US010669242B2

United States Patent
Letourneau et al.

(10) Patent No.: US 10,669,242 B2
(45) Date of Patent: Jun. 2, 2020

(54) CLOSTRIDIUM DIFFICILE TOXIN INHIBITORS

(71) Applicant: Venenum Biodesign, LLC, Lawrence Township, NJ (US)

(72) Inventors: Jeffrey J. Letourneau, East Windsor, NJ (US); Andrew G. Cole, Cranbury, NJ (US); Brett A. Marinelli, Hamilton, NJ (US); Jorge G. Quintero, Sayreville, NJ (US)

(73) Assignee: Venenum Biodesign, LLC, Hamilton, NJ (US)

( * ) Notice: Subject to any disclaimer, the term of this patent is extended or adjusted under 35 U.S.C. 154(b) by 13 days.

(21) Appl. No.: 16/308,041

(22) PCT Filed: Jun. 8, 2017

(86) PCT No.: PCT/US2017/036494
§ 371 (c)(1),
(2) Date: Dec. 7, 2018

(87) PCT Pub. No.: WO2017/214359
PCT Pub. Date: Dec. 14, 2017

(65) Prior Publication Data
US 2019/0194147 A1    Jun. 27, 2019

Related U.S. Application Data

(60) Provisional application No. 62/348,327, filed on Jun. 10, 2016.

(51) Int. Cl.
| | | |
|---|---|---|
| *C07D 401/06* | (2006.01) | |
| *C07D 401/08* | (2006.01) | |
| *C07D 401/10* | (2006.01) | |
| *C07D 401/12* | (2006.01) | |
| *C07D 401/14* | (2006.01) | |
| *C07D 403/06* | (2006.01) | |
| *C07D 403/08* | (2006.01) | |
| *C07D 403/10* | (2006.01) | |
| *C07D 403/12* | (2006.01) | |
| *C07D 403/14* | (2006.01) | |
| *C07D 413/04* | (2006.01) | |
| *C07D 413/06* | (2006.01) | |
| *C07D 413/08* | (2006.01) | |
| *C07D 413/10* | (2006.01) | |
| *C07D 413/12* | (2006.01) | |
| *C07D 413/14* | (2006.01) | |
| *C07D 417/04* | (2006.01) | |
| *C07D 417/06* | (2006.01) | |
| *C07D 417/08* | (2006.01) |
| *C07D 417/10* | (2006.01) |
| *C07D 417/12* | (2006.01) |
| *C07D 417/14* | (2006.01) |
| *C07D 243/32* | (2006.01) |
| *C07D 471/04* | (2006.01) |
| *C07D 243/14* | (2006.01) |
| *C07D 403/04* | (2006.01) |
| *A61P 31/04* | (2006.01) |
| *C07D 409/14* | (2006.01) |

(52) U.S. Cl.
CPC ............ *C07D 243/32* (2013.01); *A61P 31/04* (2018.01); *C07D 243/14* (2013.01); *C07D 401/06* (2013.01); *C07D 401/12* (2013.01); *C07D 401/14* (2013.01); *C07D 403/04* (2013.01); *C07D 403/12* (2013.01); *C07D 403/14* (2013.01); *C07D 409/14* (2013.01); *C07D 413/14* (2013.01); *C07D 417/14* (2013.01); *C07D 471/04* (2013.01)

(58) Field of Classification Search
CPC .. C07D 401/06; C07D 401/08; C07D 401/10; C07D 401/12; C07D 401/14; C07D 403/06; C07D 403/08; C07D 403/10; C07D 403/12; C07D 403/14; C07D 413/04; C07D 413/06; C07D 413/08; C07D 413/10; C07D 413/12; C07D 413/14; C07D 417/04; C07D 417/06; C07D 417/08; C07D 417/10; C07D 417/12; C07D 417/14
See application file for complete search history.

(56) References Cited

U.S. PATENT DOCUMENTS

2012/0196851 A1*   8/2012   Varrone ............... C07D 217/14
514/221

* cited by examiner

*Primary Examiner* — Bruck Kifle
(74) *Attorney, Agent, or Firm* — Arnold Braun; Terence Bogie

(57) ABSTRACT

The present invention relates to benzodiazepine derivative compounds of formula (I), or pharmaceutically acceptable salts thereof. The present benzodiazepine compounds are useful *Clostridium difficile* inhibitors in the treatment of *Clostridium difficile* infection in humans. The present invention provides a pharmaceutical composition containing benzodiazepine compounds of formula (I) and a method of making as well as a method of using the same in treating patients infected with *Clostridium difficile* infection by administering the same. The compounds of the present invention may be used in combination with additional antibiotics or anti-toxin antibody drugs.

27 Claims, 14 Drawing Sheets

1a

1b

1c

2a

2b

2c

10a

10b

10c

10d

14a

14b

14c

14d

CLOSTRIDIUM DIFFICILE TOXIN INHIBITORS

FIELD OF THE INVENTION

The present invention relates to novel benzodiazepine derivatives and pharmaceutically acceptable salts thereof that are useful as *Clostridium difficile* toxin inhibitors. The present invention also relates to compositions containing such compounds, processes of preparing and methods of use thereof.

BACKGROUND OF THE INVENTION

*Clostridium difficile* (*C. difficile*) infection (CDI) is a serious disease caused by colon infection with *C. difficile* bacteria in humans. There are ~500,000 CDI infections per year in the U.S., resulting in 15,000-20,000 deaths. The healthcare cost for CDI is estimated to be $4.8 billion (See Rupnik et al., *Nat. Rev. Microbiol.*, 2009, 7, 526-36; Dubberke et al., *Clin. Infect. Dis.*, 2012, 55, S88-92). Recurrent CDI affects about 30% of patients (Rupnik et al., *N. Engl. Med.*, 2011, 364, 422-31). CDI is primarily caused by: (i) the disruption of the gut microbiome by the broad-spectrum antibiotic therapy; and (ii) the failure to produce neutralizing anti-toxin antibodies in patients (Chang et al., *J. Infect. Dis.*, 2008, 197, 435-38; Kyne et al., *Lancet*, 2001, 357, 189-93). *C. difficile* bacteria produces two main toxins (namely, toxin A and toxin B), which glucosylate Rho-GTPases inside the epithelial cells, and lead to fever, abdominal pain, diarrhea, and colon inflammation (Rupnik et al., *Nat. Rev. Microbiol.*, 2009, 7, 526-36).

Treatment of CDI focuses on the use of several different antibiotics. These antibiotics include: (i) vancomycin (FDA-approved in 1986); (ii) metronidazole (not FDA-approved but is used "off-label"); and (iii) fidaxomicin (FDA-approved in 2011), a more narrow-spectrum antibiotic in comparison to vancomycin or metronidazole. Fidaxomicin reduces CDI recurrence from 25% (with vancomycin treatment) to 8% (with fidaxomicin treatment) (Louie et al., *N. Engl. J. Med.*, 2011, 364, 422-31). Recently, there are reports indicating the rise of new strains of *C. difficile* bacteria that exhibit an increased toxin production and resistance to fluoroquinolones (Lessa et al., *Clin. Infect. Dis.*, 2012, 55, S65-70). For example, the epidemic BI/NAP1/O27 strain now accounts for 51% of isolates from hospital outbreaks in the U.S. (McDonald et al., *N. Engl. J. Med.*, 2005, 353, 2433-41). There is a need for developing new narrow-spectrum antibiotics in treating CDI. Several narrow-spectrum antibiotics are in pre-clinical and early clinical development; however, their efficacy remains unknown.

An alternative means to treat CDI involves the use of anti-toxin antibodies. Active immunization using bacterial toxin as a vaccine is presently in clinical trials. However, the efficacy remains unknown. Passive immunization with monoclonal anti-toxin antibodies has been reported to reduce CDI recurrence from 32% to 8% when used in combination with vancomycin in a Phase II clinical trial (Lowy et al., *N. Engl. J. Med.*, 2010, 362, 197-205). The high cost of monoclonal antibody may hinder the immunization approach for its clinical application in non-hospitalized CDI patients, which account for 42% of cases in a large study (8,569 patients) (Kasper et al., *Infect. Control Hosp. Epidemiol.*, 2012, 33, 470-76).

Another emerging approach involves the use of novel compounds that inhibit the *C. difficile* toxins directly. Pruitt et al. disclose inositol hexaphosphate (InsP6) can induce an autocatalytic cleavage of *C. difficile* toxin A (*J. Biol. Chem.*, 2009, 284, 21934-40). Savidge et al. showed that S-nitrosylation of the toxins inhibits the toxin activity in vitro (*Nat. Med.*, 2011, 17, 1136-41). These studies open up windows towards identifying novel compounds that can neutralize the toxin's activity. Abdeen et al. disclose a peptide that is active against both *C. difficile* toxin A and toxin B (*ACS Chem. Biol.*, 2010, 5, 1097-1103). Puri et al. disclose the rational design of covalent small molecule inhibitors of *C. difficile* toxin B (*Chem. & Biol.*, 2010, 17, 1201-11). In particular, di-peptides and tri-peptides have been identified to uniquely inhibit the cysteine protease domain of toxin and reduce the toxicity. However, there has been no report regarding the in vivo activity of these compounds. An oral toxin-binding polymer (Tolevamer) has been developed to bind to *C. difficile* toxins, but was reported to fail in a Phase II trial (Johnson et al., *Antimicrob. Agents Chemother.*, 2012, 56, 4043-45).

Accordingly, there is a continuing need for identifying a novel compound that can inhibit *C. difficile* toxins and thus provide a new approach for CDI treatment.

SUMMARY OF THE INVENTION

The present invention relates to compounds represented by formula (I):

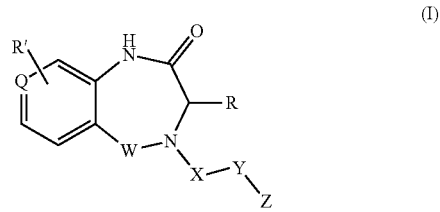

(I)

and pharmaceutically acceptable salts thereof.

The present benzodiazepine derivative compounds of formula (I) possess neutralizing activity towards *C. difficile* toxins A and B and are useful *C. difficile* inhibitors to treat CDI. The present invention relates to a pharmaceutical composition containing such compounds as well as a process of preparing them and a method of administering same to treat patients suffering from CDI. The present compounds may be used in combination with other anti-bacterial drugs.

Figure 3:
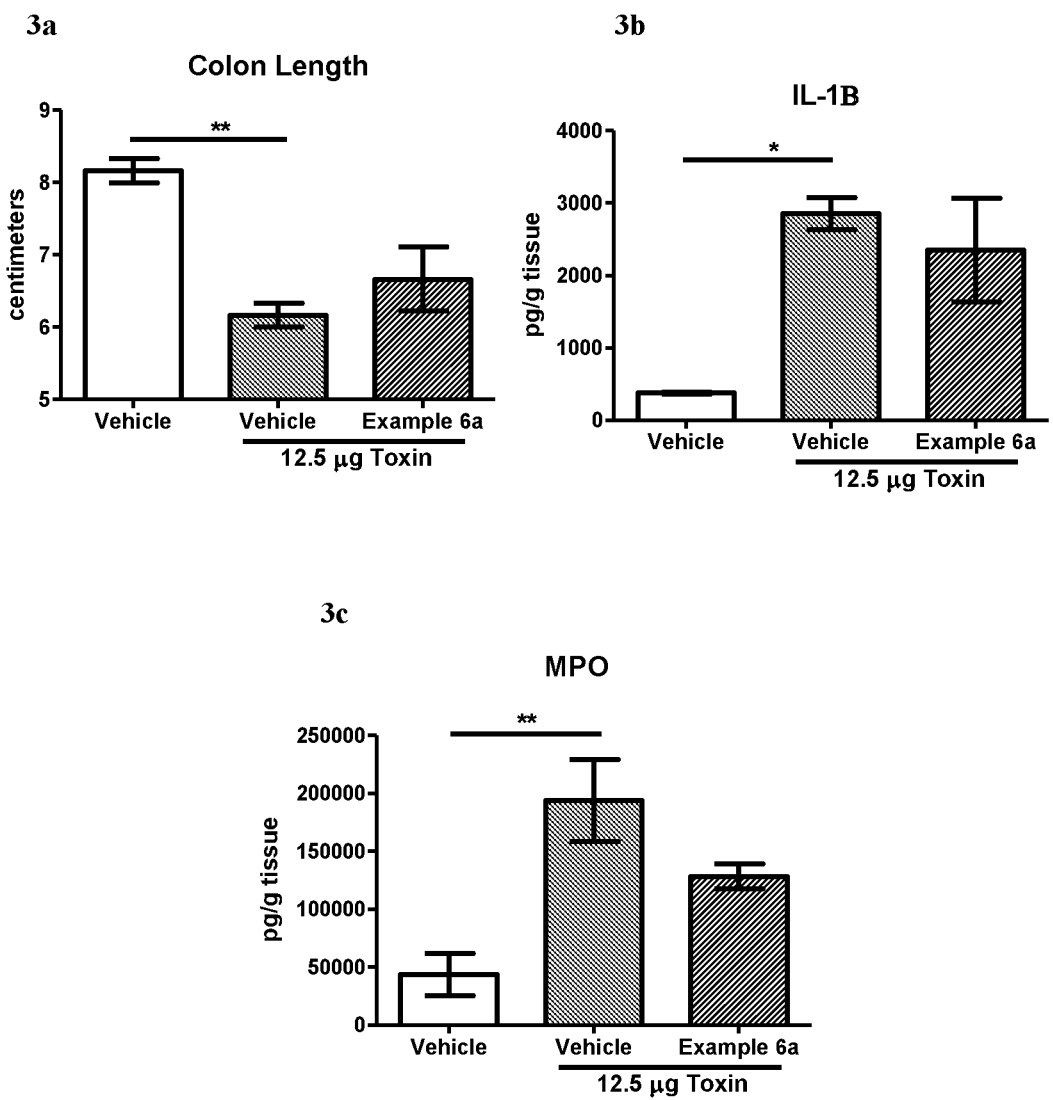

FIGS. 3a, 3b, and 3c depict the protective effect of Example 6a via intrarectal administration in the murine *C. difficile* toxin model. Three (3) animals were used in each group. Example 6a was co-administered at 25 mg/kg with *C. difficile* toxin (12.5 μg). Example 6a reduced the *C. difficile* toxin-mediated effects on colon length (FIG. 3a), decreased the *C. difficile* toxin-induced IL-1β (FIG. 3b) as well as MPO (FIG. 3c). Bars represent the mean±standard error of the mean (SEM). P values:*<0.05 and **<0.01 (one-way ANOVA followed by Dunnett post-test comparing all columns to vehicle plus toxin control).

Figure 4:
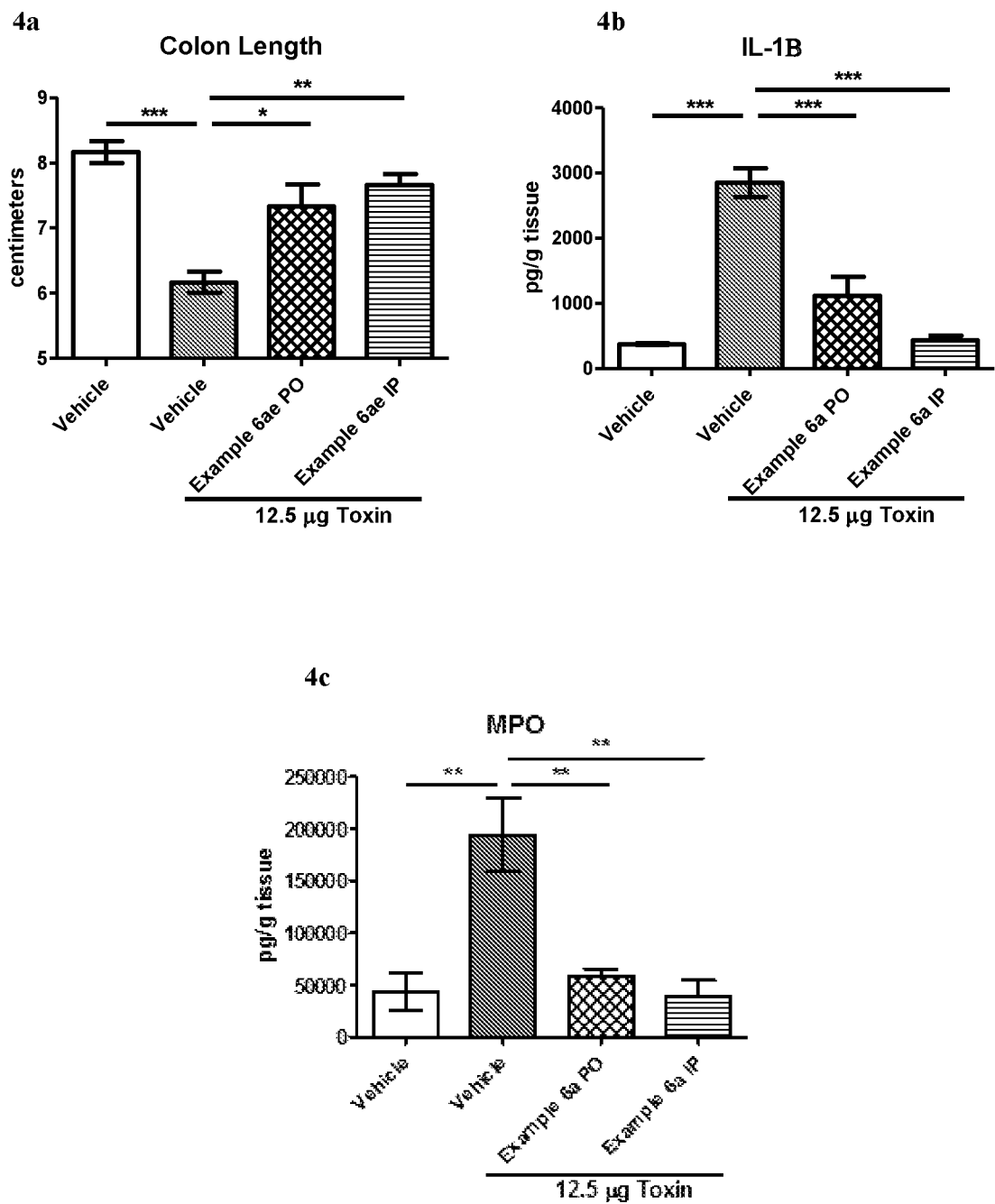

FIGS. 4a, 4b, and 4c depict the protective effect of Example 6a via oral (PO) and intraperitoneal (IP) administration in murine *C. difficile* toxin model. *C. difficile* toxin (12.5 μg) was administered intrarectally. Three (3) animals were used in each group. Example 6a was dosed at 50 mg/kg body weight. Example 6a reduced the *C. difficile* toxin-mediated effects on colon length (FIG. 4a), decreased the *C. difficile* toxin-induced IL-1β (FIG. 4b) as well as MPO (FIG. 4c). Bars represent the mean±standard error of the mean (SEM). P values:*<0.05, <0.01 and *<0.001 (one-way ANOVA followed by Dunnett post-hoc comparing all columns to vehicle plus toxin control).

Figure 5:
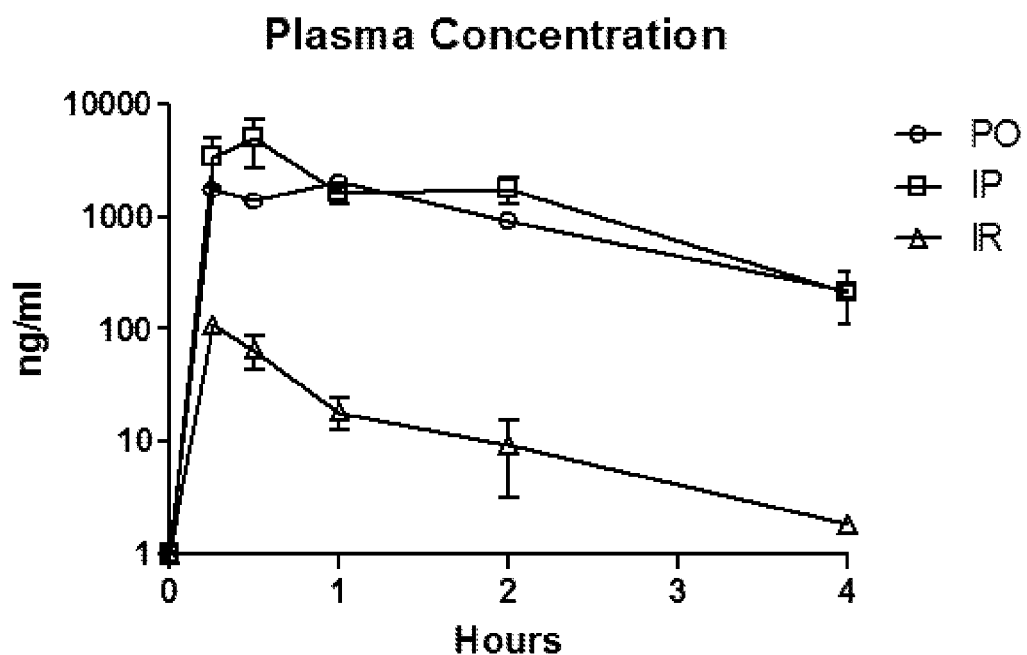

FIG. 5 depicts the plasma concentration of Example 6a via different routes of administration (i.e., PO, IP or IR) during the course of the study in the murine *C. difficile* toxin model. Each group contains three (3) mice. Bars represent the mean±standard error of the mean (SEM). Plasma exposure was higher with PO or IP administration (P<0.001) compared to IR administration (two-way ANOVA).

Figure 6:
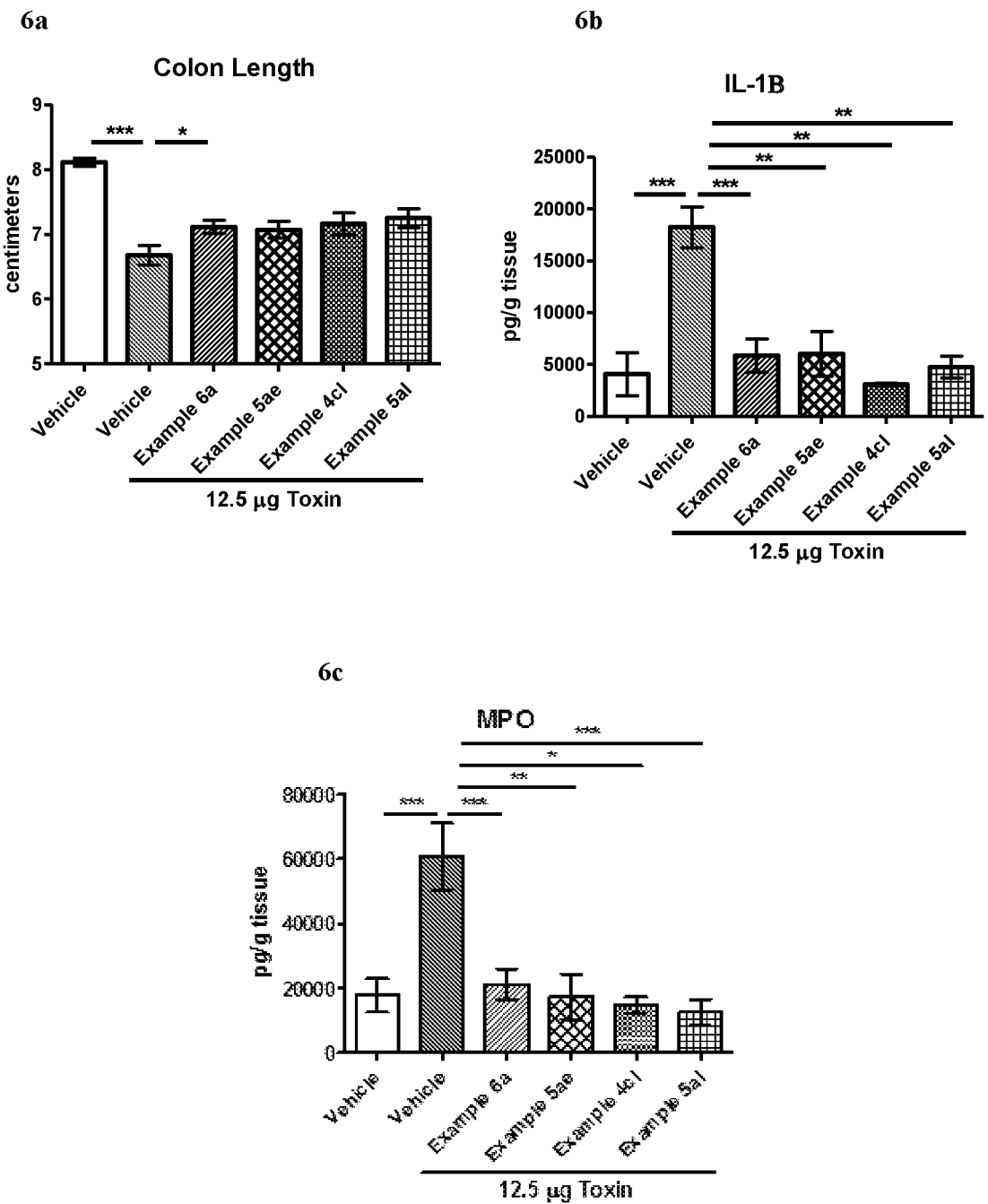

FIGS. 6a, 6b, and 6c depict the effect of Example 6a, (R)-2-Chloro-4-((8-chloro-2,5-dioxo-3-(pyridin-2-ylmethyl)-2,3-dihydro-1H-benzo[e][1,4]diazepin-4(5H)-yl) methyl)-N-(5-(trifluoromethyl)pyridin-2-yl)benzamide (Example 5ae), (R)-4-((8-Chloro-2,5-dioxo-3-(pyridin-2-ylmethyl)-2,3-dihydro-1H-benzo[e][1,4]diazepin-4(5H)-yl) methyl)-N-(5-methoxypyridin-2-yl)-2-methylbenzamide (Example 4cl) and (R)-4-((8-Chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl) pyridin-2-yl) benzamide (Example 5al) via PO administration in murine *C. difficile* toxin model. Data are pooled from three (3) experiments and between three (3) and fourteen (14) animals were used in each group. The compounds were dosed at 50 mg/kg body weight. *C. difficile* toxin (12.5 μg) was administered intrarectally. All of the four (4) tested compounds reduced the *C. difficile* toxin-mediated effects on colon length (FIG. 6a), and reduced the levels of IL-1β (FIG. 6b) as well as MPO (FIG. 6c). Bars represent the mean±standard error of the mean (SEM). P values: *<0.05, <0.01 and *<0.001 (one-way ANOVA followed by Dunnett post-test comparing all columns to toxin plus vehicle control).

Figure 7:
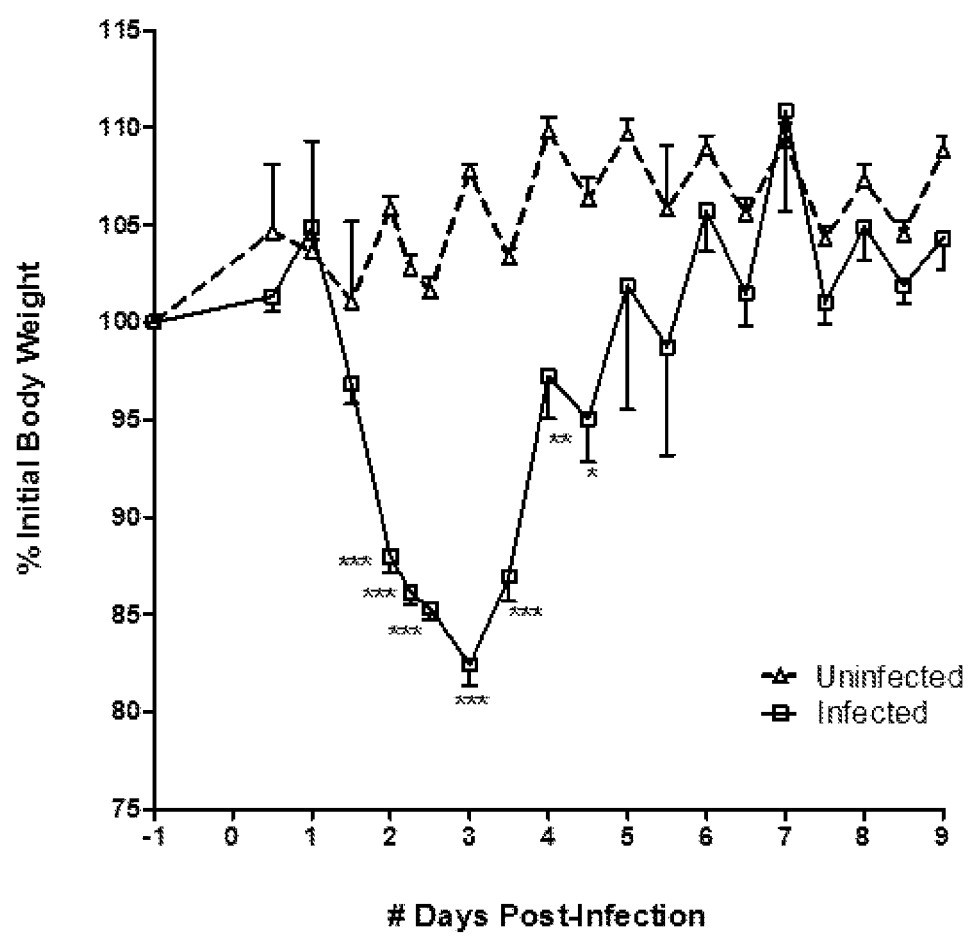

FIG. 7 depicts the acute murine infection model. There were five (5) uninfected mice and eight (8) infected mice. Five (5) of the eight (8) infected mice were euthanized on Day 3 due to body weight loss of >20%. Points represent the mean±standard error of the mean (SEM). P values: *<0.05, <0.01 and *<0.001 (two-way ANOVA followed by Bonferroni post-test excluding euthanized animals).

Figure 8:
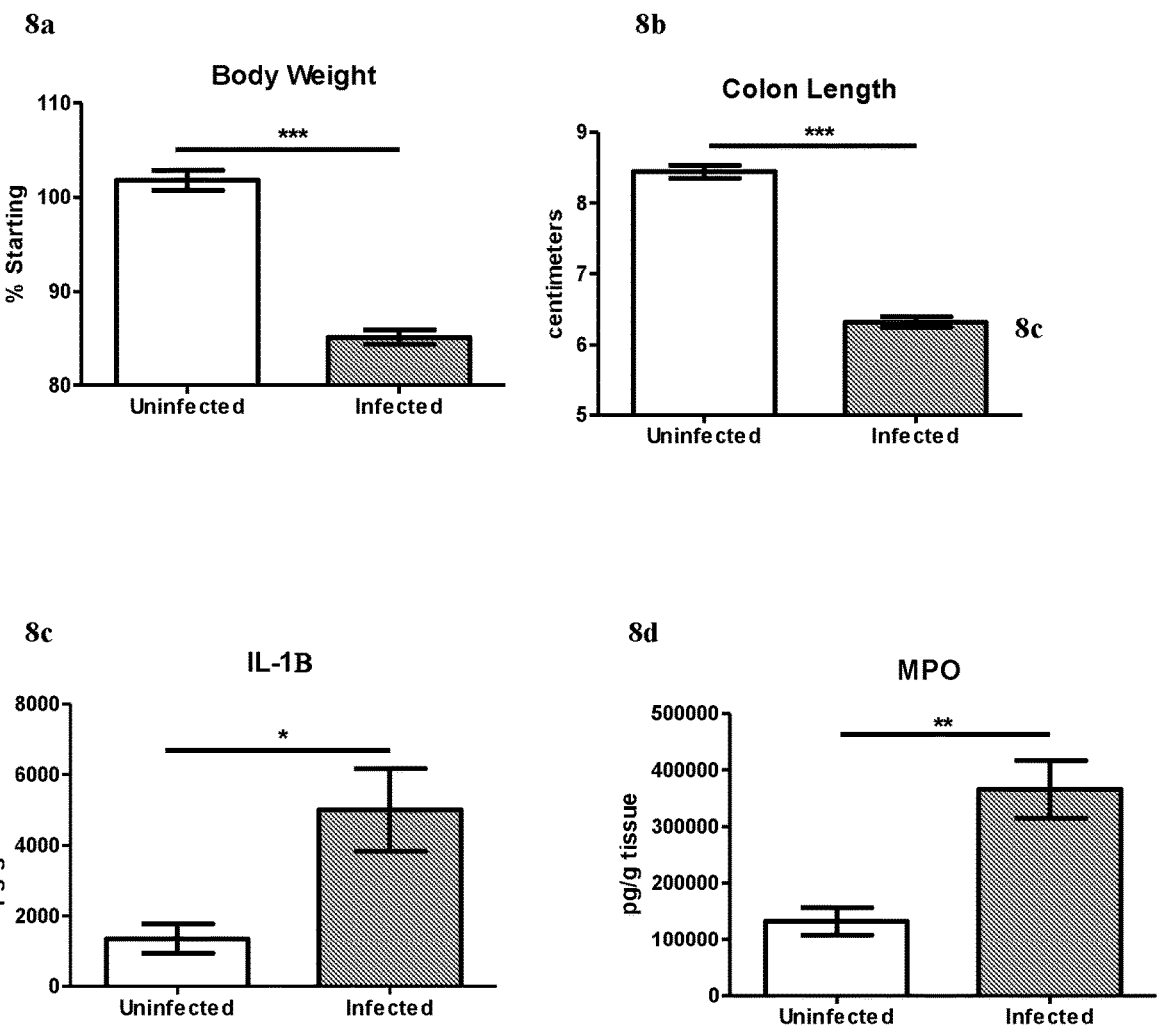

FIGS. 8a, 8b, and 8c depict the effects of *C. difficile* toxin in the acute murine infection model. Data are pooled from three (3) studies in which a total of between thirteen (13) and twenty-nine (29) animals were used in the control group and the treatment groups. Body weight, colon length, IL-1β, and MPO were determined 52 hours after infection. Infection with *C. difficile* causes a reduction in colon length (FIG. 8a), increase in IL-1β (FIG. 8b) and MPO (FIG. 8c). Bars represent the mean±standard error of the mean (SEM). P values: *<0.05, <0.01 and *<0.001 (t-test).

Figure 9:
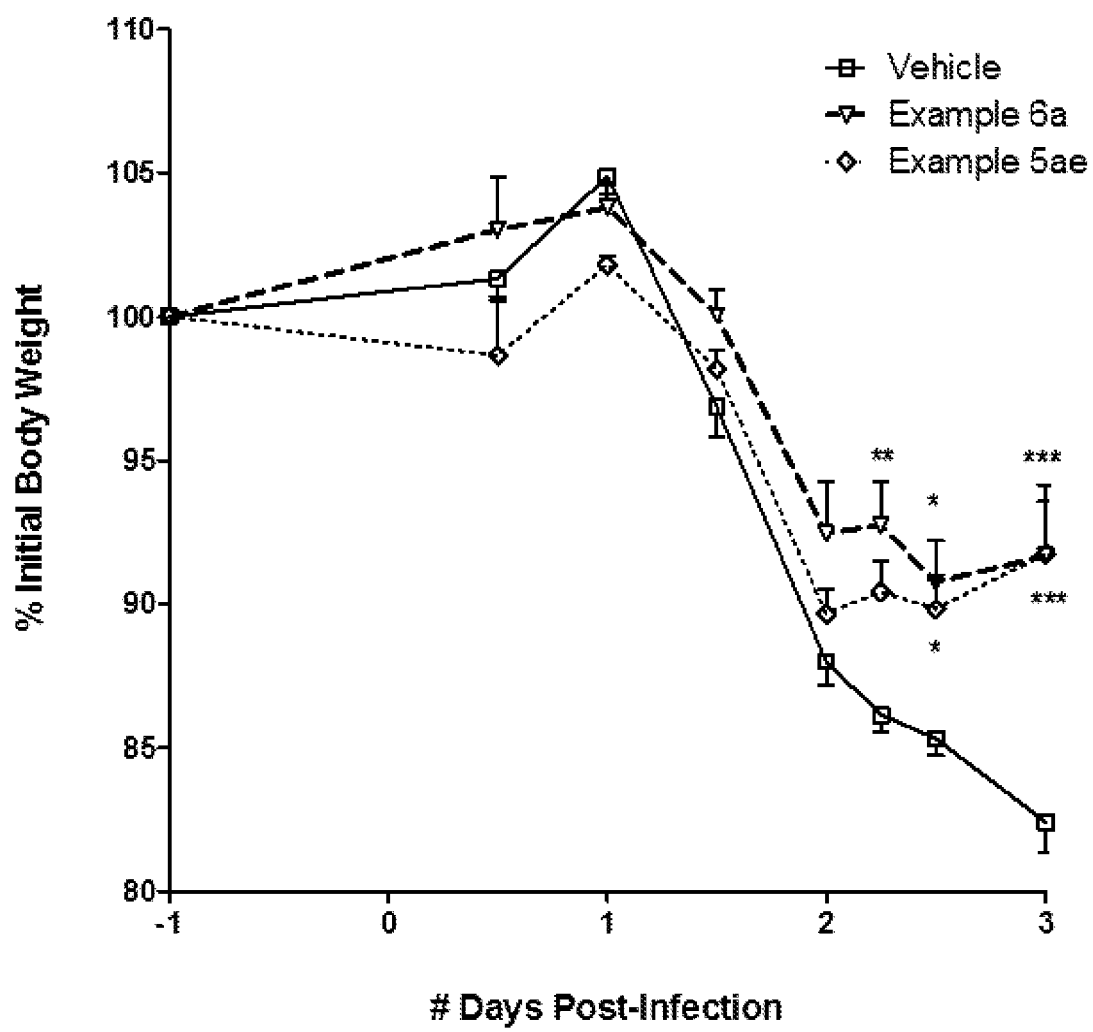

FIG. 9 depicts treatment with Example 6a or Example 5ae in the acute murine infection model. Eight (8) mice were in each group. Points represent the mean±standard error of the mean (SEM). P values: *<0.05, <0.01 and *<0.001 (two-way ANOVA followed by Bonferroni post-hoc analyzing data up to Day 3).

Figure 10:
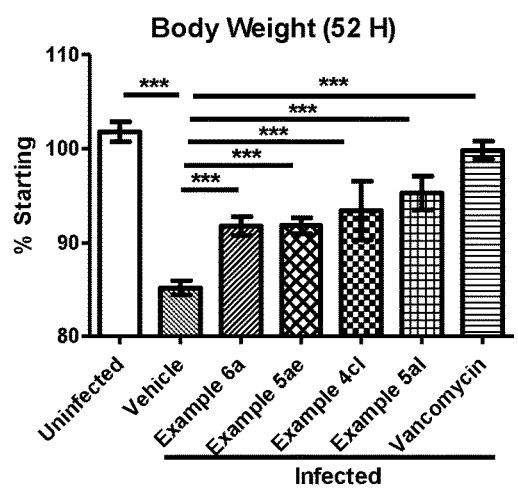
Figure 10:
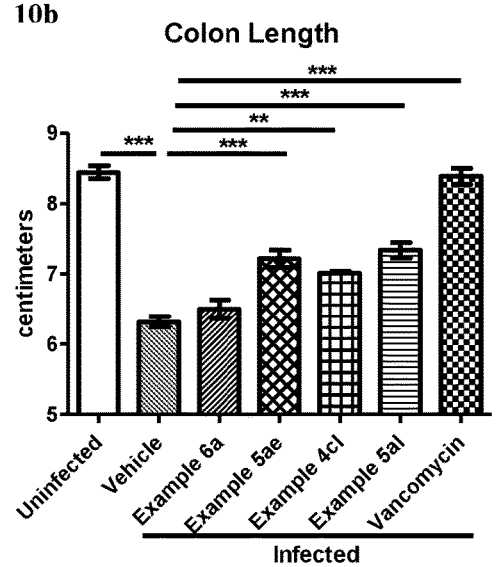
Figure 10:
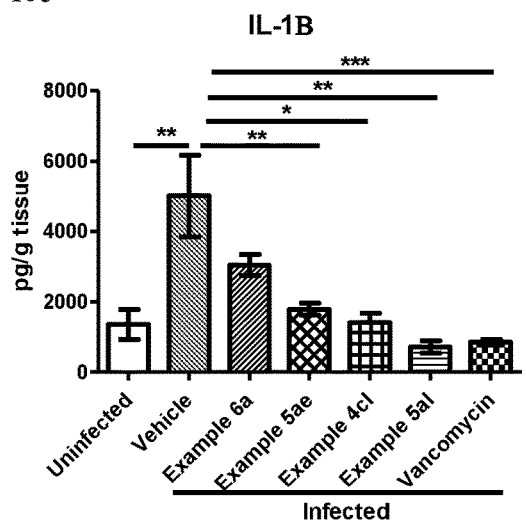
Figure 10:
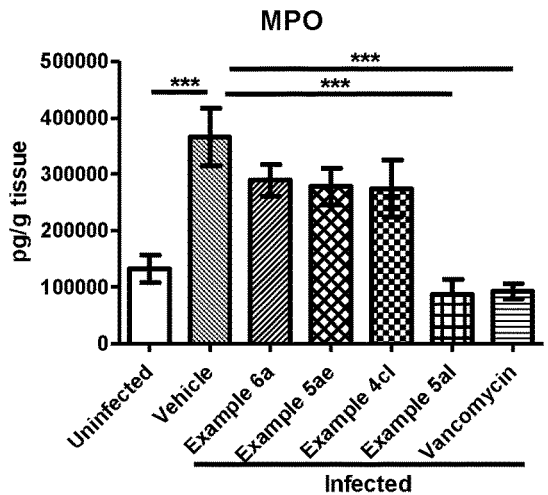

FIGS. 10a, 10b, and 10c depict the effect of Example 6a, Example 5ae, Example 4cl and Example 5al via PO administration in acute murine *C. difficile* infection model. Data are pooled from three experiments in which between five (5) and sixteen (16) animals were used in each group in each individual study. Body weight (FIG. 10a), colon length (FIG. 10b), IL-1β (FIG. 10c) and MPO (FIG. 10d) were determined 52 hours after infection. Bars represent the mean±standard error of the mean (SEM). P values: *<0.05, <0.01 and *<0.001 (one-way ANOVA followed by Dunnett post-test comparing all columns to infected vehicle control).

Figure 11:
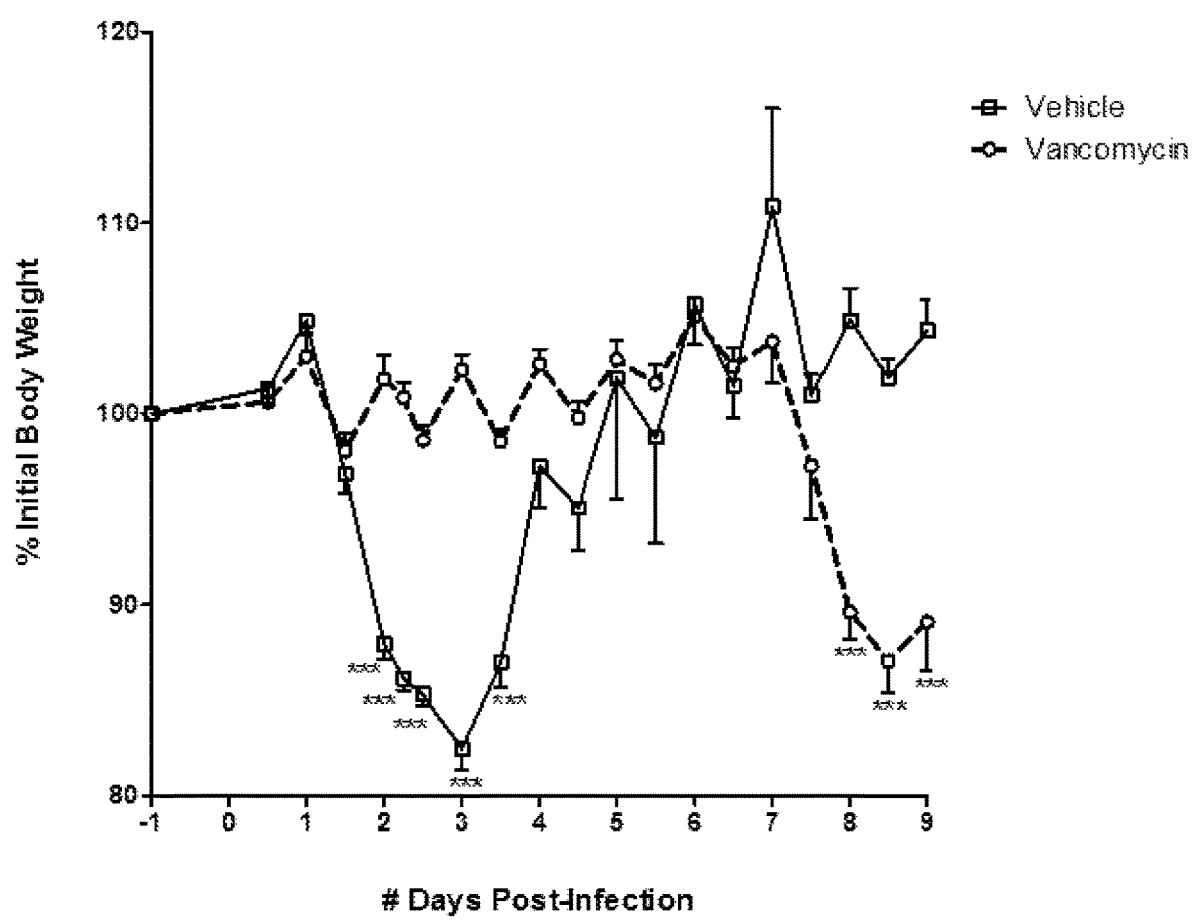

FIG. 11 depicts relapsing disease after vancomycin treatment in the murine infection model. Eight (8) mice were in each group. Five (5) of the eight (8) vehicle-treated mice were euthanized on Day 3 due to body weight loss of >20%. Six (6) of the eight (8) vancomycin-treated mice died on Days 8-9. Points represent the mean±standard error of the mean (SEM). P values: ***<0.001 (two-way ANOVA followed by Bonferroni post-hoc excluding euthanized vehicle-treated animals and using last recorded body weight for vancomycin-treated animals for post-mortality time points).

Figure 12:
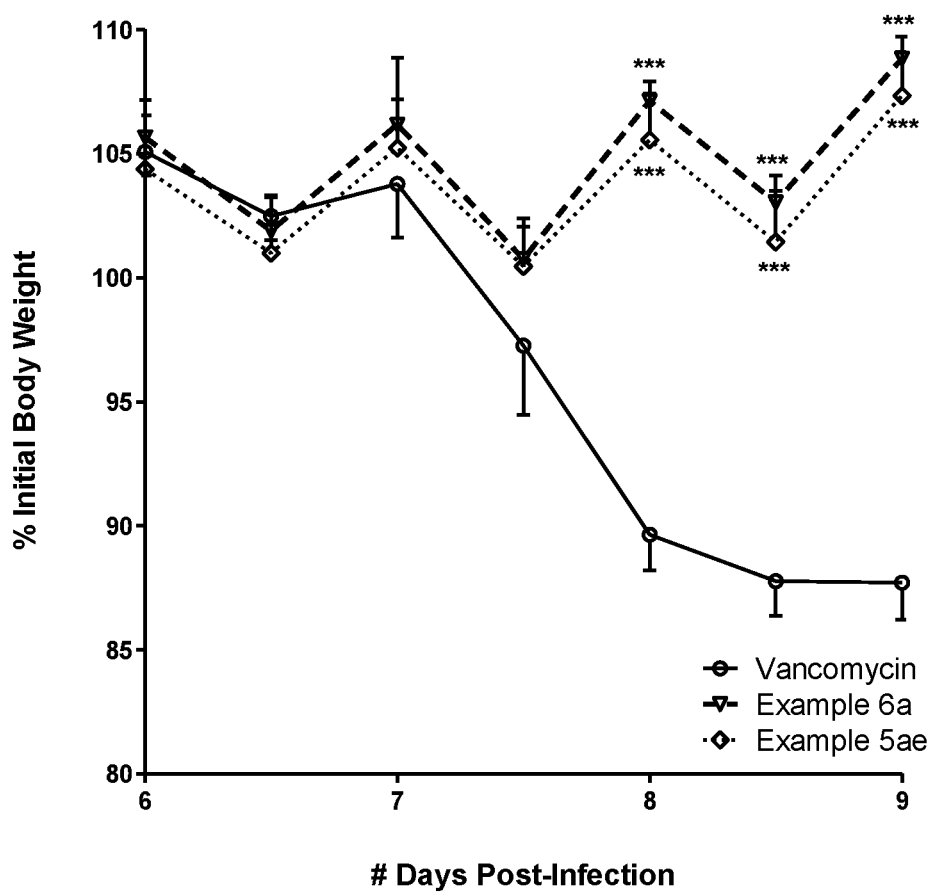

FIG. 12 depicts prevention of relapsing disease by treatment with Example 6a or Example 5ae in the relapsing murine infection model. Eight (8) mice were in each group. One (1) mouse in the Example 5ae group was euthanized on Day 4 due to body weight loss of >20%. Six (6) of the eight (8) vancomycin-treated mice died on Days 8-9. Points represent the mean±standard error of the mean (SEM). P values: *<0.05, <0.01 and *<0.001 (two-way ANOVA followed by Bonferroni post-test excluding the euthanized mouse from the Example 5ae group and using last recorded body weight for vancomycin-treated animals for post-mortality time points).

Figure 13:
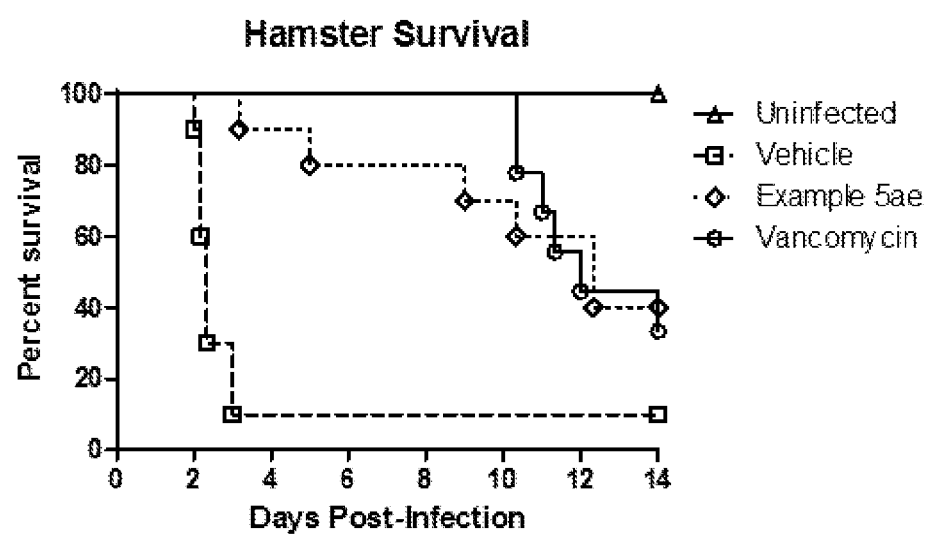

FIG. 13 depicts the effect of Example 5ae on survival in the hamster infection model. Nine (9) or ten (10) animals were used for each group. Animals were dosed twice per day via PO administration for either 5 days or 7 days post-infection.

Figure 14:
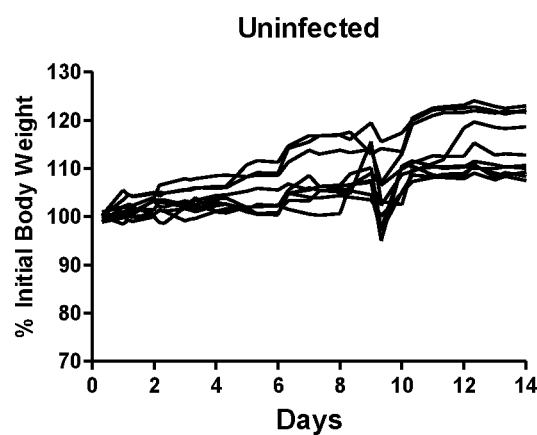
Figure 14:
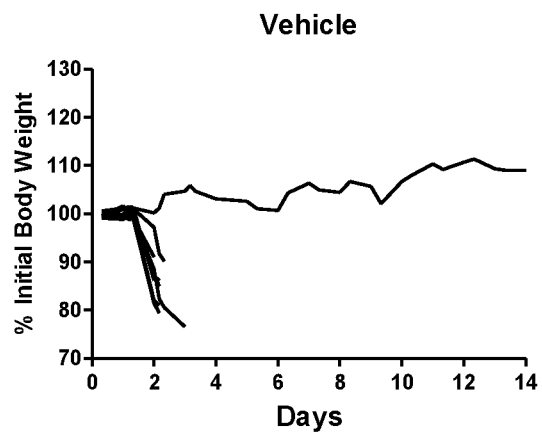
Figure 14:
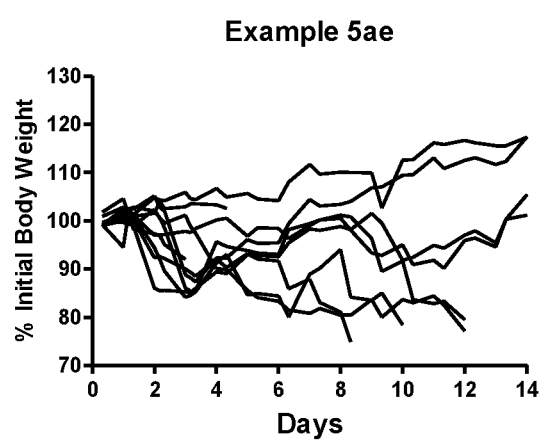
Figure 14:
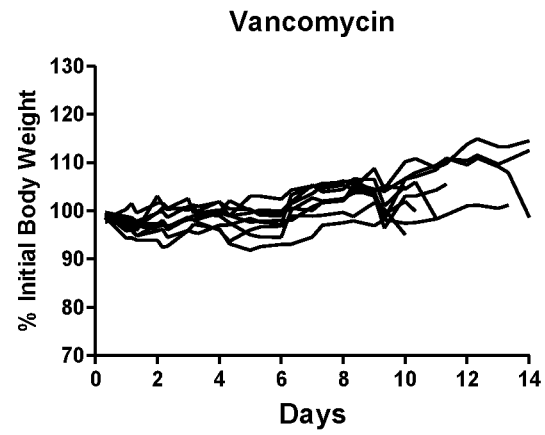

FIGS. 14a, 14b, 14c, and 14d depict the effect of Example 5ae on body weight in the hamster infection model. Groups of animals were uninfected (FIG. 14a), or infected and treated with vehicle (FIG. 14b), Example 5ae (FIG. 14c) or vancomycin (FIG. 14d). Nine (9) or ten (10) animals were used for each group. Animals were dosed twice per day via PO administration for either 5 days (vancomycin 5 mg/kg) or 7 days (Example 5ae 50 mg/kg) post-infection. Each line represents an individual hamster.

DETAILED DESCRIPTION OF THE INVENTION

Definitions

As used herein, number ranges where provided (e.g., 1-6) refer to each and every number in that range as a discrete embodiment.

As used herein, the term "alkyl" refers to a saturated carbon chain up to 10 carbons that may be linear, branched or a combination thereof. Exemplary alkyl includes methyl, ethyl, n-propyl, isopropyl, n-butyl, sec- and tert-butyl, pentyl, hexyl and the like. $C_{1-6}$alkyl refers to a saturated carbon chain that may be linear, branched or a combination thereof which contains one to six carbon atoms.

As used herein, the term "alkenyl" refers a carbon chain up to 10 carbons that contains at least one carbon-carbon double bond, and that may be linear, branched or a combination thereof. Exemplary alkenyl includes vinyl, allyl, isopropenyl, pentneyl, hexenyl, heptenyl, 1-propenyl, 2-butenyl, 2-methyl-2-butenyl and the like.

As used herein, the term "alkynyl" refers a carbon chain up to 10 carbons that contains at least one carbon-carbon triple bond, and that may be linear, branched or a combination thereof. Exemplary alkynyl includes ethynyl, propargyl, 3-methyl-1-pentynyl, 2-heptynyl and the like.

As used herein, the term "alkoxy" refers to an alkyl up to 10 carbons linked to the parent structure through an oxygen. Exemplary alkoxy includes methoxy, ethoxy, propoxy, isopropoxy, butoxy and the like.

As used herein, the term "cycloalkyl" refers to a monocyclic, bicyclic, tricyclic or bridged saturated hydrocarbon ring system containing 3-14 carbons. Exemplary cycloalkyl includes cyclopropyl, cyclobutyl, cyclopentyl, cyclohexyl, cycloheptyl, decahydronaphthyl and the like.

As used herein, the term "cycloalkenyl" refers a monocyclic, bicyclic, tricyclic or bridged non-aromatic hydrocarbon ring system containing 3-14 carbons and at least one double bond. Exemplary cycloalkenyl includes cyclopropenyl, cyclobutenyl, cyclopentenyl, cyclohexenyl, cycloheptenyl and the like.

As used herein, the term "heterocycloalkyl" refers to a monocyclic, bicyclic, tricyclic or bridged saturated hydrocarbon ring system containing 2-14 carbons and 1, 2, 3, 4 or 5 heteroatoms selected from oxygen ("O"), sulfur ("S") and nitrogen ("N") atoms. Exemplary heterocycloalkyl includes aziridinyl, azetidinyl, tetrahydrofuranyl, dioxanyl, oxanyl, morpholinyl, dithianyl, thiomorpholinyl, piperazinyl, piperidinyl, 1,3-dioxolanyl, imidazolidinyl, pyrrolidinyl, pyrazolidinyl, tetrahydropyranyl and the like.

As used herein, the term "aryl" refers to a monocyclic, bicyclic or tricyclic hydrocarbon ring system containing 5-14 carbon atoms, wherein at least one of the rings is aromatic. Aryl includes a ring system in which an aromatic ring is fused to a non-aromatic ring, such as a cycloalkyl or a cycloalkenyl ring. Exemplary aryl includes phenyl, naphthyl, indanyl, benzocyclobutanyl, tetrahydronaphthyl and the like.

As used herein, the term "heteroaryl" refers to a monocyclic, bicyclic or tricyclic hydrocarbon ring system containing 5-14 carbon atoms and containing 1, 2, 3, 4 or 5 heteroatoms selected from oxygen ("O"), sulfur ("S") and nitrogen ("N") atoms, wherein at least one of the heteroatoms containing rings is aromatic. "Heteroaryl" also refers to a ring system in which an aromatic heteroatom containing ring is fused to a non-aromatic ring such as a cycloalkyl, cycloalkenyl or heterocycloalkyl ring, and refers to a ring system in which an aryl is fused to a non-aromatic heteroatom containing ring, such as a heterocycloalkyl ring. Exemplary heteroaryl includes pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, oxo-dihydroqunoline, indolyl, oxindole, isoquinolyl, dibenzofuranyl, 1,3-benzodioxolyl, dihydroisoindolyl, dihydrobenzodioxinyl, dihydroindolyl, isoindolinyl and the like.

As used herein, the term "halogen" refers to fluorine, chlorine, bromine and iodine.

As used herein, the term "floating bond", when used in connection with a substituent depicted in a formula (e.g., —(R)), refers to that substituent (e.g., R) permitted on any available carbon or nitrogen atom in the ring to which the substituent is attached, unless expressly depicted or described.

As used herein, the term that a certain group "is optionally substituted" refers to any group having that particular component thereof can be further substituted. For example, "alkyl group is optionally further substituted with" refers to any group possessing an alkyl component that can be further substituted thereof. The term includes "mono-", "di-" or "tri-" substitutions.

As used herein, the term "ortho," "meta" and "para" (abbreviated as "o-," "m-" and "p-") refers to the position of two identical or different substituents relative to each other in a benzene ring. For example, ortho substitution refers to two substituents that are located in the 1, 2 positions of a benzene ring; meta substitution refers to two substituents that are located in the 1, 3 positions of a benzene ring; para substitution refers to two substituents that are located in the 1, 4 positions of a benzene ring.

When any variable (e.g., $R^1$, R') occurs more than one time in any substituent, its definition on each occurrence is independent of its definition at every other occurrence. Also combinations of substituents and/or variables are permissible only if such combinations result in stable compounds, and conform to well-known principles of chemical structure connectivity and stability. A squiggly line "〜〜〜" across a bond in a substituent variable represents the points of attachment.

As used herein, the term "pharmaceutically acceptable" refers to compositions, polymers, solvates, and dosage forms which are, within the scope of sound medical judgment, suitable for use in contact with the tissues of human beings and animals without causing excessive toxicity, irritation, allergic response, or other problem or complication, commensurate with a reasonable benefit and risk ratio.

As used herein, the term "pharmaceutically acceptable salt" refers to a derivative of a compound of the present invention wherein the parent compound is modified by making acid or base salts thereof. It includes inorganic or organic acid salts of basic residues such as amines; and inorganic or organic basic salts of acidic residues such as carboxylic acids. Exemplary pharmaceutically acceptable salt includes acetate, bicarbonate, bisulfate, formate, hydrochloride, sulfate, phosphate and the like.

As used herein, the term "pharmaceutical composition" refers to a composition comprising a compound of the present invention together with a pharmaceutically acceptable carrier.

As used herein, the term "pharmaceutically acceptable excipient" refers to an excipient that is not injurious to a patient. Exemplary pharmaceutically acceptable excipient includes starch, cellulose, gelatin, talc, glycol, polyol, ester, agar, buffering agents, alginic acid and the like that are employed in pharmaceutical formulations.

As used herein, the term "administering" or "administration" refers to providing a compound, a pharmaceutically acceptable salt, solvate or prodrug thereof to a human subject in need of treatment by oral administration.

As used herein, the term "mammal" refers to animal species that has the distinguished features by the presence of sweat glands, including those that are specialized to produce milk to nourish the young. Exemplary mammal includes human, mouse, rat, dog and the like.

As used herein, the term "treating" or "treatment" refers to an intervention (e.g., the administration of an agent to a subject) which cures, ameliorates or lessens the symptoms of a disease or removes (or lessens the impacts of) its cause(s) (e.g., the causative bacterium). The treatment of *C. difficile* infection according to the present invention may be characterized by inhibiting the *C. difficile* toxins without bacteriostatic and/or bacteriocidal action against *C. difficile*.

As used herein, the term "*Clostridium difficile* infection" (CDI) refers to an infection that involves (e.g., is caused, exacerbated, associated with or characterized by the presence of) *C. difficile* residing and/or replicating in the body of a subject.

As used herein, the terms "bacteriostatic" and "bacteriocidal" refer to the ability to prevent (or reduce the rate of) bacterial growth and to mediate (directly or indirectly) the cellular destruction of bacterial cells, respectively. The terms are not mutually exclusive, and many agents exert both bacteriostatic and bacteriocidal effects.

As used herein, the term "therapeutically effective amount" refers to an amount of a compound of the present invention which, as compared to a corresponding human subject who has not received such an amount, results in improved treatment, prevention, or amelioration of *C. difficile* infection. The amount will depend on the particular condition, co-administered compounds if any, and the characteristics of the human subject, such as general health, other diseases, age, sex, genotype, body weight and tolerance to drugs. Those skilled in the art will be able to determine appropriate dosages depending on these and other factors.

As used herein, the term "combination" refers to a compound of the present invention and an additional therapeutic agent useful for the treatment of CDI. Exemplary therapeutic agent includes antibiotics such as metronidazole, vancomycin, Fidaxomicin, anti-*C. difficile* antibodies, anti-*C. difficile* toxin A antibodies, anti-*C. difficile* toxin B antibodies and the like.

The present invention relates to novel benzodiazepine derivatives and pharmaceutically acceptable salts thereof that are useful in the treatment of *C. difficile* infection. The benzodiazepine derivatives are *C. difficile* toxin inhibitors. The present invention also relates to pharmaceutical compositions containing these compounds, process of making and methods of use thereof in treating *C. difficile* infection.

In one aspect, the present invention addresses a compound of formula (I)

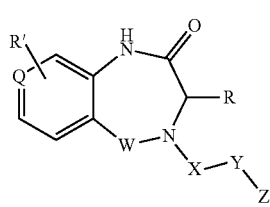
(I)

or a pharmaceutically acceptable salt thereof, wherein:

Q is CH or N;

R' is H, halogen, trifluoromethyl ($CF_3$), $C_{1-6}$alkyl, $C_{1-6}$alkoxy, CN, $NO_2$, $NH_2$, $NHS(O)_2C_{1-6}$alkyl, NHC(O)$C_{1-6}$alkyl, NHC(O)$C_{1-6}$alkylO$C_{1-6}$alkyl, NHC(O)-isoxazolyl or NHC(O)-pyridyl, wherein isoxazoly and pyridyl are each optionally mono- or di-substituted with $C_{1-3}$alkyl, and alkyl is optionally substituted with 1-4 halogen;

W is C(O) or $CH_2$;

X is $CH_2$, CH($C_{1-3}$alkyl), $C_{3-6}$cycloalkyl, C(O) or $S(O)_2$, and when W is C(O), X cannot be C(O) or $S(O)_2$;

Y is

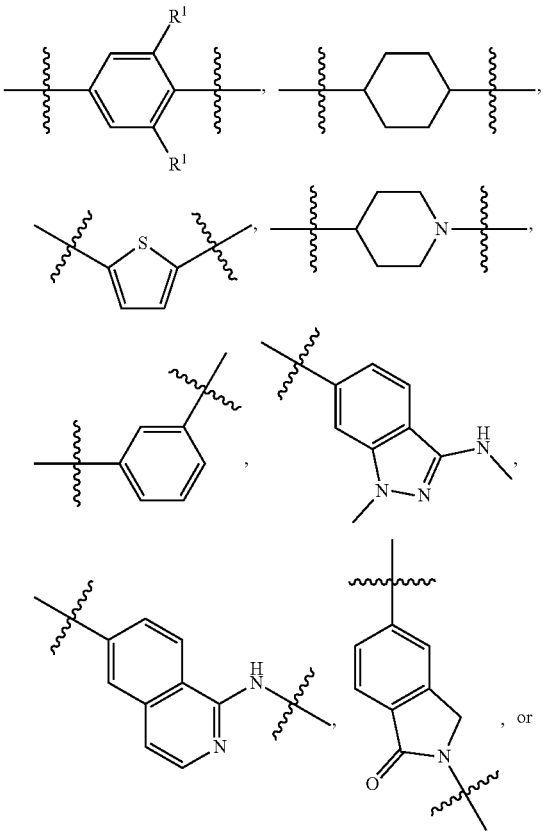

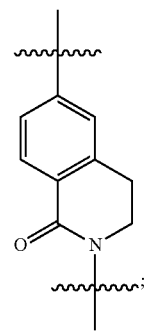

Z is CH$_2$OH, NH$_2$, C(O)OH, R$^6$,

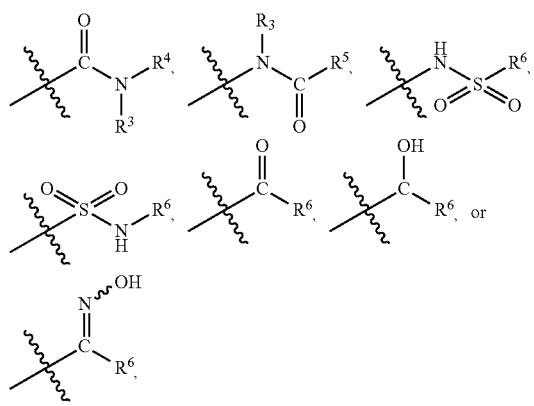

provided that only when Y is

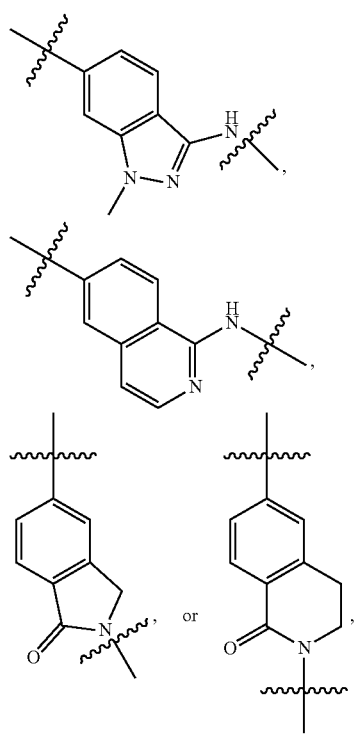

Z is R$^6$;
R is H, C$_{1-6}$alkyl, C$_{1-6}$alkyl-OH, C$_{1-6}$alkyl-N(C$_{1-6}$alkyl)C$_{1-6}$alkyl or C$_{0-3}$alkyl-R$^7$;
each R$^1$ is independently H, C$_{1-6}$alkyl, C$_{1-6}$alkoxy, halogen, NH$_2$, phenyl, pyridyl, pyrazolyl, isoxazolyl, OC$_{1-6}$alkyl-phenyl, benzodioxolyl or NHC(O)C$_{0-3}$alkyl-R$^2$, wherein phenyl, pyridyl, pyrazolyl and isoxazolyl are each optionally mono- or di-substituted with substituents independently selected from C$_{1-3}$alkyl, halogen, C$_{1-3}$alkoxy, C(O)NHC$_{1-3}$alkyl and NHC(O)C$_{1-3}$alkyl, and alkyl is optionally substituted with 1-4 halogen;
R$^2$ is OH, C$_{1-6}$alkyl, C$_{1-6}$alkoxy, N(C$_{1-6}$alkyl)C$_{1-6}$alkyl, morpholinyl, pyrrolidinyl, piperidinyl, piperizinyl, tetrahydropyranyl, cyclohexyl or pyridyl, wherein morpholinyl, pyrrolidinyl, piperidinyl, piperizinyl, tetrahydropyranyl, cyclohexyl and pyridyl are each optionally mono- or di-substituted with C$_{1-3}$alkyl, and alkyl is optionally substituted with 1-4 halogen;
R$^3$ is H or C$_{1-6}$alkyl;
R$^4$ is H, OH, C$_{1-6}$alkyl, C(O)C$_{1-6}$alkyl, C(NOH)C$_{1-6}$alkyl, S(O)$_2$C$_{1-6}$alkyl, S(O)$_2$-phenyl, or R$^6$, wherein phenyl is optionally mono- or di-substituted with substituents independently selected from halogen, C$_{1-3}$alkyl and C$_{1-3}$alkoxy, and alkyl is optionally substituted with 1-4 halogen;
or R$^3$ and R$^4$ together with the N to which they are attached form:

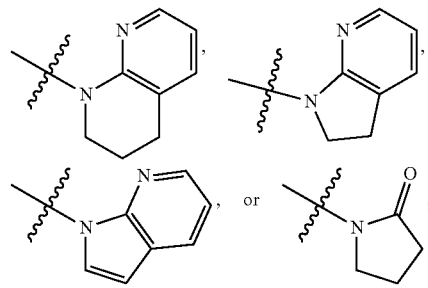

each optionally mono-, di-, or tri-substituted with substituents independently selected from halogen and C$_{1-3}$alkyl, wherein alkyl is optionally substituted with 1-4 halogen;
R$^5$ is C$_{1-6}$alkyl-SH, C$_{1-6}$alkyl-OH, C$_{1-6}$alkylOC$_{1-6}$alkyl or R$^6$;
or R$^3$, R$^5$ together with the N and C(O) to which they are respectively attached form:

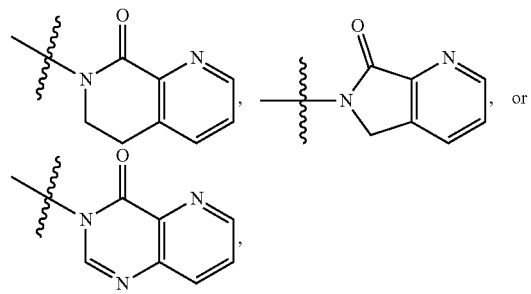

each optionally mono- or di-substituted with C$_{1-3}$alkyl, wherein alkyl is optionally substituted with 1-4 halogen;
R$^6$ is

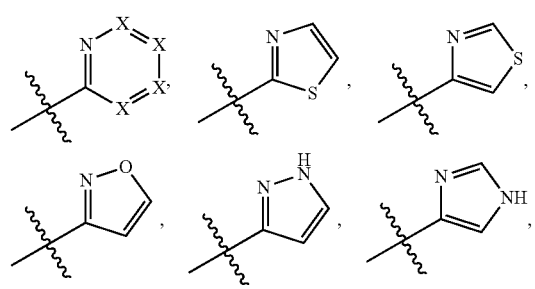

-continued

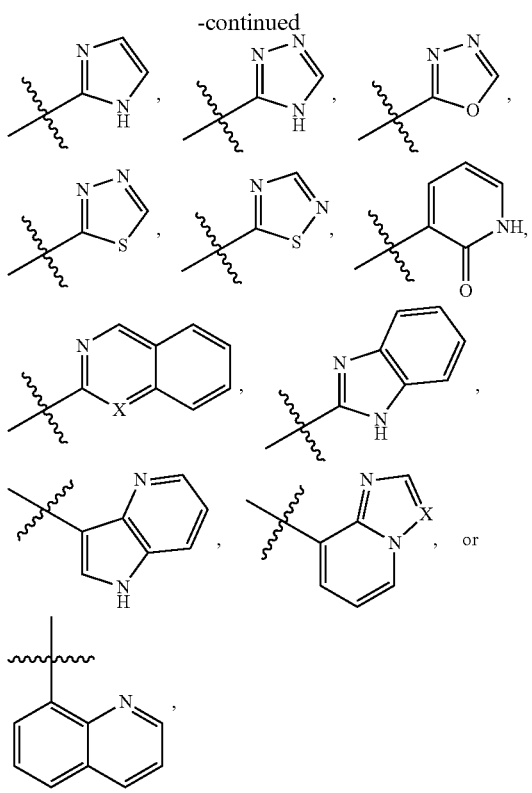

each optionally mono- or di-substituted with substituents independently selected from $C_{1-3}$alkyl, $C_{1-3}$alkoxy, halogen, CN, $NH_2$, $S(O)_2C_{1-3}$alkyl, phenyl, morpholinyl, piperidinyl and piperazinyl, wherein piperidinyl and piperazinyl are each optionally substituted with $C_{1-3}$alkyl and tert-butyloxycarbonyl, and alkyl is optionally substituted with 1-4 halogen;

$R^7$ is

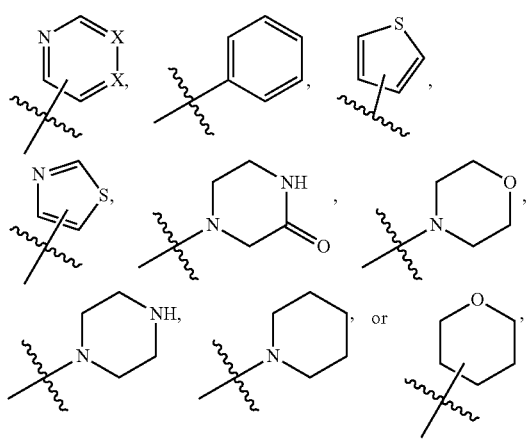

each optionally mono- or di-substituted with substituents independently selected from $C_{1-3}$alkyl, $C_{1-3}$alkoxy, halogen, CN, and OH, and alkyl is optionally substituted with 1-4 halogen; and X is CH or N, and no more one X can be N.

As used herein, the symbol ∽∽∽ when drawn through a bond refers to the point of attachment of a functional group to the parent molecule. When the functional group has two symbols ∽∽∽ present, it means the functional group has two points of attachment. For purpose of the present application, the left-hand point of attachment of the functional group is attached to the left-hand side of the parent molecule. While the right-hand point of attachment of the functional group is attached to the right-hand side of the parent molecule. For example, the left-hand side of Y is attached to X of the parent molecule, while the right-hand side of the Y is attached to Z.

In one embodiment, Q is CH. In another embodiment, W is C(O); and X is $CH_2$, $CH(C_{1-3}alkyl)$ or $C_{3-6}$cycloalkyl. In yet another embodiment, Y is

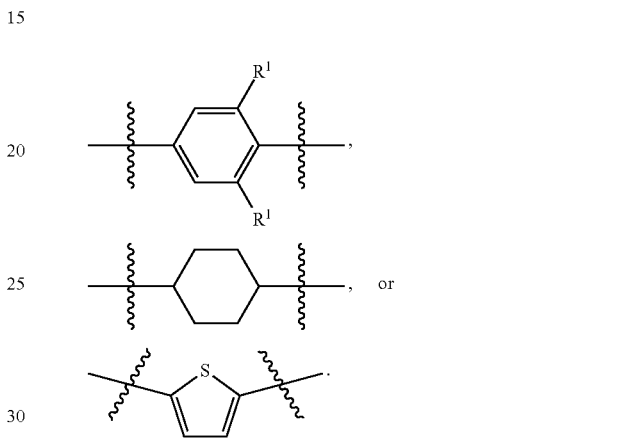

In one embodiment, R' is halogen, $C_{1-6}$alkyl, $C_{1-6}$alkoxy, CN, $NO_2$ or $NH_2$, wherein alkyl is optionally substituted with 1-4 halogen;

Z is C(O)OH,

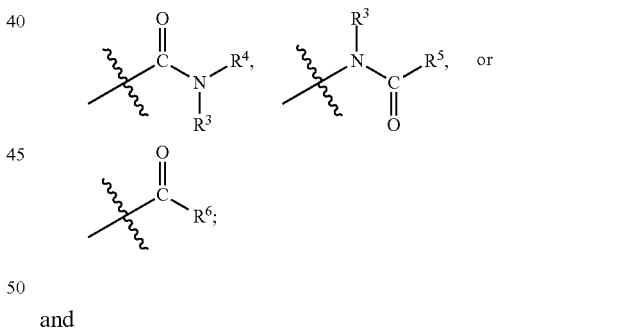

and

R is H, $C_{1-6}$alkyl, $C_{1-6}$alkyl-OH or $CH_2$—$R^7$.

In one embodiment, R' is halogen, $C_{1-3}$alkyl, $C_{1-3}$alkoxy, CN or $NO_2$;

R is H, $C_{1-3}$alkyl, $C_{1-3}$alkyl-OH or $CH_2$—$R^7$;

each $R^1$ is independently H, $C_{1-3}$alkyl, $C_{1-3}$alkoxy, halogen, phenyl or benzodioxolyl, wherein phenyl is optionally mono- or di-substituted with substituents independently selected from $C_{1-3}$alkyl, halogen, $C_{1-3}$alkoxy;

$R^3$ is H or $C_{1-3}$alkyl;

$R^4$ is H, OH, $C(O)C_{1-3}$alkyl or $R^6$;

or $R^3$ and $R^4$ together with the N to which they are attached form:

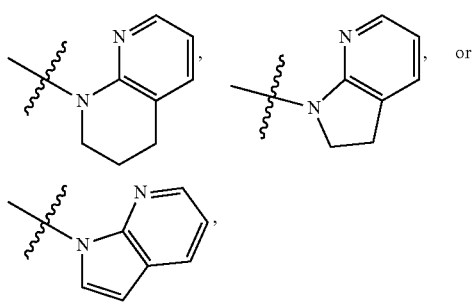

each optionally mono-, di- or tri-substituted with substituents independently selected from halogen and $C_{1-3}$alkyl, wherein alkyl is optionally substituted with 1-4 halogen;

$R^5$ is $R^6$;

or $R^3$, $R^5$ together with the N and C(O) to which they are respectively attached form:

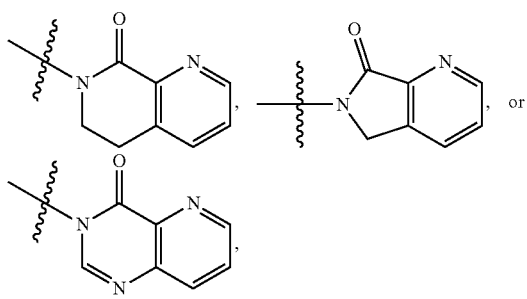

each optionally mono- or di-substituted with $C_{1-3}$alkyl, wherein alkyl is optionally substituted with 1-4 halogen;

$R^7$ is

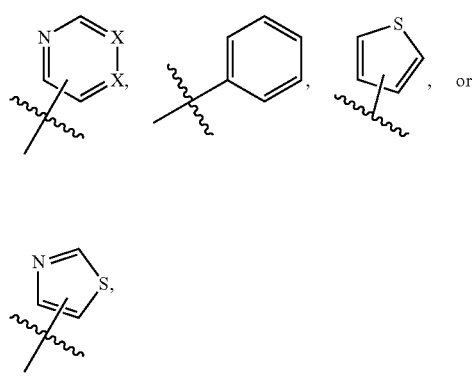

each optionally mono- or di-substituted with substituents independently selected from $C_{1-3}$alkyl, $C_{1-3}$alkoxy, halogen, CN, and OH, wherein alkyl is optionally substituted with 1-4 halogen.

In one embodiment, R' is Cl, Br, $OCH_3$, CN or $NO_2$;

W is C(O);

X is $CH_2$ or $CH(CH_3)$;

Y is

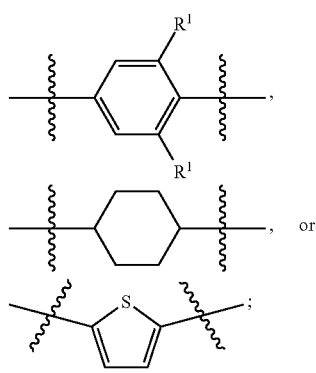

Z is C(O)OH,

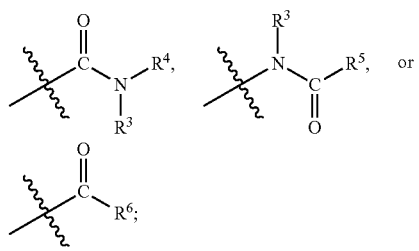

R is H, $CH_3$, $CH(CH_3)_2$ or $CH_2$—$R^7$;

each $R^1$ is independently H, $CH_3$, $OCH_3$, halogen, phenyl or benzodioxolyl, wherein phenyl is optionally mono- or di-substituted with substituents independently selected from $CH_3$, $OCH_3$ and halogen;

$R^3$ is H;

$R^4$ is OH, $C(O)CH_3$ or $R^6$;

or $R^3$ and $R^4$ together with the N to which they are attached form:

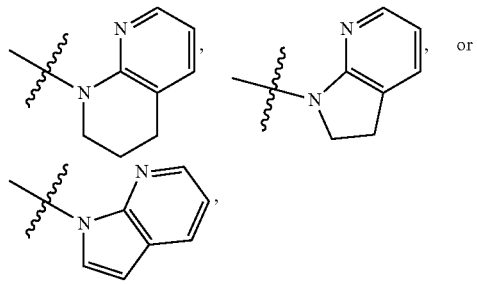

each optionally mono-, di- or tri-substituted with substituents independently selected from $CH_3$ and $CF_3$;

$R^5$ is $R^6$;

or $R^3$, $R^5$ together with the N and C(O) to which they are respectively attached form:

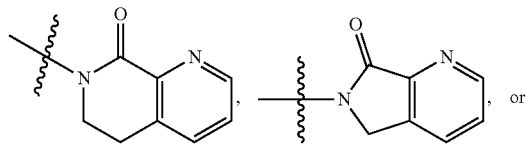

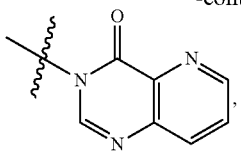

each optionally mono- or di-substituted with CH₃ and CF₃;

R⁷ is

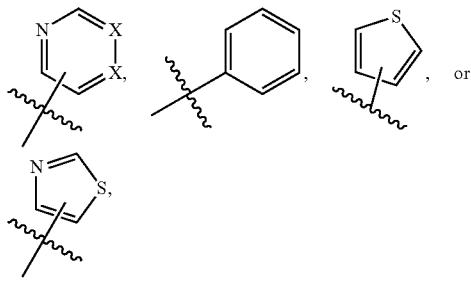

each optionally mono- or di-substituted with substituents independently selected from CH₃, CF₃, OCH₃, halogen and CN.

In one embodiment, R is other than H, and the carbon to which R is attached is of the configuration shown:

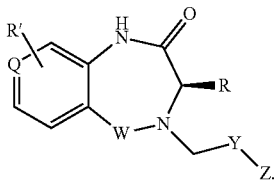

In one embodiment, W is CH₂; and X is S(O)₂, C(O) or CH₂.

In one preferred embodiment, X is S(O)₂.

In one embodiment, Y is

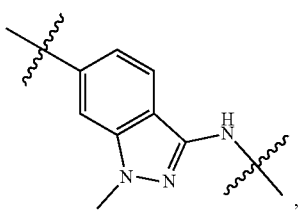

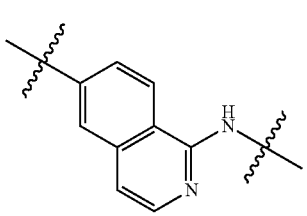

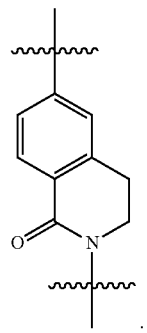

In one embodiment, R' is Cl, Br, OCH₃, CN or NO₂; W is C(O); X is CH₂ or CH(CH₃);

Z is R⁶; R is H, CH₃, CH(CH₃)₂ or CH₂—R⁷; R⁶ is

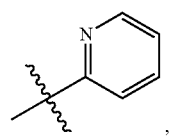 [SMILES: *c1ccccn1 ; ","]

optionally mono- or di-substituted with substituents independently selected from C₁₋₃alkyl, C₁₋₃alkoxy, halogen, CN and NH₂, wherein alkyl is optionally substituted with 1-4 halogen.

In one preferred embodiment, the present compounds include: (R)-4-((8-Chloro-2,5-dioxo-3-(pyridin-2-ylmethyl)-2,3-dihydro-1H-benzo[e][1,4]diazepin-4(5H)-yl) methyl)benzoic acid; (R)-4-((8-fluoro-2,5-dioxo-3-(pyridin-3-ylmethyl)-2,3-dihydro-1H-benzo[e][1,4]diazepin-4(5H)-yl)methyl)benzoic acid; (R)-4-((8-chloro-2,5-dioxo-3-(pyridin-4-ylmethyl)-2,3-dihydro-1H-benzo[e][1,4]diazepin-4(5H)-yl)methyl)benzoic acid; (R)-4-((8-chloro-3-(3,4-dichlorobenzyl)-2,5-dioxo-2,3-dihydro-1H-benzo[e][1,4]diazepin-4(5H)-yl)methyl)benzoic acid; (R)-4-((3-(3,4-dichlorobenzyl)-8-methyl-2,5-dioxo-2,3-dihydro-1H-benzo[e][1,4]diazepin-4(5H)-yl)methyl)benzoic acid; (S)-4-((8-chloro-2,5-dioxo-3-(pyridin-2-ylmethyl)-2,3-dihydro-1H-benzo[e][1,4]diazepin-4(5H)-yl)methyl)benzoic acid; (R)-4-((8-bromo-2,5-dioxo-3-(pyridin-3-ylmethyl)-2,3-dihydro-1H-benzo[e][1,4]diazepin-4(5H)-yl)methyl)benzoic acid; (R)-5-((8-chloro-2,5-dioxo-3-(pyridin-2-ylmethyl)-2,3-dihydro-1H-benzo[e][1,4]diazepin-4(5H)-yl)methyl)thiophene-2-carboxylic acid; (R)-4-((8-chloro-2,5-dioxo-3-(pyridin-2-ylmethyl)-2,3-dihydro-1H-benzo[e][1,4]diazepin-4(5H)-yl)methyl)-2-fluorobenzoic acid; (1R,4r)-4-(((R)-8-chloro-2,5-dioxo-3-(pyridin-2-ylmethyl)-2,3-dihydro-1H-benzo[e][1,4]diazepin-4(5H)-yl)methyl) cyclohexanecarboxylic acid; (R)-4-((8-chloro-2,5-dioxo-3-(thiophen-2-ylmethyl)-2,3-dihydro-1H-benzo[e][1,4]diazepin-4(5H)-yl)methyl)benzoic acid; 4-((8-chloro-2,5-dioxo-3-(pyrazin-2-ylmethyl)-2,3-dihydro-1H-benzo[e][1,4]diazepin-4(5H)-yl)methyl)benzoic acid; (R)-4-((8-chloro-2,5-dioxo-3-(thiazol-4-ylmethyl)-2,3-dihydro-1H-benzo[e][1,4]diazepin-4(5H)-yl)methyl)benzoic acid; (R)-2-bromo-4-((8-chloro-3-methyl-2,5-dioxo-2,3-dihydro-1H-benzo[e][1,4]diazepin-4(5H)-yl)methyl)benzoic acid; (R)-4-((8-Chloro-2,5-dioxo-3-(pyridin-3-ylmethyl)-2,3-dihydro-1H-benzo[e][1,4]diazepin-4(5H)-yl)methyl)benzoic acid; (S)-4-((8-chloro-3-(3,4-dichlorobenzyl)-2,5-dioxo-2,3-dihydro-1H-benzo[e][1,4]diazepin-4(5H)-yl)methyl)benzoic acid;

(S)-4-((8-chloro-3-(4-hydroxybenzyl)-2,5-dioxo-2,3-dihydro-1H-benzo[e][1,4]diazepin-4(5H)-yl)methyl)benzoic acid; (R)-4-((8-chloro-3-(4-hydroxybenzyl)-2,5-dioxo-2,3-dihydro-1H-benzo[e][1,4]diazepin-4(5H)-yl)methyl)benzoic acid; (R)-4-((8-methoxy-2,5-dioxo-3-(pyridin-3-ylmethyl)-2,3-dihydro-1H-benzo[e][1,4]diazepin-4(5H)-yl)methyl)benzoic acid; (R)-4-((3-(3,4-dichlorobenzyl)-8-methoxy-2,5-dioxo-2,3-dihydro-1H-benzo[e][1,4]diazepin-4(5H)-yl)methyl)benzoic acid; (R)-4-((3-(3,4-dichlorobenzyl)-8-fluoro-2,5-dioxo-2,3-dihydro-1H-benzo[e][1,4]diazepin-4(5H)-yl)methyl)benzoic acid; (R)-4-((3-(3,4-dichlorobenzyl)-8-nitro-2,5-dioxo-2,3-dihydro-1H-benzo[e][1,4]diazepin-4(5H)-yl)methyl)benzoic acid; (R)-4-((8-nitro-2,5-dioxo-3-(pyridin-3-ylmethyl)-2,3-dihydro-1H-benzo[e][1,4]diazepin-4(5H)-yl)methyl)benzoic acid; (R)-4-((3-Benzyl-8-chloro-2,5-dioxo-2,3-dihydro-1H-benzo[e][1,4]diazepin-4(5H)-yl)methyl)benzoic acid; (S)-4-((8-chloro-3-methyl-2,5-dioxo-2,3-dihydro-1H-benzo[e][1,4]diazepin-4(5H)-yl)methyl)benzoic acid; (R)-4-((8-chloro-2,5-dioxo-3-phenethyl-2,3-dihydro-1H-benzo[e][1,4]diazepin-4(5H)-yl)methyl)benzoic acid; (R)-4-((8-chloro-3-(4-fluorobenzyl)-2,5-dioxo-2,3-dihydro-1H-benzo[e][1,4]diazepin-4(5H)-yl)methyl)benzoic acid; (R)-4-((8-chloro-3-(4-chlorobenzyl)-2,5-dioxo-2,3-dihydro-1H-benzo[e][1,4]diazepin-4(5H)-yl)methyl)benzoic acid; (R)-4-((8-chloro-3-(3-chlorobenzyl)-2,5-dioxo-2,3-dihydro-1H-benzo[e][1,4]diazepin-4(5H)-yl)methyl)benzoic acid; (R)-4-((8-chloro-3-methyl-2,5-dioxo-2,3-dihydro-1H-benzo[e][1,4]diazepin-4(5H)-yl)methyl)benzoic acid; (R)-4-((8-chloro-3-(4-methylbenzyl)-2,5-dioxo-2,3-dihydro-1H-benzo[e][1,4]diazepin-4(5H)-yl)methyl)benzoic acid; (R)-4-((8-chloro-3-(2-chlorobenzyl)-2,5-dioxo-2,3-dihydro-1H-benzo[e][1,4]diazepin-4(5H)-yl)methyl)benzoic acid; (R)-4-((8-chloro-3-(2-fluorobenzyl)-2,5-dioxo-2,3-dihydro-1H-benzo[e][1,4]diazepin-4(5H)-yl)methyl)benzoic acid; (R)-4-((8-chloro-3-isopropyl-2,5-dioxo-2,3-dihydro-1H-benzo[e][1,4]diazepin-4(5H)-yl)methyl)benzoic acid; (R)-4-((8-chloro-3-(2-methylbenzyl)-2,5-dioxo-2,3-dihydro-1H-benzo[e][1,4]diazepin-4(5H)-yl)methyl)benzoic acid; (R)-4-((8-chloro-3-(3-methylbenzyl)-2,5-dioxo-2,3-dihydro-1H-benzo[e][1,4]diazepin-4(5H)-yl)methyl)benzoic acid; (R)-4-((8-chloro-3-(3-cyanobenzyl)-2,5-dioxo-2,3-dihydro-1H-benzo[e][1,4]diazepin-4(5H)-yl)methyl)benzoic acid; 4-((8-chloro-2,5-dioxo-2,3-dihydro-1H-benzo[e][1,4]diazepin-4(5H)-yl)methyl)benzoic acid; (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(thiazol-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(1-methyl-1H-pyrazol-3-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(5-methylisoxazol-3-yl)benzamide; (S)-4-((8-chloro-3-methyl-2,5-dioxo-2,3-dihydro-1H-benzo[e][1,4]diazepin-4(5H)-yl)methyl)-N-(pyridin-2-yl)benzamide; (R)-4-((8-chloro-2,5-dioxo-3-phenethyl-2,3-dihydro-1H-benzo[e][1,4]diazepin-4(5H)-yl)methyl)-N-(pyridin-2-yl)benzamide; (R)-4-((3-benzyl-8-chloro-2,5-dioxo-2,3-dihydro-1H-benzo[e][1,4]diazepin-4(5H)-yl)methyl)-N-(pyridin-2-yl)benzamide; (R)-4-((8-chloro-3-(4-fluorobenzyl)-2,5-dioxo-2,3-dihydro-1H-benzo[e][1,4]diazepin-4(5H)-yl)methyl)-N-(pyridin-2-yl)benzamide; (R)-4-((8-chloro-3-(4-chlorobenzyl)-2,5-dioxo-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(3-methylpyridin-2-yl)benzamide; (R)-4-((3-(3,4-dichlorobenzyl)-8-methoxy-2,5-dioxo-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-methyl-N-(pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(5-methylpyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(6-methylpyridin-2-yl)benzamide; (R)-4-((8-methoxy-2,5-dioxo-3-(pyridin-3-ylmethyl)-2,3-dihydro-1H-benzo[e][1,4]diazepin-4(5H)-yl)methyl)-N-(pyridin-2-yl)benzamide; (R)-4-((3-(3,4-dichlorobenzyl)-8-fluoro-2,5-dioxo-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(4-chloropyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(4-methylpyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(pyrimidin-4-yl)benzamide; (R)-4-((8-chloro-2,5-dioxo-3-(pyridin-4-ylmethyl)-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide; (R)-4-((8-chloro-3-(2-chlorobenzyl)-2,5-dioxo-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide; (R)-8-chloro-4-(4-(2,3-dihydro-1H-pyrrolo[2,3-b]pyridine-1-carbonyl)benzyl)-3-methyl-3,4-dihydro-1H-benzo[e][1,4]diazepine-2,5-dione; (R)-4-((8-chloro-3-methyl-2,5-dioxo-2,3-dihydro-1H-benzo[e][1,4]diazepin-4(5H)-yl)methyl)-N-(pyridin-2-yl)benzamide; (R)-4-((8-chloro-3-(3-chlorobenzyl)-2,5-dioxo-2,3-dihydro-1H-benzo[e][1,4]diazepin-4(5H)-yl)methyl)-N-(pyridin-2-yl)benzamide; (R)-8-chloro-4-(3-chloro-4-(1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-4-((3-(3,4-dichlorobenzyl)-8-methyl-2,5-dioxo-2,3-dihydro-1H-benzo[e][1,4]diazepin-4(5H)-yl)methyl)-N-(pyridin-2-yl)benzamide; (R)-8-chloro-4-(3-chloro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-4-((3-(3,4-dichlorobenzyl)-8-nitro-2,5-dioxo-2,3-dihydro-1H-benzo[e][1,4]diazepin-4(5H)-yl)methyl)-N-(pyridin-2-yl)benzamide; (R)-8-chloro-4-(4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-8-chloro-3-(pyridin-2-ylmethyl)-4-(4-(1,2,3,4-tetrahydro-1,8-naphthyridine-1-carbonyl)benzyl)-3,4-dihydro-1H-benzo[e][1,4]diazepine-2,5-dione; (R)-8-chloro-4-(4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-4-((8-chloro-3-(2-methylbenzyl)-2,5-dioxo-2,3-dihydro-1H-benzo[e][1,4]diazepin-4(5H)-yl)methyl)-N-(pyridin-2-yl)benzamide; (R)-4-((8-chloro-3-(3-methylbenzyl)-2,5-dioxo-2,3-dihydro-1H-benzo[e][1,4]diazepin-4(5H)-yl)methyl)-N-(pyridin-2-yl)benzamide; (R)-4-((8-chloro-3-(3- cyanobenzyl)-2,5-dioxo-2,3-dihydro-1H-benzo[e][1,4]
diazepin-4(5H)-yl)methyl)-N-(pyridin-2-yl)benzamide;
(R)-4-((8-chloro-2,5-dioxo-3-(thiazol-4-ylmethyl)-2,3-di-
hydro-1H-benzo[e][1,4]diazepin-4(5H)-yl)methyl)-N-(5-
methylpyridin-2-yl)benzamide; 4-((8-chloro-2,5-dioxo-2,3-
dihydro-1H-benzo[e][1,4]diazepin-4(5H)-yl)methyl)-N-
(pyridin-2-yl)benzamide; (R)-4-((8-chloro-3-(2-
fluorobenzyl)-2,5-dioxo-2,3-dihydro-1H-benzo[e][1,4]
diazepin-4(5H)-yl)methyl)-N-(pyridin-2-yl)benzamide;
(R)-4-((8-chloro-2,5-dioxo-3-(pyridin-2-ylmethyl)-2,3-di-
hydro-1H-benzo[e][1,4]diazepin-4(5H)-yl)methyl)-N-(5-
methoxypyridin-2-yl)benzamide; (R)-4-((8-chloro-2,5-di-
oxo-3-(pyridin-2-ylmethyl)-2,3-dihydro-1H-benzo[e][1,4]
diazepin-4(5H)-yl)methyl)-N-(5-ethylpyridin-2-yl)
benzamide; (S)-4-((8-chloro-2,5-dioxo-3-(pyridin-2-
ylmethyl)-2,3-dihydro-1H-benzo[e][1,4]diazepin-4(5H)-yl)
methyl)-N-(pyridin-2-yl)benzamide; (R)-8-chloro-4-(3-
chloro-4-(2,2-dimethyl-2,3-dihydro-1H-pyrrolo[2,3-b]
pyridine-1-carbonyl)benzyl)-3-(pyridin-2-ylmethyl)-3,4-
dihydro-1H-benzo[e][1,4]diazepine-2,5-dione; (R)-8-
chloro-4-(3-chloro-4-(3,3-dimethyl-2,3-dihydro-1H-pyrrolo
[2,3-b]pyridine-1-carbonyl)benzyl)-3-(pyridin-2-ylmethyl)-
3,4-dihydro-1H-benzo[e][1,4]diazepine-2,5-dione; (R)-4-
((8-chloro-2,5-dioxo-3-(pyridin-2-ylmethyl)-2,3-dihydro-
1H-benzo[e][1,4]diazepin-4(5H)-yl)methyl)-N-(5-
isopropylpyridin-2-yl)benzamide; (R)-4-((8-chloro-2,5-
dioxo-3-(pyridin-2-ylmethyl)-2,3-dihydro-1H-benzo[e][1,
4]diazepin-4(5H)-yl)methyl)-2-methoxy-N-(5-
(trifluoromethyl)pyridin-2-yl)benzamide; (R)-4-((8-chloro-
2,5-dioxo-3-(pyridin-2-ylmethyl)-2,3-dihydro-1H-benzo[e]
[1,4]diazepin-4(5H)-yl)methyl)-N-(5-morpholinopyridin-2-
yl)benzamide; (R)-tert-butyl 4-(6-(4-((8-chloro-2,5-dioxo-
3-(pyridin-2-ylmethyl)-2,3-dihydro-1H-benzo[e][1,4]
diazepin-4(5H)-yl)methyl)benzamido)pyridin-3-yl)
piperazine-1-carboxylate; (R)-4-((8-chloro-2,5-dioxo-3-
(pyridin-2-ylmethyl)-2,3-dihydro-1H-benzo[e][1,4]
diazepin-4(5H)-yl)methyl)-N-(5-(4-methylpiperazin-1-yl)
pyridin-2-yl)benzamide; (R)-4-((8-chloro-3-methyl-2,5-
dioxo-2,3-dihydro-1H-benzo[e][1,4]diazepin-4(5H)-yl)
methyl)-N-(5-ethylpyridin-2-yl)benzamide; (R)-4-((8-
chloro-3-methyl-2,5-dioxo-2,3-dihydro-1H-benzo[e][1,4]
diazepin-4(5H)-yl)methyl)-N-(5-isopropylpyridin-2-yl)
benzamide; (R)-4-((8-chloro-3-methyl-2,5-dioxo-2,3-
dihydro-1H-benzo[e][1,4]diazepin-4(5H)-yl)methyl)-N-(5-
methoxypyridin-2-yl)benzamide; (R)-4-((8-chloro-3-
methyl-2,5-dioxo-2,3-dihydro-1H-benzo[e][1,4]diazepin-4
(5H)-yl)methyl)-N-(isoquinolin-3-yl)benzamide; (R)-4-((8-
chloro-3-methyl-2,5-dioxo-2,3-dihydro-1H-benzo[e][1,4]
diazepin-4(5H)-yl)methyl)-N-(5-phenylpyridin-2-yl)
benzamide; (R)-4-((8-bromo-2,5-dioxo-3-(pyridin-3-
ylmethyl)-2,3-dihydro-1H-benzo[e][1,4]diazepin-4(5H)-yl)
methyl)-N-(pyridin-2-yl)benzamide; (R)-4-((8-chloro-3-
methyl-2,5-dioxo-2,3-dihydro-1H-benzo[e][1,4]diazepin-4
(5H)-yl)methyl)-N-(5-methoxypyrimidin-2-yl)benzamide;
(R)-4-((8-chloro-3-methyl-2,5-dioxo-2,3-dihydro-1H-benzo
[e][1,4]diazepin-4(5H)-yl)methyl)-N-(5-morpholinopyri-
din-2-yl)benzamide; (R)-tert-butyl 4-(6-(4-((8-chloro-3-
methyl-2,5-dioxo-2,3-dihydro-1H-benzo[e][1,4]diazepin-4
(5H)-yl)methyl)benzamido)pyridin-3-yl)piperazine-1-
carboxylate; (R)-4-((8-chloro-3-methyl-2,5-dioxo-2,3-
dihydro-1H-benzo[e][1,4]diazepin-4(5H)-yl)methyl)-N-(5-
(4-methylpiperazin-1-yl)pyridin-2-yl)benzamide; (R)-4-((8-
chloro-3-methyl-2,5-dioxo-2,3-dihydro-1H-benzo[e][1,4]
diazepin-4(5H)-yl)methyl)-N-(5-methylpyrazin-2-yl)
benzamide; (R)-4-((8-chloro-2,5-dioxo-3-(pyridin-2-
ylmethyl)-2,3-dihydro-1H-benzo[e][1,4]diazepin-4(5H)-yl)
methyl)-N-(5-methyl-4H-1,2,4-triazol-3-yl)benzamide; (R)-
4-((8-chloro-2,5-dioxo-3-(pyridin-2-ylmethyl)-2,3-dihydro-
1H-benzo[e][1,4]diazepin-4(5H)-yl)methyl)-N-(3-methyl-
1,2,4-thiadiazol-5-yl)benzamide; (R)-4-((8-chloro-2,5-
dioxo-3-(pyridin-2-ylmethyl)-2,3-dihydro-1H-benzo[e][1,
4]diazepin-4(5H)-yl)methyl)-N-(pyridazin-3-yl)benzamide;
(R)-4-((8-chloro-2,5-dioxo-3-(pyridin-2-ylmethyl)-2,3-di-
hydro-1H-benzo[e][1,4]diazepin-4(5H)-yl)methyl)-N-(6-
methoxypyridazin-3-yl)benzamide; (R)-4-((8-chloro-2,5-di-
oxo-3-(pyridin-2-ylmethyl)-2,3-dihydro-1H-benzo[e][1,4]
diazepin-4(5H)-yl)methyl)-N-(5-methyl-1,3,4-thiadiazol-2-
yl)benzamide; (R)-4-((8-chloro-2,5-dioxo-3-(pyridin-2-
ylmethyl)-2,3-dihydro-1H-benzo[e][1,4]diazepin-4(5H)-yl)
methyl)-N-(5-methyl-1,3,4-oxadiazol-2-yl)benzamide; (R)-
4-((8-chloro-2,5-dioxo-3-(pyridin-2-ylmethyl)-2,3-dihydro-
1H-benzo[e][1,4]diazepin-4(5H)-yl)methyl)-N-(1,3,4-
thiadiazol-2-yl)benzamide; (R)-5-((8-chloro-2,5-dioxo-3-
(pyridin-2-ylmethyl)-2,3-dihydro-1H-benzo[e][1,4]
diazepin-4(5H)-yl)methyl)-N-(pyridin-2-yl)thiophene-2-
carboxamide; (R)-5-((8-chloro-2,5-dioxo-3-(pyridin-2-
ylmethyl)-2,3-dihydro-1H-benzo[e][1,4]diazepin-4(5H)-yl)
methyl)-N-(5-methoxypyridin-2-yl)thiophene-2-
carboxamide; (R)-5-((8-chloro-2,5-dioxo-3-(pyridin-2-
ylmethyl)-2,3-dihydro-1H-benzo[e][1,4]diazepin-4(5H)-yl)
methyl)-N-(5-methylpyridin-2-yl)thiophene-2-
carboxamide; (R)-5-((8-chloro-2,5-dioxo-3-(pyridin-2-
ylmethyl)-2,3-dihydro-1H-benzo[e][1,4]diazepin-4(5H)-yl)
methyl)-N-(5-(trifluoromethyl)pyridin-2-yl)thiophene-2-
carboxamide; 4-((8-chloro-2,5-dioxo-3-(pyrazin-2-
ylmethyl)-2,3-dihydro-1H-benzo[e][1,4]diazepin-4(5H)-yl)
methyl)-N-(pyridin-2-yl)benzamide; (R)-4-((8-chloro-2,5-
dioxo-3-(pyridin-3-ylmethyl)-2,3-dihydro-1H-benzo[e][1,
4]diazepin-4(5H)-yl)methyl)-N-(1-(hydroxyimino)ethyl)
benzamide; (R)-4-((8-chloro-2,5-dioxo-3-(pyridin-2-
ylmethyl)-2,3-dihydro-1H-benzo[e][1,4]diazepin-4(5H)-yl)
methyl)-N-(5-methylthiazol-2-yl)benzamide; (1R,4r)-4-
(((R)-8-chloro-2,5-dioxo-3-(pyridin-2-ylmethyl)-2,3-
dihydro-1H-benzo[e][1,4]diazepin-4(5H)-yl)methyl)-N-(5-
methylpyridin-2-yl)cyclohexanecarboxamide; (R)-2-chloro-
4-((8-chloro-2,5-dioxo-3-(pyridin-2-ylmethyl)-2,3-dihydro-
1H-benzo[e][1,4]diazepin-4(5H)-yl)methyl)-N-(5-
methoxypyridin-2-yl)benzamide; (1R,4r)-4-(((R)-8-chloro-
2,5-dioxo-3-(pyridin-2-ylmethyl)-2,3-dihydro-1H-benzo[e]
[1,4]diazepin-4(5H)-yl)methyl)-N-(5-methoxypyridin-2-yl)
cyclohexanecarboxamide; (1R,4r)-4-(((R)-8-chloro-2,5-
dioxo-3-(pyridin-2-ylmethyl)-2,3-dihydro-1H-benzo[e][1,
4]diazepin-4(5H)-yl)methyl)-N-(5-fluoropyridin-2-yl)
cyclohexanecarboxamide; (R)-2-chloro-4-((8-chloro-2,5-
dioxo-3-(pyridin-2-ylmethyl)-2,3-dihydro-1H-benzo[e][1,
4]diazepin-4(5H)-yl)methyl)-N-(5-methylpyridin-2-yl)
benzamide; (R)-2-chloro-4-((8-chloro-2,5-dioxo-3-(pyridin-
2-ylmethyl)-2,3-dihydro-1H-benzo[e][1,4]diazepin-4(5H)-
yl)methyl)-N-(5-methylthiazol-2-yl)benzamide; (R)-8-
chloro-4-(3-chloro-4-(2,3-dihydro-1H-pyrrolo[2,3-b]
pyridine-1-carbonyl)benzyl)-3-(pyridin-2-ylmethyl)-3,4-
dihydro-1H-benzo[e][1,4]diazepine-2,5-dione; (1R,4r)-4-
(((R)-8-chloro-2,5-dioxo-3-(pyridin-2-ylmethyl)-2,3-
dihydro-1H-benzo[e][1,4]diazepin-4(5H)-yl)methyl)-N-(5-
methoxypyrazin-2-yl)cyclohexanecarboxamide; (1R,4r)-4-
(((R)-8-chloro-2,5-dioxo-3-(pyridin-2-ylmethyl)-2,3-
dihydro-1H-benzo[e][1,4]diazepin-4(5H)-yl)methyl)-N-(5-
methylpyrazin-2-yl)cyclohexanecarboxamide; (R)-8-
chloro-4-(((1r,4R)-4-(2,3-dihydro-1H-pyrrolo[2,3-b]
pyridine-1-carbonyl)cyclohexyl)methyl)-3-(pyridin-2-
ylmethyl)-3,4-dihydro-1H-benzo[e][1,4]diazepine-2,5-
dione; (R)-8-chloro-3-(pyridin-2-ylmethyl)-4-(((1r,4R)-4-
(1,2,3,4-tetrahydro-1,8-naphthyridine-1-carbonyl)
cyclohexyl)methyl)-3,4-dihydro-1H-benzo[e][1,4]

diazepine-2,5-dione; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyridin-2-yl)benzamide; (R)-4-((8-chloro-3-(4-methylbenzyl)-2,5-dioxo-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(pyrazin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(5-chloropyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(3-chloropyridin-2-yl)benzamide; (R)-2-(benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(5-methoxypyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(5-methylpyrimidin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(4-methylpyrimidin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(6-methoxypyrimidin-4-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(5-ethylpyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(5-methoxypyrimidin-2-yl)benzamide; (R)-4-((8-chloro-3-methyl-2,5-dioxo-2,3-dihydro-1H-benzo[e][1,4]diazepin-4(5H)-yl)methyl)-N-(quinazolin-2-yl)benzamide; (R)-4-((8-chloro-3-methyl-2,5-dioxo-2,3-dihydro-1H-benzo[e][1,4]diazepin-4(5H)-yl)methyl)-N-(6-methylpyrazin-2-yl)benzamide; (R)—N-(1H-benzo[d]imidazol-2-yl)-4-((8-chloro-3-methyl-2,5-dioxo-2,3-dihydro-1H-benzo[e][1,4]diazepin-4(5H)-yl)methyl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide; (R)-5-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)thiophene-2-carboxamide; (R)-5-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)thiophene-2-carboxamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(pyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide; 4-((8-chloro-2,5-dioxo-3-(pyrazin-2-ylmethyl)-2,3-dihydro-1H-benzo[e][1,4]diazepin-4(5H)-yl)methyl)-N-(5-methoxypyridin-2-yl)benzamide; 4-((8-chloro-2,5-dioxo-3-(pyrazin-2-ylmethyl)-2,3-dihydro-1H-benzo[e][1,4]diazepin-4(5H)-yl)methyl)-N-(5-methylpyridin-2-yl)benzamide; 4-((8-chloro-2,5-dioxo-3-(pyrazin-2-ylmethyl)-2,3-dihydro-1H-benzo[e][1,4]diazepin-4(5H)-yl)methyl)-N-(5-methoxypyrimidin-2-yl)benzamide; 4-((8-chloro-2,5-dioxo-3-(pyrazin-2-ylmethyl)-2,3-dihydro-1H-benzo[e][1,4]diazepin-4(5H)-yl)methyl)-N-(5-methylpyrimidin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(3-fluoropyridin-2-yl)benzamide; (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)cyclohexanecarboxamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrimidin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl)pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrimidin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrimidin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)-2-methylbenzamide; (R)-4-((8-chloro-2,5-dioxo-3-(pyridin-2- ylmethyl)-2,3-dihydro-1H-benzo[e][1,4]diazepin-4(5H)-yl)methyl)-N-(5-fluoropyridin-2-yl)-2-methoxybenzamide; (R)-2-bromo-4-((8-chloro-3-methyl-2,5-dioxo-2,3-dihydro-1H-benzo[e][1,4]diazepin-4(5H)-yl)methyl)-N-(5-(trifluoromethyl)pyridin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)-2-methylbenzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(methylsulfonyl)pyridin-2-yl)benzamide; (R)-8-chloro-4-(3-chloro-4-(3,3-dimethyl-5-(trifluoromethyl)-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)cyclohexanecarboxamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(methylsulfonyl)pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methoxypyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-fluoropyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methylpyridin-2-yl)benzamide; (R)-8-chloro-4-(4-(2,3-dihydro-1H-pyrrolo[2,3-b]pyridine-1-carbonyl)-3-fluorobenzyl)-3-(pyridin-2-ylmethyl)-3,4-dihydro-1H-benzo[e][1,4]diazepine-2,5-dione; (R)-8-chloro-4-(3-fluoro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-2-chloro-4-((8-chloro-2,5-dioxo-3-(pyridin-2-ylmethyl)-2,3-dihydro-1H-benzo[e][1,4]diazepin-4(5H)-yl)methyl)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-methylbenzoic acid; (R)-2,6-dichloro-4-((8-chloro-2,5-dioxo-3-(pyridin-2-ylmethyl)-2,3-dihydro-1H-benzo[e][1,4]diazepin-4(5H)-yl)methyl)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-methoxybenzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(pyridin-4-yl)benzoic acid; (R)-5-((8-chloro-2,5-dioxo-3-(pyridin-2-ylmethyl)-2,3-dihydro-1H-benzo[e][1,4]diazepin-4(5H)-yl)methyl)-3'-methoxy-[1,1'-biphenyl]-2-carboxylic acid; (R)-2-(benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)benzoic acid; (R)-5-((8-chloro-2,5-dioxo-3-(pyridin-2-ylmethyl)-2,3-dihydro-1H-benzo[e][1,4]diazepin-4(5H)-yl)methyl)-4'-fluoro-[1,1'-biphenyl]-2-carboxylic acid; (R)-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid; (R)-5-((8-chloro-2,5-dioxo-3-(pyridin-2-ylmethyl)-2,3-dihydro-1H-benzo[e][1,4]diazepin-4(5H)-yl)methyl)-4'-methoxy-[1,1'-biphenyl]-2-carboxylic acid; (R)-5-((8-chloro-2,5-dioxo-3-(pyridin-2-ylmethyl)-2,3-dihydro-1H-benzo[e][1,4]diazepin-4(5H)-yl)methyl)-4'-methyl-[1,1'-biphenyl]-2-carboxylic acid; (R)-5-((8-chloro-2,5-dioxo-3-(pyridin-2-ylmethyl)-2,3-dihydro-1H-benzo[e][1,4]diazepin-4(5H)-yl)methyl)-3'-methyl-[1,1'-biphenyl]-2-carboxylic acid; (R)-4'-chloro-5-((8-chloro-2,5-dioxo-3-(pyridin-2-ylmethyl)-2,3-dihydro-1H-benzo[e][1,4]diazepin-4(5H)-yl)methyl)[1,1'-biphenyl]-2-carboxylic acid; (R)-3'-chloro-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid; (R)-5-((8-chloro-2,5-dioxo-3-(pyridin-2-ylmethyl)-2,3-dihydro-1H-benzo[e][1,4]diazepin-4(5H)-yl)methyl)-3'-fluoro-[1,1'-biphenyl]-2-carboxylic acid; (R)-3'-chloro-5-((8-chloro-2,5-dioxo-3-(pyridin-2-ylmethyl)-2,3-dihydro-1H-benzo[e][1,4]diazepin-4(5H)-yl)methyl)-4'-fluoro-[1,1'-biphenyl]-2-carboxylic acid; (R)-4-((8-chloro-2,5-dioxo-3-(pyridin-2-ylmethyl)-2,3-dihydro-1H-benzo[e][1,4]diazepin-4(5H)-yl)methyl)-2-(pyridin-3-yl)benzoic acid; (R)-4'-acetamido-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid; (R)-5-((8-chloro-2,5-dioxo-3-(pyridin-2-ylmethyl)-2,3-dihydro-1H-benzo[e][1,4]diazepin-4(5H)-yl)methyl)-4'-(methylcarbamoyl)-[1,1'-biphenyl]-2-carboxylic acid; (R)-5-((8-chloro-2,5-dioxo-3-(pyridin-2-ylmethyl)-2,3-dihydro-1H-benzo[e][1,4]diazepin-4(5H)-yl)methyl)-3'-(methylcarbamoyl)-[1,1'-biphenyl]-2-carboxylic acid; (R)-3'-acetamido-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid; (R)-4-((8-chloro-2,5-dioxo-3-(pyridin-2-ylmethyl)-2,3-dihydro-1H-benzo[e][1,4]diazepin-4(5H)-yl)methyl)-2-(1H-pyrazol-4-yl)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(1-methyl-1H-pyrazol-5-yl)benzoic acid; 4-(((R)-8-chloro-2,5-dioxo-3-(pyridin-2-ylmethyl)-2,3-dihydro-1H-benzo[e][1,4]diazepin-4(5H)-yl)methyl)-2-(3,5-dimethylisoxazol-4-yl)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(1-methyl-1H-pyrazol-4-yl)benzoic acid; (R)-4-((8-chloro-3-(2-hydroxyethyl)-2,5-dioxo-2,3-dihydro-1H-benzo[e][1,4]diazepin-4(5H)-yl)methyl)-N-(5-methylpyridin-2-yl)benzamide; (R)-4-((8-chloro-3-(2-morpholinoethyl)-2,5-dioxo-2,3-dihydro-1H-benzo[e][1,4]diazepin-4(5H)-yl)methyl)-N-(5-methylpyridin-2-yl)benzamide; (R)-4-((8-chloro-2,5-dioxo-3-(2-(piperidin-1-yl)ethyl)-2,3-dihydro-1H-benzo[e][1,4]diazepin-4(5H)-yl)methyl)-N-(5-methylpyridin-2-yl)benzamide; (R)-4-((8-chloro-3-(2-(4-hydroxypiperidin-1-yl)ethyl)-2,5-dioxo-2,3-dihydro-1H-benzo[e][1,4]diazepin-4(5H)-yl)methyl)-N-(5-methylpyridin-2-yl)benzamide; (R)-4-((8-chloro-3-(2-(4-methylpiperazin-1-yl)ethyl)-2,5-dioxo-2,3-dihydro-1H-benzo[e][1,4]diazepin-4(5H)-yl)methyl)-N-(5-methylpyridin-2-yl)benzamide; (R)-4-((8-chloro-2,5-dioxo-3-(2-(3-oxopiperazin-1-yl)ethyl)-2,3-dihydro-1H-benzo[e][1,4]diazepin-4(5H)-yl)methyl)-N-(5-methylpyridin-2-yl)benzamide; (R)-4-((8-chloro-3-(2-(dimethylamino)ethyl)-2,5-dioxo-2,3-dihydro-1H-benzo[e][1,4]diazepin-4(5H)-yl)methyl)-N-(5-methylpyridin-2-yl)benzamide; (R)-8-chloro-4-(4-picolinoylbenzyl)-3-(pyridin-2-ylmethyl)-3,4-dihydro-1H-benzo[e][1,4]diazepine-2,5-dione; (R)-8-chloro-4-(4-(5-methylpicolinoyl)benzyl)-3-(pyridin-2-ylmethyl)-3,4-dihydro-1H-benzo[e][1,4]diazepine-2,5-dione; (R)-8-chloro-4-((4-picolinoylcyclohexyl)methyl)-3-(pyridin-2-ylmethyl)-3,4-dihydro-1H-benzo[e][1,4]diazepine-2,5-dione; (R)-8-chloro-4-(4-(4-methylpicolinoyl)benzyl)-3-

(pyridin-2-ylmethyl)-3,4-dihydro-1H-benzo[e][1,4]diazepine-2,5-dione; (R)-8-chloro-4-(4-(6-methylpicolinoyl)benzyl)-3-(pyridin-2-ylmethyl)-3,4-dihydro-1H-benzo[e][1,4]diazepine-2,5-dione; (R)-8-chloro-4-(3-fluoro-4-picolinoylbenzyl)-3-(pyridin-2-ylmethyl)-3,4-dihydro-1H-benzo[e][1,4]diazepine-2,5-dione; (R)-8-chloro-4-(3-chloro-4-picolinoylbenzyl)-3-(pyridin-2-ylmethyl)-3,4-dihydro-1H-benzo[e][1,4]diazepine-2,5-dione; (R)-8-chloro-4-(3-methyl-4-picolinoylbenzyl)-3-(pyridin-2-ylmethyl)-3,4-dihydro-1H-benzo[e][1,4]diazepine-2,5-dione; (R)-8-chloro-4-(3-fluoro-4-(3-methylpicolinoyl)benzyl)-3-(pyridin-2-ylmethyl)-3,4-dihydro-1H-benzo[e][1,4]diazepine-2,5-dione; (R)-8-chloro-4-(3-methoxy-4-picolinoylbenzyl)-3-(pyridin-2-ylmethyl)-3,4-dihydro-1H-benzo[e][1,4]diazepine-2,5-dione; (R)—N-acetyl-4-((8-chloro-2,5-dioxo-3-(pyridin-2-ylmethyl)-2,3-dihydro-1H-benzo[e][1,4]diazepin-4(5H)-yl)methyl)benzamide; (R)-8-chloro-4-(4-(2-oxopyrrolidine-1-carbonyl)benzyl)-3-(pyridin-2-ylmethyl)-3,4-dihydro-1H-benzo[e][1,4]diazepine-2,5-dione; (S)-4-((8-chloro-3-(3,4-dichlorobenzyl)-2,5-dioxo-2,3-dihydro-1H-benzo[e][1,4]diazepin-4(5H)-yl)methyl)benzamide; (R)-4-((8-chloro-2,5-dioxo-3-(pyridin-3-ylmethyl)-2,3-dihydro-1H-benzo[e][1,4]diazepin-4(5H)-yl)methyl)-N,N-dimethylbenzamide; (R)-4-((8-chloro-2,5-dioxo-3-(pyridin-3-ylmethyl)-2,3-dihydro-1H-benzo[e][1,4]diazepin-4(5H)-yl)methyl)benzamide; (R)-4-((8-chloro-2,5-dioxo-3-(pyridin-2-ylmethyl)-2,3-dihydro-1H-benzo[e][1,4]diazepin-4(5H)-yl)methyl)benzamide; (R)-4-((8-cyano-2,5-dioxo-3-(pyridin-3-ylmethyl)-2,3-dihydro-1H-benzo[e][1,4]diazepin-4(5H)-yl)methyl)-N-(pyridin-2-yl)benzamide hydrochloride; (R)-4-((8-chloro-2,5-dioxo-3-(pyridin-3-ylmethyl)-2,3-dihydro-1H-benzo[e][1,4]diazepin-4(5H)-yl)methyl)-N-(phenylsulfonyl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(methylsulfonyl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-((4-chlorophenyl)sulfonyl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-((4-methoxyphenyl)sulfonyl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-tosylbenzamide; (R)-4-((8-amino-3-methyl-2,5-dioxo-2,3-dihydro-1H-benzo[e][1,4]diazepin-4(5H)-yl)methyl)-N-(5-methylpyridin-2-yl)benzamide; (R)-4-((8-acetamido-3-methyl-2,5-dioxo-2,3-dihydro-1H-benzo[e][1,4]diazepin-4(5H)-yl)methyl)-N-(5-methylpyridin-2-yl)benzamide; (R)-4-((8-(3-methoxypropanamido)-3-methyl-2,5-dioxo-2,3-dihydro-1H-benzo[e][1,4]diazepin-4(5H)-yl)methyl)-N-(5-methylpyridin-2-yl)benzamide; (R)-4-((8-isobutyramido-3-methyl-2,5-dioxo-2,3-dihydro-1H-benzo[e][1,4]diazepin-4(5H)-yl)methyl)-N-(5-methylpyridin-2-yl)benzamide; (R)-5-methyl-N-(3-methyl-4-(4-((5-methylpyridin-2-yl)carbamoyl)benzyl)-2,5-dioxo-2,3,4,5-tetrahydro-1H-benzo[e][1,4]diazepin-8-yl)isoxazole-3-carboxamide; (R)—N-(3-methyl-4-(4-((5-methylpyridin-2-yl)carbamoyl)benzyl)-2,5-dioxo-2,3,4,5-tetrahydro-1H-benzo[e][1,4]diazepin-8-yl)picolinamide; (R)—N-(3-methyl-4-(4-((5-methylpyridin-2-yl)carbamoyl)benzyl)-2,5-dioxo-2,3,4,5-tetrahydro-1H-benzo[e][1,4]diazepin-8-yl)nicotinamide; (R)-4-((8-chloro-2-oxo-3-(pyridin-2-ylmethyl)-2,3-dihydro-1H-benzo[e][1,4]diazepin-4(5H)-yl)sulfonyl)-N-(5-methylpyridin-2-yl)benzamide; (R)-4-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide; (S)-4-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide; (S)-4-((8-chloro-2-oxo-3-(pyridin-2-ylmethyl)-2,3-dihydro-1H-benzo[e][1,4]diazepin-4(5H)-yl)sulfonyl)-N-(5-methoxypyridin-2-yl)benzamide; (S)-4-((8-chloro-2-oxo-3-(pyridin-2-ylmethyl)-2,3-dihydro-1H-benzo[e][1,4]diazepin-4(5H)-yl)sulfonyl)-N-(5-methylpyrimidin-2-yl)benzamide; (R)-4-((8-chloro-2-oxo-3-(pyridin-2-ylmethyl)-2,3-dihydro-1H-benzo[e][1,4]diazepin-4(5H)-yl)sulfonyl)-N-(5-methoxypyridin-2-yl)benzamide; (R)-4-((8-chloro-2-oxo-3-(pyridin-2-ylmethyl)-2,3-dihydro-1H-benzo[e][1,4]diazepin-4(5H)-yl)sulfonyl)-N-(5-methylpyrimidin-2-yl)benzamide; (R)-4-((8-chloro-2-oxo-3-(pyridin-2-ylmethyl)-2,3-dihydro-1H-benzo[e][1,4]diazepin-4(5H)-yl)sulfonyl)-N-(5-methoxypyrimidin-2-yl)benzamide; (R)-4-(8-chloro-2-oxo-3-(pyridin-2-ylmethyl)-2,3,4,5-tetrahydro-1H-benzo[e][1,4]diazepine-4-carbonyl)-N-(pyridin-2-yl)benzamide; (R)-3-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide; (R)-4-((8-chloro-2-oxo-3-(pyridin-2-ylmethyl)-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-(picolinamido)benzoic acid; (R)-2-acetamido-4-((8-chloro-2,5-dioxo-3-(pyridin-2-ylmethyl)-1H-benzo[e][1,4]diazepin-4(5H)-yl)methyl)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(2-methoxyacetamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(cyclohexanecarboxamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(2-(dimethylamino)acetamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(3-methoxypropanamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(isonicotinamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(nicotinamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(2-morpholinoacetamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(1-methylpiperidine-4-carboxamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(2-(4-methylpiperazin-1-yl)acetamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(3-(dimethylamino)propanamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(2-(1-methylpiperidin-4-yl)acetamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(tetrahydro-2H-pyran-4-carboxamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(2-(pyrrolidin-1-yl)acetamido)benzoic acid; (R)-4-((8-chloro-2,5-dioxo-3-(pyridin-2-ylmethyl)-2,3-dihydro-1H-benzo[e][1,4]diazepin-4(5H)-yl)methyl)-2-(2-hydroxyacetamido)benzoic acid; (R)-4-(4-aminobenzyl)-8-chloro-3-(pyridin-2-ylmethyl)-3,4-dihydro-1H-benzo[e][1,4]diazepine-2,5-dione; (R)-4-(4-amino-3,5-dimethylbenzyl)-8-chloro-3-(pyridin-2- ylmethyl)-3,4-dihydro-1H-benzo[e][1,4]diazepine-2,5-dione; N-((1R,4r)-4-(((R)-8-chloro-2,5-dioxo-3-(pyridin-2-ylmethyl)-2,3-dihydro-1H-benzo[e][1,4]diazepin-4(5H)-yl)methyl)cyclohexyl)-5-methylpicolinamide; (R)-tert-butyl (4-((8-chloro-2,5-dioxo-3-(pyridin-2-ylmethyl)-2,3-dihydro-1H-benzo[e][1,4]diazepin-4(5H)-yl)methyl)phenyl) carbamate; (R)—N-(4-((8-chloro-2,5-dioxo-3-(pyridin-2-ylmethyl)-2,3-dihydro-1H-benzo[e][1,4]diazepin-4(5H)-yl)methyl)phenyl)picolinamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-4-methylpicolinamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-6-methylpicolinamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-3-methylpicolinamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-5-methylpicolinamide; (R)-3-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide; (R)-4-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide; (R)-5-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide; N-((1R,4r)-4-(((R)-8-chloro-2,5-dioxo-3-(pyridin-2-ylmethyl)-2,3-dihydro-1H-benzo[e][1,4]diazepin-4(5H)-yl)methyl)cyclohexyl)picolinamide; (R)—N-(4-((8-chloro-2,5-dioxo-3-(pyridin-2-ylmethyl)-2,3-dihydro-1H-benzo[e][1,4]diazepin-4(5H)-yl)methyl)-2,6-dimethylphenyl)picolinamide; (R)—N-(4-((8-chloro-2,5-dioxo-3-(pyridin-2-ylmethyl)-2,3-dihydro-1H-benzo[e][1,4]diazepin-4(5H)-yl)methyl)-2,6-dimethylphenyl)-5-methylpicolinamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-2-hydroxynicotinamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-2-hydroxyacetamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)pyrimidine-4-carboxamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)pyrazine-2-carboxamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)thiazole-2-carboxamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)thiazole-4-carboxamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-5-methylisoxazole-3-carboxamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-1H-imidazole-2-carboxamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-1-methyl-1H-imidazole-2-carboxamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-1H-imidazole-4-carboxamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-1-methyl-1H-imidazole-4-carboxamide; (R)—N-(3-((8-chloro-2,5-dioxo-3-(pyridin-2-ylmethyl)-2,3-dihydro-1H-benzo[e][1,4]diazepin-4(5H)-yl)methyl)phenyl)picolinamide; (R)—N-(3-((8-chloro-2,5-dioxo-3-(pyridin-2-ylmethyl)-2,3-dihydro-1H-benzo[e][1,4]diazepin-4(5H)-yl)methyl)phenyl)-2-methoxyacetamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-2-mercaptoacetamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)methanesulfonamide; (R)—N-(4-((8-chloro-2,5-dioxo-3-(pyridin-2-ylmethyl)-2,3-dihydro-1H-benzo[e][1,4]diazepin-4(5H)-yl)methyl)phenyl)-2-methoxyacetamide; (R)—N-(3-((8-chloro-2,5-dioxo-3-(pyridin-2-ylmethyl)-2,3-dihydro-1H-benzo[e][1,4]diazepin-4(5H)-yl)methyl)phenyl)pyridine-2-sulfonamide; (R)-8-chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione; (R)-8-chloro-3-(pyridin-2-ylmethyl)-4-(4-(quinoline-8-carbonyl)benzyl)-3,4-dihydro-1H-benzo[e][1,4]diazepine-2,5-dione; (R)-8-chloro-4-(4-(1-methyl-1H-imidazole-2-carbonyl)benzyl)-3-(pyridin-2-ylmethyl)-3,4-dihydro-1H-benzo[e][1,4]diazepine-2,5-dione; (R)-8-chloro-4-(4-(1-methyl-1H-imidazole-4-carbonyl)benzyl)-3-(pyridin-2-ylmethyl)-3,4-dihydro-1H-benzo[e][1,4]diazepine-2,5-dione; (R)-8-chloro-4-(4-(6-methylimidazo[1,2-a]pyridine-8-carbonyl)benzyl)-3-(pyridin-2-ylmethyl)-3,4-dihydro-1H-benzo[e][1,4]diazepine-2,5-dione; (R)-4-(4-([1,2,4]triazolo[1,5-a]pyridine-8-carbonyl)benzyl)-8-chloro-3-(pyridin-2-ylmethyl)-3,4-dihydro-1H-benzo[e][1,4]diazepine-2,5-dione; 4-(4-(1H-pyrrolo[3,2-b]pyridine-3-carbonyl)benzyl)-8-chloro-3-(pyridin-2-ylmethyl)-3,4-dihydro-1H-benzo[e][1,4]diazepine-2,5-dione; (R)-8-chloro-3-(pyridin-2-ylmethyl)-4-(((1r,4R)-4-(quinoline-8-carbonyl)cyclohexyl)methyl)-3,4-dihydro-1H-benzo[e][1,4]diazepine-2,5-dione; (R)-8-chloro-4-(((1r,4R)-4-(1-methyl-1H-pyrrolo[3,2-b]pyridine-3-carbonyl)cyclohexyl)methyl)-3-(pyridin-2-ylmethyl)-3,4-dihydro-1H-benzo[e][1,4]diazepine-2,5-dione; (R)-8-chloro-4-(((1r,4R)-4-(1-methyl-1H-imidazole-2-carbonyl)cyclohexyl)methyl)-3-(pyridin-2-ylmethyl)-3,4-dihydro-1H-benzo[e][1,4]diazepine-2,5-dione; (R)-8-chloro-4-(((1r,4R)-4-(1-methyl-1H-imidazole-4-carbonyl)cyclohexyl)methyl)-3-(pyridin-2-ylmethyl)-3,4-dihydro-1H-benzo[e][1,4]diazepine-2,5-dione; (R)-8-chloro-4-(4-(imidazo[1,2-α]pyridine-8-carbonyl)benzyl)-3-(pyridin-2-ylmethyl)-3,4-dihydro-1H-benzo[e][1,4]diazepine-2,5-dione; (R)-8-chloro-4-(((1r,4R)-4-(imidazo[1,2-α]pyridine-8-carbonyl)cyclohexyl)methyl)-3-(pyridin-2-ylmethyl)-3,4-dihydro-1H-benzo[e][1,4]diazepine-2,5-dione; (S)-4-((8-chloro-2,5-dioxo-3-(thiazol-4-ylmethyl)-2,3-dihydro-1H-benzo[e][1,4]diazepin-4(5H)-yl)methyl)-N-(5-methylpyridin-2-yl)benzamide; (R)-4-((8-chloro-2,5-dioxo-3-(thiophen-2-ylmethyl)-2,3-dihydro-1H-benzo[e][1,4]diazepin-4(5H)-yl)methyl)-N-(5-methylpyridin-2-yl)benzamide; (R)-4-((8-chloro-2,5-dioxo-3-phenyl-2,3-dihydro-1H-benzo[e][1,4]diazepin-4(5H)-yl)methyl)-N-(pyridin-2-yl)benzamide; (R)-4-((8-chloro-3-(4-methoxybenzyl)-2,5-dioxo-2,3-dihydro-1H-benzo[e][1,4]diazepin-4(5H)-yl)methyl)-N-(pyridin-2-yl)benzamide; 4-((8-chloro-2,5-dioxo-3-((tetrahydro-2H-pyran-4-yl)methyl)-2,3-dihydro-1H-benzo[e][1,4]diazepin-4(5H)-yl)methyl)-N-(pyridin-2-yl)benzamide; (R)-4-((3-(3,4-dichlorobenzyl)-2,5-dioxo-8-(trifluoromethyl)-2,3-dihydro-1H-benzo[e][1,4]diazepin-4(5H)-yl)methyl)-N-(pyridin-2-yl)benzamide; (R)-4-((2,5-dioxo-3-(pyridin-3-ylmethyl)-2,3-dihydro-1H-benzo[e][1,4]diazepin-4(5H)-yl)methyl)-N-(pyridin-2-yl)benzamide; (R)-4-((7-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide; (R)-4-((9-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide; (R)-4-((8-chloro-3-(3-fluorobenzyl)-2,5-dioxo-2,3-dihydro-1H-benzo[e][1,4]diazepin-4(5H)-yl)methyl)-N-(pyridin-2-yl)benzamide; (R)-4-((8-chloro-3-isobutyl-2,5-dioxo-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)cyclohexanecarboxamide; (S)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide; (R)-4-((2,5-dioxo-3-(pyridin-3-ylmethyl)-2,3-dihydro-1H-pyrido[3,4-e][1,4]diazepin-4(5H)-yl)methyl)-N-(pyridin-2-yl)benzamide; (R)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)benzenesulfonamide; (R)-8-chloro-4-((1-oxo-2-(pyridin-2-yl)-1,2,3,4-tetrahydroisoquinolin-6-yl)methyl)-3-(pyridin-2-ylmethyl)-3,4-dihydro-1H-benzo[e][1,4]diazepine-2,5-dione; (R)-2-(4-methoxybenzyloxy)-4-((8-chloro-3-methyl-2,5-dioxo-2,3-dihydro-1H-benzo[e][1,4]diazepin-4(5H)-yl)methyl)benzoic acid; (R)-4-((3-methyl-8-(methylsulfonamido)-2,5-dioxo-2,3-dihydro-1H-benzo[e][1,4]diazepin-4(5H)-yl)methyl)-N-(5-methylpyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-hydroxybenzamide; 8-Chloro-4-(4-(hydroxymethyl)benzyl)-3-(pyridin-2-ylmethyl)-3,4-dihydro-1H-benzo[e][1,4]diazepine-2,5-dione; (R)-4-((8-Chloro-2,5-dioxo-3-(pyridin-2-ylmethyl)-2,3-dihydro-1H-benzo[e][1,4]diazepin-4(5H)-yl)methyl)-N-(pyridin-2-yl)piperidine-1-carboxamide; (R)-8-chloro-4-((1-(1-methyl-1H-pyrrolo[3,2-b]pyridine-3-carbonyl)piperidin-4-yl)methyl)-3-(pyridin-2-ylmethyl)-3,4-dihydro-1H-benzo[e][1,4]diazepine-2,5-dione; (R)-4-((3-Bromo-1-methyl-1H-indazol-6-yl)methyl)-8-chloro-3-(pyridin-2-ylmethyl)-3,4-dihydro-1H-benzo[e][1,4]diazepine-2,5-dione; (R)-3-Amino-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide; (R)-8-Chloro-4-(4-(4-oxopyrido[3,2-d]pyrimidin-3(4H)-yl)benzyl)-3-(pyridin-2-ylmethyl)-3,4-dihydro-1H-benzo[e][1,4]diazepine-2,5-dione; (R)-8-Chloro-4-(4-(2-methyl-4-oxopyrido[3,2-d]pyrimidin-3(4H)-yl)benzyl)-3-(pyridin-2-ylmethyl)-3,4-dihydro-1H-benzo[e][1,4]diazepine-2,5-dione; (R)-4-((8-chloro-2,5-dioxo-3-(pyridin-2-ylmethyl)-2,3-dihydro-1H-benzo[e][1,4]diazepin-4(5H)-yl)methyl)-N-(5-(piperazin-1-yl)pyridin-2-yl)benzamide hydrochloride; (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyrimidin-2-yl)benzamide; (R)-8-chloro-4-(4-(8-oxo-5,6-dihydro-1,7-naphthyridin-7(8H)-yl)benzyl)-3-(pyridin-2-ylmethyl)-3,4-dihydro-1H-benzo[e][1,4]diazepine-2,5-dione; (R)-8-chloro-4-(4-(7-oxo-5H-pyrrolo[3,4-b]pyridin-6(7H)-yl)benzyl)-3-(pyridin-2-ylmethyl)-3,4-dihydro-1H-benzo[e][1,4]diazepine-2,5-dione; (R)-8-chloro-4-((1-oxo-2-(pyridin-2-yl)isoindolin-5-yl)methyl)-3-(pyridin-2-ylmethyl)-3,4-dihydro-1H-benzo[e][1,4]diazepine-2,5-dione; (R)-8-chloro-4-((1-(pyridin-2-ylamino)isoquinolin-6-yl)methyl)-3-(pyridin-2-ylmethyl)-3,4-dihydro-1H-benzo[e][1,4]diazepine-2,5-dione; 8-chloro-4-(1-(4-(imidazo[1,2-α]pyridine-8-carbonyl)phenyl)cyclopropyl)-3-methyl-3,4-dihydro-1H-benzo[e][1,4]diazepine-2,5-dione; (3R)-8-chloro-4-(4-(hydroxy(pyridin-2-yl)methyl)benzyl)-3-(pyridin-2-ylmethyl)-3,4-dihydro-1H-benzo[e][1,4]diazepine-2,5-dione; (R)-8-chloro-4-(4-((hydroxyimino)(pyridin-2-yl)methyl)benzyl)-3-(pyridin-2-ylmethyl)-3,4-dihydro-1H-benzo[e][1,4]diazepine-2,5-dione; (R)-8-chloro-4-(4-((hydroxyimino)(pyridin-2-yl)methyl)benzyl)-3-(pyridin-2-ylmethyl)-3,4-dihydro-1H-benzo[e][1,4]diazepine-2,5-dione; (R)-2-(benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide; (R)-2-amino-4-((8-chloro-2,5-dioxo-3-(pyridin-2-ylmethyl)-2,3-dihydro-1H-benzo[e][1,4]diazepin-4(5H)-yl)methyl)benzoic acid; 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)benzoic acid; 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-(trifluoromethyl)pyridin-2-yl)benzamide; 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methylpyridin-2-yl)benzamide; 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methoxypyridin-2-yl)benzamide; and 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methylpyridin-2-yl)benzamide, or pharmaceutically acceptable salts thereof.

In another preferred embodiment, the present compounds include: (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide; (R)-8-chloro-4-(3-chloro-4-(1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-8-chloro-4-(3-chloro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-8-chloro-4-(4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-8-chloro-4-(4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-ethylpyridin-2-yl)benzamide; (S)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide; (R)-8-chloro-4-(3-chloro-4-(3,3-dimethyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-4-((8-chloro-2,5-dioxo-3-(pyridin-2-ylmethyl)-2,3-dihydro-1H-benzo[e][1,4]diazepin-4(5H)-yl)methyl)-N-(5-morpholinopyridin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide; (R)-8-chloro-4-(3-chloro-4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5- methylpyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl) methyl)-2-methoxy-N-(5-methylpyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(3-fluoropyridin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrimidin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl)pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrimidin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrimidin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)-2-methylbenzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)-2-methylbenzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)benzamide; (R)-8-chloro-4-(3-chloro-4-(3,3-dimethyl-5-(trifluoromethyl)-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methoxypyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-fluoropyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methylpyridin-2-yl)benzamide; (R)-8-chloro-4-(3-fluoro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione; (R)-8-chloro-4-(4-(5-methylpicolinoyl)benzyl)-3-(pyridin-2-ylmethyl)-3,4-dihydro-1H-benzo[e][1,4]diazepine-2,5-dione; (R)-8-chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione; (R)-8-chloro-4-(((1r,4R)-4-(1-methyl-1H-pyrrolo[3,2-b]pyridine-3-carbonyl)cyclohexyl)methyl)-3-(pyridin-2-ylmethyl)-3,4-dihydro-1H-benzo[e][1,4]diazepine-2,5-dione; (R)-8-chloro-4-(4-(imidazo[1,2-a]pyridine-8-carbonyl)benzyl)-3-(pyridin-2-ylmethyl)-3,4-dihydro-1H-benzo[e][1,4]diazepine-2,5-dione; and (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyrimidin-2-yl)benzamide, or a pharmaceutically acceptable salt thereof.

In one preferred embodiment, the present compounds include: (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyridin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin- 2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)-2-methylbenzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrazin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl)pyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)-2-methylbenzamide; (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)benzamide; (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methoxypyridin-2-yl)benzamide; and (R)-8-chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione, or pharmaceutically acceptable salts thereof.

The compounds of the present invention may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures, as well as mixtures of diastereomers thereof. Except where otherwise specified, the formulae encompassing compounds of the present invention are shown without a definitive stereochemistry at certain positions. The present invention therefore may be understood to include all stereoisomers of compounds and pharmaceutically acceptable salts thereof. It is generally preferable to administer compounds of the present invention as enantiomerically pure formulations.

Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the present invention may be obtained by stereospecific synthesis using optically pure starting materials or reagents of known configuration.

The compounds of the present invention include tautomers of such compounds. Tautomers are defined as compounds that undergo rapid proton shifts from one atom of the compound to another atom of the compound. Some of the compounds described herein may exist as tautomers with different points of attachment of hydrogen. Exemplary tautomers include a ketone and its enol form known as keto-enol tautomers.

Accordingly, the compounds within the generic structural formulas, embodiments and specific compounds described and claimed herein are intended to encompass salts, all possible stereoisomers and tautomers.

In one embodiment, the present invention provides a composition comprising a compound of the present invention or a pharmaceutically acceptable salt, solvate, or prodrug thereof.

In one embodiment, the present invention relates to a method of treating diseases in a subject by administering a therapeutically effective amount of a compound of the present invention or a pharmaceutically acceptable salt, solvate, or prodrug thereof.

The compounds of the present invention include all suitable isotopic variations of such compounds. An isotopic variation of a compound is defined as one in which at least one atom is replaced by an atom having the same atomic number but an atomic mass different from the atomic mass usually found in nature. Exemplary isotopes include isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{188}$F, $^{36}$Cl, $^{123}$I and the like. Certain isotopic variations of the compounds are useful in drug or substrate tissue distribution studies. Others may afford certain therapeutic advantages resulting from greater metabolic stability, such as increased or decreased in vivo half-life or reduced dosage requirements. Isotopic variations of the compounds of the present invention provided herein are prepared by conventional procedures using appropriate isotopic variations of suitable reagents.

In one aspect, the present invention provides a pharmaceutical composition comprising the novel compounds of the present invention described herein, method of preparation and use of same in treatment or prophylaxis of *C. difficile* colitis in a mammal, preferably a human.

In one embodiment, the present invention provides a pharmaceutical composition containing a compound of formula (I) for use in therapy in humans with CDI.

In one aspect, the present invention provides pharmaceutical compositions that may be administered to a subject in need of *C. difficile* treatment via different administration routes. Exemplary routes of administration include, for example, oral, sublingual, intranasal, inhalation as an aerosol, parenteral administration and the like.

Pharmaceutical formulations include those suitable for oral, nasal, parenteral or intrarectal administration. Parenteral administration includes, for example, intravenous, intramuscular, subcutaneous, intraperitoneal, parenteral, intradermal administration, or any combination thereof. Intrarectal administration includes rectal suppositories.

The pharmaceutical formulations may conveniently be presented in unit dosage form using methods that are known in the art of pharmacy. The nature, availability and sources, and the administration of all the compounds including the effective amounts necessary to produce desirable effects in a subject are well known in the art. The composition may be administered by any convenient route, for example by infusion or bolus injection, by absorption through epithelial or mucocutaneous linings (e.g., oral mucosa, and intestinal mucosa, etc.). Preferably, administration can be systemic or local.

Pharmaceutical compositions of the present invention generally comprise one or more pharmaceutically acceptable excipients (also known as vehicles such as pharmaceutically acceptable carriers). Pharmaceutical acceptable excipients encompass, for example, antiadherents, binders, coatings, colors, disintegrants, flavors, glidants, lubricants, preservatives, sorbents, sweeteners, vehicles, and the like. One function of the pharmaceutical acceptable excipient is to facilitate drug absorption, reducing viscosity, enhancing solubility, and manufacturing process, handling of the active substance concerned such as facilitating powder flowability or non-stick properties, aiding in vitro stability such as prevention of denaturation or aggregation over the expected shelf life. The administration of therapeutic compositions in accordance with the invention will be administered with suitable pharmaceutical acceptable excipients that are incorporated into formulations to provide improved transfer, delivery, tolerance, and the like.

Exemplary pharmaceutically acceptable excipients include lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate, solvents, dispersion media, coatings, antibacterial and antifungal agents, and the like.

Pharmaceutically acceptable excipients are commonly known to a skilled artisan and include a variety of organic or inorganic carriers including starch, cellulose, gelatin, talc, glycol, polyol, ester, agar, buffering agents, alginic acid and the like that are employed in pharmaceutical formulations. Such excipients include, for solid preparations, diluents, lubricants, binders, and disintegrants, and for liquid preparations, solvents, solubilizing agents, suspending agents, isotonic agents, buffer agents, soothing agents, and the like.

Suitable exemplary diluents include lactose, sucrose, D-mannitol, starch, crystalline cellulose, light silica anhydrate, and the like. Suitable exemplary lubricants include magnesium stearate, calcium stearate, talc, colloidal silica, and the like. Suitable exemplary binders include crystalline cellulose, sucrose, D-mannitol, dextrin, hydroxypropylcellulose, hydroxypropylmethylcellulose, polyvinylpyrrolidone, and the like. Suitable exemplary disintegrants include starch, carboxymethylcellulose, calcium carboxymethylcellulose, croscarmellose sodium, sodium carboxymethylstarch, and the like.

Suitable exemplary solvents or dispersion media include water, alcohol (for example, ethanol), polyol (for example, glycerol, propylene glycol, and polyethylene glycol, sesame oil, corn oil, and the like), and suitable mixtures thereof that are physiologically compatible. Suitable exemplary solubilizing agents include polyethylene glycol, propylene glycol, D-mannitol, benzylbenzoate, ethanol, trisaminomethane, cholesterol, triethanolamine, sodium carbonate, sodium citrate, and the like. Suitable exemplary suspending agents include surfactants such as stearyltriethanolamine, sodium laurylsulfate, laurylaminopropionic acid, lecithin, benzalkonium chloride, benzethonium chloride, glycerin monostearate, and the like; and hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose, and the like. Suitable exemplary isotonic agent includes sodium chloride, glycerin, D-mannose, and the like. Suitable exemplary buffer agents include buffer solutions of salts, such as phosphate, acetates, carbonates, and citrates. Suitable exemplary soothing agents include benzyl alcohol, and the like. Suitable exemplary antiseptic substances include para-oxybenzoic acid esters, chlorobutanol, benzyl alcohol, phenethyl alcohol, dehydroacetic acid, sorbic acid, and the like. Suitable exemplary antioxidants include sulfite salts, ascorbic acid, and the like. Suitable exemplary sealers include, but are not limited to HPMC (or hypromellose), HPC, PEG and combinations thereof.

In some embodiments, disintegrants are added to the formulation to help the all or part of the dosage form disintegrate after consumption, thereby releasing at least a portion of the active ingredients. Some common disintegrants include several modified cellulose derivatives, such as croscarmellose sodium and other modified starch derivatives such as sodium starch glycolate. It will also be understood by one of ordinary skill in the art that a pharmaceutical composition may contain other suitable ingredients, binders and lubricants that provide optimal dissolution profiles of dosage forms.

In one aspect, the present invention provides a pharmaceutical composition that can be administered into a subject in need of therapy for *C. difficile* associated diseases. In one embodiment, the present pharmaceutical composition may be delivered orally. In another embodiment, the present pharmaceutical composition may be administered intravenously or subcutaneously with a standard needle and syringe.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Pharmaceutical acceptable excipients for the dosage form for oral administration (such as liquid, tablet or capsule) include, for example, ethanol, glycerol, water and the like. When required, suitable binders, lubricants, disintegrating agents and coloring and flavoring agents can be incorporated into the mixture. Stabilizing agents such as antioxidants, propyl gallate, sodium ascorbate, citric acid, calcium metabisulphite, hydroquinone, and 7-hydroxycoumarin can be added to stabilize the dosage forms. Other suitable compounds include gelatin, sweeteners, natural and synthetic gums such as acacia, tragacanth, or alginates, carboxymethylcellulose, polyethylene, glycol, waxes and the like.

The present invention, in various embodiments, provides an oral composition suitable for human administration. The present oral composition encompasses various dosage forms. For example, the oral composition can be a tablet, coated tablet, capsule, caplet, cachet, lozenges, gel capsule, hard gelatin capsule, soft gelatin capsule, troche, dragee, dispersion, powder, granule, pill, liquid, an aqueous or non-aqueous liquid suspension, an oil-in-liquid or oil-in-water emulsion, including sustained release formulations that are known in the art.

For oral dosage, the pharmaceutical composition may be a solid formulation, such as tablets and capsules. Delayed release or enterically coated preparations may also be devised. For pediatric and geriatric applications, suspensions, syrups and chewable tablets are especially suitable.

The preparation of pharmaceutical compositions is well known in the art and has been described in many articles and textbooks (See, e.g., Introduction to Pharmaceutical Dosage Forms, 1985, Ansel, H. C., Lea and Febiger, Philadelphia, Pa.; *Remington's Pharmaceutical Sciences,* 1995, Mack Publ. Co., Easton, Pa.)

When the dosage form of the pharmaceutical composition is a capsule, it may contain a liquid carrier. Other materials may be present as coatings or to otherwise modify the physical form of the dosage form. For instance, tablets, pills, or capsules may be coated with shellac, sugar or both. A syrup or elixir may contain sucrose as a sweetening agent and methyl and propylparabens as preservatives, a dye and flavoring, such as cherry or orange flavor. Of course, materials used in preparing any dosage form should be pharmaceutically pure and substantially non-toxic in the amounts employed. Pharmaceutical additives such as antiseptic substances, antioxidants, coloring agents, and sweeteners may also be added if necessary.

These dosage forms can be prepared using standard procedures that are known to the art, including but not limited to encapsulating procedures. In one embodiment, the dosage form provides a low blood profile of *C. difficile* inhibitors (*C. difficile* compounds) after ingestion but continues to release *C. difficile* compounds in the gut compartment over time to permit low pharmaceutical exposure (i.e., *C. difficile* compounds are restricted to the gut compartment). Preferably, the oral compositions (after ingestion) provide a plasma level of *C. difficile* compounds at 0.1-10 nM.

In one embodiment, the present compositions are formulated into a dosage form releasing *C. difficile* compounds for a period of 1 to 12, typically 3 to 12 hours, more typically 6-12 hours after ingestion. Preferably, the oral pharmaceutical compositions of the present invention may be administered in single or divided doses, from one to four times a day. The oral dosage forms may be conveniently presented in unit dosage forms and prepared by any methods well known in the art of pharmacy. In another embodiment, the present composition contains a predetermined amount of a therapeutic amount of *C. difficile* compound effective in treating *C. difficile* colitis.

In one embodiment, the pharmaceutical composition can be delivered in a controlled release system. In one embodiment, a pump may be used. In another embodiment, polymeric materials may be used. In yet another embodiment, a controlled release system may be placed in proximity of the composition's target, thus requiring only a fraction of the systemic dose.

The present formulations can be prepared by any suitable method of pharmacy which includes the step of bringing into association the therapeutic *C. difficile* compound compositions and a suitable carrier (which can contain one or more accessory ingredients as noted above). In general, the pharmaceutical compositions according to embodiments of the present invention are prepared by uniformly and intimately admixing the *C. difficile* compounds with a liquid or finely divided solid carrier, or both, and then, if necessary, shaping the resulting mixture. For example, tablets may be prepared by compressing or molding powders or granules containing the therapeutic *C. difficile* compounds, optionally with one or more accessory ingredients. Compressed tablets can be prepared by compressing, in a suitable machine, the therapeutic *C. difficile* compounds in a free-flowing form, including a powder or granules optionally mixed with a binder, lubricant, inert diluent, and/or surface active or dispersing agent(s). Molded tablets can be made by molding, in a suitable machine, the powdered compound moistened with an inert liquid binder. The tablets can optionally be coated or scored and can be formulated so as to provide slow or controlled release of the active ingredient *C. difficile* compounds therein.

When the pharmaceutical compositions are applied to humans, they are desirably administered via the oral route. The therapeutic effective dose of each *C. difficile* active compounds depends on the age or symptom of the patient to be treated. Generally, the pharmaceutical preparations may contain about 50 mg, 100 mg, 250 mg, 500 mg or 1,000 mg of the *C. difficile* compounds per unit dosage form and may be administered to humans or animals at a daily dose of 0.1-100 mg per kilogram of body weight. The optimal dose suitable for a particular patient can be conveniently determined (by a physician) without undue experimentation.

The pharmaceutical compositions generally are administered in a therapeutic effective amount for treatment or prophylaxis of *C. difficile* colitis. Initial dosing in human can be accompanied by clinical monitoring of symptoms for the selected condition (for example, diarrhea, fever, intestinal integrity, and the like) for administration particularly to mammals, and particularly humans, it is expected that the daily dosage level of the *C. difficile* compounds may be determined to maintain a sufficient blood level of the compounds to achieve the therapeutic improvement of reducing the symptom conditions such as diarrhea, fever, intestinal integrity and the like.

It will be appreciated that optimum dosage will be determined by standard methods for each treatment modality and indication, taking into account the indication, its severity, route of administration, complicating conditions and the like. The physician in any event will determine the actual dosage that will be most suitable for an individual and will vary with the age, weight and response of the particular individual. The effectiveness of a selected actual dose can readily be determined, for example, by measuring clinical symptoms after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

For purposes of the present invention, "treating" or "treatment" in the present context includes alleviating symptoms (such as, for example, diarrhea, fever, or intestinal integrity, or abdominal pain), slowing, retarding or stabilizing progression of a condition or a physiological or morphological marker thereof, or improving clinical outcome, for example as measured by quality of life, incidence or severity of adverse symptoms or survival time.

The present inventors hypothesize that when administered via an oral route, the present compounds can best provide adequate and fast delivery of the compounds to the gut compartment where gut inflammation occurs. It is further believed that the present compounds can work in conjunction with the antibiotics or antibody treatment approaches to achieve an additive or synergistic clinical benefit in improving the symptoms affected by *C. difficile* infection.

In one aspect, the present invention provides a pharmaceutical composition comprising the novel compounds of the present invention in combination with an additional therapeutic agent. The additional therapeutic agent functions in a synergistic or additive manner to enhance the therapeutic efficacy of the present compounds in the treatment of *C. difficile* infection in humans. Exemplary additional therapeutic agent includes, but not limited to, an antibiotic, antibody against the *C. difficile* (e.g., anti-toxins (toxin A or toxin B) or anti-endospores) and the like. The pharmaceutical composition includes a pharmaceutical acceptable excipient for purposes of administration into a patient.

In one aspect, the present invention provides a method of treating *C. difficile* infection (CDI) in a human in need thereof, comprising the step of: administering to said human a therapeutically effective amount of the compounds of the present invention.

In one aspect, the present invention provides a combination therapy using the compounds as described herein and one or more of an additional therapeutic agent(s). The additional therapeutic agents preferably include medications commonly prescribed for *C. difficile* treatments. Exemplary additional therapeutic agents include, but are not limited to an antibiotic, or an antibody against the *C. difficile*. Exemplary anti-*C. difficile* antibodies include, for example, anti-toxins (toxin A or toxin B) antibodies, anti-endospores antibodies, and any combination thereof.

Once an individual is diagnosed with *C. difficile* infection, a physician can prescribe a pharmaceutical composition comprising the compounds of the present invention for treatment options. *C. difficile* infection may be diagnosed by stool test, flexible sigmoidscopy, imaging scans, and the like. Conventional treatment options for *C. difficile* include, for example, antibiotics, probiotics, or surgery. Preferably, *C. difficile* infection may be treated with antibiotics. Exemplary antibiotics include, but not limited to, metronidazole, vancomycin, fidaxomicin, and the like.

For purposes of this application, *C. difficile* infection is classified, based on disease severity, into mild, moderate and severe. Mild infection is defined as *C. difficile* infection with diarrhea as the only symptom. Moderate infection is defined as *C. difficile* infection with diarrhea but without additional symptoms/signs meeting the definition of severe *C. difficile* infection. Severe infection is defined as *C. difficile* infection that presents with or develops during the course of the disease with hypoalbuminemia (serum albumin <3 g/dl) and either of the following: (i) a white blood cell count ≥15,000 cells/mm² or (2) abdominal tenderness without criteria of complicated disease. (See, Guidelines for Diagnosis, Treatment, and Prevention of *C. difficile* infection, *Am. J. Gastroenterol* 2013, 108: 478-498).

For mild to moderate infection, antibiotic such as metronidazole (Flagyl) in oral dosage form is preferred. Metronidazole is not FDA approved for the treatment of *C. difficile* infection (i.e., physicians often off-label use the antibiotic). Metronidazole is shown to be effective in treating subjects with mild to moderate *C. difficile* infection. For more severe and recurrent cases, vancomycin (Vancocin) in oral dosage form is often prescribed. It is common practice to prescribe 1-14 days of treatment for *C. difficile* infection. While the dosage may vary from individual to individual, vancomycin delivered orally (125 mg four times per day) plus intravenous metronidazole (500 mg three times a day) represents an exemplary treatment of choice in patients with severe complicated *C. difficile* infection. For example, vancomycin delivered orally (500 mg four times per day) and per rectum (500 mg in a volume of 500 ml four times a day) plus intravenous metronidazole (500 mg three times a day) is the treatment of choice for patients with complicated *C. difficile* infection. (See, Guidelines for Diagnosis, Treatment, and Prevention of *C. difficile* infection, *Am. J. Gastroenterol* 2013, 108: 478-498).

In another aspect, the present invention provides a method of treating *C. difficile* infection (CDI) in a human in need thereof comprising the steps of: (a) administering to said human a therapeutically effective amount of the compounds of the present invention; and (b) administering to said human a therapeutically effective amount of an additional therapeutic agent useful for the treatment of CDI.

It is well recognized that recurrent of *C. difficile* infection is quite common. Up to 20 percent of people with *C. difficile* infection will get sick again. The exact mechanism for *C. difficile* recurrent is not known. It may be because the initial *C. difficile* infection never went away or because the subject is re-infected with a different strain of the bacteria. Human intestine is known to contain millions of different types of bacteria. Antibiotics treatment may destroy healthy bacteria and attribute to the recurrent of *C. difficile* infection. It is noted that once after one or more recurrences, the rate of further recurrence increases (e.g., 65 percent). The treatment choice is limited to fecal microbiota transplant.

Antibiotic therapy for recurrence of *C. difficile* infection involves one or more courses of a medication (typically vancomycin) (i.e., promote acquisition of vancomycin-resistant enterococcus), a gradually tapered dose of medication or an antibiotic given once every few days, a method known as a pulsed regimen. For a first recurrence, the effectiveness of antibiotic therapy is around 60 percent but declines with each subsequent recurrence.

Another oral antibiotic, fidaxomicin (Dificid), has been FDA approved to treat *C. diffilcile*. Fidaxomicin is often prescribed at 200 mg orally 2 times per day for 10 days for the treatment of mild to moderate *C. difficile* infection. (See, Guidelines for Diagnosis, Treatment, and Prevention of *C. difficile* infection, Am. J. Gastroenterol 2013, 108: 478-498). The recurrence rate of *C. difficile* in people who took fidaxomicin is shown to have a lower recurrent rate than among those who took vancomycin. Cost of fidaxomicin is significantly more than that of metronidazole and vancomycin.

An important step in the treatment of *C. difficile* infection is cessation of the inciting antibiotic as soon as possible. Treatment with concomitant antibiotics (i.e., antibiotics other than those given to treat *C. difficile* infection) is associated both with significant prolongation of diarrhea and with increased risk of recurrent *C. difficile* infection. If ongoing antibiotics are essential for treatment of the primary infection, one physician may select antibiotic therapy that is less frequently implicated in antibiotic-associated *C. difficile* infection, such as parenteral aminoglycosides, sulfonamides, macrolides, vancomycin, or tetracycline.

In one aspect, the present invention provides a method for the treatment or prophylaxis of at least one symptom of *C. difficile* associated disease in a subject. In one embodiment, the pharmaceutical composition is effective to reduce, eliminate, or prevent *C. difficile* bacterial infection in a subject.

The pharmaceutical composition of the present invention can be used in the therapy *C. difficile* associated diseases and can be carried out by administering a therapeutically effective amount of the compounds in the composition to a subject in need of such treatment or prophylaxis. The need for a prophylactic administration according to the methods of the present invention is determined via the use of the well-known risk factors as described herein.

The magnitude of prophylactic or therapeutic dose of the active ingredients can, of course, vary with the nature of the severity of the condition to be treated. It can also vary according to the age, weight and response of the individual patient, and may be administered in subject in single or divided doses. On the other hand, it may be necessary to use dosages outside the ranges provided herein in some cases.

In one embodiment, the composition is administered for at least 3, 4, 5, 6, or 7 days prior to an increased risk of acquiring *C. difficile* infection. In another embodiment, the composition is administered prior to admission to a hospital or a nursing home. In another embodiment, the composition is administered after admission to a hospital or a nursing home.

In one embodiment, the composition is administered following infection with *C. difficile*. For example, a composition of the present invention can be administered at least 2 hours following infection, at least 4 hours following infection, at least 12 hours following infection or at least 24 hours following infection with *C. difficile*.

In yet another aspect, the present invention provides a method of preventing a relapse of a prior *C. difficile* infection (CDI) in a human, comprising the step of: administering to said human a therapeutically effective amount of the compounds of the present invention. In one embodiment, the composition is administered to prevent re-lapse of a prior *C. difficile* infection.

In one aspect, the present method comprises administering to the subject a composition comprising the compound of the present invention and an additional therapeutic agent. The additional therapeutic agent used to treat *C. difficile* associated diseases includes, for example, antibiotics and antibodies against *C. difficile*. In one example, the additional therapeutic agent is an antibiotic, e.g., vancomycin or metronidazole. In another example, the additional therapeutic agent is an antibody.

*C. difficile* antibodies include, for example, (i) antibodies that bind to a *C. difficile* toxin A; (ii) antibodies that bind to a *C. difficile* toxin B; (iii) antibodies that bind to both *C. difficile* toxin A and toxin B; (iv) antibodies that bind to a *C. difficile* vegetative cell antigen; and (v) antibodies that bind to a *C. difficile* endospore antigen.

Exemplary anti-*C. difficile* toxin A antibodies include, for example, those disclosed in U.S. Pat. Nos. 8,236,311 and 8,986,697, U.S. 2013/0230531, WO 2014/144292, and WO2013/028810. Exemplary anti-*C. difficile* toxin B antibodies include, for example, those disclosed in U.S. Pat. Nos. 8,236,311 and 8,986,697, U.S. 2013/0230531, WO 2014/144292, WO 2014/169344, and WO 2013/028810. Exemplary anti-*C. difficile* toxin A and toxin B antibodies include, for example, those disclosed in U.S. Pat. No. 8,236,311, U.S. 2013/0230531, and WO 2014/144292. Exemplary anti-*C. difficile* vegetative cell antigen or endospore antibodies include, for example, those disclosed in U.S. Pat. No. 8,697,374.

Anti-*C. difficile* toxin B is shown to have promising clinical efficacy in the early clinical trial. The phase II clinical trial of an anti-*C. difficile* toxin B in 200 patients showed a reduction in the incidence of *C. difficile* infection as compared to that of placebo. Through a license agreement with Medarex and Massachusetts Biologic Laboratories, Merck has the worldwide rights to market and develop the anti-*C. difficile* toxins (CDA-1 and CDB-1) based on the success of clinical trial.

Anti-*C. difficile* antibodies may encompass chimeric and humanized antibodies. These antibodies offer less antigenity upon administration into a human. Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (See, e.g., U.S. Pat. No. 4,816,567). Chimeric antibodies can also be created by recombinant DNA techniques where DNA encoding murine V regions can be ligated to DNA encoding the human constant regions.

Humanized anti-*C. difficile* antibodies can be prepared by methods known in the art. For example, once murine antibodies are obtained, variable regions can be sequenced. The location of the CDRs and framework residues can be determined. The light and heavy chain variable regions can, optionally, be ligated to corresponding constant regions. Fully human antibodies can further be altered (e.g., by mutation, substitution) to contain a substitute constant region, e.g., Fc region, or portion(s) thereof to achieve, for example, a desired antibody structure, function (e.g., effector function), subtype, allotype, subclass, or the like. CDR-grafted antibody molecules or immunoglobulins can be produced by CDR-grafting or CDR substitution, wherein one, two, or all CDRs of an immunoglobulin chain can be replaced. (See, e.g., U.S. Pat. Nos. 5,225,539 and 5,225,539).

In one preferred embodiment, the invention provides a method of treating *C. difficile* infection in a subject by administering to the subject the compounds of the present invention and an isolated human monoclonal antibody or antigen binding portion thereof that specifically binds to toxins A and/or B of *C. difficile* in an amount effective to inhibit *C. difficile* associated symptoms such as *C. difficile*-mediated colitis, antibiotic-associated colitis, *C. difficile*-mediated pseudomembranous colitis (PMC), or diarrhea, or relapse of *C. difficile*-mediated disease. The human antibody or antigen binding portion thereof can be administered, e.g., intravenously, intramuscularly, or subcutaneously, to the subject.

In one embodiment, anti-*C. difficile* antibody or antigen binding portion thereof includes administration of a combination of two or more anti-*C. difficile* antibody or antigen binding portion thereof. In one example, the antibody or antigen binding portion thereof specifically binds to *C. difficile* toxin A, and the second human monoclonal antibody or antigen binding portion thereof specifically binds to *C. difficile* toxin B.

For purposes of this application, the antibodies against *C. difficile* are intended to encompass both the full-length antibodies as well as their antigen-binding fragments thereof "Antigen-binding fragments thereof" of an antibody, as used herein, refers to a portion of an antibody that specifically binds to a toxin of *C. difficile* (e.g., toxin A), e.g., a molecule in which one or more immunoglobulin chains is not full length, but which specifically binds to a toxin. Examples of binding portions encompassed within the term "antigen-binding fragments thereof" of an antibody include (i) a Fab fragment, a monovalent fragment consisting of the VLC, VHC, CL and CH1 domains; (ii) a F(ab')₂ fragment, a bivalent fragment comprising two Fab fragments linked by a disulfide bridge at the hinge region; (iii) a Fd fragment consisting of the VHC and CH1 domains; (iv) a Fv fragment consisting of the VLC and VHC domains of a single arm of an antibody, (v) a dAb fragment (Ward et al., Nature 341:544-546, 1989), which consists of a VHC domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen-binding fragments thereof" of an antibody. These antibody portions are obtained using conventional techniques known to those with skill in the art, and the portions are screened for utility in the same manner as are intact antibodies.

In one aspect, the present invention provides compositions containing the compounds of the present invention, together with an anti-*C. difficile* antibody or antigen-binding portion thereof, and a pharmaceutically acceptable carrier. The compounds of the present invention as well as the anti-toxin A and anti-toxin B antibodies, or portions thereof, can be provided according to dosage regimens that may be adjusted to provide the optimum desired response, such as a therapeutic or prophylactic response, in an individual subject. Illustratively, a single bolus may be administered, several divided doses may be administered over time, or the dose may be reduced or increased proportionally, as may be indicated by a particular therapeutic situation.

Parenteral compositions may be packaged or prepared in unit dosage form for ease of administration and uniformity of dosage. Unit dosage form refers to physically discrete units provided as unitary dosages for the subjects to be treated, wherein each unit contains a predetermined quantity of active compound calculated to produce the desired therapeutic effect in association with the required pharmaceutical carrier (e.g., excipient). The specification for the unit dosage forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The present pharmaceutical compositions suitable for parenteral administration conveniently comprise a sterile aqueous or non-aqueous preparation, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables.

The amount of the aforesaid antibody contained in the pharmaceutical composition generally about 5 to about 500 mg per dosage form in a unit dose; especially in the form of injection, it is preferred that the aforesaid antibody is contained in about 5 to about 100 mg and in about 10 to about 250 mg for the other dosage forms.

The combined composition, when administered to a patient in need of treatment or prophylaxis against *C. difficile* infection, is believed to have an additive or synergistic effect on the treatment.

When administered orally, the present compositions containing the compounds of the present invention as well as the antibodies against *C. difficile* may require protection from enzymatic digestion within the digestive tracks. This can be accomplished either by complexing the compounds of the present invention as well as the antibody or antigen-binding portion thereof with a composition to render it resistant to acidic and enzymatic hydrolysis or by packaging the antibody or antigen-binding portion thereof in an appropriately resistant carrier such as a liposome. Means of protecting compounds from digestion are well known in the art. (See, Fix, *Pharm Res.* 13: 1760-1764, 1996; Samanen, *J. Pharm. Pharmacol.* 48: 119-135, 1996; and U.S. Pat. No. 5,391,377).

The present pharmaceutical compositions can be administered in sustained delivery or sustained release mechanisms. For example, biodegradable microspheres or capsules or other biodegradable polymer configurations capable of sustained delivery of a peptide can be included in the formulations of the invention (See, e.g., Putney, *Nat. Biotechnol.* 16: 153-157, 1998).

The combination therapy provides the beneficial effect from the co-action of these therapeutic agents, due to synergistic or additive effects. Therapeutic agents are preferably administered simultaneous, or carried out over a defined time interval (e.g., minutes or hours depending upon the combination selected). In one embodiment, co-administration can be accomplished, for example, by administering to the subject a single dosage form (e.g., capsule) having a fixed ratio of each therapeutic agent. In another embodiment, while the *C. difficile* compound of the present invention is administered by oral route, the second therapeutic agent can be administered by the same route or by different routes (e.g., orally, intravenous injection, intramuscular or nasally). In one embodiment, the combined therapy composition includes an oral *C. difficile* compound and an injectable antibiotic or antibodies or a combination thereof.

Additional therapeutic agent includes antibiotics that are used in the treatment of *C. difficile*. Such antibiotics may be used in combination with the present novel compounds. Treatment of *C. difficile* infection by antibiotics relies on the ability of the antibiotics to kill off the *C. difficile* bacteria. Currently, there are at least three antibiotics commonly used in the clinics to treat *C. difficile* infection; namely, metronidazole, fidaxomicin and vancomycin. Metronidazole is marketed under the brand name "Flagyl" and is a drug of choice for first episodes of mild-to-moderate *C. difficile* colitis. Several randomized controlled trials have demonstrated equivalent efficacy of oral metronidazole and oral vancomycin in treating the *C. difficile* colitis. (See, e.g., Zar, F. A. et al., "A comparison of vancomycin and metronidazole for the treatment of *C. difficile*-associated diarrhea" *Clinical Infectious Diseases* 45(3): 302-307, 2007) Fidaxomicin has the trade names "Dificid or Dificlir" (marketed under Cubist Pharmaceuticals) and it selectively eradicates the pathogenic *C. difficile* upon oral administration with minimal disruption of multiple species that made up the normal, healthy intestinal flora. Vancomycin has the trade name of "Vancocin" and was first sold in 1954 and is available as a generic medication. Vancomycin is recommended by mouth as a treatment for severe *C. difficile* colitis. Accordingly, the present invention provides a pharmaceutical composition comprising the novel compounds of the present invention with an antibiotic. Exemplary antibiotics include, but not limited to, metronidazole, fidaxomicin, vancomycin and the like. Preferably, antibiotic is vancomycin.

Antibiotic treatment often involves administration of the antibiotic intravenously for a duration of 5-7 days. The efficacy of antibiotic treatment is about 50%. It is known by clinicians that antibiotic treatment at the late stage of *C. difficile* infection is not effective (mortality >90%). The pharmaceutical composition combining the present compounds with an antibiotic represents an improved useful alternative to the current antibiotic treatment alone.

In another embodiment, the present invention provides a pharmaceutical composition comprising the novel compounds of the present invention with an antibody against *C.*

*difficile*. There are generally two known classes of anti-*C. difficile* antibodies. First, the anti-*C. difficile* recognizes the *C. difficile* bacteria; preferably the endospores of *C. difficile*. Second, the anti-*C. difficile* recognizes *C. difficile* toxins. *C. difficile* toxins include toxin A and toxin B.

U.S. Pat. No. 8,697,374 discloses a monoclonal antibody that binds to the endospores of the *C. difficile* bacteria, but not the vegetative cells or the derived toxins. The antibody is an IgG or IgM that recognize the surface epitope on the *C. difficile*. WO 2013/028810 discloses an antibody specific for toxin A. WO 2014/069344 discloses an antibody specific for toxin B. WO 2010/094970, WO 2014/144292, WO 2015/123767 and U.S. Patent Application No. 2013/0231531 disclose antibodies against toxins A and B.

WO 2013/028810, WO 2011/063146, WO 2015/123767, U.S. Patent Application No. 2013/0230531, U.S. Pat. Nos. 8,697,374 and 8,986,697 disclose humanized *C. difficile* antibodies. In a preferred embodiment, humanized *C. difficile* antibodies may be used for administration in humans to treat *C. difficile* infection as these forms of antibodies have reduced immune-reactivity for repeated administrations. In another preferred embodiments, antigen-binding fragments (e.g., Fab or F(ab)$_2$) of the *C. difficile* antibodies may be used to treat *C. difficile* infection as these fragments also exhibit reduced the immune-reactivity complexity due to a Fc involvement.

It is believed that the compounds of the present invention neutralize the toxin activities of *C. difficile* (i.e., toxins A and B). The present compounds are shown to inhibit the hydrolysis of UDP-glucose which is essential for the glycosylation of the Rho-GTPases. When administered, the present compounds help to maintain epithelial integrity and attenuate inflammation at the site of *C. difficile* infection in the gut compartment. Without bound by a theory, it is believed that the compounds of the present invention function via binding to the active sites of toxins A and B and neutralizing the toxin activities. Crystallography data reveals direct binding between the present compounds and the active site of *C. difficile* toxin B.

It is generally known that *C. difficile* antibiotic functions to kill the *C. difficile* bacteria and thus reduce the derived toxins (i.e., toxin A or toxin B) in the gut. The present combined therapy is superior to the antibiotic treatment alone where the toxins A or B are neutralized without any effects on the production of the *C. difficile* toxins. By the same token, because the antibodies or antigen-fragment thereof act via neutralizing toxins A or B, the combination of the present compounds may add additional protective benefits by virtue of its ability to stop the toxin production.

All publications and patents cited in this specification are herein incorporated by reference in their entirety. While the invention has been described in conjunction with the detailed description thereof, the foregoing description is intended to illustrate and not limit the scope of the invention, which is defined by the scope of the appended claims. Other embodiments, advantages, and modifications are within the scope of the following claims. It will be understood by those skilled in the art that various modifications and variations of the described composition, method, and systems of the invention will be apparent to those skilled in the art without departing from the scope and spirit of the invention.

EXAMPLES

The compounds of the present invention were prepared using the experimental procedures described herein. Those skilled in the art will recognize that other procedures may also be suitable to prepare the compounds of the present invention.

Techniques, solvents and reagents may be referred to by the following abbreviations:
ACN=acetonitrile
AIBN=2,2'-azobis(2-methylpropionitrile)
Brine=saturated sodium chloride
Boc=t-butoxy-carbonyl
Cbz=carbobenzoxy=benzyloxycarbonyl
CDI=1,1'-carbonyldiimidazole
d=day
DCM=dichloromethane
DIEA=DIPEA=N,N-diisopropylethylamine
DMA=dimethylacetamide
DMAP=dimethylaminopyridine
DMF=dimethylformamide
DMSO=dimethylsulfoxide
DPPA=diphenylphosphorylazide
DVB=divinylbenzene
EDC=1-ethyl-3-(3-dimethylaminopropyl)carbodiimide
EtOH=ethanol
EtOAc=ethyl acetate
FCC=flash column chromatography
h=hour
HATU=O-(7-azabenzotriazol-1-yl)-N,N,N',N'-tetramethyluronium hexafluorophosphate
HMDS=hexamethyldisilazide
HOBt=1-hydroxybenzotriazole
HPLC=high performance liquid chromatography
IPA=isopropyl alcohol
KHMDS=potassium bis(trimethylsilyl)amide
LCMS=liquid chromatography-mass spectrometry
MeOH=methanol
Min=minute
Ms=mesyl
NBS=N-bromosuccinimide
NMM=N-methylmorpholine
NMP=N-methylpyrrolidinone
PS=polystyrene
PyBOP=(benzotriazol-1-yloxy)tripyrrolidinophosphonium hexafluorophosphate
Sat.=saturated
TBAF=tetrabutylammonium fluoride
TBDMSCl=tert-butyldimethylsilyl chloride
TFA=trifluoroacetic acid
THF=tetrahydrofuran
TMSCl=tetramethylsilyl chloride
TPAP=tetrapropylammonium perruthenate
p-TsOH=para-toluenesulfonic acid LC/MS Analysis Methods
Method A—Compounds were analyzed on an Acquity Ultra Performance Liquid Chromatography system employing an Acquity UPLC BEH C18, 1.7 μm, 2.1×50 mm column. Detection was via an Acquity PDA detector and a Waters SQD single quadrupole mass spectrometer. The aqueous acetonitrile based solvent gradient was: 0-0.1 min—Isocratic—10% acetonitrile (0.01% TFA); 0.1-1.3 min—Linear gradient—10%-90% acetonitrile (0.01% TFA); 1.3-1.8 min—Isocratic—90% acetonitrile (0.01% TFA); 1.8-1.9 min—Linear gradient—90%-10% acetonitrile (0.01% TFA); 1.9-2.0 min—Isocratic—10% acetonitrile (0.01% TFA). Flow rate: 0.6 mL/min.

Method B—Compounds were analyzed on an Acquity Ultra Performance Liquid Chromatography system employing an Acquity UPLC BEH C18, 1.7 μm, 2.1×50 mm column. Detection was via an Acquity PDA detector and a Waters SQD single quadrupole mass spectrometer. The aqueous acetonitrile based solvent gradient was: 0-0.1 min—Isocratic—2% acetonitrile (0.01% TFA); 0.1-1.3 min—Linear gradient—2%-80% acetonitrile (0.01% TFA); 1.3-1.8 min—Isocratic—80% acetonitrile (0.01% TFA); 1.8-1.9 min—Linear gradient—80%-2% acetonitrile (0.01% TFA); 1.9-2.0 min—Isocratic—2% acetonitrile (0.01% TFA). Flow rate: 0.6 mL/min.

Method C—Compounds were analyzed on an Acquity Ultra Performance Liquid Chromatography system employing an Acquity UPLC BEH C18, 1.7 μm, 2.1×50 mm column. Detection was via an Acquity PDA detector and a Waters SQD single quadrupole mass spectrometer. The aqueous acetonitrile based solvent gradient was: 0-0.1 min—Isocratic—20% acetonitrile (0.01% TFA); 0.1-1.3 min—Linear gradient—20%-95% acetonitrile (0.01% TFA); 1.3-1.8 min—Isocratic—95% acetonitrile (0.01% TFA); 1.8-1.9 min—Linear gradient—95%-20% acetonitrile (0.01% TFA); 1.9-2.0 min—Isocratic—20% acetonitrile (0.01% TFA). Flow rate: 0.6 mL/min.

Method D—Compounds were analyzed on an Acquity Ultra Performance Liquid Chromatography system employing an Acquity UPLC BEH C18, 1.7 μm, 2.1×50 mm column. Detection was via an Acquity PDA detector and a Waters SQD single quadrupole mass spectrometer. The aqueous acetonitrile based solvent gradient was: 0-0.1 min—Isocratic—40% acetonitrile (0.01% TFA); 0.1-1.3 min—Linear gradient—5%-95% acetonitrile (0.01% TFA); 1.3-1.8 min—Isocratic—95% acetonitrile (0.01% TFA); 1.8-1.9 min—Linear gradient—60%-40% acetonitrile (0.01% TFA); 1.9-2.0 min—Isocratic—40% acetonitrile (0.01% TFA). Flow rate: 0.6 mL/min.

Method E—Compounds were analyzed on an Aquity Ultra Performance Liquid Chromatography system employing an Acquity UPLC BEH C18, 1.7 μm, 2.1×50 mm column. Detection was via an Acquity PDA detector and a Waters SQD single quadrupole mass spectrometer. The aqueous acetonitrile based solvent gradient was: 0-0.1 min—Isocratic—1% acetonitrile (0.01% TFA); 0.1-1.3 min—Linear gradient—50%-50% acetonitrile (0.01% TFA); 1.3-1.8 min—Isocratic—50% acetonitrile (0.01% TFA); 1.8-1.9 min—Linear gradient—99%-1% acetonitrile (0.01% TFA); 1.9-2.0 min—Isocratic—1% acetonitrile (0.01% TFA). Flow rate: 0.6 mL/min.

Method F—Compounds were analyzed on an Aquity Ultra Performance Liquid Chromatography system employing an Acquity UPLC BEH C18, 1.7 μm, 2.1×50 mm column. Detection was via an Acquity PDA detector and a Micromass Quattro Micro triple quadrupole mass spectrometer. The aqueous acetonitrile based solvent gradient was: 0-0.1 min—Isocratic—2% acetonitrile (0.01% TFA); 0.1-1.3 min—Linear gradient—2%—80% acetonitrile (0.01% TFA); 1.3-1.8 min—Isocratic—80% acetonitrile (0.01% TFA); 1.8-1.9 min—Linear gradient—80%-2% acetonitrile (0.01% TFA); 1.9-2.0 min—Isocratic—2% acetonitrile (0.01% TFA). Flow rate: 0.6 mL/min.

NMR Spectroscopy $^1$H NMR Spectroscopy was performed on a Bruker 400 MHz Avance II FTNMR Spectrometer.

General Synthetic Schemes

The compounds of the present invention were prepared by methods well known in the art of synthetic organic chemistry. During synthetic sequences it was necessary or desirable to protect sensitive or reactive groups on any of the molecules concerned. This was achieved by means of conventional protecting groups, such as those described in T. W. Greene and P. G. M. Wuts 'Protective Groups in Organic Synthesis' 2$^{nd}$ edition, John Wiley and Sons, 1991. The protecting groups were removed at a convenient subsequent stage using methods well known in the art.

In general, the compounds of the present invention were prepared by the methods illustrated in the general reaction schemes described below, or by modifications thereof, using readily available starting materials, reagents and conventional synthetic procedures. However, those skilled in the art will recognize that other methods may also be suitable. Also, in these reactions, it is possible to make use of variants that are in themselves known, but are not mentioned here. In the schemes below, the variables shown are defined as in Formula I.

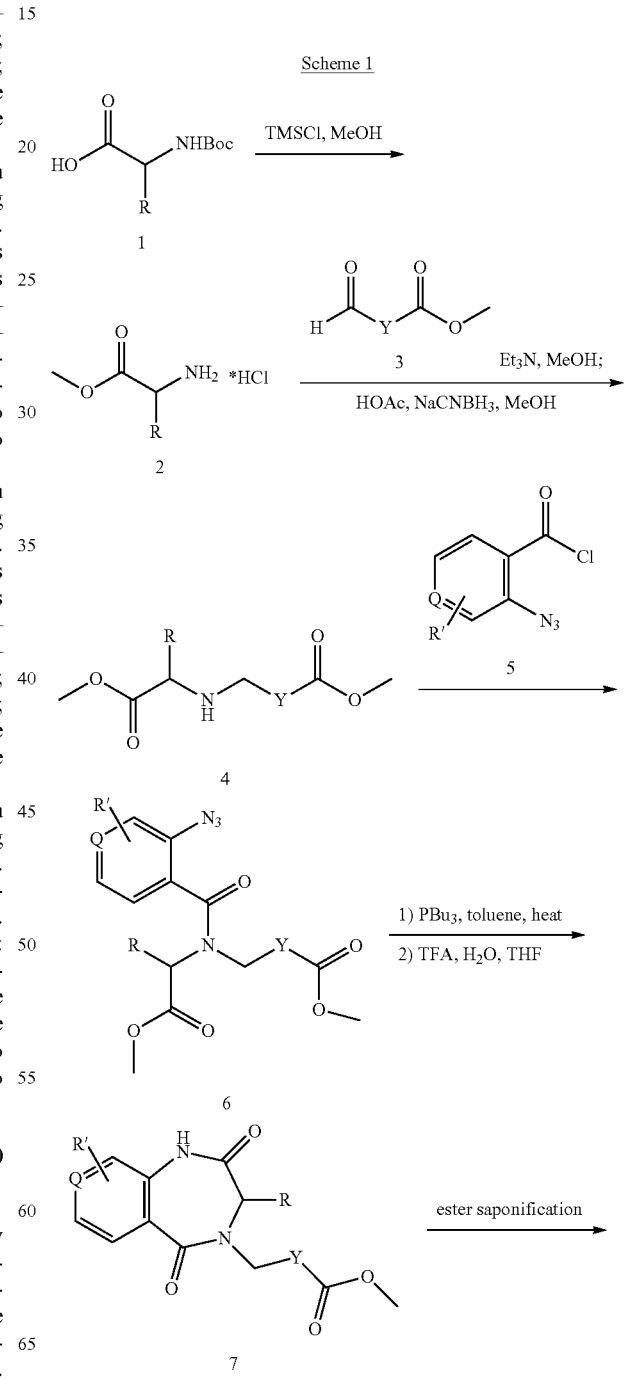

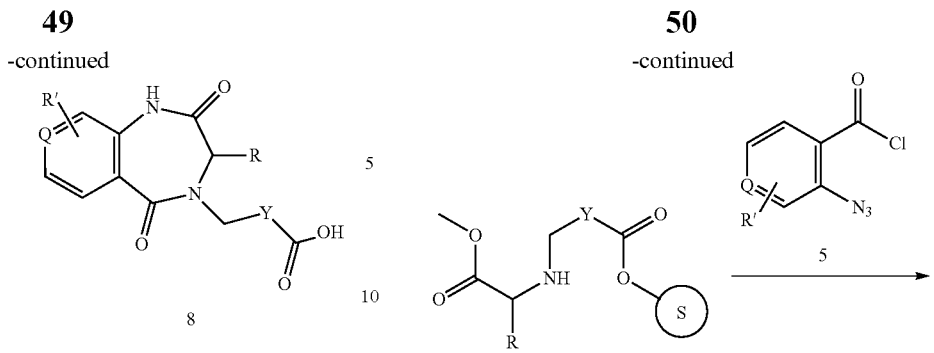

Compounds of formula I wherein X is —CH₂—, W is C(O) and Z is —COOH (shown as 8 below) can be prepared by the general synthetic sequence shown in Scheme 1. First, a Boc-protected amino acid 1 is converted to the amino acid methyl ester hydrochloride 2 by treatment with TMSCl in MeOH. Reductive amination of the hydrochloride salt of primary amine 2 with an aldehyde 3 in the presence of a suitable base such as triethylamine will give secondary amine 4. The necessary Boc-protected amino acids 1 and aldehydes 3 are either commercially available or they can be readily prepared by procedures well known in the art. Acylation of the intermediate secondary amine 4 with azido acid chloride 5 will provide amide 6. The necessary azido-acid chlorides 5 are prepared using methods well known in the art. Compound of general formula 7 is then formed by treatment of 6 with tributylphosphine (via generation of the phosphorimine) and heating the reaction mixture in a suitable solvent such as toluene, followed by aqueous acid-mediated hydrolysis of the resultant imino ether intermediate. Subsequent saponification, with lithium hydroxide for example, of the ester provides carboxylic acid 8.

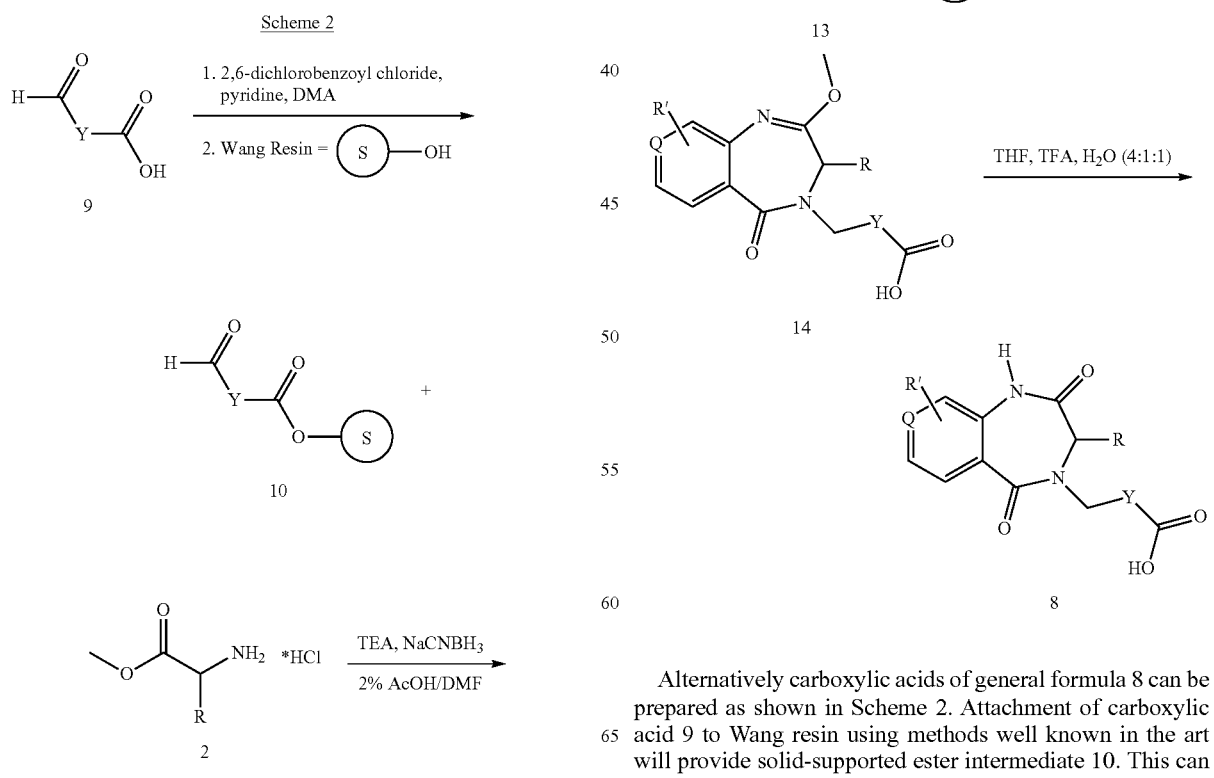

Alternatively carboxylic acids of general formula 8 can be prepared as shown in Scheme 2. Attachment of carboxylic acid 9 to Wang resin using methods well known in the art will provide solid-supported ester intermediate 10. This can be converted to the desired solid-supported amine 11 by treatment with amine hydrochloride 2 in the presence of a suitable base such as triethylamine and a suitable reducing agent such as sodium cyanoborohyride. The necessary carboxylic acids 9 and amino acid methyl esters 2 are commercially available or prepared by methods well known in the art. Acylation of solid-supported secondary amine 11 with azido-acid chloride 5 followed by phosphine-mediated aza-Wittig reaction will afford the solid supported imino ether intermediate 13 which can be cleaved from the solid support by treatment with trifluoroacetic acid in dichloromethane to give carboxylic acid 14. Subsequent aqueous acid-mediated hydrolysis of the imino ether gives 8.

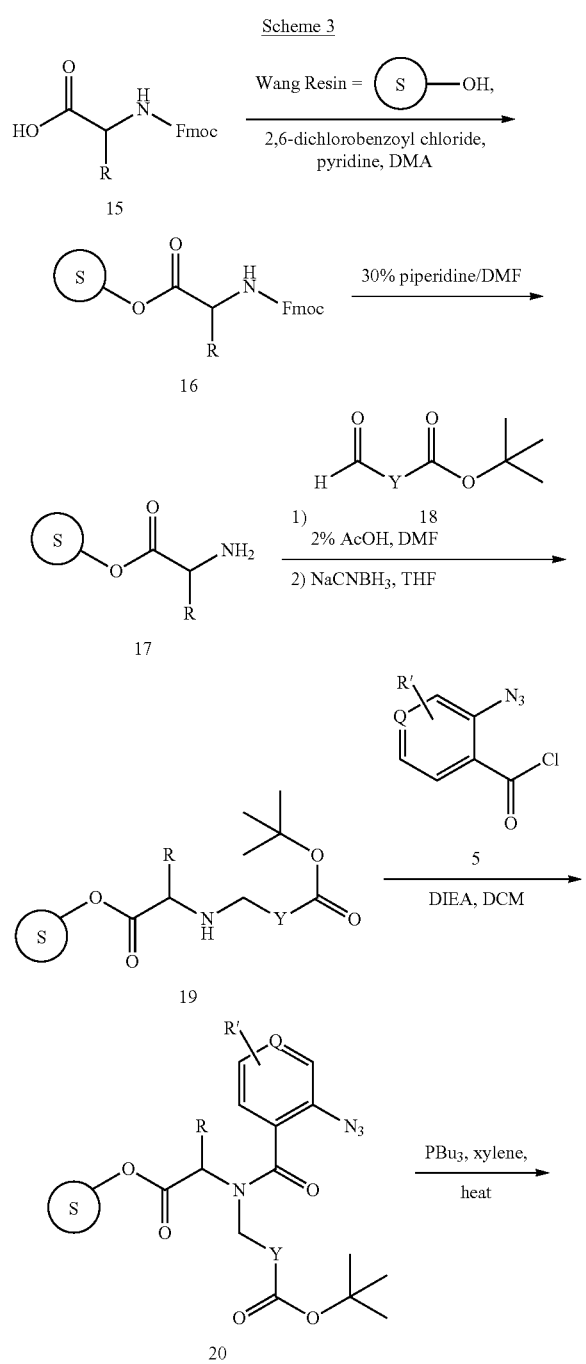

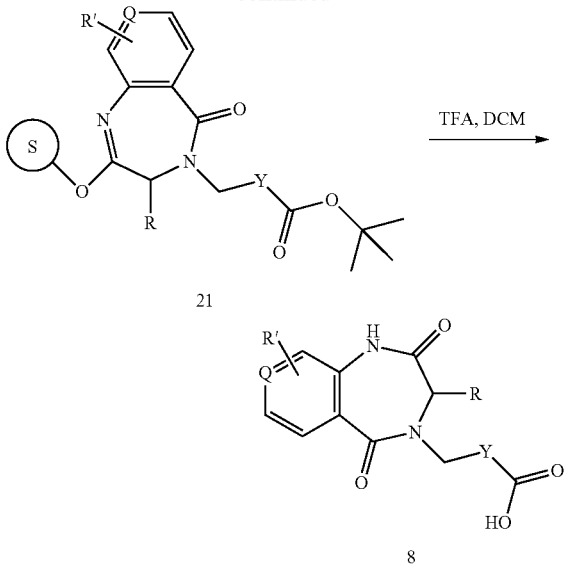

Carboxylic acids of general formula 8 can also be prepared on solid phase as shown in Scheme 3. Attachment of Fmoc-protected amino acid 15 to Wang resin will provide 16. Removal of the Fmoc protecting group with piperidine in DMF will give solid supported amine 17. This amine can be converted to the desired solid-supported secondary amine 19 by treatment with aldehyde 18 which contains a tert-butyl ester moiety in the presence of a suitable reducing agent such as sodium borohyride. The necessary Fmoc-protected amino acids 15 and aldehydes 18 are commercially available or they are prepared using methods well known in the art. Acylation of 19 with acid chloride 5 followed by phosphine-mediated aza-Wittig reaction will afford the solid supported imino ether intermediate 21. Finally, the tert-butyl ester can be deprotected and the resin bound imino ether simultaneously cleaved from the resin to provide 8 by treatment with trifluoroacetic acid in dichloromethane.

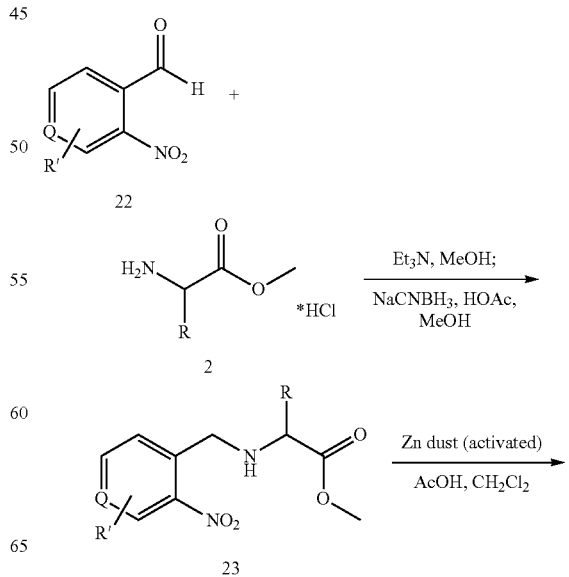

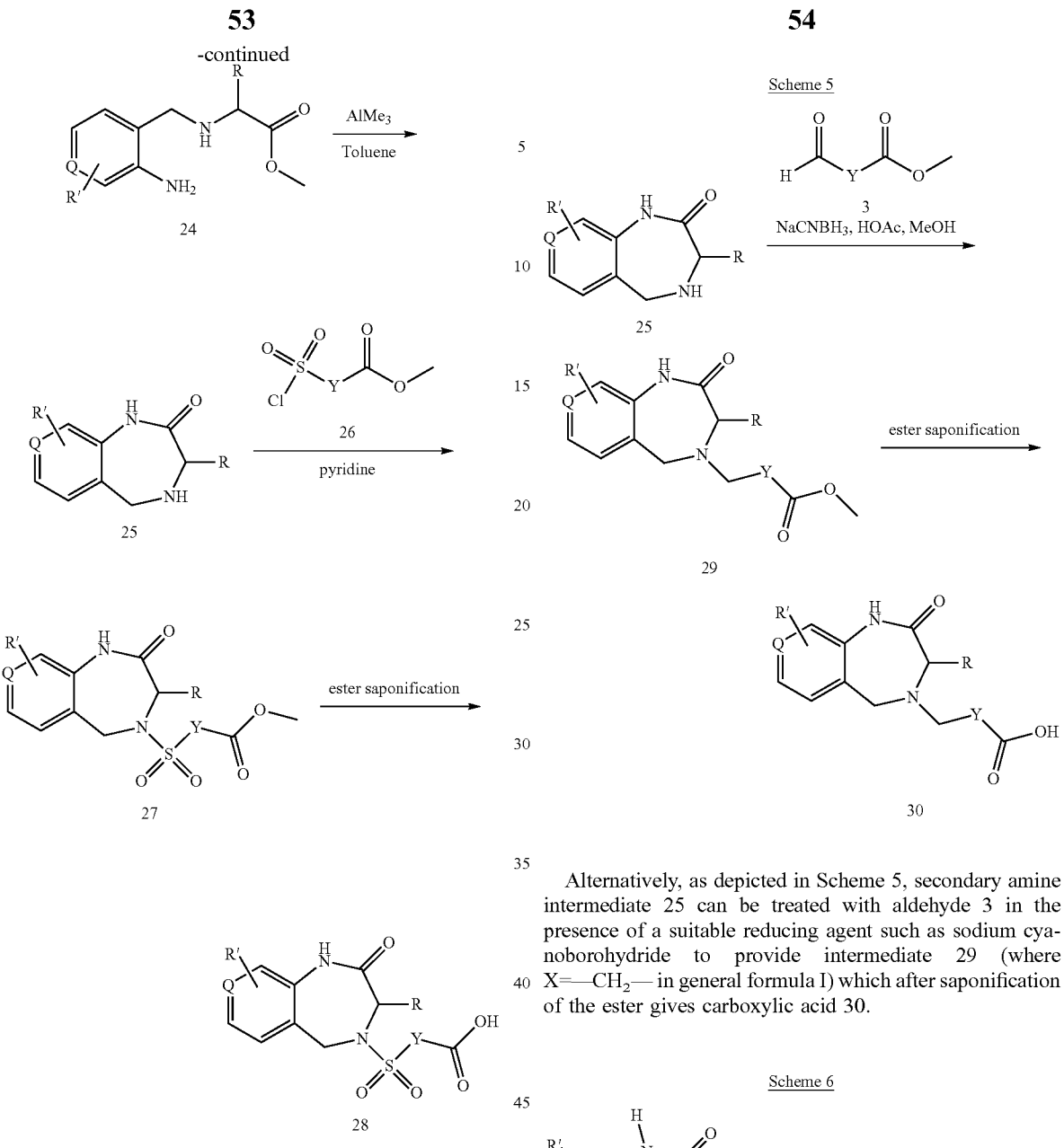

Compounds of formula I wherein X is —SO$_2$—, W is —CH$_2$— and Z is —COOH (shown as 28) can be prepared by the general synthetic sequence shown in Scheme 4. First, secondary amine intermediate 23 can be prepared by treatment of aldehyde 22 with amine hydrochloride 2 in the presence of a tertiary amine base such as triethylamine and a suitable reducing agent such as sodium borohydride. The requisite aldehyde intermediates 22 and amino acid methyl ester hydrochloride intermediates 2 are commercially available or prepared using methods well known in the art. Reduction of the nitro group in 23 with a suitable reducing reagent such as activated zinc dust in the presence of acetic acid will provide 24. 24 can then be cyclized in the presence of a suitable Lewis acid such as trimethylaluminum to provide 25. Finally, sulfonylation of the secondary amine in 25 with sulfonyl chloride 26 in pyridine followed by saponification of the methyl ester gives 28. The requisite sulfonyl chloride intermediates 26 are commercially available or prepared using methods well known to those skilled in the art.

Alternatively, as depicted in Scheme 5, secondary amine intermediate 25 can be treated with aldehyde 3 in the presence of a suitable reducing agent such as sodium cyanoborohydride to provide intermediate 29 (where X=—CH$_2$— in general formula I) which after saponification of the ester gives carboxylic acid 30.

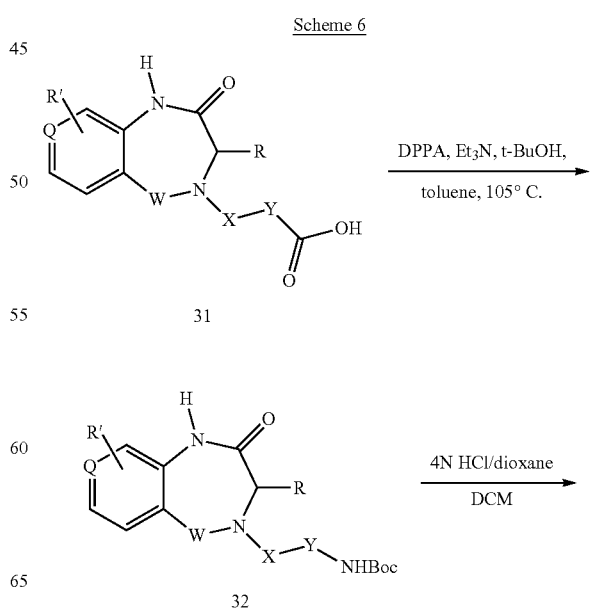

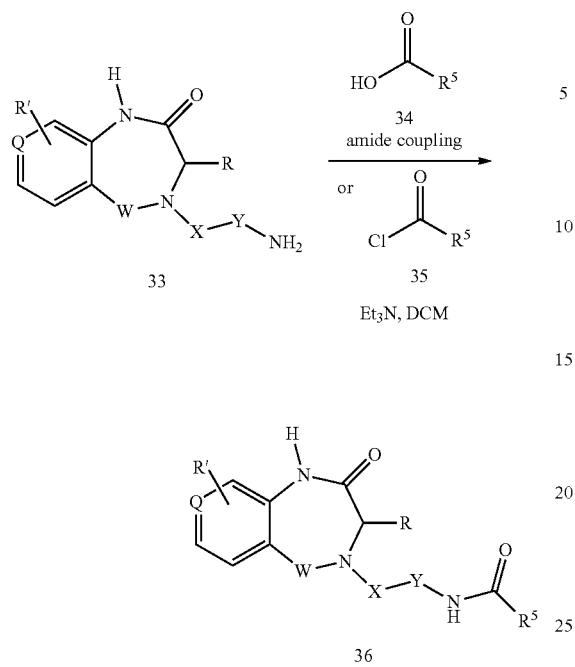

Compounds of the invention wherein Z is —NHC(O)R⁵ can be prepared as illustrated in Scheme 6. First, carboxylic acid 31, either prepared as described in Schemes 1-5 or prepared by other suitable methods, can undergo a Curtius rearrangement after treatment with DPPA in the presence of tert-butanol in an appropriate solvent such as toluene at elevated temperature to provide Boc-protected amine 32. Removal of the Boc protecting group with TFA in DCM or with HCl in dioxane or by any other suitable method will provide amine 33 which can either be reacted with a carboxylic acid 34, using a suitable coupling reagent, or acylated with an acid chloride 35 in the presence of a suitable base such as triethylamine to provide amide 36.

Scheme 7

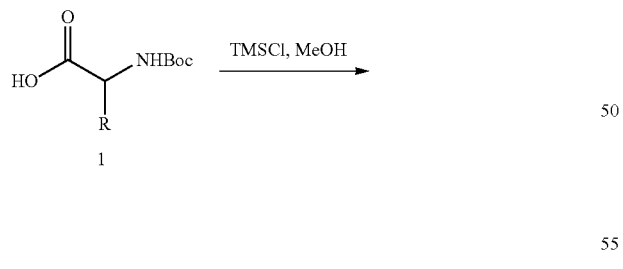

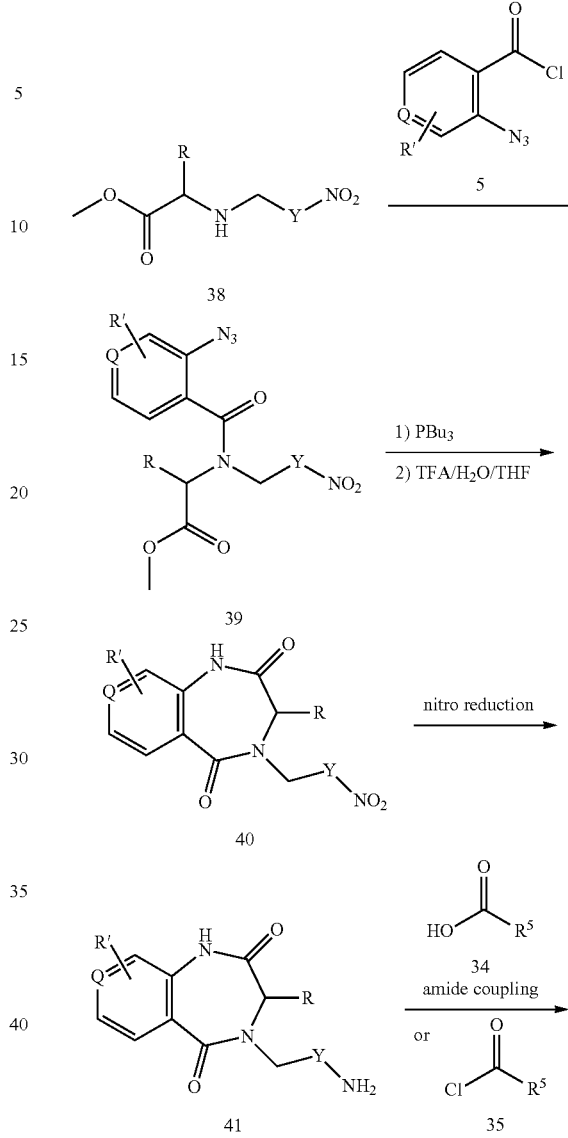

Alternatively, as shown in Scheme 7, certain compounds of the invention wherein Z is —NHC(O)R⁵, X is —CH₂— and W is —C(O)— can be prepared from nitro intermediate 40 which is prepared similarly to compound 7 (Scheme 1), but utilizing an appropriate nitro substituted aldehyde 37 (Scheme 7). The nitro substituted aldehydes 37 are commercially available or can be prepared by methods well known to those skilled in the art. Reduction of the nitro group followed by acylation of amine 41 with either carboxylic acid 34 or acid chloride 35 will provide amide 42.

Scheme 8

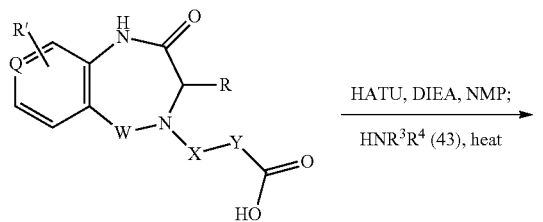

31

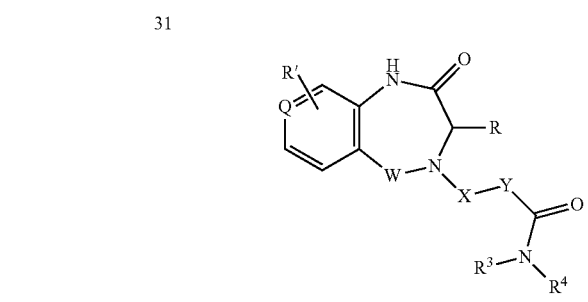

44

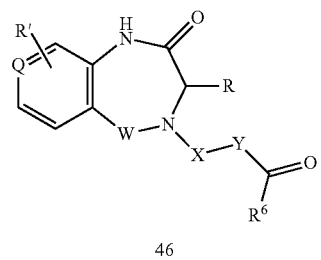

46

Further compounds of the invention wherein Z is —C(O)NR³R⁴ can be prepared as shown in Scheme 8. Compound 44 can be prepared by treatment of carboxylic acid 31 with amine HNR³R⁴ (43) in the presence of a suitable coupling reagent such as HATU. The amide coupling reaction is generally heated in the range of 80° C. to 120° C. when heteroaryl amines are employed. The reaction is preferably heated to 120° C. when particularly unreactive heteroaryl amines are employed.

Scheme 9

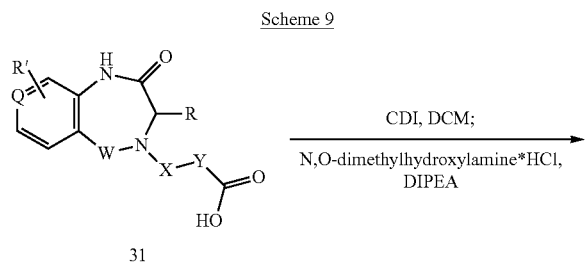

31

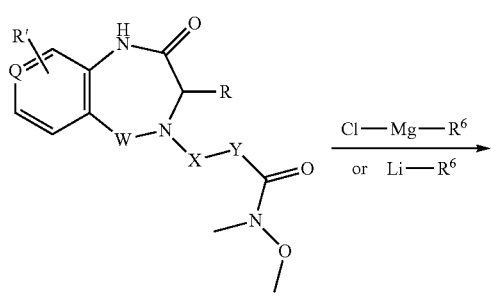

45

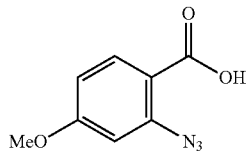

Further compounds of the invention wherein Z is —C(O)R⁶ can be prepared by a two-step procedure involving first, conversion of the carboxylic acid in 8 to the Weinreb amide, followed by reaction of the subsequent Weinreb amide intermediate 45 with an appropriate Grignard or aryllithium reagent to give ketone 46 (Scheme 9). The requisite Grignard or aryllithium reagents are either commercially available or prepared using methods well known in the art.

SYNTHESIS OF INTERMEDIATES

2-Azido-4-methoxybenzoic Acid (Intermediate I.1)

Intermediate I.1

2-Azido-4-methoxybenzoic acid (Intermediate I.1) was prepared from 2-amino-4-methoxybenzoic acid in 92% yield according to the synthetic procedure described by Lamara et al. (Lamara, K. et al. *Tetrahedron*, 1994, 50, (18), 5515-5526). ¹H NMR (400 MHz, d₆-DMSO): δ ppm 12.83 (br s, 1H), 7.81 (d, 1H), 6.86-6.82 (m, 2H), 3.85 (s, 1H).

Using the method outlined above for the preparation of Intermediate I.1, the following intermediates were made from the corresponding reagents as indicated in Table 1.

TABLE 1

| Intermediate | Structure | Reagent |
|---|---|---|
| I.2 | 4-F, 2-N₃ benzoic acid | 4-F, 2-NH₂ benzoic acid |
| I.3 | 4-O₂N, 2-N₃ benzoic acid | 4-O₂N, 2-NH₂ benzoic acid |

TABLE 1-continued

| Intermediate | Structure | Reagent |
|---|---|---|
| I.4 | 4-Cl, 2-N₃ benzoic acid | 4-Cl, 2-NH₂ benzoic acid |
| I.5 | 3-azido pyridine-4-carboxylic acid | 3-amino pyridine-4-carboxylic acid |
| I.6 | 4-CF₃, 2-N₃ benzoic acid | 4-CF₃, 2-NH₂ benzoic acid |
| I.7 | 4-Me, 2-N₃ benzoic acid | 4-Me, 2-NH₂ benzoic acid |
| I.8 | 2-N₃ benzoic acid | 2-NH₂ benzoic acid |
| I.9 | 5-Cl, 2-N₃ benzoic acid | 5-Cl, 2-NH₂ benzoic acid |
| I.10 | 3-Cl, 2-N₃ benzoic acid | 3-Cl, 2-NH₂ benzoic acid |
| I.11 | 4-Br, 2-N₃ benzoic acid | 4-Br, 2-NH₂ benzoic acid |

D-2-Pyridylalanine Methyl Ester Dihydrochloride Salt (Intermediate II.1)

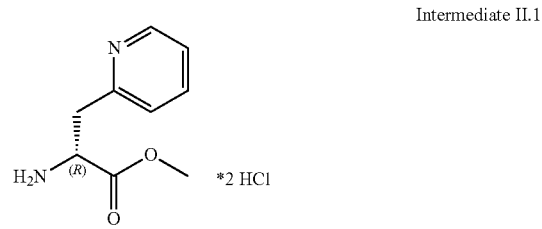

Intermediate II.1

D-2-Pyridylalanine methyl ester dihydrochloride salt (Intermediate II.1) was prepared from Boc-D-2-pyridylalanine according to the synthetic procedure described by Chen et al. (Chen, B. C. et al. *J. Org. Chem.*, 1999, 64, 9294-9296). $^1$H NMR (400 MHz, $d_6$-DMSO): δ ppm 8.91 (br s, 3H), 8.72 (d, 1H), 8.24 (br t, 1H), 7.81 (br d, 1H), 7.71 (br t, 1H), 4.64 (br m, 1H), 3.67 (s, 3H), 3.59 (d, 2H).

Following the method described above for the preparation of Intermediate II.1, the following intermediates were made from the corresponding reagents as indicated in Table 2.

TABLE 2

| Intermediate | Structure | Reagent |
|---|---|---|
| II.2 | D-3-pyridylalanine methyl ester *2HCl | Boc-D-3-pyridylalanine |
| II.3 | D-phenylglycine methyl ester *HCl | Boc-D-phenylglycine |
| II.4 | D-homophenylalanine methyl ester *HCl | Boc-D-homophenylalanine |
| II.5 | D-4-fluorophenylalanine methyl ester *HCl | Boc-D-4-fluorophenylalanine |

TABLE 2-continued

| Intermediate | Structure | Reagent |
|---|---|---|
| II.6 | H₂N-CH(CH₂Ph)-C(O)OMe · HCl | BocHN-CH(CH₂Ph)-COOH |
| II.7 | H₂N-CH(CH₂-C₆H₄-4-Cl)-C(O)OMe · HCl | BocHN-CH(CH₂-C₆H₄-4-Cl)-COOH |
| II.8 | H₂N-CH(CH₂-4-pyridyl)-C(O)OMe · 2 HCl | BocHN-CH(CH₂-4-pyridyl)-COOH |
| II.9 | H₂N-CH(CH₂-C₆H₄-2-Cl)-C(O)OMe · HCl | BocHN-CH(CH₂-C₆H₄-2-Cl)-COOH |
| II.10 | H₂N-CH(CH₂-C₆H₄-4-Me)-C(O)OMe · HCl | bocHN-CH(CH₂-C₆H₄-4-Me)-COOH |
| II.11 | H₂N-CH(CH₂-C₆H₄-4-OMe)-C(O)OMe · HCl | bocHN-CH(CH₂-C₆H₄-4-OMe)-COOH |
| II.12 | H₂N-CH(CH₂-cyclohexyl)-C(O)OMe · HCl | BocHN-CH(CH₂-cyclohexyl)-COOH |
| II.13 | H₂N-CH(CH₂-C₆H₄-3-Cl)-C(O)OMe · HCl | BocHN-CH(CH₂-C₆H₄-3-Cl)-COOH |
| II.14 | H₂N-CH(CH₂-(4-tetrahydropyranyl))-C(O)OMe · HCl | BocHN-CH(CH₂-(4-tetrahydropyranyl))-COOH |
| II.15 | H₂N-CH(CH₂-C₆H₄-2-Me)-C(O)OMe · HCl | BocHN-CH(CH₂-C₆H₄-2-Me)-COOH |
| II.16 | H₂N-CH(CH₂-C₆H₄-3-Me)-C(O)OMe · HCl | BocHN-CH(CH₂-C₆H₄-3-Me)-COOH |
| II.17 | H₂N-CH(CH₂-C₆H₄-3-CN)-C(O)OMe · HCl | BocHN-CH(CH₂-C₆H₄-3-CN)-COOH |

TABLE 2-continued

| Intermediate | Structure | Reagent |
|---|---|---|
| II.18 | (3-fluorophenyl)alanine methyl ester·HCl | Boc-(3-fluorophenyl)alanine |
| II.19 | (2-fluorophenyl)alanine methyl ester·HCl | Boc-(2-fluorophenyl)alanine |
| II.20 | 3-(pyridin-2-yl)alanine methyl ester·2HCl | Boc-3-(pyridin-2-yl)alanine |
| II.21 | 3-(pyridin-3-yl)alanine methyl ester·2HCl | Boc-3-(pyridin-3-yl)alanine |
| II.22 | 3-(3,4-dichlorophenyl)alanine methyl ester·HCl | Boc-3-(3,4-dichlorophenyl)alanine |
| II.23 | 3-(thiazol-4-yl)alanine methyl ester·HCl | Boc-3-(thiazol-4-yl)alanine |
| II.24 | 3-(thiazol-4-yl)alanine methyl ester·HCl | Boc-3-(thiazol-4-yl)alanine |
| II.25 | 3-(thiophen-2-yl)alanine methyl ester·HCl | Boc-3-(thiophen-2-yl)alanine |

(±)-Ethyl 2-Amino-3-(pyrazin-2-yl)propanoate Hydrochloride Salt (Intermediate II.26)

Intermediate II.26

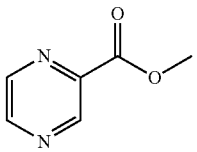

Step 1: Methyl Pyrazine-2-carboxylate

To pyrazinecarboxylic acid (5.80 g, 46.5 mmol) in dichloromethane (100 mL) was added oxalyl chloride (5.10 mL, 60.4 mmol) followed by catalytic DMF. The reaction mixture was stirred at 23° C. for 6 h. Methanol (30 mL) was then added, and the mixture was stirred for an additional 30 min. The reaction mixture was concentrated in vacuo. The residue was taken up in EtOAc (200 mL), and washed with sat. NaHCO$_3$ (aq) (1×100 mL) and brine (1×100 mL). The organic layer was dried (MgSO$_4$), and concentrated in vacuo to provide 3.38 g (53%) of methyl pyrazine-2-carboxylate which was used without further purification in the next step. $^1$H NMR (400 MHz, CDCl$_3$): δ ppm 9.34 (d, 1H), 8.79 (d, 1H), 8.74 (dd, 1H), 4.06 (s, 3H); LCMS (Method A): t$_R$=0.48 min, m/z 139.3 (M+H)$^+$.

Step 2: Pyrazin-2-ylmethanol

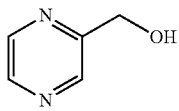

To methyl pyrazine-2-carboxylate (3.35 g, 24.3 mmol) in EtOH (60 mL) was added calcium chloride (4.03 g, 36.4 mmol) followed by sodium borohydride (1.38 g, 36.4 mmol). The reaction mixture was stirred at 23° C. for 5 h. The mixture was quenched with a mixture of acetic acid (4.20 mL, 72.8 mmol) and water (1.31 mL, 72.8 mmol), and stirred for 30 min. The mixture was filtered through a pad a silica gel, and the pad was washed with 5-10% MeOH/DCM containing 0.3% conc. NH$_3$ (aq). The combined filtrates were concentrated in vacuo, and the crude residue was purified by FCC (SiO$_2$, elution with 0-10% MeOH/DCM) to provide 2.01 g (75%) of pyrazin-2-ylmethanol. $^1$H NMR (400 MHz, d$_6$-DMSO): δ ppm 8.71 (m, 1H), 8.56 (dd, 1H), 8.54 (d, 1H), 5.61 (t, 1H), 4.63 (d, 2H); LCMS (Method E): t$_R$=0.56 min, m/z 111.3 (M+H)$^+$.

Step 3: 2-(Chloromethyl)pyrazine

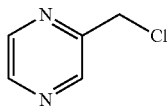

To pyrazin-2-ylmethanol (1.23 g, 11.2 mmol) in SOCl$_2$ (0.98 mL, 13.4 mmol) was added catalytic DMF. The mixture was stirred at 23° C. for 2 h. The mixture was concentrated in vacuo, and the crude product was used directly in the following step.

Step 4: Ethyl 2-((diphenylmethylene)amino)-3-(pyrazin-2-yl)propanoate

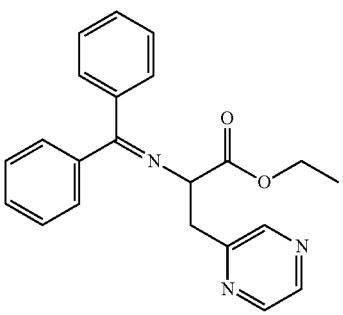 [SMILES: CCOC(=O)C(Cc1cnccn1)N=C(c1ccccc1)c1ccccc1]

To N-(diphenylmethylene)glycine ethyl ester (5.98 g, 22.4 mmol) in DMF (6 mL) at 0° C. was added KHMDS drop wise (1.0 M in THF, 28.0 mL, 28.0 mmol). The mixture was stirred at 0° C. for 10 min, and then 2-(chloromethyl)pyrazine (1.44 g, 11.2 mmol) in DMF (12 ml) was added drop wise at 0° C. The mixture was stirred at 0° C. for 1 h, and then allowed to warm to room temperature over 1 h. The mixture was then quenched with sat. NH$_4$Cl (aq) (100 mL), and extracted with EtOAc (3×100 mL). The combined organic extracts were washed with brine (1×100 mL), dried (MgSO$_4$), and concentrated in vacuo. The crude residue was purified by FCC (SiO$_2$, elution with 0-50% EtOAc/hexanes) to provide 1.43 g (18%) of ethyl 2-((diphenylmethylene)amino)-3-(pyrazin-2-yl)propanoate. $^1$H NMR (400 MHz, CDCl$_3$): δ ppm 8.47 (d, 1H), 8.38-8.36 (m, 2H), 7.56-7.52 (m, 2H), 7.41-7.27 (m, 6H), 6.81 (br d, 2H), 4.57 (dd, 1H), 4.27-4.14 (m, 2H), 3.50-3.39 (m, 2H), 1.26 (t, 3H); LCMS (Method A): t$_R$=1.22 min, m/z 360.4 (M+H)$^+$.

Step 5: (±)-Ethyl 2-amino-3-(pyrazin-2-yl)propanoate Hydrochloride Salt (Intermediate II.26)

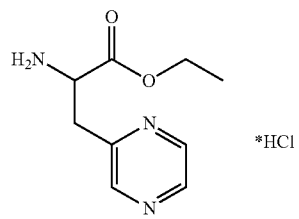

Intermediate II.26

To a solution of ethyl 2-((diphenylmethylene)amino)-3-(pyrazin-2-yl)propanoate (1.42 g, 3.95 mmol) in EtOH (10 mL) was added conc. HCl (aq) (0.32 mL). The mixture was stirred at 23° C. for 5 h. The mixture was then concentrated in vacuo. The crude residue was taken up in water (100 mL), washed with EtOAc (2×50 mL), and the aqueous phase concentrated in vacuo. The residue was treated with DCM, and then concentrated in vacuo to provide 0.91 g (99%) of Intermediate II.26. $^1$H NMR (400 MHz, d$_6$-DMSO): δ ppm 8.65 (br s, 3H), 8.63 (d, 1H), 8.58 (dd, 1H), 8.56 (d, 1H), 4.49 (m, 1H), 4.12 (m, 2H), 3.39 (m, 2H), 1.08 (t, 3H); LCMS (Method E): t$_R$=0.70 min, m/z 196.4 (M+H)$^+$.

Methyl 2-amino-4-((tert-butyldimethylsilyl)oxy)butanoate (Intermediate II.27)

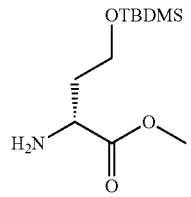

Intermediate II.27

Step 1: (R)-4-tert-butyl 1-methyl 2-(((benzyloxy)carbonyl)amino)succinate

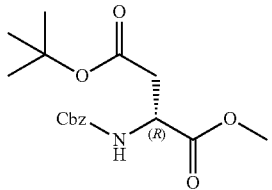

To a solution of Z-D-Asp(Ot-Bu)-OH (2.0 g, 6.2 mmol) in acetone (10 mL) was added K$_2$CO$_3$ (1.2 g, 8.7 mmol) followed by methyl iodide (0.39 mL, 6.2 mmol). The reaction mixture was stirred at 23° C. for 2.5 h over which time a thick white precipitate had formed. More acetone was added (20 mL), and the mixture was stirred at 23° C. for an additional 16 h. Additional methyl iodide was then added (0.20 mL, 3.1 mmol), and the mixture was stirred for an additional 24 h. The mixture was concentrated in vacuo. The crude residue was taken up in EtOAc (100 mL), and washed with sat. NaHCO$_3$ (aq) (1×100 mL) and brine (1×50 mL). The organic layer was dried (Na$_2$SO$_4$), filtered, and concentrated in vacuo to provide 2.0 g (96%) of (R)-4-tert-butyl 1-methyl 2-(((benzyloxy)carbonyl)amino)succinate. $^1$H NMR (400 MHz, CDCl$_3$): δ ppm 8.71 (m, 1H), 8.56 (dd, 1H), 8.54 (d, 1H), 5.61 (t, 1H), 4.63 (d, 2H); LCMS (Method A) $t_R$=1.28 min, m/z 360.3 (M+Na)$^+$.

Step 2: (R)-3-(((benzyloxy)carbonyl)amino)-4-methoxy-4-oxobutanoic Acid

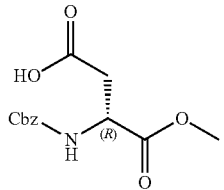

(R)-4-tert-butyl 1-methyl 2-(((benzyloxy)carbonyl)amino)succinate (2.0 g, 5.9 mmol) was treated with 20 mL of 30% TFA in DCM. The mixture was allowed to stand for 2 h at 23° C. The mixture was then concentrated in vacuo to provide 1.7 g (100%) of (R)-3-(((benzyloxy)carbonyl)amino)-4-methoxy-4-oxobutanoic acid. LCMS (Method B) $t_R$=1.05 min, m/z 282.2 (M+H)$^+$, 304.2 (M+Na)$^+$.

Step 3: (R)-methyl 2-(((benzyloxy)carbonyl)amino)-4-hydroxybutanoate

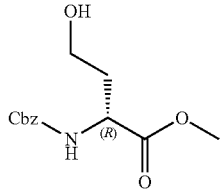

To a solution of (R)-3-(((benzyloxy)carbonyl)amino)-4-methoxy-4-oxobutanoic acid (2.0 g, 7.1 mmol) in THF (10 mL) at 0° C. was slowly added BH$_3$.THF (1 M in THF, 10.7 mL, 10.7 mmol). The reaction mixture was stirred at 0° C. for 2 h. Additional BH$_3$.THF (1 M in THF, 4.0 mL, 4.0 mmol) was added, and the mixture stirred at 0° C. for 3 h. The mixture was then quenched with 1 N citric acid (aq) (50 mL), and extracted with Et$_2$O (3×50 mL). The combined organic extracts were washed with a 1:1 mixture of H$_2$O and brine (100 mL), dried (Na$_2$SO$_4$), filtered, and concentrated in vacuo. The crude residue was purified by FCC (SiO$_2$, elution with 0-80% EtOAc/hexanes) to provide 1.2 g (63%) of (R)-methyl 2-(((benzyloxy)carbonyl)amino)-4-hydroxybutanoate. $^1$H NMR (400 MHz, CDCl$_3$): δ ppm 7.41-7.30 (m, 5H), 5.67 (br d, 1H), 5.13 (ABq, 2H), 4.56 (m, 1H), 3.77 (s, 3H), 3.77-3.64 (m, 2H), 2.17 (m, 1H), 1.71 (m, 1H); LCMS (Method B) $t_R$=1.02 min, m/z 290.3 (M+Na)$^+$.

Step 4: (R)-methyl 2-(((benzyloxy)carbonyl)amino)-4-((tert-butyldimethylsilyl)oxy)butanoate

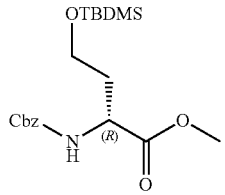

To a solution of (R)-methyl 2-(((benzyloxy)carbonyl)amino)-4-hydroxybutanoate (1.2 g, 4.5 mmol) in DMF (10 mL) was added imidazole (736 mg, 10.8 mmol) followed by TBDMSCl (813 mg, 5.39 mmol). The reaction mixture was stirred at 23° C. for 16 h. The mixture was then diluted with EtOAc (200 mL), and washed with 1 N HCl (aq) (1×100 mL), sat. NaHCO$_3$ (aq) (1×100 mL) and brine (1×100 mL). The organic layer was dried (Na$_2$SO$_4$), filtered, and concentrated in vacuo. The crude residue was purified by FCC (SiO$_2$, elution with 0-50% EtOAc/hexanes) to provide 1.5 g (90%) of (R)-methyl 2-(((benzyloxy)carbonyl)amino)-4-((tert-butyldimethylsilyl)oxy)butanoate. $^1$H NMR (400 MHz, CDCl$_3$): δ ppm 7.36-7.29 (m, 5H), 5.93 (br d, 1H), 5.11 (ABq, 2H), 4.46 (m, 1H), 3.74 (s, 3H), 3.74-3.66 (m, 2H), 2.11-1.94 (m, 2H), 0.88 (s, 9H), 0.041 (s, 3H), 0.035 (s, 3H); LCMS (Method B) $t_R$=1.77 min, m/z 382.4 (M+H)$^+$.

Step 5: Methyl 2-amino-4-((tert-butyldimethylsilyl)oxy)butanoate (Intermediate II.27)

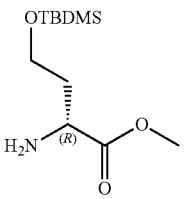

Intermediate II.27

To a solution of (R)-methyl 2-(((benzyloxy)carbonyl)amino)-4-((tert-butyldimethylsilyl)oxy)butanoate (1.5 g, 3.9 mmol) in MeOH (10 mL) under inert atmosphere of N$_2$ (g)

was added 10% Pd/C (100 mg). The reaction mixture was then placed under an atmosphere of H$_2$ (g) (1 atm., balloon), and stirred vigorously for 3 d. The mixture was then filtered through a pad of CELITErinsing with MeOH, and the combined filtrates were concentrated in vacuo to provide 0.80 g (82%) of Intermediate II.27. $^1$H NMR (400 MHz, CDCl$_3$): δ ppm 3.77-3.71 (m, 2H), 3.72 (s, 3H), 3.62 (m, 1H), 1.98 (m, 1H), 1.73 (m, 1H), 1.54 (br s, 2H, —NH$_2$), 0.88 (s, 9H), 0.049 (s, 6H).

Tert-Butyl 2-chloro-4-formylbenzoate (Intermediate III.1)

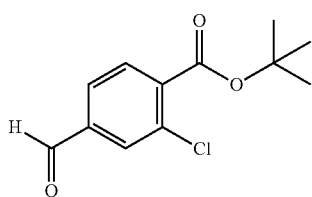

Intermediate III.1

Step 1: Tert-Butyl 4-bromo-2-chlorobenzoate

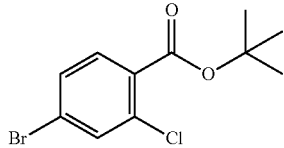

To a suspension of 4-bromo-2-chlorobenzoic acid (5.03 g, 21.4 mmol) in DCM (40 mL) were added oxalyl chloride (2.4 mL, 28 mmol) and catalytic DMF. The reaction mixture was stirred at 23° C. for 4 h. The mixture was then concentrated in vacuo, and the residue was azeotroped with toluene (2×20 mL). The residue was then dissolved in THF (10 mL), and the mixture was added to a suspension of potassium tert-butoxide (3.6 g, 32 mmol) in THF (20 mL) at 0° C. The reaction mixture was allowed to slowly warm to room temperature and stirred for 16 h. The mixture was then poured into ice water (200 mL), and extracted with EtOAc (3×100 mL). The combined organic extracts were washed with brine (1×100 mL), dried (Na$_2$SO$_4$), filtered, and concentrated in vacuo. The crude residue was purified by FCC (SiO$_2$, elution with 0-10% EtOAc/hexanes) to provide 2.83 g (45%) of tert-butyl 4-bromo-2-chlorobenzoate. $^1$H NMR (400 MHz, CDCl$_3$): δ ppm 7.62 (d, 1H), 7.59 (d, 1H), 7.43 (d, 1H), 1.59 (s, 9H).

Step 2: Tert-Butyl 2-chloro-4-formylbenzoate (Intermediate III.1)

Intermediate III.1

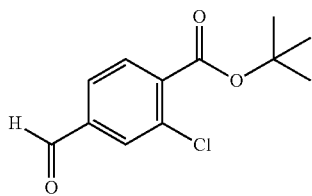

To a solution of tert-butyl 4-bromo-2-chlorobenzoate (2.83 g, 9.71 mmol) in THF (30 mL) at −100° C. (dry ice/Et$_2$O cooling bath) was added n-BuLi (2.5 M in hexanes, 4.3 mL, 11 mmol) drop wise. The resultant mixture was stirred at −100° C. for 30 min, and then DMF (2.25 mL, 29.1 mmol) was added. The reaction mixture was stirred at −100° C. for an additional 45 min, and then quenched with sat. NH$_4$Cl (aq) (20 mL). The mixture was allowed to warm up to room temperature. It was added more NH$_4$Cl (aq) (100 mL), and extracted with EtOAc (3×100 mL). The combined organic extracts were washed with water (1×100 mL) and brine (1×100 mL), dried (Na$_2$SO$_4$), filtered, and concentrated in vacuo. The crude residue was purified by FCC (SiO$_2$, elution with 0-10% EtOAc/hexanes) to provide 0.98 g (42%) of tert-butyl 2-chloro-4-formylbenzoate (Intermediate III.1). $^1$H NMR (400 MHz, CDCl$_3$): δ ppm 10.01 (s, 1H), 7.92 (d, 1H), 7.83 (d, 1H), 7.79 (dd, 1H), 1.62 (s, 9H).

Using the method outlined above for the preparation of Intermediate III.1, the following intermediates were made from the corresponding reagents as indicated in Table 3.

TABLE 3

| Intermediate | Structure | Reagent |
|---|---|---|
| III.2 | 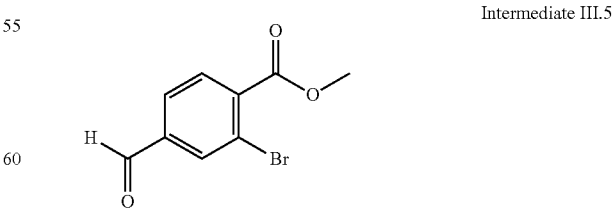 | |
| III.3 | 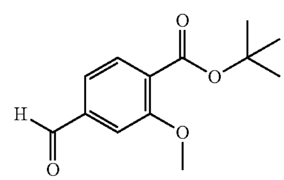 [SMILES: COc1cc(C=O)ccc1C(=O)OC(C)(C)C] | |
| III.4 | 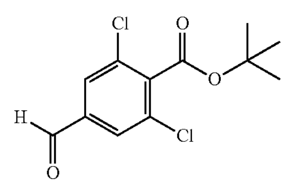 [SMILES: CC(C)(C)OC(=O)c1c(Cl)cc(C=O)cc1Cl] | |

Methyl 2-bromo-4-formylbenzoate (Intermediate III.5)

Intermediate III.5

Methyl 2-bromo-4-formylbenzoate was prepared from 2-bromo-4-methylbenzoic acid as described by Renold, et al. (Renold, P. et al. Insecticidal compounds, PCT Int. Appl. (2009), WO 2009080250).

Methyl 4-formyl-2-nitrobenzoate (Intermediate III.6)

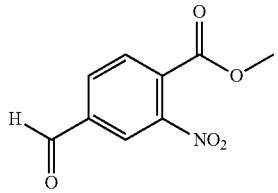

Intermediate III.6

Methyl 4-formyl-2-nitrobenzoate was prepared from 4-formylbenzoic acid as described by Cassayre, et al. (Cassayre, J. Y. et al. Isoxazoline derivatives as insecticidal compounds, PCT Int. Appl. (2013), WO 2013026931).

4-Formyl-N-(pyridin-2-yl)benzenesulfonamide (Intermediate III.7)

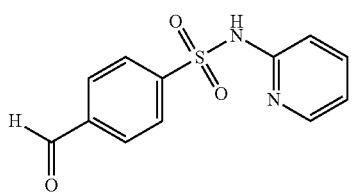

Intermediate III.7

To a solution of 2-aminopyridine (0.02 g, 0.27 mmol) in DCM (3 mL) was added pyridine (0.02 mL, 0.27 mmol) followed by 4-formylbenzenesulfonyl chloride (0.05 g, 0.24 mmol). The reaction mixture was stirred at 23° C. for 16 h. The mixture was then concentrated in vacuo, and the crude residue was purified directly by FCC (SiO$_2$, gradient elution with 0-5% MeOH/DCM) to give 45 mgs (70%) of Intermediate III.7. $^1$H NMR (400 MHz, CDCl$_3$): δ ppm 14.20 (br s, 1H, N—H), 10.10 (s, 1H), 8.35 (d, 1H), 8.10 (d, 2H), 7.98 (d, 2H), 7.75 (m, 1H), 7.45 (d, 1H), 6.85 (t, 1H); LCMS (Method A) $t_R$=0.65 min, m/z 263.1 (M+H)$^+$.

1-Oxo-2-(pyridin-2-yl)-1,2,3,4-tetrahydroisoquinoline-6-carbaldehyde (Intermediate III.8)

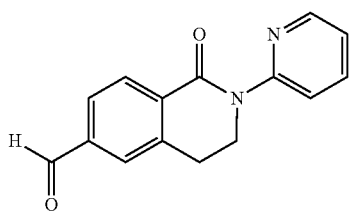

Intermediate III.8

Step 1: Methyl 1-oxo-2-(pyridin-2-yl)-1,2,3,4-tetrahydroisoquinoline-6-carboxylate

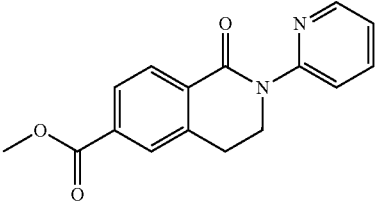 [SMILES: COC(=O)c1ccc2c(c1)CCN(c1ccccn1)C2=O]

A 2-5 mL capacity microwave vessel was charged with 1-oxo-1,2,3,4-tetrahydroisoquinoline-6-carboxylate (0.420 g, 2.05 mmol, for preparation; see: Brenneman, J. B. et al., Soluble Guanylate Cyclase Activators, PCT Int. Appl., (2012) WO 2012122340), 2-bromopyridine (0.323 g, 2.05 mmol), xantphos (0.142 g, 0.246 mmol), cesium carbonate (0.934 g, 2.87 mmol) and dioxane (3 mL). The resultant mixture was then degassed by bubbling N$_2$ (g) through for 5 min, and then added Pd$_2$(dba)$_3$, and bubbled N$_2$ (g) through for an additional 5 min. The vessel was then tightly sealed, and the reaction mixture was stirred at 100° C. for 18 h. The mixture was cooled to room temperature, diluted with DCM (20 mL), filtered through CELITE, and concentrated in vacuo. The crude residue was purified by FCC (SiO$_2$; 0-5% MeOH/DCM) to provide 0.257 g (44%) of methyl 1-oxo-2-(pyridin-2-yl)-1,2,3,4-tetrahydroisoquinoline-6-carboxylate. $^1$H NMR (400 MHz, CDCl$_3$): δ ppm 8.46 (ddd, 1H), 8.25 (d, 1H), 8.03 (m, 2H), 7.96 (d, 1H), 7.74 (ddd, 1H), 7.12 (ddd, 1H), 4.34 (t, 2H), 3.96 (s, 3H), 3.18 (t, 2H); LCMS (Method A) $t_R$=1.03, m/z 283.2 (M+H)$^+$.

Step 2: 6-(hydroxymethyl)-2-(pyridin-2-yl)-3,4-dihydroisoquinolin-1(2H)-one

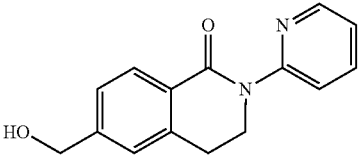 [SMILES: O=C1c2ccc(CO)cc2CCN1c1ccccn1]

To a solution of methyl 1-oxo-2-(pyridin-2-yl)-1,2,3,4-tetrahydroisoquinoline-6-carboxylate (0.40 g, 1.4 mmol) in THF (15 mL) was added LiBH$_4$ (2 M in THF, 4.1 mL, 8.2 mmol) drop wise. The reaction mixture stirred at 23° C. for 6 h. It was then quenched with 0.5 N NaOH (20 mL), and extracted with EtOAc (3×20 mL). The combined organics layers were washed with 0.5 N NaOH (1×30 mL) and brine (1×20 mL), then dried (Na$_2$SO$_4$), filtered, and concentrated in vacuo. The crude residue was purified by FCC (SiO$_2$; elution with 0-100% EtOAc/hexanes) to provide 172 mg (48%) of 6-(hydroxymethyl)-2-(pyridin-2-yl)-3,4-dihydroisoquinolin-1(2H)-one. $^1$H NMR (400 MHz, CDCl$_3$): δ ppm 8.44 (ddd, 1H), 8.15 (d, 1H), 8.01 (d, 1H), 7.72 (ddd, 1H), 7.35 (d, 1H), 7.30 (s, 1H), 7.10 (ddd, 1H), 4.77 (s, 2H), 4.29 (t, 2H), 3.11 (t, 2H); LCMS (Method A) $t_R$=0.77, m/z 255.1 (M+H)$^+$.

Step 3: 1-Oxo-2-(pyridin-2-yl)-1,2,3,4-tetrahydroisoquinoline-6-carbaldehyde (Intermediate III.8)

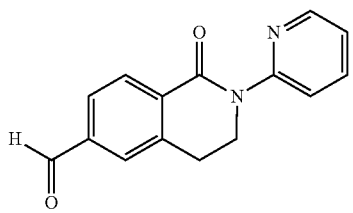

Intermediate III.8

To a solution of 6-(hydroxymethyl)-2-(pyridin-2-yl)-3,4-dihydroisoquinolin-1(2H)-one (0.107 g, 0.421 mmol) in DCM (5 mL) were added powdered 4 Angstrom molecular sieves (1.5 g), 4-methylmorpholino-N-oxide (0.074 g, 0.63 mmol) and tetrapropylammonium perruthenate (7 mg, 0.02 mmol). The mixture was stirred at 23° C. for 1.5 h. The mixture was then diluted with DCM (20 mL), filtered through a pad of CELITE, and the filtrate was concentrated in vacuo. The crude residue was purified by FCC (SiO$_2$, elution with 0-50% EtOAc/hexanes) to provide 50 mg (47%) of 1-oxo-2-(pyridin-2-yl)-1,2,3,4-tetrahydroisoquinoline-6-carbaldehyde. $^1$H NMR (400 MHz, CDCl$_3$): δ ppm 10.10 (s, 1H), 8.47 (m, 1H), 8.36 (d, 1H), 8.03 (d, 1H), 7.89 (d, 1H), 7.77 (m, 2H), 7.14 (m, 1H), 4.36 (t, 2H), 3.22 (t, 2H); LCMS (Method A) t$_R$=0.90, m/z 253.1 (M+H)$^+$.

1-(Pyridin-2-ylamino)isoquinoline-6-carbaldehyde (Intermediate III.9)

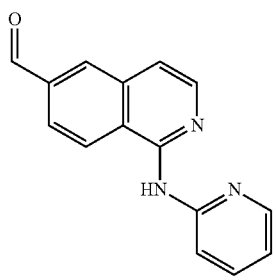

Intermediate III.9

Step 1:
6-Bromo-N-(pyridin-2-yl)isoquinolin-1-amine

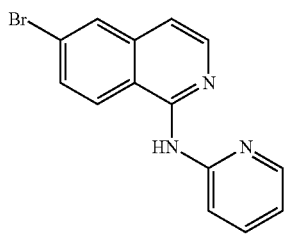 [SMILES: Brc1ccc2c(Nc3ccccn3)nccc2c1]

To a solution of 2-aminopyridine (58 mg, 0.62 mmol) in THF (1 mL) was added NaH (66 mg, 1.7 mmol, 60% in mineral oil). The resulting mixture was stirred at 0° C. for 30 min. 6-Bromo-1-chloroisoquinoline (0.1 g, 0.41 mmol) in THF (1.0 mL) was added, and the resulting mixture was stirred at 70° C. for 2 h. The mixture was cooled to room temperature, diluted with DCM (30 mL), and washed successively with H$_2$O (1×15 mL) and brine (1×15 mL). The organic layer was then dried (Na$_2$SO$_4$), filtered, and concentrated in vacuo. The crude residue was purified by FCC (SiO$_2$; elution with 0-10% CH$_3$OH/DCM) to provide 86 mg (70%) of 6-Bromo-N-(pyridin-2-yl)isoquinolin-1-amine. $^1$H NMR (400 MHz, d$_6$-DMSO) δ ppm 9.84 (s, 1H), 8.55 (d, 1H), 8.32 (dd, 1H), 8.26 (d, 1H), 8.17 (d, 1H), 8.12 (d, 1H), 7.75 (m, 2H), 7.31 (d, 1H), 7.01 (ddd, 1H).

Step 2:
1-(Pyridin-2-ylamino)isoquinoline-6-carbaldehyde (Intermediate III.9)

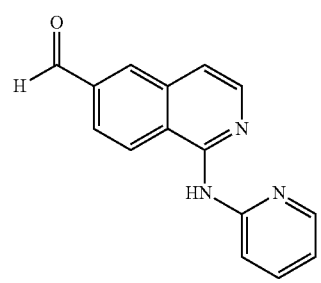

Intermediate III.9

To a solution of 6-Bromo-N-(pyridin-2-yl)isoquinolin-1-amine (0.48 g, 1.6 mmol) in THF (14 mL) at −78° C. was added n-BuLi (1.4 mL, 3.5 mmol, 2.5 M in hexanes) drop wise over 15 min. DMF (1.2 g, 16 mmol) was added, and the mixture was stirred at −78° C. for 1 h. The reaction was quenched with sat. NH$_4$Cl (aq) (20 mL), and then warmed to room temperature. The mixture was extracted with EtOAc (2×30 mL). The organic phases were combined, washed with brine (1×50 mL), dried (Na$_2$SO$_4$), filtered, and concentrated in vacuo. The crude residue was purified by FCC (SiO$_2$; elution with 0-10% CH$_3$OH/DCM) to provide 280 mg of an inseparable mixture (~50/50) of desired product 1-(Pyridin-2-ylamino)isoquinoline-6-carbaldehyde (Intermediate III.9) and by-product N-(pyridin-2-yl)isoquinolin-1-amine. This mixture was used directly without further purification. LCMS (Method A) t$_R$=0.66 min, m/z 250.1 (M+H)$^+$.

4-(8-Oxo-5,6-dihydro-1,7-naphthyridin-7(8H)-yl)benzaldehyde (Intermediate III.10)

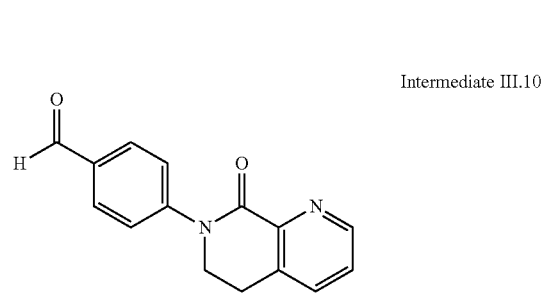 [SMILES: O=Cc1ccc(N2CCc3cccnc3C2=O)cc1]

Intermediate III.10

Step 1: Ethyl 3-methylpicolinate

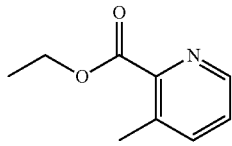

To a solution of 3-methylpicolinic acid (10 g, 73 mmol) at 0° C. in DCM (250 mL) was added catalytic DMF followed by oxalyl chloride (12.3 mL, 146 mmol) drop wise over 15 min. The mixture was warmed to 23° C., stirred for 3 h, and then concentrated in vacuo. The residue was dissolved in DCM (100 mL), and then DIEA (25 mL, 146 mmol) in EtOH (20 mL) was added. The resulting mixture was stirred at 23° C. for 45 min, and then concentrated in vacuo. The crude residue was purified by FCC (SiO$_2$; elution with 0-60% EtOAc/Hexanes) to provide 7.3 g (61%) of ethyl 3-methylpicolinate. $^1$H NMR (400 MHz, CDCl$_3$) δ ppm 8.56 (dd, 1H), 7.61 (dd, 1H), 7.34 (dd, 1H), 4.47 (q, 2H), 2.59 (s, 3H), 1.45 (t, 3H); LCMS (Method A) t$_R$=0.84 min, m/z 166.2 (M+H)$^+$.

Step 2: Ethyl 3-(bromomethyl)picolinate

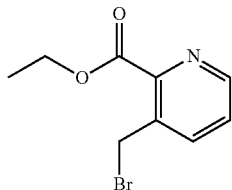

To a solution of ethyl 3-methylpicolinate (3.4 g, 21 mmol) and AIBN (5.1 g, 31 mmol) in chloroform (45 mL) was added NBS (5.5 g, 31 mmol). The mixture was heated to 100° C. in a sealed tube. The mixture was then cooled to 80° C., and heated at this temperature for 3 h. It was then cooled to room temperature, and concentrated in vacuo. The crude residue was purified by FCC (SiO$_2$; elution with 0-2% CH$_3$OH/DCM) to provide 3.0 g (60%) of ethyl 3-(bromomethyl)picolinate which was used immediately in the next step. LCMS (Method A) t$_R$=0.99 min, m/z 244.2/246.2 (M+H)$^+$.

Step 3: Ethyl 3-(cyanomethyl)picolinate

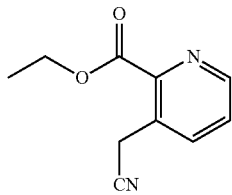

To a solution of 3-(bromomethyl)picolinate (3.0 g, 12 mmol) in DCM (45 mL) and H$_2$O (45 mL) were added sodium cyanide (1.8 g, 37 mmol) and tetrabutylammonium iodide (14 g, 37 mmol). The resulting mixture was stirred at 23° C. for 18 h. The layers were separated, and the organic phase was washed successively with sat. NaHCO$_3$ (aq) (1×30 mL) and brine (1×30 mL). The organic layer was then dried (Na$_2$SO$_4$), filtered, and concentrated in vacuo. The crude residue was purified by FCC (SiO$_2$; elution with 0-80% EtOAc/Hexanes) to provide 1.3 g (56%) of ethyl 3-(cyanomethyl)picolinate. $^1$H NMR (400 MHz, CDCl$_3$) δ ppm 8.76 (dd, 1H), 8.01 (dd, 1H), 7.55 (dd, 1H), 4.50 (q, 2H), 4.29 (s, 2H), 1.47 (t, 3H); LCMS (Method A) t$_R$=0.76 min, m/z 191.2 (M+H)$^+$.

Step 4: 6,7-Dihydro-1,7-naphthyridin-8(5H)-one

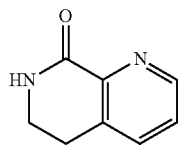

To a solution of 3-(cyanomethyl)picolinate (1.3 g, 6.9 mmol) in EtOH (75 mL) under nitrogen atmosphere was added Raney Nickel (4.0 mL, slurry in H$_2$O). The mixture was then placed under hydrogen atmosphere (balloon), and stirred vigorously at 50° C. for 7 h. The mixture was cooled, filtered through a pad of CELITE, and concentrated in vacuo. The crude residue was purified by FCC (SiO$_2$; elution with 0-15% CH$_3$OH/DCM) to provide 0.58 g (57%) of 6,7-dihydro-1,7-naphthyridin-8(5H)-one. $^1$H NMR (400 MHz, d$_6$-DMSO) δ ppm 8.57 (dd, 1H), 8.14 (br s, 1H, N—H), 7.76 (dd, 1H), 7.46 (dd, 1H), 3.38 (td, 2H), 2.96 (t, 2H).

Step 5: 4-(8-Oxo-5,6-dihydro-1,7-naphthyridin-7(8H)-yl)benzaldehyde (Intermediate III.10)

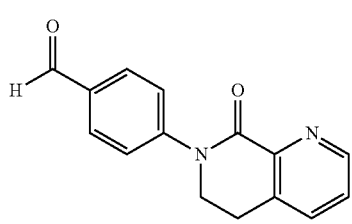

Intermediate III.10

To a solution of 6,7-dihydro-1,7-naphthyridin-8(5H)-one (50 mg, 0.34 mmol) and 4-iodobenzaldehyde (160 mg, 0.67 mmol) in DMF (0.6 mL) was added K$_2$CO$_3$ (47 mg, 0.34 mmol). The mixture was degassed by bubbling nitrogen gas through for 15 min. To this mixture was then added CuI (6 mg, 0.034 mmol), and the reaction vessel was sealed and heated at 150° C. for 6 h. The mixture was cooled to room temperature, and then diluted with EtOAc (20 mL) and water, and added concentrated NH$_3$ (aq). The aqueous phase was extracted with EtOAc (2×20 mL). The combined organic extracts were washed with brine (1×30 mL), dried (Na$_2$SO$_4$), filtered, and concentrated in vacuo. The crude residue was purified by FCC (SiO$_2$; elution with 0-10% CH$_3$OH/DCM) to provide 55 mg (65%) of Intermediate III.10. $^1$H NMR (400 MHz, d$_6$-DMSO) δ ppm 10.00 (s, 1H), 8.66 (dd, 1H), 7.98 (d, 2H), 7.87 (dd, 1H), 7.69 (d, 2H), 7.56

(dd, 1H), 4.09 (t, 2H), 3.21 (t, 2H); LCMS (Method A) $t_R$=0.71 min, m/z 253.5 (M+H)⁺.

4-(7-Oxo-5H-pyrrolo[3,4-b]pyridin-6(7H)-yl)benzaldehyde (Intermediate III.11)

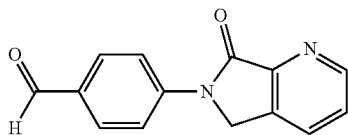

Intermediate III.11

Step 1: Ethyl 3-(azidomethyl)picolinate

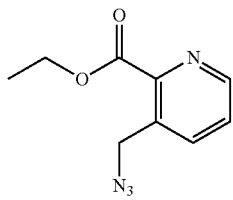

To a solution of ethyl 3-(bromomethyl)picolinate (0.90 g, 3.7 mmol, prepared from 3-methylpicolinic acid as described in steps 1 and 2 of preparation of Intermediate III.10) in EtOH (10 mL) was added NaN₃ (0.36 g, 5.5 mmol) in H₂O (0.79 mL). The resulting mixture was stirred at 60° C. for 1 h. The mixture was concentrated in vacuo, and partitioned between EtOAc (50 mL) and H₂O (25 mL). The organic phase was washed with brine (1×30 mL), dried (Na₂SO₄), filtered, and concentrated in vacuo to provide 0.62 g (81%) of ethyl 3-(azidomethyl)picolinate. ¹H NMR (400 MHz, CDCl₃) δ ppm 8.71 (dd, 1H), 7.94 (dd, 1H), 7.51 (dd, 1H), 4.89 (s, 2H), 4.49 (q, 2H), 1.47 (t, 3H).

Step 2: 5H-Pyrrolo[3,4-b]pyridin-7(6H)-one

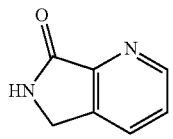

To a solution of ethyl 3-(azidomethyl)picolinate (0.62 g, 3.0 mmol) in EtOH (5 mL) under a nitrogen atmosphere was added Pd/C (120 mg). The mixture was then placed under 1 atm hydrogen gas (balloon), and stirred vigorously at 23° C. for 2 h. The mixture was filtered through a pad of CELITE and concentrated in vacuo. The crude residue was purified by FCC (SiO₂; elution with 0-10% CH₃OH/DCM) to provide 0.19 g (48%) of 5H-pyrrolo[3,4-b]pyridin-7(6H)-one. ¹H NMR (400 MHz, d₆-DMSO) δ ppm 8.96 (bs, 1H, N—H), 8.71 (dd, 1H), 8.04 (dd, 1H), 7.56 (dd, 1H), 4.40 (s, 2H).

Step 3: 4-(7-Oxo-5H-pyrrolo[3,4-b]pyridin-6(7H)-yl)benzaldehyde (Intermediate III.11)

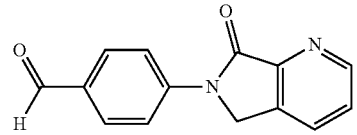

Intermediate III.11

To a solution of 5H-pyrrolo[3,4-b]pyridin-7(6H)-one (190 mg, 1.4 mmol) and 4-iodobenzaldehyde (640 mg, 2.8 mmol) in DMF (2.0 mL) was added K₂CO₃ (190 mg, 1.4 mmol). The mixture was degassed by bubbling nitrogen gas through for 10 min. To this mixture was then added CuI (26 mg, 0.14 mmol). The reaction vessel was sealed, and heated at 150° C. for 6 h. The mixture was cooled to room temperature, and then diluted with EtOAc (20 mL) and water, and added concentrated NH₃ (aq). The aqueous phase was extracted with EtOAc (2×20 mL). The combined organic extracts were washed with brine (1×30 mL), dried (Na₂SO₄), filtered, and concentrated in vacuo. The crude residue was purified by FCC (SiO₂; elution with 0-10% CH₃OH/DCM) to provide 81 mg (33%) of Intermediate III.11. ¹H NMR (400 MHz, d₆-DMSO) δ ppm 9.98 (s, 1H), 8.81 (dd, 1H), 8.21 (d, 2H), 8.18 (dd, 1H), 8.02 (m, 2H), 7.69 (dd, 1H), 5.13 (s, 2H); LCMS (Method A) $t_R$=0.80 min, m/z 239.3 (M+H)⁺.

1-Oxo-2-(pyridin-2-yl)isoindoline-5-carbaldehyde (Intermediate III.12)

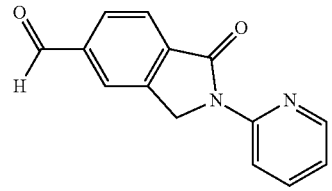

Intermediate III.12

Step 1: Dimethyl 2-cyanoterephthalate

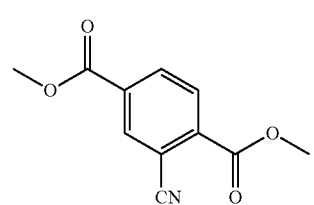

To a suspension of dimethyl aminoterephthalate (2.31 g, 11.0 mmol) in water (14 mL) was added conc. HCl (aq) (2.8 mL). The mixture was cooled to −5° C. (brine/ice bath). A solution of sodium nitrite (838 mg, 12.1 mmol) in water (1.8 mL) was added drop wise. The resultant mixture was stirred at 0° C. for 10 min. This was then neutralized to pH 7 by careful addition of K₂CO₃ (s). This mixture was then added to a mixture of CuCN (1.19 g, 13.3 mmol) and NaCN (1.30 g, 26.5 mmol) in water (4 mL) at 60° C. The reaction mixture was then heated to 110° C. for 15 min, then cooled to room temperature, and extracted with EtOAc (200 mL). The organic phase was washed with sat. NaHCO₃ (aq) (1×50 mL) and brine (1×50 mL), dried (Na₂SO₄), filtered, and concentrated in vacuo. The crude yellow solid was purified by FCC (SiO₂; elution with 0-40% EtOAc/Hexanes) to provide 1.32 g (57%) of dimethyl 2-cyanoterephthalate. ¹H NMR (400 MHz, d₆-DMSO) δ ppm 8.42 (d, 1H), 8.34 (dd, 1H), 8.25 (d, 1H), 3.95 (s, 3H), 3.92 (s, 3H).

Step 2: Methyl 1-oxoisoindoline-5-carboxylate

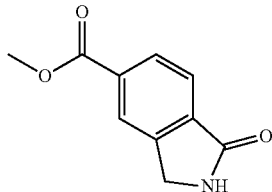

To a solution of dimethyl 2-cyanoterephthalate (2.54 g, 12.0 mmol) in methanol (60 mL) under nitrogen atmosphere was added Raney Nickel (2.0 mL, slurry in H₂O). The resulting mixture was shaken in a Parr apparatus under hydrogen atmosphere (45 psi) for 6 h. The mixture was then filtered through a pad of CELITE, and the filter cake was rinsed with methanol and THF. The filter cake was then broken up, slurried in a mixture of DCM/CH₃OH (80:20), and then filtered. The combined organic filtrates were concentrated in vacuo, and the crude residue was purified by FCC (SiO₂; elution with 0-10% CH₃OH/DCM) to provide 1.27 g (57%) of methyl 1-oxoisoindoline-5-carboxylate. ¹H NMR (400 MHz, d₆-DMSO) δ ppm 8.83 (br s, 1H), 8.16 (d, 1H), 8.06 (dd, 1H), 7.79 (d, 1H), 4.45 (s, 2H), 3.90 (s, 3H); LCMS (Method A) t$_R$=0.73 min, m/z 192.2 (M+H)⁺.

Step 3: Ethyl 1-oxo-2-(pyridin-2-yl)isoindoline-5-carboxylate

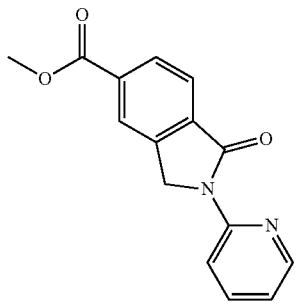 [SMILES: COC(=O)c1ccc2c(c1)CN(c1ccccn1)C2=O]

To a reaction vial under nitrogen atmosphere were added methyl 1-oxoisoindoline-5-carboxylate (100 mg, 0.52 mmol), Xantphos (18 mg, 0.031 mmol), Cs₂CO₃ (240 mg, 0.73 mmol) and Pd₂(dba)₃ (19 mg, 0.021 mmol) followed by 2-bromopyridine (50 µL, 0.52 mmol) and dioxane (1.0 mL). The vial was sealed, and mixture was heated at 100° C. for 25 h. The mixture was cooled to room temperature, filtered through a pad of CELITE, and the filter cake was rinsed with DCM. The combined filtrates were concentrated, and the residue was purified by FCC (SiO₂; elution with 0-10% CH₃OH/DCM) to provide 56 mg (40%) of ethyl 1-oxo-2-(pyridin-2-yl)isoindoline-5-carboxylate. ¹H NMR (400 MHz, d₆-DMSO) δ ppm 8.54 (d, 1H), 8.47 (dd, 1H), 8.30 (s, 1H), 8.12 (dd, 1H), 7.94 (d, 1H), 7.92 (ddd, 2H), 7.23 (dd, 1H), 5.18 (s, 2H), 3.92 (s, 3H); LCMS (Method A) t$_R$=1.15 min, m/z 269.3 (M+H)⁺.

Step 4: 5-(Hydroxymethyl)-2-(pyridin-2-yl)isoindolin-1-one

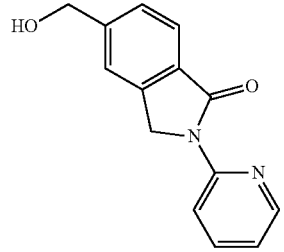 [SMILES: O=C1c2ccc(CO)cc2CN1c1ccccn1]

To a solution of ethyl 1-oxo-2-(pyridin-2-yl)isoindoline-5-carboxylate (0.34 g, 1.2 mmol) in THF (16 mL) was added LiBH₄ (3.7 mL, 2.0 M in THF, 7.3 mmol). The resulting mixture was stirred at 23° C. for 6 h. The reaction was quenched with 0.5 N NaOH (20 mL), and extracted with EtOAc (2×20 mL). The combined organic extracts were washed with brine (1×20 mL), dried (Na₂SO₄), filtered, and concentrated in vacuo. The crude residue was purified by FCC (SiO₂; elution with 0-10% CH₃OH/DCM) to provide 0.19 g (63%) of 5-(Hydroxymethyl)-2-(pyridin-2-yl)isoindolin-1-one. ¹H NMR (400 MHz, d₆-DMSO) δ ppm 8.54 (d, 1H), 8.44 (ddd, 1H), 7.89 (ddd, 1H), 7.77 (d, 1H), 7.65 (s, 1H), 7.48 (d, 1H), 7.19 (dd, 1H), 5.46 (t, 1H, O—H), 5.10 (s, 2H), 4.65 (d, 2H); LCMS (Method A) t$_R$=0.84 min, m/z 241.1 (M+H)⁺.

Step 5: 1-Oxo-2-(pyridin-2-yl)isoindoline-5-carbaldehyde (Intermediate III.12)

Intermediate III.12

To a solution of 5-(hydroxymethyl)-2-(pyridin-2-yl)isoindolin-1-one (0.19 g, 0.79 mmol) in DCM (8 mL) were added 4 Angstrom molecular sieves (300 mg), 4-methylmorpholine-n-oxide (0.14 g, 1.9 mmol), and TPAP (14 mg, 0.040 mmol). The resulting mixture was stirred at 23° C. for 2 h. The mixture was filtered through a pad of silica gel, and rinsed with DCM. The combined filtrates were concentrated in vacuo, and the crude residue was purified by FCC (SiO₂; elution with 0-10% CH₃OH/DCM) to provide 0.11 g (61%) of Intermediate III.12. ¹H NMR (400 MHz, d₆-DMSO) δ ppm 10.18 (s, 1H), 8.55 (d, 1H), 8.48 (ddd, 1H), 8.24 (s, 1H), 8.09 (d, 1H), 8.03 (d, 1H), 7.93 (ddd, 1H), 7.24 (dd, 1H), 5.21 (s, 2H); LCMS (Method A) t$_R$=1.02 min, 239.1 (M+H)⁺.

3-Bromo-1-methyl-1H-indazole-6-carbaldehyde (Intermediate III.13)

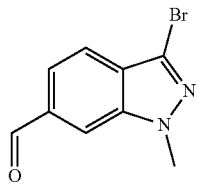

Intermediate III.13

N-Bromosuccinimide (0.73 g, 4.13 mmol) was added to a solution of 1-methyl-1H-indazole-6-carbaldehyde (0.66 g, 4.13 mmol) in acetonitrile (10 mL). The mixture was stirred at 23° C. for 16 h. The solvent was removed in vacuo, and the residue was re-dissolved in EtOAc (50 mL). The organic solution was washed with sat. $Na_2CO_3$ (aq) (30 mL), dried ($Na_2SO_4$), and concentrated in vacuo. The residue was purified by FCC ($SiO_2$; elution with 10-50% EtOAc/hexanes) to provide 0.85 g (86%) of Intermediate III.13. $^1$H NMR (400 MHz, $d_6$-DMSO): δ ppm 10.16 (s, 1H), 8.41 (d, 1H), 7.76 (d, 2H), 7.71 (dd, 1H), 4.16 (s, 3H).

4-formyl-N-(5-(trifluoromethyl)pyrimidin-2-yl)benzamide (Intermediate III.14)

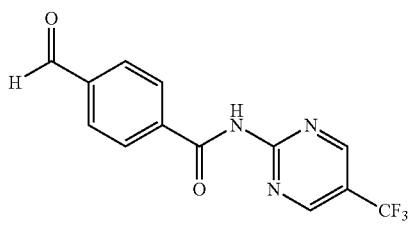

Intermediate III.14

To a suspension of 4-formylbenzoic acid (580 mg, 3.86 mmol) in DCM (20 mL) were added oxalyl chloride (0.46 mL, 5.4 mmol) and catalytic DMF. The reaction mixture was stirred at 23° C. for 3 h. Then the mixture was concentrated in vacuo, and the crude residue was azeotroped with toluene (2×) to give crude 4-formylbenzoylchloride which was used directly as described below. To a solution of 2-amino-5-trifluoromethylpyrimidine (1.26 g, 7.73 mmol) in THF 30 mL was added NaH (60% dispersion in mineral oil, 340 mg, 8.49 mmol). The mixture was stirred at 23° C. for 30 min. To this mixture was added 4-formylbenzoylchloride (prepared as described above) as a solution in THF (15 mL). The reaction mixture was stirred at 23° C. for 3.5 h. The mixture was then quenched with saturated $NH_4Cl$ (aq) (20 mL), and extracted with EtOAc (3×50 mL). The combined organic extracts were dried ($Na_2SO_4$), filtered, and concentrated in vacuo. The crude residue was purified by FCC ($SiO_2$, elution with 0-30% EtOAc/hexanes) to provide 407 mg (36%) of Intermediate III.14. $^1$H NMR (400 MHz, $CDCl_3$) δ ppm 10.14 (s, 1H), 8.93 (s, 2H), 8.84 (br s, 1H), 8.12 (d, 2H), 8.05 (d, 2H).

5-Methyl-2,3-dihydro-7-aza-indole Hydrochloride (Intermediate IV.1)

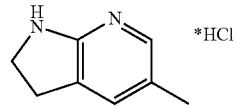

Intermediate IV.1

Step 1: Tert-Butyl-5-bromo-2,3-dihydro-7-aza Indole-1-carboxylate

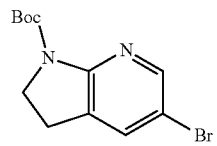

A mixture of 5-bromo-2,3-dihydro-7-aza-indole (0.40 g, 2.0 mmol, prepared from 2,3-dihydro-7-aza-indole according to the procedure described by Graczyk, P. et al., Synthesis of 5-Substituted 7-Azaindoles and 7-Azaindonines, PCT Int. App (2004), WO 2004078757), di-tert-butyl dicarbonate (0.52 g, 2.4 mmol) and N,N-diisopropylethylamine (0.30 mL, 2.2 mmol) in DMF (8 mL) was heated at 150° C. for 1 h. Additional di-tert-butyl dicarbonate (0.05 g, 0.23 mmol) and DIEA (0.05 mL, 0.36 mmol) were added, and the mixture was heated at 150° C. for an additional 20 min. The solvent was removed in vacuo, and water (10 mL) was added. The mixture was extracted with $CH_2Cl_2$, and the organic layer was washed with brine. The organic phase was then dried ($Na_2SO_4$), and the solvent was removed in vacuo. The residue was purified by FCC ($SiO_2$; elution with 0-15% EtOAc/hexanes) to provide 0.55 g (92%) of tert-Butyl-5-bromo-2,3-dihydro-7-aza indole-1-carboxylate. LCMS (Method A): $t_R$=0.82 min, m/z 299.3/301.2 (M+H)$^+$.

Step 2: Tert-Butyl-5-methyl-2,3-dihydro-7-azaindole-1-carboxylate

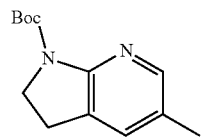 [SMILES: Cc1cnc2c(c1)CCN2C(=O)OC(C)(C)C]

To a mixture of degassed (by bubbling nitrogen gas through for 10 min) p-dioxane (8 mL) and water (2 mL) were added tert-Butyl-5-bromo-2,3-dihydro-7-aza indole-1-carboxylate (0.3 g, 1.3 mmol), trimethylboroxine (0.22 mL, 1.57 mmol) and $Cs_2CO_3$ (1.27 g, 3.9 mmol), followed by $PdCl_2(dppf)CH_2Cl_2$ (0.11 g, 0.13 mmol). The mixture was subjected to microwave irradiation maintaining a reaction temperature of 100° C. for 15 minutes, cooled to room temperature, and then diluted with EtOAc and water. The organic layer was washed with brine, dried ($Na_2SO_4$), and the solvent was removed in vacuo. The residue was purified by FCC ($SiO_2$; elution with 0-5% [2 M $NH_3$ in MeOH]/$CH_2Cl_2$) to provide 0.24 g (68%) of tert-Butyl-5-methyl-2, 3-dihydro-7-azaindole-1-carboxylate. $^1$H NMR (400 MHz, d$_6$-DMSO) δ ppm 7.87 (s, 1H), 7.37 (s, 1H), 3.9 (t, 2H), 2.97 (t, 2H), 2.19 (s, 3H), 1.47 (s, 9H); LCMS (Method A): t$_R$=1.01 min, m/z 235.2 (M+H)$^+$.

Step 3: 5-Methyl-2,3-dihydro-7-azaindole Hydrochloride (Intermediate IV.1)

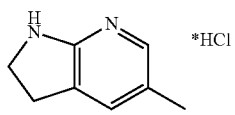

Intermediate IV.1

To a solution of tert-Butyl-5-methyl-2,3-dihydro-7-azain-dole-1-carboxylate (0.23 g, 1.0 mmol) in p-dioxane (0.5 mL) was added 4 M HCl in dioxane (0.10 mL). The mixture was stirred at 23° C. for 18 h. An additional aliquot of 4 M HCl in dioxane (0.50 mL) was added, and the mixture was stirred for an additional 30 min. Volatiles were removed in vacuo to provide 0.24 g of 5-Methyl-2,3-dihydro-7-azaindole as the hydrochloride salt (Intermediate IV.1) which was used directly without further purification. LCMS (Method B): t$_R$=0.66 min, m/z 135.2 (M+H)$^+$.

5-Morpholinopyridin-2-amine (Intermediate IV.2)

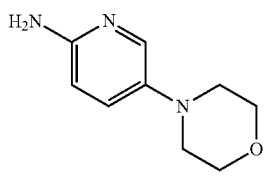

Intermediate IV.2

Step 1: 4-(6-Nitropyridin-3-yl)morpholine

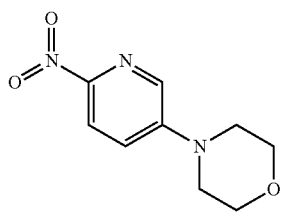 [SMILES: O=[N+]([O-])c1ccc(N2CCOCC2)cn1]

To a solution of 5-bromo-2-nitropyridine (1.0 g, 4.93 mmol) in DMSO (4 mL) was added morpholine (0.43 mL, 4.9 mmol) followed by DIPEA (0.94 mL, 5.4 mmol). The reaction mixture was then subjected to microwave irradiation maintaining a reaction temperature of 120° C. for 3 h. The mixture was cooled to room temperature, added more DIPEA (0.94 mL, 5.4 mmol), and then subjected to microwave irradiation maintaining a reaction temperature of 120° C. for 3 h. The mixture was then cooled to room temperature, diluted with EtOAc (50 mL) and washed with water (50 mL). The aqueous phase was back extracted with EtOAc (2×50 mL) and the organic layers combined and washed with brine (1×50 mL). The organic phase was then dried (Na$_2$SO$_4$), filtered, and concentrated in vacuo. The crude residue was purified by FCC (SiO$_2$, elution with 0-100% EtOAc/hexanes) to provide 0.76 g (74%) of 4-(6-nitropyri-din-3-yl)morpholine. $^1$H NMR (400 MHz, CDCl$_3$) δ ppm 8.19 (d, 1H), 8.15 (d, 1H), 7.22 (dd, 1H), 3.90 (m, 4H), 3.42 (m, 4H); LCMS (Method B): t$_R$=0.92 min, m/z 210.2 (M+H)$^+$.

Step 2: 5-Morpholinopyridin-2-amine (Intermediate IV.2)

To a suspension of 4-(6-nitropyridin-3-yl)morpholine (0.76 g, 3.7 mmol) in EtOAc (5 mL) and EtOH (5 mL) under nitrogen (g) atmosphere was added 10% Pd/C (50 mg). The mixture was then placed under an atmosphere of H$_2$ (g) (balloon) and stirred vigorously for 16 h. The mixture was then filtered through a pad of CELITE, and concentrated in vacuo to provide 0.63 g (96%) of Intermediate IV.2 which was used without further purification. $^1$H NMR (400 MHz, CDCl$_3$) δ pp 7.76 (dd, 1H), 7.17 (d, 1H), 6.50 (dd, 1H), 4.23 (br s, 2H, N—H), 3.85 (m, 4H), 3.01 (m, 4H); LCMS (Method B): t$_R$=0.61 min, m/z 180.2 (M+H)$^+$.

Using the method outlined above for the preparation of Intermediate IV.2, the following intermediates were made from the corresponding reagents as indicated in Table 4.

TABLE 4

| Intermediate | Structure | Reagent |
|---|---|---|
| IV.3 | ![H2N-pyridine-piperazine-NBoc] | HN-CH2CH2-NBoc |
| IV.4 | ![H2N-pyridine-piperazine-N-Me] | HN-piperazine-N-Me |

(±)-Methyl 4-(1-((1-methoxy-1-oxopropan-2-yl)amino)cyclopropyl)benzoate (Intermediate V.1)

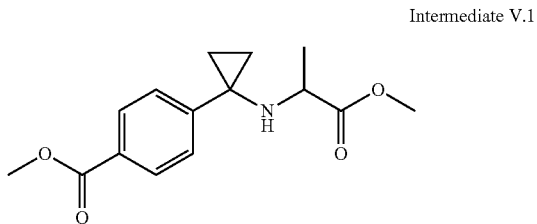

Intermediate V.1

To a solution of methyl-4-(1-aminocyclopropyl)benzoate hydrochloride (100 mg, 0.44 mmol) in DMSO (0.5 mL) were added (±)-methyl-2-bromopropionate (49 μL, 0.44 mmol) and DIEA (168 μL, 0.97 mmol). The reaction mixture was heated to 60° C. for 16 h. The mixture was then heated to 80° C. for an additional 24 h. The mixture was cooled, diluted with EtOAc (30 mL), and washed with water (2×20 mL) and brine (1×20 mL). The organic phase was dried ($Na_2SO_4$), filtered, and concentrated in vacuo. The crude residue was purified by FCC ($SiO_2$, elution with 0-100% EtOAc/hexanes) to provide 74 mg (61%) of Intermediate V.1. $^1$H NMR (400 MHz, $CDCl_3$) δ ppm 7.97 (d, 2H), 7.38 (d, 2H), 3.91 (s, 3H), 3.51 (d, 1H), 3.37 (q, 1H), 2.49 (br s, 1H, N—H), 1.23 (d, 3H), 1.12-0.97 (m, 3H), 0.88 (ddd, 1H).

SYNTHESIS OF EXAMPLES

Example 1a (R)-4-((8-Chloro-2,5-dioxo-3-(pyridin-2-ylmethyl)-2,3-dihydro-1H-benzo[e][1,4]diazepin-4(5H)-yl)methyl)benzoic Acid Step 1: (R)-Methyl 4-(((1-methoxy-1-oxo-3-(pyridin-2-yl)propan-2-yl)amino)methyl)benzoate (1-1)

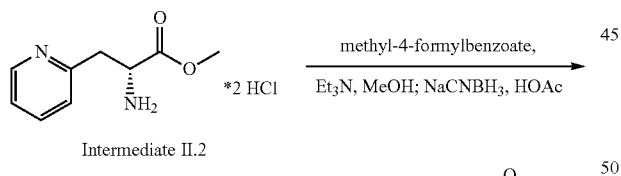

Intermediate II.2

1-1

To a suspension of Intermediate II.2 (2.0 g, 8.5 mmol) in MeOH (40 mL) was added triethylamine (2.4 mL, 17 mmol) followed by methyl-4-formylbenzoate (1.4 g, 8.6 mmol). The resulting mixture was stirred at 23° C. for 45 min. Sodium cyanoborohydride (0.54 g, 8.5 mmol) was added followed by acetic acid (0.97 mL, 17 mmol). The reaction mixture was stirred at 23° C. for 16 h. The mixture was concentrated in vacuo, and the crude residue was taken up in EtOAc (100 mL), and washed with 1 N NaOH (aq) (1×100 mL). The aqueous phase was then extracted with EtOAC (2×100 mL). The combined organic extracts were washed with brine (1×100 mL), dried ($Na_2SO_4$), filtered, and concentrated in vacuo. The crude residue was purified by FCC ($SiO_2$; elution with 0-100% EtOAc/hexanes) to provide 1.8 g (65%) of (R)-methyl 4-(((1-methoxy-1-oxo-3-(pyridin-2-yl)propan-2-yl)amino)methyl)benzoate (1-1) as clear oil. $^1$H NMR (400 MHz, $CDCl_3$): δ ppm 8.53 (m, 1H), 7.92 (d, 2H), 7.60 (dt, 1H), 7.26 (d, partially obscured by solvent peak, 2H), 7.17-7.13 (m, 2H), 3.90 (s, 3H), 3.76-3.68 (m, 2H), 3.69 (s, 3H), 3.19 (dd, 1H), 3.08 (dd, 1H); LCMS (Method A) $t_R$=0.76 min, m/z 329.4 $(M+H)^+$.

Step 2: 2-Azido-4-chlorobenzoyl Chloride (1-2)

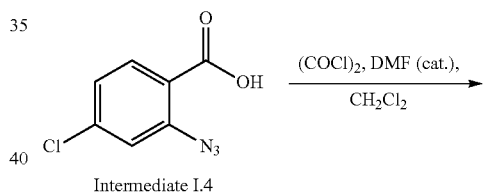

Intermediate I.4

1-2

To a solution of Intermediate I.4 (5.2 g, 26 mmol) in DCM (150 mL) were added oxalyl chloride (3.3 mL, 40 mmol) and catalytic DMF. The reaction mixture was stirred at 23° C. for 3 h. The mixture was concentrated in vacuo, and the crude residue was then azeotroped with toluene (2×). The resultant acid chloride intermediate 1-2 was used directly in the next step.

Step 3: (R)-Methyl 4-((2-azido-4-chloro-N-(1-methoxy-1-oxo-3-(pyridin-2-yl)propan-2-yl)benzamido)methyl)benzoate (1-3)

Step 4: (R)-Methyl 4-((8-chloro-2,5-dioxo-3-(pyridin-2-ylmethyl)-2,3-dihydro-1H-benzo[e][1,4]diazepin-4(5H)-yl)methyl)benzoate (1-4)

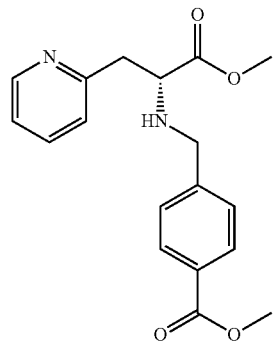

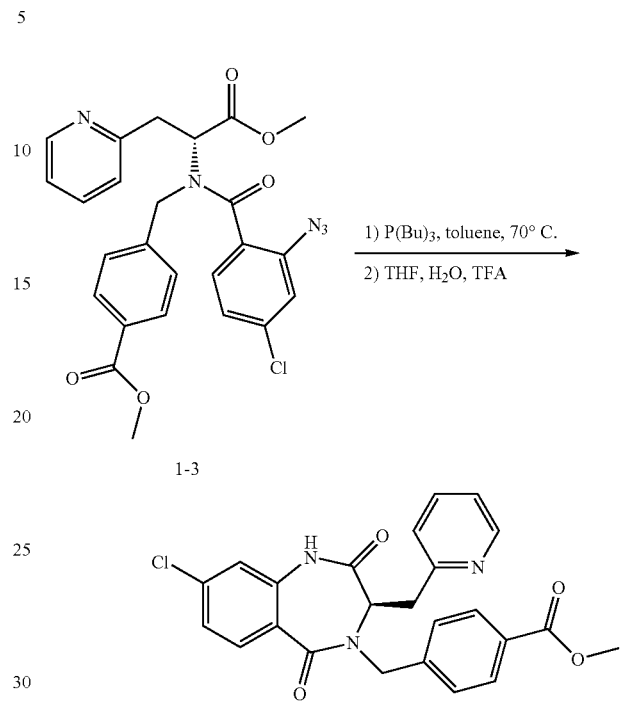

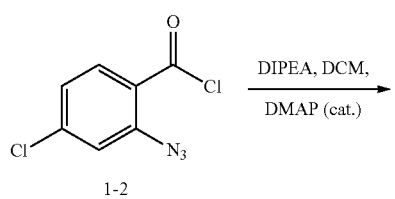

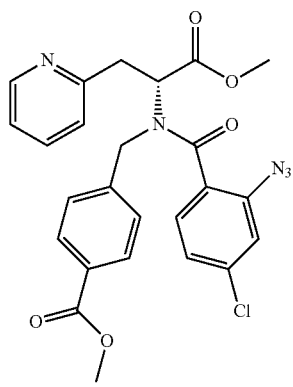

To a solution of 1-3 (9.7 g, 19.1 mmol) in toluene (100 mL) was added tri-n-butylphosphine (5.2 mL, 21 mmol). The reaction mixture was heated to 70° C., and stirred at this temperature for 16 h. The mixture was then cooled, and concentrated in vacuo. The residue was dissolved in THF (60 mL), H$_2$O (5 mL) and TFA (5 mL), and the resulting mixture was stirred at 23° C. for 16 h. The mixture was then concentrated in vacuo, and the residue was taken up in EtOAc (200 mL), and washed with sat. NaHCO$_3$ (aq) (1×100 mL) and brine (1×100 mL). The organic layer was dried (Na$_2$SO$_4$), filtered, and concentrated in vacuo. The crude residue was purified by FCC (elution with 0-5% MeOH/DCM) to provide 9.1 g of semi pure 1-4 which was used in the next step without further purification. LCMS (Method A) t$_R$=0.98 min, m/z 450.2/452.2 (M+H)$^+$.

To a solution of 1-1 (7.2 g, 22 mmol) in DCM (60 mL) was added crude acid chloride 1-2 (5.7 g, 26 mmol) from the previous step, as a solution in DCM (10 mL). To this mixture were added DIEA (5.7 mL, 33 mmol) and catalytic DMAP (20 mg). The reaction mixture was stirred at 23° C. for 18 h. The mixture was diluted with EtOAc (200 mL), and washed successively with sat. NH$_4$Cl (aq) (1×100 mL), sat. NaHCO$_3$ (aq) (1×100 mL), and brine (1×100 mL). The organic layer was dried (Na$_2$SO$_4$), filtered, and concentrated in vacuo. The crude product was purified by FCC (SiO$_2$; elution with 0-5% MeOH/DCM) to provide 9.7 g (87%) of 1-3. LCMS (Method A): t$_R$=1.11 min, m/z 508.3/510.3 (M+H)$^+$

Step 5: (R)-4-((8-Chloro-2,5-dioxo-3-(pyridin-2-ylmethyl)-2,3-dihydro-1H-benzo[e][1,4]diazepin-4(5H)-yl)methyl)benzoic Acid (Example 1a)

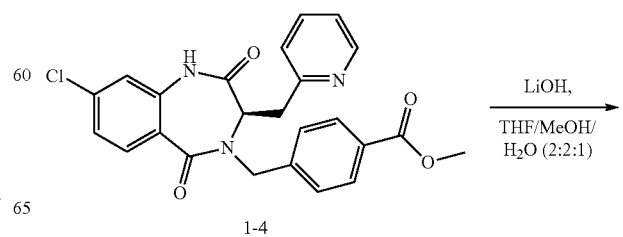

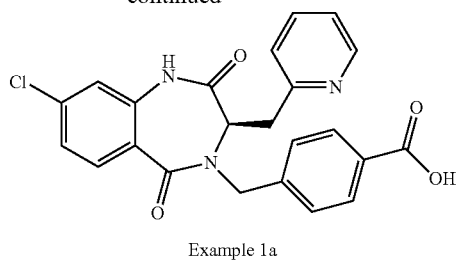

Example 1a

To a solution of 1-4 (2.9 g, 6.5 mmol) in THF (20 mL), MeOH (20 mL) and H₂O (10 mL) was added LiOH (0.31 g, 13 mmol). The reaction mixture was stirred at 23° C. for 16 h. The mixture was then concentrated in vacuo. The residue was taken up in H₂O (100 mL), and washed with EtOAc (1×100 mL). The aqueous layer was acidified to pH 5 with 1N HCl (aq), and then extracted with a 3:1 mixture of CHCl₃/IPA (6×50 mL). The combined organic phases were washed with brine (1×100 mL). The organic phase was then dried (Na₂SO₄), filtered, and concentrated in vacuo to give 2.5 g (88%) of Example 1a. ¹H NMR (400 MHz, d₆-DMSO, ~1.5:1 mixture of 7-membered ring conformers observed) δ ppm 12.89 (br s, 1H), 10.74 and 10.64 (2s, 1H, N—H), 8.47-7.00 (m, 11H), 5.07-4.21 (m, 3H), 3.51-2.79 (m, 2H); LCMS (Method A) $t_R$=0.81 min, m/z 436.3/438.3 (M+H)⁺.

Following the method described above for Example 1a and substituting the corresponding intermediates and reagents, the following Examples were prepared as indicated in Table 5.

TABLE 5

| Example | Structure | Intermediates | Reagent | LCMS Method | $t_R$ (min) | (M + H)⁺ observed |
|---|---|---|---|---|---|---|
| 1b | (R)-4-((8-fluoro-2,5-dioxo-3-(pyridin-3-ylmethyl)-2,3-dihydro-1H-benzo[e][1,4]diazepin-4(5H)-yl)methyl)benzoic acid | I.2 and II.2 | | F | 0.81 | 420.3 |
| 1c | (R)-4-((8-chloro-2,5-dioxo-3-(pyridin-4-ylmethyl)-2,3-dihydro-1H-benzo[e][1,4]diazepin-4(5H)-yl)methyl)benzoic acid | I.4 and II.8 | | A | 1.67 | 436.3/ 438.3 |
| 1d | (R)-4-((8-chloro-3-(3,4-dichlorobenzyl)-2,5-dioxo-2,3-dihydro-1H-benzo[e][1,4]diazepin-4(5H)-yl)methyl)benzoic acid | I.4 and II.22 | | A | 0.68 | 505.2/ 507.2/ 509.2 |

TABLE 5-continued

| Example | Structure | Intermediates | Reagent | LCMS Method | $t_R$ (min) | $(M + H)^+$ observed |
|---|---|---|---|---|---|---|
| 1e | (R)-4-((3-(3,4-dichlorobenzyl)-8-methyl-2,5-dioxo-2,3-dihydro-1H-benzo[e][1,4]diazepin-4(5H)-yl)methyl)benzoic acid | I.7 and II.22 | methyl 4-formylbenzoate | C | 1.21 | 483.3/ 485.3/ 487.3 |
| 1f | (S)-4-((8-chloro-2,5-dioxo-3-(pyridin-2-ylmethyl)-2,3-dihydro-1H-benzo[e][1,4]diazepin-4(5H)-yl)methyl)benzoic acid | I.4 and II.20 | methyl 4-formylbenzoate | A | 1.05 | 436.2/ 438.2 |
| 1g | (R)-4-((8-bromo-2,5-dioxo-3-(pyridin-3-ylmethyl)-2,3-dihydro-1H-benzo[e][1,4]diazepin-4(5H)-yl)methyl)benzoic acid | I.11 and II.2 | methyl 4-formylbenzoate | A | 0.81 | 480.2/ 482.2 |
| 1h | (R)-5-((8-chloro-2,5-dioxo-3-(pyridin-2-ylmethyl)-2,3-dihydro-1H-benzo[e][1,4]diazepin-4(5H)-yl)methyl)thiophene-2-carboxylic acid | I.4 and II.1 | methyl 5-formylthiophene-2-carboxylate | A | 0.77 | 442.3/ 444.3 |

TABLE 5-continued

| Example | Structure | Intermediates | Reagent | LCMS Method | $t_R$ (min) | $(M + H)^+$ observed |
|---|---|---|---|---|---|---|
| 1i | (R)-4-((8-chloro-2,5-dioxo-3-(pyridin-2-ylmethyl)-2,3-dihydro-1H-benzo[e][1,4]diazepin-4(5H)-yl)methyl)-2-fluorobenzoic acid | I.4 and II.1 | | A | 0.84 | 454.4/ 456.4 |
| 1j | (1R,4r)-4-(((R)-8-chloro-2,5-dioxo-3-(pyridin-2-ylmethyl)-2,3-dihydro-1H-benzo[e][1,4]diazepin-4(5H)-yl)methyl)cyclohexanecarboxylic acid | I.4 and II.1 | | A | 0.87 | 442.5/ 444.5 |
| 1k | (R)-4-((8-chloro-2,5-dioxo-3-(thiophen-2-ylmethyl)-2,3-dihydro-1H-benzo[e][1,4]diazepin-4(5H)-yl)methyl)benzoic acid | I.4 and II.25 | | A | 1.12 | 441.3/ 443.3 |
| 1l | 4-((8-chloro-2,5-dioxo-3-(pyrazin-2-ylmethyl)-2,3-dihydro-1H-benzo[e][1,4]diazepin-4(5H)-yl)methyl)benzoic acid | I.4 and II.26 | | A | 0.87 | 437.4/ 439.4 |

TABLE 5-continued

| Example | Structure | Intermediates | Reagent | LCMS Method | $t_R$ (min) | $(M + H)^+$ observed |
|---|---|---|---|---|---|---|
| 1m | (R)-4-((8-chloro-2,5-dioxo-3-(thiazol-4-ylmethyl)-2,3-dihydro-1H-benzo[e][1,4]diazepin-4(5H)-yl)methyl)benzoic acid | I.4 and II.24 | | A | 0.96 | 442.4/ 444.4 |
| 1n | (R)-2-bromo-4-((8-chloro-3-methyl-2,5-dioxo-2,3-dihydro-1H-benzo[e][1,4]diazepin-4(5H)-yl)methyl)benzoic acid | I.4 and III.5 | | A | 1.00 | 437.2/ 439.2/ 441.2 |

Example 2a (R)-4-((8-Chloro-2,5-dioxo-3-(pyridin-3-ylmethyl)-2,3-dihydro-1H-benzo[e][1,4]diazepin-4(5H)-yl)methyl)benzoic Acid Step 1: Resin-Bound Fmoc Protected Amine 2-1

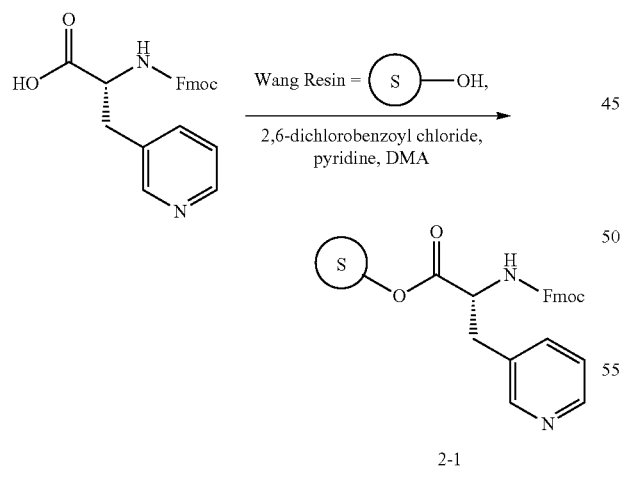

To a solution of Fmoc-3-pyridyl-D-Ala-OH (1.3 g, 3.4 mmol) in DMA (30 mL) in a 100 mL capacity solid-phase synthesis reaction vessel, was added 2,6-dichlorobenzoyl-chloride (1.9 mL, 14 mmol) followed by pyridine (1.8 mL, 23 mmol). The reaction mixture was shaken on a wrist action shaking apparatus for 30 min. Wang Resin (0.75 g, 2.3 mmol, HS, 100-200 mesh, 1% DVB, 3 mmol/g loading) was added and the reaction mixture was shaken for 16 h. The reaction vessel was drained, and the resin was washed successively with 3×30 mL each of DMF, MeOH, and DCM. The resin was then dried in vacuo to provide resin-bound Fmoc-protected amine 2-1.

Step 2: Resin-Bound Amine 2-2

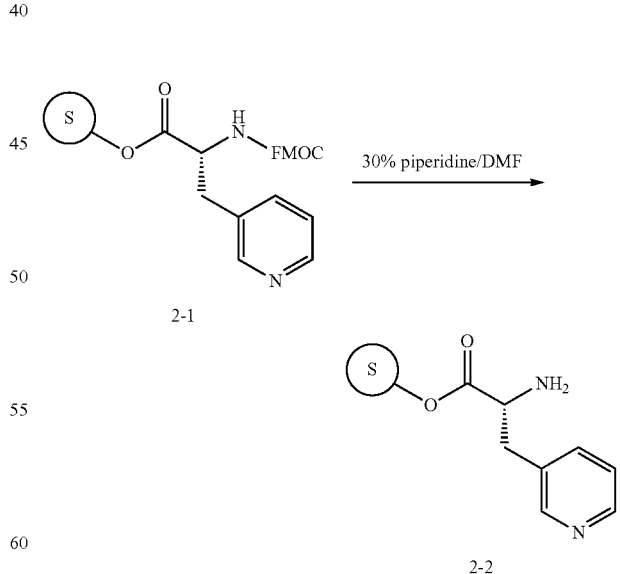

To the resin-bound Fmoc protected amine 2-1 was added 30% piperidine/DMF (45 mL). The reaction mixture was shaken on a wrist action shaking apparatus for 2 h. The reaction vessel was then drained, and the resin was washed successively with 3×30 mL each of DMF and 1% acetic acid/DMF. The resin was then dried in vacuo to provide resin-bound amine 2-2.

Step 3: Resin-Bound Intermediate 2-3

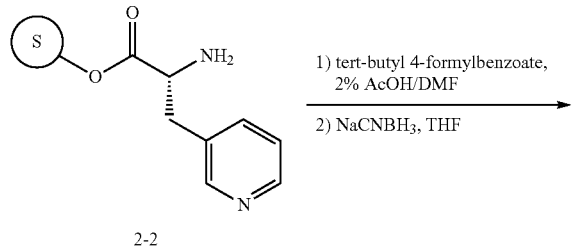

2-2

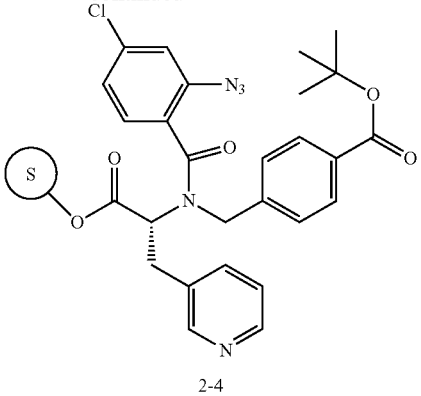

2-4

To the resin-bound secondary amine 2-3 suspended in DCM (30 mL) was added 2-azido-4-chlorobenzoyl chloride 1-2 (1.4 g, 6.8 mmol, prepared as described in step 2 of Example 1a) followed by DIEA (3.9 mL, 23 mmol). The reaction mixture was shaken on a wrist action shaking apparatus for 16 h. The vessel was drained, and the resin washed successively with 3×30 mL each of DCM and o-xylenes. The resin was then dried in vacuo to provide resin-bound amide 2-4.

Step 5: Resin-Bound Intermediate 2-5

2-3

To the resin-bound amine 2-2 was added tert-butyl 4-formylbenzoate (1.4 g, 6.8 mmol) followed by 1% (v/v) acetic acid/DMF (30 mL). This mixture was shaken on a wrist action shaking apparatus for 2 hours. Sodium cyanoborohydride (1.6 g, 23 mmol) was then added, and the reaction mixture was shaken for an additional 16 h. The vessel was drained, and the resin washed successively with 3×30 mL each of DMF and DCM. The resin was then dried in vacuo to provide resin-bound secondary amine 2-3.

Step 4: Resin-Bound Amide 2-4

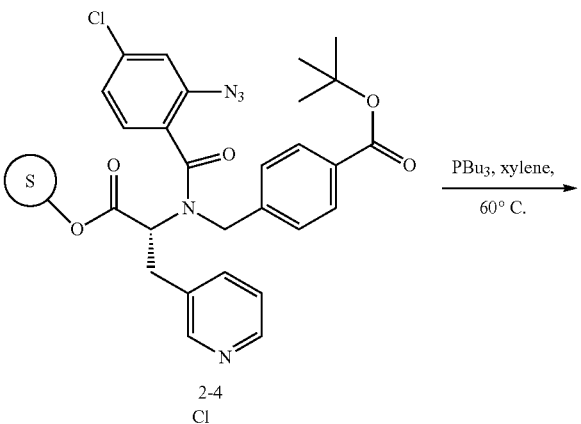

2-5

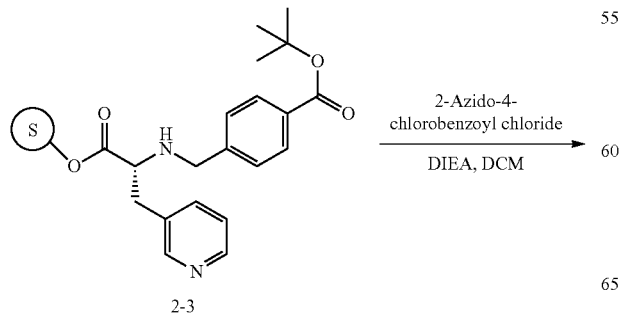

2-3

To the resin-bound amide 2-4 in a 100 mL round bottom flask under N$_2$ atmosphere was added o-xylenes (10 mL) followed by tri-n-butylphosphine (1.7 mL, 6.8 mmol). The reaction mixture was heated to 60° C. for 16 h. The mixture was cooled to room temperature, and transferred to a 100 mL capacity solid-phase synthesis reaction vessel. The vessel was drained, and the resin washed successively with 2×30 mL each of toluene and DCM. The resin was then dried in vacuo to provide resin-bound intermediate 2-5.

Step 6: (R)-4-((8-Chloro-2,5-dioxo-3-(pyridin-3-ylmethyl)-2,3-dihydro-1H-benzo[e][1,4]diazepin-4(5H)-yl)methyl)benzoic Acid (Example 2a)

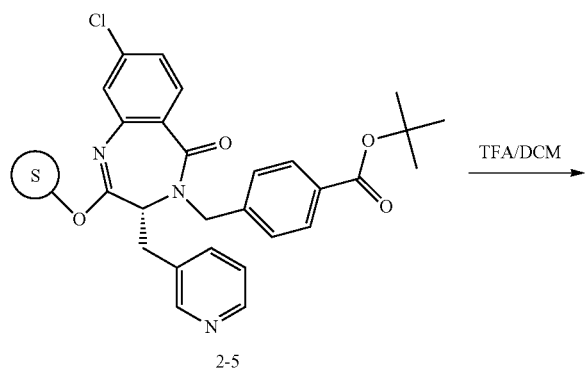

2-5

TFA/DCM

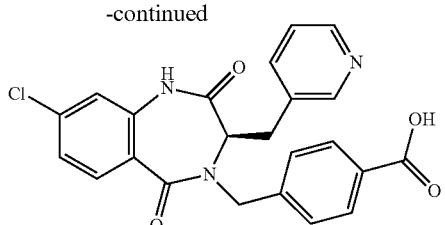

Example 2a

To a 100 mL capacity solid-phase synthesis vessel containing resin-bound intermediate 2-5 was added 10% (v/v) TFA/DCM (30 mL). The resin suspension was shaken on a wrist action shaking apparatus for 2 h. The vessel was then drained collecting the filtrate. The resin was washed successively with 2×30 mL each of DCM and MeOH, and the combined filtrates were concentrated in vacuo. The crude residue was purified by FCC (SiO$_2$; elution with 0-5% MeOH/DCM) to provide 0.14 g (14% over 6 steps) of Example 2a. $^1$H NMR (400 MHz, d$_6$-DMSO, ~1.5:1 mixture of 7-membered ring conformers observed): δ ppm 12.95 (br s, 1H), 10.77 and 10.65 (2s, 1H), 8.48-7.10 (m, 11H), 5.05-4.30 (m, 3H), 3.35-2.71 (m, partially obscured by H$_2$O peak, 2H); LCMS (Method B) t$_R$=1.81 min, m/z 436.2/438.2 (M+H)$^+$.

Following the method described above for Example 2a and substituting the corresponding azido carboxylic acid intermediates and Fmoc-protected amino acid reagents, the following Examples were prepared as indicated in Table 6.

TABLE 6

| Example | Structure | Intermediate and Reagent | LCMS Method | t$_R$ (min) | (M + H)$^+$ observed |
|---|---|---|---|---|---|
| 2b | (S)-4-((8-chloro-3-(3,4-dichlorobenzyl)-2,5-dioxo-2,3-dihydro-1H-benzo[e][1,4]diazepin-4(5H)-yl)methyl)benzoic acid | I.4 and [Fmoc-3,4-dichlorophenylalanine] | A | 1.27 | 503.1/ 505.1/ 507.1 |
| 2c | (S)-4-((8-chloro-3-(4-hydroxybenzyl)-2,5-dioxo-2,3-dihydro-1H-benzo[e][1,4]diazepin-4(5H)-yl)methyl)benzoic acid | I.4 and [Fmoc-tyrosine] | A | 1.02 | 451.1/ 453.1 |

TABLE 6-continued

| Example | Structure | Intermediate and Reagent | LCMS Method | $t_R$ (min) | $(M + H)^+$ observed |
|---|---|---|---|---|---|
| 2d | 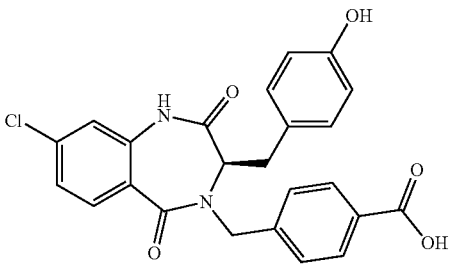<br>(R)-4-((8-chloro-3-(4-hydroxybenzyl)-2,5-dioxo-2,3-dihydro-1H-benzo[e][1,4]diazepin-4(5H)-yl)methyl)benzoic acid | I.4 and<br>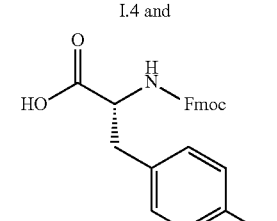 | A | 1.02 | 451.1/<br>453.1 |
| 2e | 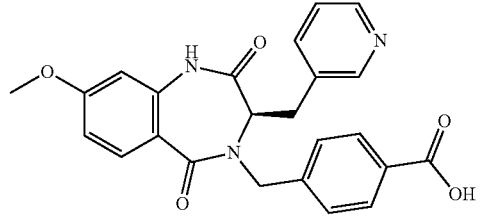<br>(R)-4-((8-methoxy-2,5-dioxo-3-(pyridin-3-ylmethyl)-2,3-dihydro-1H-benzo[e][1,4]diazepin-4(5H)-yl)methyl)benzoic acid | I.1 and<br>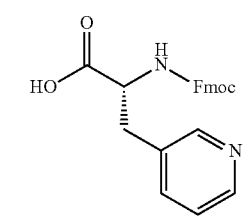 | B | 0.78 | 432.4 |
| 2f | 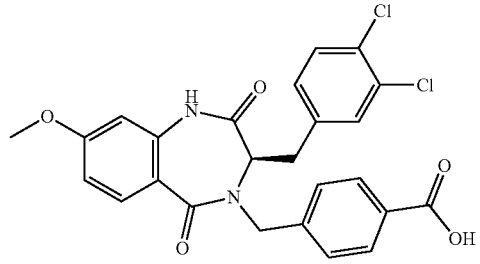<br>(R)-4-((3-(3,4-dichlorobenzyl)-8-methoxy-2,5-dioxo-2,3-dihydro-1H-benzo[e][1,4]diazepin-4(5H)-yl)methyl)benzoic acid | I.1 and<br>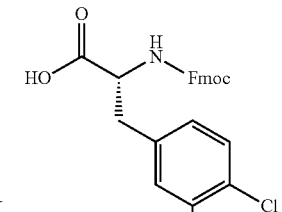 | B | 1.27 | 499.3/<br>501.3/<br>503.3 |
| 2g | 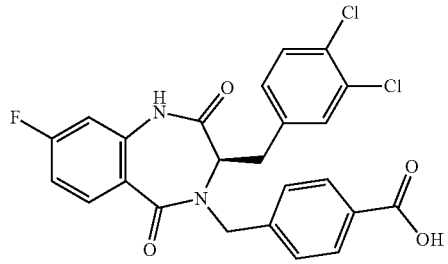<br>(R)-4-((3-(3,4-dichlorobenzyl)-8-fluoro-2,5-dioxo-2,3-dihydro-1H-benzo[e][1,4]diazepin-4(5H)-yl)methyl)benzoic acid | I.2 and<br>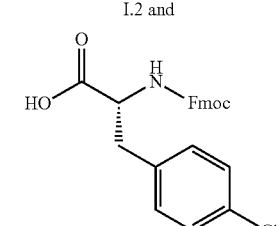 | B | 1.28 | 487.3/<br>489.3/<br>491.3 |

TABLE 6-continued

| Example | Structure | Intermediate and Reagent | LCMS Method | $t_R$ (min) | $(M + H)^+$ observed |
|---|---|---|---|---|---|
| 2h | (R)-4-((3-(3,4-dichlorobenzyl)-8-nitro-2,5-dioxo-2,3-dihydro-1H-benzo[e][1,4]diazepin-4(5H)-yl)methyl)benzoic acid | I.3 and | A | 1.25 | 514.4/ 516.5/ 518.5 |
| 2i | (R)-4-((8-nitro-2,5-dioxo-3-(pyridin-3-ylmethyl)-2,3-dihydro-1H-benzo[e][1,4]diazepin-4(5H)-yl)methyl)benzoic acid | I.3 and | B | 0.83 | 447.3 |

Example 3a (R)-4-((3-Benzyl-8-chloro-2,5-dioxo-2,3-dihydro-1H-benzo[e][1,4]diazepin-4(5H)-yl)methyl)benzoic Acid Step 1: Resin-Bound Aldehyde 3-1

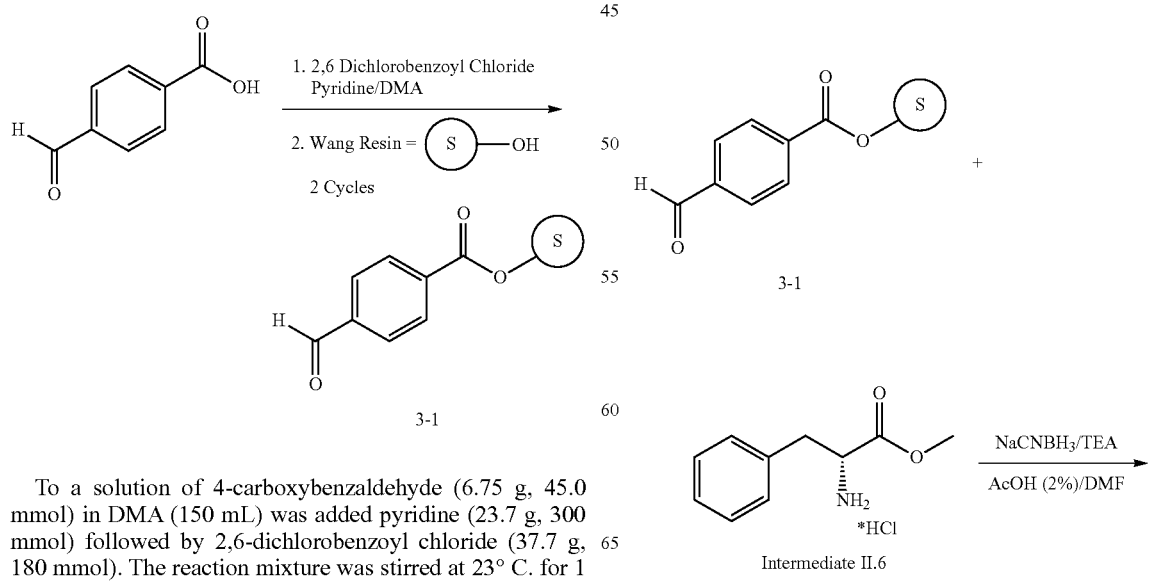

To a solution of 4-carboxybenzaldehyde (6.75 g, 45.0 mmol) in DMA (150 mL) was added pyridine (23.7 g, 300 mmol) followed by 2,6-dichlorobenzoyl chloride (37.7 g, 180 mmol). The reaction mixture was stirred at 23° C. for 1 h. Wang resin (10.0 g, 30.0 mmol, HS, 100-200 mesh, 1% DVB, 3 mmol/g loading) was then added, and the mixture was stirred at 23° C. gently for 20 h. The resin was filtered, washed with dimethylacetamide (3×), and then washed alternately with methanol (3×) and DCM (3×). The resin was then dried in vacuo. The above procedure was repeated a second time to provide resin-bound aldehyde 3-1.

Step 2: Resin-Bound Secondary Amine 3-2

-continued

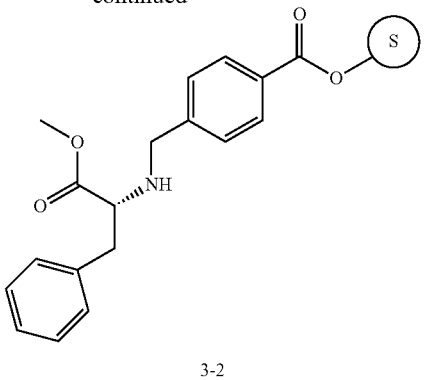

3-2

To (R)-methyl 2-amino-3-phenylpropanoate hydrochloride (Intermediate II.6) in 2% AcOH/DMF (20 mL) was added triethylamine (0.65 g, 6.4 mmol). The mixture was then agitated on an orbital shaker for 5 min. Resin from Step 1 (0.8 g, 1.1 mmol) was added, and the mixture was sonicated briefly, and then placed on an orbital shaker and agitated for 2 h. Sodium cyanoborohydride (0.67 g, 3.2 mmol) was added, and the mixture was agitated on an orbital shaker for 18 h. The resin was filtered and washed successively with DMF (3×) and DCM (3×), and then dried in vacuo to provide resin-bound secondary amine 3-2.

Step 3: Resin-Bound Amide 3-3

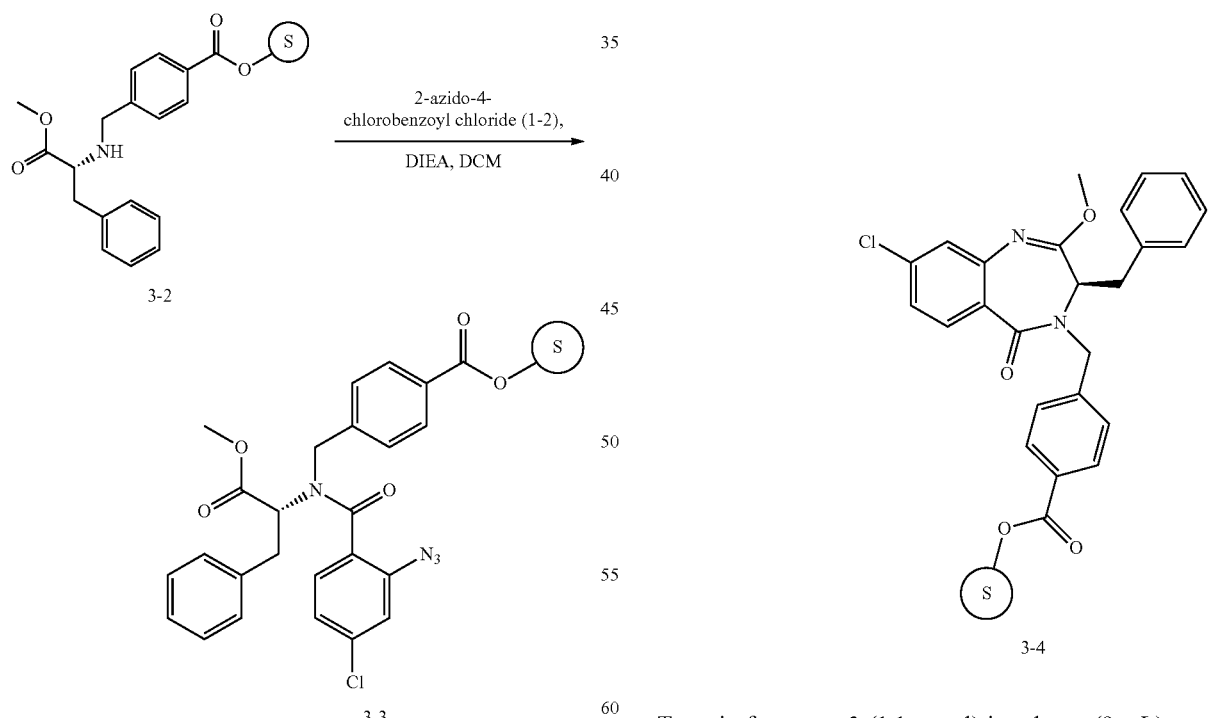

To the resin from step 2 (1.1 mmol) was added a solution of 2-azido-4-chlorobenzoyl chloride (1-2) (0.69 g, 3.2 mmol, prepared as described in step 2 of Example 1a) in DCM (15 mL) followed by DIEA (0.61 g, 5.4 mmol). The mixture was agitated on an orbital shaker for 20 h. The resin was filtered, washed successively with DCM (3×) and toluene (3×), and then dried in vacuo to provide resin-bound amide 3-3.

Step 4: Resin-Bound Intermediate 3-4

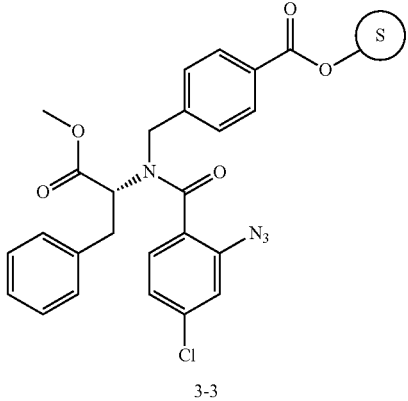

To resin from step 3 (1.1 mmol) in toluene (9 mL) was added tri-n-butylphosphine (0.80 mL, 1.1 mmol). The reaction mixture was heated to 65° C., and stirred gently for 20 h. The mixture was cooled to room temperature. The resin was filtered, washed successively with toluene (2×) and DCM (2×), and then dried in vacuo to provide resin-bound intermediate 3-4.

Step 5: (R)-4-((3-benzyl-8-chloro-2-methoxy-5-oxo-3H-benzo[e][1,4]diazepin-4(5H)-yl)methyl)benzoic Acid (3-5)

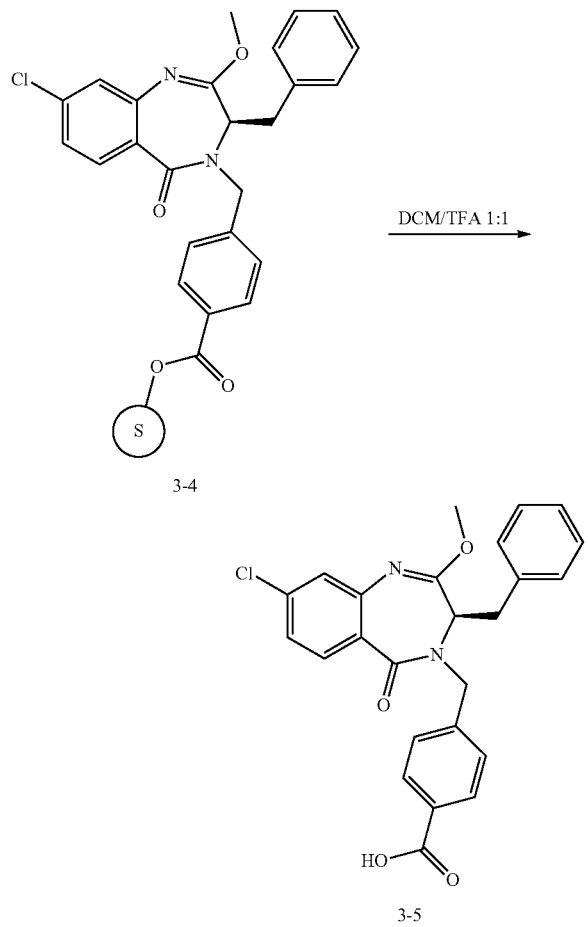

To resin from step 4 (1.1 mmol) was added 50% (v/v) TFA/DCM (10 mL). The mixture was agitated on an orbital stir plate for 45 min. The resin was filtered, washed with DCM (3×), and the combined filtrates were concentrated in vacuo to provide crude benzoic acid 3-5 which was used in the following step without further purification.

Step 6: (R)-4-((3-benzyl-8-chloro-2,5-dioxo-2,3-dihydro-1H-benzo[e][1,4]diazepin-4(5R)-yl)methyl)benzoic Acid (Example 3a)

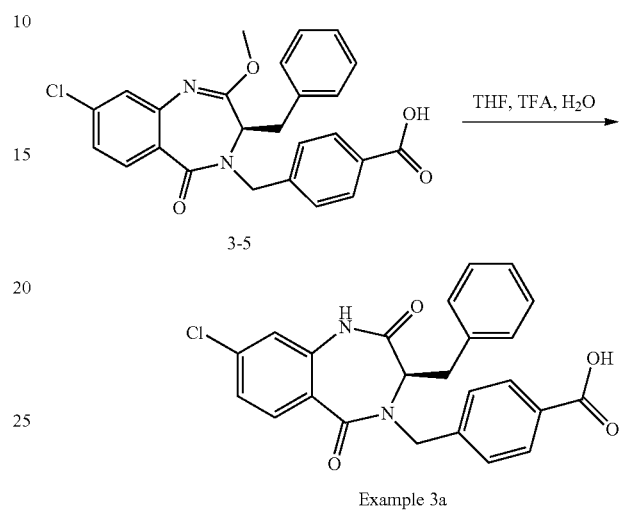

To benzoic acid 3-5 from the previous step were added THF (4 mL), TFA (0.3 mL), and $H_2O$ (0.3 mL). The mixture was stirred at 23° C. for 45 min. The mixture was concentrated in vacuo, and the crude residue was purified by FCC ($SiO_2$, elution with 0-10% MeOH/DCM) to provide 0.10 g (22% over 6 steps) of Example 3a. $^1$H NMR (400 MHz, $d_6$-DMSO, ~1.8:1 mixture of 7-membered ring conformers observed): δ ppm 12.94 (bs, 1H), 10.74 and 10.63 (2 s, 1H, N—H), 7.94-6.97 (m, 12H), 5.06-4.22 (m, 3H), 3.34-2.62 (m, 2H, partially obscured by $H_2O$ peak); LCMS (Method A) $t_R$=1.10 min, m/z 435.3/437.3 (M+H)$^+$.

Following the method described above for Example 3a and substituting the corresponding intermediates or reagents in Step 2, the following Examples were prepared as indicated in Table 7.

TABLE 7

| Example | Structure | Intermediate/reagent | LCMS Method | $t_R$ (min) | (M + H)$^+$ observed |
|---|---|---|---|---|---|
| 3b | (S)-4-((8-chloro-3-methyl-2,5-dioxo-2,3-dihydro-1H-benzo[e][1,4]diazepin-4(5H)-yl)methyl)benzoic acid | | A | 0.88 | 359.2/361.2 |

TABLE 7-continued

| Example | Structure | Intermediate/reagent | LCMS Method | $t_R$ (min) | $(M + H)^+$ observed |
|---|---|---|---|---|---|
| 3c | (R)-4-((8-chloro-2,5-dioxo-3-phenethyl-2,3-dihydro-1H-benzo[e][1,4]diazepin-4(5H)-yl)methyl)benzoic acid | II.4 | A | 1.13 | 449.3/451.3 |
| 3d | (R)-4-((8-chloro-3-(4-fluorobenzyl)-2,5-dioxo-2,3-dihydro-1H-benzo[e][1,4]diazepin-4(5H)-yl)methyl)benzoic acid | II.5 | A | 1.11 | 453.3/455.3 |
| 3e | (R)-4-((8-chloro-3-(4-fluorobenzyl)-2,5-dioxo-2,3-dihydro-1H-benzo[e][1,4]diazepin-4(5H)-yl)methyl)benzoic acid | II.7 | A | 1.18 | 473.3/471.3/473.3 |
| 3f | (R)-4-((8-chloro-3-(3-chlorobenzyl)-2,5-dioxo-2,3-dihydro-1H-benzo[e][1,4]diazepin-4(5H)-yl)methyl)benzoic acid | II.13 | A | 1.16 | 469.3/471.3/473.3 |

TABLE 7-continued

| Example | Structure | Intermediate/ reagent | LCMS Method | $t_R$ (min) | $(M + H)^+$ observed |
|---|---|---|---|---|---|
| 3g | (R)-4-((8-chloro-3-methyl-2,5-dioxo-2,3-dihydro-1H-benzo[e][1,4]diazepin-4(5H)-yl)methyl)benzoic acid | methyl alaninate *HCl | A | 0.88 | 359.2/ 361.2 |
| 3h | (R)-4-((8-chloro-3-(4-methylbenzyl)-2,5-dioxo-2,3-dihydro-1H-benzo[e][1,4]diazepin-4(5H)-yl)methyl)benzoic acid | II.10 | A | 1.16 | 449.3/ 451.3 |
| 3i | (R)-4-((8-chloro-3-(2-chlorobenzyl)-2,5-dioxo-2,3-dihydro-1H-benzo[e][1,4]diazepin-4(5H)-yl)methyl)benzoic acid | II.9 | A | 1.13 | 469.3/ 471.3/ 473.3 |
| 3j | (R)-4-((8-chloro-3-(2-fluorobenzyl)-2,5-dioxo-2,3-dihydro-1H-benzo[e][1,4]diazepin-4(5H)-yl)methyl)benzoic acid | II.19 | A | 1.09 | 453.3/ 455.3 |

TABLE 7-continued

| Example | Structure | Intermediate/reagent | LCMS Method | $t_R$ (min) | $(M + H)^+$ observed |
|---|---|---|---|---|---|
| 3k | (R)-4-((8-chloro-3-isopropyl-2,5-dioxo-2,3-dihydro-1H-benzo[e][1,4]diazepin-4(5H)-yl)methyl)benzoic acid | methyl valinate *HCl | A | 1.03 | 387.2/389.2 |
| 3l | (R)-4-((8-chloro-3-(2-methylbenzyl)-2,5-dioxo-2,3-dihydro-1H-benzo[e][1,4]diazepin-4(5H)-yl)methyl)benzoic acid | II.15 | A | 1.13 | 449.2/451.2 |
| 3m | (R)-4-((8-chloro-3-(3-methylbenzyl)-2,5-dioxo-2,3-dihydro-1H-benzo[e][1,4]diazepin-4(5H)-yl)methyl)benzoic acid | II.16 | A | 1.15 | 449.2/451.2 |
| 3n | (R)-4-((8-chloro-3-(3-cyanobenzyl)-2,5-dioxo-2,3-dihydro-1H-benzo[e][1,4]diazepin-4(5H)-yl)methyl)benzoic acid | II.17 | A | 1.02 | 460.2/462.2 |

TABLE 7-continued

| Example | Structure | Intermediate/reagent | LCMS Method | $t_R$ (min) | $(M + H)^+$ observed |
|---|---|---|---|---|---|
| 3o | ![structure] 4-((8-chloro-2,5-dioxo-2,3-dihydro-1H-benzo[e][1,4]diazepin-4(5H)-yl)methyl)benzoic acid | ![reagent structure] | A | 0.83 | 345.2/347.1 |

Example 4a (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide

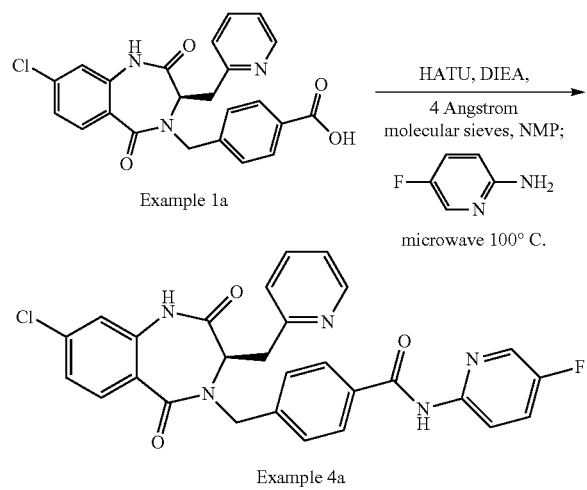

To a mixture of carboxylic acid Example 1a (1.0 g, 2.3 mmol) and powdered 4 Å molecular sieves (100 mg) in NMP (8 mL) in an oven-dried, 5-10 mL capacity microwave vial, were added HATU (0.96 g, 2.5 mmol) and DIEA (0.44 mL, 2.5 mmol). The mixture was stirred under $N_2$ atmosphere for 15 min. 2-Amino-5-fluoropyridine (0.39 g, 3.4 mmol) was then added. The vial was tightly capped, and the mixture was heated to 100° C. in a microwave reactor for 15 minute intervals until LCMS analysis of the reaction mixture indicated complete reaction. The mixture was diluted with EtOAc (100 mL), and washed successively with sat. $NH_4Cl$ (aq) (1×50 mL), sat. $NaHCO_3$ (aq) (1×50 mL), and brine (1×50 mL). The organic layer was dried ($Na_2SO_4$), filtered, and concentrated in vacuo. The crude residue was purified by FCC ($SiO_2$, elution with 0-80% EtOAc/hexanes) followed by further purification by FCC ($SiO_2$; elution with 0-5% MeOH/DCM) to provide 0.78 g (64%) of Example 4a. $^1$H NMR (400 MHz, $CDCl_3$, ~1.7:1 mixture of 7-membered ring conformers observed): δ ppm 8.71-6.75 (m, 15H, partially obscured by solvent peak), 5.15-4.32 (m, 3H), 3.62-2.80 (m, 2H); LCMS (Method A) $t_R$=1.01 min, m/z 530.5/532.5 (M+H)$^+$.

Following the method described above for Example 4a and substituting the corresponding carboxylic acid-based precursors and reagents or intermediates, the following Examples were prepared as indicated in Table 8.

TABLE 8

| Example | Structure | Precursor | Reagent/Intermediate | LCMS Method | $t_R$ (min) | $(M + H)^+$ observed |
|---|---|---|---|---|---|---|
| 4b | ![structure] (R)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide | 1a | ![reagent] | A | 0.73 | 512.4/514.4 |

TABLE 8-continued

| Example | Structure | Precursor | Reagent/ Intermediate | LCMS Method | $t_R$ (min) | $(M + H)^+$ observed |
|---|---|---|---|---|---|---|
| 4c | (R)-4-((8-chloro-2,5-dioxo-3-(pyridin-3-ylmethyl)-2,3-dihydro-1H-benzo[e][1,4]diazepin-4(5H)-yl)methyl)-N-(thiazol-2-yl)benzamide | 2a | H₂N-thiazole | A | 0.80 | 518.3/ 520.3 |
| 4d | (R)-4-((8-chloro-2,5-dioxo-3-(pyridin-3-ylmethyl)-2,3-dihydro-1H-benzo[e][1,4]diazepin-4(5H)-yl)methyl)-N-(1-methyl-1H-pyrazol-3-yl)benzamide | 2a | H₂N-(1-methylpyrazol-3-yl) | A | 0.72 | 515.4/ 517.4 |
| 4e | (R)-4-((8-chloro-2,5-dioxo-3-(pyridin-3-ylmethyl)-2,3-dihydro-1H-benzo[e][1,4]diazepin-4(5H)-yl)methyl)-N-(5-methylisoxazol-3-yl)benzamide | 2a | H₂N-(5-methylisoxazol-3-yl) | A | 0.81 | 516.4/ 518.4 |
| 4f | (S)-4-((8-chloro-3-methyl-2,5-dioxo-2,3-dihydro-1H-benzo[e][1,4]diazepin-4(5H)-yl)methyl)-N-(pyridin-2-yl)benzamide | 3b | H₂N-pyridin-2-yl | A | 0.87 | 435.3/ 437.3 |
| 4g | (R)-4-((8-chloro-2,5-dioxo-3-phenethyl-2,3-dihydro-1H-benzo[e][1,4]diazepin-4(5H)-yl)methyl)-N-(pyridin-2-yl)benzamide | 3c | H₂N-pyridin-2-yl | B | 2.79 | 525.3/ 527.3 |

TABLE 8-continued

| Example | Structure | Precursor | Reagent/ Intermediate | LCMS Method | $t_R$ (min) | $(M + H)^+$ observed |
|---|---|---|---|---|---|---|
| 4h | (R)-4-((3-benzyl-8-chloro-2,5-dioxo-2,3-dihydro-1H-benzo[e][1,4]diazepin-4(5H)-yl)methyl)-N-(pyridin-2-yl)benzamide | 3a | H₂N-pyridin-2-yl | B | 2.70 | 511.2/ 513.2 |
| 4i | (R)-4-((8-chloro-3-(4-fluorobenzyl)-2,5-dioxo-2,3-dihydro-1H-benzo[e][1,4]diazepin-4(5H)-yl)methyl)-N-(pyridin-2-yl)benzamide | 3d | H₂N-pyridin-2-yl | B | 2.74 | 529.3/ 531.2 |
| 4j | (R)-4-((8-chloro-3-(4-chlorobenzyl)-2,5-dioxo-2,3-dihydro-1H-benzo[e][1,4]diazepin-4(5H)-yl)methyl)-N-(pyridin-2-yl)benzamide | 3e | H₂N-pyridin-2-yl | B | 2.87 | 545.3/ 547.2/ 549.2 |
| 4k | (R)-4-((8-chloro-2,5-dioxo-3-(pyridin-3-ylmethyl)-2,3-dihydro-1H-benzo[e][1,4]diazepin-4(5H)-yl)methyl)-N-(3-methylpyridin-2-yl)benzamide | 2a | H₂N-(3-methylpyridin-2-yl) | A | 0.70 | 526.4/ 528.4 |

TABLE 8-continued

| Example | Structure | Precursor | Reagent/Intermediate | LCMS Method | $t_R$ (min) | $(M + H)^+$ observed |
|---|---|---|---|---|---|---|
| 4l | (R)-4-((3-(3,4-dichlorobenzyl)-8-methoxy-2,5-dioxo-2,3-dihydro-1H-benzo[e][1,4]diazepin-4(5H)-yl)methyl)-N-(pyridin-2-yl)benzamide | 2f | H₂N-pyridine | A | 1.11 | 575.4/ 577.4/ 579.4 |
| 4m | (R)-4-((8-chloro-2,5-dioxo-3-(pyridin-3-ylmethyl)-2,3-dihydro-1H-benzo[e][1,4]diazepin-4(5H)-yl)methyl)-N-methyl-N-(pyridin-2-yl)benzamide | 2a | MeHN-pyridine | A | 0.76 | 526.4/ 528.4 |
| 4n | (R)-4-((8-chloro-2,5-dioxo-3-(pyridin-3-ylmethyl)-2,3-dihydro-1H-benzo[e][1,4]diazepin-4(5H)-yl)methyl)-N-(5-methylpyridin-2-yl)benzamide | 2a | H₂N-(5-methylpyridine) | A | 0.76 | 526.3/ 528.3 |
| 4o | (R)-4-((8-chloro-2,5-dioxo-3-(pyridin-3-ylmethyl)-2,3-dihydro-1H-benzo[e][1,4]diazepin-4(5H)-yl)methyl)-N-(6-methylpyridin-2-yl)benzamide | 2a | H₂N-(6-methylpyridine) | A | 0.77 | 526.3/ 528.3 |

TABLE 8-continued

| Example | Structure | Precursor | Reagent/ Intermediate | LCMS Method | $t_R$ (min) | $(M + H)^+$ observed |
|---|---|---|---|---|---|---|
| 4p | (R)-4-((8-methoxy-2,5-dioxo-3-(pyridin-3-ylmethyl)-2,3-dihydro-1H-benzo[e][1,4]diazepin-4(5H)-yl)methyl)-N-(pyridin-2-yl)benzamide | 2e | H₂N-(2-pyridyl) | A | 0.68 | 508.4 |
| 4q | (R)-4-((3-(3,4-dichlorobenzyl)-8-fluoro-2,5-dioxo-2,3-dihydro-1H-benzo[e][1,4]diazepin-4(5H)-yl)methyl)-N-(pyridin-2-yl)benzamide | 2g | H₂N-(2-pyridyl) | A | 1.13 | 563.3/ 565.3/ 567.3 |
| 4r | (R)-4-((8-chloro-2,5-dioxo-3-(pyridin-3-ylmethyl)-2,3-dihydro-1H-benzo[e][1,4]diazepin-4(5H)-yl)methyl)-N-(4-chloropyridin-2-yl)benzamide | 2a | H₂N-(4-chloro-2-pyridyl) | A | 0.90 | 546.3/ 548.3/ 550.3 |
| 4s | (R)-4-((8-chloro-2,5-dioxo-3-(pyridin-3-ylmethyl)-2,3-dihydro-1H-benzo[e][1,4]diazepin-4(5H)-yl)methyl)-N-(4-methylpyridin-2-yl)benzamide | 2a | H₂N-(4-methyl-2-pyridyl) | A | 0.72 | 526.4/ 528.4 |

TABLE 8-continued

| Example | Structure | Precursor | Reagent/ Intermediate | LCMS Method | $t_R$ (min) | $(M + H)^+$ observed |
|---|---|---|---|---|---|---|
| 4t | (R)-4-((8-chloro-2,5-dioxo-3-(pyridin-3-ylmethyl)-2,3-dihydro-1H-benzo[e][1,4]diazepin-4(5H)-yl)methyl)-N-(pyrimidin-4-yl)benzamide | 2a | H$_2$N-pyrimidin-4-yl | A | 0.72 | 513.4/ 515.4 |
| 4u | (R)-4-((8-chloro-2,5-dioxo-3-(pyridin-4-ylmethyl)-2,3-dihydro-1H-benzo[e][1,4]diazepin-4(5H)-yl)methyl)-N-(pyridin-2-yl)benzamide | 1c | H$_2$N-pyridin-2-yl | A | 0.71 | 512.3/ 514.4 |
| 4v | (R)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide | 1a | H$_2$N-pyridin-2-yl | A | 0.83 | 512.3/ 514.4 |
| 4w | (R)-4-((8-chloro-3-(2-chlorobenzyl)-2,5-dioxo-2,3-dihydro-1H-benzo[e][1,4]diazepin-4(5H)-yl)methyl)-N-(pyridin-2-yl)benzamide | 3i | H$_2$N-pyridin-2-yl | A | 1.12 | 545.3/ 547.3 |
| 4x | (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide | 1a | H$_2$N-5-methylpyridin-2-yl | A | 0.85 | 526.3/ 528.3 |

TABLE 8-continued

| Example | Structure | Precursor | Reagent/ Intermediate | LCMS Method | $t_R$ (min) | $(M + H)^+$ observed |
|---|---|---|---|---|---|---|
| 4y | (R)-8-chloro-4-(4-(2,3-dihydro-1H-pyrrolo[2,3-b]pyridine-1-carbonyl)benzyl)-3-methyl-3,4-dihydro-1H-benzo[e][1,4]diazepine-2,5-dione | 3g | 2,3-dihydro-1H-pyrrolo[2,3-b]pyridine | A | 0.91 | 461.5/ 463.5 |
| 4z | (R)-4-((8-chloro-3-methyl-2,5-dioxo-2,3-dihydro-1H-benzo[e][1,4]diazepin-4(5H)-yl)methyl)-N-(pyridin-2-yl)benzamide | 3g | 2-aminopyridine | A | 0.87 | 435.3/ 437.3 |
| 4aa | (R)-4-((8-chloro-3-(3-chlorobenzyl)-2,5-dioxo-2,3-dihydro-1H-benzo[e][1,4]diazepin-4(5H)-yl)methyl)-N-(pyridin-2-yl)benzamide | 3f | 2-aminopyridine | A | 1.13 | 545.3/ 547.3/ 549.3 |
| 4ab | (R)-8-chloro-4-(3-chloro-4-(1H-pyrrolo[2,3-b]pyridine-1-carbonyl)benzyl)-3-(pyridin-2-ylmethyl)-3,4-dihydro-1H-benzo[e][1,4]diazepine-2,5-dione | 7a | 1H-pyrrolo[2,3-b]pyridine | A | 1.13 | 570.3/ 572.3/ 574.3 |
| 4ac | (R)-4-((3-(3,4-dichlorobenzyl)-8-methyl-2,5-dioxo-2,3-dihydro-1H-benzo[e][1,4]diazepin-4(5H)-yl)methyl)-N-(pyridin-2-yl)benzamide | 1e | 2-aminopyridine | D | 0.77 | 559.3/ 561.3/ 562.3 |

TABLE 8-continued

| Example | Structure | Precursor | Reagent/Intermediate | LCMS Method | $t_R$ (min) | $(M + H)^+$ observed |
|---|---|---|---|---|---|---|
| 4ad | (R)-8-chloro-4-(3-chloro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | 7a | Intermediate IV.1 | A | 1.05 | 586.5/ 588.5/ 590.5 |
| 4ae | (R)-4-((3-(3,4-dichlorobenzyl)-8-nitro-2,5-dioxo-2,3-dihydro-1H-benzo[e][1,4]diazepin-4(5H)-yl)methyl)-N-(pyridin-2-yl)benzamide | 2h | H₂N-pyridine | A | 1.15 | 590.3/ 592.3/ 593.4 |
| 4af | (R)-8-chloro-4-(4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | 1a | Intermediate IV.1 | A | 1.02 | 552.5/ 554.5 |
| 4ag | (R)-8-chloro-3-(pyridin-2-ylmethyl)-4-(4-(1,2,3,4-tetrahydro-1,8-naphthyridine-1-carbonyl)benzyl)-3,4-dihydro-1H-benzo[e][1,4]diazepine-2,5-dione | 1a | 1,2,3,4-tetrahydro-1,8-naphthyridine | A | 0.95 | 552.5/ 554.5 |

TABLE 8-continued

| Example | Structure | Precursor | Reagent/Intermediate | LCMS Method | $t_R$ (min) | (M + H)+ observed |
|---|---|---|---|---|---|---|
| 4ah | (R)-8-chloro-4-(4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | 1a | 2,3-dihydro-1H-pyrrolo[2,3-b]pyridine | A | 0.87 | 538.5/ 540.5 |
| 4ai | (R)-4-((8-chloro-3-(2-methylbenzyl)-2,5-dioxo-2,3-dihydro-1H-benzo[e][1,4]diazepin-4(5H)-yl)methyl)-N-(pyridin-2-yl)benzamide | 3l | 2-aminopyridine | A | 1.16 | 525.3/ 527.3 |
| 4aj | (R)-4-((8-chloro-3-(3-methylbenzyl)-2,5-dioxo-2,3-dihydro-1H-benzo[e][1,4]diazepin-4(5H)-yl)methyl)-N-(pyridin-2-yl)benzamide | 3m | 2-aminopyridine | A | 1.18 | 525.3/ 527.3 |
| 4ak | (R)-4-((8-chloro-3-(3-cyanobenzyl)-2,5-dioxo-2,3-dihydro-1H-benzo[e][1,4]diazepin-4(5H)-yl)methyl)-N-(pyridin-2-yl)benzamide | 3n | 2-aminopyridine | A | 1.05 | 536.3/ 538.3 |
| 4al | (R)-4-((8-chloro-2,5-dioxo-3-(thiazol-4-ylmethyl)-2,3-dihydro-1H-benzo[e][1,4]diazepin-4(5H)-yl)methyl)-N-(5-methylpyridin-2-yl)benzamide | 1m | 2-amino-5-methylpyridine | A | 0.94 | 532.3/ 534.3 |

TABLE 8-continued

| Example | Structure | Precursor | Reagent/ Intermediate | LCMS Method | $t_R$ (min) | $(M + H)^+$ observed |
|---|---|---|---|---|---|---|
| 4am | 4-((8-chloro-2,5-dioxo-2,3-dihydro-1H-benzo[e][1,4]diazepin-4(5H)-yl)methyl)-N-(pyridin-2-yl)benzamide | 3o | H₂N-pyridin-2-yl | A | 0.89 | 421.2/ 423.2 |
| 4an | (R)-4-((8-chloro-3-(2-fluorobenzyl)-2,5-dioxo-2,3-dihydro-1H-benzo[e][1,4]diazepin-4(5H)-yl)methyl)-N-(pyridin-2-yl)benzamide | 3j | H₂N-pyridin-2-yl | A | 1.14 | 529.3/ 531.3 |
| 4ao | (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide | 1a | H₂N-(5-methoxypyridin-2-yl) | B | 1.11 | 542.3/ 544.3 |
| 4ap | (R)-4-((8-chloro-2,5-dioxo-3-(pyridin-2-ylmethyl)-2,3-dihydro-1H-benzo[e][1,4]diazepin-4(5H)-yl)methyl)-N-(5-ethylpyridin-2-yl)benzamide | 1a | H₂N-(5-ethylpyridin-2-yl) | B | 1.14 | 540.4/ 542.3 |
| 4aq | (S)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide | 1f | H₂N-pyridin-2-yl | A | 0.90 | 512.3/ 514.2 |

TABLE 8-continued

| Example | Structure | Precursor | Reagent/ Intermediate | LCMS Method | $t_R$ (min) | (M + H)+ observed |
|---|---|---|---|---|---|---|
| 4ar | (R)-8-chloro-4-(3-chloro-4-(2,2-dimethyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | 7a | 2,2-dimethyl-2,3-dihydro-1H-pyrrolo[2,3-b]pyridine | A | 1.19 | 600.3/ 602.3/ 604.3 |
| 4as | (R)-8-chloro-4-(3-chloro-4-(3,3-dimethyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | 7a | 3,3-dimethyl-2,3-dihydro-1H-pyrrolo[2,3-b]pyridine | A | 1.13 | 600.3/ 602.3/ 604.3 |
| 4at | (R)-4-((8-chloro-2,5-dioxo-3-(pyridin-3-ylmethyl)-2,3-dihydro-1H-benzo[e][1,4]diazepin-4(5H)-yl)methyl)-N-(5-isopropylpyridin-2-yl)benzamide | 2a | 5-isopropylpyridin-2-amine | A | 0.95 | 544.4/ 556.4 |
| 4au | (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-(trifluoromethyl)pyridin-2-yl)benzamide | 7d | 5-(trifluoromethyl)pyridin-2-amine | A | 1.28 | 610.2/ 612.2 |

TABLE 8-continued

| Example | Structure | Precursor | Reagent/ Intermediate | LCMS Method | $t_R$ (min) | $(M + H)^+$ observed |
|---|---|---|---|---|---|---|
| 4av | (R)-4-((8-chloro-2,5-dioxo-3-(pyridin-2-ylmethyl)-2,3-dihydro-1H-benzo[e][1,4]diazepin-4(5H)-yl)methyl)-N-(5-morpholinopyridin-2-yl)benzamide | 1a | Intermediate IV.2 | B | 1.04 | 597.4/ 599.4 |
| 4aw | (R)-tert-butyl 4-(6-(4-((8-chloro-2,5-dioxo-3-(pyridin-2-ylmethyl)-2,3-dihydro-1H-benzo[e][1,4]diazepin-4(5H)-yl)methyl)benzamido)pyridin-3-yl)piperazine-1-carboxylate | 1a | Intermediate IV.3 | B | 1.24 | 696.5/ 698.4 |
| 4ax | (R)-4-((8-chloro-2,5-dioxo-3-(pyridin-2-ylmethyl)-2,3-dihydro-1H-benzo[e][1,4]diazepin-4(5H)-yl)methyl)-N-(5-(4-methylpiperazin-1-yl)pyridin-2-yl)benzamide | 1a | Intermediate IV.4 | B | 0.92 | 610.4/ 612.4 |
| 4ay | (R)-4-((8-chloro-3-methyl-2,5-dioxo-2,3-dihydro-1H-benzo[e][1,4]diazepin-4(5H)-yl)methyl)-N-(5-ethylpyridin-2-yl)benzamide | 3g | H₂N-pyridine-ethyl | A | 1.02 | 463.3/ 465.3 |
| 4az | (R)-4-((8-chloro-3-methyl-2,5-dioxo-2,3-dihydro-1H-benzo[e][1,4]diazepin-4(5H)-yl)methyl)-N-(5-isopropylpyridin-2-yl)benzamide | 3g | H₂N-pyridine-isopropyl | A | 1.08 | 477.3/ 479.3 |

TABLE 8-continued

| Example | Structure | Precursor | Reagent/ Intermediate | LCMS Method | $t_R$ (min) | (M + H)+ observed |
|---|---|---|---|---|---|---|
| 4ba | (R)-4-((8-chloro-3-methyl-2,5-dioxo-2,3-dihydro-1H-benzo[e][1,4]diazepin-4(5H)-yl)methyl)-N-(5-methoxypyridin-2-yl)benzamide | 3g | H₂N-pyridine-OMe | A | 1.02 | 465.3/ 467.3 |
| 4bb | (R)-4-((8-chloro-3-methyl-2,5-dioxo-2,3-dihydro-1H-benzo[e][1,4]diazepin-4(5H)-yl)methyl)-N-(isoquinolin-3-yl)benzamide | 3g | H₂N-isoquinoline | A | 1.18 | 485.3/ 487.3 |
| 4bc | (R)-4-((8-chloro-3-methyl-2,5-dioxo-2,3-dihydro-1H-benzo[e][1,4]diazepin-4(5H)-yl)methyl)-N-(5-phenylpyridin-2-yl)benzamide | 3g | H₂N-pyridine-phenyl | A | 1.24 | 511.3/ 513.3 |
| 4bd | (R)-4-((8-bromo-2,5-dioxo-3-(pyridin-3-ylmethyl)-2,3-dihydro-1H-benzo[e][1,4]diazepin-4(5H)-yl)methyl)-N-(pyridin-2-yl)benzamide | 1g | H₂N-pyridine | A | 0.81 | 558.2/ 560.2 |
| 4be | (R)-4-((8-chloro-3-methyl-2,5-dioxo-2,3-dihydro-1H-benzo[e][1,4]diazepin-4(5H)-yl)methyl)-N-(5-methoxypyrimidin-2-yl)benzamide | 3g | H₂N-pyrimidine-OMe | A | 0.92 | 466.3/ 468.3 |

TABLE 8-continued

| Example | Structure | Precursor | Reagent/ Intermediate | LCMS Method | $t_R$ (min) | $(M + H)^+$ observed |
|---|---|---|---|---|---|---|
| 4bf | 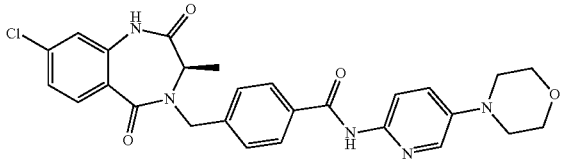 [SMILES: C[C@@H]1C(=O)Nc2cc(Cl)ccc2C(=O)N1Cc1ccc(C(=O)Nc2ccc(N3CCOCC3)cn2)cc1]<br>(R)-4-((8-chloro-3-methyl-2,5-dioxo-2,3-dihydro-1H-benzo[e][1,4]diazepin-4(5H)-yl)methyl)-N-(5-morpholinopyridin-2-yl)benzamide | 3g | Intermediate IV.2 | A | 0.92 | 520.3/ 522.3 |
| 4bg | 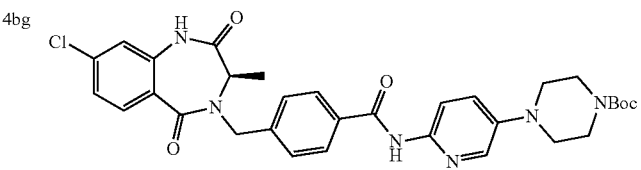<br>(R)-tert-butyl 4-(6-(4-((8-chloro-3-methyl-2,5-dioxo-2,3-dihydro-1H-benzo[e][1,4]diazepin-4(5H)-yl)methyl)benzamido)pyridin-3-yl)piperazine-1-carboxylate | 3g | Intermediate IV.3 | A | 1.12 | 619.4/ 621.4 |
| 4bh | 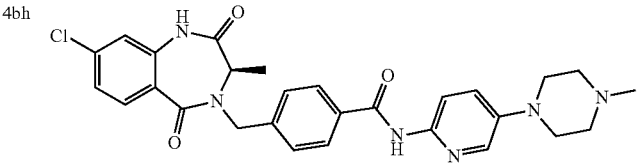<br>(R)-4-((8-chloro-3-methyl-2,5-dioxo-2,3-dihydro-1H-benzo[e][1,4]diazepin-4(5H)-yl)methyl)-N-(5-(4-methylpiperazin-1-yl)pyridin-2-yl)benzamide | 3g | Intermediate IV.4 | A | 0.79 | 533.3/ 535.4 |
| 4bi | 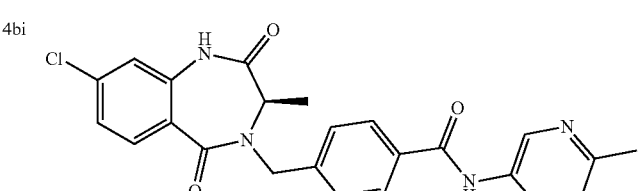<br>(R)-4-((8-chloro-3-methyl-2,5-dioxo-2,3-dihydro-1H-benzo[e][1,4]diazepin-4(5H)-yl)methyl)-N-(5-methylpyrazin-2-yl)benzamide | 3g | 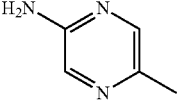 | A | 0.99 | 450.2/ 452.3 |
| 4bj | 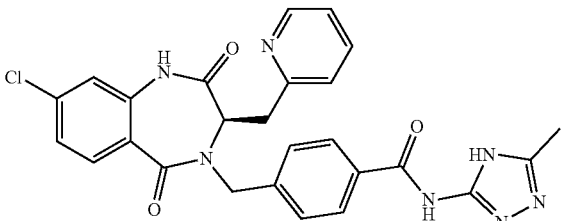<br>(R)-4-((8-chloro-2,5-dioxo-3-(pyridin-2-ylmethyl)-2,3-dihydro-1H-benzo[e][1,4]diazepin-4(5H)-yl)methyl)-N-(5-methyl-4H-1,2,4-triazol-3-yl)benzamide | 1a | 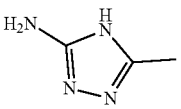 | A | 0.87 | 516.3/ 518.3 |

TABLE 8-continued

| Example | Structure | Precursor | Reagent/ Intermediate | LCMS Method | $t_R$ (min) | (M + H)+ observed |
|---|---|---|---|---|---|---|
| 4bk | (R)-4-((8-chloro-2,5-dioxo-3-(pyridin-2-ylmethyl)-2,3-dihydro-1H-benzo[e][1,4]diazepin-4(5H)-yl)methyl)-N-(3-methyl-1,2,4-thiadiazol-5-yl)benzamide | 1a | H2N-(3-methyl-1,2,4-thiadiazol-5-yl) | A | 0.95 | 533.3/ 535.3 |
| 4bl | (R)-4-((8-chloro-2,5-dioxo-3-(pyridin-2-ylmethyl)-2,3-dihydro-1H-benzo[e][1,4]diazepin-4(5H)-yl)methyl)-N-(pyridazin-3-yl)benzamide | 1a | H2N-pyridazin-3-yl | A | 0.86 | 513.3/ 515.3 |
| 4bm | (R)-4-((8-chloro-2,5-dioxo-3-(pyridin-2-ylmethyl)-2,3-dihydro-1H-benzo[e][1,4]diazepin-4(5H)-yl)methyl)-N-(6-methoxypyridazin-3-yl)benzamide | 1a | H2N-(6-methoxypyridazin-3-yl) | A | 0.93 | 543.4/ 545.3 |
| 4bn | (R)-4-((8-chloro-2,5-dioxo-3-(pyridin-2-ylmethyl)-2,3-dihydro-1H-benzo[e][1,4]diazepin-4(5H)-yl)methyl)-N-(5-methyl-1,3,4-thiadiazol-2-yl)benzamide | 1a | H2N-(5-methyl-1,3,4-thiadiazol-2-yl) | A | 0.92 | 533.3/ 535.3 |
| 4bo | (R)-4-((8-chloro-2,5-dioxo-3-(pyridin-2-ylmethyl)-2,3-dihydro-1H-benzo[e][1,4]diazepin-4(5H)-yl)methyl)-N-(5-methyl-1,3,4-oxadiazol-2-yl)benzamide | 1a | H2N-(5-methyl-1,3,4-oxadiazol-2-yl) | A | 0.82 | 517.4/ 519.4 |

TABLE 8-continued

| Example | Structure | Precursor | Reagent/Intermediate | LCMS Method | $t_R$ (min) | $(M + H)^+$ observed |
|---|---|---|---|---|---|---|
| 4bp | (R)-4-((8-chloro-2,5-dioxo-3-(pyridin-2-ylmethyl)-2,3-dihydro-1H-benzo[e][1,4]diazepin-4(5H)-yl)methyl)-N-(1,3,4-thiadiazol-2-yl)benzamide | 1a | H2N— (1,3,4-thiadiazol-2-amine) | A | 0.88 | 519.3/ 521.3 |
| 4bq | (R)-5-((8-chloro-2,5-dioxo-3-(pyridin-2-ylmethyl)-2,3-dihydro-1H-benzo[e][1,4]diazepin-4(5H)-yl)methyl)-N-(pyridin-2-yl)thiophene-2-carboxamide | 1h | H2N—pyridin-2-yl | A | 0.90 | 518.4/ 520.4 |
| 4br | (R)-5-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)thiophene-2-carboxamide | 1h | H2N—(5-methoxypyridin-2-yl) | A | 0.97 | 548.4/ 550.4 |
| 4bs | (R)-5-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)thiophene-2-carboxamide | 1h | H2N—(5-methylpyridin-2-yl) | A | 0.93 | 532.4/ 534.4 |
| 4bt | (R)-5-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)thiophene-2-carboxamide | 1h | H2N—(5-(trifluoromethyl)pyridin-2-yl) | A | 1.16 | 586.4/ 588.4 |

TABLE 8-continued

| Example | Structure | Precursor | Reagent/ Intermediate | LCMS Method | $t_R$ (min) | $(M + H)^+$ observed |
|---|---|---|---|---|---|---|
| 4bu | 4-((8-chloro-2,5-dioxo-3-(pyrazin-2-ylmethyl)-2,3-dihydro-1H-benzo[e][1,4]diazepin-4(5H)-yl)methyl)-N-(pyridin-2-yl)benzamide | 1l | | A | 0.90 | 513.5/ 515.5 |
| 4bv | (R)-4-((8-chloro-2,5-dioxo-3-(pyridin-3-ylmethyl)-2,3-dihydro-1H-benzo[e][1,4]diazepin-4(5H)-yl)methyl)-N-(1-(hydroxyimino)ethyl)benzamide | 2a | | A | 0.72 | 492.5/ 494.5 |
| 4bw | (R)-4-((8-chloro-2,5-dioxo-3-(pyridin-2-ylmethyl)-2,3-dihydro-1H-benzo[e][1,4]diazepin-4(5H)-yl)methyl)-N-(5-methylthiazol-2-yl)benzamide | 1a | | A | 1.01 | 532.5/ 534.5 |
| 4bx | (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)cyclohexanecarboxamide | 1j | | A | 0.88 | 532.6/ 534.6 |

TABLE 8-continued

| Example | Structure | Precursor | Reagent/ Intermediate | LCMS Method | $t_R$ (min) | $(M + H)^+$ observed |
|---|---|---|---|---|---|---|
| 4by | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide | 7a | H$_2$N-pyridine-OMe (5-methoxy) | A | 1.04 | 576.5/ 578.5/ 580.5 |
| 4bz | (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)cyclohexanecarboxamide | 1j | H$_2$N-pyridine-OMe (5-methoxy) | A | 0.93 | 548.6/ 550.6 |
| 4ca | (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)cyclohexanecarboxamide | 1j | H$_2$N-pyridine-F (5-fluoro) | A | 1.00 | 536.5/ 538.5 |
| 4cb | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide | 7a | H$_2$N-pyridine-Me (5-methyl) | A | 1.03 | 560.5/ 562.5/ 564.5 |
| 4cc | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylthiazol-2-yl)benzamide | 7a | H$_2$N-thiazole-Me (5-methyl) | A | 1.08 | 566.4/ 568.4/ 570.4 |

TABLE 8-continued

| Example | Structure | Precursor | Reagent/Intermediate | LCMS Method | $t_R$ (min) | $(M + H)^+$ observed |
|---|---|---|---|---|---|---|
| 4cd | (R)-8-chloro-4-(3-chloro-4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | 7a | 7-azaindoline | A | 1.01 | 572.5/ 574.5/ 576.5 |
| 4ce | (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)cyclohexanecarboxamide | 1j | 2-amino-5-methoxypyrazine | A | 0.99 | 549.6/ 551.6 |
| 4cf | (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)cyclohexanecarboxamide | 1j | 2-amino-5-methylpyrazine | A | 0.93 | 533.5/ 535.5 |
| 4cg | (R)-8-chloro-4-(((1r,4R)-4-(2,3-dihydro-1H-pyrrolo[2,3-b]pyridine-1-carbonyl)cyclohexyl)methyl)-3-(pyridin-2-ylmethyl)-3,4-dihydro-1H-benzo[e][1,4]diazepine-2,5-dione | 1j | 7-azaindoline | A | 0.91 | 544.5/ 546.5 |

TABLE 8-continued

| Example | Structure | Precursor | Reagent/ Intermediate | LCMS Method | $t_R$ (min) | $(M + H)^+$ observed |
|---|---|---|---|---|---|---|
| 4ch | (R)-8-chloro-3-(pyridin-2-ylmethyl)-4-(((1r,4R)-4-(1,2,3,4-tetrahydro-1,8-naphthyridine-1-carbonyl)cyclohexyl)methyl)-3,4-dihydro-1H-benzo[e][1,4]diazepine-2,5-dione | 1j | 1,2,3,4-tetrahydro-1,8-naphthyridine | A | 0.93 | 558.5/ 560.5 |
| 4ci | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide | 7a | 5-methoxypyrazin-2-amine | A | 1.06 | 577.5/ 579.4/ 581.4 |
| 4cj | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide | 7a | pyridin-2-amine | A | 1.00 | 546.4/ 548.3/ 550.3 |
| 4ck | (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyridin-2-yl)benzamide | 7b | 5-methylpyridin-2-amine | A | 0.96 | 540.4/ 542.4 |
| 4cl | (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)-2-methylbenzamide | 7b | 5-methoxypyridin-2-amine | A | 0.99 | 556.5/ 558.5 |

TABLE 8-continued

| Example | Structure | Precursor | Reagent/ Intermediate | LCMS Method | $t_R$ (min) | (M + H)+ observed |
|---|---|---|---|---|---|---|
| 4cm | (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyridin-2-yl)benzamide | 7d | H₂N-pyridine-methyl | A | 1.02 | 556.4/ 558.4 |
| 4cn | (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyridin-2-yl)benzamide | 7d | H₂N-pyridine-OMe | A | 1.04 | 572.4/ 574.4 |
| 4co | (R)-4-((8-chloro-3-(4-methylbenzyl)-2,5-dioxo-2,3-dihydro-1H-benzo[e][1,4]diazepin-4(5H)-yl)methyl)-N-(pyridin-2-yl)benzamide | 3h | H₂N-pyridine | A | 1.13 | 525.4/ 527.4 |

Example 5a (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide

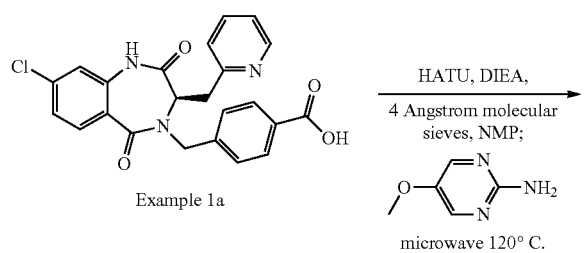

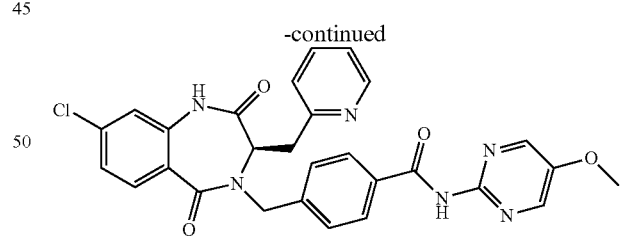

Example 5a

To a mixture of carboxylic acid Example 1a (0.10 g, 0.23 mmol) and powdered 4 Å molecular sieves (40 mg) in NMP (1 mL) in an oven dried, 0.5-2 mL capacity microwave vial, were added HATU (0.11 g, 0.28 mmol) and DIEA (0.048 mL, 0.28 mmol). The mixture was stirred under N₂ atmosphere for 15 min. 2-Amino-5-methoxypyrimidine (0.14 g, 1.2 mmol) was added. The vial was tightly capped, and the mixture was heated in a microwave reactor at 120° C. for 1 h intervals until LCMS analysis of the reaction mixture indicated complete reaction. The mixture was diluted with EtOAc (30 mL), and washed successively with sat. NH₄Cl (aq) (1×10 mL), sat. NaHCO₃ (aq) (1×10 mL), and brine (1×10 mL). The organic phase was dried (Na₂SO₄), filtered, and concentrated in vacuo. The crude residue was purified by FCC (12 g SiO₂, gradient elution with 0-5% MeOH/DCM) followed by further purification by reverse-phase semi-preparative scale HPLC to give 21 mgs (17% yield) of Example 5a. ¹H NMR (400 MHz, CDCl₃, ~1.6:1 mixture of 7-membered ring conformers observed): δ ppm 8.84-6.73 (m, 15H, partially obscured by solvent peak), 5.15-4.38 (m, 3H), 3.91 (s, 3H), 3.61-2.78 (m, 2H); LCMS (Method A) $t_R$=0.85 min, m/z 543.5/545.5 (M+H)⁺.

Following the method described above for Example 5a and substituting the corresponding carboxylic acid-based precursors and reagents, the following Examples were prepared as indicated in Table 9.

TABLE 9

| Example | Structure | Precursor | Reagent | LCMS Method | $t_R$ (min) | (M + H)⁺ observed |
|---|---|---|---|---|---|---|
| 5b | (R)-4-((8-chloro-2,5-dioxo-3-(pyridin-3-ylmethyl)-2,3-dihydro-1H-benzo[e][1,4]diazepin-4(5H)-yl)methyl)-N-(pyrimidin-2-yl)benzamide | 2a | H₂N-pyrimidin-2-yl | B | 0.80 | 513.4/ 515.3 |
| 5c | (R)-4-((8-chloro-2,5-dioxo-3-(pyridin-3-ylmethyl)-2,3-dihydro-1H-benzo[e][1,4]diazepin-4(5H)-yl)methyl)-N-(pyrazin-2-yl)benzamide | 2a | H₂N-pyrazin-2-yl | A | 0.73 | 513.4/ 515.4 |
| 5d | (R)-4-((8-chloro-2,5-dioxo-3-(pyridin-3-ylmethyl)-2,3-dihydro-1H-benzo[e][1,4]diazepin-4(5H)-yl)methyl)-N-(5-chloropyridin-2-yl)benzamide | 2a | H₂N-(5-chloropyridin-2-yl) | A | 0.90 | 546.4/ 548.4/ 550.4 |
| 5e | (R)-4-((8-chloro-2,5-dioxo-3-(pyridin-3-ylmethyl)-2,3-dihydro-1H-benzo[e][1,4]diazepin-4(5H)-yl)methyl)-N-(3-chloropyridin-2-yl)benzamide | 2a | H₂N-(3-chloropyridin-2-yl) | A | 0.76 | 546.3/ 548.3/ 550.4 |

TABLE 9-continued

| Example | Structure | Precursor | Reagent | LCMS Method | $t_R$ (min) | $(M + H)^+$ observed |
|---|---|---|---|---|---|---|
| 5f | (R)-2-(benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide | 8c | H2N—pyridine-CF3 | A | 1.28 | 700.5/ 702.5 |
| 5g | (R)-4-((8-chloro-2,5-dioxo-3-(pyridin-3-ylmethyl)-2,3-dihydro-1H-benzo[e][1,4]diazepin-4(5H)-yl)methyl)-N-(5-methoxypyridin-2-yl)benzamide | 2a | H2N—pyridine-OMe | A | 0.80 | 542.3/ 544.3 |
| 5h | (R)-4-((8-chloro-2,5-dioxo-3-(pyridin-3-ylmethyl)-2,3-dihydro-1H-benzo[e][1,4]diazepin-4(5H)-yl)methyl)-N-(5-methylpyrimidin-2-yl)benzamide | 2a | H2N—pyrimidine-Me | B | 0.89 | 527.3/ 529.3 |
| 5i | (R)-4-((8-chloro-2,5-dioxo-3-(pyridin-3-ylmethyl)-2,3-dihydro-1H-benzo[e][1,4]diazepin-4(5H)-yl)methyl)-N-(4-methylpyrimidin-2-yl)benzamide | 2a | H2N—pyrimidine-Me | A | 0.73 | 527.3/ 529.3 |

TABLE 9-continued

| Example | Structure | Precursor | Reagent | LCMS Method | $t_R$ (min) | $(M + H)^+$ observed |
|---|---|---|---|---|---|---|
| 5j | (R)-4-((8-chloro-2,5-dioxo-3-(pyridin-3-ylmethyl)-2,3-dihydro-1H-benzo[e][1,4]diazepin-4(5H)-yl)methyl)-N-(6-methoxypyridin-4-yl)benzamide | 2a | H₂N-(6-methoxypyridin-4-yl) | A | 0.85 | 543.3/ 545.4 |
| 5k | (R)-4-((8-chloro-2,5-dioxo-3-(pyridin-3-ylmethyl)-2,3-dihydro-1H-benzo[e][1,4]diazepin-4(5H)-yl)methyl)-N-(5-ethylpyridin-2-yl)benzamide | 2a | H₂N-(5-ethylpyridin-2-yl) | A | 0.86 | 540.4/ 542.4 |
| 5l | (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)benzamide | 1a | H₂N-(5-methylpyrimidin-2-yl) | B | 0.98 | 527.3/ 529.3 |
| 5m | (R)-4-((8-chloro-2,5-dioxo-3-(pyridin-3-ylmethyl)-2,3-dihydro-1H-benzo[e][1,4]diazepin-4(5H)-yl)methyl)-N-(5-methoxypyrimidin-2-yl)benzamide | 2a | H₂N-(5-methoxypyrimidin-2-yl) | A | 0.76 | 543.3/ 545.3 |
| 5n | (R)-4-((8-chloro-3-methyl-2,5-dioxo-2,3-dihydro-1H-benzo[e][1,4]diazepin-4(5H)-yl)methyl)-N-(quinazolin-2-yl)benzamide | 3g | H₂N-quinazolin-2-yl | A | 0.99 | 486.3/ 488.3 |

TABLE 9-continued

| Example | Structure | Precursor | Reagent | LCMS Method | $t_R$ (min) | $(M + H)^+$ observed |
|---|---|---|---|---|---|---|
| 5o | (R)-4-((8-chloro-3-methyl-2,5-dioxo-2,3-dihydro-1H-benzo[e][1,4]diazepin-4(5H)-yl)methyl)-N-(6-methylpyrazin-2-yl)benzamide | 3g | H₂N-pyrazine-methyl | A | 0.89 | 450.3/ 452.3 |
| 5p | (R)-N-(1H-benzo[d]imidazol-2-yl)-4-((8-chloro-3-methyl-2,5-dioxo-2,3-dihydro-1H-benzo[e][1,4]diazepin-4(5H)-yl)methyl)benzamide | 3g | 2-aminobenzimidazole | A | 0.91 | 474.3/ 476.2 |
| 5q | (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide | 1a | H₂N-pyridine-CF₃ | A | 1.15 | 580.4/ 582.4 |
| 5r | (R)-5-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)thiophene-2-carboxamide | 1h | H₂N-pyrimidine-OMe | A | 0.84 | 549.4/ 551.4 |
| 5s | (R)-5-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)thiophene-2-carboxamide | 1h | H₂N-pyrimidine-methyl | A | 0.84 | 533.5/ 535.5 |

TABLE 9-continued

| Example | Structure | Precursor | Reagent | LCMS Method | $t_R$ (min) | $(M + H)^+$ observed |
|---|---|---|---|---|---|---|
| 5t | (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide | 1a | H₂N-(5-methylpyrazin-2-yl) | A | 0.91 | 527.5/ 529.5 |
| 5u | (R)-4-((8-chloro-2,5-dioxo-3-(pyridin-2-ylmethyl)-2,3-dihydro-1H-benzo[e][1,4]diazepin-4(5H)-yl)methyl)-N-(pyrazin-2-yl)benzamide | 1a | H₂N-(pyrazin-2-yl) | A | 0.88 | 513.5/ 515.5 |
| 5v | (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide | 1a | H₂N-(5-methoxypyrazin-2-yl) | A | 1.01 | 543.5/ 545.5 |
| 5w | 4-((8-chloro-2,5-dioxo-3-(pyrazin-2-ylmethyl)-2,3-dihydro-1H-benzo[e][1,4]diazepin-4(5H)-yl)methyl)-N-(5-methoxypyridin-2-yl)benzamide | 1l | H₂N-(5-methoxypyridin-2-yl) | A | 1.03 | 543.5/ 545.5 |
| 5x | 4-((8-chloro-2,5-dioxo-3-(pyrazin-2-ylmethyl)-2,3-dihydro-1H-benzo[e][1,4]diazepin-4(5H)-yl)methyl)-N-(5-methylpyridin-2-yl)benzamide | 1l | H₂N-(5-methylpyridin-2-yl) | A | 1.01 | 527.5/ 529.5 |

TABLE 9-continued

| Example | Structure | Precursor | Reagent | LCMS Method | $t_R$ (min) | $(M + H)^+$ observed |
|---|---|---|---|---|---|---|
| 5y | 4-((8-chloro-2,5-dioxo-3-(pyrazin-2-ylmethyl)-2,3-dihydro-1H-benzo[e][1,4]diazepin-4(5H)-yl)methyl)-N-(5-methoxypyrimidin-2-yl)benzamide | 11 | H₂N-pyrimidine-OMe | A | 0.99 | 544.5/ 546.5 |
| 5z | 4-((8-chloro-2,5-dioxo-3-(pyrazin-2-ylmethyl)-2,3-dihydro-1H-benzo[e][1,4]diazepin-4(5H)-yl)methyl)-N-(5-methylpyrimidin-2-yl)benzamide | 11 | H₂N-pyrimidine-Me | A | 1.02 | 528.5/ 530.5 |
| 5aa | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide | 7a | H₂N-pyrazine-Me | A | 0.99 | 561.5/ 563.5/ 565.5 |
| 5ab | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide | 7a | H₂N-pyrimidine-OMe | A | 0.92 | 577.5/ 579.5/ 581.5 |
| 5ac | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(3-fluoropyridin-2-yl)benzamide | 7a | H₂N-pyridine-F | A | 0.95 | 564.4/ 566.5/ 568.5 |

TABLE 9-continued

| Example | Structure | Precursor | Reagent | LCMS Method | $t_R$ (min) | $(M + H)^+$ observed |
|---|---|---|---|---|---|---|
| 5ad | (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)cyclohexanecarboxamide | 1j | 2-amino-5-methylpyrimidine | A | 1.00 | 533.5/ 535.5 |
| 5ae | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide | 7a | 2-amino-5-(trifluoromethyl)pyridine | A | 1.21 | 614.3/ 616.3/ 618.3 |
| 5af | (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)-2-methylbenzamide | 7b | 2-amino-5-methoxypyrazine | A | 1.02 | 557.5/ 559.4/ |
| 5ag | (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrimidin-2-yl)benzamide | 7b | 2-amino-5-methylpyrimidine | A | 0.88 | 541.4/ 543.4 |
| 5ah | (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrazin-2-yl)benzamide | 7b | 2-amino-5-methylpyrazine | A | 0.95 | 541.4/ 543.4 |

TABLE 9-continued

| Example | Structure | Precursor | Reagent | LCMS Method | $t_R$ (min) | $(M + H)^+$ observed |
|---|---|---|---|---|---|---|
| 5ai | (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)-2-methylbenzamide | 7b | H₂N-(5-methoxypyrimidin-2-yl) | A | 0.89 | 557.4/ 559.4 |
| 5aj | (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrazin-2-yl)benzamide | 7d | H₂N-(5-methylpyrazin-2-yl) | A | 1.01 | 557.4/ 559.4 |
| 5ak | (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrazin-2-yl)benzamide | 7d | H₂N-(5-methoxypyrazin-2-yl) | A | 1.09 | 573.3/ 575.3/ |
| 5al | (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl)pyridin-2-yl)benzamide | 7b | H₂N-(5-(trifluoromethyl)pyridin-2-yl) | A | 1.18 | 594.3/ 596.3 |
| 5am | (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrimidin-2-yl)benzamide | 7d | H₂N-(5-methylpyrimidin-2-yl) | A | 0.97 | 557.2/ 559.2 |

TABLE 9-continued

| Example | Structure | Precursor | Reagent | LCMS Method | $t_R$ (min) | $(M + H)^+$ observed |
|---|---|---|---|---|---|---|
| 5an | (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrimidin-2-yl)benzamide | 7d | H₂N-pyrimidine-OMe | A | 0.98 | 573.2/ 575.2 |
| 5ao | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide | 7a | H₂N-pyridine-F | A | 1.07 | 564.1/ 566.1/ 568.1 |
| 5ap | (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)-2-methylbenzamide | 7b | H₂N-pyridine-F | A | 1.03 | 544.2/ 546.2 |
| 5aq | (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)-2-methoxybenzamide | 7d | H₂N-pyridine-F | A | 1.08 | 560.2/ 562.2 |
| 5ar | (R)-2-bromo-4-((8-chloro-3-methyl-2,5-dioxo-2,3-dihydro-1H-benzo[e][1,4]diazepin-4(5H)-yl)methyl)-N-(5-(trifluoromethyl)pyridin-2-yl)benzamide | 1n | H₂N-pyridine-CF₃ | A | 1.30 | 581.3/ 583.3/ 585.2 |

TABLE 9-continued

| Example | Structure | Precursor | Reagent | LCMS Method | $t_R$ (min) | $(M + H)^+$ observed |
|---|---|---|---|---|---|---|
| 5as | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)benzamide | 7a | H₂N-(5-methylpyrimidin-2-yl) | A | 0.92 | 561.5/ 563.5/ 565.5 |
| 5at | (R)-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)-2-methylbenzamide | 7b | H₂N-(5-cyanopyridin-2-yl) | A | 1.04 | 551.4/ 553.4 |
| 5au | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)benzamide | 7a | H₂N-(5-cyanopyridin-2-yl) | A | 1.09 | 571.4/ 573.4/ 575.4 |
| 5av | (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(methylsulfonyl)pyridin-2-yl)benzamide | 7a | H₂N-(5-SO₂Me-pyridin-2-yl) | A | 1.18 | 624.4/ 626.4/ 628.4 |
| 5aw | (R)-8-chloro-4-(3-chloro-4-(3,3-dimethyl-5-(trifluoromethyl)-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | 7a | 3,3-dimethyl-5-(trifluoromethyl)-2,3-dihydro-1H-pyrrolo[2,3-b]pyridine | A | 1.31 | 668.4/ 670.4/ 672.4 |

TABLE 9-continued

| Example | Structure | Precursor | Reagent | LCMS Method | $t_R$ (min) | $(M + H)^+$ observed |
|---|---|---|---|---|---|---|
| 5ax | (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)cyclohexanecarboxamide | 1j | H₂N-pyrimidine-OMe | A | 1.00 | 549.5/ 551.5 |
| 5ay | (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(methylsulfonyl)pyridin-2-yl)benzamide | 7b | H₂N-pyridine-SO₂Me | A | 0.96 | 604.5/ 606.4 |

Example 6a (R)-4-((8-Chloro-2,5-dioxo-3-(pyridin-2-ylmethyl)-2,3-dihydro-1H-benzo[e][1,4]diazepin-4(5H)-yl)methyl)-2-fluoro-N-(5-methoxypyridin-2-yl)benzamide

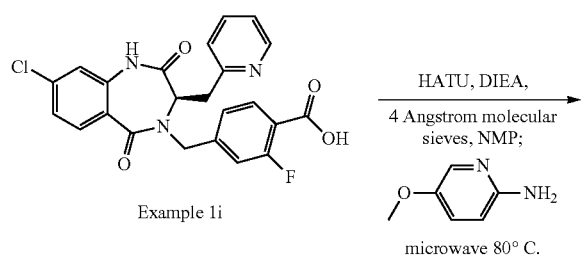

Example 1i → HATU, DIEA, 4 Angstrom molecular sieves, NMP; microwave 80° C.

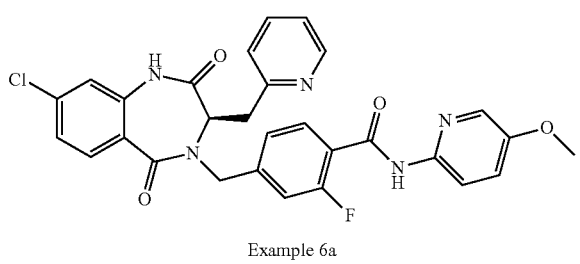

Example 6a

To a mixture of carboxylic acid Example 1i (0.50 g, 1.1 mmol) and powdered 4 Å molecular sieves (100 mg) in NMP (5 mL) in an oven dried, 2-5 mL capacity microwave vial, were added HATU (0.11 g, 0.28 mmol) and DIEA (0.048 mL, 0.28 mmol). The mixture was stirred under N₂ atmosphere for 15 min. 2-Amino-5-methoxypyridine (0.21 g, 1.7 mmol) was added. The vial was tightly capped, and the mixture was heated in a microwave reactor at 80° C. for 5 min intervals until LCMS analysis of the reaction mixture indicated complete reaction. The mixture was diluted with EtOAc (100 mL), and washed successively with sat. NH₄Cl (aq) (1×10 mL), sat. NaHCO₃ (aq) (1×10 mL), and brine (1×10 mL). The organic phase was dried (Na₂SO₄), filtered, and concentrated in vacuo. The crude residue was purified by FCC (SiO₂, elution with 0-80% EtOAc/hexanes). The semi-pure material was further purified by FCC (SiO₂, elution with 0-5% MeOH/EtOAc) to give 459 mgs (75%) of Example 6a. $^1$H NMR (400 MHz, CDCl₃, ~1.8:1 mixture of 7-membered ring conformers observed): δ ppm 10.81 and 10.71 (2s, 1H, N—H), 10.61 and 10.57 (2s, 1H, N—H), 8.47-7.03 (m, 13H), 5.07-4.32 (m, 3H), 3.58-2.81 (m, 2H); LCMS (Method A) $t_R$=1.02 min, m/z 560.5/562.5 (M+H)⁺.

Following the method described above for Example 6a and substituting the corresponding reagents, the following Examples were prepared as indicated in Table 10.

TABLE 10

| Example | Structure | Reagent | LCMS Method | $t_R$ (min) | $(M + H)^+$ observed |
|---|---|---|---|---|---|
| 6b | (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(pyridin-2-yl)benzamide | 2-aminopyridine | A | 1.08 | 530.5/ 532.5 |
| 6c | (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-fluoropyridin-2-yl)benzamide | 2-amino-5-fluoropyridine | A | 1.16 | 548.5/ 550.5 |
| 6d | (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methylpyridin-2-yl)benzamide | 2-amino-5-methylpyridine | A | 1.00 | 544.5/ 546.5 |
| 6e | (R)-8-chloro-4-(4-(2,3-dihydro-1H-pyrrolo[2,3-b]pyridine-1-carbonyl)-3-fluorobenzyl)-3-(pyridin-2-ylmethyl)-3,4-dihydro-1H-benzo[e][1,4]diazepine-2,5-dione | 2,3-dihydro-1H-pyrrolo[2,3-b]pyridine | A | 0.96 | 556.5/ 558.5 |

TABLE 10-continued

| Example | Structure | Reagent | LCMS Method | $t_R$ (min) | $(M + H)^+$ observed |
|---|---|---|---|---|---|
| 6f | (R)-8-chloro-4-(3-fluoro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | | A | 1.01 | 570.4/ 572.4 |

Example 7a (R)-2-Chloro-4-((8-chloro-2,5-dioxo-3-(pyridin-2-ylmethyl)-2,3-dihydro-1H-benzo[e][1,4]diazepin-4(5H)-yl)methyl)benzoic Acid Steps 1-2: (R)-Methyl 4-((2-azido-4-chloro-N-(1-methoxy-1-oxo-3-(pyridin-2-yl)propan-2-yl)benzamido)methyl)-2-chlorobenzoate (7-2)

Intermediate II.2 *2 HCl  →  Intermediate III.1, Et₃N, MeOH; NaCNBH₃, HOAc 7-1  +  1-2  →  DIPEA, DCM, DMAP (cat.)  →  7-2

(R)-Methyl 4-((2-azido-4-chloro-N-(1-methoxy-1-oxo-3-(pyridin-2-yl)propan-2-yl)benzamido)methyl)-2-chlorobenzoate (7-2) was prepared from Intermediate II.2, Intermediate III.1 and acid chloride 1-2 using the same general procedures described for the preparation of compound 1-3 in Example 1a. LCMS (Method A) $t_R$=1.34 min, m/z 584.2/586.2/588.2 (M+H)⁺.

Step 3: (R)-2-Chloro-4-((8-chloro-2,5-dioxo-3-(pyridin-2-ylmethyl)-2,3-dihydro-1H-benzo[e][1,4]diazepin-4(5H)-yl)methyl)benzoic Acid (Example 7a)

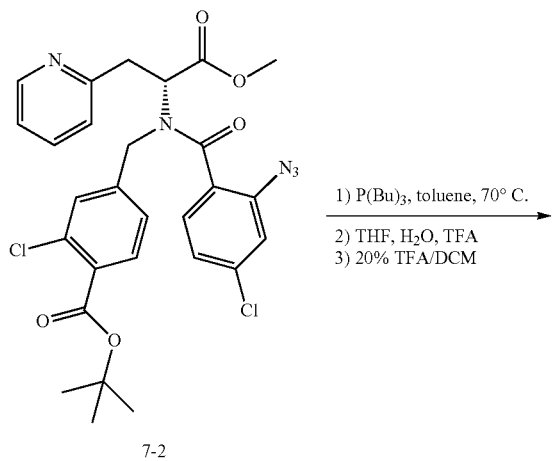

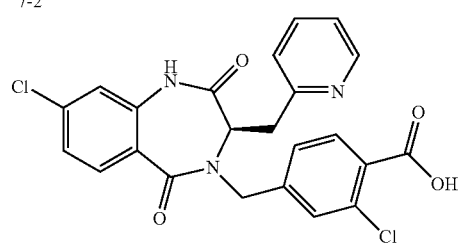

Example 7a

To a solution of 7-2 (1.5 g, 2.6 mmol) in toluene (20 mL) was added tri-n-butylphosphine (0.71 mL, 2.8 mmol). The reaction mixture was heated to 70° C., and stirred at this temperature for 16 h. The mixture was then cooled, and concentrated in vacuo. The residue was dissolved in THF (20 mL), H$_2$O (2 mL) and TFA (2 mL), and the resultant mixture was stirred at 23° C. for 16 h. The mixture was then concentrated in vacuo, and the residue was treated with 20% TFA/DCM (20 mL). The mixture was allowed to stand for 2 h at ambient temperature. This was then concentrated in vacuo. The residue was taken up in 1N NaOH (aq) (50 mL) and washed with EtOAc (3×50 mL). The aqueous phase was then acidified to pH 5 with 1 N HCl (aq) and extracted with 3:1 CHCl$_3$/i-PrOH (3×100 mL). The combined organic extracts were dried (Na$_2$SO$_4$), filtered, and concentrated in vacuo. The crude residue was purified by FCC (elution with 0-20% MeOH/DCM) to provide 0.82 g (68%) of Example 7a. $^1$H NMR (400 MHz, d$_6$-DMSO, ~1.7:1 mixture of 7-membered ring conformers observed) δ ppm 13.37 (br s, 1H), 10.79 and 10.69 (2s, 1H, N—B), 8.44-7.01 (m, 10H), 5.04-4.26 (m, 3H), 3.52-2.78 (m, 2H); LCMS (Method A) t$_R$=0.90 min, m/z 470.2/472.2/474.2 (M+H)$^+$.

Following the method described above for Example 7a and substituting the corresponding intermediates, the following Examples were prepared as indicated in Table 11.

TABLE 11

| Example | Structure | Intermediates | LCMS Method | t$_R$ (min) | (M + H)$^+$ observed |
|---|---|---|---|---|---|
| 7b | (R)-4-((8-chloro-2,5-dioxo-3-(pyridin-2-ylmethyl)-2,3-dihydro-1H-benzo[e][1,4]diazepin-4(5H)-yl)methyl)-2-methylbenzoic acid | II.1 and III.2 | A | 0.90 | 450.4/452.3 |
| 7c | (R)-2,6-dichloro-4-((8-chloro-2,5-dioxo-3-(pyridin-2-ylmethyl)-2,3- | II.1 and III.4 | A | 0.86 | 504.3/506.3/508.3/ |

TABLE 11-continued

| Example | Structure | Intermediates | LCMS Method | $t_R$ (min) | (M + H)+ observed |
|---|---|---|---|---|---|
| | dihydro-1H-benzo[e][1,4]diazepin-4(5H)-yl)methyl)benzoic acid | | | | |
| 7d | 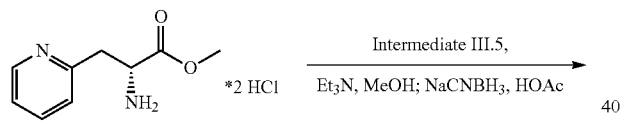<br>(R)-4-((8-chloro-2,5-dioxo-3-(pyridin-2-ylmethyl)-2,3-dihydro-1H-benzo[e][1,4]diazepin-4(5H)-yl)methyl)-2-methoxybenzoic acid | II.1 and III.3 | A | 0.88 | 466.4/<br>468.4 |

Example 8a (R)-4-((8-Chloro-2,5-dioxo-3-(pyridin-2-ylmethyl)-2,3-dihydro-1H-benzo[e][1,4]diazepin-4(5H)-yl)methyl)-2-(pyridin-4-yl)benzoic Acid Steps 1-3: (R)-Methyl 2-bromo-4-((8-chloro-2,5-dioxo-3-(pyridin-2-ylmethyl)-2,3-dihydro-1H-benzo[e][1,4]diazepin-4(5H)-yl)methyl)benzoate (8-3)

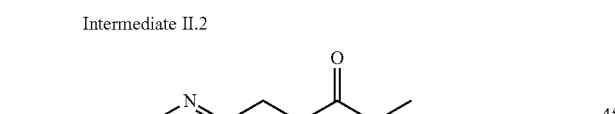

Intermediate II.2

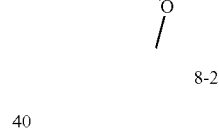
Intermediate III.5,
Et₃N, MeOH; NaCNBH₃, HOAc

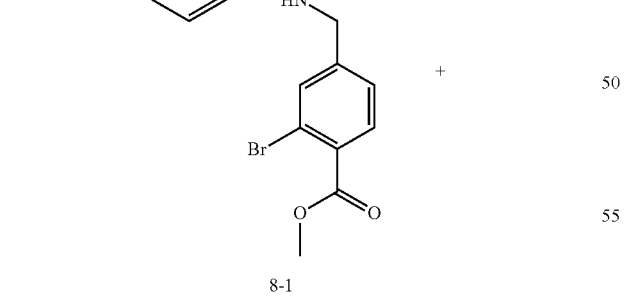

8-1

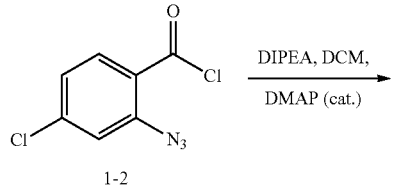

1-2

DIPEA, DCM,
DMAP (cat.)

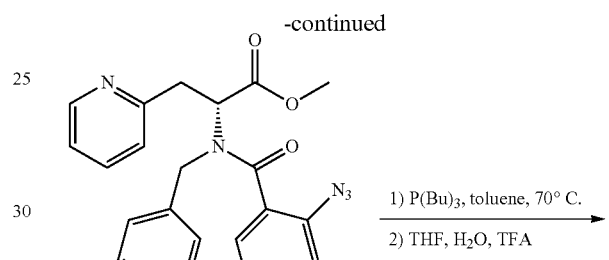

8-2

1) P(Bu)₃, toluene, 70° C.
2) THF, H₂O, TFA

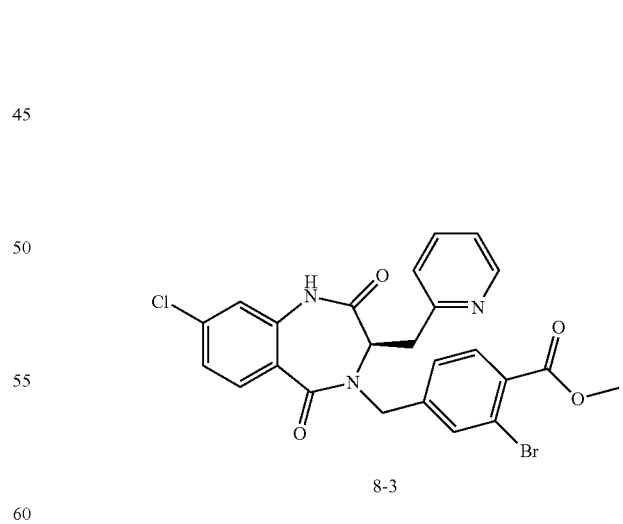

8-3

(R)-Methyl 2-bromo-4-((8-chloro-2,5-dioxo-3-(pyridin-2-ylmethyl)-2,3-dihydro-1H-benzo[e][1,4]diazepin-4(5H)-yl)methyl)benzoate (8-3) was prepared from Intermediate II.2, Intermediate III.5 and acid chloride 1-2 using the same general procedures described for the preparation of compound 1-4 in the synthesis of Example 1a.

Step 4: (R)-Methyl 4-((8-chloro-2,5-dioxo-3-(pyridin-2-ylmethyl)-2,3-dihydro-1H-benzo[e][1,4]diazepin-4(5H)-yl)methyl)-2-(pyridin-4-yl)benzoate (8-4)

Step 5: (R)-4-((8-Chloro-2,5-dioxo-3-(pyridin-2-ylmethyl)-2,3-dihydro-1H-benzo[e][1,4]diazepin-4(5H)-yl)methyl)-2-(pyridin-4-yl)benzoic Acid (Example 8a)

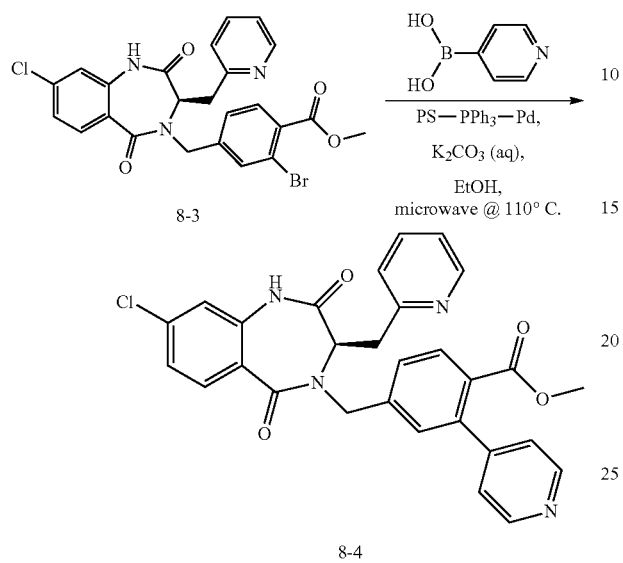

8-3

8-4

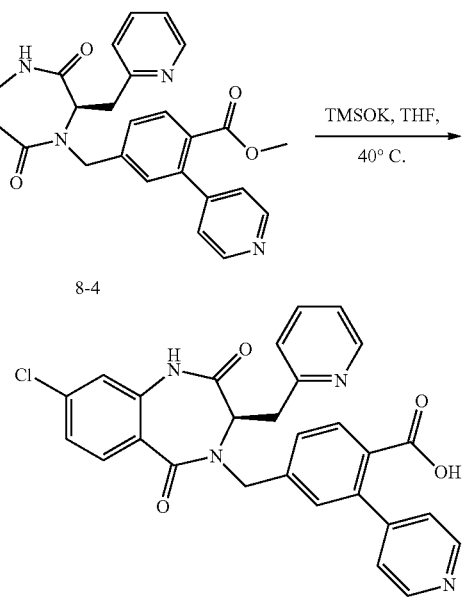

8-4

Example 8a

A 0.5-2 mL capacity microwave vessel was charged with 8-3 (53 mg, 0.10 mmol), 4-pyridinylboronic acid (17 mg, 0.14 mmol), and EtOH (1 mL). To this mixture were added 1 N K$_2$CO$_3$ (aq) (140 mL) and PS-PPh$_3$-Pd (Biotage, loading 0.11 mmol/g, 45 mg, 0.0050 mmol). The vessel was tightly capped, and heated to 110° C. in a microwave reactor for 15 minute intervals until LCMS analysis of the reaction mixture indicated complete reaction. The reaction mixture was then applied to a cartridge containing 1 g of 3-(trimethylammonium)propyl-functionalized silica gel, carbonate (Aldrich, loading 0.8 mmol/g) which had been preconditioned with 1:1 MeOH/DCM. The cartridge was further eluted with 1:1 MeOH/DCM (3×2 mL) collecting the eluent by gravity filtration. The combined eluent was concentrated in vacuo, and the crude product 8-4 was carried into the next step without further purification.

To a solution of methyl ester 8-4 from the previous step in THF (1 mL) was added potassium trimethylsilanolate (64 mg, 0.50 mmol). The reaction mixture was heated at 40° C. for 2 h. The mixture was then cooled to room temperature, and concentrated in vacuo. The crude residue was purified by reverse-phase semi-preparative scale HPLC to provide 20 mg (39% for 2 steps) of Example 8a. $^1$H NMR (400 MHz, CDCl$_3$ w/drop of CD$_3$OD, ~1.2:1 mixture of 7-membered ring conformers observed): δ ppm 8.54-6.77 (m, 14H, partially obscured by solvent peak), 5.13-4.13 (m, 3H), 3.59-2.82 (m, 2H); LCMS (Method A) t$_R$=0.76 min, m/z 513.3/515.3 (M+H)$^+$.

Following the method described above for Example 8a and substituting the corresponding reagents, the following Examples were prepared as indicated in Table 12.

TABLE 12

| Example | Structure | Reagent | LCMS Method | t$_R$ (min) | (M + H)$^+$ observed |
|---|---|---|---|---|---|
| 8b | (R)-5-((8-chloro-2,5-dioxo-3-(pyridin-2-ylmethyl)-2,3-dihydro-1H-benzo[e][1,4]diazepin-4(5H)- | (HO)$_2$B-aryl-OMe | A | 1.02 | 542.4/ 544.4 |

TABLE 12-continued

| Example | Structure | Reagent | LCMS Method | $t_R$ (min) | $(M + H)^+$ observed |
|---|---|---|---|---|---|
| | yl)methyl)-3'-methoxy-[1,1'-biphenyl]-2-carboxylic acid | | | | |
| 8c | (R)-2-(benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)benzoic acid | (HO)₂B—benzo[1,3]dioxole | A | 1.00 | 556.3/ 558.3 |
| 8d | (R)-5-((8-chloro-2,5-dioxo-3-(pyridin-2-ylmethyl)-2,3-dihydro-1H-benzo[e][1,4]diazepin-4(5H)-yl)methyl)-4'-fluoro-[1,1'-biphenyl]-2-carboxylic acid | (HO)₂B—C₆H₄—F | A | 1.04 | 530.3/ 532.3 |
| 8e | (R)-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid | (HO)₂B—C₆H₅ | A | 1.01 | 512.3/ 514.3 |

TABLE 12-continued

| Example | Structure | Reagent | LCMS Method | $t_R$ (min) | $(M + H)^+$ observed |
|---|---|---|---|---|---|
| 8f | (R)-5-((8-chloro-2,5-dioxo-3-(pyridin-2-ylmethyl)-2,3-dihydro-1H-benzo[e][1,4]diazepin-4(5H)-yl)methyl)-4'-methoxy-[1,1'-biphenyl]-2-carboxylic acid | (HO)₂B—C₆H₄—OMe | A | 1.01 | 542.3/ 544.3 |
| 8g | (R)-5-((8-chloro-2,5-dioxo-3-(pyridin-2-ylmethyl)-2,3-dihydro-1H-benzo[e][1,4]diazepin-4(5H)-yl)methyl)-4'-methyl-[1,1'-biphenyl]-2-carboxylic acid | (HO)₂B—C₆H₄—CH₃ (para) | A | 1.06 | 526.3/ 528.3 |
| 8h | (R)-5-((8-chloro-2,5-dioxo-3-(pyridin-2-ylmethyl)-2,3-dihydro-1H-benzo[e][1,4]diazepin-4(5H)-yl)methyl)-3'-methyl-[1,1'-biphenyl]-2-carboxylic acid | (HO)₂B—C₆H₄—CH₃ (meta) | A | 1.06 | 526.3/ 528.3 |

TABLE 12-continued

| Example | Structure | Reagent | LCMS Method | $t_R$ (min) | $(M + H)^+$ observed |
|---|---|---|---|---|---|
| 8i | (R)-4'-chloro-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid | (HO)₂B—⟨⟩—Cl | A | 1.09 | 546.3/ 548.3/ 550.3 |
| 8j | (R)-3'-chloro-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid | (HO)₂B—⟨⟩—Cl | A | 1.09 | 546.2/ 548.2/ 550.2 |
| 8k | (R)-5-((8-chloro-2,5-dioxo-3-(pyridin-2-ylmethyl)-2,3-dihydro-1H-benzo[e][1,4]diazepin-4(5H)-yl)methyl)-3'-fluoro-[1,1'-biphenyl]-2-carboxylic acid | (HO)₂B—⟨⟩—F | A | 1.04 | 530.3/ 532.3 |

TABLE 12-continued

| Example | Structure | Reagent | LCMS Method | $t_R$ (min) | $(M + H)^+$ observed |
|---|---|---|---|---|---|
| 8l | (R)-3'-chloro-5-((8-chloro-2,5-dioxo-3-(pyridin-2-ylmethyl)-2,3-dihydro-1H-benzo[e][1,4]diazepin-4(5H)-yl)methyl)-4'-fluoro-[1,1'-biphenyl]-2-carboxylic acid | (HO)₂B—C₆H₃(Cl)(F) | A | 1.11 | 564.3/ 566.3/ 568.3 |
| 8m | (R)-4-((8-chloro-2,5-dioxo-3-(pyridin-2-ylmethyl)-2,3-dihydro-1H-benzo[e][1,4]diazepin-4(5H)-yl)methyl)-2-(pyridin-3-yl)benzoic acid | (HO)₂B—pyridin-3-yl | A | 0.78 | 513.3/ 515.3 |
| 8n | (R)-4'-acetamido-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid | (HO)₂B—C₆H₄—NHAc | A | 0.89 | 569.4/ 571.4 |

TABLE 12-continued

| Example | Structure | Reagent | LCMS Method | $t_R$ (min) | $(M + H)^+$ observed |
|---|---|---|---|---|---|
| 8o | (R)-5-((8-chloro-2,5-dioxo-3-(pyridin-2-ylmethyl)-2,3-dihydro-1H-benzo[e][1,4]diazepin-4(5H)-yl)methyl)-4'-(methylcarbamoyl)-[1,1'-biphenyl]-2-carboxylic acid | (HO)₂B—C₆H₄—C(O)NHMe | A | 0.87 | 569.4/ 571.4 |
| 8p | (R)-5-((8-chloro-2,5-dioxo-3-(pyridin-2-ylmethyl)-2,3-dihydro-1H-benzo[e][1,4]diazepin-4(5H)-yl)methyl)-3'-(methylcarbamoyl)-[1,1'-biphenyl]-2-carboxylic acid | (HO)₂B—C₆H₄—C(O)NHMe (meta) | A | 0.90 | 569.4/ 571.4 |
| 8q | (R)-3'-acetamido-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid | (HO)₂B—C₆H₄—NHAc | A | 0.91 | 569.3/ 571.3 |

TABLE 12-continued

| Example | Structure | Reagent | LCMS Method | $t_R$ (min) | $(M + H)^+$ observed |
|---|---|---|---|---|---|
| 8r | (R)-4-((8-chloro-2,5-dioxo-3-(pyridin-2-ylmethyl)-2,3-dihydro-1H-benzo[e][1,4]diazepin-4(5H)-yl)methyl)-2-(1H-pyrazol-4-yl)benzoic acid | (HO)₂B-pyrazole | A | 0.81 | 502.4/504.2 |
| 8s | (R)-4-((8-chloro-2,5-dioxo-3-(pyridin-2-ylmethyl)-2,3-dihydro-1H-benzo[e][1,4]diazepin-4(5H)-yl)methyl)-2-(1-methyl-1H-pyrazol-5-yl)benzoic acid | (HO)₂B-(1-methylpyrazole) | A | 0.90 | 516.3/518.2 |
| 8t | 4-(((R)-8-chloro-2,5-dioxo-3-(pyridin-2-ylmethyl)-2,3-dihydro-1H-benzo[e][1,4]diazepin-4(5H)-yl)methyl)-2-(3,5-dimethylisoxazol-4-yl)benzoic acid | (HO)₂B-(3,5-dimethylisoxazole) | A | 0.95 | 531.3/533.4 |

TABLE 12-continued

| Example | Structure | Reagent | LCMS Method | $t_R$ (min) | $(M + H)^+$ observed |
|---|---|---|---|---|---|
| 8u | (R)-4-((8-chloro-2,5-dioxo-3-(pyridin-2-ylmethyl)-2,3-dihydro-1H-benzo[e][1,4]diazepin-4(5H)-yl)methyl)-2-(1-methyl-1H-pyrazol-4-yl)benzoic acid | $(HO)_2B$ attached to 1-methyl-1H-pyrazol-4-yl | A | 0.85 | 516.4/ 518.4 |

Example 9a (R)-4-((8-Chloro-3-(2-hydroxyethyl)-2,5-dioxo-2,3-dihydro-1H-benzo[e][1,4]diazepin-4(5H)-yl)methyl)-N-(5-methylpyridin-2-yl)benzamide Step 1: (R)-Methyl 4-((8-chloro-3-(2-hydroxyethyl)-2,5-dioxo-2,3-dihydro-1H-benzo[e][1,4]diazepin-4(5H)-yl)methyl)benzoate (9-1)

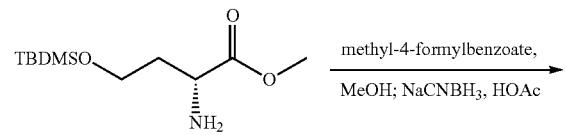

Intermediate II.27

To a solution of Intermediate II.27 (0.80 g, 3.2 mmol) in MeOH (15 mL) was added methyl-4-formylbenzoate (584 mg, 3.56 mmol). The resultant mixture was stirred at 23° C. for 10 min. Then sodium cyanoborohydride (224 mg, 3.56 mmol) was added followed by acetic acid (0.18 mL, 3.2 mmol), and the reaction mixture was stirred at 23° C. for 16 h. The mixture was then concentrated in vacuo, and the crude residue was taken up in EtOAc (50 mL) and washed with 1 N NaOH (aq). The aqueous phase was extracted with EtOAc (2×50 mL), and the combined organic extracts were washed with brine (1×50 mL), dried ($Na_2SO_4$), filtered and concentrated in vacuo. The crude residue was purified by FCC ($SiO_2$, elution with 0-5% MeOH/DCM) to provide 737 mg (58%) of 9-1. $^1$H NMR (400 MHz, $CDCl_3$): δ ppm 7.99 (d, 2H), (m, 3H), 7.41 (d, 2H), 3.92-3.66 (m, 4H), 3.92 (s, 3H), 3.73 (s, 3H), 3.44 (dd, 1H), 1.92 (m, 1H), 1.77 (m, 1H), 0.87 (s, 9H), 0.038 (s, 6H); LCMS (Method B) $t_R$=1.26 min, m/z 396.3 $(M+H)^+$.

Step 2: (R)-Methyl 4-((2-azido-N-(4-((tert-butyldimethylsilyl)oxy)-1-methoxy-1-oxobutan-2-yl)-4-chlorobenzamido)methyl)benzoate (9-2)

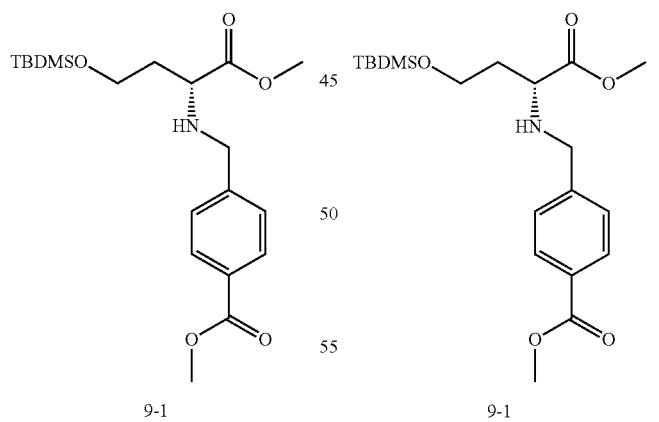

9-1

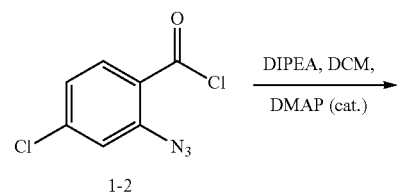

1-2

-continued

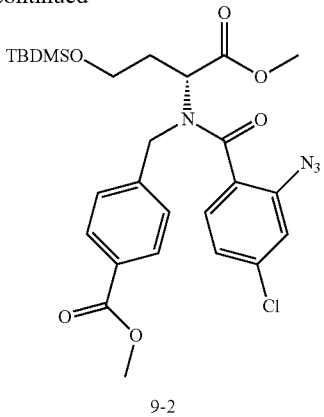

9-2

To a solution of acid chloride 1-2 (0.67 g, 3.1 mmol) (for preparation see step 2 of Example 1a) in DCM (6 mL) was added amine 9-1 (1.1 g, 2.8 mmol) as a solution in DCM (5 mL) followed by DIPEA (0.68 mL, 3.9 mmol) and catalytic DMAP. The reaction mixture was stirred at 23° C. for 3 d. The mixture was then concentrated in vacuo. The crude residue was taken up in EtOAc (200 mL), and washed successively with 1 N HCl (aq) (1×100 mL), sat. NaHCO$_3$ (aq) (1×100 mL), and brine (1×100 mL). The organic phase was then dried (Na$_2$SO$_4$), filtered, and concentrated in vacuo. The crude residue was purified by FCC (SiO$_2$, elution with 0-50% EtOAc/hexanes) to provide 1.4 g (89%) of 9-2. LCMS (Method D) $t_R$=1.57 min, m/z 575.4/577.4 (M+H)$^+$.

Step 3: (R)-Methyl 4-((8-chloro-3-(2-hydroxyethyl)-2,5-dioxo-2,3-dihydro-1H-benzo[e][1,4]diazepin-4(5H)-yl)methyl)benzoate (9-3)

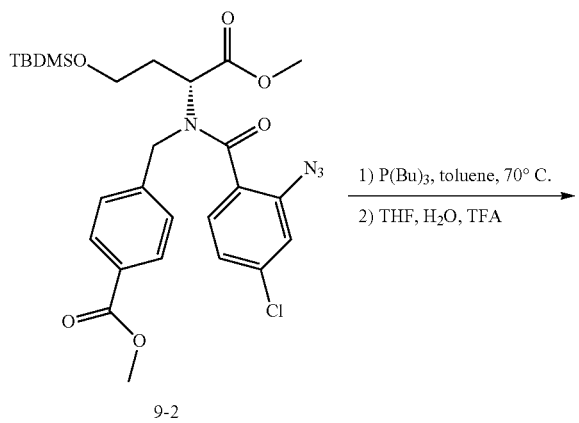

Following the general procedure described in Step 4 of Example 1a, 9-2 (1.43 g, 2.49 mmol) was reacted with PBu$_3$ (0.68 mL, 2.74 mmol) to provide 0.93 g (93%) of 9-3 after purification by FCC (SiO$_2$, elution with 0-100% EtOAc/hexanes). LCMS (Method A) $t_R$=0.95 min, m/z 403.3/405.3 (M+H)$^+$.

Step 4: (R)-Methyl 4-((3-(2-((tert-butyldimethylsilyl)oxy)ethyl)-8-chloro-2,5-dioxo-2,3-dihydro-1H-benzo[e][1,4]diazepin-4(5H)-yl)methyl)benzoate (9-4)

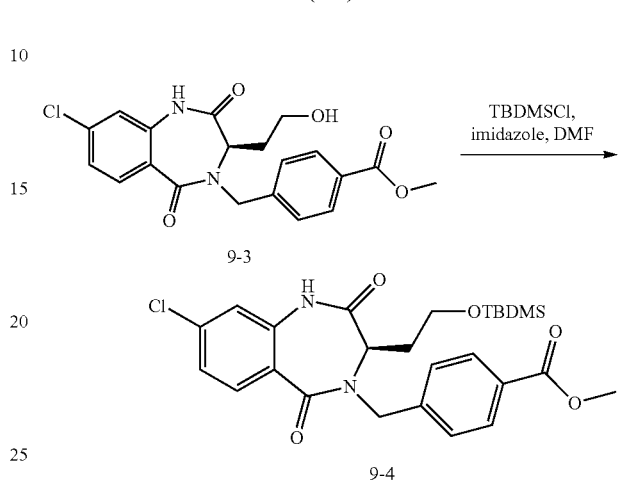

To a solution of alcohol 9-3 (1.03 g, 2.56 mmol) in DMF (10 mL) were added TBDMSCl (463 mg, 3.07 mmol) and imidazole (420 mg, 6.14 mmol). The reaction mixture was stirred at 23° C. for 24 h. The mixture was then diluted with EtOAc (100 mL), and washed successively with 1 N HCl (aq) (1×100 mL), sat. NaHCO$_3$ (aq) (1×100 mL) and brine (1×100 mL). The organic phase was then dried (Na$_2$SO$_4$), filtered, and concentrated in vacuo. The crude residue was purified by FCC (SiO$_2$, elution with 0-50% EtOAc/hexanes) to provide 0.96 g (73%) of 9-4. $^1$H NMR (400 MHz, CDCl$_3$, ~1.4:1 mixture of 7-membered ring conformers observed): δ ppm 8.02-6.88 (m, 8H, partially obscured by solvent peak), 5.23-4.62 (m, 2H), 4.47 and 4.33 (2m, 1H), 3.89 and 3.88 (2s, 3H), 3.59-3.43 (m, 2H), 2.33-1.47 (m, 2H), 0.86 and 0.65 (2s, 9H), 0.01, −0.12 and −0.14 (3s, 6H); LCMS (Method D) $t_R$=1.36 min, m/z 517.4/519.4 (M+H)$^+$.

Step 5: (R)-4-((3-(2-((tert-Butyldimethylsilyl)oxy)ethyl)-8-chloro-2,5-dioxo-2,3-dihydro-1H-benzo[e][1,4]diazepin-4(5H)-yl)methyl)benzoic Acid (9-5)

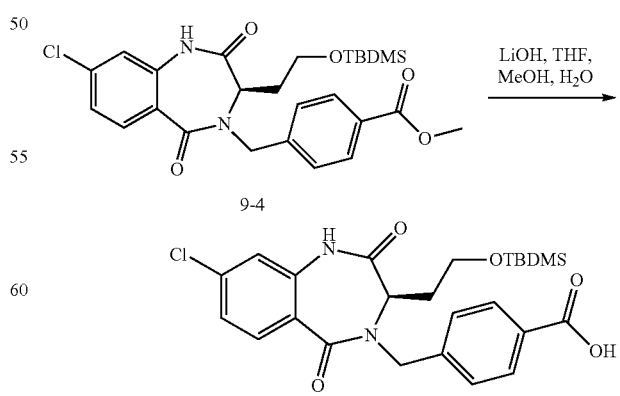

To a solution of methyl ester 9-4 (961 mg, 1.86 mmol) in THF (4 mL), MeOH (4 mL) and water (2 mL) was added LiOH (134 mg, 5.58 mmol). The reaction mixture was stirred at 23° C. for 3 d. The mixture was then concentrated in vacuo. The residue was taken up in water (50 mL), and washed with Et$_2$O (2×50 mL). The aqueous phase was acidified to pH 1 with 1 N HCl (aq), and then extracted with EtOAc (3×50 mL). The combined organic extracts were then dried (Na$_2$SO$_4$), filtered, and concentrated in vacuo to provide 944 mg of crude product which was used without purification in the next step.

Step 6: (R)-4-((8-Chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide (9-6)

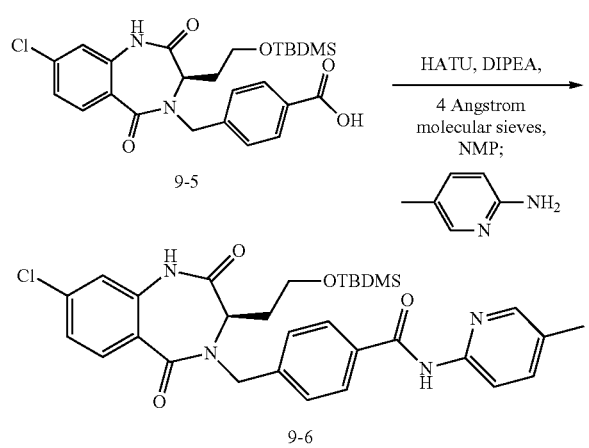

Following the general procedure described in Example 4a, carboxylic acid 9-5 (51 mg, 0.10 mmol) was coupled with 6-amino-3-picoline (55 mg, 0.51 mmol). After workup as described in Example 4a, the crude product was used in the next step without further purification.

Step 7: (R)-4-((8-Chloro-3-(2-hydroxyethyl)-2,5-dioxo-2,3-dihydro-1H-benzo[e][1,4]diazepin-4(5H)-yl)methyl)-N-(5-methylpyridin-2-yl)benzamide (Example 9a)

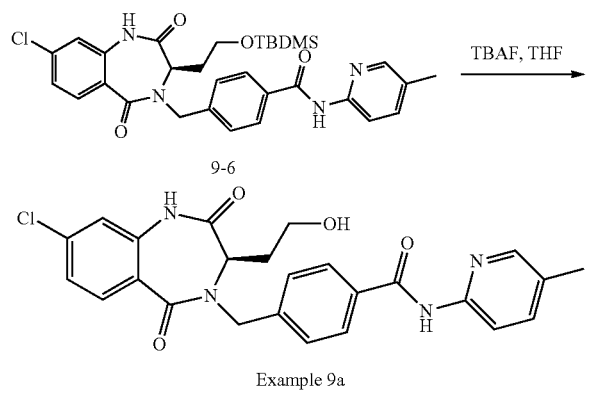

To a solution of 9-6 in THF (5 mL) was added TBAF (1 N in THF, 0.12 mL, 0.12 mmol) and the reaction mixture was stirred at 23° C. for 0.5 h. Additional TBAF (1 N in THF, 0.12 mL, 0.12 mmol) was then added and the mixture was stirred at 23° C. for an additional 2h. The mixture was then diluted with EtOAc (30 mL), and washed successively with sat. NH$_4$Cl (aq) (1×20 mL), water (1×20 mL) and brine (1×20 mL). The organic phase was dried (Na$_2$SO$_4$), filtered, and concentrated in vacuo. The crude residue was purified by FCC (SiO$_2$, elution with 0-5% MeOH/DCM) to give semi pure product which was further purified by reverse-phase semi-preparative scale HPLC to provide 18 mg (38%) for 3 steps) of Example 9a. $^1$H NMR (400 MHz, CDCl$_3$, ~1.3:1 mixture of 7-membered ring conformers observed): δ ppm 8.91-6.93 (m, 12H, partially obscured by solvent peak), 5.14-4.75 (m, 2H), 4.42 and 4.35 (2m, 1H), 3.69 and 3.38 (m, 2H), 2.48-1.68 (m, 2H), 2.32 (s, 3H); LCMS (Method B) t$_R$=0.98 min, m/z 479.4/481.4 (M+H)$^+$.

Example 10a (R)-4-((8-Chloro-3-(2-morpholinoethyl)-2,5-dioxo-2,3-dihydro-1H-benzo[e][1,4]diazepin-4(5H)-yl)methyl)-N-(5-methylpyridin-2-yl)benzamide Step 1: (R)-2-(8-Chloro-4-(4-((5-methylpyridin-2-yl)carbamoyl)benzyl)-2,5-dioxo-2,3,4,5-tetrahydro-1H-benzo[e][1,4]diazepin-3-yl)ethyl Methanesulfonate (10-1)

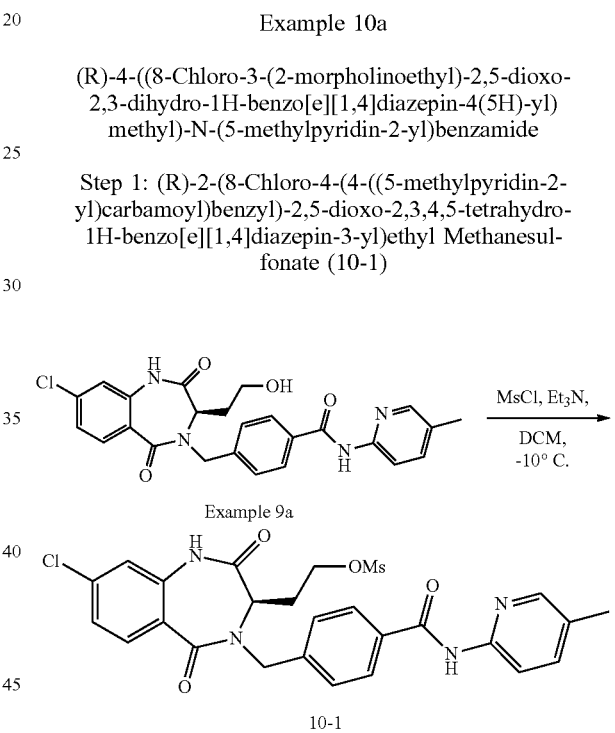

To a solution of Example 9a (616 mg, 1.3 mmol) in DCM (13 mL) at −10° C. were added triethylamine (0.22 mL, 1.6 mmol) followed by MsCl (0.10 mL, 1.4 mmol). The reaction mixture was stirred at −10° C. for 10 min. More MsCl (0.030 mL, 0.39 mmol) was added and the mixture was stirred at −10° C. for an additional 10 min. The mixture was added more triethylamine (0.10 mL, 0.72 mmol) followed by MsCl (0.030 mL, 0.39 mmol), and stirred at −10° C. for 20 min. The mixture was then quenched with sat. NaHCO$_3$ (aq) (20 mL), and extracted with EtOAc (3×20 mL). The combined organic extracts were dried (Na$_2$SO$_4$), filtered, and concentrated in vacuo to provide 406 mg (56%) of 10-1 which was used directly in the next step without further purification. $^1$H NMR (400 MHz, CDCl$_3$, ~1.1:1 mixture of 7-membered ring conformers observed): δ ppm 8.85-6.97 (m, 12H, partially obscured by solvent peak), 5.12-4.77 (m, 2H), 4.37-4.00 (2m, 3H), 2.96 and 2.90 (2s, 3H), 2.60-1.74 (m, 2H), 2.32 (s, 3H); LCMS (Method A) t$_R$=0.94 min, m/z 557.2/559.3 (M+H)$^+$.

Step 2: (R)-4-((8-Chloro-3-(2-morpholinoethyl)-2,5-dioxo-2,3-dihydro-1H-benzo[e][1,4]diazepin-4(5H)-yl)methyl)-N-(5-methylpyridin-2-yl)benzamide (Example 10a)

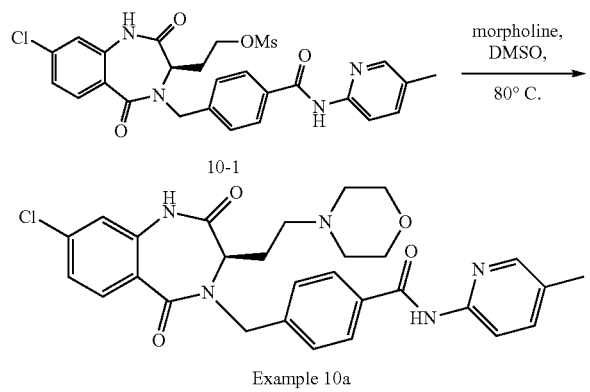

Example 10a

To a solution of 10-1 (32 mg, 0.057 mmol) in DMSO (0.5 mL) was added morpholine (0.050 mL, 0.57 mmol). The reaction mixture was heated to 80° C. for 40 min. The mixture was then cooled to room temperature, and diluted with MeOH (1.5 mL). The mixture was purified directly by reverse-phase semi-preparative scale HPLC to provide 5 mg (16%) of Example 10a. $^1$H NMR (400 MHz, CD$_3$OD, ~1.1:1 mixture of 7-membered ring conformers observed): δ ppm 8.28-7.16 (m, 10H, partially obscured by solvent peak), 5.19-4.80 (m, 2H, partially obscured by H$_2$O peak), 4.38-4.30 (m, 1H), 3.61 (m, 4H), 2.51-1.50 (m, 8H), 2.34 (s, 3H); LCMS (Method A) $t_R$=0.77 min, m/z 548.3/550.3 (M+H)$^+$.

Following the method described above for Example 10a and substituting the corresponding reagents, the following Examples were prepared as indicated in Table 13.

TABLE 13

| Example | Structure | Reagent | LCMS Method | $t_R$ (min) | (M + H)$^+$ observed |
|---|---|---|---|---|---|
| 10b | (R)-4-((8-chloro-2,5-dioxo-3-(2-(piperidin-1-yl)ethyl)-2,3-dihydro-1H-benzo[e][1,4]diazepin-4(5H)-yl)methyl)-N-(5-methylpyridin-2-yl)benzamide | HN piperidine | A | 0.80 | 546.3/ 548.3 |
| 10c | (R)-4-((8-chloro-3-(2-(4-hydroxypiperidin-1-yl)ethyl)-2,5-dioxo-2,3-dihydro-1H-benzo[e][1,4]diazepin-4(5H)-yl)methyl)-N-(5-methylpyridin-2-yl)benzamide | HN—OH | A | 0.75 | 562.4/ 564.4 |
| 10d | (R)-4-((8-chloro-3-(2-(4-methylpiperazin-1-yl)ethyl)-2,5-dioxo-2,3-dihydro-1H-benzo[e][1,4]diazepin-4(5H)-yl)methyl)-N-(5-methylpyridin-2-yl)benzamide | HN N— | A | 0.76 | 561.3/ 563.3 |

TABLE 13-continued

| Example | Structure | Reagent | LCMS Method | $t_R$ (min) | $(M + H)^+$ observed |
|---|---|---|---|---|---|
| 10e | (R)-4-((8-chloro-2,5-dioxo-3-(2-(3-oxopiperazin-1-yl)ethyl)-2,3-dihydro-1H-benzo[e][1,4]diazepin-4(5H)-yl)methyl)-N-(5-methylpyridin-2-yl)benzamide | 2-oxopiperazine | A | 0.76 | 561.3/ 563.3 |
| 10f | (R)-4-((8-chloro-3-(2-(dimethylamino)ethyl)-2,5-dioxo-2,3-dihydro-1H-benzo[e][1,4]diazepin-4(5H)-yl)methyl)-N-(5-methylpyridin-2-yl)benzamide | NHMe₂ | A | 0.75 | 506.4/ 508.4 |

Example 11a (R)-8-Chloro-4-(4-picolinoylbenzyl)-3-(pyridin-2-ylmethyl)-3,4-dihydro-1H-benzo[e][1,4]diazepine-2,5-dione Step 1: (R)-4-((8-Chloro-2,5-dioxo-3-(pyridin-2-ylmethyl)-2,3-dihydro-1H-benzo[e][1,4]diazepin-4(5H)-yl)methyl)-N-methoxy-N-methylbenzamide (11-1)

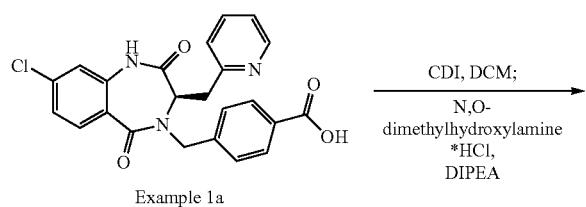

Example 1a

CDI, DCM;
N,O-dimethylhydroxylamine *HCl,
DIPEA

-continued

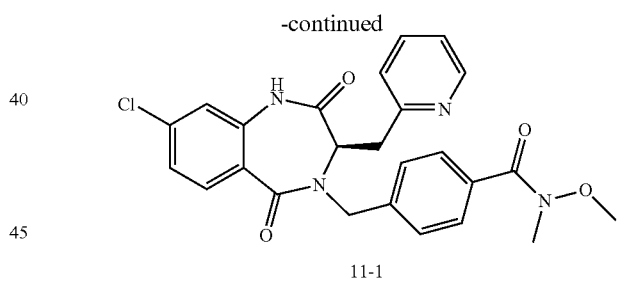

11-1

To a suspension of Example 1a (254 mg, 0.583 mmol) in DCM (5 mL) was added CDI (113 mg, 0.699 mmol). The resulting mixture was stirred at 23° C. for 3 h. N,O-dimethylhydroxylamine hydrochloride salt (68 mg, 0.70 mmol) was then added followed by DIPEA (0.20 mL, 1.2 mmol). The mixture stirred at 23° C. for 16 h. The mixture was then concentrated in vacuo. The residue was taken up in EtOAc (30 mL), and washed with sat. NaHCO₃ (aq) (1×20 mL) and brine (1×20 mL). The organic layer was then dried (Na₂SO₄), filtered, and concentrated in vacuo. The crude residue was purified by FCC (SiO₂, elution with 0-100% EtOAc/hexanes) to provide 198 mg (71%) of Weinreb amide 11-1. ¹H NMR (400 MHz, CHCl₃, ~1.6:1 mixture of 7-membered ring conformers observed): δ ppm 8.49-6.71 (m, 12H, partially obscured by solvent peak), 5.12-4.38 (m, 3H), 4.38-4.30 (m, 1H), 3.61-2.75 (m, 2H), 3.53 and 3.51 (2s, 3H), 3.34 (s, 3H); LCMS (Method A) $t_R$=0.91 min, m/z 479.5/481.5 (M+H)⁺.

Step 2: (R)-8-Chloro-4-(4-picolinoylbenzyl)-3-(pyridin-2-ylmethyl)-3,4-dihydro-1H-benzo[e][1,4]diazepine-2,5-dione (Example 11a)

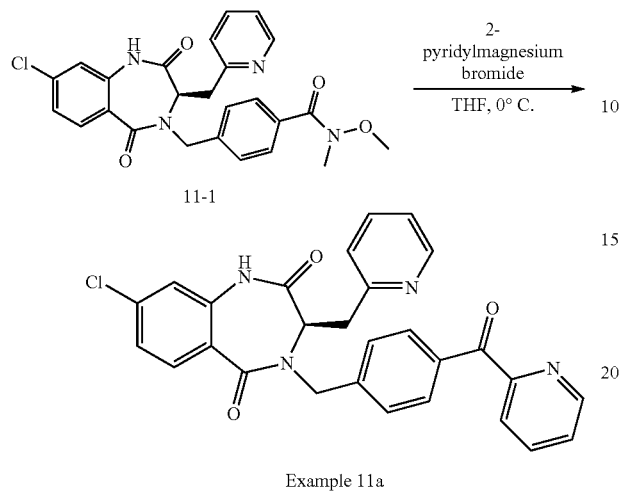

11-1

Example 11a

To a solution of 11-1 (70 mg, 0.15 mmol) in THF (1 mL) at 0° C. was added 2-pyridylmagnesium bromide (0.25 M in THF, 2.9 mL, 0.73 mmol). The reaction mixture was stirred at 0° C. for 3 h. The mixture was then quenched with $NH_4Cl$ (aq) (20 mL), and extracted with EtOAc (3×20 mL). The combined organic extracts were dried ($Na_2SO_4$), filtered, and concentrated in vacuo. The crude residue was purified by FCC ($SiO_2$, elution with 0-100% EtOAc/hexanes) to provide 34 mg (47%) of Example 11a. $^1$H NMR (400 MHz, $CHCl_3$, ~1.6:1 mixture of 7-membered ring conformers observed): δ ppm 8.72-6.74 (m, 16H, partially obscured by solvent peak), 5.15-4.43 (m, 3H), 3.63-2.79 (m, 2H); LCMS (Method A) $t_R$=1.00 min, m/z 497.5/499.5 $(M+H)^+$.

Following the method described above for Example 11a and substituting the corresponding precursors and reagents, the following Examples were prepared as indicated in Table 14.

TABLE 14

| Example | Structure | Precursor | Reagent | LCMS Method | $t_R$ (min) | $(M + H)^+$ observed |
|---|---|---|---|---|---|---|
| 11b | (R)-8-chloro-4-(4-(5-methylpicolinoyl)benzyl)-3-(pyridin-2-ylmethyl)-3,4-dihydro-1H-benzo[e][1,4]diazepine-2,5-dione | 1a | BrMg-(5-methylpyridin-2-yl) | A | 1.06 | 511.5/ 513.5 |
| 11c | (R)-8-chloro-4-((4-picolinoylcyclohexyl)methyl)-3-(pyridin-2-ylmethyl)-3,4-dihydro-1H-benzo[e][1,4]diazepine-2,5-dione | 1j | BrMg-(pyridin-2-yl) | A | 1.04 | 503.4/ 505.4 |

TABLE 14-continued

| Example | Structure | Precursor | Reagent | LCMS Method | $t_R$ (min) | $(M + H)^+$ observed |
|---|---|---|---|---|---|---|
| 11d | (R)-8-chloro-4-(4-(4-methylpicolinoyl)benzyl)-3-(pyridin-2-ylmethyl)-3,4-dihydro-1H-benzo[e][1,4]diazepine-2,5-dione | 1a | BrMg-(4-methylpyridin-2-yl) | A | 1.19 | 511.3/ 513.3 |
| 11e | (R)-8-chloro-4-(4-(6-methylpicolimoyl)benzyl)-3-(pyridin-2-ylmethyl)-3,4-dihydro-1H-benzo[e][1,4]diazepine-2,5-dione | 1a | BrMg-(6-methylpyridin-2-yl) | A | 1.18 | 511.4/ 513.3 |
| 11f | (R)-8-chloro-4-(3-fluoro-4-picolinoylbenzyl)-3-(pyridin-2-ylmethyl)-3,4-dihydro-1H-benzo[e][1,4]diazepine-2,5-dione | 1i | BrMg-(pyridin-2-yl) | A | 1.03 | 515.4/ 517.4 |
| 11g | (R)-8-chloro-4-(3-chloro-4-picolinoylbenzyl)-3-(pyridin-2-ylmethyl)-3,4-dihydro-1H-benzo[e][1,4]diazepine-2,5-dione | 7a | BrMg-(pyridin-2-yl) | A | 1.07 | 531.4/ 533.4/ 535.4 |

TABLE 14-continued

| Example | Structure | Precursor | Reagent | LCMS Method | $t_R$ (min) | $(M + H)^+$ observed |
|---|---|---|---|---|---|---|
| 11h | (R)-8-chloro-4-(3-methyl-4-picolinoylbenzyl)-3-(pyridin-2-ylmethyl)-3,4-dihydro-1H-benzo[e][1,4]diazepine-2,5-dione | 7b | BrMg-pyridin-2-yl | A | 1.02 | 511.4/ 513.4/ |
| 11i | (R)-8-chloro-4-(3-fluoro-4-(3-methylpicolinoyl)benzyl)-3-(pyridin-2-ylmethyl)-3,4-dihydro-1H-benzo[e][1,4]diazepine-2,5-dione | 1i | BrMg-(3-methylpyridin-2-yl) | A | 1.09 | 529.4/ 531.4 |
| 11j | (R)-8-chloro-4-(3-methoxy-4-picolinoylbenzyl)-3-(pyridin-2-ylmethyl)-3,4-dihydro-1H-benzo[e][1,4]diazepine-2,5-dione | 7d | BrMg-pyridin-2-yl | A | 1.01 | 527.1/ 529.1 |

Example 12a (R)—N-Acetyl-4-((8-chloro-2,5-dioxo-3-(pyridin-2-ylmethyl)-2,3-dihydro-1H-benzo[e][1,4]diazepin-4(5H)-yl)methyl)benzamide

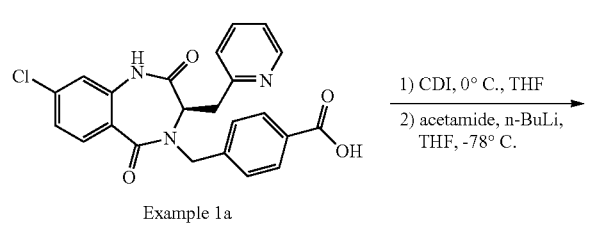

Example 1a

1) CDI, 0° C., THF
2) acetamide, n-BuLi, THF, -78° C.

-continued

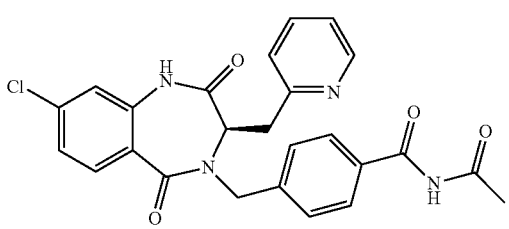

Example 12a

To a suspension of Example 1a (100 mg, 0.229 mmol) in THF (2 mL) at −5° C. was added CDI (45 mg, 0.28 mmol).

The mixture was stirred at −5° C. for 5 min. DMF (0.2 mL) was then added, and the mixture stirred at −5° C. for 1 h. Meanwhile, to a solution of acetamide (41 mg, 0.69 mmol) in THF (1 mL) at −78° C. was added n-BuLi (2.5 M in hexanes, 0.20 mL, 0.50 mmol). This mixture was then warmed to 0° C., and then the reaction mixture of Example 1a and CDI was added via cannula. The resultant mixture was stirred at 0° C. for 10 min, and then quenched with sat. NH$_4$Cl (aq) (10 mL). This was then extracted with EtOAc (3×15 mL), dried (Na$_2$SO$_4$), filtered, and concentrated in vacuo. The crude residue was purified by FCC (SiO$_2$, elution with 0-5% MeOH/DCM) to provide 37 mg (34%) of Example 12a. $^1$H NMR (400 MHz, CHCl$_3$, ~1.6:1 mixture of 7-membered ring conformers observed): δ ppm 10.99 and 10.97 (2s, 1H, N—H), 10.75 and 10.65 (2s, 1H, N—H), 8.47-7.02 (m, 11H), 5.06-4.24 (m, 3H), 3.54-2.80 (m, 2H), 2.34 (s, 3H); LCMS (Method A) t$_R$=0.86 min, m/z 477.5/479.5 (M+H)$^+$.

Following the method described above for Example 12a and substituting the corresponding reagent, the following Example was prepared as indicated in Table 15.

TABLE 15

| Example | Structure | Reagent | LCMS Method | t$_R$ (min) | (M + H)$^+$ observed |
|---|---|---|---|---|---|
| 12b | (R)-8-chloro-4-(4-(2-oxopyrrolidine-1-carbonyl)benzyl)-3-(pyridin-2-ylmethyl)-3,4-dihydro-1H-benzo[e][1,4]diazepine-2,5-dione | | A | 0.91 | 503.5/505.5 |

Example 13a (S)-4-((8-Chloro-3-(3,4-dichlorobenzyl)-2,5-dioxo-2,3-dihydro-1H-benzo[e][1,4]diazepin-4(5H)-yl)methyl)benzamide

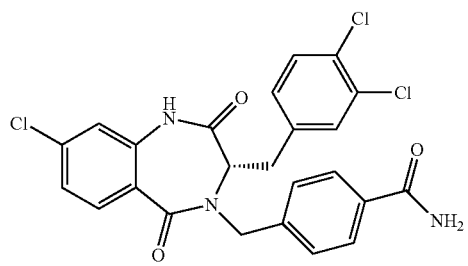

Example 13a

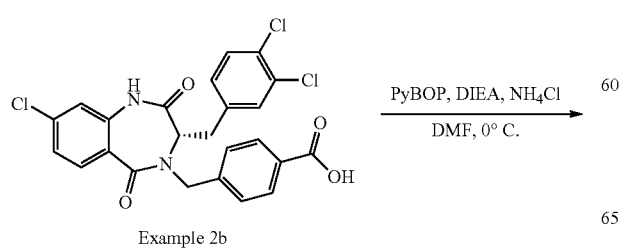

To a solution of Example 2b (0.10 g, 0.20 mmol) in DMF (5 mL) was added PyBOP (0.11 g, 0.22 mmol). The mixture was stirred at 23° C. for 5 min. This was then cooled to 0° C., and DIEA (0.12 mL, 0.64 mmol) was added followed by ammonium chloride (0.02 g, 0.40 mmol). The mixture was stirred at 0° C. for 2 h. The mixture was then diluted with water (30 mL), and extracted with EtOAc (3×10 mL). The organic phase was dried (Na$_2$SO$_4$), filtered, and concentrated in vacuo. The crude residue was purified by FCC (SiO$_2$, elution with 0-5% MeOH/DCM), followed by further purification by reverse-phase semi-preparative scale HPLC to give 58 mgs (58%) of Example 13a. $^1$H NMR (400 MHz, CDCl$_3$, ~2:1 mixture of 7-membered ring conformers observed): δ ppm 8.40-5.60 (m, 12H, partially obscured by solvent peak), 5.00-4.20 (m, 3H), 3.65-2.45 (m, 2H); LCMS (Method A) t$_R$=1.19 min, m/z 502.2/504.2/506.2 (M+H)$^+$.

Following the method described above for Example 13a and substituting the corresponding precursors and reagents, the following Examples were prepared as indicated in Table 16.

TABLE 16

| Example | Structure | Precursor | Reagent | LCMS Method | $t_R$ (min) | $(M + H)^+$ observed |
|---|---|---|---|---|---|---|
| 13b | (R)-4-((8-chloro-2,5-dioxo-3-(pyridin-3-ylmethyl)-2,3-dihydro-1H-benzo[e][1,4]diazepin-4(5H)-yl)methyl)-N,N-dimethylbenzamide | 2a | dimethyl amine | A | 0.71 | 463.4/ 465.4 |
| 13c | (R)-4-((8-chloro-2,5-dioxo-3-(pyridin-3-ylmethyl)-2,3-dihydro-1H-benzo[e][1,4]diazepin-4(5H)-yl)methyl)benzamide | 2a | ammonium chloride | B | 1.04 | 435.3/ 437.3 |
| 13d | (R)-4-((8-chloro-2,5-dioxo-3-(pyridin-2-ylmethyl)-2,3-dihydro-1H-benzo[e][1,4]diazepin-4(5H)-yl)methypbenzamide | 1a | ammonium chloride | A | 0.79 | 435.5/ 437.5 |

Example 14a (R)-4-((8-Cyano-2,5-dioxo-3-(pyridin-3-ylmethyl)-2,3-dihydro-1H-benzo[e][1,4]diazepin-4(5H)-yl)methyl)-N-(pyridin-2-yl)benzamide Hydrochloride

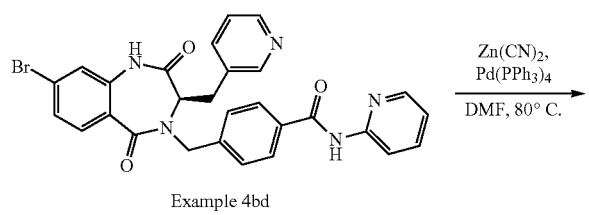

Example 4bd

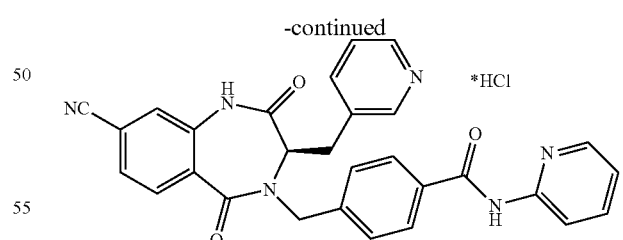

Example 14a

To an oven dried, 100 mL round bottom flask charged with Example 4bd (0.12 g, 0.22 mmol), zinc cyanide (0.025 g, 0.22 mmol), and tetrakis[triphenylphosphine]palladium (O) (0.025 g, 0.02 mmol), was added 2 mL of anhydrous DMF. The reaction mixture was heated to 80° C., and stirred at this temperature for 16 h. The mixture was then cooled to room temp, diluted with EtOAc (100 mL), and washed with water (1×20 mL), sat. ammonium chloride (1×20 mL), and brine (1×20 mL). The organic phase was dried (Na$_2$SO$_4$), filtered, and concentrated in vacuo. The crude residue was purified by FCC (SiO$_2$, gradient elution with 0-5% MeOH/DCM) followed by further purification by reverse-phase semi-preparative scale HPLC. The purified product was dissolved in 5 mL of methanol to which 10 drops of 3M HCl in methanol were added. The mixture was then concentrated in vacuo, and this process was repeated 2 more times to provide 50 mg (53%) of Example 14a. $^1$H NMR (400 MHz, CD$_3$OD, ~1.3:1 mixture of 7-membered ring conformers observed): δ ppm 8.80-7.40 (m, 15H), 5.20-4.64 (m, 3H, partially obscured by H$_2$O peak), 3.80-3.00 (m, 2H, partially obscured by solvent peak); LCMS (Method A) t$_R$=0.73 min, m/z 503.3 (M+H)$^+$.

Example 15a (R)-4-((8-Chloro-2,5-dioxo-3-(pyridin-3-ylmethyl)-2,3-dihydro-1H-benzo[e][1,4]diazepin-4(5H)-yl)methyl)-N-(phenylsulfonyl)benzamide

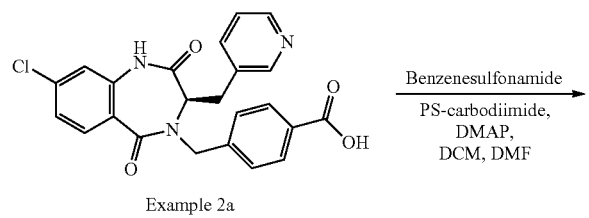

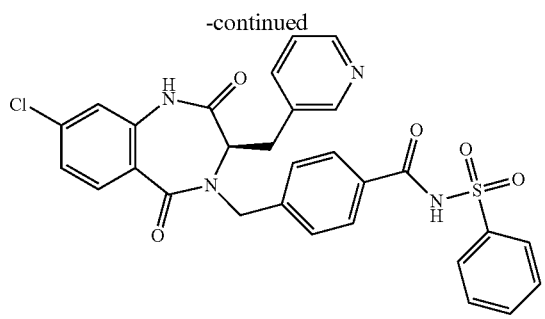

Example 15a

To a mixture of Example 2a (75 mg, 0.17 mmol) in DCM (1 mL) and DMF (0.1 mL) was added benzenesulfonamide (27 mg, 0.17 mmol) followed by PS-carbodiimide (185 mg, 0.258 mmol, 1.4 mmol/g loading) and DMAP (21 mg, 0.17 mmol). The reaction mixture was shaken on an orbital shaker for 16 h. The mixture was then filtered, and the resin was washed alternately with DCM (5 mL) and MeOH (5 mL) (3×). The combined filtrates were concentrated in vacuo, and the crude residue was purified directly by reverse-phase semi-preparative scale HPLC. The semi pure material was then further purified by FCC (SiO$_2$, elution with 0-5% MeOH/DCM) to provide 37 mg (37%) of Example 15a. $^1$H NMR (400 MHz, CDCl$_3$, ~1.2:1 mixture of 7-membered ring conformers observed): δ ppm 9.80 (br s, 1H, N—H), 8.95 (br s, 1H, N—H), 8.54-7.05 (m, 16H, partially obscured by solvent peak), 5.07-4.27 (m, 3H), 3.60-2.62 (m, 2H); LCMS (Method A) t$_R$=0.84 min, m/z 575.3/577.3 (M+H)$^1$.

Following the method described above for Example 15a and substituting the corresponding reagents, the following Examples were prepared as indicated in Table 17.

TABLE 17

| Example | Structure | Reagent | LCMS Method | t$_R$ (min) | (M + H)$^+$ observed |
|---|---|---|---|---|---|
| 15b | (R)-4-((8-chloro-2,5-dioxo-3-(pyridin-3-ylmethyl)-2,3-dihydro-1H-benzo[e][1,4]diazepin-4(5H)-yl)methyl)-N-(methylsulfonyl)benzamide | H$_2$N—S(=O)(=O)—CH$_3$ | B | 0.84 | 513.3/ 515.3 |
| 15c | (R)-4-((8-chloro-2,5-dioxo-3-(pyridin-3-ylmethyl)-2,3-dihydro-1H-benzo[e][1,4]diazepin-4(5H)-yl)methyl)-N-((4-chlorophenyl)sulfonyl)benzamide | H$_2$N—S(=O)(=O)—(4-Cl-C$_6$H$_4$) | A | 0.92 | 609.3/ 611.3/ 613.3 |

TABLE 17-continued

| Example | Structure | Reagent | LCMS Method | $t_R$ (min) | $(M + H)^+$ observed |
|---|---|---|---|---|---|
| 15d | (R)-4-((8-chloro-2,5-dioxo-3-(pyridin-3-ylmethyl)-2,3-dihydro-1H-benzo[e][1,4]diazepin-4(5H)-yl)methyl)-N-((4-methoxyphenyl)sulfonyl)benzamide | | A | 0.86 | 605.3/ 607.3 |
| 15e | (R)-4-((8-chloro-2,5-dioxo-3-(pyridin-3-ylmethyl)-2,3-dihydro-1H-benzo[e][1,4]diazepin-4(5H)-yl)methyl)-N-tosylbenzamide | | A | 0.89 | 589.3/ 591.3 |

Example 16a (R)-4-((8-Amino-3-methyl-2,5-dioxo-2,3-dihydro-1H-benzo[e][1,4]diazepin-4(5H)-yl)methyl)-N-(5-methylpyridin-2-yl)benzamide Steps 1-4: (R)-4-((3-Methyl-8-nitro-2,5-dioxo-2,3-dihydro-1H-benzo[e][1,4]diazepin-4(5H)-yl)methyl) benzoic Acid (16-4)

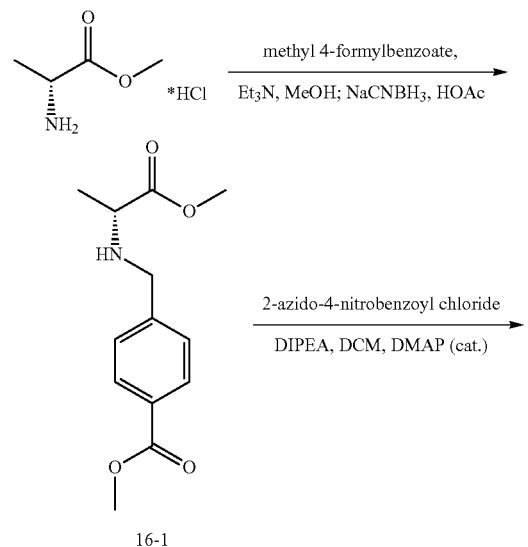

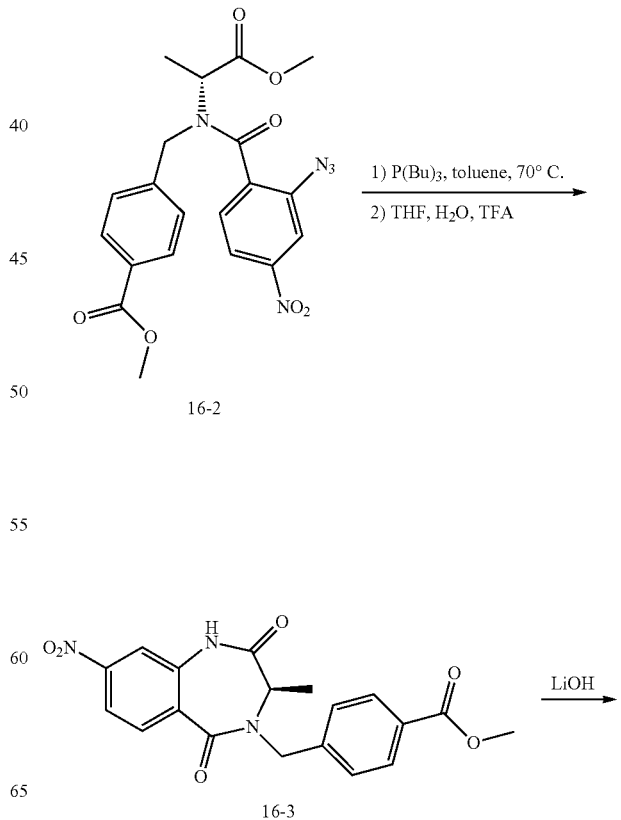

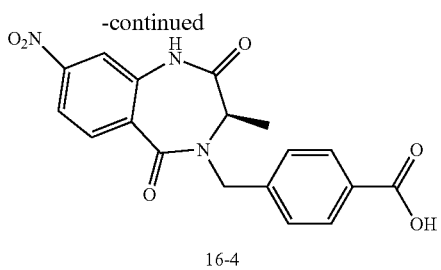

16-4

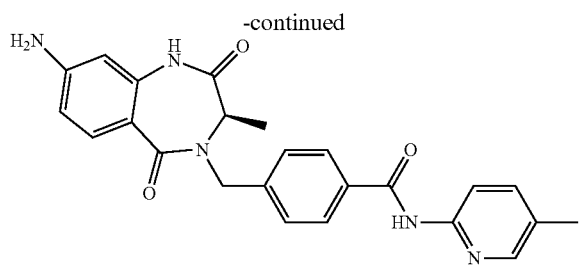

Example 16a

Carboxylic acid 16-4 was prepared from D-alanine methyl ester hydrochloride, methyl 4-formylbenzoate and 2-azido-4-nitrobenzoyl chloride (prepared from Intermediate I.3 following the general method described in step 2 of Example 1a) using the same general procedure described for the preparation of Example 1a.

Step 5: (R)-4-((3-Methyl-8-nitro-2,5-dioxo-2,3-dihydro-1H-benzo[e][1,4]diazepin-4(5H)-yl)methyl)-N-(5-methylpyridin-2-yl)benzamide (16-5)

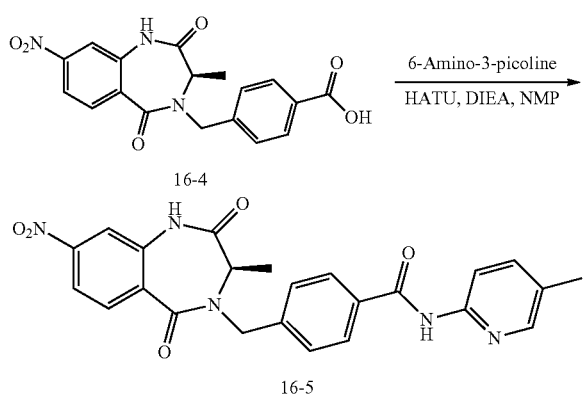

Following the general procedure described for the preparation of Example 4a, carboxylic acid 16-4 (1.0 g, 2.7 mmol) and 6-amino-3-picoline (0.88 g, 8.1 mmol) were reacted to provide 0.64 g (51%) of 16-5. $^1$H NMR (400 MHz, d$_6$-DMSO, mixture of 7-membered ring conformers observed): δ ppm 10.88 (br s, 1H, N—H), 10.68 (br s, 1H, N—H), 8.22 (d, 1H), 8.10-7.97 (m, 6H), 7.66 (dd, 1H), 7.40 (m, 2H), 5.13-4.29 (m, 3H), 2.28 (s, 3H), 1.29 and 1.09 (2 br d, 3H); LCMS (Method A) $t_R$=0.91, m/z 460.5 (M+H)$^1$.

Step 6: (R)-4-((8-Amino-3-methyl-2,5-dioxo-2,3-dihydro-1H-benzo[e][1,4]diazepin-4(5H)-yl)methyl)-N-(5-methylpyridin-2-yl)benzamide (Example 16a)

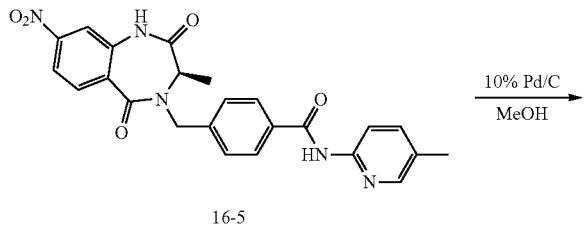

To a solution of 16-5 (50 mg, 0.11 mmol) in MeOH (2 mL) under an inert atmosphere of N$_2$ (g) was added 10% Pd/C (5 mg). The mixture was then placed under an atmosphere (balloon) of H$_2$ (g), and stirred vigorously for 2 d. The mixture was then filtered through a pad of CELITE rinsing with MeOH, and the combined filtrates were concentrated in vacuo. The crude residue was purified by FCC (SiO$_2$, elution with 0-100% EtOAc/hexanes) to provide 4 mg (9%) of Example 16a. LCMS (Method A) $t_R$=0.76 min, m/z 430.5 (M+H)$^+$.

Example 17a (R)-4-((8-Acetamido-3-methyl-2,5-dioxo-2,3-dihydro-1H-benzo[e][1,4]diazepin-4(5H)-yl)methyl)-N-(5-methylpyridin-2-yl)benzamide

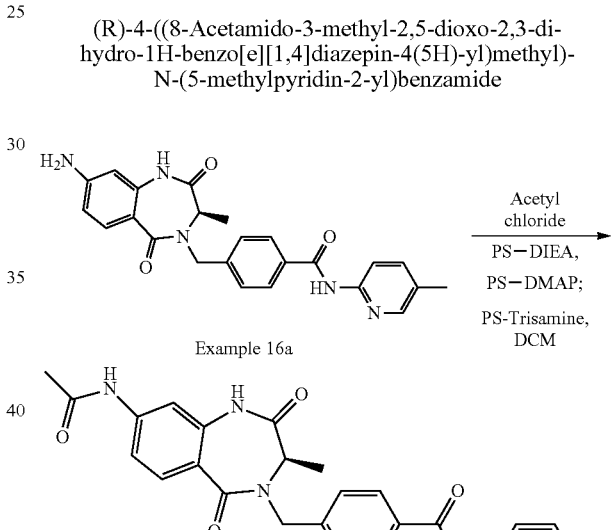

To a mixture of Example 16a (10 mg, 0.023 mmol), PS-DIEA (19 mg, 0.070 mmol, 3.68 mmol/g) and PS-DMAP (3 mg, 0.005 mmol, 1.49 mmol/g) in DCM (1 mL) was added acetyl chloride as a solution in DCM (0.3 M, 0.12 mL, 0.035 mmol). The reaction mixture was shaken on an orbital stir plate for 18 h. More acetyl chloride was added as a solution in DCM (0.1 M, 0.11 mL, 0.011 mmol), and the mixture was shaken for an additional 4 h. PS-Trisamine (0.018 g, 0.070 mmol, 3.95 mmol/g) was then added followed by additional DCM (0.5 mL), and the mixture was shaken for 18 h. The mixture was then filtered, and the resin washed successively with DCM (3×2 mL) then MeOH (3×2 mL). The combined filtrates were concentrated in vacuo, and the residue was taken up in MeOH (3 mL), and added K$_2$CO$_3$ (32 mg). The mixture was shaken on an orbital stir plate for 10 min, and then concentrated in vacuo. The crude residue was then purified directly by FCC (SiO$_2$, elution with 0-100% EtOAc/hexane then 0-10% MeOH/EtOAc) to provide 6 mg (51%) of Example 17a. ¹H NMR (400 MHz, CDCl₃, mixture of 7-membered ring conformers observed): δ ppm 8.73-7.00 (m, 13H), 4.97-4.16 (m, 3H), 2.31 (s, 3H), 2.20 (s, 3H), 1.42 and 1.10 (br s, 3H); LCMS (Method A) t$_R$=0.77 min, m/z 472.5 (M+H)⁺.

Example 18a (R)-4-((8-(3-Methoxypropanamido)-3-methyl-2,5-dioxo-2,3-dihydro-1H-benzo[e][1,4]diazepin-4(5H)-yl)methyl)-N-(5-methylpyridin-2-yl)benzamide

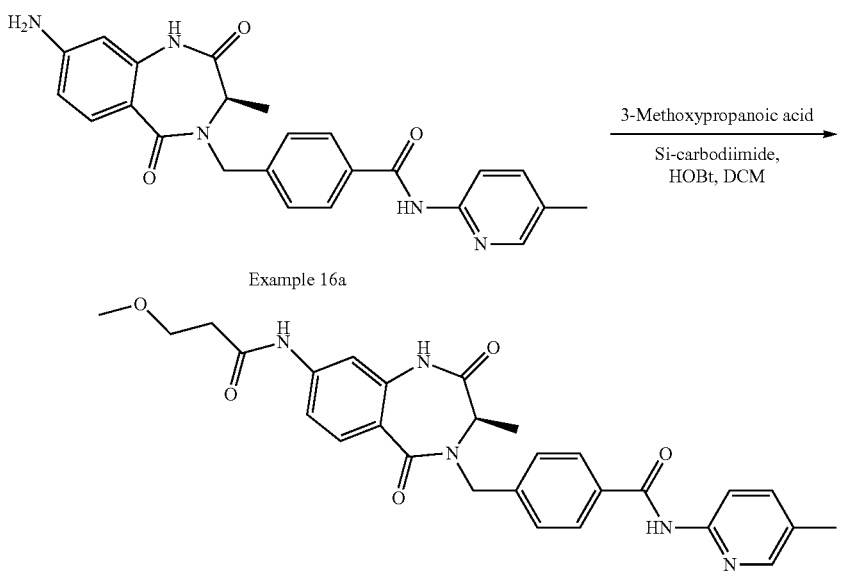

Example 16a

Example 18a

To a solution of 3-Methoxypropanoic acid (4 mg, 0.04 mmol) in DCM (1 mL) were added Si-carbodiimide (1.1 mmol/g, 45 mg, 0.049 mmol) and HOBt (6 mg, 0.04 mmol). The resulting mixture was stirred at 23° C. for 15 min. A solution of Example 16a (10 mg, 0.025 mmol) in DCM (0.5 mL) was then added, and the resulting mixture was stirred at 23° C. for 18 h. To the mixture was added Si-carbonate (0.8 mmol/g, 0.19 g, 0.15 mmol), and the resulting mixture was stirred at 23° C. for 1.5 h. The mixture was filtered rinsing with DCM (2×5 mL). The combined organic filtrates were concentrated in vacuo, and the crude residue was purified by FCC (SiO₂; elution with 0-10% CH₃OH/CH₂Cl₂) to provide 2 mg (16%) of Example 18a. LCMS (Method A) t$_R$=0.91 min, m/z 535.6 (M+H)⁺.

Following the method described above for Example 18a and substituting the corresponding reagents, the following Examples were prepared as indicated in Table 18.

TABLE 18

| Example | Structure | Reagent | LCMS Method | t$_R$ (min) | (M + H)⁺ observed |
|---|---|---|---|---|---|
| 18b | -4-((8-isobutyramido-3-methyl-2,5-dioxo-2,3-dihydro-1H-benzo[e][1,4]diazepin-4(5H)-yl)methyl)-N-(5-methylpyridin-2-yl)benzamide | isobutyric acid | A | 0.87 | 500.6 |

TABLE 18-continued

| Example | Structure | Reagent | LCMS Method | $t_R$ (min) | $(M + H)^+$ observed |
|---|---|---|---|---|---|
| 18c | (R)-5-methyl-N-(3-methyl-4-(4-((5-methylpyridin-2-yl)carbamoyl)benzyl)-2,5-dioxo-2,3,4,5-tetrahydro-1H-benzo[e][1,4]diazepin-8-yl)isoxazole-3-carboxamide | | A | 0.91 | 539.6 |
| 18d | (R)-N-(3-methyl-4-(4-((5-methylpyridin-2-yl)carbamoyl)benzyl)-2,5-dioxo-2,3,4,5-tetrahydro-1H-benzo[e][1,4]diazepin-8-yl)picolinamide | | A | 0.91 | 535.6 |
| 18e | (R)-N-(3-methyl-4-(4-((5-methylpyridin-2-yl)carbamoyl)benzyl)-2,5-dioxo-2,3,4,5-tetrahydro-1H-benzo[e][1,4]diazepin-8-yl)nicotinamide | | A | 0.79 | 535.6 |

Example 19a (R)-4-((8-Chloro-2-oxo-3-(pyridin-2-ylmethyl)-2,3-dihydro-1H-benzo[e][1,4]diazepin-4(5H)-yl)sulfonyl)-N-(5-methylpyridin-2-yl)benzamide Step 1: (R)-Methyl 2-((4-chloro-2-nitrobenzyl)amino)-3-(pyridin-2-yl)propanoate (19-1)

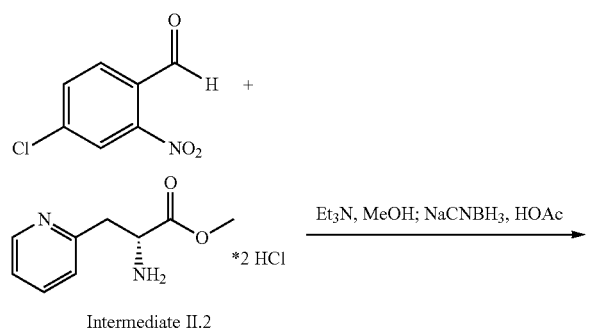

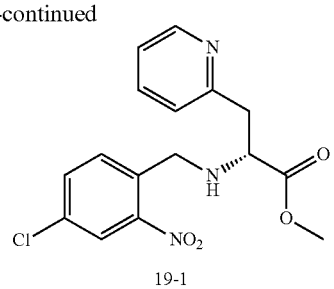

19-1

To a suspension of Intermediate II.2 (5.5 g, 22 mmol) in MeOH (200 mL) was added triethylamine (6.0 mL, 43 mmol). To this clear solution was added 4-chloro-2-nitrobenzaldehde (4.0 g, 22 mmol), and the resulting mixture was stirred at 23° C. for 1 h. Sodium cyanoborohydride (1.4 g, 22 mmol) was added followed by acetic acid (2.5 mL, 43 mmol). The reaction mixture was stirred at 23° C. for 18 h. The mixture was concentrated in vacuo. The crude residue was taken up in EtOAc (100 mL), and washed with 0.5 N NaOH (aq) (1×100 mL). The aqueous phase was then extracted with EtOAc (2×100 mL), and the combined organic extracts were washed with brine (1×100 mL), dried ($Na_2SO_4$), filtered, and concentrated in vacuo. The crude residue was purified by FCC ($SiO_2$; elution with 0-5%

CH$_3$OH/DCM) to provide 3.8 g (51%) of 19-1. $^1$H NMR (400 MHz, CDCl$_3$): δ ppm 8.50 (m, 1H), 7.88 (m, 1H), 7.60 (td, 1H), 7.43 (m, 2H), 7.17-7.11 (m, 2H), 4.01 (ABq, 2H), 3.73 (dd, 1H), 3.69 (s, 3H), 3.18 (dd, 1H), 3.03 (dd, 1H), 2.34 (br s, 1H, N—H); LCMS (Method A) $t_R$=0.89 min, m/z 350.2/352.2 (M+H)$^+$.

Step 2: (R)-Methyl 2-((2-amino-4-chlorobenzyl) amino)-3-(pyridin-2-yl)propanoate (19-2)

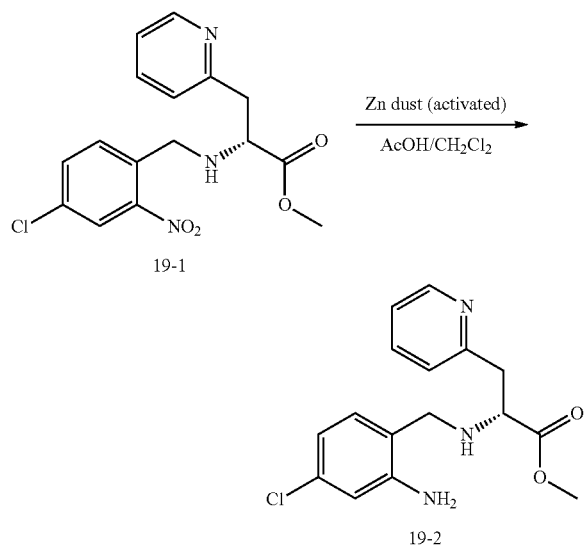

To a solution of 19-1 (3.8 g, 11 mmol) in DCM (250 mL) was added activated zinc dust (14 g, 220 mmol). To this mixture was added acetic acid (13 mL) drop wise over 3 min, and the resulting mixture was stirred at 23° C. for 30 min. The mixture was filtered to remove zinc, and then diluted with NaHCO$_3$ (sat. aq.) (100 mL). The resulting bi-phasic mixture was filtered to remove precipitated solids, and then separated. The aqueous phase was extracted with CH$_2$Cl$_2$ (2×100 mL). The combined organic extracts were washed with brine (1×100 mL), dried (Na$_2$SO$_4$), filtered, and concentrated in vacuo. The crude residue was purified by FCC (SiO$_2$; elution with 0-5% CH$_3$OH/DCM) to provide 2.8 g (80%) of 19-2. $^1$H NMR (400 MHz, CDCl$_3$): δ ppm 8.52 (ddd, 1H), 7.59 (td, 1H), 7.15 (ddd, 1H), 7.10 (d, 1H), 6.84 (d, 1H), 6.58 (d, 1H), 6.53 (d, 1H), 4.41 (br s, 2H, N—H$_2$), 3.79 (dd, 1H), 3.74 (s, 3H), 3.67 (ABq, 2H), 3.20 (dd, 1H), 2.98 (dd, 1H), 1.90 (br s, 1H, N—H); LCMS (Method A) $t_R$=0.81 min, m/z 320.2/322.2 (M+H)$^+$.

Step 3: (R)-8-Chloro-3-(pyridin-2-ylmethyl)-4,5-dihydro-1H-benzo[e][1,4]diazepin-2(3H)-one (19-3)

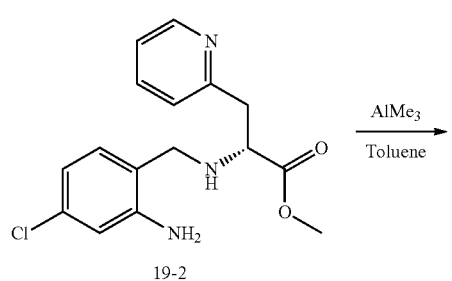

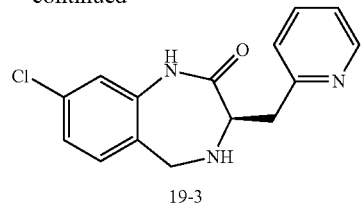

To a solution of 19-2 (2.8 g, 8.8 mmol) in toluene (75 mL) at 0° C. was added Al(Me)$_3$ (2.0 M in toluene, 18 mL, 35 mmol) drop wise over 15 min. The reaction mixture was stirred at 0° C. for 15 min, and then the ice bath was removed. The mixture was stirred for 30 min. The mixture was again cooled to 0° C., and quenched with methanol (24 mL). The mixture was stirred for 15 minutes, and then diluted with EtOAc (100 mL) and sat. NaHCO$_3$ (aq) (100 mL). The mixture was filtered through a pad of CELITE. The layers were separated, and the aqueous phase was extracted with EtOAc (2×50 mL). The combined organic extracts were washed with brine (1×100 mL), dried (Na$_2$SO$_4$), filtered, and concentrated in vacuo to give 2.3 g (92%) of 19-3 which was used directly in the next step without further purification. $^1$H NMR (400 MHz, CDCl$_3$): δ ppm 8.42 (ddd, 1H), 7.73 (br s, 1H, N—H), 7.57 (td, 1H), 7.22 (d, 1H), 7.14-7.07 (m, 3H), 6.92 (d, 1H), 4.08 (dd, 1H), 3.97 (ABq, 2H), 3.36 (dd, 1H), 3.14 (dd, 1H), 2.56 (br s, 1H, N—H); LCMS (Method A) $t_R$=0.65 min, m/z 288.2/290.2 (M+H)$^+$.

Step 4: (R)-Methyl 4-((8-chloro-2-oxo-3-(pyridin-2-ylmethyl)-2,3-dihydro-1H-benzo[e][1,4]diazepin-4(5H)-yl)sulfonyl)benzoate (19-4)

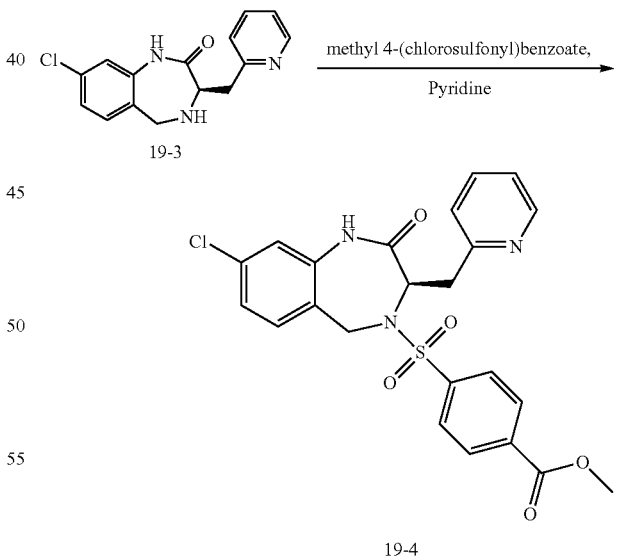

To a solution of 19-3 (500 mg, 1.7 mmol) in pyridine (15 ml) was added 4-(chlorosulfonyl)benzoyl chloride (610 mg, 2.6 mmol). The reaction mixture was stirred at 23° C. for 4 h, and then concentrated in vacuo. The crude residue was dissolved in EtOAc (100 mL), and then washed successively with sat. NH$_4$Cl (aq) (1×50 mL) and brine (aq.) (1×50 mL). The organic phase was dried (Na$_2$SO$_4$), filtered, and concentrated in vacuo to give 790 mg (93%) of 19-4 which was used directly in the next step without further purification. LCMS (Method A) $t_R$=0.94 min, m/z 486.4/488.4 (M+H)$^+$.

Step 5: (R)-4-((8-Chloro-2-oxo-3-(pyridin-2-ylmethyl)-2,3-dihydro-1H-benzo[e][1,4]diazepin-4(5H)-yl)sulfonyl)benzoic Acid (19-5)

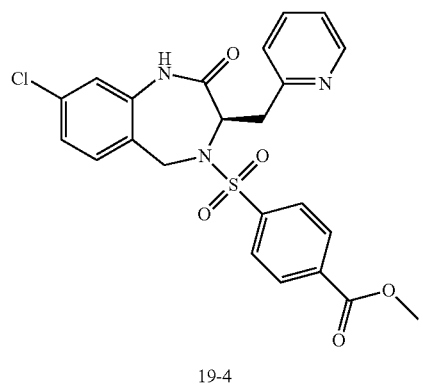

To a solution of 19-4 (790 mg, 1.6 mmol) in THF (10 mL) and MeOH (10 mL) was added LiOH (77 mg, 3.2 mmol) in H$_2$O (4 mL). The resulting mixture was stirred at 23° C. for 7 h. Additional LiOH (20 mg, 0.84 mmol) was added, and the mixture was stirred at 23° C. for 18 h. The mixture was then concentrated in vacuo. The residue was dissolved in H$_2$O (50 mL), and the pH was adjusted to 5 by addition of 1 N HCl (aq). The mixture was extracted with 3:1 CHCl$_3$/i-PrOH (3×50 mL), and the combined organic extracts were washed with brine (1×100 mL), dried (Na$_2$SO$_4$), filtered, and concentrated in vacuo to give 420 mg (56%) of 19-5 which was used directly in the next step without further purification. $^1$H NMR (400 MHz, d$_6$-DMSO): δ ppm 13.46 (br s, 1H, O—H), 10.07 (s, 1H, N—H), 8.43 (ddd, 1H), 7.84 (d, 2H), 7.67 (td, 1H), 7.47 (d, 2H), 7.31 (d, 1H), 7.24-7.18 (m, 2H), 7.07 (dd, 1H), 6.86 (d, 1H) 5.10 (dd, 1H), 4.65 (ABq, 2H), 3.32 (m, 2H, partially obscured by H$_2$O peak).

Step 6: (R)-4-((8-Chloro-2-oxo-3-(pyridin-2-ylmethyl)-2,3-dihydro-1H-benzo[e][1,4]diazepin-4(5H)-yl)sulfonyl)-N-(5-methylpyridin-2-yl)benzamide (Example 19a)

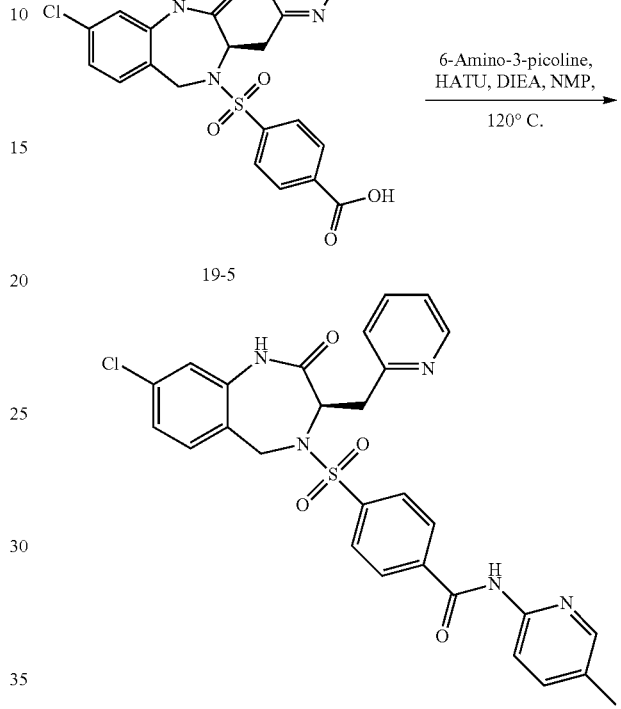

To a solution of 19-5 (80 mg, 0.17 mmol) in NMP (0.5 mL) in an oven dried microwave vial were added HATU (97 mg, 0.25 mmol) and DIEA (59 µL, 0.34 mmol). The mixture was stirred for 30 min. 6-Amino-3-picoline (92 mg, 0.85 mmol) was added. The vial was tightly capped, and the mixture was heated in a microwave reactor at 120° C. for 30 min intervals until LCMS analysis of the reaction mixture indicated complete reaction. The mixture was diluted with EtOAc (30 mL), and washed successively with sat. NaHCO$_3$ (aq) (1×20 mL) and brine (1×20 mL). The organic phase was dried (Na$_2$SO$_4$), filtered, and concentrated in vacuo. The crude residue was purified by FCC (SiO$_2$, elution with 0-5% MeOH/DCM). The semi pure material was then further purified by FCC (SiO$_2$, elution with 0-100% EtOAc/Hexanes to provide 16 mg (16%) of Example 19a. $^1$H NMR (400 MHz, d$_6$-DMSO) δ ppm 10.87 (s, 1H, N—H), 10.09 (s, 1H, N—H), 8.42 (ddd, 1H), 8.24 (m, 1H), 8.08 (d, 1H), 7.96 (d, 2H), 7.66 (m, 2H), 7.49 (d, 2H), 7.33 (d, 1H), 7.21-7.17 (m, 2H), 7.08 (dd, 1H), 6.93 (d, 1H), 5.08 (dd, 1H), 4.64 (ABq, 2H), 3.33-3.20 (m, 2H, partially obscured by H$_2$O peak), 2.29 (s, 3H); LCMS m/z 562.3/564.3 (M+H)$^1$.

Following the method described above for Example 19a and substituting the corresponding Intermediates in Step 1 and reagents in Step 6, the following Examples were prepared as indicated in Table 19.

TABLE 19

| Example | Structure | Intermediate | Reagent | LCMS Method | $t_R$ (min) | (M + H)$^+$ observed |
|---|---|---|---|---|---|---|
| 19b | (R)-4-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide | II.1 | H$_2$N-pyridin-2-yl | A | 0.90 | 548.2/ 550.2 |
| 19c | (S)-4-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide | II.20 | H$_2$N-pyridin-2-yl | A | 0.90 | 548.3/ 550.3 |
| 19d | (S)-4-((8-chloro-2-oxo-3-(pyridin-2-ylmethyl)-2,3- | II.20 | H$_2$N-5-methoxypyridin-2-yl | A | 0.94 | 578.3/ 580.3 |

TABLE 19-continued

| Example | Structure | Intermediate | Reagent | LCMS Method | $t_R$ (min) | (M + H)+ observed |
|---|---|---|---|---|---|---|
| | dihydro-1H-benzo[e][1,4]diazepin-4(5H)-yl)sulfonyl)-N-(5-methoxypyridin-2-yl)benzamide | | | | | |
| 19e | 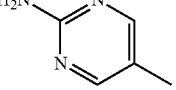<br>(S)-4-((8-chloro-2-oxo-3-(pyridin-2-ylmethyl)-2,3-dihydro-1H-benzo[e][1,4]diazepin-4(5H)-yl)sulfonyl)-N-(5-methylpyrimidin-2-yl)benzamide | II.20 | 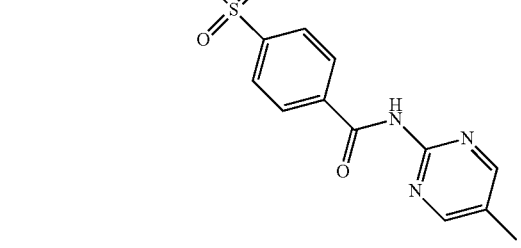 | A | 0.82 | 563.4/<br>565.4 |
| 19f | 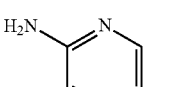<br>(R)-4-((8-chloro-2-oxo-3-(pyridin-2-ylmethyl)-2,3-dihydro-1H-benzo[e][1,4]diazepin-4(5H)-yl)sulfonyl)-N-(5-methoxypyridin-2-yl)benzamide | II.1 | 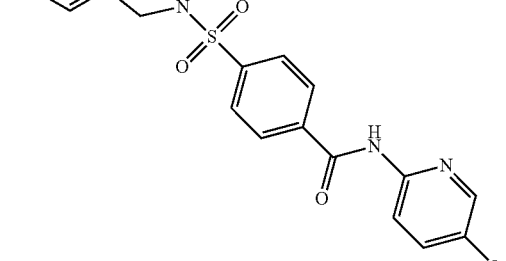 | A | 0.94 | 578.4/<br>580.4 |

TABLE 19-continued

| Example | Structure | Intermediate | Reagent | LCMS Method | $t_R$ (min) | $(M + H)^+$ observed |
|---|---|---|---|---|---|---|
| 19g | (R)-4-((8-chloro-2-oxo-3-(pyridin-2-ylmethyl)-2,3-dihydro-1H-benzo[e][1,4]diazepin-4(5H)-yl)sulfonyl)-N-(5-methylpyrimidin-2-yl)benzamide | II.1 | H₃N-pyrimidine-5-methyl | A | 0.82 | 563.5/ 565.5 |
| 19h | (R)-4-((8-chloro-2-oxo-3-(pyridin-2-ylmethyl)-2,3-dihydro-1H-benzo[e][1,4]diazepin-4(5H)-yl)sulfonyl)-N-(5-methoxypyrimidin-2-yl)benzamide | II.1 | H₂N-5-methoxypyrimidine | A | 0.82 | 579.5/ 581.5 |

Following the method described above for Example 19a and substituting the corresponding reagents in Step 4 and utilizing 2-aminopyridine in Step 6, the following Examples were prepared as indicated in Table 20.

TABLE 20

| Example | Structure | Reagent | LCMS Method | $t_R$ (min) | $(M + H)^+$ observed |
|---|---|---|---|---|---|
| 19i | (R)-4-(8-chloro-2-oxo-3-(pyridin-2-ylmethyl)-2,3,4,5-tetrahydro-1H-benzo[e][1,4]diazepine-4-carbonyl)-N-(pyridin-2-yl)benzamide | | A | 0.89 | 512.3/ 514.3 |
| 19j | (R)-3-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide | | A | 0.90 | 548.3/ 550.3 |

Example 20a (R)-4-((8-Chloro-2-oxo-3-(pyridin-2-ylmethyl)-2,3-dihydro-1H-benzo[e][1,4]diazepin-4(5H)-yl)methyl)-N-(pyridin-2-yl)benzamide Step 1: (R)-Methyl 4-((8-chloro-2-oxo-3-(pyridin-2-ylmethyl)-2,3-dihydro-1H-benzo[e][1,4]diazepin-4(5H)-yl)methyl)benzoate (20-1)

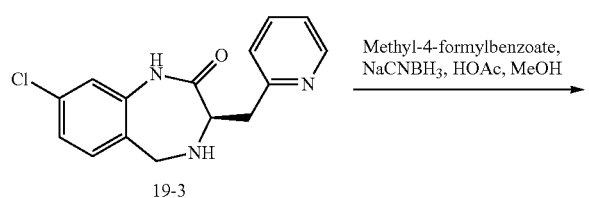

19-3

Methyl-4-formylbenzoate, NaCNBH$_3$, HOAc, MeOH →

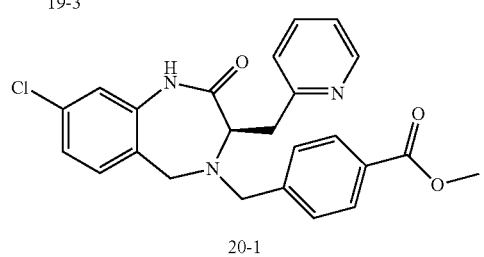

20-1

To a solution of 19-3 (100 mg, 0.35 mmol) in MeOH (3 mL) was added methyl-4-formylbenzoate (57 mg, 0.35 mmol). The resulting mixture was stirred at 23° C. for 30 min. Acetic acid (40 µL, 0.70 mmol) was added followed by NaCNBH$_3$ (22 mg, 0.35 mmol). The resulting mixture was stirred at 23° C. for 18 h. More methyl-4-formylbenzoate (29 mg, 0.18 mmol) and NaCNBH$_3$ (10 mg, 0.18 mmol) were added, and the resulting mixture was stirred at 23° C. for an additional 18 h. The mixture was concentrated in vacuo. The crude residue was taken up in EtOAc (30 mL), and washed with 0.5 N NaOH (aq) (20 mL). The aqueous phase was then extracted with EtOAc (2×30 mL). The combined organic extracts were washed with brine (1×50 mL), dried (Na$_2$SO$_4$), filtered, and concentrated in vacuo. The crude residue was purified by FCC (SiO$_2$; elution with 0-5% CH$_3$OH/CH$_2$Cl$_2$) to provide 59 mg (39%) of 20-1. LCMS (Method A) t$_R$=0.99 min, m/z 436.3/438.3 (M+H)$^+$.

Step 2: (R)-4-((8-Chloro-2-oxo-3-(pyridin-2-ylmethyl)-2,3-dihydro-1H-benzo[e][1,4]diazepin-4(5H)-yl)methyl)benzoic Acid (20-2)

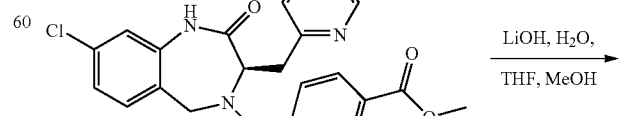

20-1

LiOH, H$_2$O, THF, MeOH →

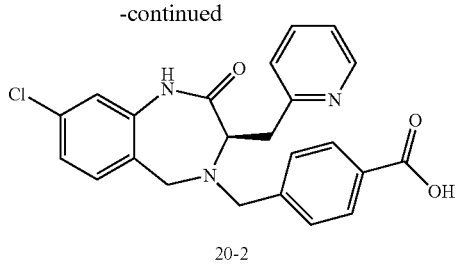

20-2

To a solution of 20-1 (59 mg, 0.14 mmol) in THF (1.0 mL) and MeOH (1.0 mL) was added LiOH (5 mg, 0.20 mmol) in H$_2$O (0.5 mL). The resulting mixture was stirred at 23° C. for 6 h, and then concentrated in vacuo. The residue was dissolved in H$_2$O (20 mL), and the pH was adjusted to 5 with 1 N HCl (aq.). The mixture was extracted with CHCl$_3$/i-PrOH (3:1) (3×20 mL). The combined organic extracts were washed with brine (1×50 mL), dried (Na$_2$SO$_4$), filtered, and concentrated in vacuo to give 50 mg (88%) of 20-2. LCMS (Method A) t$_R$=0.86 min, m/z 422.2/424.2 (M+H)$^+$.

Step 3: (R)-4-((8-Chloro-2-oxo-3-(pyridin-2-ylmethyl)-2,3-dihydro-1H-benzo[e][1,4]diazepin-4(5H)-yl)methyl)-N-(pyridin-2-yl)benzamide (Example 20a)

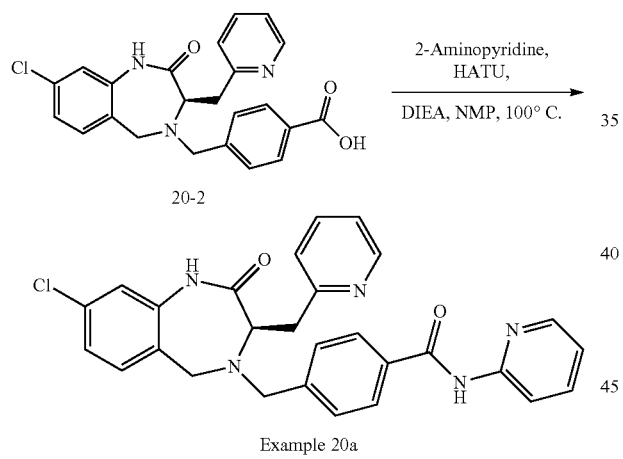

To a solution of 20-2 (50 mg, 0.12 mmol) in NMP in an oven dried microwave vial were added HATU (106 mg, 0.28 mmol) and DIEA (66 µL, 0.28 mmol). The mixture was stirred under N$_2$ atmosphere for 1 hour. 2-Aminopyridine (88 mg, 0.93 mmol) was added. The vial was tightly capped, and the mixture was heated in a microwave reactor at 100° C. for 15 minute intervals until LCMS analysis of the reaction mixture indicated complete reaction. The mixture was diluted with EtOAc (30 mL), and washed successively with sat. NaHCO$_3$ (aq) (1×20 mL) and brine (1×20 mL). The organic phase was dried (Na$_2$SO$_4$), filtered, and concentrated in vacuo. The crude residue was purified by FCC (SiO$_2$, elution with 0-5% MeOH/DCM to give 32 mg (54%) of Example 20a. $^1$H NMR (400 MHz, d$_6$-DMSO): δ ppm 10.72 (s, 1H), 10.16 (s, 1H), 8.45 (m, 1H), 8.39 (m, 1H), 8.18 (d, 1H), 7.92 (d, 2H), 7.84 (m, 1H), 7.71 (td, 1H), 7.29 (d, 1H), 7.23 (ddd, 1H), 7.19-7.08 (m, 6H), 4.08 (app t, 1H), 3.82 (m, 2H), 3.59 (m, 2H), 3.33 (dd, 1H, partially obscured by H$_2$O peak), 3.14 (dd, 1H); LCMS (Method A) t$_R$=0.91 min, m/z 498.3/500.3 (M+H)$^+$.

Example 21a (R)-4-((8-Chloro-2,5-dioxo-3-(pyridin-2-ylmethyl)-2,3-dihydro-1H-benzo[e][1,4]diazepin-4(5H)-yl)methyl)-2-(picolinamido)benzoic Acid Steps 1-3: (R)-Methyl 4-((8-chloro-2,5-dioxo-3-(pyridin-2-ylmethyl)-2,3-dihydro-1H-benzo[e][1,4]diazepin-4(5H)-yl)methyl)-2-nitrobenzoate (21-3)

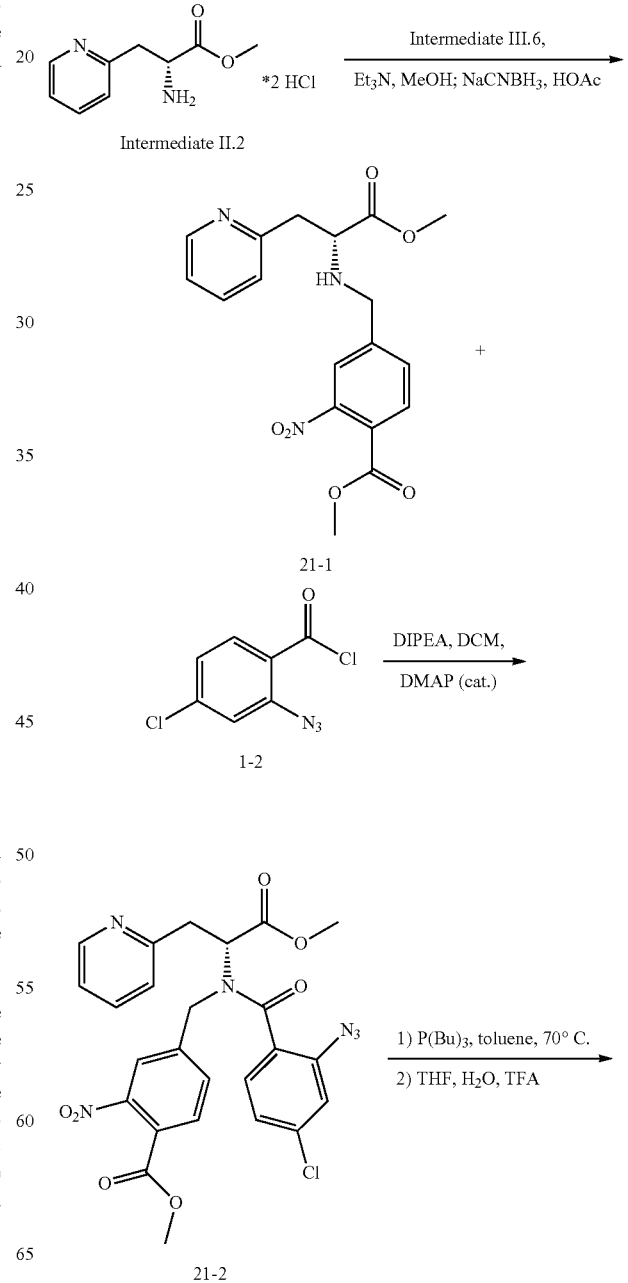

-continued

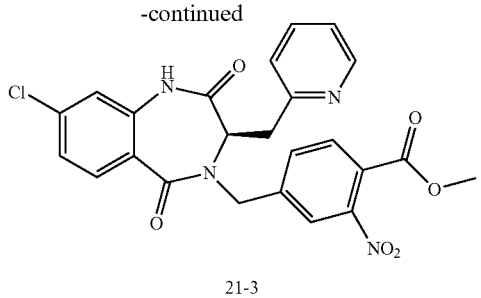

21-3

(R)-Methyl 4-((8-chloro-2,5-dioxo-3-(pyridin-2-ylmethyl)-2,3-dihydro-1H-benzo[e][1,4]diazepin-4(5H)-yl)methyl)-2-nitrobenzoate (21-3) was prepared from Intermediate II.2, Intermediate III.6 and acid chloride 1-2 using the same general procedures described for the preparation of compound 1-4 in Example 1a.

Step 4: (R)-Methyl 2-amino-4-((8-chloro-2,5-dioxo-3-(pyridin-2-ylmethyl)-2,3-dihydro-1H-benzo[e][1,4]diazepin-4(5H)-yl)methyl)benzoate (21-4)

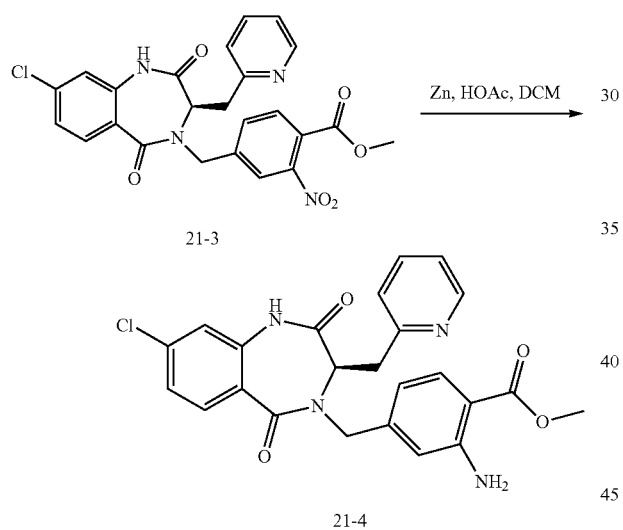

To a suspension of 21-3 (1.0 g, 2.0 mmol) in DCM (10 mL) were added activated Zn powder (2.6 g, 40 mmol) and HOAc (1 mL). The resulting mixture was stirred at 23° C. for 0.5 h. More HOAc (1 mL) was added, and the mixture was stirred an additional 3 h. The mixture was added more DCM (10 mL), HOAc (1 mL) and activated Zn (1.3 g, 20 mmol), and continued to stir at ambient temperature for 16 h. The mixture was then filtered through a pad of CELITE rinsing with DCM, and the combined filtrates were concentrated in vacuo. The crude residue was azeotroped with toluene, and then purified by FCC (SiO$_2$, elution with 0-100% EtOAc/hexanes). The semi pure material obtained was further purified by FCC (SiO$_2$, elution with 0-2% MeOH/DCM) to provide 0.92 g (98%) of 21-4. $^1$H NMR (400 MHz, CDCl$_3$, ~1.6:1 mixture of 7-membered ring conformers observed): δ ppm 8.50-6.54 (m, 11H), 5.73 (br s, 2H), 5.10-4.24 (m, 3H), 3.84 (s, 3H), 3.60 and 2.76 (m, 2H); LCMS (Method A) $t_R$=0.97 min, m/z 465.3/467.3 (M+H)$^+$.

Step 5: (R)-Methyl 4-((8-chloro-2,5-dioxo-3-(pyridin-2-ylmethyl)-2,3-dihydro-1H-benzo[e][1,4]diazepin-4(5H)-yl)methyl)-2-(picolinamido)benzoate (21-5)

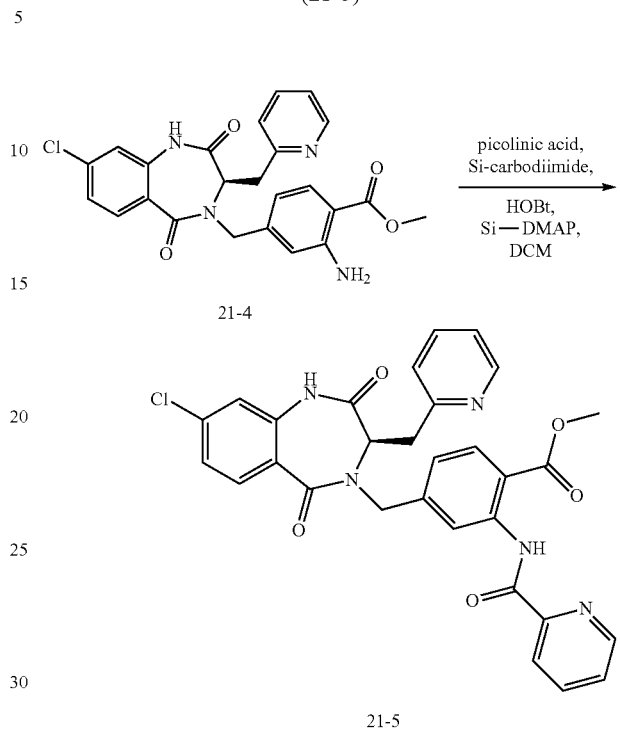

To a solution of picolinic acid (8 mg, 0.07 mmol) in DCM (1 mL) were added Si-carbodiimide (1.1 mmol/g, 78 mg, 0.086 mmol) and HOBt (10 mg, 0.073 mmol). The resulting mixture was stirred at 23° C. for 10 min, and to this were then added 21-4 (20 mg, 0.043 mmol) and Si-DMAP (0.93 mmol/g, 9 mg, 0.009 mmol). The reaction mixture was then stirred at 23° C. for 2 d, and then added Si-carbonate (0.8 mmol/g, 323 mg, 0.258 mmol) and DCM (1 mL), and continued to stir for 2 h. The mixture was then filtered, rinsed with DCM (~10 mL), and the combined filtrates were concentrated in vacuo to give 20 mg of 21-5 which was used without further purification in the next step. LCMS (Method A) $t_R$=1.10 min, m/z 570.4/572.3 (M+H)$^+$.

Step 6: (R)-4-((8-Chloro-2,5-dioxo-3-(pyridin-2-ylmethyl)-2,3-dihydro-1H-benzo[e][1,4]diazepin-4(5H)-yl)methyl)-2-(picolinamido)benzoic Acid (Example 21a)

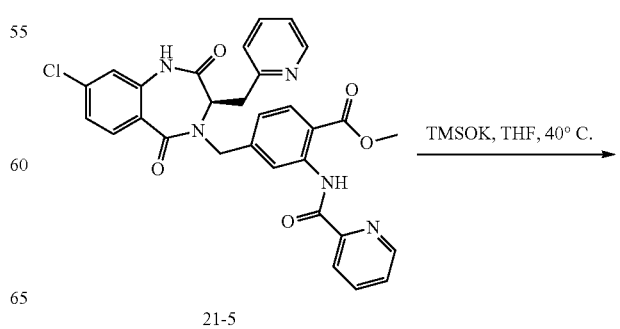

-continued

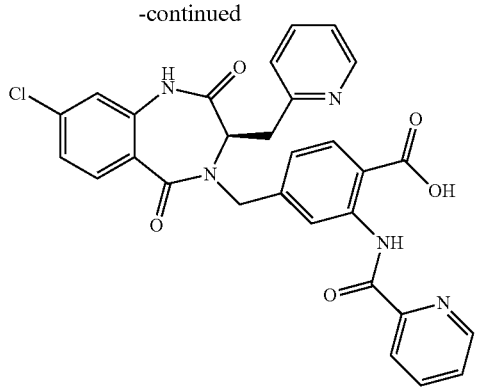

Example 21a

To a solution of 21-5 (20 mg, 0.043 mmol) in THF (1 mL) was added potassium trimethylsilanoate (28 mg, 0.22 mmol). The reaction mixture was heated to 40° C. for 2 h. The mixture was then cooled, concentrated in vacuo, and the residue was purified directly by reverse-phase semi-preparative scale HPLC to provide 12 mg (50%) of Example 21a. LCMS (Method A) $t_R$=0.95 min, m/z 556.4/558.4 (M+H)$^+$.

Example 22a (R)-2-Acetamido-4-((8-chloro-2,5-dioxo-3-(pyridin-2-ylmethyl)-2,3-dihydro-1H-benzo[e][1,4]diazepin-4(5H)-yl)methyl)benzoic Acid Step 1: (R)-Methyl 2-acetamido-4-((8-chloro-2,5-dioxo-3-(pyridin-2-ylmethyl)-2,3-dihydro-1H-benzo[e][1,4]diazepin-4(5H)-yl)methyl)benzoate (22-1)

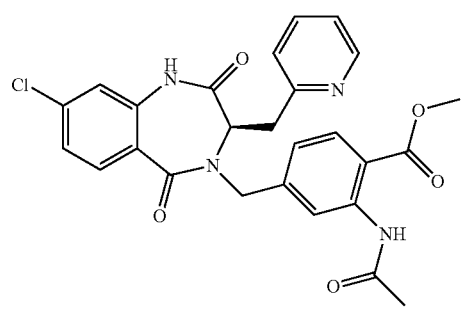

To a mixture of 21-4 (20 mg, 0.044 mmol), PS-DIEA (3.68 mmol/g, 35 mg, 0.13 mmol) and PS-DMAP (1.49 mmol/g, 6 mg, 0.009 mmol) in DCM (1 mL) was added acetyl chloride (5 µL, 0.06 mmol). The resulting mixture was shaken on an orbital stir plate for 18 h. PS-trisamine (3.85 mmol/g, 17 mg, 0.066 mmol) was then added, and the mixture was shaken on an orbital stir plate for an additional 3 h. The mixture was then filtered, rinsed with DCM, and the combined filtrates were concentrated in vacuo to provide crude 22-1 which was used directly in the next step without further purification.

Step 2: (R)-2-Acetamido-4-((8-chloro-2,5-dioxo-3-(pyridin-2-ylmethyl)-2,3-dihydro-1H-benzo[e][1,4]diazepin-4(5H)-yl)methyl)benzoic Acid (Example 22a)

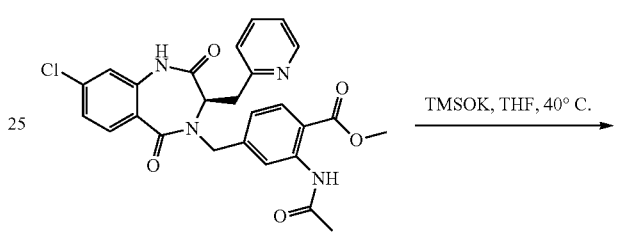

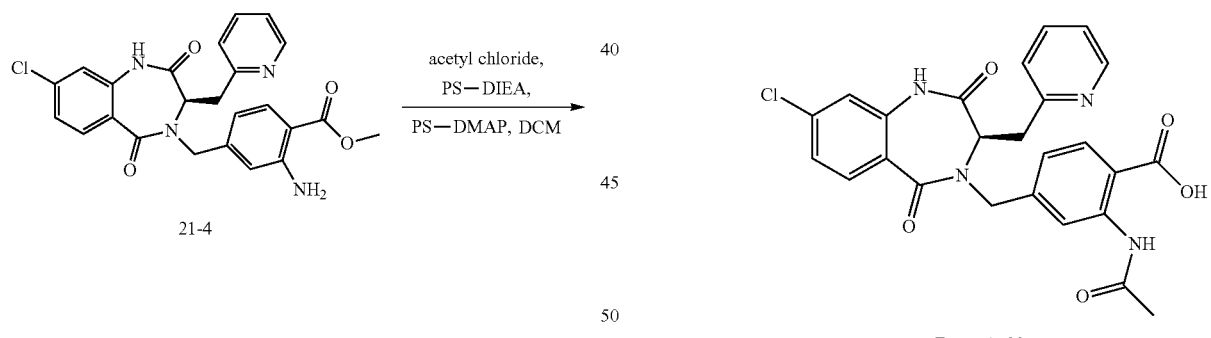

Example 22a

Following the general procedure described for Step 6 in Example 21a, compound 22-1 was reacted with potassium trimethylsilanoate (17 mg, 0.13 mmol) to provide 5 mg (23% for 2 steps) of Example 22a. $^1$H NMR (400 MHz, CDCl$_3$, ~1.2:1 mixture of 7-membered ring conformers observed): δ ppm 13.54 (br s, 1H), 11.18 (br s, 1H), 10.74 and 10.62 (2 s, 1H), 8.50-6.92 (m, 10H), 5.02-4.17 (m, 3H), 3.51-2.82 (m, 2H, partially obscured by H$_2$O peak), 2.124 (s, 3H); LCMS (Method A) $t_R$=0.83 min, m/z 493.3/495.3 (M+H)$^1$.

Following the method described above for Example 22a and substituting the corresponding reagents in step 1, the following Examples were prepared as indicated in Table 21.

TABLE 21

| Example | Structure | Reagent | LCMS Method | $t_R$ (min) | $(M + H)^+$ observed |
|---|---|---|---|---|---|
| 22b | 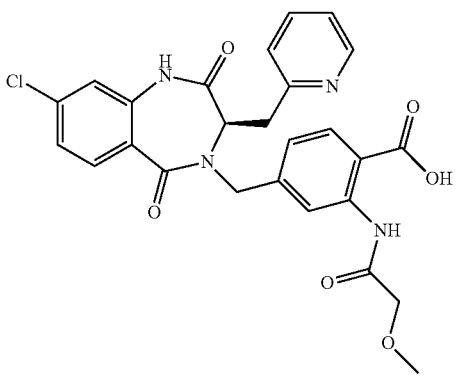<br>(R)-4-((8-chloro-2,5-dioxo-3-(pyridin-2-ylmethyl)-2,3-dihydro-1H-benzo[e][1,4]diazepin-4(5H)-yl)methyl)-2-(2-methoxyacetamido)benzoic acid | 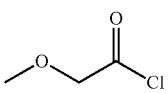 | A | 0.86 | 523.3/525.3 |
| 22c | 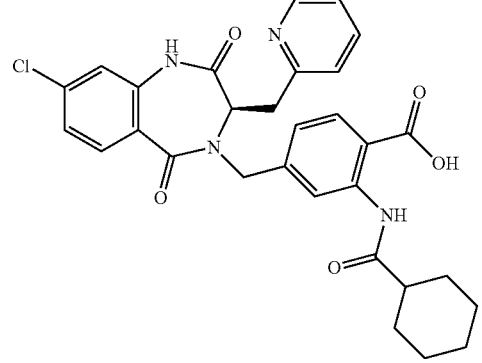<br>(R)-4-((8-chloro-2,5-dioxo-3-(pyridin-2-ylmethyl)-2,3-dihydro-1H-benzo[e][1,4]diazepin-4(5H)-yl)methyl)-2-(cyclohexanecarboxamido)benzoic acid | 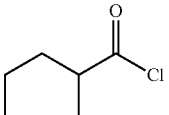 | A | 1.06 | 561.4/563.4 |
| 22d | 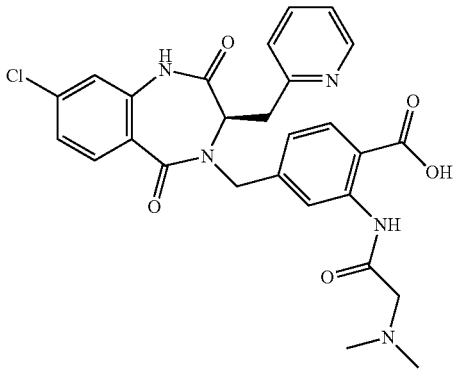<br>(R)-4-((8-chloro-2,5-dioxo-3-(pyridin-2-ylmethyl)-2,3-dihydro-1H-benzo[e][1,4]diazepin-4(5H)-yl)methyl)-2-(2-(dimethylamino)acetamido)benzoic acid | 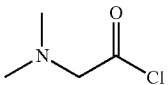 | A | 0.74 | 536.5/538.4 |

TABLE 21-continued

| Example | Structure | Reagent | LCMS Method | $t_R$ (min) | $(M + H)^+$ observed |
|---|---|---|---|---|---|
| 22e | (R)-4-((8-chloro-2,5-dioxo-3-(pyridin-2-ylmethyl)-2,3-dihydro-1H-benzo[e][1,4]diazepin-4(5H)-yl)methyl)-2-(3-methoxypropanamido)benzoic acid | 3-methoxypropanoyl chloride | A | 0.87 | 537.4/539.5 |
| 22f | (R)-4-((8-chloro-2,5-dioxo-3-(pyridin-2-ylmethyl)-2,3-dihydro-1H-benzo[e][1,4]diazepin-4(5H)-yl)methyl)-2-(isonicotinamido)benzoic acid | isonicotinoyl chloride | A | 0.86 | 556.4/558.4 |
| 22g | (R)-4-((8-chloro-2,5-dioxo-3-(pyridin-2-ylmethyl)-2,3-dihydro-1H-benzo[e][1,4]diazepin-4(5H)-yl)methyl)-2-(nicotinamido)benzoic acid | nicotinoyl chloride | A | 0.88 | 556.4/558.5 |

TABLE 21-continued

| Example | Structure | Reagent | LCMS Method | $t_R$ (min) | $(M + H)^+$ observed |
|---|---|---|---|---|---|
| 22h | (R)-4-((8-chloro-2,5-dioxo-3-(pyridin-2-ylmethyl)-2,3-dihydro-1H-benzo[e][1,4]diazepin-4(5H)-yl)methyl)-2-(2-morpholinoacetamido)benzoic acid | | A | 0.79 | 578.5/580.5 |
| 22i | (R)-4-((8-chloro-2,5-dioxo-3-(pyridin-2-ylmethyl)-2,3-dihydro-1H-benzo[e][1,4]diazepin-4(5H)-yl)methyl)-2-(1-methylpiperidine-4-carboxamido)benzoic acid | | A | 0.77 | 576.5/578.5 |
| 22j | (R)-4-((8-chloro-2,5-dioxo-3-(pyridin-2-ylmethyl)-2,3-dihydro-1H-benzo[e][1,4]diazepin-4(5H)-yl)methyl)-2-(2-(4-methylpiperazin-1-yl)acetamido)benzoic acid | | A | 0.83 | 591.5/593.5 |

TABLE 21-continued

| Example | Structure | Reagent | LCMS Method | $t_R$ (min) | $(M + H)^+$ observed |
|---|---|---|---|---|---|
| 22k | (R)-4-((8-chloro-2,5-dioxo-3-(pyridin-2-ylmethyl)-2,3-dihydro-1H-benzo[e][1,4]diazepin-4(5H)-yl)methyl)-2-(3-(dimethylamino)propanamido)benzoic acid | | A | 0.82 | 550.5/552.5 |
| 22l | (R)-4-((8-chloro-2,5-dioxo-3-(pyridin-2-ylmethyl)-2,3-dihydro-1H-benzo[e][1,4]diazepin-4(5H)-yl)methyl)-2-(2-(1-methylpiperidin-4-yl)acetamido)benzoic acid | | A | 0.83 | 590.5/592.5 |
| 22m | (R)-4-((8-chloro-2,5-dioxo-3-(pyridin-2-ylmethyl)-2,3-dihydro-1H-benzo[e][1,4]diazepin-4(5H)-yl)methyl)-2-(tetrahydro-2H-pyran-4-carboxamido)benzoic acid | | A | 0.96 | 563.5/565.5 |

TABLE 21-continued

| Example | Structure | Reagent | LCMS Method | $t_R$ (min) | $(M + H)^+$ observed |
|---|---|---|---|---|---|
| 22n | (R)-4-((8-chloro-2,5-dioxo-3-(pyridin-2-ylmethyl)-2,3-dihydro-1H-benzo[e][1,4]diazepin-4(5H)-yl)methyl)-2-(2-(pyrrolidin-1-yl)acetamido)benzoic acid | | A | 0.83 | 562.5.564.5 |
| 22o | (R)-4-((8-chloro-2,5-dioxo-3-(pyridin-2-ylmethyl)-2,3-dihydro-1H-benzo[e][1,4]diazepin-4(5H)-yl)methyl)-2-(2-hydroxyacetamido)benzoic acid | | A | 0.88 | 509.4/511.4 |

Example 23a (R)-4-(4-Aminobenzyl)-8-chloro-3-(pyridin-2-ylmethyl)-3,4-dihydro-1H-benzo[e][1,4]diazepine-2,5-dione Step 1: (R)-tert-Butyl (4-((8-chloro-2,5-dioxo-3-(pyridin-2-ylmethyl)-2,3-dihydro-1H-benzo[e][1,4]diazepin-4(5H)-yl)methyl)phenyl)carbamate (23-1)

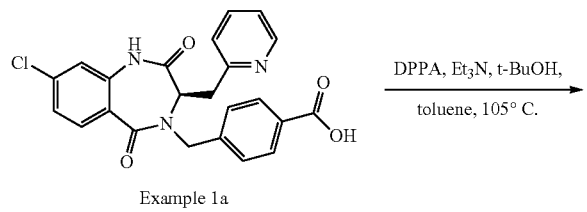

Example 1a

DPPA, Et₃N, t-BuOH,
toluene, 105° C.

-continued

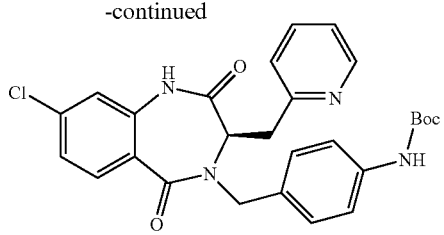

23-1

To a suspension of Example 1a (0.25 g, 0.57 mmol) in toluene (5 mL) and t-BuOH (5 mL) were added 4 Angstrom molecular sieves (1 g), triethylamine (0.10 mL, 0.72 mmol) and DPPA (0.14 mL, 0.63 mmol). The reaction mixture was heated to 105° C. for 18 h. The mixture was then cooled to room temperature, filtered to remove the molecular sieves, and the filtrate was concentrated in vacuo. The crude residue was purified by FCC (SiO₂, elution with 0-100% EtOAc/hexanes) to provide 0.19 g (65%) of 23-1. ¹H NMR (400 MHz, CDCl₃, ~1.7:1 mixture of 7-membered ring conformers observed): δ ppm 8.58-6.55 (m, 13H), 5.05-4.23 (m, 3H), 3.60-2.71 (m, 2H), 1.50 and 1.49 (2 s, 9H); LCMS (Method A) $t_R$=1.08 min, m/z 507.5/509.5 (M+H)⁺.

Step 2: (R)-4-(4-Aminobenzyl)-8-chloro-3-(pyridin-2-ylmethyl)-3,4-dihydro-1H-benzo[e][1,4]diazepine-2,5-dione (Example 23a)

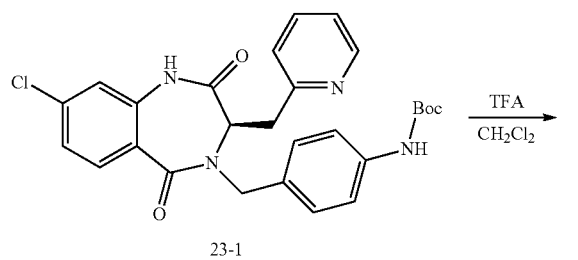

23-1

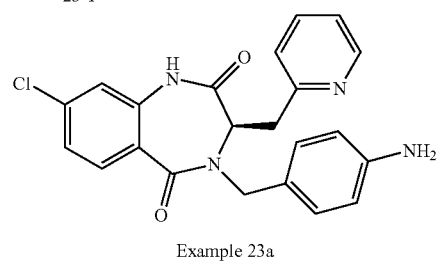

Example 23a

To a solution of 23-1 (0.84 g, 1.7 mmol) in DCM (6 mL) was added TFA (6 mL). The resultant mixture was stirred at 23° C. for 4 h, and then concentrated in vacuo. To the residue was slowly added sat. NaHCO₃ (aq) (50 mL), and the resulting mixture was stirred for 5 min. The mixture was extracted with EtOAc (3×50 mL). The combined organic extracts were washed with brine (1×100 mL), dried (Na$_2$SO$_4$), filtered, and concentrated in vacuo. The crude residue was purified by FCC (SiO$_2$; elution with 0-100% EtOAc/hexanes) to provide 0.5 g (74%) of Example 23a. $^1$H NMR (400 MHz, d$_6$-DMSO, ~1.1:1 mixture of 7-membered ring conformers observed): δ ppm 10.62 and 10.51 (2 br s, 1H, N—H), 8.49 and 8.36 (2 d, 1H), 7.89 and 7.83 (2 d, 1H), 7.68 (m, 1H), 7.34-6.45 (m, 8H), 5.05 and 4.98 (2 s, 2H), 4.91-3.87 (m, 3H), 3.52-2.67 (m, 2H, partially obscured by H$_2$O peak); LCMS (Method A) $t_R$=0.73 min, m/z 407.4/409.4 (M+H)$^+$.

Example 24a (R)-4-(4-Amino-3,5-dimethylbenzyl)-8-chloro-3-(pyridin-2-ylmethyl)-3,4-dihydro-1H-benzo[e][1,4]diazepine-2,5-dione Steps 1-3: (R)-8-Chloro-4-(3,5-dimethyl-4-nitrobenzyl)-3-(pyridin-2-ylmethyl)-3,4-dihydro-1H-benzo[e][1,4]diazepine-2,5-dione (24-3)

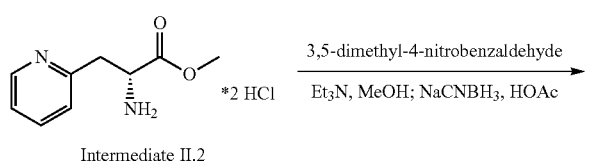

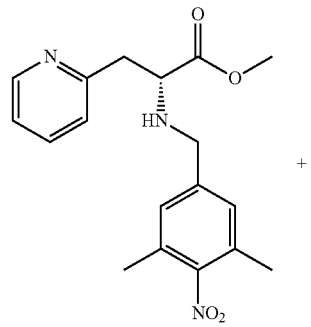

24-1

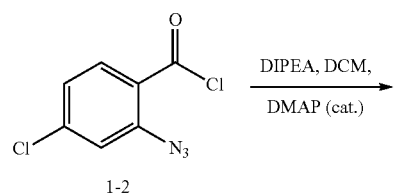

1-2

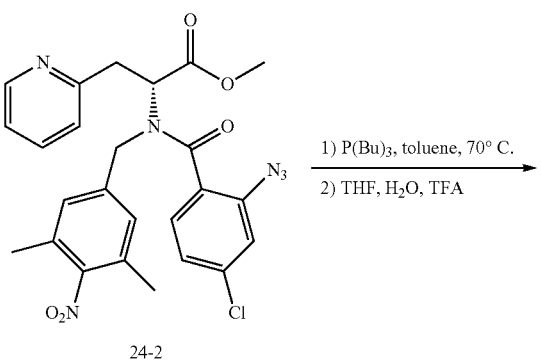

24-2

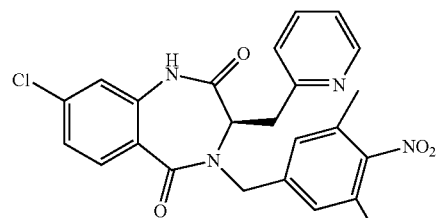

24-3

(R)-4-(4-Amino-3,5-dimethylbenzyl)-8-chloro-3-(pyridin-2-ylmethyl)-3,4-dihydro-1H-benzo[e][1,4]diazepine-2,5-dione (24-3) was prepared from Intermediate II.2, 3,5-dimethyl-4-nitrobenzaldehyde and acid chloride 1-2 using the same general procedures described for the preparation of compound 1-4 in Example 1a. LCMS (Method A) $t_R$=1.13 min, m/z 465.5/467.5 (M+H)$^1$.

Step 4: (R)-4-(4-Amino-3,5-dimethylbenzyl)-8-chloro-3-(pyridin-2-ylmethyl)-3,4-dihydro-1H-benzo[e][1,4]diazepine-2,5-dione (Example 24a)

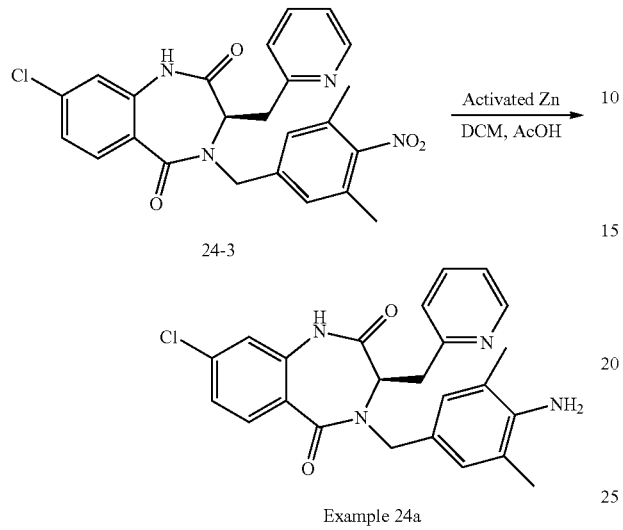

To a solution of 24-3 (50 mg, 0.11 mmol) in DCM (3 mL) were added activated zinc powder (141 mg, 2.2 mmol) and acetic acid (0.17 mL). The resultant mixture was stirred at 23° C. for 2 h, and then filtered rinsing with additional DCM (40 mL). The filtrate was washed successively with sat. NaHCO$_3$ (aq) (1×20 mL) and brine (aq) (1×20 mL), dried (Na$_2$SO$_4$), filtered, and concentrated in vacuo. The crude residue was purified by FCC (SiO$_2$; elution with 0-100% EtOAc/hexanes) to provide 17 mg (36%) of Example 24a. $^1$H NMR (400 MHz, d$_6$-DMSO, ~1.2:1 mixture of 7-membered ring conformers observed) δ ppm 10.66 and 10.55 (2 s, 1H, N—H), 8.47 and 8.36 (2 d, 1H), 7.89 and 7.83 (2 d, 1H), 7.66 (m, 1H), 7.35-6.90 (m, 4H), 6.73 and 6.67 (2 s, 2H), 4.92-3.82 (m, 3H), 4.53 and 4.46 (2 s, 2H), 3.50-2.67 (m, 2H, partially obscured by H$_2$O peak), 2.02 (s, 6H); LCMS (Method A) $t_R$=0.84 min, m/z 435.5/437.5 (M+H)$^+$.

Example 25a

N-((1R,4r)-4-(((R)-8-Chloro-2,5-dioxo-3-(pyridin-2-ylmethyl)-2,3-dihydro-1H-benzo[e][1,4]diazepin-4(5H)-yl)methyl)cyclohexyl)-5-methylpicolinamide Step 1: Tert-Butyl ((1R,4r)-4-(((R)-8-chloro-2,5-dioxo-3-(pyridin-2-ylmethyl)-2,3-dihydro-1H-benzo[e][1,4]diazepin-4(5H)-yl)methyl)cyclohexyl)carbamate (25-1)

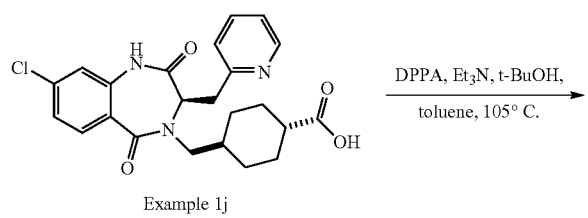

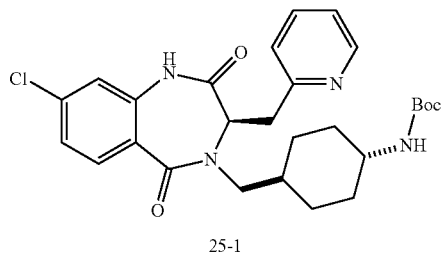

To a solution of Example 1j (0.25 g, 0.57 mmol) in toluene (5 mL) and t-BuOH (5 mL) were added 4 Angstrom molecular sieves (1 g), triethylamine (0.090 mL, 0.62 mmol) and DPPA (0.13 mL, 0.62 mmol). The reaction mixture was heated to 105° C. for 18 h. The mixture was then cooled to room temperature, filtered to remove the molecular sieves, and the filtrate was concentrated in vacuo. The crude residue was purified by FCC (SiO$_2$, elution with 0-100% EtOAc/hexanes) to provide 81 mg (28%) of 25-1. LCMS (Method A) $t_R$=1.11 min, m/z 513.6/515.6 (M+H)$^+$.

Step 2: (R)-4-(((1r,4R)-4-Aminocyclohexyl)methyl)-8-chloro-3-(pyridin-2-ylmethyl)-3,4-dihydro-1H-benzo[e][1,4]diazepine-2,5-dione Hydrochloride (25-2)

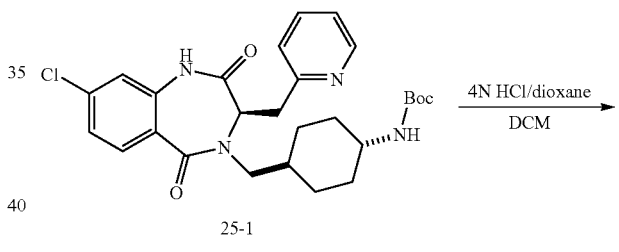

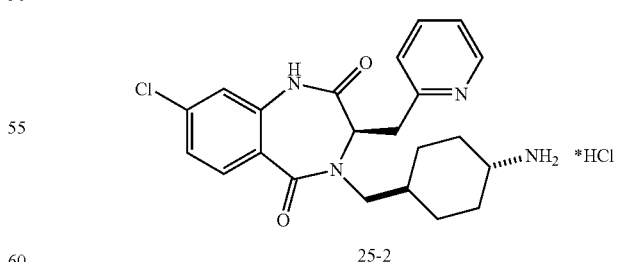

To a solution of 25-1 (81 mg, 0.16 mmol) in DCM (1 mL) was added 4 N HCl in dioxane (1 mL). The resultant mixture was stirred at 23° C. for 1 h then concentrated in vacuo to provide 72 mg (100%) of 25-2. LCMS (Method A) $t_R$=0.74 min, m/z 413.5/415.5 (M+H)$^+$.

Step 3: N-((1R,4r)-4-(((R)-8-Chloro-2,5-dioxo-3-(pyridin-2-ylmethyl)-2,3-dihydro-1H-benzo[e][1,4]diazepin-4(5H)-yl)methyl)cyclohexyl)-5-methylpicolinamide (Example 25a)

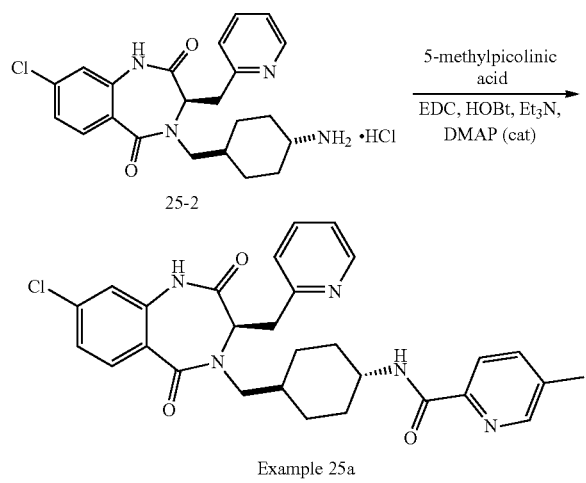

Example 25a

To a mixture of 25-2 (32 mg, 0.071 mmol) and 5-methylpicolinic acid (10 mg, 0.071 mmol) in DCM (1 mL) were added triethylamine (0.020 mL, 0.14 mmol) followed by EDC (16 mg, 0.085 mmol) and HOBt (12 mg, 0.085 mmol). The resulting mixture was stirred at 23° C. for 2 h, and then catalytic DMAP (5 mg, 0.04 mmol) was added. The mixture was stirred for another 3 d. The mixture was then diluted with EtOAc (30 mL), and washed successively with sat. NH$_4$Cl (aq) (1×15 mL), sat. NaHCO$_3$ (aq) (1×15 mL) and brine (1×10 mL). The organic phase was dried (Na$_2$SO$_4$), filtered, and concentrated in vacuo. The crude residue was purified by FCC (SiO$_2$, elution with 0-5% MeOH/DCM) to provide 25 mg (66%) of Example 25a. $^1$H NMR (400 MHz, d$_6$-DMSO ~1.3:1 mixture of 7-membered ring conformers observed): δ ppm 8.59-6.82 (m, 12H), 4.99 and 4.72 (2 m, 1H), 4.13-2.69 (m, 2H), 2.39 (s, 3H), 2.17-1.09 (m, 9H); LCMS (Method A) t$_R$=1.01 min, m/z 532.5/534.5 (M+H)$^+$.

Example 26a (R)-tert-Butyl (4-((8-chloro-2,5-dioxo-3-(pyridin-2-ylmethyl)-2,3-dihydro-1H-benzo[e][1,4]diazepin-4(5H)-yl)methyl)phenyl)carbamate

Steps 1-2: (R)-4-(4-Aminobenzyl)-8-chloro-3-(pyridin-3-ylmethyl)-3,4-dihydro-1H-benzo[e][1,4]diazepine-2,5-dione (26-1)

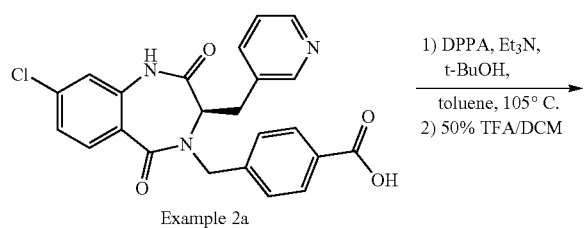

Example 2a

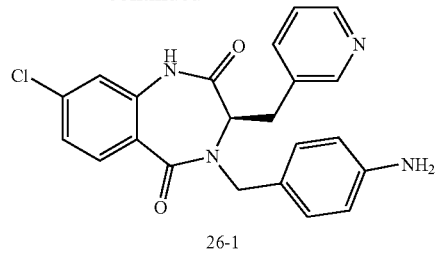

26-1

(R)-4-(4-Aminobenzyl)-8-chloro-3-(pyridin-3-ylmethyl)-3,4-dihydro-1H-benzo[e][1,4]diazepine-2,5-dione (26-1) was prepared from carboxylic acid Example 2a using the same general procedures described for the preparation of Example 23a. LCMS (Method A) t$_R$=0.64 min, m/z 407.4/409.4 (M+H)$^+$.

Step 3: (R)—N-(4-((8-Chloro-2,5-dioxo-3-(pyridin-3-ylmethyl)-2,3-dihydro-1H-benzo[e][1,4]diazepin-4(5H)-yl)methyl)phenyl)picolinamide (Example 26a)

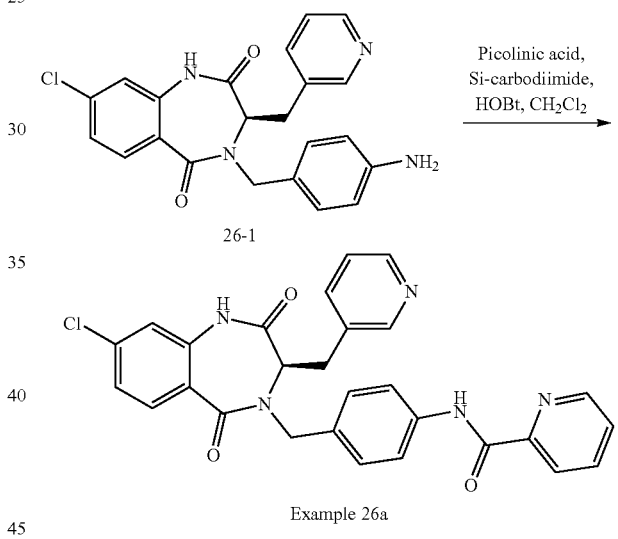

Example 26a

To a solution of picolinic acid (5 mg, 0.04 mmol) in DCM (1 mL) were added Si-carbodiimide (1.1 mmol/g, 45 mg, 0.049 mmol) and HOBt (6 mg, 0.04 mmol). The resulting mixture was stirred at 23° C. for 15 min. A solution of 26-1 (10 mg, 0.025 mmol) in DCM (0.5 mL) was added, and resulting mixture was stirred at 23° C. for 18 h. To the mixture was added Si-carbonate (0.8 mmol/g, 0.19 g, 0.15 mmol), and the resulting mixture was stirred at 23° C. for 1.5 h. The mixture was filtered rinsing with DCM (2×5 mL). The combined organic filtrates were concentrated in vacuo, and the crude residue was purified by FCC (SiO$_2$; elution with 0-10% CH$_3$OH/DCM) to provide 9 mg (68%) of Example 26a. $^1$H NMR (400 MHz, d$_6$-DMSO ~1.7:1 mixture of 7-membered ring conformers observed) δ ppm 10.75-10.63 (m, 2H, N—H's), 8.75-7.09 (m, 15H), 4.97-4.21 (m, 3H), 3.38-2.65 (m, 2H, partially obscured by H$_2$O peak); LCMS (Method A) t$_R$=0.88 min, m/z 512.5/514.5 (M+H)$^+$.

Following the method described above for Step 3 of Example 26a and substituting the corresponding precursors and reagents, the following Examples were prepared as indicated in Table 22.

TABLE 22

| Example | Structure | Precursor | Reagent | LCMS Method | $t_R$ (min) | $(M + H)^+$ observed |
|---|---|---|---|---|---|---|
| 26b | (R)-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide | 23a | pyridine-2-carboxylic acid | A | 0.98 | 512.5/ 514.5 |
| 26c | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-4-methylpicolinamide | 23a | 4-methylpyridine-2-carboxylic acid | A | 1.05 | 526.5/ 528.5 |
| 26d | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-6-methylpicolinamide | 23a | 6-methylpyridine-2-carboxylic acid | A | 1.05 | 526.5/ 528.5 |
| 26e | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-3-methylpicolinamide | 23a | 3-methylpyridine-2-carboxylic acid | A | 1.02 | 526.5/ 528.5 |
| 26f | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-5-methylpicolinamide | 23a | 5-methylpyridine-2-carboxylic acid | A | 1.02 | 526.5/ 528.5 |

TABLE 22-continued

| Example | Structure | Precursor | Reagent | LCMS Method | $t_R$ (min) | $(M + H)^+$ observed |
|---|---|---|---|---|---|---|
| 26g | (R)-3-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide | 23a | 3-chloropicolinic acid | A | 0.96 | 546.5/ 548.5/ 550.5 |
| 26h | (R)-4-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide | 23a | 4-chloropicolinic acid | A | 1.09 | 546.5/ 548.5/ 550.5 |
| 26i | (R)-5-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide | 23a | 5-chloropicolinic acid | A | 1.10 | 546.5/ 548.5/ 550.5 |
| 26j | N-((1R,4r)-4-(((R)-8-chloro-2,5-dioxo-3-(pyridin-2-ylmethyl)-2,3-dihydro-1H-benzo[e][1,4]diazepin-4(5H)-yl)methyl)cyclohexyl)picolinamide | 25-2 | picolinic acid | A | 0.97 | 518.5/ 520.5 |
| 26k | (R)-N-(4-((8-chloro-2,5-dioxo-3-(pyridin-2-ylmethyl)-2,3-dihydro-1H-benzo[e][1,4]diazepin-4(5H)-yl)methyl)-2,6-dimethylphenyl)picolinamide | 24a | picolinic acid | A | 1.01 | 540.5/ 542.5 |

TABLE 22-continued

| Example | Structure | Precursor | Reagent | LCMS Method | $t_R$ (min) | $(M + H)^+$ observed |
|---|---|---|---|---|---|---|
| 26l | 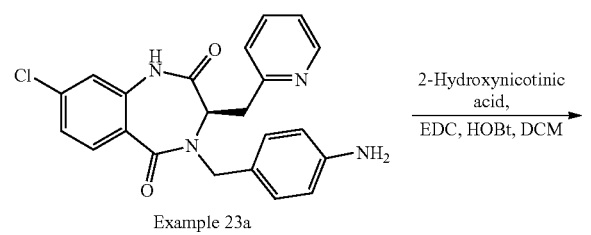  (R)-N-(4-((8-chloro-2,5-dioxo-3-(pyridin-2-ylmethyl)-2,3-dihydro-1H-benzo[e][1,4]diazepin-4(5H)-yl)methyl)-2,6-dimethylphenyl)-5-methylpicolinamide | 24a | 5-methylpyridine-2-carboxylic acid | A | 1.07 | 554.6/556.6 |

Example 27a (R)—N-(4-((8-Chloro-2,5-dioxo-3-(pyridin-2-ylmethyl)-2,3-dihydro-1H-benzo[e][1,4]diazepin-4(5H)-yl)methyl)phenyl)-2-hydroxynicotinamide

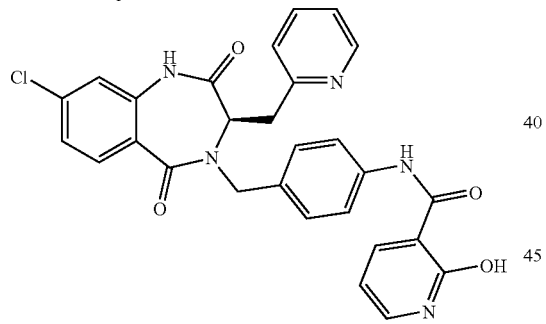

Example 27a

To a solution of Example 23a (50 mg, 0.12 mmol) in DCM (2.0 mL) were added EDC (26 mg, 0.14 mmol) and HOBt (18 mg, 0.14 mmol). The resultant mixture was stirred at 23° C. for 15 min. 2-Hydroxynicotinic acid (17 mg, 0.12 mmol) was added, and the resulting mixture was stirred at 23° C. for 18 h, and then concentrated in vacuo. The residue was dissolved in EtOAc (30 mL), and then washed successively with sat. $NH_4Cl$ (aq) (1×15 mL), sat. $NaHCO_3$ (aq) (1×15 mL) and brine (1×10 mL). The organic layer was dried ($Na_2SO_4$), filtered, and concentrated in vacuo, and the crude residue was purified by FCC ($SiO_2$; elution with 0-100% EtOAc/hexanes) to provide 8 mg (12%) of Example 27a. $^1$H NMR (400 MHz, $d_6$-DMSO ~1.4:1 mixture of 7-membered ring conformers observed): δ ppm 12.75 (br s, 1H, O—H), 12.21 and 12.18 (2 s, 1H, N—H), 10.70 and 10.60 (2 s, 1H, N—H), 8.49-6.55 (m, 14H), 5.99-4.07 (m, 3H), 3.54-2.75 (m, 2H, partially obscured by $H_2O$ peak); LCMS (Method A) $t_R$=0.85 min, m/z 528.5/530.5 (M+H)$^+$.

Following the method described above for Example 27a and substituting the corresponding reagents, the following Examples were prepared as indicated in Table 23.

TABLE 23

| Example | Structure | Reagent | LCMS Method | $t_R$ (min) | $(M + H)^+$ observed |
|---|---|---|---|---|---|
| 27b | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-2-hydroxyacetamide | glycolic acid | A | 0.80 | 465.5/467.5 |

TABLE 23-continued

| Example | Structure | Reagent | LCMS Method | $t_R$ (min) | $(M + H)^+$ observed |
|---|---|---|---|---|---|
| 27c | (R)-N-(4-((8-chloro-2,5-dioxo-3-(pyridin-2-ylmethyl)-2,3-dihydro-1H-benzo[e][1,4]diazepin-4(5H)-yl)methyl)phenyl)pyrimidine-4-carboxamide | pyrimidine-4-carboxylic acid | A | 0.99 | 513.5/515.5 |
| 27d | (R)-N-(4-((8-chloro-2,5-dioxo-3-(pyridin-2-ylmethyl)-2,3-dihydro-1H-benzo[e][1,4]diazepin-4(5H)-yl)methyl)phenyl)pyrazine-2-carboxamide | pyrazine-2-carboxylic acid | A | 1.00 | 513.5/515.5 |
| 27e | (R)-N-(4-((8-chloro-2,5-dioxo-3-(pyridin-2-ylmethyl)-2,3-dihydro-1H-benzo[e][1,4]diazepin-4(5H)-yl)methyl)phenyl)thiazole-2-carboxamide | thiazole-2-carboxylic acid | A | 1.06 | 518.5/520.5 |
| 27f | (R)-N-(4-((8-chloro-2,5-dioxo-3-(pyridin-2-ylmethyl)-2,3-dihydro-1H-benzo[e][1,4]diazepin-4(5H)-yl)methyl)phenyl)thiazole-4-carboxamide | thiazole-4-carboxylic acid | A | 1.02 | 518.5/520.5 |
| 27g | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-5-methylisoxazole-3-carboxamide | 5-methylisoxazole-3-carboxylic acid | A | 1.07 | 516.5/518.5 |

TABLE 23-continued

| Example | Structure | Reagent | LCMS Method | $t_R$ (min) | $(M + H)^+$ observed |
|---|---|---|---|---|---|
| 27h | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-1H-imidazole-2-carboxamide | 1H-imidazole-2-carboxylic acid | A | 0.94 | 501.5/503.5 |
| 27i | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-1-methyl-1H-imidazole-2-carboxamide | 1-methyl-1H-imidazole-2-carboxylic acid | A | 1.01 | 515.5/517.5 |
| 27j | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-1H-imidazole-4-carboxamide | 1H-imidazole-4-carboxylic acid | A | 0.87 | 501.5/503.5 |
| 27k | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-1-methyl-1H-imidazole-4-carboxamide | 1-methyl-1H-imidazole-4-carboxylic acid | A | 0.91 | 515.5/517.5 |

Example 28a (R)—N-(3-((8-Chloro-2,5-dioxo-3-(pyridin-2-ylmethyl)-2,3-dihydro-1H-benzo[e][1,4]diazepin-4(5H)-yl)methyl)phenyl)picolinamide Steps 1-3: (R)-8-Chloro-4-(3-nitrobenzyl)-3-(pyridin-2-ylmethyl)-3,4-dihydro-1H-benzo[e][1,4]diazepine-2,5-dione (28-3)

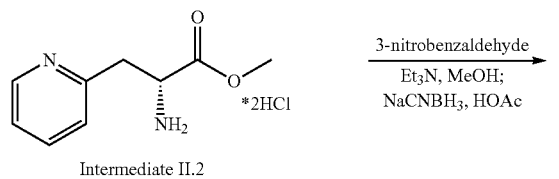

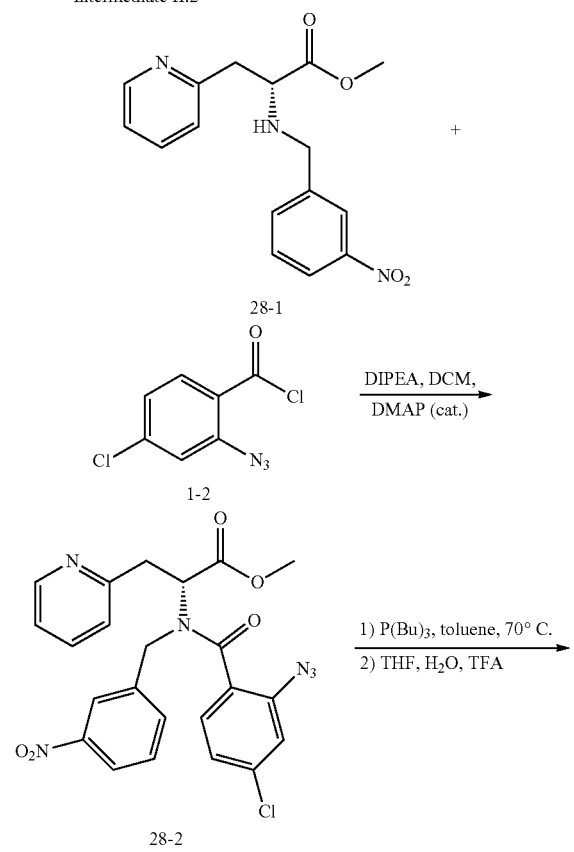

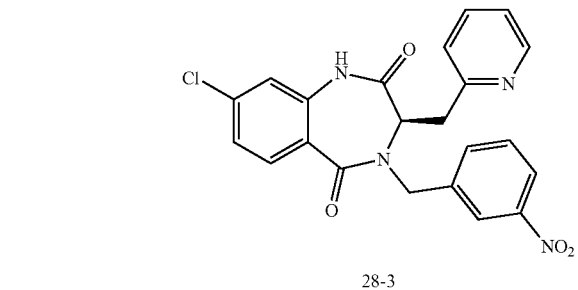

(R)-8-Chloro-4-(3-nitrobenzyl)-3-(pyridin-2-ylmethyl)-3,4-dihydro-1H-benzo[e][1,4]diazepine-2,5-dione (28-3) was prepared from Intermediate II.2, 3-nitrobenzaldehyde and acid chloride 1-2 using the same general procedures described for the preparation of compound 1-4 in Example 1a.

Step 4: (R)-4-(3-Aminobenzyl)-8-chloro-3-(pyridin-2-ylmethyl)-3,4-dihydro-1H-benzo[e][1,4]diazepine-2,5-dione (28-4)

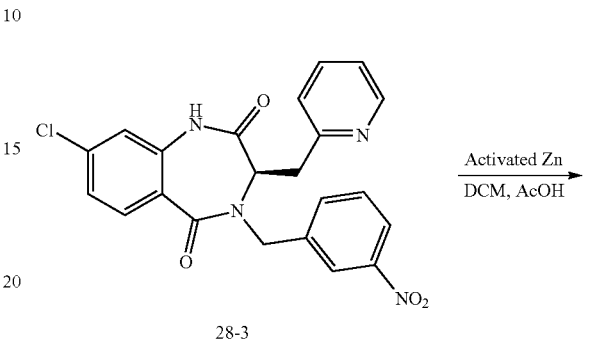

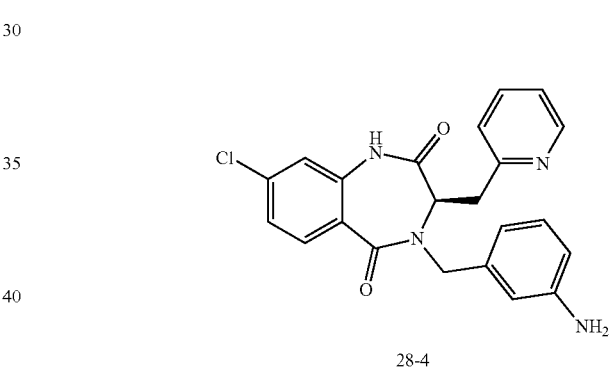

Following the general procedure described in Step 4 of Example 24a, compound 28-4 was prepared from 28-3.

Step 5: (R)—N-(3-((8-Chloro-2,5-dioxo-3-(pyridin-2-ylmethyl)-2,3-dihydro-1H-benzo[e][1,4]diazepin-4(5H)-yl)methyl)phenyl)picolinamide (Example 28a)

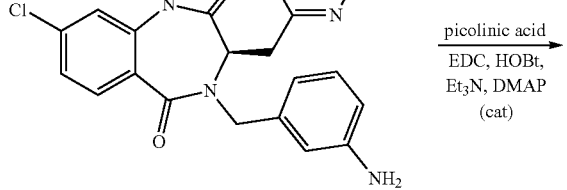

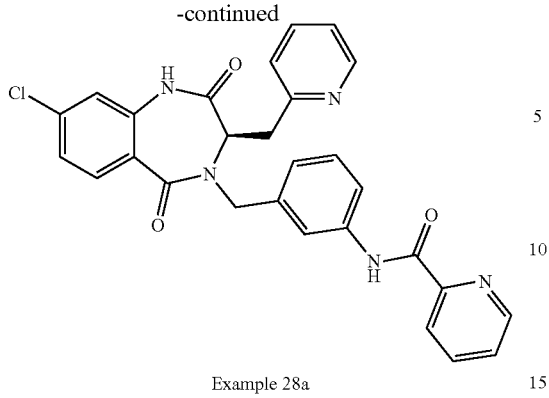

Example 28a

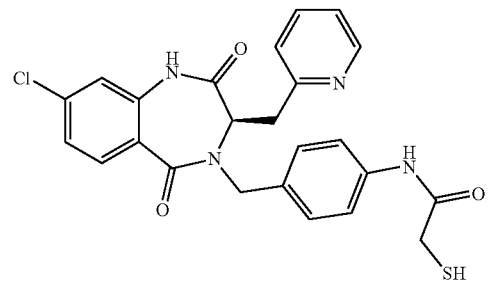

Example 29a

Following the general procedure described for Step 3 of Example 25a, compound 28-4 was reacted with picolinic acid to provide Example 28a. $^1$H NMR (400 MHz, d$_6$-DMSO, ~1.3:1 mixture of 7-membered ring conformers observed): δ ppm 10.72-10.61 (m, 2H, N—H's), 8.74-6.96 (m, 14H), 5.04-4.09 (m, 3H), 3.55-2.80 (m, partially obscured by H$_2$O peak, 2H); LCMS (Method A) t$_R$=0.85 min, m/z 512.5/514.5 (M+H)$^+$.

Following the method described above for Example 28a and substituting the corresponding reagent in Step 5, the following Example was prepared as indicated in Table 24.

To a solution of Example 23a (50 mg, 0.12 mmol) in toluene (0.5 mL) was added thioglycolic acid (43 μL, 0.61 mmol). The resulting mixture was stirred at 100° C. in a sealed reaction tube for 24 h. The mixture was cooled to 50°

TABLE 24

| Example | Structure | Reagent | LCMS Method | t$_R$ (min) | (M + H)$^+$ observed |
|---|---|---|---|---|---|
| 28b | (R)-N-(3-((8-chloro-2,5-dioxo-3-(pyridin-2-ylmethyl)-2,3-dihydro-1H-benzo[e][1,4]diazepin-4(5H)-yl)methyl)phenyl)-2-methoxyacetamide | HO—C(O)—CH$_2$—O—CH$_3$ | A | 0.98 | 479.5/481.5 |

Example 29a (R)—N-(4-((8-Chloro-2,5-dioxo-3-(pyridin-2-ylmethyl)-2,3-dihydro-1H-benzo[e][1,4]diazepin-4(5H)-yl)methyl)phenyl)-2-mercaptoacetamide

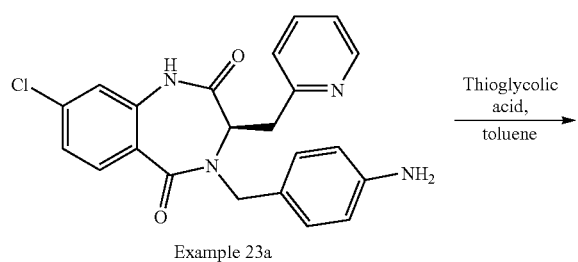

Example 23a

→ Thioglycolic acid, toluene

C., diluted with EtOAc (20 mL), and stirred until precipitated solids were dissolved. The resulting solution was cooled to room temperature, and then washed successively with sat. NaHCO$_3$ (aq) (1×10 mL), sat. NH$_4$Cl (aq) (1×10 mL), and brine (1×10 mL). The organic phase was then dried (Na$_2$SO$_4$), filtered, and concentrated in vacuo. The crude residue was purified by FCC (SiO$_2$; elution with 0-10% CH$_3$OH/CH$_2$Cl$_2$) to provide 28 mg (47%) of Example 29a. $^1$H NMR (400 MHz, d$_6$-DMSO, ~1.2:1 mixture of 7-membered ring conformers observed): δ ppm 10.67 and 10.57 (2 s, 1H, N—H), 10.09 and 10.06 (2 s, 1H, N—H), 8.47 and 8.36 (2 d, 1H), 7.90-6.96 (m, 10H), 4.96-4.03 (m, 3H), 3.51-2.72 (m, 2H, partially obscured by H$_2$O peak), 3.27 (br s, 2H), 2.94 (br s, 1H); LCMS (Method A) t$_R$=0.89 min, m/z 481.5/483.5 (M+H)$^+$.

Example 30a (R)—N-(4-((8-Chloro-2,5-dioxo-3-(pyridin-2-ylmethyl)-2,3-dihydro-1H-benzo[e][1,4]diazepin-4(5H)-yl)methyl)phenyl)methanesulfonamide

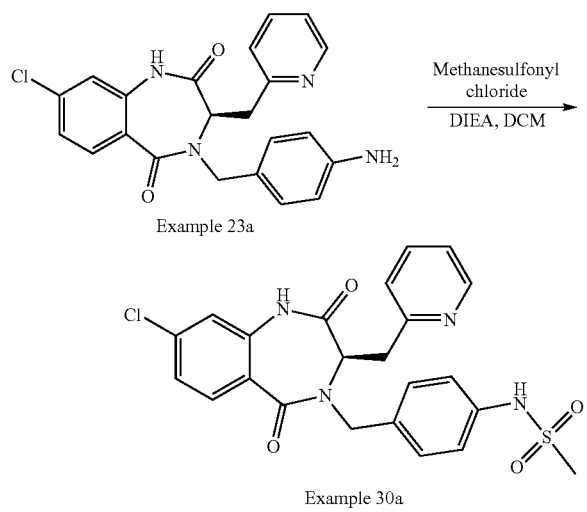

To a solution of Example 23a (25 mg, 0.061 mmol) in CH$_2$Cl$_2$ (0.5 mL) were added DIEA (16 µL, 0.092 mmol) and methane sulfonylchloride (5.2 µL, 0.068 mmol). The resultant mixture was stirred at 23° C. for 6 h. The mixture was diluted with EtOAc, washed successively with sat. NH$_4$Cl (aq), sat. NaHCO$_3$ (aq) and brine, and then concentrated in vacuo. The crude residue was purified by FCC (SiO$_2$; elution with 0-100% EtOAc/hexanes) to provide 11 mg (37%) of Example 30a. $^1$H NMR (400 MHz, d$_6$-DMSO ~1.3:1 mixture of 7-membered ring conformers observed): δ ppm 10.70 and 10.61 (2 s, 1H, N—H), 9.74 and 9.69 (2 s, 1H, N—H), 8.47 and 8.37 (2 d, 1H), 7.89 and 7.84 (2 d, 1H), 7.67 (m, 1H), 7.38-6.98 (m, 8H), 4.98-4.06 (m, 3H), 3.52-2.74 (m, 2H), 2.96 and 2.95 (2 s, 3H); LCMS (Method A) t$_R$=0.87 min, m/z 485.5/487.5 (M+H)$^+$.

Following the method described above for Example 30a and substituting the corresponding precursors and/or reagents, the following Examples were prepared as indicated in Table 25.

TABLE 25

| Example | Structure | Precursor | Reagent | LCMS Method | t$_R$ (min) | (M + H)$^+$ observed |
|---|---|---|---|---|---|---|
| 30b | (R)-N-(4-((8-chloro-2,5-dioxo-3-(pyridin-2-ylmethyl)-2,3-dihydro-1H-benzo[e][1,4]diazepin-4(5H)-yl)methyl)phenyl)-2-methoxyacetamide | 23a | | A | 0.85 | 479.5/481.5 |
| 30c | (R)-N-(3-((8-chloro-2,5-dioxo-3-(pyridin-2-ylmethyl)-2,3-dihydro-1H-benzo[e][1,4]diazepin-4(5H)-yl)methyl)phenyl)pyridine-2-sulfonamide | 28-4 | | A | 1.04 | 548.5/550.5 |

Example 31a (R)-8-Chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione

Step 1: 3-Bromo-1-methyl-4-azaindole (31-1)

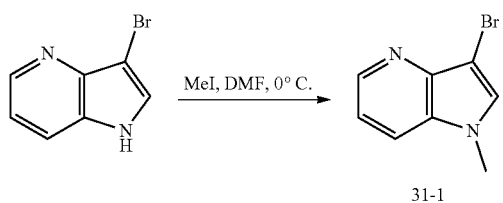

To a solution of 3-bromo-4-azaindole (0.70 g, 3.6 mmol, for preparation see: Ebetino, F. H. et al. 4-Azaindole Bisphosphonates, PCT Int. Appl. (2010) WO 2010033980) in anhydrous DMF (16 mL) at 0° C. was added sodium hydride (0.22 g, 5.3 mmol, 60% dispersion in mineral oil). The mixture was allowed to warm to room temperature over approximately 15 min, and methyl iodide (0.27 mL, 4.3 mmol) was added. The mixture was stirred at 23° C. for 1 h, and then quenched with water. The mixture was diluted with DCM (100 mL), and washed with water (1×100 mL) and brine (1×50 mL). The organic layer was dried ($Na_2SO_4$), filtered, and concentrated in vacuo. The crude residue was purified by FCC ($SiO_2$; elution with 0-4% MeOH/$CH_2Cl_2$) to provide 0.6 g (36%) of 31-1. $^1$H NMR (400 MHz, $d_6$-DMSO): δ ppm 8.41 (dd, 1H), 7.96 (dd, 1H), 7.86 (s, 1H), 7.25 (dd, 1H), 3.83 (s, 3H).

Step 2: (R)-8-Chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione (Example 31a)

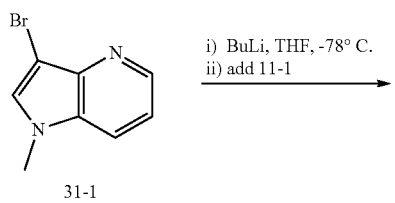

i) BuLi, THF, -78° C.
ii) add 11-1

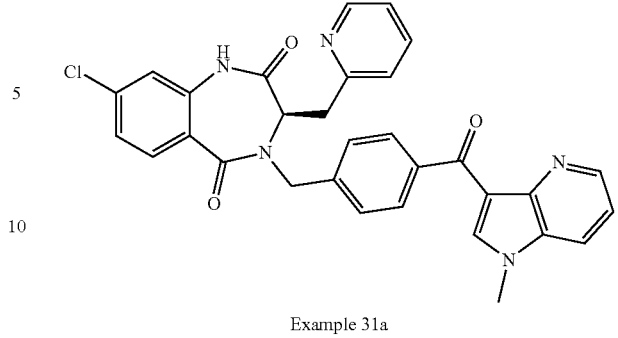

Example 31a

To a solution of 31-1 (0.17 g, 0.80 mmol) in anhydrous THF (4 mL) at −78° C. under nitrogen atmosphere was added n-BuLi (0.43 mL, 1.6 M in hexane, 0.68 mmol). The mixture was stirred at −78° C. for 20 min, and a solution of Weinreb amide 11-1 (0.10 g, 0.23 mmol) in anhydrous THF (1 mL) was added. The mixture was allowed to warm to −10° C., and the reaction mixture was stirred for 1.5 h. The reaction was quenched by the addition of sat. $NH_4Cl$ (aq), and then diluted with EtOAc. Saturated $Na_2CO_3$ (aq) was added, and the layers were separated. The organic phase was washed with brine, dried ($Na_2SO_4$), filtered, and concentrated in vacuo. The residue was purified by FCC ($SiO_2$; elution with 0-5% 2M $NH_3$ in MeOH/DCM) to provide 23 mg (18%) of Example 31a. $^1$H NMR (400 MHz, $CD_3OD$, ~1.2:1 mixture of 7-membered ring conformers observed): δ ppm 8.54-6.93 (m, 15H), 5.13-4.36 (m, 3H, partially obscured by $H_2O$ peak), 3.93 (s, 3H), 3.66-2.88 (m, 2H); LCMS (Method A): $t_R$=0.80 min, m/z 550.4/552.4 (M+H)$^+$.

Following the method described above for step 2 of Example 31a and substituting the corresponding reagents, the following Examples were prepared as indicated in Table 26.

TABLE 26

| Example | Structure | Reagent | LCMS Method | $t_R$ (min) | (M + H)$^+$ observed |
|---|---|---|---|---|---|
| 31b | (R)-8-chloro-3-(pyridin-2-ylmethyl)-4-(4-(quinoline-8-carbonyl)benzyl)-3,4-dihydro-1H-benzo[e][1,4]diazepine-2,5-dione | | A | 1.01 | 547.2/549.2 |

TABLE 26-continued

| Example | Structure | Reagent | LCMS Method | $t_R$ (min) | (M + H)+ observed |
|---|---|---|---|---|---|
| 31c | (R)-8-chloro-4-(4-(1-methyl-1H-imidazole-2-carbonyl)benzyl)-3-(pyridin-2-ylmethyl)-3,4-dihydro-1H-benzo[e][1,4]diazepine-2,5-dione | 2-bromo-1-methyl-1H-imidazole | A | 1.21 | 499.2/502.0 |
| 31d | (R)-8-chloro-4-(4-(1-methyl-1H-imidazole-4-carbonyl)benzyl)-3-(pyridin-2-ylmethyl)-3,4-dihydro-1H-benzo[e][1,4]diazepine-2,5-dione | 4-bromo-1-methyl-1H-imidazole | A | 0.85 | 500.1/502.2 |
| 31e | (R)-8-chloro-4-(4-(6-methyl)midazo[1,2-a]pyridine-8-carbonyl)benzyl)-3-(pyridin-2-ylmethyl)-3,4-dihydro-1H-benzo[e][1,4]diazepine-2,5-dione | 8-bromo-6-methylimidazo[1,2-a]pyridine | A | 0.99 | 550.5/552.5 |
| 31f | (R)-4-(4-([1,2,4]triazolo[1,5-a]pyridine-8-carbonyl)benzyl)-8-chloro-3-(pyridin-2-ylmethyl)-3,4-dihydro-1H-benzo[e][1,4]diazepine-2,5-dione | 8-bromo-[1,2,4]triazolo[1,5-a]pyridine | A | 0.97 | 537.5/539.5 |

Example 32a 4-(4-(1H-Pyrrolo[3,2-b]pyridine-3-carbonyl)benzyl)-8-chloro-3-(pyridin-2-ylmethyl)-3,4-dihydro-1H-benzo[e][1,4]diazepine-2,5-dione

Step 1: tert-Butyl-3-bromo-4-azaindole-1-carboxylate (32-1)

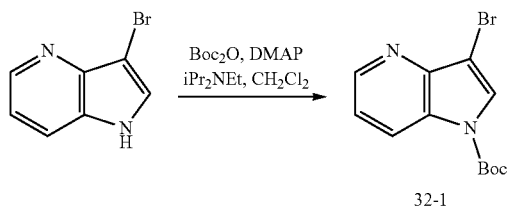 [SMILES: Brc1c[nH]c2cccnc12 ; CC(C)(C)OC(=O)n1cc(Br)c2ncccc21]

32-1

To a solution of 3-bromo-4-azaindole (1.6 g, 0.8 mmol, for preparation see: Ebetino, F. H. et al. 4-Azaindole Bisphosphonates, PCT Int. Appl. (2010) WO 2010033980) in DCM (25 mL) were added di-tert-butyl dicarbonate (2.6 g, 12.0 mmol) and N,N-diisopropylethylamine (2.1 mL, 12.0 mmol) followed by catalytic 4-dimethylaminopyridine. The reaction mixture was stirred at 23° C. for 3 h, and then diluted with EtOAc (100 mL) and water (50 mL). The layers were separated, and the organic layer was washed with sat. NaHCO$_3$ (aq) (1×50 mL) and brine (1×50 mL). The organic layer was dried (Na$_2$SO$_4$), filtered, and concentrated in vacuo. The crude residue was purified by FCC (SiO$_2$; elution with 0-10% EtOAc/Hex) to provide 1.45 g (61%) of 32-1. $^1$H NMR (400 MHz, d$_6$-DMSO): δ ppm 8.23 (s, 1H), 7.46 (dd, 1H), 7.37 (d, 1H), 6.58 (dd, 1H), 1.64 (s, 9H); LCMS (Method A): t$_R$=1.38 min, m/z 297.3/299.3 (M+H)$^+$.

Step 2: 4-(4-(1H-Pyrrolo[3,2-b]pyridine-3-carbonyl)benzyl)-8-chloro-3-(pyridin-2-ylmethyl)-3,4-dihydro-1H-benzo[e][1,4]diazepine-2,5-dione (Example 32a)

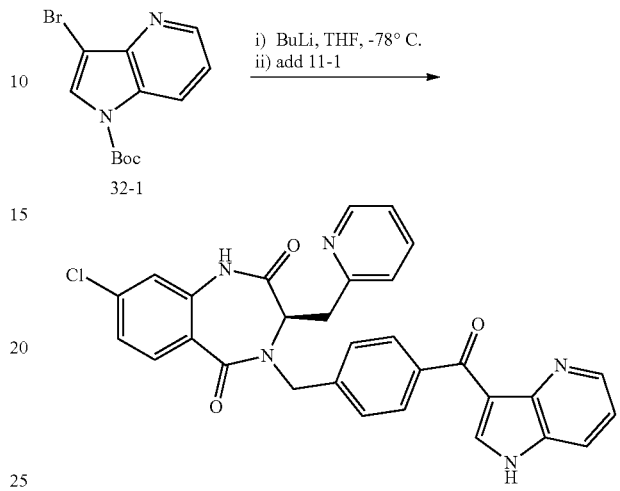

Example 32a

Following the general procedure described for step 2 of Example 32a tert-butyl-3-bromo-4-azaindole-1-carboxylate was reacted with Weinreb amide 11-1 to provide Example 32a. $^1$H NMR (400 MHz, CD$_3$OD, ~1.2:1 mixture of 7-membered ring conformers observed) δ ppm 8.51-6.93 (m, 15H), 5.13-4.40 (m, 3H, partially obscured by H$_2$O peak), 3.65-2.87 (m, 2H, partially obscured by solvent peak); LCMS (Method A): t$_R$=0.94 min, m/z 536.2/538.2 (M+H)$^+$.

Example 33a (R)-8-Chloro-3-(pyridin-2-ylmethyl)-4-(((1r,4R)-4-(quinoline-8-carbonyl)cyclohexyl)methyl)-3,4-dihydro-1H-benzo[e][1,4]diazepine-2,5-dione Step 1: (1R,4r)-4-(((R)-8-Chloro-2,5-dioxo-3-(pyridin-2-ylmethyl)-2,3-dihydro-1H-benzo[e][1,4]diazepin-4(5H)-yl)methyl)-N-methoxy-N-methylcyclohexanecarboxamide (33-1)

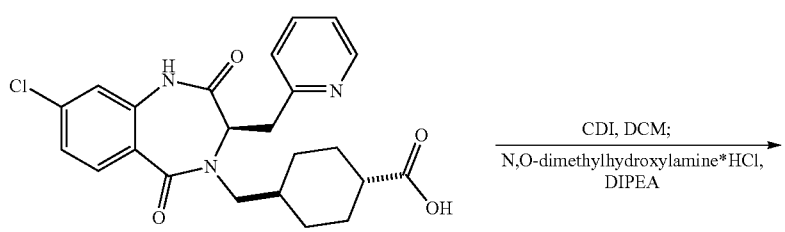

Example 1j

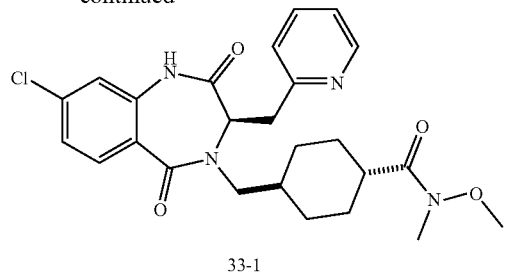

33-1

Following the general procedure described in Step 1 of Example 11a, Example 1j (1 g, 2.263 mmol) was coupled with N,O-dimethylhydroxylamine hydrochloride to provide 1.03 g (94%), of Weinreb amide 33-1. ¹H NMR (400 MHz, CDCl₃, ~1:1 mixture of 7-membered ring conformers observed): δ ppm 8.58-6.82 (m, 8H, partially obscured by solvent peak), 4.96 and 4.69 (2 dd, 1H), 4.05-3.32 (m, 2H), 3.67 and 3.66 (2 s, 3H), 3.16 and 3.15 (2 s, 3H), 3.12-2.83 (m, 2H), 2.60 (m, 1H), 1.86-0.95 (m, 9H); LCMS (Method A) $t_R$=0.96 min, m/z 485.3/487.3 (M+H)⁺.

Step 2: (R)-8-Chloro-3-(pyridin-2-ylmethyl)-4-(((1r, 4R)-4-(quinoline-8-carbonyl)cyclohexyl)methyl)-3, 4-dihydro-1H-benzo[e][1,4]diazepine-2,5-dione (33a)

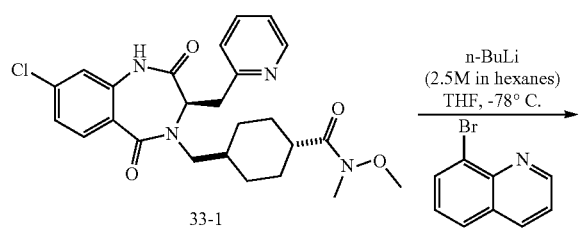

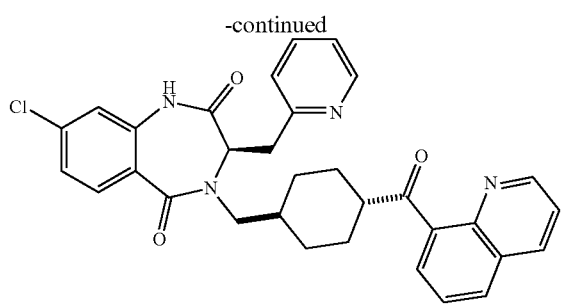

Example 33a

Following the general procedure described in Step 2 of Example 31a, 33-1 (0.10 g, 0.21 mmol) was reacted with 8-bromoquinoline (0.22 g, 1.0 mmol) to give 72 mg (63%) of Example 33a. ¹H NMR (400 MHz, CDCl₃, ~1:1 mixture of 7-membered ring conformers observed): δ ppm 8.92-6.81 (m, 14H, partially obscured by solvent peak), 4.95 and 4.68 (2 dd, 1H), 4.09-3.31 (m, 3H), 3.09-2.76 (m, 2H) 2.11-0.95 (m, 9H); LCMS (Method A) $t_R$=0.92 min, m/z 553.3/555.3 (M+H)⁺.

Following the method described above for Example 33a and substituting the corresponding bromide precursors in step 2, the following Examples were prepared as indicated in Table 27.

TABLE 27

| Example | Structure | Precursor | LCMS Method | $t_R$ (min) | (M + H)⁺ observed |
|---|---|---|---|---|---|
| 33b | (R)-8-chloro-4-(((1r,4R)-4-(1-methyl-1H-pyrrolo[3,2-b]pyridine-3-carbonyl)cyclohexyl)methyl)-3-(pyridin-2-ylmethyl)-3,4-dihydro-1H-benzo[e][1,4]diazepine-2,5-dione | 31-1 | A | 0.81 | 556.3/558.3 |

TABLE 27-continued

| Example | Structure | Precursor | LCMS Method | $t_R$ (min) | $(M + H)^+$ observed |
|---|---|---|---|---|---|
| 33c | (R)-8-chloro-4-(((1r,4R)-4-(1-methyl-1H-imidazole-2-carbonyl)cyclohexyl)methyl)-3-(pyridin-2-ylmethyl)-3,4-dihydro-1H-benzo[e][1,4]diazepine-2,5-dione | Br / 2-bromo-1-methylimidazole | A | 0.80 | 506.3/508.2 |
| 33d | (R)-8-chloro-4-(((1r,4R)-4-(1-methyl-1H-imidazole-4-carbonyl)cyclohexyl)methyl)-3-(pyridin-2-ylmethyl)-3,4-dihydro-1H-benzo[e][1,4]diazepine-2,5-dione | Br / 4-bromo-1-methylimidazole | A | 0.84 | 506.2/508.2 |

Example 34a (R)-8-Chloro-4-(4-(imidazo[1,2-α]pyridine-8-carbonyl)benzyl)-3-(pyridin-2-ylmethyl)-3,4-dihydro-1H-benzo[e][1,4]diazepine-2,5-dione

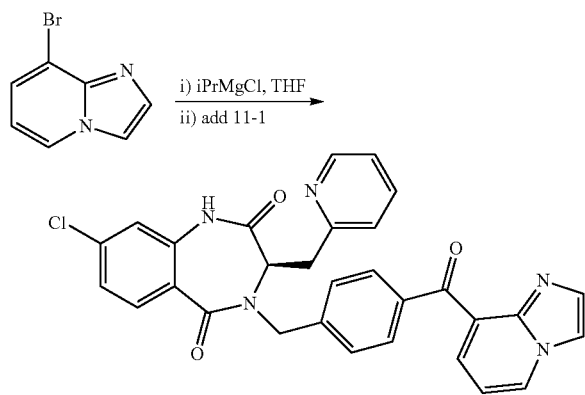

Example 34a

To a solution of 8-bromoimidazo[1,2-α]pyridine (70 mg, 0.36 mmol) in anhydrous THF (0.5 mL) was added a solution of isopropylmagnesium chloride (0.21 mL, 2 M in THF). The reaction mixture was stirred at 23° C. for 40 min, and then a solution of Weinreb amide 11-1 (57 mg, 0.12 mmol) in THF (0.2 mL) was added. The mixture was stirred at 23° C. for 40 min, and a second portion of imidazo[1,2-α]pyridine anion (generated by the addition of a solution of isopropylmagnesium chloride (0.21 mL, 2 M in THF) to 8-bromoimidazo[1,2-α]pyridine (70 mg, 0.36 mmol) in THF (0.5 mL) at room temperature and stirring for 40 min) was added. The reaction mixture was stirred at 23° C. for an additional 1 h, cooled to 0° C., and quenched by the addition of sat. NH$_4$Cl (aq). The mixture was allowed to warm to room temperature, and diluted with EtOAc (30 mL). The mixture was basified with sat. NaHCO$_3$ (aq) (20 mL), and the layers were separated. The organic phase was washed with water (1×10 mL) and brine (1×10 mL), dried (Na$_2$SO$_4$), filtered, and concentrated in vacuo. The crude residue was purified by FCC (SiO$_2$; elution with 0-5% 2 M NH$_3$ in MeOH/DCM) to provide 20 mg (31%) of Example 34a. $^1$H NMR (400 MHz, CD$_3$OD, ~1.2:1 mixture of 7-membered ring conformers observed): δ ppm 8.66-6.91 (m, 16H), 5.12-4.42 (m, 3H, partially obscured by H$_2$O peak), 3.63-2.86 (m, 2H, partially obscured by solvent peak); LCMS (Method A): $t_R$=0.78 min, m/z 536.2/538.2 (M+H)$^+$.

Following the general method described above for Example 34a, and substituting the corresponding Weinreb amide precursor, the following Example was prepared as indicated in Table 28.

TABLE 28

| Example | Structure | Precursor | LCMS Method | $t_R$ (min) | $(M + H)^+$ observed |
|---|---|---|---|---|---|
| 34b | (R)-8-chloro-4-(((1r,4R)-4-(imidazo[1,2-a]pyridine-8-carbonyl)cyclohexyl)methyl)-3-(pyridin-2-ylmethyl)-3,4-dihydro-1H-benzo[e][1,4]diazepine-2,5-dione | 33-1 | A | 0.75 | 542.2/544.2 |

Example 35a (S)-4-((8-Chloro-2,5-dioxo-3-(thiazol-4-ylmethyl)-2,3-dihydro-1H-benzo[e][1,4]diazepin-4(5H)-yl)methyl)-N-(5-methylpyridin-2-yl)benzamide Step 1: (S)-Methyl 4-(((1-methoxy-1-oxo-3-(thiazol-4-yl)propan-2-yl)amino)methyl)benzoate (35-1)

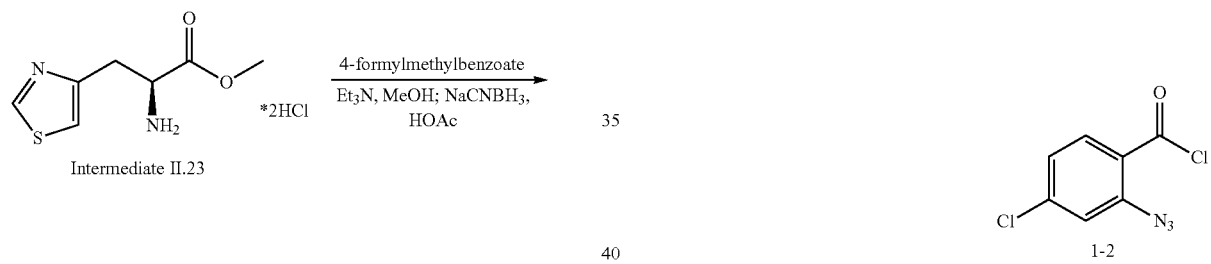

Step 2: 2-Azido-4-chlorobenzoyl Chloride (1-2)

2-Azido-4-chlorobenzoyl chloride (1-2) was prepared as described in Step 2 of Example 1a.

Steps 3-5: (S)-2-Chloro-4-((8-chloro-2,5-dioxo-3-(thiazol-4-ylmethyl)-2,3-dihydro-1H-benzo[e][1,4]diazepin-4(5H)-yl)methyl)benzoic Acid (35-4)

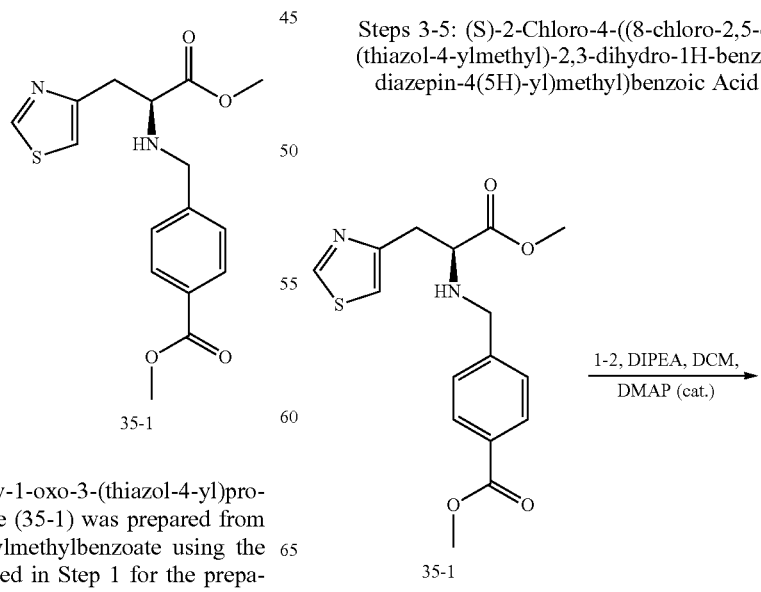

(S)-Methyl 4-(((1-methoxy-1-oxo-3-(thiazol-4-yl)propan-2-yl)amino)methyl)benzoate (35-1) was prepared from Intermediate II.23 and 4-formylmethylbenzoate using the same general procedure described in Step 1 for the preparation of Example 1a.

293

-continued

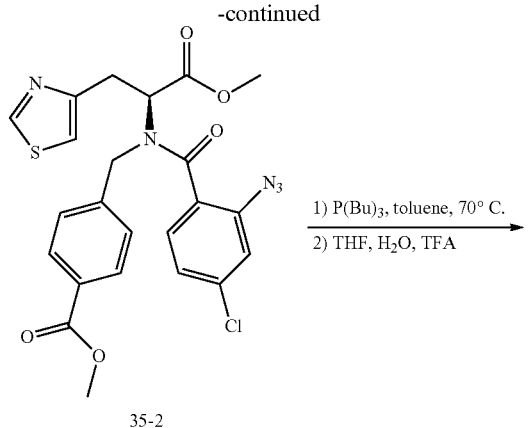

35-2

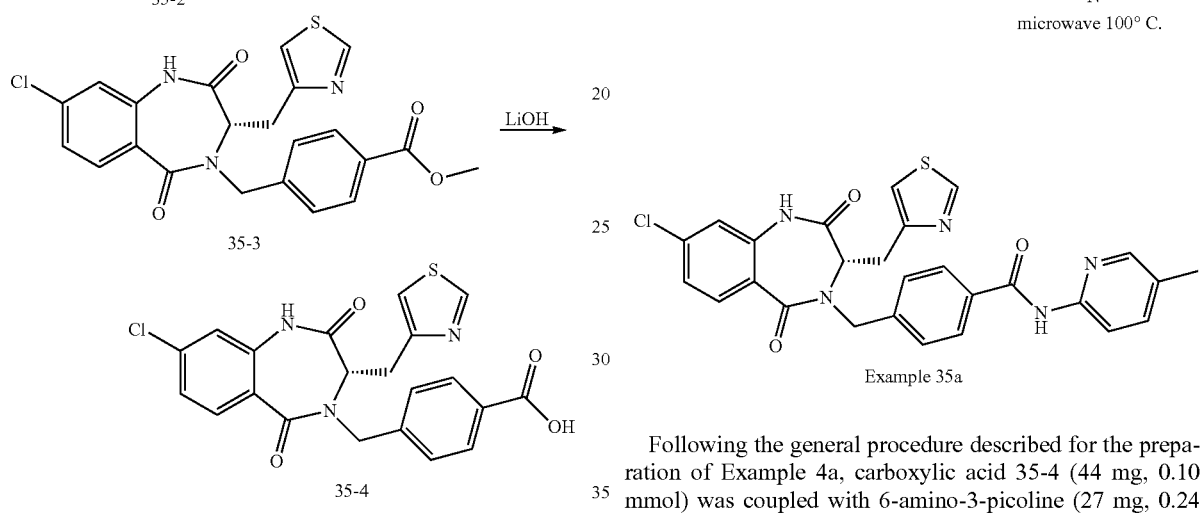

(S)-2-Chloro-4-((8-chloro-2,5-dioxo-3-(thiazol-4-ylmethyl)-2,3-dihydro-1H-benzo[e][1,4]diazepin-4(5H)-yl)methyl)benzoic acid (35-4) was prepared from 35-1, acid chloride 1-2 using the same general procedures described in Steps 3-5 for the preparation of Example 1a. $^1$H NMR (400 MHz, CD$_3$OD, mixture of 7-membered ring conformers observed): δ ppm 8.88-7.09 (m, 9H), 5.09-4.31 (m, 3H, partially obscured by H$_2$O peak), 3.57-2.89 (m, 2H, partially obscured by solvent peak); LCMS (Method A): $t_R$=0.97 min, m/z 442.2/444.2 (M+H)$^+$.

294

Step 5: (S)-4-((8-Chloro-2,5-dioxo-3-(thiazol-4-ylmethyl)-2,3-dihydro-1H-benzo[e][1,4]diazepin-4(5H)-yl)methyl)-N-(5-methylpyridin-2-yl)benzamide (Example 35a)

Following the general procedure described for the preparation of Example 4a, carboxylic acid 35-4 (44 mg, 0.10 mmol) was coupled with 6-amino-3-picoline (27 mg, 0.24 mmol) to provide 38 mg (71%) of Example 35a. $^1$H NMR (400 MHz, CD$_3$OD, ~1.2:1 mixture of 7-membered ring conformers observed): δ ppm 9.24 and 9.06 (2 d, 1H), 8.38-7.16 (m, 11H), 7.37 (m, 1H), 5.21-4.34 (m, 3H), 3.67-2.98 (m, 2H), 2.49 (s, 3H); LCMS (Method A): $t_R$=0.97 min, m/z 532.3/534.3 (M+H)$^+$.

Following the method described above for Example 35a and substituting the corresponding amino acid methyl ester intermediates/reagents and aldehyde (Step 1) and amine (Step 5) reagents the following Examples were prepared as indicated in Table 29.

TABLE 29

| Example | Structure | Inter-Mediates | Aldehyde | Amine | LCMS Method | $t_R$ (min) | $(M+H)^+$ observed |
|---|---|---|---|---|---|---|---|
| 35b | (R)-4-((8-chloro-2,5-dioxo-3-(thiophen-2-ylmethyl)-2,3-dihydro-1H-benzo[e][1,4]diazepin-4(5H)-yl)methyl)-N-(5-methylpyridin-2-yl)benzamide | I.4 and II.25 | | | A | 1.11 | 531.5/533.4 |
| 35c | (R)-4-((8-chloro-2,5-dioxo-3-phenyl-2,3-dihydro-1H-benzo[e][1,4]diazepin-4(5H)-yl)methyl)-N-(pyridin-2-yl)benzamide | I.4 and II.3 | | | B | 2.56 | 497.3/499.2 |
| 35d | (R)-4-((8-chloro-3-(4-methoxybenzyl)-2,5-dioxo-2,3-dihydro-1H-benzo[e][1,4]diazepin-4(5H)-yl)methyl)-N-(pyridin-2-yl)benzamide | I.4 and II.11 | | | A | 1.07 | 541.3/543.3 |

TABLE 29-continued

| Example | Structure | Inter-Mediates | Aldehyde | Amine | LCMS Method | $t_R$ (min) | $(M+H)^+$ observed |
|---|---|---|---|---|---|---|---|
| 35e | 4-((8-chloro-2,5-dioxo-3-((tetrahydro-2H-pyran-4-yl)methyl)-2,3-dihydro-1H-benzo[e][1,4]diazepin-4(5H)-yl)methyl)-N-(pyridin-2-yl)benzamide | I.4 and II.14 | | | A | 0.91 | 519.3/521.3 |
| 35f | (R)-4-((3-(3,4-dichlorobenzyl)-2,5-dioxo-8-(trifluoromethyl)-2,3-dihydro-1H-benzo[e][1,4]diazepin-4(5H)-yl)methyl)-N-(pyridin-2-yl)benzamide | I.6 and II.22 | | | C | 1.11 | 613.3/615.3/617.3 |
| 35g | (R)-4-((2,5-dioxo-3-(pyridin-3-ylmethyl)-2,3-dihydro-1H-benzo[e][1,4]diazepin-4(5H)-yl)methyl)-N-(pyridin-2-yl)benzamide | I.8 and II.2 | | | A | 0.65 | 478.3 |

TABLE 29-continued

| Example | Structure | Inter-Mediates | Aldehyde | Amine | LCMS Method | $t_R$ (min) | $(M + H)^+$ observed |
|---|---|---|---|---|---|---|---|
| 35h | (R)-4-((7-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide | I.9 and II.2 | | | A | 0.75 | 512.3/514.3 |
| 35i | (R)-4-((9-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide | I.10 and II.2 | | | A | 0.75 | 512.3/514.3 |
| 35j | (R)-4-((8-chloro-3-(3-fluorobenzyl)-2,5-dioxo-2,3-dihydro-1H-benzo[e][1,4]diazepin-4(5H)-yl)methyl)-N-(pyridin-2-yl)benzamide | I.4 and II.18 | | | A | 1.13 | 529.3/531.3 |

TABLE 29-continued

| Example | Structure | Inter-Mediates | Aldehyde | Amine | LCMS Method | $t_R$ (min) | $(M + H)^+$ observed |
|---|---|---|---|---|---|---|---|
| 35k | (R)-4-((8-chloro-3-isobutyl-2,5-dioxo-2,3-dihydro-1H-benzo[e][1,4]diazepin-4(5H)-yl)methyl)-N-(pyridin-2-yl)benzamide | L4 and (Leu-OMe·HCl) | methyl 4-formylbenzoate | 2-aminopyridine | A | 1.41 | 477.4/479.4 |
| 35l | (R)-4-(8-chloro-2,5-dioxo-3-(pyridin-3-ylmethyl)-2,3-dihydro-1H-benzo[e][1,4]diazepin-4(5H)-yl)methyl)-N-(pyridin-2-yl)cyclohexanecarboxamide | L4 and II.2 | methyl 4-formylcyclohexanecarboxylate | 2-aminopyridine | B | 0.91 | 518.3/520.3 |
| 35m | (S)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide | L4 and II.21 | methyl 4-formylbenzoate | 2-aminopyridine | A | 0.81 | 512.3/514.3 |

TABLE 29-continued

| Example | Structure | Inter-Mediates | Aldehyde | Amine | LCMS Method | $t_R$ (min) | $(M + H)^+$ observed |
|---|---|---|---|---|---|---|---|
| 35n | (R)-4-((2,5-dioxo-3-(pyridin-3-ylmethyl)-2,3-dihydro-1H-pyrido[3,4-e][1,4]diazepin-4(5H)-yl)methyl)-N-(pyridin-2-yl)benzamide | I.5 and II.2 | | | E | 0.93 | 479.4 |

Example 36a (R)-4-((8-Chloro-2,5-dioxo-3-(pyridin-3-ylmethyl)-2,3-dihydro-1H-benzo[e][1,4]diazepin-4(5H)-yl)methyl)-N-(pyridin-2-yl)benzenesulfonamide

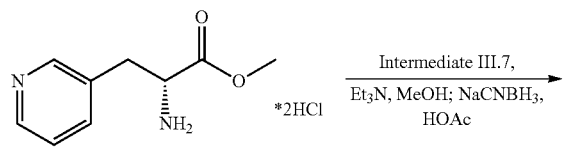

Intermediate II.2

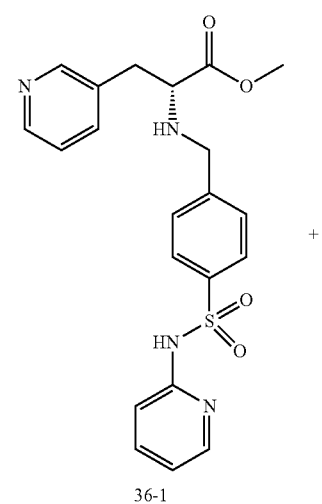

36-1

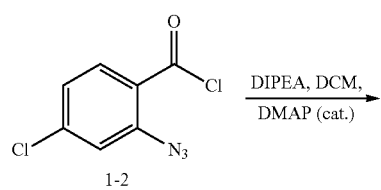

1-2

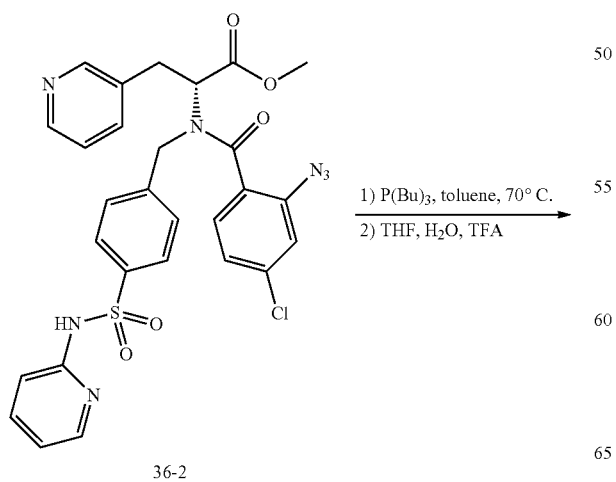

36-2

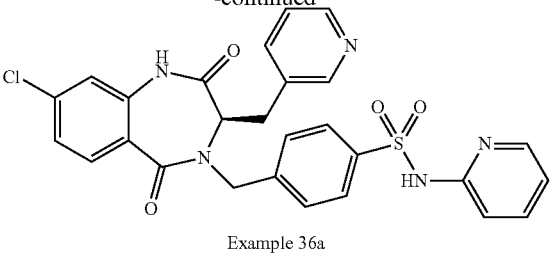

Example 36a (R)-4-((8-Chloro-2,5-dioxo-3-(pyridin-3-ylmethyl)-2,3-dihydro-1H-benzo[e][1,4]diazepin-4(5H)-yl)methyl)-N-(pyridin-2-yl)benzenesulfonamide (Example 36a) was prepared from Intermediate II.2, Intermediate III.7 and acid chloride 1-2 using the same general procedures described for the preparation of compound 1-4 in Example 1a. $^1$H NMR (400 MHz, CD$_3$OD, ~1.5:1 mixture of 7-membered ring conformers observed): δ ppm 8.71-6.98 (m, 15H), 5.01-4.53 (m, 3H, partially obscured by H$_2$O peak), 3.72-2.94 (m, 2H, partially obscured by solvent peak); LCMS (Method B) t$_R$=0.82 min, m/z 548.3/550.3 (M+H)$^+$.

Example 37a (R)-8-Chloro-4-((1-oxo-2-(pyridin-2-yl)-1,2,3,4-tetrahydroisoquinolin-6-yl)methyl)-3-(pyridin-2-ylmethyl)-3,4-dihydro-1H-benzo[e][1,4]diazepine-2,5-dione

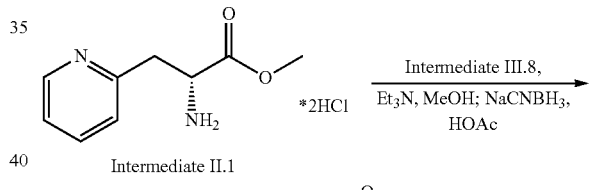

Intermediate II.1

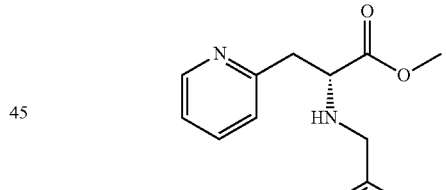

37-1

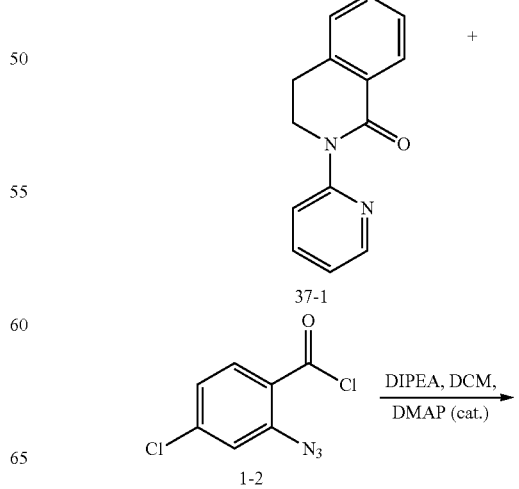

1-2

307
-continued

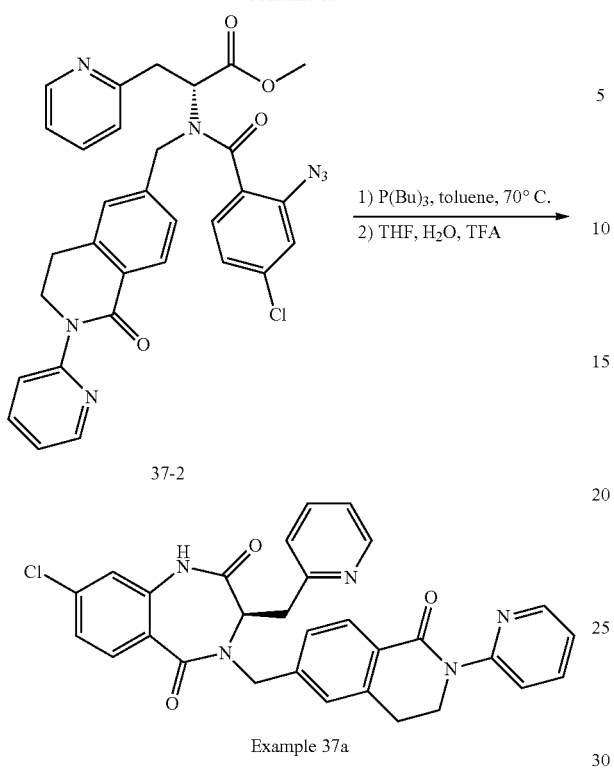

Example 37a (R)-8-Chloro-4-((1-oxo-2-(pyridin-2-yl)-1,2,3,4-tetrahydroisoquinolin-6-yl)methyl)-3-(pyridin-2-ylmethyl)-3,4-dihydro-1H-benzo[e][1,4]diazepine-2,5-dione (Example 37a) was prepared from Intermediate II.1, Intermediate III.8 and acid chloride 1-2 using the same general procedures described for the preparation of compound 1-4 in Example 1a. $^1$H NMR (400 MHz, CDCl$_3$, ~1.7:1 mixture of 7-membered ring conformers observed): δ ppm 8.50-6.74 (m, 15H), 5.14 and 4.82 (2 dd, 1H), 4.89 and 4.67 (2 ABq, 2H), 4.27 (t, 2H), 3.63-2.79 (m, 2H), 3.06 (t, 2H); LCMS (Method B) $t_R$=0.82 min, m/z 548.3/550.3 (M+H)$^+$.

Example 38a (R)-2-(4-Methoxybenzyloxy)-4-((8-chloro-3-methyl-2,5-dioxo-2,3-dihydro-1H-benzo[e][1,4]diazepin-4(5H)-yl)methyl)benzoic Acid Steps 1-3: (R)-Methyl 4-((8-chloro-3-methyl-2,5-dioxo-2,3-dihydro-1H-benzo[e][1,4]diazepin-4(5H)-yl)methyl)-2-((4-methoxybenzyl)oxy)benzoate (38-3)

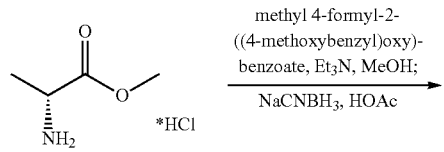

308
-continued

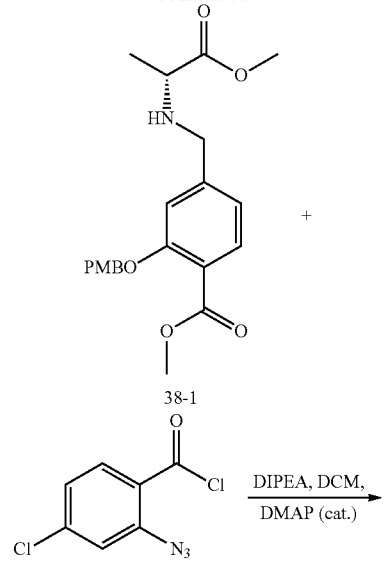

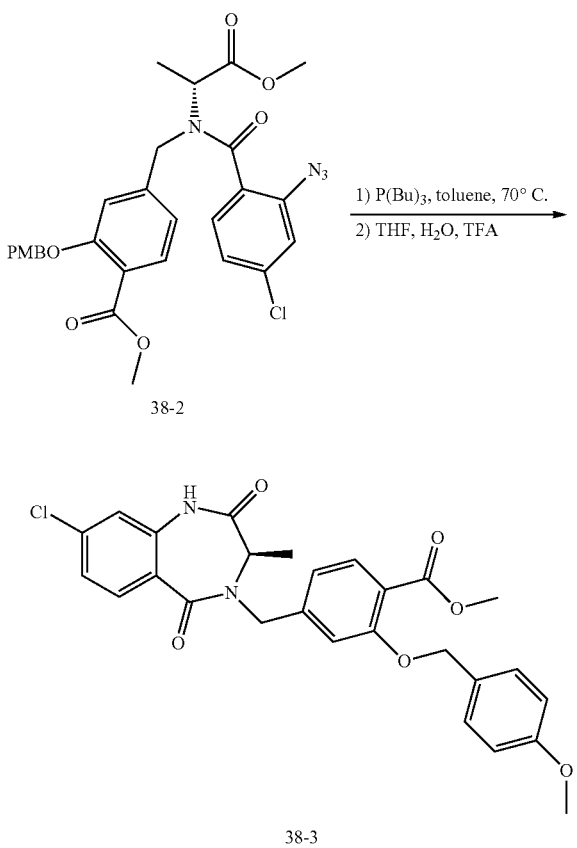

(R)-Methyl 4-((8-chloro-3-methyl-2,5-dioxo-2,3-dihydro-1H-benzo[e][1,4]diazepin-4(5H)-yl)methyl)-2-((4-methoxybenzyl)oxy)benzoate (38-3) was prepared from D-alanine methyl ester hydrochloride, methyl 4-formyl-2-((4-methoxybenzyl)oxy)benzoate, and acid chloride 1-2 using the same general procedures described for the preparation of compound 1-4 in Example 1a.

Step 4: (R)-2-(4-Methoxybenzyloxy)-4-((8-chloro-3-methyl-2,5-dioxo-2,3-dihydro-1H-benzo[e][1,4]diazepin-4(5H)-yl)methyl)benzoic Acid (Example 38a)

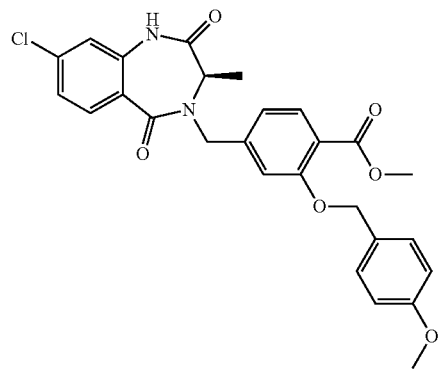

38-3

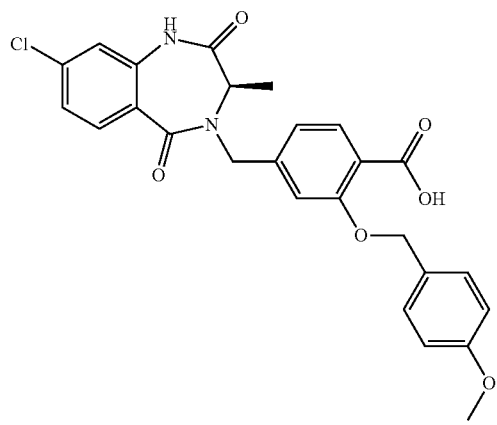

Example 38a

To a solution of methyl ester 38-3 (0.10 g, 0.20 mmol) in THF (2 mL) was added potassium trimethylsilanolate (0.76 g, 0.59 mmol). The reaction mixture was stirred at 40° C. for 2 h. The mixture was then cooled to room temperature, and concentrated in vacuo. The residue was taken up in EtOAc (30 mL), and washed with 0.5 N HCl (2×20 mL). The combined aqueous layers were then extracted with EtOAc (2×20 mL). The combined organics were dried ($Na_2SO_4$), filtered, and concentrated in vacuo to provide 97 mg (100%) of Example 38a. LCMS (Method A) $t_R$=1.13, m/z 495.3/497.3 (M+H)$^+$.

Example 39a (R)-4-((3-Methyl-8-(methylsulfonamido)-2,5-dioxo-2,3-dihydro-1H-benzo[e][1,4]diazepin-4(5H)-yl)methyl)-N-(5-methylpyridin-2-yl)benzamide

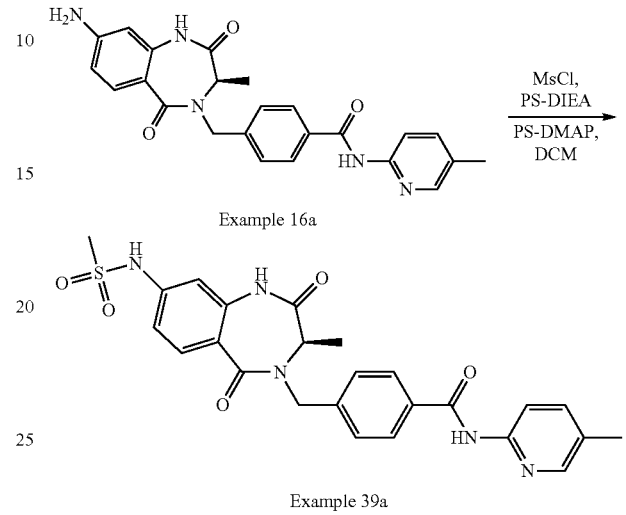

Example 16a

Example 39a

Following the general procedure described for the preparation of Example 17a, (R)-4-((8-amino-3-methyl-2,5-dioxo-2,3-dihydro-1H-benzo[e][1,4]diazepin-4(5H)-yl)methyl)-N-(5-methylpyridin-2-yl)benzamide (Example 16a) (10 mg, 0.023 mmol) was reacted with methanesulfonyl chloride (4 mg, 0.035 mmol) to provide 2 mg (16%) of Example 39a. LCMS (Method A) $t_R$=0.80 min, m/z 508.5 (M+H)$^+$.

Example 40a (R)-4-((8-Chloro-2,5-dioxo-3-(pyridin-2-ylmethyl)-2,3-dihydro-1H-benzo[e][1,4]diazepin-4(5H)-yl)methyl)-N-hydroxybenzamide

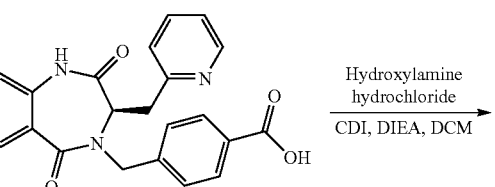

Example 1a

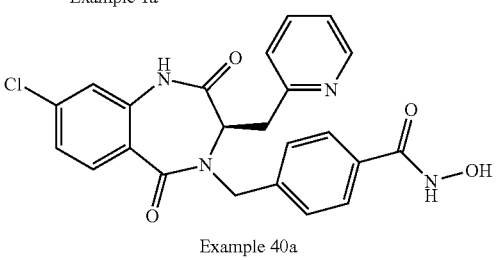

Example 40a

To a solution of Example 1a (100 mg, 0.23 mmol) in DCM (2 mL) was added CDI (45 mg, 0.27 mmol) and the

Example 41a

8-Chloro-4-(4-(hydroxymethyl)benzyl)-3-(pyridin-2-ylmethyl)-3,4-dihydro-1H-benzo[e][1,4]diazepine-2,5-dione

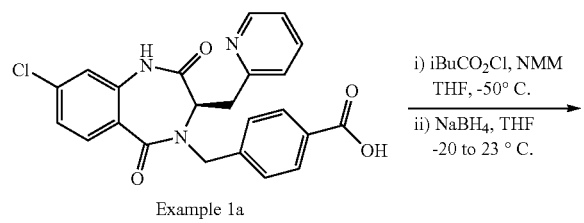

i) iBuCO₂Cl, NMM
THF, -50° C.
ii) NaBH₄, THF
-20 to 23 ° C.

Example 1a

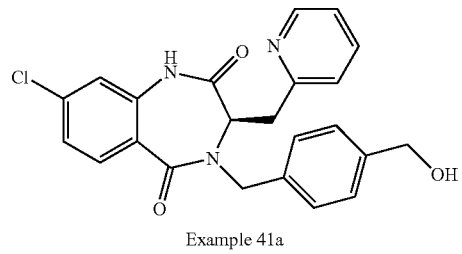

Example 41a

To a solution of Example 1a (100 mg, 0.25 mmol) in anhydrous THF (2 mL) at −50° C. under a nitrogen atmosphere were added N-methylmorpholine (0.027 mL, 0.25 mmol) followed by iso-butyl chloroformate (0.032 mL, 0.25 mmol). The mixture was stirred for 5 min, and then filtered into a cooled solution of sodium borohydride (6.4 mg, 0.18 mmol) in THF (1 mL) at −20° C. The reaction mixture was allowed to warm to room temperature, and stirred for 60 h. Methanol (0.5 mL) was added, and stirring was continued for 10 minutes. Volatiles were removed in vacuo, and the residue was purified by reverse-phase semi-preparative scale HPLC to provide 6 mg (6%) of Example 41a. ¹H NMR (400 MHz, CD₃OD, ~1.4:1 mixture of 7-membered ring conformers observed): δ ppm 8.50-7.12 (m, 11H), 5.00-4.54 (m, 5H, partially obscured by H₂O peak), 3.79-2.92 (m, 2H); LCMS (Method A): $t_R$=0.82 min, m/z 422.4/424.4 (M+H)⁺.

resultant mixture was stirred at 23° C. for 1.5 h. Hydroxylamine hydrochloride (80 mg, 1.1 mmol) was then added followed by DIEA (177 μL, 1.40 mmol), and the resultant mixture was stirred at 23° C. for 18 h. The mixture was concentrated in vacuo, and the residue was purified by reverse-phase semi-preparative scale HPLC to provide 21 mg (20%) of Example 40a. ¹H NMR (400 MHz, d₆-DMSO ~1.4:1 mixture of 7-membered ring conformers observed): δ ppm 11.19 (br s 1H), 10.74 and 10.64 (2 s, 1H), 9.02 (br s, 1H), 8.46 and 8.36 (2 d, 1H), 7.90-7.00 (m, 9H), 5.03-4.18 (m, 3H), 3.53-2.79 (m, 2H); LCMS (Method A) $t_R$=0.77 min, m/z 451.4/453.4 (M+H)⁺.

Example 42a (R)-4-((8-Chloro-2,5-dioxo-3-(pyridin-2-ylmethyl)-2,3-dihydro-1H-benzo[e][1,4]diazepin-4(5H)-yl)methyl)-N-(pyridin-2-yl)piperidine-1-carboxamide Step 1: (R)-tert-Butyl 4-((2-azido-4-chloro-N-(1-methoxy-1-oxo-3-(pyridin-2-yl)propan-2-yl)benzamido)methyl)piperidine-1-carboxylate (42-1)

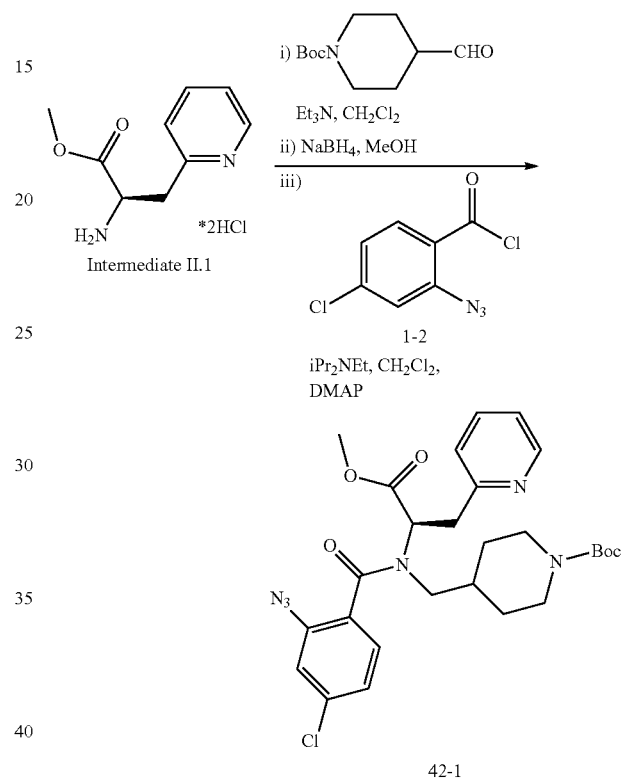

42-1

To a solution of Intermediate II.1 (1.0 g, 4.0 mmol) in THF (10 mL) containing triethylamine (1.4 mL, 9.9 mmol) was added N-Boc-4-piperidine carboxaldehyde (0.9 g, 4.2 mmol) followed by sodium sulfate (0.5 g, 7.0 mmol) and the mixture was stirred at 23° C. for 3 h. The mixture was filtered, and the filtrate diluted with MeOH (10 mL). Solid sodium borohydride (0.3 g, 8.1 mmol) was added portion wise, and the resulting mixture was stirred at 23° C. for 30 min. Acetone (10 mL) was then added, and the mixture stirred at 23° C. for further 30 min. The solvent was removed in vacuo, and the residue was partitioned between EtOAc (50 mL) and sat. Na₂CO₃ (aq) (30 mL). The layers were separated. The organic phase was dried (Na₂SO₄), and the solvent was removed in vacuo. The crude secondary amine was dissolved in DCM (2 mL), and added drop wise to a solution of acid chloride 1-2 in CH₂Cl₂ (7 mL) containing N,N-diisopropylethylamine (1.1 mL, 6.3 mmol). N,N-Dimethylaminopyridine (5 mg, catalytic) was added, and the mixture was stirred at 23° C. for 16 h. The mixture was diluted with DCM (50 mL), and washed with sat. NaHCO₃ (aq) (30 mL). The organic phase was dried (Na₂SO₄), and the solvent was removed in vacuo. The residue was purified by FCC (SiO₂, elution with 25-100% EtOAc/hexanes) to provide 1.5 g (68% from Intermediate II.1) of 42-1. LCMS (Method A): $t_R$=1.01 min, m/z 527.2/529.2 (M+H)$^+$.

Step 2: (R)-8-Chloro-4-(piperidin-4-ylmethyl)-3-(pyridin-2-ylmethyl)-3,4-dihydro-1H-benzo[e][1,4]diazepine-2,5-dione (42-2)

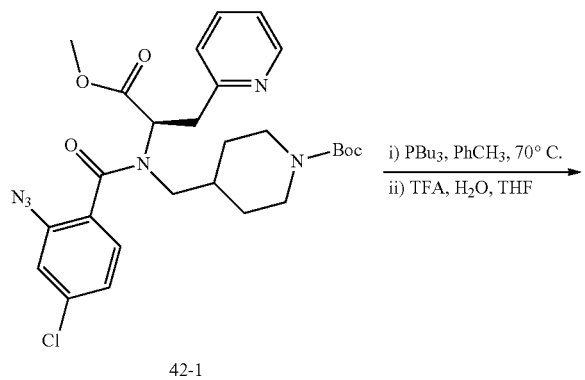

42-1

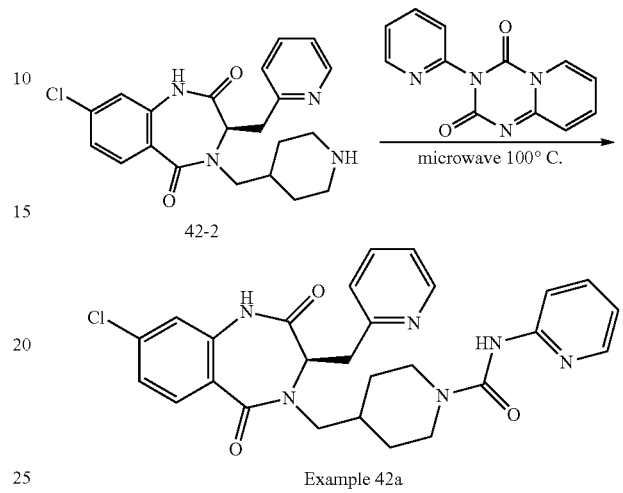

42-2

Tri-n-butyl phosphine (0.40 mL, 1.62 mmol) was added to a solution of 42-1 in anhydrous toluene (5 mL). The mixture was stirred at 23° C. for 30 min. The mixture was then heated to 70° C. for 18 h. The mixture was then allowed to cool to room temperature, and the solvent was removed in vacuo. The residue was redissolved in THF (5 mL), and trifluoroacetic acid (3 mL) and water (3 mL) were added. The mixture was stirred at 23° C. for 72 h, and the solvent was removed in vacuo. The residue was redissolved in CH$_2$Cl$_2$ (10 mL), and trifluoroacetic acid (3 mL) was added. The mixture was stirred at 23° C. for 1 h, and the solvent was removed in vacuo. The residue was partitioned between HCl (1.0 M, 20 mL) and CH$_2$Cl$_2$ (30 mL). The organic phase was extracted with HCl (1.0 M, 20 mL), and the combined aqueous layers were basified with sat. aqueous Na$_2$CO$_3$ (20 mL). The aqueous phase was extracted with EtOAc (2×100 mL), and then further extracted with CHCl$_3$ (2×100 mL). The organic extracts were dried (Na$_2$SO$_4$), and the solvents removed in vacuo to provide 0.56 g (86%) of 42-2. $^1$H NMR (400 MHz, CD$_3$OD, ~1.2:1 mixture of 7-membered ring conformers observed): δ ppm 8.59 and 8.40 (2 m, 1H), 7.97 and 7.90 (2 d, 1H), 7.60 (m, 1H), 7.32-6.82 (m, 4H), 4.97 and 4.71 (2 dd, 1H), 4.11 and 3.88 (2 dd, 1H), 3.76-1.33 (m, 10H); LCMS (Method A): $t_R$=0.70 min, m/z 399.2/401.2 (M+H)$^1$.

(R)-4-((8-Chloro-2,5-dioxo-3-(pyridin-2-ylmethyl)-2,3-dihydro-1H-benzo[e][1,4]diazepin-4(5H)-yl)methyl)-N-(pyridin-2-yl)piperidine-1-carboxamide (Example 42a)

A solution of 42-2 (35 mg, 0.088 mmol) and 2-pyridine isocyanate dimer (20 mg, 0.18 mmol, prepared as described by Duffy K. J., et al. Prolyl Hydroxylase Inhibitors, PCT Int. Appl. (2007) WO 2007150011) in DCM (0.5 mL) was stirred at 23° C. for 16 h. The mixture was then subjected to microwave irradiation maintaining a reaction temperature of 65° C. for 15 min, and then further subjected to microwave irradiation maintaining a reaction temperature of 100° C. for an additional 2 h. The mixture was allowed to cool to room temperature, and the solvent was removed in vacuo. The residue was purified by FCC (SiO$_2$; elution with 25-100% EtOAc/hexanes) to provide 35 mg (76%) of Example 42a. $^1$H NMR (400 MHz, d$_6$-DMSO, ~1.3:1 mixture of 7-membered ring conformers observed): δ ppm 10.77 and 10.73 (2 s, 1H), 9.08 (s, 1H), 8.50 and 8.38 (2 m, 1H), 8.19 (m, 1H), 7.86-7.60 (m, 4H), 7.44-6.91 (m, 5H), 4.88 and 4.52 (2 m, 1H), 4.09 (m, 2H), 3.91 and 3.67 (2dd, 1H), 3.52-1.36 (m, 8H); LCMS (Method A): $t_R$=0.79 min, m/z 519.2/521.2 (M+H)$^+$.

Example 43a (R)-8-Chloro-4-((1-1-methyl-1H-pyrrolo[3,2-b]pyridine-3-carbonyl)piperidin-4-yl)methyl)-3-(pyridin-2-ylmethyl)-3,4-dihydro-1H-benzo[e][1,4]diazepine-2,5-dione Step 1: Ethyl 1-methyl-1H-pyrrolo[3,2-b]pyridine-3-carboxylate (43-1)

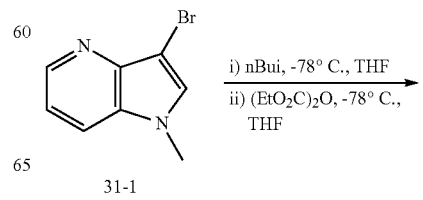

31-1

315
-continued

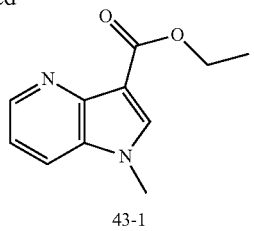

43-1

To a solution of 3-Bromo-1-methyl-4-azaindole (31-1) (0.55 g, 2.61 mmol) in THF (50 mL) at −78° C. was added a solution of n-BuLi (1.79 mL, 1.6 M in hexanes, 2.86 mmol) drop wise. The reaction mixture was stirred at −78° C. for 30 min, and a solution of diethyl pyrocarbonate (0.46 mL, 3.13 mmol) in anhydrous THF (2 mL) was added drop wise. The reaction mixture was then allowed to warm to −10° C., and quenched with sat. NH$_4$Cl (aq) (0.5 mL). The mixture was allowed to warm to room temperature, and diluted with EtOAc and basified with sat. NaHCO$_3$ (aq). The organic phase was washed with brine, and dried (Na$_2$SO$_4$). The solvent was removed in vacuo, and the residue was purified by FCC (SiO$_2$; elution with 0-4% MeOH/CH$_2$Cl$_2$) to provide 0.43 g (81%) of 43-1. LCMS (Method A): t$_R$=0.56 min, m/z 205.1 (M+H)$^+$.

Step 2: 1-Methyl-1H-pyrrolo[3,2-b]pyridine-3-carboxylic Acid (43-2)

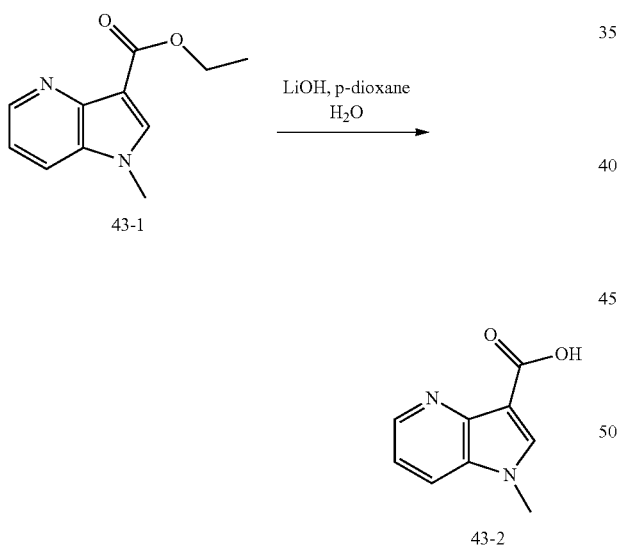

To a solution of 43-1 (0.43 g, 2.1 mmol) in p-dioxane (15 mL) was added a solution of LiOH (0.44 g, 10.5 mmol) in water (5 mL). The reaction mixture was stirred at 23° C. for 18 h. A solution of aqueous HCl (1N) was added drop wise to pH 3-4, and the mixture was extracted with 5% isopropanol/chloroform (×10). The combined organic extracts were dried (Na$_2$SO$_4$), and the solvent was removed in vacuo to provide 0.20 g (54%) of 43-2. $^1$H NMR (400 MHz, CD$_3$OD): δ ppm 8.50 (dd, 1H), 8.22 (s, 1H), 8.11 (dd, 1H), 7.40 (dd, 1H), 3.95 (s, 3H); LCMS (Method B): t$_R$=0.56 min, m/z 177.1 (M+H)$^+$.

316

Step 3: (R)-8-Chloro-4-((1-(1-methyl-1H-pyrrolo[3,2-b]pyridine-3-carbonyl)piperidin-4-yl)methyl)-3-(pyridin-2-ylmethyl)-3,4-dihydro-1H-benzo[e][1,4]diazepine-2,5-dione (Example 43a)

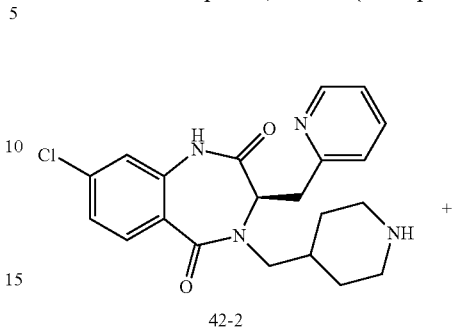

42-2

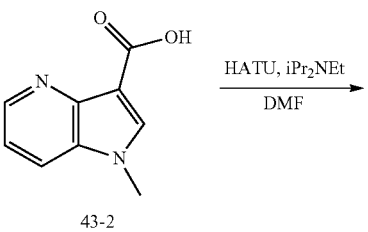

43-2

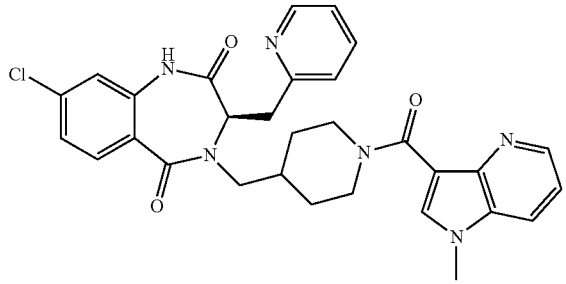

Example 43a

To a solution of carboxylic acid 43-2 (18 mg, 0.10 mmol) in DMF (0.5 mL) were added HATU (67 mg, 0.17 mmol) and N,N-diisopropylethylamine (35 μL, 0.20 mmol) followed by amine 42-2 (35 mg, 0.090 mmol). The mixture was stirred at 23° C. for 20 min. The mixture was then diluted with DCM, and washed successively with sat. Na$_2$CO$_3$ (aq) (1×) and brine (1×). The organic layer was then dried (Na$_2$SO$_4$), filtered, and concentrated in vacuo. The residue was purified by FCC (SiO$_2$; elution with 0-7% MeOH/CH$_2$Cl$_2$) to provide 25 mg (50%) of Example 43a. $^1$H NMR (400 MHz, CD$_3$OD, ~1.2:1 mixture of 7-membered ring conformers observed): δ ppm 8.52-6.99 (m, 11H), 4.98-2.89 (m, 9H, partially obscured by H$_2$O and solvent peaks) 3.91 (s, 3H), 2.16-1.22 (m, 5H); LCMS (Method A): t$_R$=0.89 min, m/z 557.3/559.3 (M+H)$^+$.

Example 44a

(R)-4-((3-Bromo-1-methyl-1H-indazol-6-yl)methyl)-8-chloro-3-(pyridin-2-ylmethyl)-3,4-dihydro-1H-benzo[e][1,4]diazepine-2,5-dione Steps 1-3: (R)-4-((3-Bromo-1-methyl-1H-indazol-6-yl)methyl)-8-chloro-3-(pyridin-2-ylmethyl)-3,4-dihydro-1H-benzo[e][1,4]diazepine-2,5-dione (44-3)

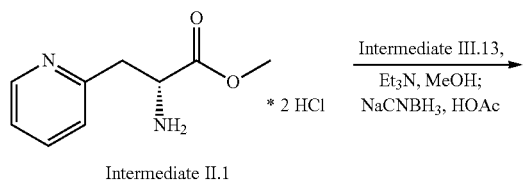

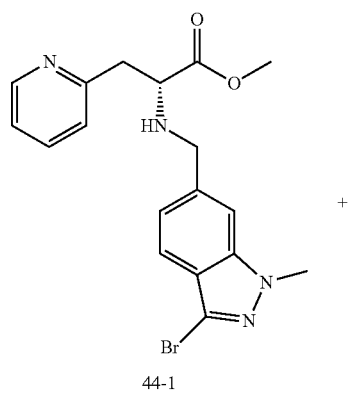

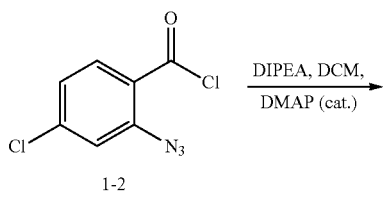

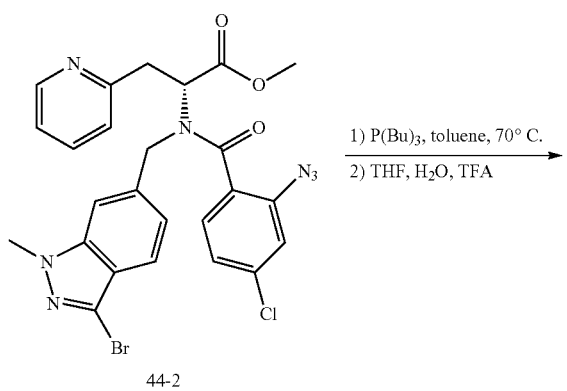

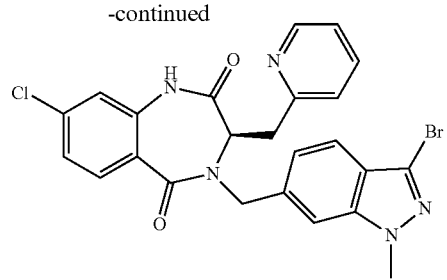

(R)-4-((3-Bromo-1-methyl-1H-indazol-6-yl)methyl)-8-chloro-3-(pyridin-2-ylmethyl)-3,4-dihydro-1H-benzo[e][1,4]diazepine-2,5-dione (44-3) was prepared from Intermediate II.1, Intermediate III.13 and acid chloride 1-2 using the same general procedures described for the preparation of compound 1-4 in Example 1a. $^1$H NMR (400 MHz, CDCl$_3$, ~1.5:1 mixture of 7-membered ring conformers observed): δ ppm 8.39 and 8.34 (2 m, 1H), 8.06 and 8.03 (2 d, 1H), 7.96 and 7.80 (2 s, 1H), 7.55-7.30 (m, 2H), 7.18-6.65 (m, 4H), 5.17-4.55 (m, 3H), 3.64-2.73 (m, 2H), 1.55 (s, 3H); LCMS (Method A): t$_R$=1.02 min, m/z 524.1/526.1/528.1 (M+H)$^+$.

Step 4: (R)-8-Chloro-4-((1-methyl-3-((5-methylpyridin-2-yl)amino)-1H-indazol-6-yl)methyl)-3-(pyridin-2-ylmethyl)-3,4-dihydro-1H-benzo[e][1,4]diazepine-2,5-dione (Example 44a)

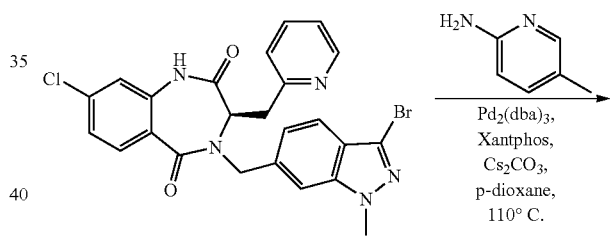

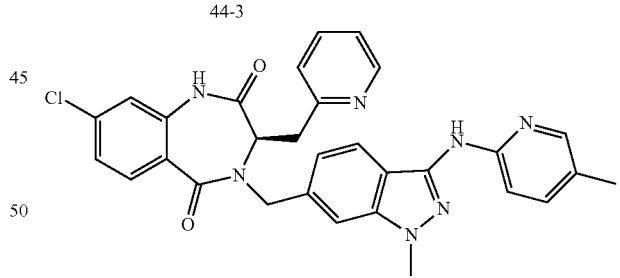

Example 44a

To a suspension of 44-3 (50 mg, 0.10 mmol), 2-amino-5-methylpyridine (31 mg, 0.29 mmol) and cesium carbonate (45 mg, 0.14 mmol) in degassed p-dioxane (0.5 mL) under a nitrogen atmosphere were added tris(dibenyzlideneacetone)dipalladium (O) (9 mg, 0.01 mmol) and xantphos (55 mg, 0.10 mmol). The reaction vessel was sealed, and the mixture was heated at 100° C. for 2 h, and then further heated at 110° C. for 18 h. The mixture was allowed to cool to room temperature, and diluted with EtOAc (10 mL) and water (5 mL). The layers were separated. The organic phase was washed with sat. aqueous Na$_2$CO$_3$ (5 mL), dried (Na$_2$SO$_4$), and the solvent was removed in vacuo. The residue was purified by reverse-phase semi-preparative scale HPLC and subsequently by FCC (SiO$_2$; elution with 0-8% MeOH/CH$_2$Cl$_2$) to provide 19 mg (36%) of Example 44a. $^1$H NMR (400 MHz, CDCl$_3$, ~1.9:1 mixture of 7-membered ring conformers observed): δ ppm 8.50 and 8.43 (2m, 1H), 8.08-6.75 (m, 14H), 5.19-4.27 (m, 3H), 3.78-2.78 (m, 5H), 2.26 (s, 3H); LCMS (Method A): t$_R$=0.89 min, m/z 552.3/554.3 (M+H)$^+$.

Example 45a (R)-3-Amino-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide

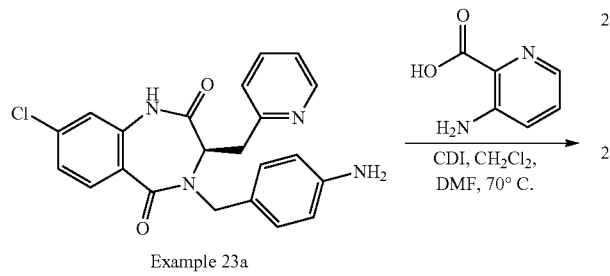

Example 23a

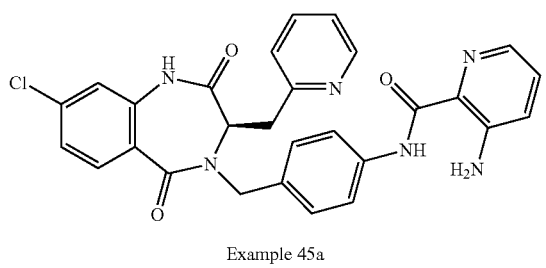

Example 45a 1,1'-Carbonyl diimidazole (0.076 g, 0.47 mmol) was added to a suspension of 3-aminopicolinic acid (0.065 g, 0.47 mmol) in DCM (1.0 mL), and DMF (0.6 mL) was then added. The mixture was stirred at 23° C. for 2 h, and Example 23a (0.15 g, 0.37 mmol) and DMF (0.4 mL) were added. The mixture was heated at 70° C. for 2 h, and then allowed to cool to room temperature. The mixture was diluted with EtOAc (20 mL) and sat. Na$_2$CO$_3$ (aq) (10 mL). The layers were separated. The organic phase was washed with sat. aqueous NaCl (10 mL), dried (Na$_2$SO$_4$), and the solvent removed in vacuo. The residue was purified by FCC (SiO$_2$; elution with 30-90% EtOAc/hexanes) to provide 0.16 g (81%) of Example 45a. $^1$H NMR (400 MHz, CDCl$_3$, ~1.3:1 mixture of 7-membered ring conformers observed): δ ppm 10.10 (m, 1H), 8.50 and 8.35 (2m, 1H), 8.47-7.00 (m, 14H), 6.02 (bs, 2H), 5.13-4.36 (m, 3H), 3.66-2.67 (m, 2H); LCMS (Method A): t$_R$=1.01 min, m/z 527.2/529.2 (M+H)$^+$.

Example 46a (R)-8-Chloro-4-(4-(4-oxopyrido[3,2-c]pyrimidin-3(4H)-yl)benzyl)-3-(pyridin-2-ylmethyl)-3,4-dihydro-1H-benzo[e][1,4]diazepine-2,5-dione

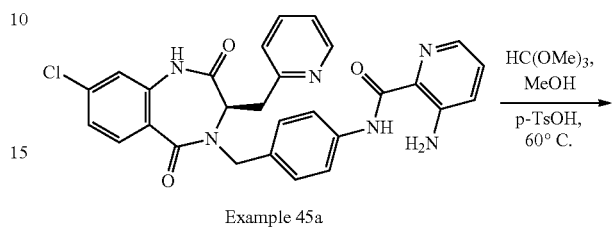

Example 45a

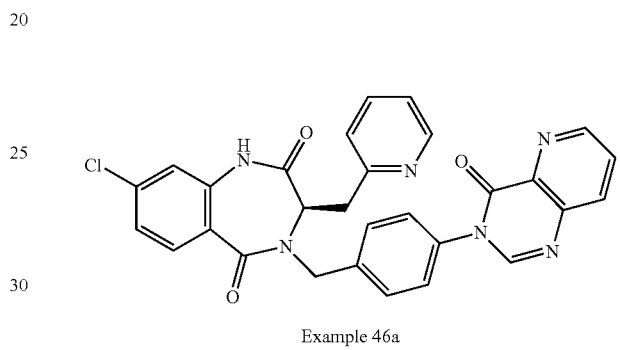

Example 46a

To a suspension of Example 45a (43 mg, 0.081 mmol) in trimethylorthoformate (2 mL) were added p-toluene sulfonic acid monohydrate (5 mg, 0.03 mmol) followed by MeOH (1.5 mL). The mixture was heated at 60° C. for 1 h, and then allowed to cool to room temperature. The solvent was removed in vacuo, and the residue was purified by reverse-phase semi-preparative scale HPLC to provide 29 mg (66%) of Example 46a. $^1$H NMR (400 MHz, CD$_3$OD, ~1.3:1 mixture of 7-membered ring conformers observed): δ ppm 8.87 (m, 1H), 8.50 (m, 1H), 8.36 (s, 1H), 8.23 (m, 1H), 8.14-7.88 (m, 3H), 7.64-7.10 (m, 8H), 5.11-4.67 (m, 3H), 3.82-2.91 (m, 2H); LCMS (Method A): t$_R$=0.84 min, m/z 537.2/539.2 (M+H)$^+$.

Example 47a (R)-8-Chloro-4-(4-(2-methyl-4-oxopyrido[3,2-d]pyrimidin-3(4H)-yl)benzyl)-3-(pyridin-2-ylmethyl)-3,4-dihydro-1H-benzo[e][1,4]diazepine-2,5-dione

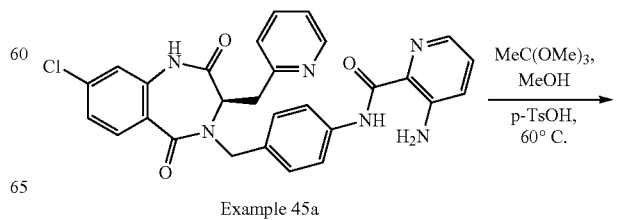

Example 45a

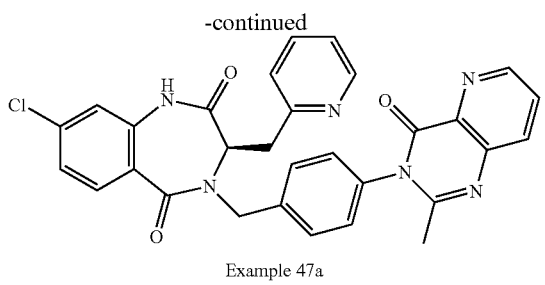

Example 47a

Following the general procedure described for the preparation of Example 46a, Example 45a was reacted with trimethylorthoacetate to provide Example 47a in 54% yield. LCMS (Method A): $t_R$=0.85 min, m/z 551.2/553.2 (M+H)$^+$.

Example 48a (R)-4-((8-Chloro-2,5-dioxo-3-(pyridin-2-ylmethyl)-2,3-dihydro-1H-benzo[e][1,4]diazepin-4(5H)-yl)methyl)-N-(5-(piperazin-1-yl)pyridin-2-yl)benzamide hydrochloride

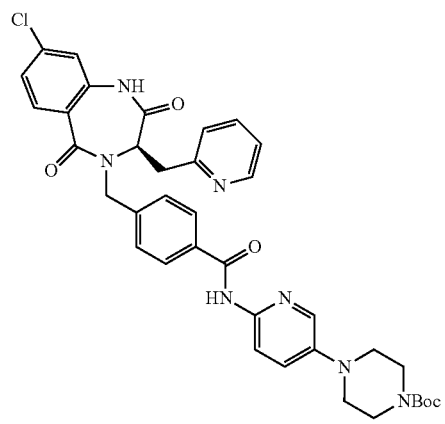

Example 4aw

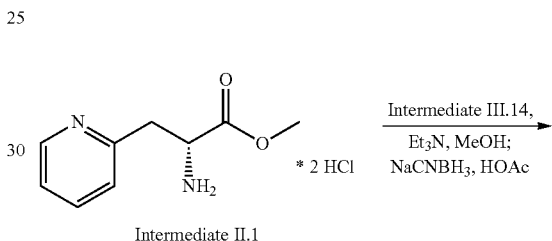

Intermediate II.1

Example 4aw (58 mg, 0.083 mmol) was taken up in 30% TFA/DCM (2 mL) and stirred at 23° C. for 3 h. The volatiles were removed in vacuo and the residue was taken up in MeOH (5 mL) and treated with 3N HCl in MeOH (1 mL). This was concentrated in vacuo and the residue was again taken up in MeOH (5 mL), treated with 3N HCl in MeOH (1 mL) and concentrated in vacuo to provide 49 mg (100%) of (R)-4-((8-chloro-2,5-dioxo-3-(pyridin-2-ylmethyl)-2,3-dihydro-1H-benzo[e][1,4]diazepin-4(5H)-yl)methyl)-N-(5-(piperazin-1-yl)pyridin-2-yl)benzamide as the hydrochloride salt (Example 48a). $^1$H NMR (400 MHz, d$_6$-DMSO, mixture of 7-membered ring conformers observed): δ 10.80-10.71 (m, 2H), 9.03 (br s, 2H), 8.57-7.17 (m, 14H), 5.11-4.30 (m, 3H), 3.63-2.96 (m, 2H), 3.40 (m, 4H), 3.25 (m, 4H) ppm; LCMS (Method B): $t_R$=0.91 min, m/z 596.3/598.3 (M+H)$^+$.

Example 49a (R)-4-((8-Chloro-2,5-dioxo-3-(pyridin-2-ylmethyl)-2,3-dihydro-1H-benzo[e][1,4]diazepin-4(5H)-yl)methyl)-N-(5-(trifluoromethyl)pyrimidin-2-yl)benzamide

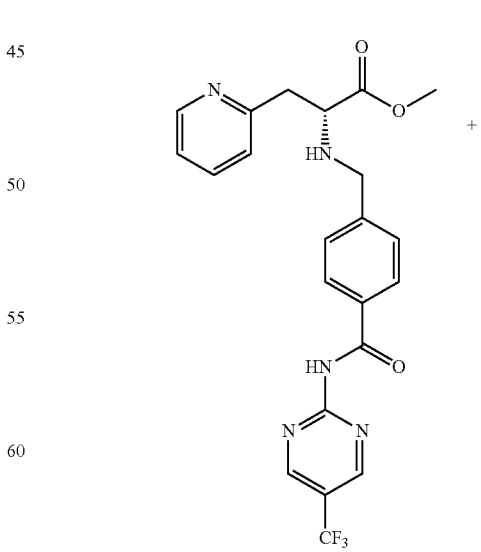

49-1

323

-continued

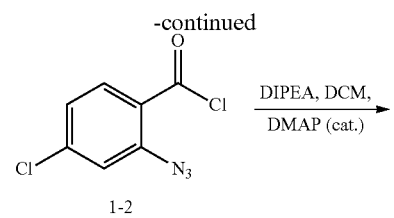

1-2

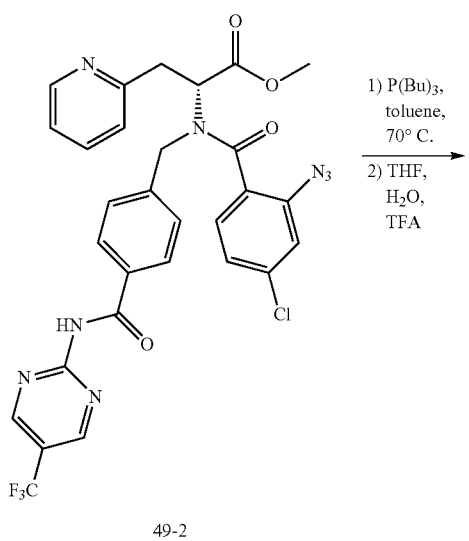

49-2

1) P(Bu)₃, toluene, 70° C.
2) THF, H₂O, TFA

324

-continued

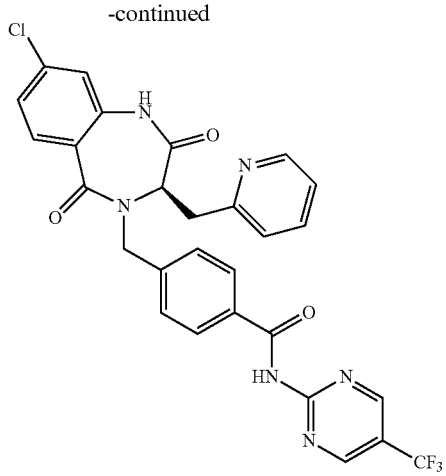

Example 49a

Example 49a was prepared from Intermediate II.1, Intermediate III.14 and acid chloride 1-2 using the same general procedures described for the preparation of compound 1-4 in Example 1a. ¹H NMR (400 MHz, CDCl₃, 1.7:1 mixture of 7-membered ring conformers observed): δ ppm 9.20 and 9.03 (2 s, 1H), 8.90 (s, 2H), 8.51-6.76 (m, 12H, partially obscured by solvent peak), 5.16-4.30 (m, 3H), 3.63-2.81 (m, 2H); LCMS (Method A): $t_R$=1.02 min, m/z 581.5/583.5 (M+H)⁺.

Following the method described above for Example 49a and substituting the corresponding intermediates the following Examples were prepared as indicated in Table 30.

TABLE 30

| Example | Structure | Intermediate | LCMS Method | $t_R$ (min) | (M + H)⁺ observed |
|---|---|---|---|---|---|
| 49b | (R)-8-chloro-4-(4-(8-oxo-5,6-dihydro-1,7-naphthyridin-7(8H)-yl)benzyl)-3-(pyridin-2-ylmethyl)-3,4-dihydro-1H-benzo[e][1,4]diazepine-2,5-dione | III.10 | A | 1.03 | 538.3/540.3 |
| 49c | (R)-8-chloro-4-(4-(7-oxo-5H-pyrrolo[3,4-b]pyridin-6(7H)-yl)benzyl)-3-(pyridin-2-ylmethyl)-3,4-dihydro-1H-benzo[e][1,4]diazepine-2,5-dione | III.11 | A | 0.88 | 524.4/526.4 |

TABLE 30-continued

| Example | Structure | Intermediate | LCMS Method | $t_R$ (min) | (M + H)+ observed |
|---|---|---|---|---|---|
| 49d | (R)-8-chloro-4-((1-oxo-2-(pyridin-2-yl)isoindolin-5-yl)methyl)-3-(pyridin-2-ylmethyl)-3,4-dihydro-1H-benzo[e][1,4]diazepine-2,5-dione | III.12 | A | 1.02 | 524.2/526.2 |
| 49e | (R)-8-chloro-4-((1-(pyridin-2-ylamino)isoquinolin-6-yl)methyl)-3-(pyridin-2-ylmethyl)-3,4-dihydro-1H-benzo[e][1,4]diazepine-2,5-dione | III.9 | A | 0.85 | 535.2/537.2 |

Example 50a

8-Chloro-4-(1-(4-(imidazo[1,2-α]pyridine-8-carbonyl)phenyl)cyclopropyl)-3-methyl-3,4-dihydro-1H-benzo[e][1,4]diazepine-2,5-dione Steps 1-2: Methyl 4-(1-(8-chloro-3-methyl-2,5-dioxo-2,3-dihydro-1H-benzo[e][1,4]diazepin-4(5H)-yl)cyclopropyl)benzoate (50-2)

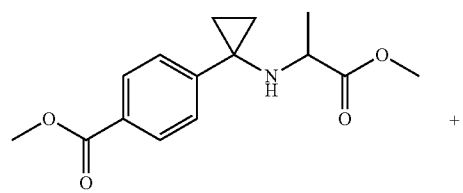

Intermediate V.1

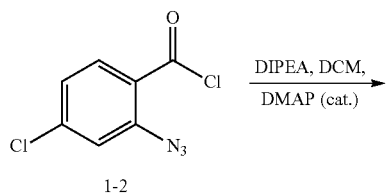

1-2

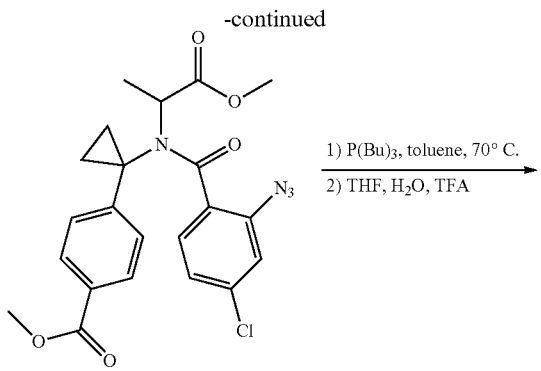

50-1

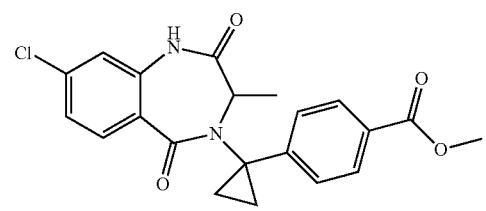

50-2

50-2 was prepared from Intermediate V.1 and acid chloride 1-2 using the same general procedures described for Steps 3 and 4 in Example 1a for the preparation of compound 1-4. LCMS (Method A): $t_R$=1.14 min, m/z 399.3/401.3 (M+H)+.

Step 3: 4-(1-(8-Chloro-3-methyl-2,5-dioxo-2,3-dihydro-1H-benzo[e][1,4]diazepin-4(5H)-yl)cyclopropyl)benzoic Acid (50-3)

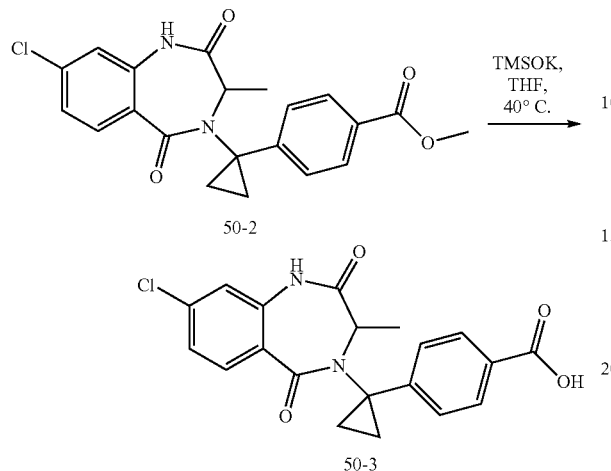

To a solution of methyl ester 50-2 (71 mg, 0.18 mmol) in THF (2 mL) was added potassium trimethylsilanoate (114 mg, 0.885 mmol). The resulting mixture was stirred at 40° C. for 16 h. The mixture was then cooled to room temperature, and concentrated in vacuo. The crude residue was taken up in water (20 mL), and washed with EtOAc (2×10 mL). The aqueous phase was then acidified to pH 1 with 2 N HCl (aq) forming a white precipitate. The aquate phase was extracted with EtOAc (3×20 mL). The combined organic extracts were dried ($Na_2SO_4$), filtered, and concentrated in vacuo to provide 44 mg (65%) of 50-3 which was used without further purification in the next step. LCMS (Method A): $t_R$=0.95 min, m/z 385.3/387.3 (M+H)$^+$.

Step 4: 4-(1-(8-Chloro-3-methyl-2,5-dioxo-2,3-dihydro-1H-benzo[e][1,4]diazepin-4(5H)-yl)cyclopropyl)-N-methoxy-N-methylbenzamide (50-4)

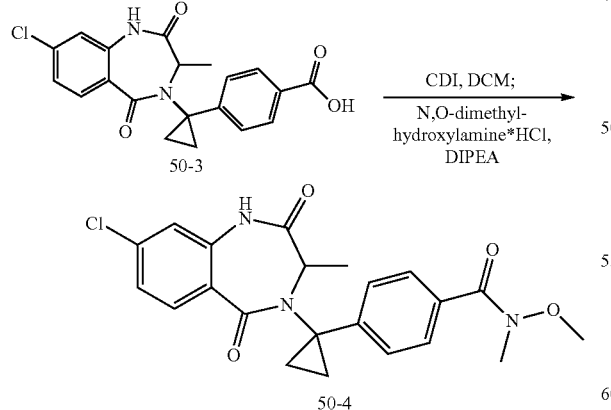

Using the same general procedure described in Step 1 of Example 11a, carboxylic acid 50-3 was reacted with CDI and N,O-dimethylhydroxylamine hydrochloride to provide Weinreb amide 50-4 in 57% yield. LCMS (Method A): $t_R$=1.00 min, m/z 428.3/430.3 (M+H)$^+$.

Step 5: 8-Chloro-4-(1-(4-(imidazo[1,2-α]pyridine-8-carbonyl)phenyl)cyclopropyl)-3-methyl-3,4-dihydro-1H-benzo[e][1,4]diazepine-2,5-dione (Example 50a)

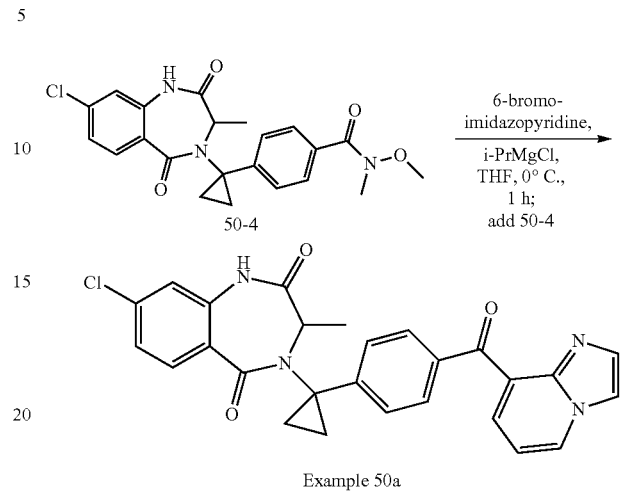

Following the same general procedure described in Example 34a, Weinreb amide 50-4 was reacted with the Grignard reagent derived from 6-bromoimidazopyridine to provide Example 50a in 35% yield. $^1$H NMR (400 MHz, CDCl$_3$, 1.8:1 mixture of 7-membered ring conformers observed): δ ppm 8.31-6.89 (m, 13H, partially obscured by solvent peak), 4.55 and 4.38 (2 q, 1H), 1.78-1.17 (m, 7H); LCMS (Method A): $t_R$=0.81 min, m/z 485.4/487.4 (M+H)$^+$.

Example 51a (3R)-8-Chloro-4-(4-(hydroxy(pyridin-2-yl)methyl)benzyl)-3-(pyridin-2-ylmethyl)-3,4-dihydro-1H-benzo[e][1,4]diazepine-2,5-dione

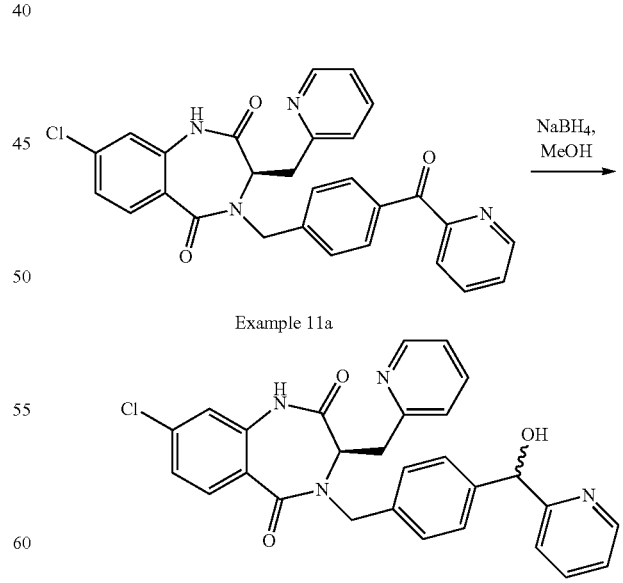

To a solution of ketone Example 11a (24 mg, 0.048 mmol) in MeOH (1 mL) was added sodium borohydride (2 mg, 0.048 mmol). The reaction mixture was stirred at 23° C. for 10 min, quenched with acetone (1 mL), and concentrated in vacuo. The residue was taken up in sat. NaHCO₃ (aq) (10 mL), and extracted with EtOAc (3×10 mL). The combined organic extracts were washed with brine (aq) (1×20 mL), dried (Na₂SO₄), filtered, and concentrated in vacuo. The crude residue was purified by FCC (SiO₂, elution with 0-10% MeOH/DCM) to provide 23 mg of semi pure material, 11 mg of which was used without further purification in a subsequent step and 12 mg of which was further purified by reverse-phase semi-preparative scale HPLC to provide 4 mg (17%) of Example 51a. ¹H NMR (400 MHz, CDCl₃, 1.7:1 mixture of 7-membered ring conformers observed): δ ppm 8.58-6.66 (m, 16H, partially obscured by solvent peak), 5.72 (br s, 1H), 5.29-4.35 (m, 4H), 3.61-2.71 (m, 2H); LCMS (Method A): $t_R$=0.79 min, m/z 499.4/501.4 (M+H)⁺.

Example 52a (R)-8-Chloro-4-(4-((hydroxyimino)(pyridin-2-yl)methyl)benzyl)-3-(pyridin-2-ylmethyl)-3,4-dihydro-1H-benzo[e][1,4]diazepine-2,5-dione

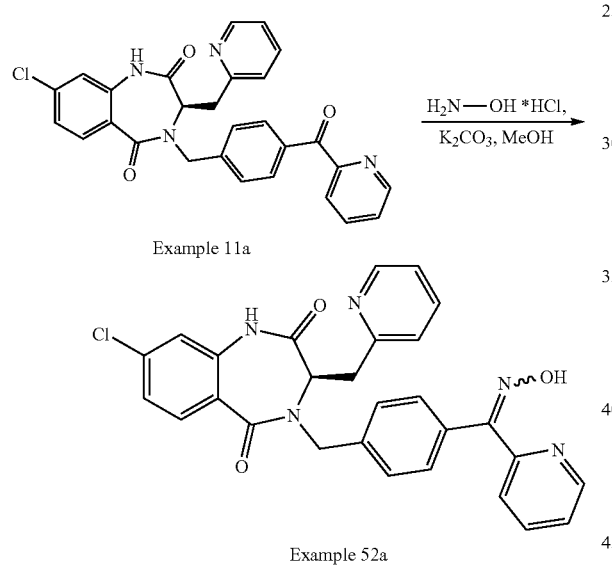

Example 52a

To a solution of ketone Example 11a (30 mg, 0.060 mmol) in methanol (1 mL) were added hydroxylamine hydrochloride (5 mg, 0.08 mmol) and potassium carbonate (17 mg, 0.12 mmol). The resultant mixture was stirred at 23° C. for 3 h at which time additional hydroxylamine hydrochloride (20 mg) and potassium carbonate (80 mg) were added. The mixture was stirred at 23° C. for another 16 h. Analysis by LC/MS showed a significant amount of starting material remaining. The mixture was heated at 50° C. for 4 h, and then added additional hydroxylamine hydrochloride (20 mg) and potassium carbonate (80 mg). The mixture was heated at 50° C. for an additional 3.5 h. It was then cooled to room temperature, and added more hydroxylamine hydrochloride (50 mg) and potassium carbonate (170 mg) followed by water (0.3 mL), and stirred at 23° C. for another 2 d. The mixture was then concentrated in vacuo. The residue was taken up in DCM, filtered, and concentrated in vacuo. The crude residue was purified by FCC (SiO₂, elution with 0-5% MeOH/DCM) to provide 16 mg (52%) of Example 52a as a ~3:1 mixture of geometrical isomers. LCMS (Method A): $t_R$=0.85 min (75%) and 0.90 min (25%) (geometrical isomers of oxime), m/z 512.4/514.4 (M+H)⁺.

Example 53a (R)-8-Chloro-4-(4-((hydroxyimino)(pyridin-2-yl)methyl)benzyl)-3-(pyridin-2-ylmethyl)-3,4-dihydro-1H-benzo[e][1,4]diazepine-2,5-dione

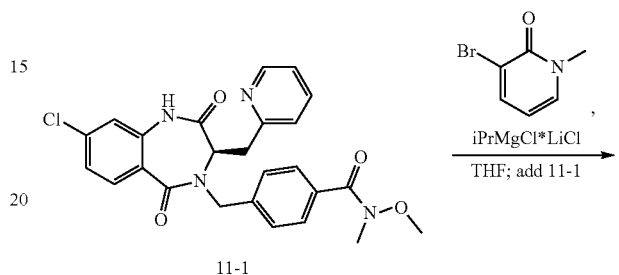

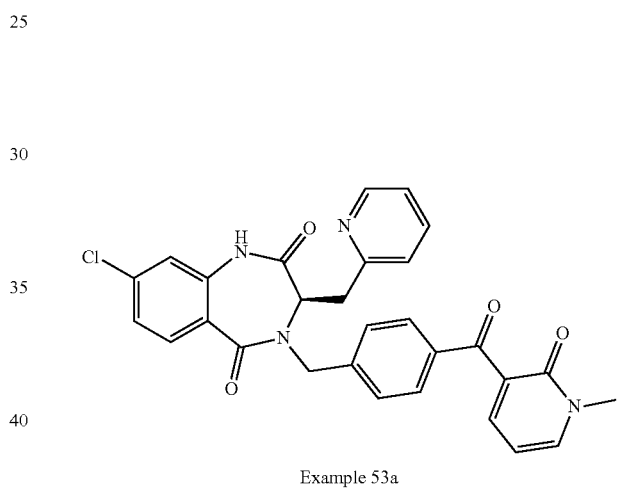

Example 53a

To a solution of 3-bromo-1-methylpyridin-2(1H)-one (165 mg, 0.88 mmol, prepared from 3-bromo-2-hydroxypyridine as described by Hilpert, K. et al., Benzamide Derivatives as P2X7 Receptor Antagonists, Their Preparation and Therapeutic Use, PCT Int. Appl. (2012), WO 2012114268) in THF (5 mL) at 23° C. was added isopropylmagnesium chloride lithium chloride complex (1.3 M in THF, 0.64 mL, 0.84 mmol) drop wise. The resulting mixture was stirred for 30 min. To the resultant orange-brown solution was added Weinreb amide 11-1 (100 mg, 0.21 mmol), and the reaction mixture was stirred at 23° C. for 16 h. The mixture was quenched with sat. NH₄Cl (aq) (20 mL), and extracted with EtOAc (3×20 mL). The combined organic extracts were washed with brine (1×30 mL), dried (Na₂SO₄), filtered, and concentrated in vacuo. The crude residue was purified by FCC (SiO₂, elution with 0-5% MeOH/DCM) to provide 51 mg (46%) of Example 53a. ¹H NMR (400 MHz, CDCl₃, 1.7:1 mixture of 7-membered ring conformers observed): δ ppm 8.47 and 8.34 (2 d, 1H), 8.05-6.71 (m, 13H, partially obscured by solvent peak), 6.28 (t, 1H), 5.14-4.45 (m, 3H), 3.60-2.75 (m, 2H), 3.59 (s, 3H); LCMS (Method A): $t_R$=0.87 min, m/z 527.3/529.3 (M+H)⁺.

Example 54a (R)-2-(Benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide Steps 1-5: (R)-2-(Benzo[d][1,3]dioxol-5-yl)-4-((8-chloro-3-methyl-2,5-dioxo-2,3-dihydro-1H-benzo[e][1,4]diazepin-4(5H)-yl)methyl)benzoic Acid (54-5)

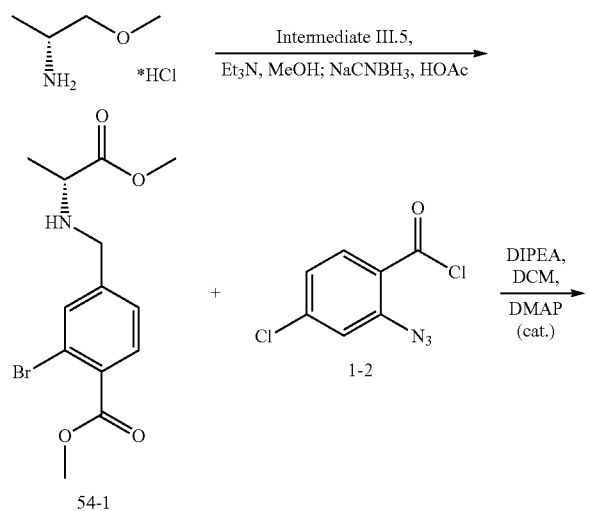

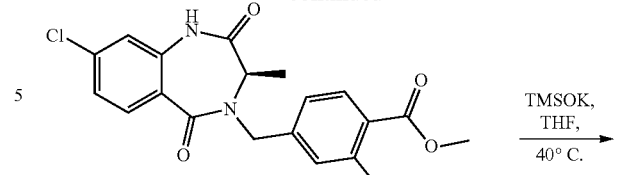

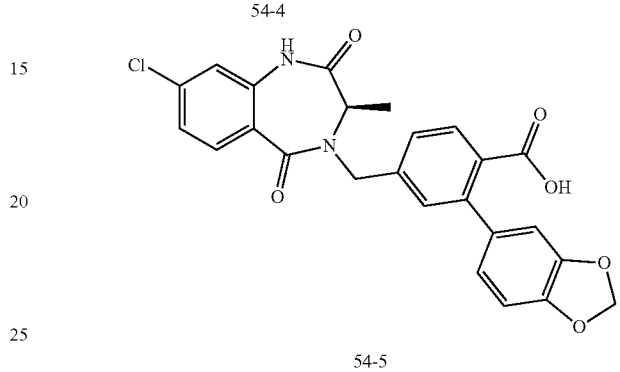

(R)-2-(Benzo[d][1,3]dioxol-5-yl)-4-((8-chloro-3-methyl-2,5-dioxo-2,3-dihydro-1H-benzo[e][1,4]diazepin-4(5H)-yl)methyl)benzoic acid (54-5) was prepared from D-alanine methylester hydrochloride, Intermediate III.5, acid chloride 1-2 and benzo[d][1,3]dioxol-5-ylboronic acid using the same general procedures described for the preparation of Example 8a. LCMS (Method A) $t_R$=1.08 min, m/z 479.3/481.4 (M+H)$^+$.

Step 6: (R)-2-(Benzo[d][1,3]dioxol-5-yl)-4-((8-chloro-3-methyl-2,5-dioxo-2,3-dihydro-1H-benzo[e][1,4]diazepin-4(5H)-yl)methyl)-N-(4-(trifluoromethyl)phenyl)benzamide (Example 54a)

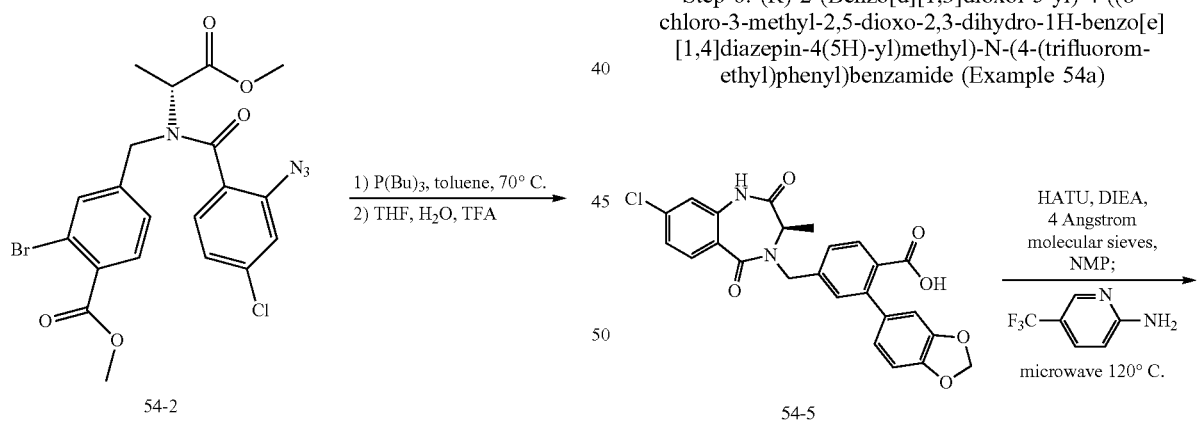

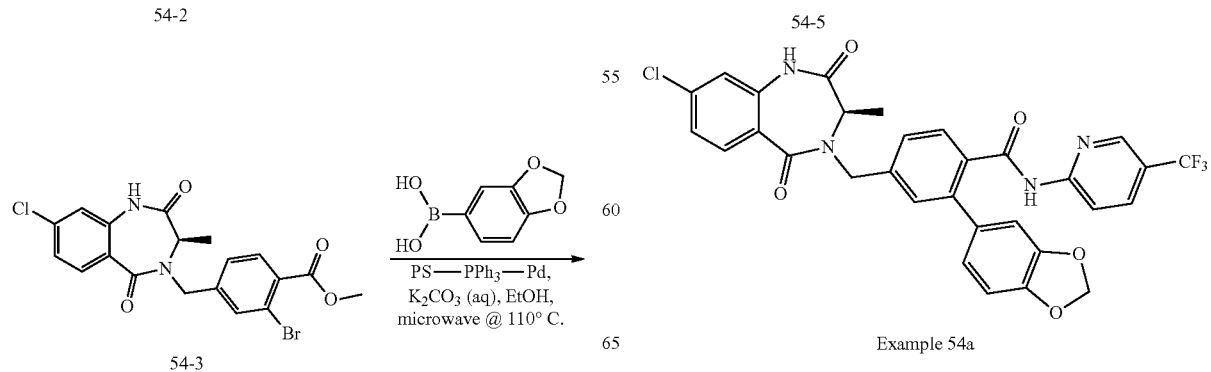

Following the same general procedure described in Example 5a, carboxylic acid 54-5 was reacted with 2-amino-5-trifluoromethylpyridine to provide Example 54a. LCMS (Method A): $t_R$=1.33 min, m/z 623.3/625.3 (M+H)$^+$.

Example 55a (R)-2-Amino-4-((8-chloro-2,5-dioxo-3-(pyridin-2-ylmethyl)-2,3-dihydro-1H-benzo[e][1,4]diazepin-4(5H)-yl)methyl)benzoic Acid Step 1: (R)-Methyl 2-(2-acetoxyacetamido)-4-((8-chloro-2,5-dioxo-3-(pyridin-2-ylmethyl)-2,3-dihydro-1H-benzo[e][1,4]diazepin-4(5H)-yl)methyl)benzoate (55-1)

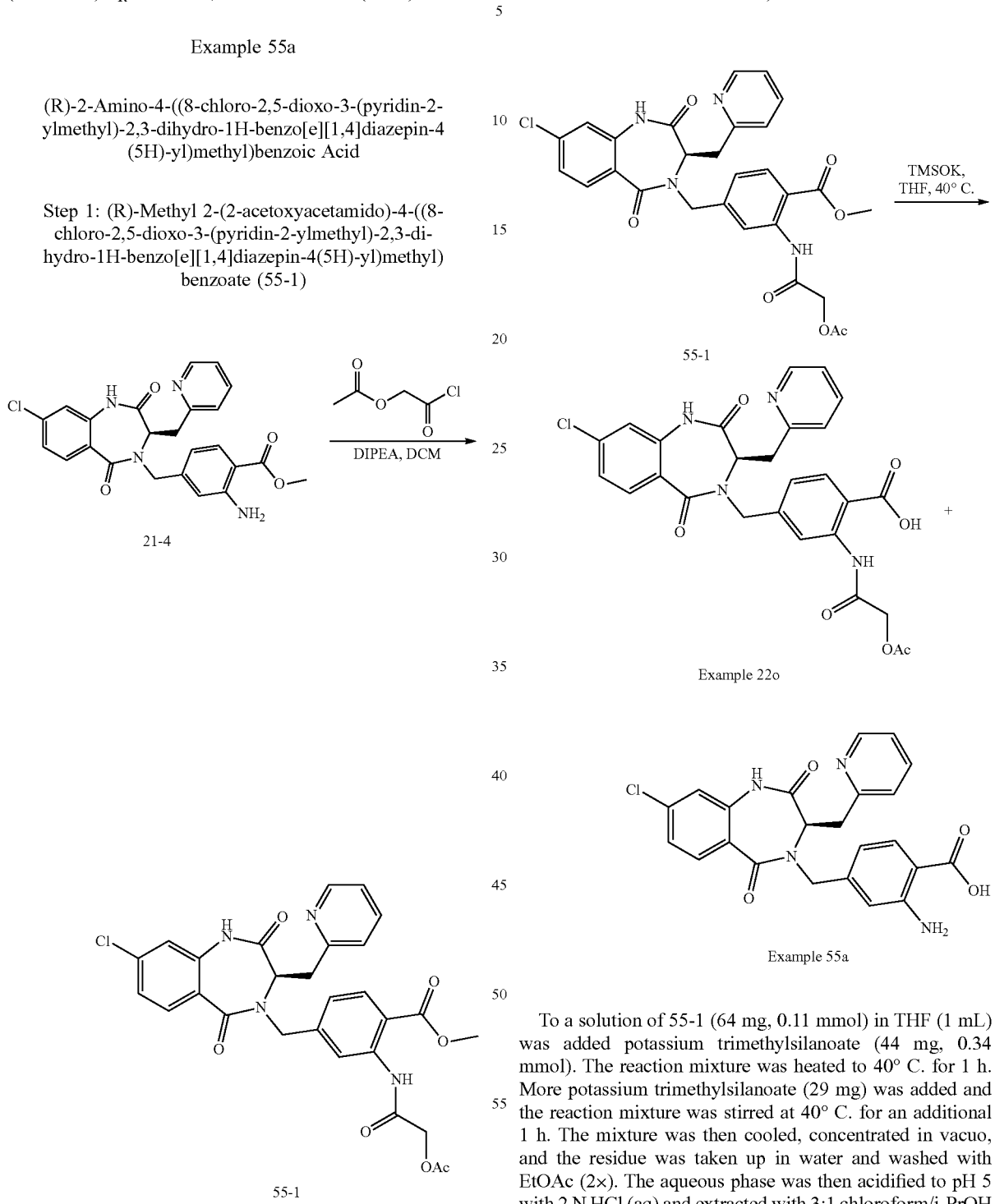

Following the same general procedure described in Step 1 of Example 22a, aniline 21-4 (53 mg, 0.11 mmol) was reacted with 2-chloro-2-oxoethyl acetate (0.015 mL, 0.14 mmol) to provide 64 mg of 55-1 which was used directly in the next step without further purification. LCMS (Method A): $t_R$=1.01 min, m/z 565.5/567.5 (M+H)$^+$.

Step 2: (R)-2-Amino-4-((8-chloro-2,5-dioxo-3-(pyridin-2-ylmethyl)-2,3-dihydro-1H-benzo[e][1,4]diazepin-4(5H)-yl)methyl)benzoic Acid (Example 55a)

To a solution of 55-1 (64 mg, 0.11 mmol) in THF (1 mL) was added potassium trimethylsilanoate (44 mg, 0.34 mmol). The reaction mixture was heated to 40° C. for 1 h. More potassium trimethylsilanoate (29 mg) was added and the reaction mixture was stirred at 40° C. for an additional 1 h. The mixture was then cooled, concentrated in vacuo, and the residue was taken up in water and washed with EtOAc (2×). The aqueous phase was then acidified to pH 5 with 2 N HCl (aq) and extracted with 3:1 chloroform/i-PrOH (3×). The combined organic extracts were dried (Na$_2$SO$_4$), filtered and concentrated in vacuo. The crude residue was purified by FCC (SiO$_2$; elution with 0-10% MeOH/DCM) to provide 14 mg (24%) of Example 22o and 12 mg of Example 55a as an unexpected by-product. Data for Example 55a: LCMS (Method A) $t_R$=0.83 min, m/z 451.4/453.4 (M+H)$^+$.

Example 56a

2-Chloro-4-(1-((R)-8-chloro-2,5-dioxo-3-(pyridin-2-ylmethyl)-2,3-dihydro-1H-benzo[e][1,4]diazepin-4(5H)-yl)ethyl)benzoic Acid

Step 1: tert-Butyl 2-chloro-4-(1-hydroxyethyl)benzoate (56-1)

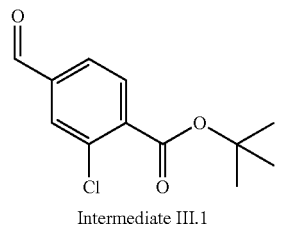

Intermediate III.1

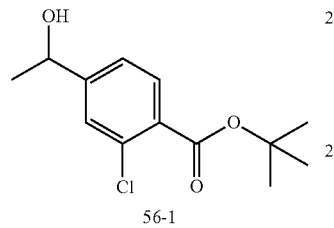

56-1

To a solution of Intermediate III.X (0.05 g, 0.21 mmol) in toluene (5 mL) and ethyl ether (5 mL) at 0° C. was added methylmagnesium bromide (3 M in ethyl ether, 0.080 mL, 0.23 mmol) drop wise and the reaction mixture was stirred at 0° C. for 30 min. The reaction was quenched with 2 mL of saturated ammonium chloride (aq), and then extracted with EtOAc (3×20 mL). The combined organic extracts were washed with brine (1×10 mL), dried (Na$_2$SO$_4$), filtered and concentrated in vacuo. The crude residue was purified by FCC (SiO$_2$, gradient elution with 0-80% DCM/Hexane) to give 40 mgs (75%) of 56-1. $^1$H NMR (400 MHz, CDCl$_3$): δ ppm 7.75 (d, 1H), 7.45 (s, 1H), 7.25 (d, 1H), 4.90 (m, 1H), 1.95 (d, 1H), 1.60 (s, 9H), 1.45 (d, 3H); LCMS (Method A) t$_R$=1.33 min, m/z 201.2/203.2 (M+H)$^+$.

Step 2: tert-Butyl 2-chloro-4-(1-((methylsulfonyl)oxy)ethyl)benzoate (56-2)

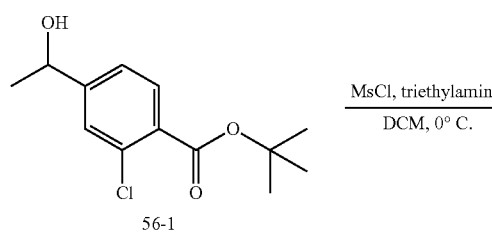

To a solution of alcohol 56-1 (1.51 g, 5.88 mmol) in DCM (20 mL) at 0° C. were added MsCl (0.50 mL, 6.5 mmol) and triethylamine (1.23 mL, 8.82 mmol) and the reaction mixture was stirred at 0° C. for 30 min. This was then diluted with additional DCM (20 mL), and washed with water (1×20 mL) and brine (1×20 mL). The organic phase was dried (Na$_2$SO$_4$), filtered and concentrated in vacuo to provide 1.98 g (100%) of 56-2 which was used without further purification in the next step.

Step 3: Tert-Butyl 2-chloro-4-(1-(((R)-1-methoxy-1-oxo-3-(pyridin-2-yl)propan-2-yl)amino)ethyl)benzoate (56-3)

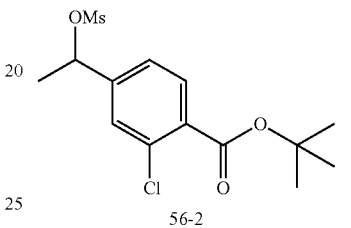

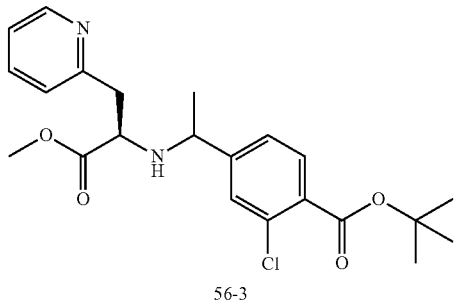

56-3

To a mixture of mesylate 56-2 (1.86 g, 5.56 mmol) and Intermediate II.1 (4.20 g, 16.7 mmol) in DMF (7 mL) were added DIPEA (7.0 mL, 40 mmol) and NaI (42 mg, 0.28 mmol). The reaction mixture was then heated to 80° C. for 66 h. The mixture was cooled to room temperature, diluted with EtOAc (100 mL) and washed with saturated NaHCO$_3$ (aq) (1×70 mL). The aqueous phase was then back-extracted with EtOAc (2×100 mL), and the organic extracts were combined, washed with water (1×100 mL) and brine (1×100 mL), dried (Na$_2$SO$_4$), filtered and concentrated in vacuo. The crude residue was purified by FCC (SiO$_2$; elution with 0-40% EtOAc/hexanes) to provide a total of 1.06 g (45%) of 56-3 as partially separable diastereomers (designated "less polar" for the first eluting diastereomer and "more polar" for the later eluting diastereomer). The initial purification by FCC provided 0.38 g of the less polar diastereomer and 0.37 g of the more polar diastereomer along with an additional 0.32 g of a mixture of the two diastereomers. The purified more polar diastereomer was carried forward into the next steps.

Step 4: Methyl 4-(1-(2-azido-4-chloro-N—((R)-1-methoxy-1-oxo-3-(pyridin-2-yl)propan-2-yl)benzamido)ethyl)-2-chlorobenzoate (56-4)

Step 5: 2-Chloro-4-(1-((R)-8-chloro-2,5-dioxo-3-(pyridin-2-ylmethyl)-2,3-dihydro-1H-benzo[e][1,4]diazepin-4(5H)-yl)ethyl)benzoic Acid (Example 56a)

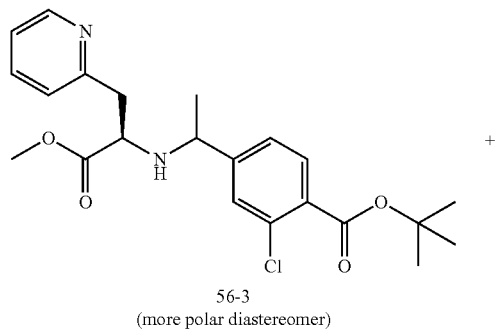

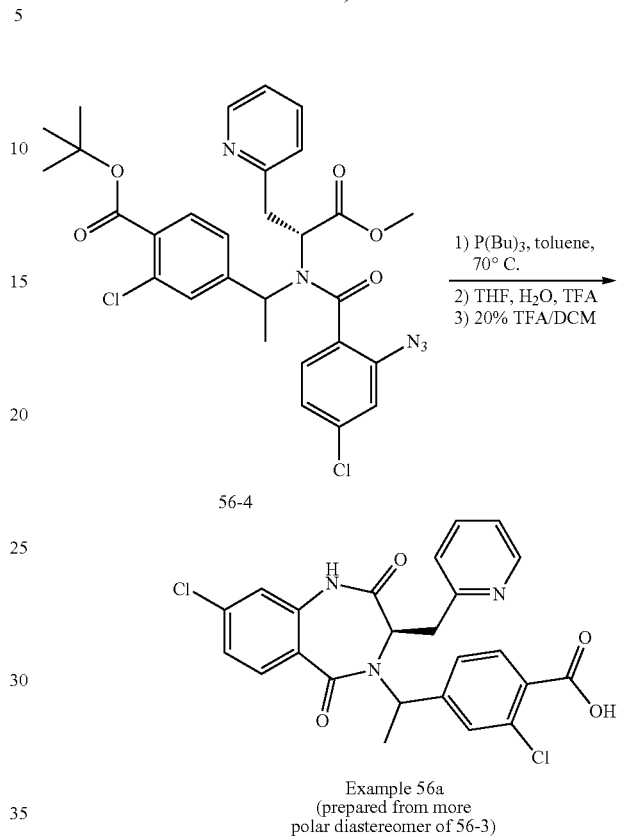

Compound 56-4 (644 mg, 1.08 mmol) was subjected to the same general procedure described in Step 3 of Example 7a to provide 270 mg (52%) of Example 56a. $^1$H NMR (400 MHz, CDCl$_3$): δ ppm 8.15 (d, 1H), 8.01 (d, 1H), 7.69 (d, 1H), 7.38 (td, 1H), 7.29 (d, 1H), 7.25 (m, 1H, partially obscured by solvent peak), 7.23 (m, 1H), 7.07 (m, 1H), 6.99 (ddd, 1H), 6.39 (d, 1H), 6.18 (q, 1H), 4.35 (t, 1H), 2.74 (dd, 1H), 2.38 (dd, 1H), 1.56 (d, 3H); LCMS (Method A): $t_R$=0.86 min, m/z 484.4/486.4/488.4 (M+H)$^+$.

Example 57a

2-Chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-(trifluoromethyl)pyridin-2-yl)benzamide

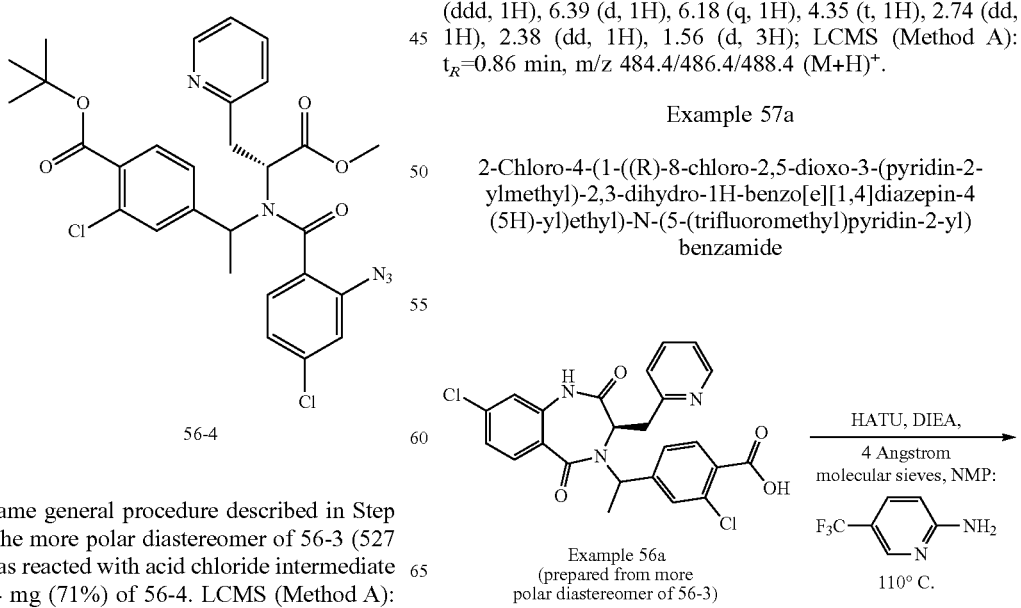

Following the same general procedure described in Step 3 of Example 1a, the more polar diastereomer of 56-3 (527 mg, 1.26 mmol) was reacted with acid chloride intermediate 1-2 to provide 644 mg (71%) of 56-4. LCMS (Method A): $t_R$=1.28 min, m/z 598.5/600.5/602.5 (M+H)$^+$.

339

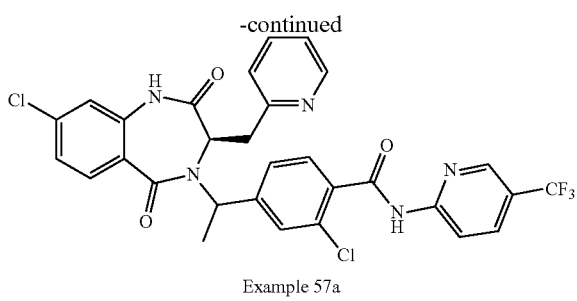

Example 57a

To a mixture of carboxylic acid Example 56a (101 mg, 0.21 mmol) and powdered 4 Å molecular sieves (20 mg) in NMP (0.5 mL) in an oven-dried, 5-10 mL capacity microwave vial, were added HATU (87 mg, 0.23 mmol) and DIEA (0.040 mL, 0.23 mmol). The mixture was stirred under $N_2$ atmosphere for 40 min. 2-Amino-5-trifluoromethylpyridine (51 mg, 0.31 mmol) was then added. The vial was tightly capped, and the mixture was heated thermally in a heating block to 110° C. for 16 h. The mixture was cooled to room temperature, diluted with EtOAc (20 mL), and washed successively with sat. $NH_4Cl$ (aq) (1×10 mL), sat. $NaHCO_3$ (aq) (1×10 mL), and brine (1×10 mL). The organic layer was dried ($Na_2SO_4$), filtered, and concentrated in vacuo. The crude residue was purified by FCC ($SiO_2$; elution with 0-5% MeOH/DCM) to provide 36 mg (27%) of Example 57a. $^1$H NMR (400 MHz, $CDCl_3$): δ ppm 8.88 (s, 1H), 8.57 (s, 1H), 8.51 (d, 1H), 8.32 (d, 1H), 8.20 (s, 1H), 8.11 (d, 1H), 8.01 (dd, 1H), 7.64 (d, 1H), 7.47-7.39 (m, 3H), 7.32 (dd, 1H), 7.07 (dd, 1H), 6.99 (m, 1H), 6.54 (d, 1H), 6.26 (q, 1H), 4.54 (td, 1H), 2.83 (dd, 1H), 2.45 (dd, 1H), 1.65 (d, 3H); LCMS (Method A) $t_R$=1.24 min, m/z 628.5/630.5 (M+H)$^+$.

Following the general procedure described above for Example 57a and substituting the corresponding reagents, the following Examples were similarly prepared as indicated in Table 31.

340

Example 58a

2-Chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methylpyridin-2-yl)benzamide Steps 1-2: 2-Chloro-4-(1-((R)-8-chloro-2,5-dioxo-3-(pyridin-2-ylmethyl)-2,3-dihydro-1H-benzo[e][1,4]diazepin-4(5H)-yl)ethyl)benzoic Acid (58-2)

TABLE 31

| Example | Structure | Reagent | LCMS Method | $t_R$ (min) | (M + H)$^+$ observed |
|---|---|---|---|---|---|
| 57b | 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methylpyridin-2-yl)benzamide | | A | 1.07 | 574.5/576.5/578.5 |
| 57c | 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methoxypyridin-2-yl)benzamide | | A | 1.08 | 590.5/592.5/594.5 |

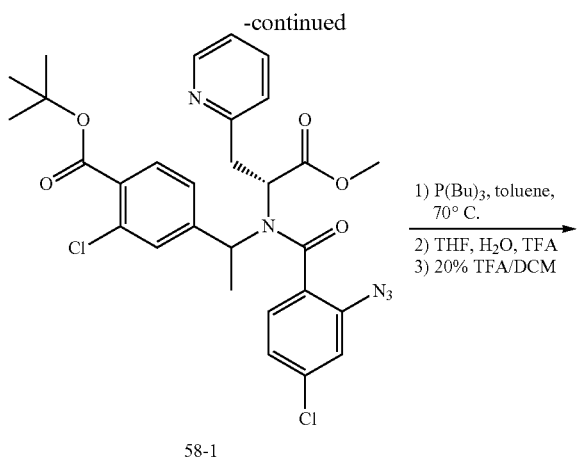

58-1

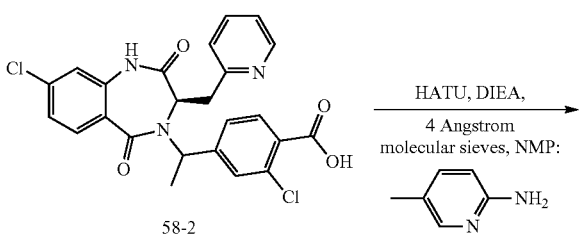

58-2

Carboxylic acid 58-2 was prepared from the less polar diastereomer of 56-3 and acid chloride 1-2 using the same general procedures described for Steps 4 and 5 for the preparation of Example 56a. LCMS (Method A): $t_R$=0.99 min, m/z 484.4/486.4/488.4 (M+H)$^+$.

Step 3: 2-Chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methylpyridin-2-yl)benzamide (Example 58a)

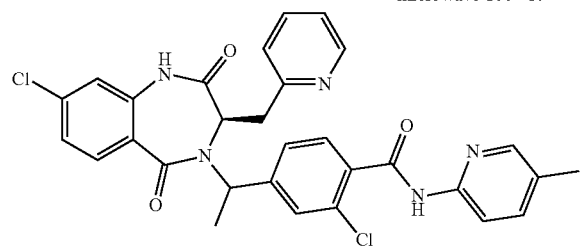

Example 58a
(prepared from less polar diastereomer of 56-3)

Following the same general procedure described for the preparation of Example 4a, carboxylic acid 58-2 (0.10 g, 0.21 mmol) was reacted with 6-amino-3-picoline (67 mg, 0.62 mmol) to provide 59 mg (50%) of Example 58a. $^1$H NMR (400 MHz, CDCl$_3$, ~6.4:1.0 mixture of 7-member ring conformers observed); data for major conformer: δ ppm 8.70 (br s, 1H), 8.59 (m, 1H), 8.24 (d, 1H), 8.11 (m, 2H), 8.08 (d, 1H), 7.69 (d, 1H), 7.60-7.54 (m, 2H), 7.38 (m, 1H), 7.31-7.27 (m, 2H), 7.17 (ddd, 1H), 6.95 (d, 1H), 6.87 (d, 1H), 6.11 (q, 1H), 4.39 (t, 1H), 2.99 (dd, 1H), 2.87 (dd, 1H), 2.31 (s, 3H), 1.23 (d, 3H); LCMS (Method A) $t_R$=1.08 min, m/z 574.5/576.5/578.5 (M+H)$^1$.

Experimental Studies—In Vitro and In Vivo Studies

Example 59: Fluorescence Polarization Assay for C. difficile TcdB Glucosyltransferase Domain UDP-Glucose Hydrolysis Activity (TcdB UDP-Glucose Hydrolysis Assay)

We evaluated the compounds of the present invention for their ability to inhibit hydrolysis of uridine-5'-diphosphoglucose (UDP-glucose) to uridine 5'-diphosphate (UDP) and glucose by purified recombinant glucosyltransferase domain of C. difficile Toxin B/TcdB. The UDP-glucose hydrolase activity of TcdB was measured using a competition assay (Transcreener® ADP2 FP Assay; BellBrook Labs, Madison, Wis.) to quantify UDP. In this assay, UDP generated as a reaction product displaces a fluorescently-labeled tracer from its binding site on an antibody that recognizes UDP and thus decreases the fluorescence polarization signal. The effect of TcdB inhibitors is to decrease UDP production and therefore increase fluorescence polarization levels.

Recombinant C. difficile Toxin B/TcdB catalytic fragment (Met1Leu543, with a C-terminal 6-His tag, accession # P18177) was purchased from R&D Systems (Minneapolis, Minn.; catalog #6246-GT). Uridine-5'-diphosphoglucose was purchased from Sigma-Aldrich (St. Louis, Mo.; catalog # U4625). ADP$^2$ antibody (catalog #2054) and fluorescent ADP Alexa633 tracer (catalog #2013) were supplied by BellBrook Labs. The assay buffer consisted of 50 mM HEPES, pH 7.5 (Life Technologies, Carlsbad, Calif.; catalog #15630), 150 mM KCl (Sigma-Aldrich, catalog # P3911), 0.05% bovine gamma globulin (Sigma-Aldrich, catalog # G7516), 0.005% Tween-20 (Sigma-Aldrich, catalog # P1379), and 2 mM MnCl$_2$ (Sigma-Aldrich, catalog #244589).

The UDP-glucose hydrolysis assay was performed in solid black 1536-well plates (Greiner Bio-One, Monroe, N.C.; catalog #782076) by adding 2 µL per well of 0.2 µg/mL TcdB diluted in assay buffer, then adding 2 µL of 40 µM UDP-glucose substrate/7.8 nM ADP Alexa633 tracer in assay buffer, incubating the assay plate for 3 hours at 25° C., and then adding 4 µL of 1 µg/mL ADP$^2$ antibody/20 mM ethylenediaminetetraacetic acid (EDTA; Sigma-Aldrich, catalog # E9884), pH 8.0 in assay buffer. Reagent additions were carried out using the JANUS Automated Workstation (PerkinElmer) with a 384-tip pipetting head. The microplate was centrifuged for 2 minutes after each addition, as well as after the incubation, at 1,500 rpm (approximately 450×g) in a tabletop centrifuge (Allegra X-12, Beckman Coulter; Brea, Calif.). After the second reagent addition (substrate with ADP-tracer), the plate was sealed with adhesive plate tape and protected from light during the 3-hour incubation, and centrifuged again prior to the third reagent addition (EDTA/antibody). After the EDTA/antibody addition, the plate was resealed and stored in the dark for 16 hours. Fluorescence polarization was detected using the EnVision 2103 Multi-Label Reader with the optimized Cy5 FP Dual Emission Label (620/40 nm excitation, 688/45 nm emission, and D658/fp688 dual mirror; PerkinElmer, Waltham, Mass.). Each assay plate contained additional control wells as follows: (1) assay buffer in all three additions ("buffer-only blank," used for blank subtraction), and (2) assay buffer alone instead of TcdB in the first addition, followed by the substrate/tracer and EDTA additions as described above ("no enzyme" control).

Fluorescence polarization (in units of mP) was calculated by first subtracting the average parallel emission channel "buffer-only blank" fluorescence value from each parallel emission reading, and similarly, subtracting the average "buffer-only blank" perpendicular emission reading from each perpendicular emission reading, and then computing polarization using a G factor of 0.3, and the equation:

$$\text{Fluorescence polarization (in units of mP)} = 1000 \times (S-GP)/(S+GP)$$

where:
S=background-subtracted parallel emission.
P=background-subtracted perpendicular emission.

For small molecule compound testing, compounds were dissolved to 10 mM in dimethylsulfoxide (Sigma-Aldrich, catalog # D8418) and arrayed by acoustic dispensing into assay plates, using the ATS-100 (BioSero). After arraying, compounds were dried down in the assay wells for 16 hours at 37° C., prior to addition of reagents for the TcdB assay. The $IC_{50}$ values reported in the present invention were derived from a four-parameter non-linear regression curve fit of the polarization values at each test compound concentration, plotting mP vs. test compound concentration expressed as log(M), using ActivityBase (IDBS; London, UK).

TcdB UDP-Glucose Hydrolysis Assay Results

In Table 32, $IC_{50}$ values are shown for Examples of the invention as determined according to the UDP-Glucose hydrolysis assay protocol described above. The $IC_{50}$ values are coded as A, B, C or D where: A<100 nM; B=100-999 nM; C=1,000-10,000 nM and D=10,001-35,000 nM.

TABLE 32

Activity of compounds of the invention (Example #) as determined in a UDP-Glucose hydrolysis assay

| Example # | TcdB UDP-Glucose hydrolysis activity |
|---|---|
| 01a | B |
| 01b | C |
| 01c | D |
| 01d | C |
| 01e | D |
| 01f | B |
| 01g | C |
| 01h | B |
| 01i | B |
| 01j | D |
| 01k | D |
| 01l | C |
| 01m | C |
| 01n | D |
| 02a | B |
| 02c | D |
| 02d | C |
| 02e | C |
| 02f | C |
| 02g | C |
| 02h | C |
| 02i | C |
| 03a | C |
| 03b | D |
| 03c | D |
| 03d | C |
| 03e | D |
| 03f | C |
| 03g | D |
| 03h | D |
| 03i | C |
| 03j | D |
| 03k | B |
| 03l | C |
| 03m | C |
| 03n | C |
| 03o | D |
| 04a | A |
| 04b | A |
| 04c | A |
| 04d | B |
| 04e | A |
| 04f | A |
| 04g | C |
| 04h | A |
| 04i | A |
| 04j | C |
| 04k | B |
| 04l | A |
| 04m | B |
| 04n | A |
| 04o | D |
| 04p | A |
| 04q | B |
| 04r | A |
| 04s | A |
| 04t | A |
| 04u | B |
| 04v | A |
| 04w | A |
| 04x | A |
| 04y | A |
| 04z | A |
| 04aa | A |
| 04ab | A |
| 04ac | B |
| 04ad | A |
| 04ae | B |
| 04af | A |
| 04ag | C |
| 04ah | A |
| 04ai | A |
| 04aj | B |
| 04ak | A |
| 04al | A |
| 04am | B |
| 04an | A |
| 04ao | A |
| 04ap | A |
| 04aq | A |
| 04ar | A |
| 04as | A |
| 04at | A |
| 04au | A |
| 04av | A |
| 04aw | B |
| 04ax | A |
| 04ay | B |
| 04az | B |
| 04ba | B |
| 04bb | B |
| 04bc | B |
| 04bd | A |
| 04be | A |
| 04bf | B |
| 04bg | B |
| 04bh | B |
| 04bi | B |
| 04bj | C |
| 04bk | D |
| 04bl | B |
| 04bm | A |

TABLE 32-continued

Activity of compounds of the invention (Example #) as determined in a UDP-Glucose hydrolysis assay

| Example # | TcdB UDP-Glucose hydrolysis activity |
|---|---|
| 04bn | C |
| 04bo | A |
| 04bp | B |
| 04bq | B |
| 04br | B |
| 04bs | B |
| 04bt | C |
| 04bu | A |
| 04bv | B |
| 04bw | A |
| 04bx | A |
| 04by | A |
| 04bz | A |
| 04ca | A |
| 04cb | A |
| 04cc | A |
| 04cd | A |
| 04ce | B |
| 04cf | A |
| 04cg | A |
| 04ch | D |
| 04ci | A |
| 04cj | A |
| 04ck | A |
| 04cl | A |
| 04cm | A |
| 04cn | A |
| 04co | B |
| 05a | A |
| 05b | A |
| 05c | A |
| 05d | A |
| 05e | B |
| 05f | B |
| 05g | A |
| 05h | A |
| 05i | A |
| 05j | A |
| 05k | A |
| 05l | A |
| 05m | A |
| 05n | B |
| 05o | B |
| 05p | C |
| 05q | A |
| 05r | B |
| 05s | B |
| 05t | A |
| 05u | A |
| 05v | A |
| 05w | A |
| 05x | A |
| 05y | A |
| 05z | A |
| 05aa | A |
| 05ab | A |
| 05ac | A |
| 05ad | A |
| 05ae | A |
| 05af | A |
| 05ag | A |
| 05ah | A |
| 05ai | A |
| 05aj | A |
| 05ak | A |
| 05al | A |
| 05am | A |
| 05an | A |
| 05ao | A |
| 05ap | A |
| 05aq | A |
| 05ar | C |
| 05as | A |
| 05at | A |
| 05au | A |
| 05av | A |
| 05aw | A |
| 05ax | A |
| 06a | A |
| 06b | A |
| 06c | A |
| 06d | A |
| 06e | B |
| 06f | A |
| 07a | B |
| 07b | B |
| 07c | C |
| 07d | B |
| 08a | B |
| 08b | B |
| 08c | B |
| 08d | B |
| 08e | B |
| 08f | B |
| 08g | B |
| 08h | B |
| 08i | B |
| 08j | B |
| 08k | B |
| 08l | B |
| 08m | C |
| 08n | B |
| 08o | C |
| 08p | B |
| 08q | B |
| 08r | B |
| 08s | C |
| 08t | C |
| 08u | C |
| 09a | B |
| 10a | C |
| 10b | D |
| 10c | C |
| 10d | C |
| 10e | C |
| 10f | D |
| 11a | A |
| 11b | A |
| 11c | A |
| 11d | A |
| 11e | B |
| 11f | A |
| 11g | A |
| 11h | A |
| 11i | C |
| 11j | A |
| 12a | A |
| 12b | C |
| 13a | D |
| 13b | D |
| 13c | C |
| 13d | B |
| 14a | A |
| 15a | C |
| 15b | C |
| 15c | C |
| 15d | C |
| 15e | C |
| 16a | C |
| 17a | B |
| 18a | C |
| 18b | D |
| 18c | C |
| 18d | D |
| 18e | C |
| 19a | B |
| 19b | A |
| 19c | B |
| 19d | B |
| 19e | B |

TABLE 32-continued

Activity of compounds of the invention (Example #) as determined in a UDP-Glucose hydrolysis assay

| Example # | TcdB UDP-Glucose hydrolysis activity |
|---|---|
| 19f | B |
| 19g | A |
| 19h | A |
| 19i | C |
| 19j | D |
| 20a | C |
| 21a | C |
| 22a | B |
| 22b | B |
| 22c | B |
| 22d | C |
| 22e | C |
| 22f | C |
| 22g | C |
| 22h | C |
| 22i | D |
| 22j | C |
| 22k | B |
| 22l | B |
| 22m | B |
| 22n | B |
| 22o | B |
| 23a | C |
| 24a | D |
| 25a | B |
| 26a | B |
| 26b | A |
| 26c | A |
| 26d | C |
| 26e | C |
| 26f | A |
| 26g | C |
| 26h | B |
| 26i | A |
| 26j | B |
| 26k | B |
| 26l | B |
| 27a | C |
| 27b | B |
| 27c | B |
| 27d | B |
| 27e | B |
| 27f | A |
| 27g | C |
| 27h | A |
| 27i | B |
| 27j | A |
| 27k | A |
| 28a | A |
| 28b | C |
| 29a | C |
| 30a | D |
| 30b | D |
| 30c | C |
| 31a | A |
| 31b | C |
| 31c | B |
| 31d | B |
| 31e | C |
| 31f | A |
| 32a | A |
| 33a | D |
| 33b | A |
| 33c | C |
| 33d | B |
| 34a | A |
| 34b | A |
| 35a | B |
| 35b | A |
| 35c | C |
| 35d | B |
| 35e | C |
| 35f | C |
| 35g | B |
| 35h | B |
| 35i | C |
| 35j | A |
| 35k | D |
| 35l | B |
| 35m | B |
| 35n | B |
| 36a | C |
| 37a | C |
| 38a | D |
| 39a | D |
| 40a | A |
| 41a | C |
| 42a | C |
| 43a | C |
| 44a | B |
| 45a | A |
| 46a | A |
| 47a | A |
| 48a | A |
| 49a | A |
| 49b | A |
| 49c | A |
| 49d | B |
| 49e | A |
| 50a | B |
| 51a | C |
| 52a | B |
| 53a | B |
| 54a | C |

Example 60: Cell-Based Assay for *C. difficile* Full-Length Toxin Activity In Vitro: Caspase 3/7 Activation We evaluated the compounds of the present invention for their ability to inhibit induction by *C. difficile* full-length toxins (TcdA or TcdB) of apoptosis in cultured mammalian cells. Apoptosis was quantified using a luciferase-based assay (Caspase 3/7 Glo™; Promega, Madison, Wis.) for activation of the caspase cascade. Briefly, following a forty-eight hour incubation with toxin, cells are lysed and a caspase substrate is hydrolyzed by caspases-3 and/or -7, producing aminoluciferin, a substrate for luciferase. In the presence of assay kit reagents luciferase and adenosine triphosphate (ATP), a luminescence signal is generated.

Chinese Hamster Ovary (CHO) cells (American Type Culture Collection, catalog # CRL-9618) were cultured at 37° C./5% $CO_2$ in Medium A [F12-Ham medium (Sigma-Aldrich, catalog # N6658), supplemented with 10% fetal bovine serum (Sigma-Aldrich, catalog # F4135), 100 U/mL penicillin, 100 μg/mL streptomycin (Pen-Strep; Sigma-Aldrich, catalog # P4333), and 2 mM L-glutamine (Corning, Tewksbury, Mass.; catalog #25-005-001. Flask cultures were grown to 70-90% confluence. The culture medium was then removed and replaced with Medium B, consisting of 17% Medium A and 83% of [L-15 medium (Leibovitz; Sigma-Aldrich, catalog #5520), supplemented with 10% fetal bovine serum (Sigma-Aldrich, catalog # F4135), 100 U/mL penicillin, 100 μg/mL streptomycin (Pen-Strep; Sigma-Aldrich, catalog # P4333), and 2 mM L-glutamine (Corning, catalog #25-005-001. After further culturing for 24 hours, the cells were rinsed twice with Dulbecco's phosphate-buffered saline (5 mL per 150 cm2 flask; Corning, catalog #21-031-CV), and detached for 5 minutes at 37° C. in 2 mL of trypsin formulated as TrypLExpress (Life Technologies, catalog #12605-010). 8 ml of Medium B was added to quench the trypsin and cells were then triturated ten times, pelleted by centrifugation, resuspended in 10 mL Medium B, and strained through a Falcon® 40 μm strainer (Corning, catalog #352340) to remove clumps. The cell density was adjusted to 800,000 cells/mL. 10 μL cells were then added to each well of a solid white 384-well plate (Greiner Bio-One, catalog #781080) already containing 10 μL of Medium B or dried test compounds that had been redissolved in 10 μL of Medium B. The plate was incubated for one hour at 37° C./5% $CO_2$ and then centrifuged for 1 minute at (500 rpm; approximately 50×g). TcdA (Enzo Life Sciences, Farmingdale, N.Y.; catalog # BML-G140-0050) or TcdB (EMD Millipore, Billerica, Mass.; catalog #616377) were added in 10 μL to final concentrations of 100 ng/mL and 0.3 ng/mL, respectively, in the final reaction volume of 30 μL. As an additional control, staurosporine (Sigma-Aldrich, catalog #5921) was added to three wells to 0.5 μM final concentration. The plate was again centrifuged at 50×g for 1 minute and incubated for 48 hours at 37° C./5% $CO_2$. Caspase 3/7 activation was detected using Caspase 3/7 Glo™ (Promega, Madison, Wis.; catalog # G-8091), according to the manufacturer's instructions, and luminescence measured in the ViewLux 1430 ultra-HTS microplate imager (PerkinElmer).

For small molecule compound testing, compounds were dissolved in dimethylsulfoxide and arrayed by acoustic dispensing into assay plates, using the ATS-100 (BioSero). Compounds were dried down for 16 hours at 37° C., prior to addition of assay reagents. $IC_{50}$ values were derived from a four-parameter non-linear regression curve fit of the luminescence values at each test compound concentration, using ActivityBase (IDBS).

Cell-Based Assay Results

In Table 33, $IC_{50}$ values are shown for some representative Examples of the invention as determined according to the cell-based assay protocol described above. The $IC_{50}$ values are coded as A, B, C or D where: A<100 nM; B=100-999 nM; C=1,000-10,000 nM and D>10,000 nM.

TABLE 33

Activity of compounds of the invention (Example #) as determined in a cell-based assay

| Example # | CHO-K1/TcdB Caspase 3/7 Glo Activity | CHO-K1/TcdA Caspase 3/7 Glo Activity |
|---|---|---|
| 04a | A | C |
| 04ad | A | B |
| 04au | B | D |
| 04by | A | B |
| 04cb | A | B |
| 04ci | B | C |
| 04ck | A | B |
| 04cl | A | B |
| 04cm | B | D |
| 05aa | B | C |
| 05ab | A | C |
| 05ae | B | C |
| 05af | B | C |
| 05ah | B | C |
| 05ai | A | B |
| 05aj | B | C |
| 05ak | B | C |
| 05al | A | C |
| 05am | B | C |
| 05an | B | C |
| 06a | A | B |
| 11a | C | D |
| 11b | C | D |
| 11g | C | D |
| 27j | C | D |
| 31a | B | C |
| 33b | B | C |
| 34a | B | D |
| 49b | C | D |
| 49c | D | D |

Example 61: Murine *C. difficile* Toxin Model

Toxin A (TcdA) and toxin B (TcdB) are two large glucosylating toxins produced by *C. difficile*. Production of these toxins during the *C. difficile* infection leads to colon inflammation and diarrhea. In initial studies, we tested whether the present compounds cause growth inhibition of multiple bacterial species, including *Clostridium difficile, Bacteriodes fragilis, Lactobacillus reuteri* and *Bifidobacterium longum*. We did not observe any significant inhibition of bacterial growth, even at a concentration of 50 μM of tested compounds.

In the following studies, we established a murine *C. difficile* toxin model with modifications from a published murine model (Hirota, Iablokov et al. 2012). Details of the murine *C. difficile* toxin model are described in the "Experimental Protocols" (below). *C. difficile* toxins were isolated from a culture of the *C. difficile* strain VPI 10463. *C. difficile* toxins consisted of TcdA and TcdB (~1:1 ratio of TcdA: TcdB). Respective TcdA and TcdB concentrations were determined by enzyme-linked immunosorbant assay (ELISA). In our mouse model, *C. difficile* toxins were administered intrarectally to evaluate their pathological effects.

We administered *C. difficile* toxin (12.5 μg/mouse) via intrarectal instillation into female C57BL/6 mice. Four (4) animals were used in each group. Four (4) hours after the toxin administration, the mice were euthanized. The colons were excised from the animals and washed with phosphate buffered saline (PBS). The colon lengths were measured. Excised colon tissues were stored at −70° C. for chemical analysis of interleukin-1β(IL-1β) and myeloperosidase (MPO) in tissues, which are the hallmarks of colon inflammation. Excised colon tissues were also stored at room temperature in 10% neutral buffered formalin for histopathological analysis.

Figure 1:
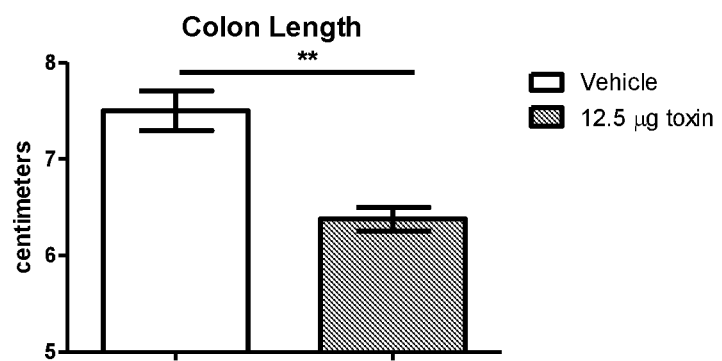
FIGS. 1a, 1b and 1c depict the effects of *C. difficile* toxin in murine toxin model. Four (4) animals were used in the control group and the treatment group. *C. difficile* toxin was administered intrarectally (12.5 µg). Colon length, IL-1β and MPO were determined. Intrarectal administration of *C. difficile* toxin causes a reduction in colon length (FIG. 1a), increase in IL-1β (FIG. 1b) and MPO (FIG. 1c). Bars represent the mean±standard error of the mean (SEM). P values:*<0.05 and **<0.01 (t-test).
Figure 1:
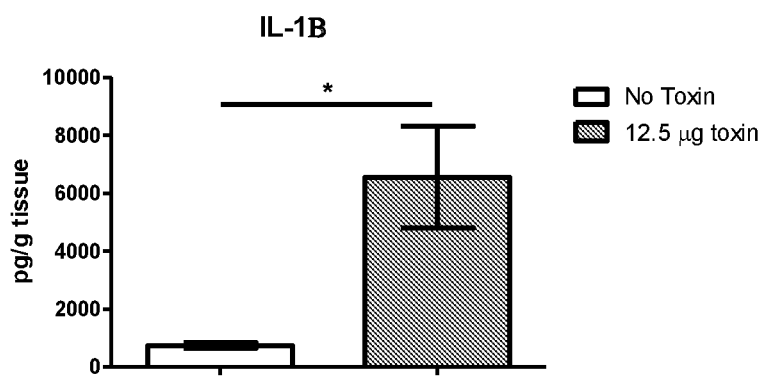
Figure 1:
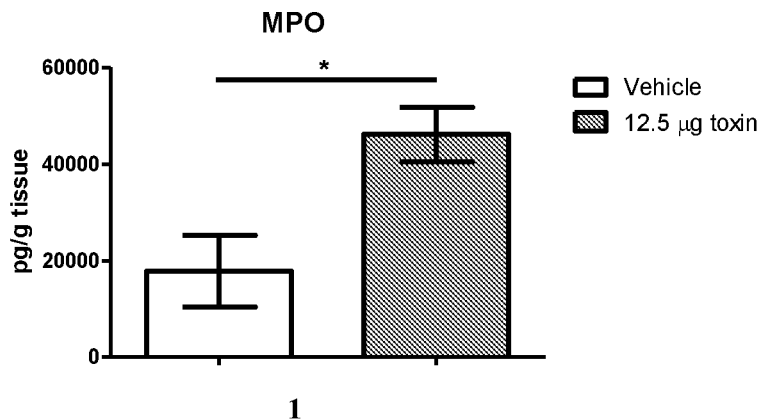
Figure 2:
FIGS. 2a, 2b and 2c depict the histopathological evaluation (100× magnification) of the colon tissue in mice. Healthy colon tissue in the absence of toxin (FIG. 2a), epithelial disintegration and submucosal edema following the intrarectal administration of *C. difficile* toxin (12.5 µg) (FIG. 2b) and prevention of tissue damage by oral co-administration of (R)-4-((8-Chloro-2,5-dioxo-3-(pyridin-2- ylmethyl)-2,3-dihydro-1H-benzo[e][1,4]diazepin-4(5H)-yl) methyl)-2-fluoro-N-(5-methoxypyridin-2-yl)benzamide (Example 6a) with intrarectal toxin (FIG. 2c).
Figure 2:
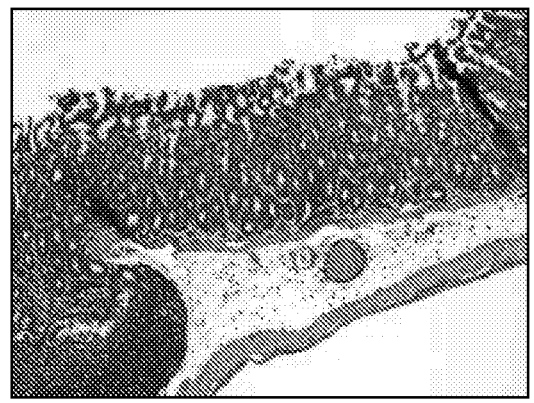
Figure 2:
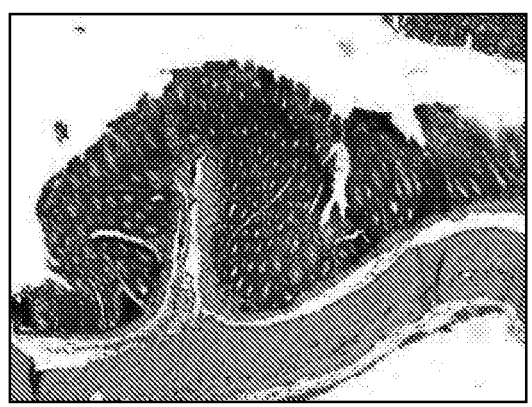

There was a significant reduction in colon length after intrarectal administration of the *C. difficile* toxin (FIG. 1a). Administration of *C. difficile* toxin increased the levels of IL-1β (FIG. 1b) and MPO (FIG. 1c), indicating cytokine generation as well as neutrophil accumulation in the colon tissues following the toxin administration. Histopathology evaluation of the colon tissues revealed that *C. difficile* toxin caused epithelial disintegration and gross submucosal edema (FIG. 2b).

Example 62: Example 6a Reduced the *C. difficile* Toxicity in the Murine Toxin Model Using the murine *C. difficile* toxin model (Example 61), we evaluated the efficacy of Example 6a in reducing the *C. difficile* toxin activity. In this study, the isolated toxin (12.5 μg) was diluted in 50 μl of PBS and mixed with a 50 μl suspension of Example 6a (10 mg/mL) in 1% carboxymethyl cellulose and 0.5% Tween 80 to achieve a fixed dose of ~12.5 mg/kg of Example 6a (0.5 mg in mice weighing ~20 g) and *C. difficile* toxin (12.5 μg). Three (3) animals were used in each group.

Co-administration of Example 6a and *C. difficile* toxin intrarectally (IR) reduced the *C. difficile* toxin effects on colon length (FIG. 3*a*). Example 6a decreased the *C. difficile* toxin-induced IL-1β (FIG. 3*b*) as well as MPO (FIG. 3*c*).

Example 63: Oral and Intraperitoneal Administrations of Example 6a were Effective In this study, we evaluated the efficacy of Example 6a via different routes of administration (i.e., oral (PO) and intraperitoneal (IP) administrations) in the same murine *C. difficile* toxin model (Example 61). In both PO and IP dosages, Example 6a was prepared as 5 mg/mL solutions in 20% PEG-400, 0.4% carboxymethyl cellulose and 0.2% Tween 80. Example 6a was administered at a final dose of 50 mg/kg body weight. Three (3) mice were used in each group (i.e., vehicle (control), PO and IP).

Both PO and IP administrations of Example 6a were effective in reducing the *C. difficile* toxin effects on colon length (FIG. 4*a*). Example 6a reduced the concentrations of IL-1β (FIG. 4*b*) as well as MPO (FIG. 4*c*) in colon tissues. Example 6a improved the colon histopathology after PO administration (FIG. 2*c*).

Example 64: Plasma Concentrations of Example 6a

We monitored the plasma concentrations of Example 6a following the IR, PO and IP administrations in the murine *C. difficile* toxin model (Example 63). Plasma concentrations of Example 6a were determined with the use of high pressure liquid chromatography (HPLC) and mass spectrometry (MS) following the administration of Example 6a. Plasma concentration curve of Example 6a was plotted over four hours (FIG. 5). While IR administration resulted in low plasma concentrations of Example 6a, both PO and IP had significantly higher plasma concentrations of Example 6a (FIG. 5). It is noted that reduction of the IL-1β and MPO levels as well as improved colon histopathology correlates with the plasma concentrations of Example 6a.

Example 65: Example 6a, Example 5ae, Example 4cl and Example 5al had Similar Protective Activities in the Murine *C. difficile* Toxin Model Using the murine *C. difficile* toxin model (Example 63), we further tested the efficacy of four (4) additional compounds (i.e., Example 6a, Example 5ae, Example 4cl, and Example 5al) via PO administration. All of the compounds were dosed orally at 50 mg/kg body weight. In three separate studies a total of three (3) to fourteen (14) mice were used in each group.

All of the four (4) tested compounds reduced the *C. difficile* toxin effects on colon length (FIG. 6*a*), reduced the colon levels of IL-1β (FIG. 6*b*) as well as MPO (FIG. 6*c*).

Example 66: Additional Compounds Tested in the Murine *C. difficile* Toxin Model We evaluated the efficacy of additional compounds in reducing *C. difficile* toxicity. Using the PO administration (Example 63), we further tested 30 compounds (Table 34). All of the compounds were dosed orally at 50 mg/kg body weight. Three (3) to fourteen (14) animals were used for each compound. % inhibition was determined by the following formula:

$$\% \text{ Inhibition} = \frac{(\text{toxin and vehicle}) - (\text{toxin and compound})}{(\text{toxin and vehicle}) - (\text{no toxin and vehicle})} \times 100$$

Table 34 summarizes the results of 30 test compounds.

TABLE 34

| Test Compounds | IL-1β (% Inhibition) | MPO (% Inhibition) |
|---|---|---|
| Example 4a: (R)-4-((8-Chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide | 30 | 51 |
| Example 6a: (R)-4-((8-Chloro-2,5-dioxo-3-(pyridin-2-ylmethyl)-2,3-dihydro-1H-benzo[e][1,4]diazepin-4(5H)-yl)methyl)-2-fluoro-N-(5-methoxypyridin-2-yl)benzamide | 80 | 81 |
| Example 4by: (R)-2-Chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide | 46 | 1 |
| Example 4cb: (R)-2-Chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide | 74 | 99 |
| Example 5aa: (R)-2-Chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide | 63 | 50 |
| Example 11b: (R)-8-Chloro-4-(4-(5-methylpicolinoyl)benzyl)-3-(pyridin-2-ylmethyl)-3,4-dihydro-1H-benzo[e][1,4]diazepine-2,5-dione | 52 | 100 |
| Example 5ab: (R)-2-Chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide | 100 | 100 |
| Example 11a: (R)-8-Chloro-4-(4-picolinoylbenzyl)-3-(pyridin-2-ylmethyl)-3,4-dihydro-1H-benzo[e][1,4]diazepine-2,5-dione | 22 | 0 |
| Example 49b: (R)-8-Chloro-4-(4-(8-oxo-5,6-dihydro-1,7-naphthyridin-7(8H)-yl)benzyl)-3-(pyridin-2-ylmethyl)-3,4-dihydro-1H- | 13 | 0 |

TABLE 34-continued

| Test Compounds | IL-1β (% Inhibition) | MPO (% Inhibition) |
|---|---|---|
| benzo[e][1,4]diazepine-2,5-dione | | |
| Example 4ci: (R)-2-Chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide | 86 | 19 |
| Example 4ad: (R)-8-Chloro-4-(3-chloro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione | 80 | 100 |
| Example 11g: (R)-8-Chloro-4-(3-chloro-4-picolinoylbenzyl)-3-(pyridin-2-ylmethyl)-3,4-dihydro-1H-benzo[e][1,4]diazepine-2,5-dione | 15 | 28 |
| Example 5ae: (R)-2-Chloro-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide | 81 | 79 |
| Example 4ck: (R)-4-((8-Chloro-2,5-dioxo-3-(pyridin-2-ylmethyl)-2,3-dihydro-1H-benzo[e][1,4]diazepin-4(5H)-yl)methyl)-2-methyl-N-(5-methylpyridin-2-yl)benzamide | 82 | 79 |
| Example 4cl: (R)-4-((8-Chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)-2-methylbenzamide | 100 | 100 |
| Example 5af: (R)-4-((8-Chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)-2-methylbenzamide | 100 | 100 |
| Example 49c: (R)-8-Chloro-4-(4-(7-oxo-5H-pyrrolo[3,4-b]pyridin-6(7H)-yl)benzyl)-3-(pyridin-2-ylmethyl)-3,4-dihydro-1H-benzo[e][1,4]diazepine-2,5-dione | 30 | 0 |
| Example 5ah: (R)-4-((8-Chloro-2,5-dioxo-3-(pyridin-2-ylmethyl)-2,3-dihydro-1H-benzo[e][1,4]diazepin-4(5H)-yl)methyl)-2-methyl-N-(5-methylpyrazin-2-yl)benzamide | 91 | 65 |
| Example 31a: (R)-8-Chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione | 100 | 100 |
| Example 5ai: (R)-4-((8-Chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)-2-methylbenzamide | 96 | 79 |
| Example 4cm: (R)-4-((8-Chloro-2,5-dioxo-3-(pyridin-2-ylmethyl)-2,3-dihydro-1H-benzo[e][1,4]diazepin-4(5H)-yl)methyl)-2-methoxy-N-(5-methylpyridin-2-yl)benzamide | 49 | 35 |
| Example 5aj: (R)-4-((8-Chloro-2,5-dioxo-3-(pyridin-2-ylmethyl)-2,3-dihydro-1H-benzo[e][1,4]diazepin-4(5H)-yl)methyl)-2-methoxy-N-(5-methylpyrazin-2-yl)benzamide | 76 | 17 |
| Example 27j: (R)-N-(4-((8-Chloro-2,5-dioxo-3-(pyridin-2-ylmethyl)-2,3-dihydro-1H-benzo[e][1,4]diazepin-4(5H)-yl)methyl)phenyl)-1H-imidazole-4-carboxamide | 41 | 1 |
| Example 5ak: (R)-4-((8-Chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrazin-2-yl)benzamide | 71 | 73 |
| Example 5al: (R)-4-((8-Chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl)pyridin-2-yl)benzamide | 81 | 91 |
| Example 4au: (R)-4-((8-Chloro-2,5-dioxo-3-(pyridin-2-ylmethyl)-2,3-dihydro-1H-benzo[e][1,4]diazepin-4(5H)-yl)methyl)-2-methoxy-N-(5-(trifluoromethyl)pyridin-2-yl)benzamide | 40 | 0 |
| Example 5am: (R)-4-((8-Chloro-2,5-dioxo-3-(pyridin-2-ylmethyl)-2,3-dihydro-1H-benzo[e][1,4]diazepin-4(5H)-yl)methyl)-2-methoxy-N-(5-methylpyrimidin-2-yl)benzamide | 54 | 31 |
| Example 5an: (R)-4-((8-Chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrimidin-2-yl)benzamide | 87 | 63 |
| Example 32a: 4-(4-(1H-Pyrrolo[3,2-b]pyridine-3-carbonyl)benzyl)-8-chloro-3-(pyridin-2-ylmethyl)-3,4-dihydro-1H-benzo[e][1,4]diazepine-2,5-dione | 72 | 76 |
| Example 33b: (R)-8-Chloro-4-(((1r,4R)-4-(1-methyl-1H-pyrrolo[3,2-b]pyridine-3-carbonyl)cyclohexyl)methyl)-3-(pyridin-2-ylmethyl)-3,4-dihydro-1H-benzo[e][1,4]diazepine-2,5-dione | 84 | 41 |

Example 67: Acute Murine *C. difficile* Infection Model

In a hospital environment, *C. difficile* infection occurs when the patient receives an antibiotic treatment that disrupts the normal gut microflora and is exposed to *C. difficile* spores. The patient often fails to mount a protective immune response against the acute *C. difficile* infection. (Rupnik, Wilcox et al. 2009). To study the acute *C. difficile* infection, we established a murine *C. difficile* infection model. Details of the infection model are provided in the "Experimental Protocol" (below).

In brief, female C57BL/6 mice were administered the following antibiotics: colistin (0.042 units/mL), gentamicin (0.035 mg/mL), kanamycin (0.4 mg/mL), metronidazole (0.215 mg/mL) and vancomycin (0.045 mg/mL) in drinking water for 3 days. The administered antibiotics disrupted the normal gut microflora in mice. On the $4^{th}$ day, mice received oral administration of 0.5 mL volume containing ~100 spores produced from a virulent clinical *C. difficile* isolate (strain VPI 10463). In this acute murine *C. difficile* infection model, we observed a similar time course of infection when compared to that of clinical patients. The *C. difficile* infected mice developed diarrhea and weight loss, exhibited gut inflammation, and in some cases, expired from the acute infection.

Time course study revealed that acute infection with *C. difficile* spores caused a significant reduction in body weight from 2.0 to 4.5 days after infection (FIG. 7). Five (5) out of eight (8) infected mice were euthanized on Day 3 due to body weight loss of >20%. After 52 hours of infection, we observed a significant reduction in body weight (FIG. 8a), colon length (FIG. 8b) and a significant increase in the concentrations of IL-1β (FIG. 8c) as well as MPO in the colon tissue (FIG. 8d).

Example 68: PO Administration of Example 6a, Example 5ae, Example 4cl, and Example 5al Reduced *C. difficile* Toxicity in an Acute Murine Infection Model Using the developed murine *C. difficile* infection model (Example 67), we evaluated our test compounds for their efficacy in reducing weight loss and gut inflammation caused by the acute *C. difficile* infection. We tested the efficacy of Example 6a and Example 5ae and used eight (8) animals in each group. Example 6a significantly reduced weight loss 2.25, 2.5 and 3.0 days after infection (FIG. 9a). Example 5ae significantly reduced weight loss 2.5 and 3.0 days after infection (FIG. 9b).

We further tested the efficacy of the Example 6a, Example 5ae, Example 4cl, and Example 5al compounds by PO administration. Vancomycin was used as a positive control. Three (3) experiments were performed utilizing a total of five (5) to sixteen (16) animals in each group.

All four (4) tested compounds significantly decreased body weight loss in the mice after 52 hours of infection (FIG. 10a). Example 5ae, Example 4cl and Example 5al significantly reduced the toxin effect on colon length (FIG. 10b). Example 5al reduced the level of IL-1β (FIG. 10c) and MPO (FIG. 10d) in colon tissues.

Example 69: Relapse Murine *C. difficile* Infection Model

Relapse or recurrent *C. difficile* infection is a major clinical problem affecting ~30% of patients with *C. difficile* infection (Aslam, Hamill et al. 2005). To study the recurrent *C. difficile* infection in humans, we developed a relapse murine *C. difficile* infection model. Details of the relapse murine *C. difficile* infection model are provided in the "Experimental Protocol" (below).

In this model, female C57/BL6 mice were administered antibiotics to disrupt gut flora and infected with *C. difficile* spores as described for the acute model. In addition, the animals were treated with vancomycin (20 mg/kg by oral dosing, once per day for five days after infection). There were eight (8) animals in each group. Treatment with vancomycin prevented weight loss during treatment (Days 1-5) but resulted in significant weight loss on days 8-9, indicative of the relapsing *C. difficile* disease (FIG. 11). Six (6) out of eight (8) mice in the vancomycin-treated group expired on Days 8-9.

Example 70: PO Administration of Example 6a and Example 5ae Reduced *C. difficile* Toxicity in a Relapse Murine *C. difficile* Infection Model Using the relapse murine *C. difficile* infection model (Example 69), we tested the efficacy of Example 6a and Example 5ae in reducing the toxin effects. Eight (8) animals were used in each group. PO administration of Example 6a and Example 5ae significantly reduced weight loss 8.0, 8.5 and 9.0 days after infection (FIG. 12). Six (6) out of eight (8) vancomycin-treated animals expired during Days 8-9. In contrast, none of the mice in the Example 6a and Example 5ae treated groups expired during this time.

Example 71: Hamster *C. difficile* Infection Model

The hamster model of *C. difficile* infection is the "gold standard" model. Hamster model has been shown to be clinically predictive and has been used to validate therapies before testing of drug candidates to advance into the clinic (Best, Freeman et al. 2012). For example, the approved agents vancomycin (Fekety, Silva et al. 1979) and fidaxomicin (Swanson, Hardy et al. 1991) are effective in this model, as are numerous agents in clinical trials, including anti-toxin antibodies (Babcock, Broering et al. 2006) and the antibiotics surotomycin (Mascio, Mortin et al. 2012), cadazolid (Locher, Seiler et al. 2014) and LFF571 (Trzasko, Leeds et al. 2012). Details of the hamster *C. difficile* infection model are provided in the "Experimental Protocol" (below).

Female Golden Syrian hamsters were administered clindamycin phosphate by oral gavage for a final dose of 30 mg/kg body weight five (5) days prior to infection. Approximately 100 spores of *C. difficile* strain 630 were administered by oral gavage.

Using the hamster *C. difficile* infection model, we evaluated test compounds for their efficacy in reducing *C. difficile* toxicity. Nine (9) or ten (10) animals were used in each group. Animals were dosed with Example 5ae beginning eight (8) hours after infection by oral gavages for a final dose of 50 mg/kg body weight. Example 5ae was dosed twice per day for 7 days by the PO route. Vancomycin was used as a positive control and dosed twice per day by the PO route for 5 days.

Vehicle treatment (control) did not protect from disease-related mortality (90% of animals expired by Day 3) (FIG. 13). In contrast, Example 5ae significantly improved the median survival time of the *C. difficile* infected hamster (70% survival until Day 10) (FIG. 13). Vancomycin exhibited a similar protective effect (FIG. 13). Vehicle treatment did not protect from significant vehicle-related weight loss (FIG. 14b). In contrast, Example 5ae-treated hamsters only exhibited a slight reduction in weight loss (FIG. 14c). Vancomycin treatment prevented any significant weight loss (FIG. 14d). Table 35 summarizes the dosing regimen and survival time in the hamster infection model.

TABLE 35

| Treatments | Regimens | Durations | Median Survival (Days) | P values* (compared to vehicle) |
|---|---|---|---|---|
| Vancomycin | 5 MPK bid | 5 days | 12.0 | 0.0055 |
| Example 5ae | 50 MPK bid | 7 days | 12.3 | 0.0022 |

*P values were determined by log-rank test.

EXPERIMENTAL PROTOCOLS

I. Murine C. difficile Toxin Model
(a) C. difficile Culture

An overnight culture of C. difficile strain VPI 10463 (American Type Culture Collection) was grown at 37° C. in Brain-Heart Infusion (BHI) broth using the GasPak EZ Anaerobe Pouch System (Becton Dickinson). 2 mL of the culture was added to 28 mL of phosphate buffered saline (PBS) in a gamma-irradiated, 10,000 molecular weight cut-off, 30-70 ml Slide-A-Lyzer G2 dialysis cassette (Pierce). This cassette was submerged in 1 L of BHI broth in a 2 L beaker and incubated under anaerobic conditions for 5 days at 37° C. The culture was then transferred to a 50 mL conical tube and the cassette was washed with 10 mL of PBS. The combined culture and wash were centrifuged at 2,000 g for 20 minutes to pellet the bacteria and the supernatant was filtered through a 0.2 μm syringe filter. The filtrate was then applied to a 20 mL 150 K molecular weight cut-off concentration column (Pierce) and centrifuged at 2,000 g for 15 minutes. Concentrated supernatant was stored at 4° C.

(b) ELISA for C. difficile Toxin

Concentration of TcdA and TcdB in the concentrated supernatant was determined by ELISA (tgcBiOMICS GmbH catalog # TGC E002-1) as per the manufacturer's instructions. This ELISA uses an antibody that recognizes both TcdA and TcdB to capture the toxin from the sample, which can then be separately detected and quantified by anti-TcdA or anti-TcdB antibodies conjugated to horseradish peroxidase. Addition of a colorimetric substrate (tetramethylbenzidine) generates a yellow color that can be measured spectrophometrically. Quantification is performed by comparing sample values to a standard curve generated by using purified TcdA or TcdB.

(c) Murine Intrarectal C. difficile Toxin Model

We used a variation of an established intrarectal C. difficile intoxication model (Hirota, Iablokov et al. 2012). Female C57BL/6 mice (~10 weeks old and weighing ~20 g) were used. 12.5 μg of isolated toxin (~1:1 ratio of TcdA: TcdB) was diluted in a volume of 100 mL of PBS and administered intrarectally using a feeding needle. When experimental compounds were co-administered intrarectally, the toxin dose was diluted into 50 μl of PBS and mixed with a 50 μl suspension of compound (5 mg/mL) in 1% carboxymethyl cellulose and 0.5% Tween 80. When compounds were dosed orally or intraperitoneally, they were prepared as 5 mg/mL solutions in 20% PEG-400, 0.4% carboxymethyl cellulose and 0.2% Tween 80 and administered at a dose of 10 mL/kg for a final dose of 25 mg/kg body weight.

(d) Colon Length Studies:

Animals were euthanized four (4) hours after toxin and compound administration. Colons were excised and measured for length excluding the cecum. Normal mice have a colon length of ~9 cm.

(e) IL-1l1 and MPO Studies:

Excised and washed colon tissues were stored at −70° C. until processing. Colons were thawed and homogenized in 500 μl lysis buffer (150 mM NaCl, 20 mM Tris pH 7.5, 1 mM EDTA, 1 mM EGTA, 1% Triton X-100 with 1 protease inhibitor tab/26 mL of buffer) using NAVY beads in Snap-Cap Eppendorf tubes (Next Advance) for 1 minute in a Bullet Blender (Next Advance) set to speed 10. After homogenization, samples were centrifuged at ~14,000 g at 4° C. for 20 minutes, and 200 μl of supernatant was transferred to a pre-chilled microcentrifuge tube and stored at −80° C. until analyzed.

(f) ELISA for IL-1β and MPO:

ELISA was used to quantify the presence of interleukin-1-β (IL-1β) (R & D Systems catalog # DY401) and myeloperoxidase (MPO) (R&D Systems catalog # DY3667) as per the manufacturer's instructions described above.

(g) Histopathology Analysis:

Colon sections were fixed in 10% neutral buffered formalin. After fixation, tissues samples were taken and embedded in paraffin wax. Each paraffin tissue block was cut into 4 μm thick sections, placed on glass slides and stained with haematoxylin eosin(H&E stain). All completed slides for this project were reviewed by a trained pathologist using Nikon Eclipse 50i microscope. The slides were examined under high and low power (100× and 400×), and the histologic characteristics, such as epithelial disintegration, neutrophil influx and submucosal edema, were documented by the pathologist.

(h) Determination of Plasma Concentrations of Anti-Toxin Compounds:

To determine plasma concentration of compounds, blood (~200 μl) was drawn by retro-orbital bleed, and compound concentration was determined by liquid chromatography (LC)/mass spectrometry (MS)(AB Sciex API-3000 LC/MS/MS system).

II. Acute Murine C. difficile Infection Model

C. difficile strain VPI 10463 was grown for four (4) days in 10 ml of BHI in a Bactron anaerobic workstation (Shel Lab). The culture was centrifuged at 2,700 g for 10 minutes. The bacterial pellet was washed with 10 mL of PBS and the centrifugation was repeated. The pellet was then re-suspended in 10 mL of PBS, incubated at 56° C. for 10 minutes, and then was frozen at −20° C. until used. Titers of spore stocks were determined by serial dilution and plating onto BHI and with 1% taurocholate and counting of colonies after incubation for 24 hours at 37° C. using the GasPak EZ Anaerobe Pouch System.

We utilized an established C. difficile murine infection model (Chen, Katchar et al. 2008). To render them susceptible to infection, female C57BL/6 mice (~10 weeks old and weighing ~20 g) were administered the following antibiotics (Sigma Aldrich) in drinking water for 3 days (Days −6 to −3): colistin (0.042 units/mL), gentamicin (0.035 mg/mL), kanamycin (0.4 mg/mL), metronidazole (0.215 mg/mL) and vancomycin (0.045 mg/mL). Based upon an expected water consumption of 100 mL/kg/day, the approximate doses of these antibiotics will be as follows: colistin (4.2 units/kg/day), gentamicin (3.5 mg/kg/day), kanamycin (40 mg/kg/ day), metronidazole (21.5 mg/kg/day) and vancomycin (4.5 mg/kg/day). The animals were provided with regular drinking water for two days (Day −2 and Day −1), and the next day (Day 0) they were administered clindamycin phosphate (1 mg/mL solution in PBS) at 10 mL/kg by intraperitoneal injection, for a final dose of 10 mg/kg body weight. The following day (Day 1), they were orally gavaged with ~100 spores in a 0.5 ml volume.

Compounds were administered beginning ~8 hours after infection, and the animals were dosed twice per day for two days (Days 2-3) with a total of four doses. Compounds were prepared as 5 mg/mL suspensions in 20% PEG-400, 0.4% carboxymethyl cellulose and 0.2% Tween 80 and administered at a dose of 10 mL/kg, for a final dose of 50 mg/kg body weight.

Animals were observed and weighed two (2) to (3) times daily. Animals that were obviously moribund or had lost >20% of their initial body weight were euthanized. Subgroups of animals were euthanized four (4) hours after the final compound dose (52 hours after infection). Colons were removed, stored, processed and analyzed as described above for the murine C. difficile toxin model.

III. Relapsing Murine Infection Model

The relapsing murine infection model was identical to the acute murine infection model except that it included a group of animals treated with vancomycin administered by oral gavage, 10 mL/kg of a 2 mg/mL solution, for a final dose of 20 mg/kg body weight, once per day.

Animals were observed and weighed two (2) to three (3) times daily. Animals that were obviously moribund or had lost >20% of their initial body weight were euthanized. Animals were observed for a total of nine (9) days after infection.

IV. Hamster Infection Model

We utilized an established C. difficile hamster infection model (Sambol, Tang et al. 2001). Female Golden Syrian hamsters (~6 weeks old and weighing ~100 g) were administered clindamycin phosphate (3 mg/mL in water) by oral gavages at a dose of 10 mL/kg of body weight, for a final dose of 30 mg/kg body weight 5 days prior to infection (Day −4). After five days, 100 spores (0.5 ml of a 200 spore/ml suspension) of C. difficile strain 630 (American Type Culture Collection), prepared using the culture methodology as described for the murine infection model, were administered by oral gavages (Day 1). This strain was utilized as it reported to cause death in three (3) days rather than two (2) days as was the case with other strains (Razaq, Sambol et al. 2007), and provided a longer opportunity to treat with anti-toxin compounds.

Animals were dosed with compound beginning ~8 hours after infection by oral gavages with a 10 mL/kg body weight dose of a 5 mg/mL suspension in 20% PEG-400, 0.4% carboxymethyl cellulose and 0.2% Tween 80, for a final dose of 50 mg/kg body weight. Animals were dosed twice daily for 7 days (Days 1-7) for a total of 14 doses. Vancomycin was administered by oral gavages with 10 mL/kg body weight with a 0.5 mg/mL solution for a final dose of 5 mg/kg body weight, twice per day for 5 days (Days 1-5). Animals were observed and weighed twice daily for a total of fourteen (14) days after infection.

All references to the literature and all patents mentioned in this specification are incorporated herein by reference in their entirety. The present invention is not to be limited in terms of the particular embodiments described in this application, which are intended as single illustrations of individual aspects of the present invention. Functionally equivalent pharmaceutical compositions and methods of treatment within the scope of the present invention, in addition to those enumerated herein, will be apparent to those skilled in the art from the foregoing description. Such modifications and variations are intended to fall within the scope of the appended claims.

What is claimed is:

1. A compound of formula (I)

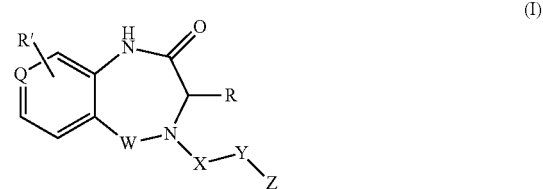

or a pharmaceutically acceptable salt thereof, wherein:

Q is CH or N;

R' is H, halogen, $C_{1-6}$alkyl, $C_{1-6}$alkoxy, CN, $NO_2$, $NH_2$, $NHS(O)_2C_{1-6}$alkyl, $NHC(O)C_{1-6}$alkyl, $NHC(O)C_{1-6}$alkyl$OC_{1-6}$alkyl, NHC(O)-isoxazolyl or NHC(O)-pyridyl, wherein isoxazoly and pyridyl are each optionally mono- or di-substituted with $C_{1-3}$alkyl, and alkyl is optionally substituted with 1-4 halogen;

W is C(O) or $CH_2$;

X is $CH_2$, $CH(C_{1-3}$alkyl), $C_{3-6}$cycloalkyl, C(O) or $S(O)_2$, and when W is C(O), X cannot be C(O) or $S(O)_2$;

Y is

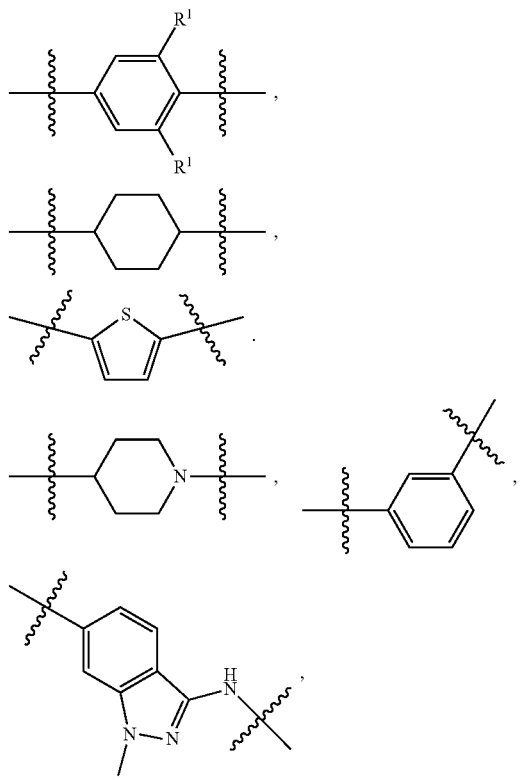

361

-continued

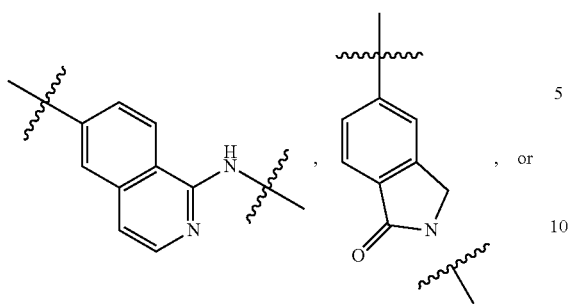

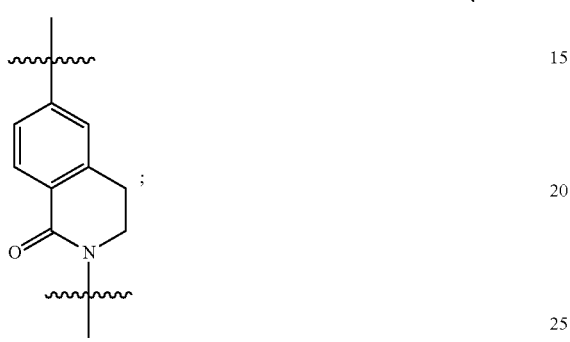

Z is CH₂OH, NH₂, C(O)OH, $R^6$,

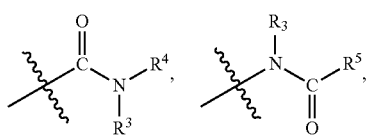

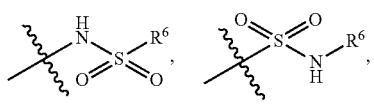

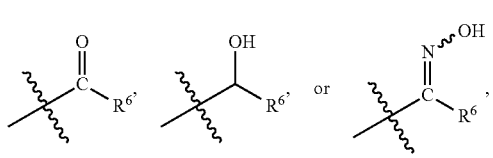

provided that only when Y is

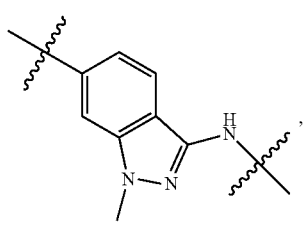

362

-continued

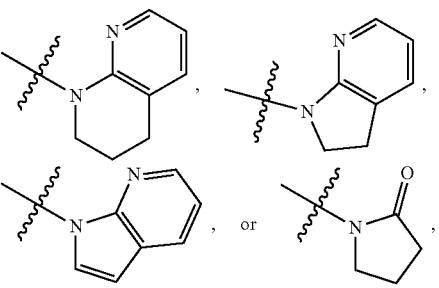

Z is $R^6$;

R is H, $C_{1-6}$alkyl, $C_{1-6}$alkyl-OH, $C_{1-6}$alkyl-N($C_{1-6}$alkyl)$C_{1-6}$alkyl or $C_{0-3}$alkyl-$R^7$;

each $R^1$ is independently H, $C_{1-6}$alkyl, $C_{1-6}$alkoxy, halogen, NH₂, phenyl, pyridyl, pyrazolyl, isoxazolyl, $OC_{1-6}$alkyl-phenyl, benzodioxolyl or NHC(O)$C_{0-3}$alkyl-$R^2$, wherein phenyl, pyridyl, pyrazolyl and isoxazolyl are each optionally mono- or di-substituted with substituents independently selected from $C_{1-3}$alkyl, halogen, $C_{1-3}$alkoxy, C(O)NH$C_{1-3}$ alkyl and NHC(O)$C_{1-3}$ alkyl, and alkyl is optionally substituted with 1-4 halogen;

$R^2$ is OH, $C_{1-6}$alkyl, $C_{1-6}$ alkoxy, N($C_{1-6}$ alkyl)$C_{1-6}$ alkyl, morpholinyl, pyrrolidinyl, piperidinyl, piperizinyl, tetrahydropyranyl, cyclohexyl or pyridyl, wherein morpholinyl, pyrrolidinyl, piperidinyl, piperizinyl, tetrahydropyranyl, cyclohexyl and pyridyl are each optionally mono- or di-substituted with $C_{1-3}$ alkyl, and alkyl is optionally substituted with 1-4 halogen;

$R^3$ is H or $C_{1-6}$alkyl;

$R^4$ is H, OH, $C_{1-6}$alkyl, C(O)$C_{1-6}$alkyl, C(NOH)$C_{1-6}$alkyl, S(O)₂$C_{1-6}$alkyl, S(O)₂-phenyl, or $R^6$, wherein phenyl is optionally mono- or di-substituted with substituents independently selected from halogen, $C_{1-3}$alkyl and $C_{1-3}$alkoxy, and alkyl is optionally substituted with 1-4 halogen;

or $R^3$ and $R^4$ together with the N to which they are attached form:

each optionally mono-, di-, or tri-substituted with substituents independently selected from halogen and $C_{1-3}$alkyl, wherein alkyl is optionally substituted with 1-4 halogen;

$R^5$ is $C_{1-6}$alkyl-SH, $C_{1-6}$alkyl-OH, $C_{1-6}$alkylO$C_{1-6}$alkyl or $R^6$;

or $R^3$, $R^5$ together with the N and C(O) to which they are respectively attached form:

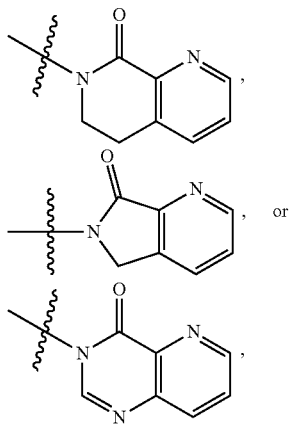

each optionally mono- or di-substituted with $C_1$-3alkyl, wherein alkyl is optionally substituted with 1-4 halogen;

$R^6$ is

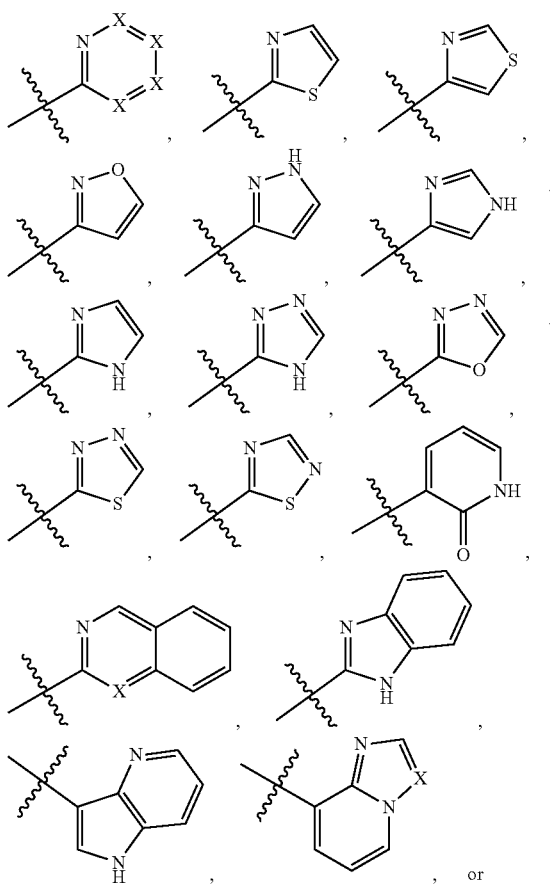

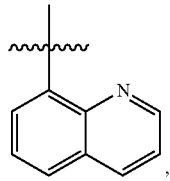

each optionally mono- or di-substituted with substituents independently selected from $C_{1-3}$alkyl, $C_{1-3}$alkoxy, halogen, CN, NH$_2$, S(O)$_2C_{1-3}$alkyl, phenyl, morpholinyl, piperidinyl and piperazinyl, wherein piperidinyl and piperazinyl are each optionally substituted with $C_{1-3}$alkyl and tert-butyloxycarbonyl, and alkyl is optionally substituted with 1-4 halogen;

$R^7$ is

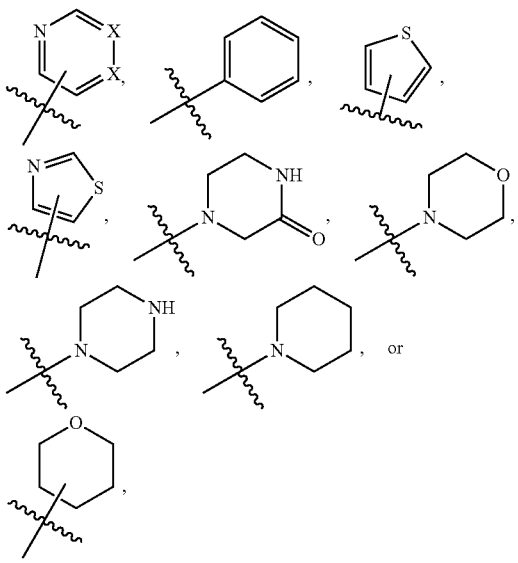

each optionally mono- or di-substituted with substituents independently selected from $C_{1-3}$alkyl, $C_{1-3}$alkoxy, halogen, CN, and OH, and alkyl is optionally substituted with 1-4 halogen; and X is CH or N, and no more one X can be N.

2. The compound of claim 1, or a pharmaceutically acceptable salt thereof, wherein Q is CH.

3. The compound of claim 2, or a pharmaceutically acceptable salt thereof, wherein:

W is C(O); and

X is CH$_2$, CH($C_{1-3}$alkyl) or $C_{3-6}$cycloalkyl.

4. The compound of claim 2, or a pharmaceutically acceptable salt thereof, wherein Y is

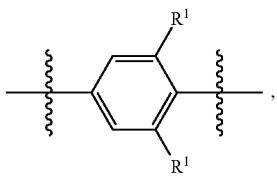

-continued

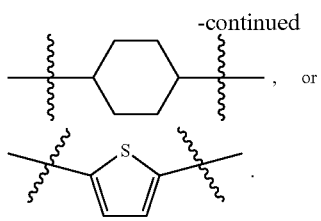 , or

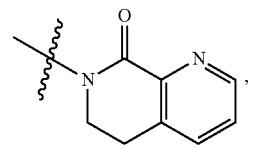 ,

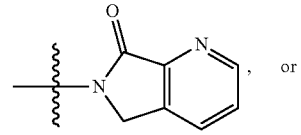 , or

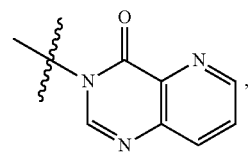 ,

5. The compound of claim 4, or a pharmaceutically acceptable salt thereof, wherein:

R' is halogen, $C_{1-6}$alkyl, $C_{1-6}$alkoxy, CN, $NO_2$ or $NH_2$, wherein alkyl is optionally substituted with 1-4 halogen;

Z is C(O)OH,

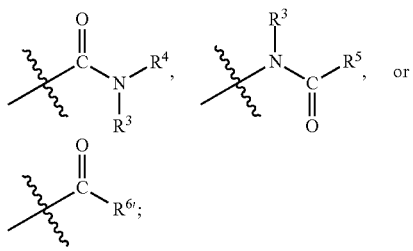 , or and

R is H, $C_{1-6}$alkyl, $C_{1-6}$alkyl-OH or $CH_2$—$R^7$.

6. The compound of claim 5, or a pharmaceutically acceptable salt thereof, wherein:

R' is halogen, $C_{1-3}$alkyl, $C_{1-3}$alkoxy, CN or $NO_2$;

R is H, $C_{1-3}$alkyl, $C_{1-3}$alkyl-OH or $CH_2$—$R^7$;

each $R^1$ is independently H, $C_{1-3}$alkyl, $C_{1-3}$alkoxy, halogen, phenyl or benzodioxolyl, wherein phenyl is optionally mono- or di-substituted with substituents independently selected from $C_{1-3}$alkyl, halogen, $C_{1-3}$alkoxy;

$R^3$ is H or $C_{1-3}$alkyl;

$R^4$ is H, OH, C(O)$C_{1-3}$alkyl or $R^6$;

or $R^3$ and $R^4$ together with the N to which they are attached form:

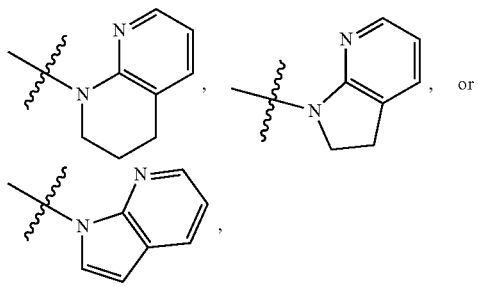

each optionally mono-, di- or tri-substituted with substituents independently selected from halogen and $C_1$-3alkyl, wherein alkyl is optionally substituted with 1-4 halogen;

$R^5$ is $R^6$;

or $R^3$, $R^5$ together with the N and C(O) to which they are respectively attached form:

each optionally mono- or di-substituted with $C_{1-3}$alkyl, wherein alkyl is optionally substituted with 1-4 halogen;

$R^7$ is

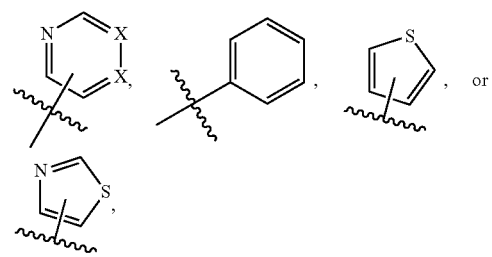

each optionally mono- or di-substituted with substituents independently selected from $C_{1-3}$alkyl, $C_{1-3}$alkoxy, halogen, CN, and OH, wherein alkyl is optionally substituted with 1-4 halogen.

7. The compound of claim 4, or a pharmaceutically acceptable salt thereof, wherein:

R' is Cl, Br, $OCH_3$, CN or $NO_2$;

W is C(O);

X is $CH_2$ or $CH(CH_3)$;

Y is

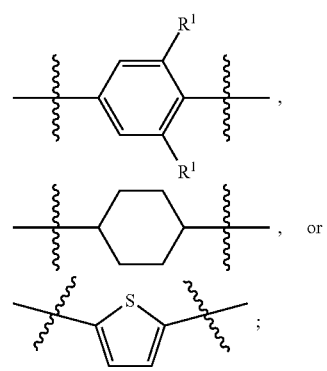

Z is C(O)OH,

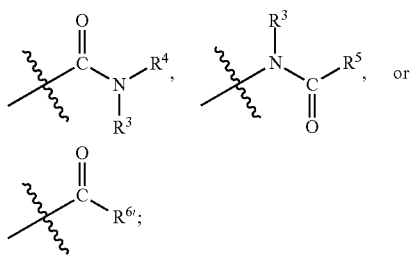

R is H, CH$_3$, CH(CH$_3$)$_2$ or CH$_2$—R$^7$;
each R$^1$ is independently H, CH$_3$, OCH$_3$, halogen, phenyl or benzodioxolyl, wherein phenyl is optionally mono- or di-substituted with substituents independently selected from CH$_3$, OCH$_3$ and halogen;
R$^3$ is H;
R$^4$ is OH, C(O)CH$_3$ or R$^6$;
or R$^3$ and R$^4$ together with the N to which they are attached form:

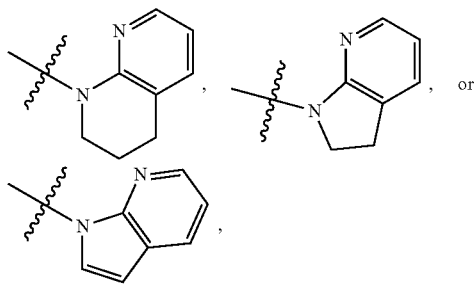

each optionally mono-, di- or tri-substituted with substituents independently selected from CH$_3$ and CF$_3$;
R$^5$ is R$^6$;
or R$^3$, R$^5$ together with the N and C(O) to which they are respectively attached form:

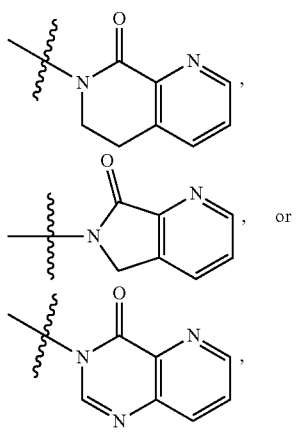

each optionally mono- or di-substituted with CH$_3$ and CF$_3$;

R$^7$ is

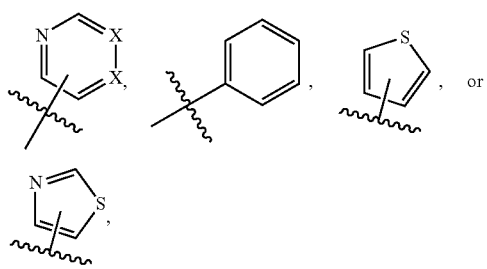

each optionally mono- or di-substituted with substituents independently selected from CH$_3$, CF$_3$, OCH$_3$, halogen and CN.

8. The compound of claim 1, or a pharmaceutically acceptable salt thereof, wherein R is other than H, and the carbon to which R is attached is of the configuration shown:

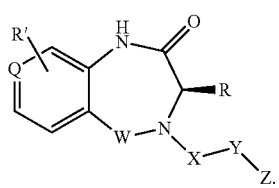

9. The compound of claim 2, or a pharmaceutically acceptable salt thereof, wherein:

W is CH$_2$; and

X is S(O)$_2$, C(O) or CH$_2$.

10. The compound of claim 9, or a pharmaceutically acceptable salt thereof, wherein X is S(O)$_2$.

11. The compound of claim 2, or a pharmaceutically acceptable salt thereof, wherein Y is

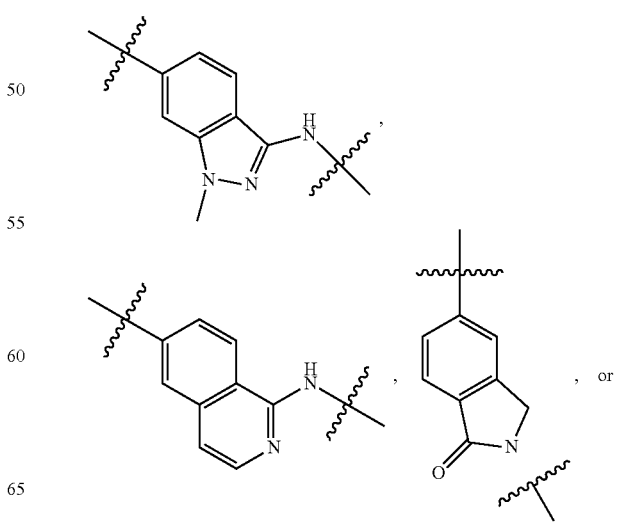

-continued

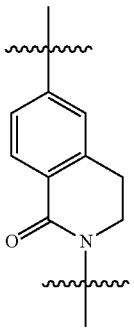

12. The compound of claim 11, or a pharmaceutically acceptable salt thereof, wherein:
R' is Cl, Br, OCH₃, CN or NO₂;
W is C(O);
X is CH₂ or CH(CH₃);
Z is R⁶;
R is H, CH₃, CH(CH₃)₂ or CH₂—R⁷;
R⁶ is

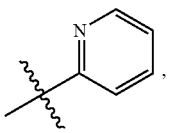 [SMILES: *c1ccccn1]

optionally mono- or di-substituted with substituents independently selected from C$_{1-3}$alkyl, C$_{1-3}$alkoxy, halogen, CN and NH₂, wherein alkyl is optionally substituted with 1-4 halogen.

13. A compound of claim 1 selected from the group consisting of:
1) (R)-4-((8-Chloro-2,5-dioxo-3-(pyridin-2-ylmethyl)-2,3-dihydro-1H-benzo[e][1,4]diazepin-4(5H)-yl)methyl)benzoic acid;
2) (R)-4-((8-fluoro-2,5-dioxo-3-(pyridin-3-ylmethyl)-2,3-dihydro-1H-benzo[e][1,4]diazepin-4(5H)-yl)methyl)benzoic acid;
3) (R)-4-((8-chloro-2,5-dioxo-3-(pyridin-4-ylmethyl)-2,3-dihydro-1H-benzo[e][1,4]diazepin-4(5H)-yl)methyl)benzoic acid;
4) (R)-4-((8-chloro-3-(3,4-dichlorobenzyl)-2,5-dioxo-2,3-dihydro-1H-benzo[e][1,4]diazepin-4(5H)-yl)methyl)benzoic acid;
5) (R)-4-((3-(3,4-dichlorobenzyl)-8-methyl-2,5-dioxo-2,3-dihydro-1H-benzo[e][1,4]diazepin-4(5H)-yl)methyl)benzoic acid;
6) (S)-4-((8-chloro-2,5-dioxo-3-(pyridin-2-ylmethyl)-2,3-dihydro-1H-benzo[e][1,4]diazepin-4(5H)-yl)methyl)benzoic acid;
7) (R)-4-((8-bromo-2,5-dioxo-3-(pyridin-3-ylmethyl)-2,3-dihydro-1H-benzo[e][1,4]diazepin-4(5H)-yl)methyl)benzoic acid;
8) (R)-5-((8-chloro-2,5-dioxo-3-(pyridin-2-ylmethyl)-2,3-dihydro-1H-benzo[e][1,4]diazepin-4(5H)-yl)methyl)thiophene-2-carboxylic acid;
9) (R)-4-((8-chloro-2,5-dioxo-3-(pyridin-2-ylmethyl)-2,3-dihydro-1H-benzo[e][1,4]diazepin-4(5H)-yl)methyl)-2-fluorobenzoic acid;
10) (1R,4r)-4-(((R)-8-chloro-2,5-dioxo-3-(pyridin-2-ylmethyl)-2,3-dihydro-1H-benzo[e][1,4]diazepin-4(5H)-yl)methyl)cyclohexanecarboxylic acid;
11) (R)-4-((8-chloro-2,5-dioxo-3-(thiophen-2-ylmethyl)-2,3-dihydro-1H-benzo[e][1,4]diazepin-4(5H)-yl)methyl)benzoic acid;
12) 4-((8-chloro-2,5-dioxo-3-(pyrazin-2-ylmethyl)-2,3-dihydro-1H-benzo[e][1,4]diazepin-4(5H)-yl)methyl)benzoic acid;
13) (R)-4-((8-chloro-2,5-dioxo-3-(thiazol-4-ylmethyl)-2,3-dihydro-1H-benzo[e][1,4]diazepin-4(5H)-yl)methyl)benzoic acid;
14) (R)-2-bromo-4-((8-chloro-3-methyl-2,5-dioxo-2,3-dihydro-1H-benzo[e][1,4]diazepin-4(5H)-yl)methyl)benzoic acid;
15) (R)-4-((8-Chloro-2,5-dioxo-3-(pyridin-3-ylmethyl)-2,3-dihydro-1H-benzo[e][1,4]diazepin-4(5H)-yl)methyl)benzoic acid;
16) (S)-4-((8-chloro-3-(3,4-dichlorobenzyl)-2,5-dioxo-2,3-dihydro-1H-benzo[e][1,4]diazepin-4(5H)-yl)methyl)benzoic acid;
17) (S)-4-((8-chloro-3-(4-hydroxybenzyl)-2,5-dioxo-2,3-dihydro-1H-benzo[e][1,4]diazepin-4(5H)-yl)methyl)benzoic acid;
18) (R)-4-((8-chloro-3-(4-hydroxybenzyl)-2,5-dioxo-2,3-dihydro-1H-benzo[e][1,4]diazepin-4(5H)-yl)methyl)benzoic acid;
19) (R)-4-((8-methoxy-2,5-dioxo-3-(pyridin-3-ylmethyl)-2,3-dihydro-1H-benzo[e][1,4]diazepin-4(5H)-yl)methyl)benzoic acid;
20) (R)-4-((3-(3,4-dichlorobenzyl)-8-methoxy-2,5-dioxo-2,3-dihydro-1H-benzo[e][1,4]diazepin-4(5H)-yl)methyl)benzoic acid;
21) (R)-4-((3-(3,4-dichlorobenzyl)-8-fluoro-2,5-dioxo-2,3-dihydro-1H-benzo[e][1,4]diazepin-4(5H)-yl)methyl)benzoic acid;
22) (R)-4-((3-(3,4-dichlorobenzyl)-8-nitro-2,5-dioxo-2,3-dihydro-1H-benzo[e][1,4]diazepin-4(5H)-yl)methyl)benzoic acid;
23) (R)-4-((8-nitro-2,5-dioxo-3-(pyridin-3-ylmethyl)-2,3-dihydro-1H-benzo[e][1,4]diazepin-4(5H)-yl)methyl)benzoic acid;
24) (R)-4-((3-Benzyl-8-chloro-2,5-dioxo-2,3-dihydro-1H-benzo[e][1,4]diazepin-4(5H)-yl)methyl)benzoic acid;
25) (S)-4-((8-chloro-3-methyl-2,5-dioxo-2,3-dihydro-1H-benzo[e][1,4]diazepin-4(5H)-yl)methyl)benzoic acid;
26) (R)-4-((8-chloro-2,5-dioxo-3-phenethyl-2,3-dihydro-1H-benzo[e][1,4]diazepin-4(5H)-yl)methyl)benzoic acid;
27) (R)-4-((8-chloro-3-(4-fluorobenzyl)-2,5-dioxo-2,3-dihydro-1H-benzo[e][1,4]diazepin-4(5H)-yl)methyl)benzoic acid;
28) (R)-4-((8-chloro-3-(4-chlorobenzyl)-2,5-dioxo-2,3-dihydro-1H-benzo[e][1,4]diazepin-4(5H)-yl)methyl)benzoic acid;
29) (R)-4-((8-chloro-3-(3-chlorobenzyl)-2,5-dioxo-2,3-dihydro-1H-benzo[e][1,4]diazepin-4(5H)-yl)methyl)benzoic acid;
30) (R)-4-((8-chloro-3-methyl-2,5-dioxo-2,3-dihydro-1H-benzo[e][1,4]diazepin-4(5H)-yl)methyl)benzoic acid;
31) (R)-4-((8-chloro-3-(4-methylbenzyl)-2,5-dioxo-2,3-dihydro-1H-benzo[e][1,4]diazepin-4(5H)-yl)methyl)benzoic acid;
32) (R)-4-((8-chloro-3-(2-chlorobenzyl)-2,5-dioxo-2,3-dihydro-1H-benzo[e][1,4]diazepin-4(5H)-yl)methyl)benzoic acid;

33) (R)-4-((8-chloro-3-(2-fluorobenzyl)-2,5-dioxo-2,3-dihydro-1H-benzo[e][1,4]diazepin-4(5H)-yl)methyl)benzoic acid;

34) (R)-4-((8-chloro-3-isopropyl-2,5-dioxo-2,3-dihydro-1H-benzo[e][1,4]diazepin-4(5H)-yl)methyl)benzoic acid;

35) (R)-4-((8-chloro-3-(2-methylbenzyl)-2,5-dioxo-2,3-dihydro-1H-benzo[e][1,4]diazepin-4(5H)-yl)methyl)benzoic acid;

36) (R)-4-((8-chloro-3-(3-methylbenzyl)-2,5-dioxo-2,3-dihydro-1H-benzo[e][1,4]diazepin-4(5H)-yl)methyl)benzoic acid;

37) (R)-4-((8-chloro-3-(3-cyanobenzyl)-2,5-dioxo-2,3-dihydro-1H-benzo[e][1,4]diazepin-4(5H)-yl)methyl)benzoic acid;

38) 4-((8-chloro-2,5-dioxo-2,3-dihydro-1H-benzo[e][1,4]diazepin-4(5H)-yl)methyl)benzoic acid;

39) (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide;

40) (R)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide;

41) (R)-4-((8-chloro-2,5-dioxo-3-(pyridin-3-ylmethyl)-2,3-dihydro-1H-benzo[e][1,4]diazepin-4(5H)-yl)methyl)-N-(thiazol-2-yl)benzamide;

42) (R)-4-((8-chloro-2,5-dioxo-3-(pyridin-3-ylmethyl)-2,3-dihydro-1H-benzo[e][1,4]diazepin-4(5H)-yl)methyl)-N-(1-methyl-1H-pyrazol-3-yl)benzamide;

43) (R)-4-((8-chloro-2,5-dioxo-3-(pyridin-3-ylmethyl)-2,3-dihydro-1H-benzo[e][1,4]diazepin-4(5H)-yl)methyl)-N-(5-methylisoxazol-3-yl)benzamide;

44) (S)-4-((8-chloro-3-methyl-2,5-dioxo-2,3-dihydro-1H-benzo[e][1,4]diazepin-4(5H)-yl)methyl)-N-(pyridin-2-yl)benzamide;

45) (R)-4-((8-chloro-2,5-dioxo-3-phenethyl-2,3-dihydro-1H-benzo[e][1,4]diazepin-4(5H)-yl)methyl)-N-(pyridin-2-yl)benzamide;

46) (R)-4-((3-benzyl-8-chloro-2,5-dioxo-2,3-dihydro-1H-benzo[e][1,4]diazepin-4(5H)-yl)methyl)-N-(pyridin-2-yl)benzamide;

47) (R)-4-((8-chloro-3-(4-fluorobenzyl)-2,5-dioxo-2,3-dihydro-1H-benzo[e][1,4]diazepin-4(5H)-yl)methyl)-N-(pyridin-2-yl)benzamide;

48) (R)-4-((8-chloro-3-(4-chlorobenzyl)-2,5-dioxo-2,3-dihydro-1H-benzo[e][1,4]diazepin-4(5H)-yl)methyl)-N-(pyridin-2-yl)benzamide;

49) (R)-4-((8-chloro-2,5-dioxo-3-(pyridin-3-ylmethyl)-2,3-dihydro-1H-benzo[e][1,4]diazepin-4(5H)-yl)methyl)-N-(3-methylpyridin-2-yl)benzamide;

50) (R)-4-((3-(3,4-dichlorobenzyl)-8-methoxy-2,5-dioxo-2,3-dihydro-1H-benzo[e][1,4]diazepin-4(5H)-yl)methyl)-N-(pyridin-2-yl)benzamide;

51) (R)-4-((8-chloro-2,5-dioxo-3-(pyridin-3-ylmethyl)-2,3-dihydro-1H-benzo[e][1,4]diazepin-4(5H)-yl)methyl)-N-methyl-N-(pyridin-2-yl)benzamide;

52) (R)-4-((8-chloro-2,5-dioxo-3-(pyridin-3-ylmethyl)-2,3-dihydro-1H-benzo[e][1,4]diazepin-4(5H)-yl)methyl)-N-(5-methylpyridin-2-yl)benzamide;

53) (R)-4-((8-chloro-2,5-dioxo-3-(pyridin-3-ylmethyl)-2,3-dihydro-1H-benzo[e][1,4]diazepin-4(5H)-yl)methyl)-N-(6-methylpyridin-2-yl)benzamide;

54) (R)-4-((8-methoxy-2,5-dioxo-3-(pyridin-3-ylmethyl)-2,3-dihydro-1H-benzo[e][1,4]diazepin-4(5H)-yl)methyl)-N-(pyridin-2-yl)benzamide;

55) (R)-4-((3-(3,4-dichlorobenzyl)-8-fluoro-2,5-dioxo-2,3-dihydro-1H-benzo[e][1,4]diazepin-4(5H)-yl)methyl)-N-(pyridin-2-yl)benzamide;

56) (R)-4-((8-chloro-2,5-dioxo-3-(pyridin-3-ylmethyl)-2,3-dihydro-1H-benzo[e][1,4]diazepin-4(5H)-yl)methyl)-N-(4-chloropyridin-2-yl)benzamide;

57) (R)-4-((8-chloro-2,5-dioxo-3-(pyridin-3-ylmethyl)-2,3-dihydro-1H-benzo[e][1,4]diazepin-4(5H)-yl)methyl)-N-(4-methylpyridin-2-yl)benzamide;

58) (R)-4-((8-chloro-2,5-dioxo-3-(pyridin-3-ylmethyl)-2,3-dihydro-1H-benzo[e][1,4]diazepin-4(5H)-yl)methyl)-N-(pyrimidin-4-yl)benzamide;

59) (R)-4-((8-chloro-2,5-dioxo-3-(pyridin-4-ylmethyl)-2,3-dihydro-1H-benzo[e][1,4]diazepin-4(5H)-yl)methyl)-N-(pyridin-2-yl)benzamide;

60) (R)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide;

61) (R)-4-((8-chloro-3-(2-chlorobenzyl)-2,5-dioxo-2,3-dihydro-1H-benzo[e][1,4]diazepin-4(5H)-yl)methyl)-N-(pyridin-2-yl)benzamide;

62) (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide;

63) (R)-8-chloro-4-(4-(2,3-dihydro-1H-pyrrolo[2,3-b]pyridine-1-carbonyl)benzyl)-3-methyl-3,4-dihydro-1H-benzo[e][1,4]diazepine-2,5-dione;

64) (R)-4-((8-chloro-3-methyl-2,5-dioxo-2,3-dihydro-1H-benzo[e][1,4]diazepin-4(5H)-yl)methyl)-N-(pyridin-2-yl)benzamide;

65) (R)-4-((8-chloro-3-(3-chlorobenzyl)-2,5-dioxo-2,3-dihydro-1H-benzo[e][1,4]diazepin-4(5H)-yl)methyl)-N-(pyridin-2-yl)benzamide;

66) (R)-8-chloro-4-(3-chloro-4-(1H-pyrrolo[2,3-b]pyridine-1-carbonyl)benzyl)-3-(pyridin-2-ylmethyl)-3,4-dihydro-1H-benzo[e][1,4]diazepine-2,5-dione;

67) (R)-4-((3-(3,4-dichlorobenzyl)-8-methyl-2,5-dioxo-2,3-dihydro-1H-benzo[e][1,4]diazepin-4(5H)-yl)methyl)-N-(pyridin-2-yl)benzamide;

68) (R)-8-chloro-4-(3-chloro-4-(5-methyl-2,3-dihydro-1H-pyrrolo[2,3-b]pyridine-1-carbonyl)benzyl)-3-(pyridine-2-ylmethyl)-3,4-dihydro-1H-benzo[e][1,4]diazepine-2,5-dione;

69) (R)-4-((3-(3,4-dichlorobenzyl)-8-nitro-2,5-dioxo-2,3-dihydro-1H-benzo[e][1,4]diazepin-4(5H)-yl)methyl)-N-(pyridin-2-yl)benzamide;

70) (R)-8-chloro-4-(4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;

71) (R)-8-chloro-3-(pyridin-2-ylmethyl)-4-(4-(1,2,3,4-tetrahydro-1,8-naphthyridine-1-carbonyl)benzyl)-3,4-dihydro-1H-benzo[e][1,4]diazepine-2,5-dione;

72) (R)-8-chloro-4-(4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;

73) (R)-4-((8-chloro-3-(2-methylbenzyl)-2,5-dioxo-2,3-dihydro-1H-benzo[e][1,4]diazepin-4(5H)-yl)methyl)-N-(pyridin-2-yl)benzamide;

74) (R)-4-((8-chloro-3-(3-methylbenzyl)-2,5-dioxo-2,3-dihydro-1H-benzo[e][1,4]diazepin-4(5H)-yl)methyl)-N-(pyridin-2-yl)benzamide;

75) (R)-4-((8-chloro-3-(3-cyanobenzyl)-2,5-dioxo-2,3-dihydro-1H-benzo[e][1,4]diazepin-4(5H)-yl)methyl)-N-(pyridin-2-yl)benzamide;

76) (R)-4-((8-chloro-2,5-dioxo-3-(thiazol-4-ylmethyl)-2,3-dihydro-1H-benzo[e][1,4]diazepin-4(5H)-yl)methyl)-N-(5-methylpyridin-2-yl)benzamide;
77) 4-((8-chloro-2,5-dioxo-2,3-dihydro-1H-benzo[e][1,4]diazepin-4(5H)-yl)methyl)-N-(pyridin-2-yl)benzamide;
78) (R)-4-((8-chloro-3-(2-fluorobenzyl)-2,5-dioxo-2,3-dihydro-1H-benzo[e][1,4]diazepin-4(5H)-yl)methyl)-N-(pyridin-2-yl)benzamide;
79) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide;
80) (R)-4-((8-chloro-2,5-dioxo-3-(pyridin-2-ylmethyl)-2,3-dihydro-1H-benzo[e][1,4]diazepin-4(5H)-yl)methyl)-N-(5-ethylpyridin-2-yl)benzamide;
81) (S)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide;
82) (R)-8-chloro-4-(3-chloro-4-(2,2-dimethyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;
83) (R)-8-chloro-4-(3-chloro-4-(3,3-dimethyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;
84) (R)-4-((8-chloro-2,5-dioxo-3-(pyridin-3-ylmethyl)-2,3-dihydro-1H-benzo[e][1,4]diazepin-4(5H)-yl)methyl)-N-(5-isopropylpyridin-2-yl)benzamide;
85) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-(trifluoromethyl)pyridin-2-yl)benzamide;
86) (R)-4-((8-chloro-2,5-dioxo-3-(pyridin-2-ylmethyl)-2,3-dihydro-1H-benzo[e][1,4]diazepin-4(5H)-yl)methyl)-N-(5-morpholinopyridin-2-yl)benzamide;
87) (R)-tert-butyl 4-(6-(4-((8-chloro-2,5-dioxo-3-(pyridin-2-ylmethyl)-2,3-dihydro-1H-benzo[e][1,4]diazepin-4(5H)-yl)methyl)benzamido)pyridin-3-yl)piperazine-1-carboxylate;
88) (R)-4-((8-chloro-2,5-dioxo-3-(pyridin-2-ylmethyl)-2,3-dihydro-1H-benzo[e][1,4]diazepin-4(5H)-yl)methyl)-N-(5-(4-methylpiperazin-1-yl)pyridin-2-yl)benzamide;
89) (R)-4-((8-chloro-3-methyl-2,5-dioxo-2,3-dihydro-1H-benzo[e][1,4]diazepin-4(5H)-yl)methyl)-N-(5-ethylpyridin-2-yl)benzamide;
90) (R)-4-((8-chloro-3-methyl-2,5-dioxo-2,3-dihydro-1H-benzo[e][1,4]diazepin-4(5H)-yl)methyl)-N-(5-isopropylpyridin-2-yl)benzamide;
91) (R)-4-((8-chloro-3-methyl-2,5-dioxo-2,3-dihydro-1H-benzo[e][1,4]diazepin-4(5H)-yl)methyl)-N-(5-methoxypyridin-2-yl)benzamide;
92) (R)-4-((8-chloro-3-methyl-2,5-dioxo-2,3-dihydro-1H-benzo[e][1,4]diazepin-4(5H)-yl)methyl)-N-(isoquinolin-3-yl)benzamide;
93) (R)-4-((8-chloro-3-methyl-2,5-dioxo-2,3-dihydro-1H-benzo[e][1,4]diazepin-4(5H)-yl)methyl)-N-(5-phenylpyridin-2-yl)benzamide;
94) (R)-4-((8-bromo-2,5-dioxo-3-(pyridin-2-ylmethyl)-2,3-dihydro-1H-benzo[e][1,4]diazepin-4(5H)-yl)methyl)-N-(pyridin-2-yl)benzamide;
95) (R)-4-((8-chloro-3-methyl-2,5-dioxo-2,3-dihydro-1H-benzo[e][1,4]diazepin-4(5H)-yl)methyl)-N-(5-methoxypyrimidin-2-yl)benzamide;
96) (R)-4-((8-chloro-3-methyl-2,5-dioxo-2,3-dihydro-1H-benzo[e][1,4]diazepin-4(5H)-yl)methyl)-N-(5-morpholinopyridin-2-yl)benzamide;
97) (R)-tert-butyl 4-(6-(4-((8-chloro-3-methyl-2,5-dioxo-2,3-dihydro-1H-benzo[e][1,4]diazepin-4(5H)-yl)methyl)benzamido)pyridin-3-yl)piperazine-1-carboxylate;
98) (R)-4-((8-chloro-3-methyl-2,5-dioxo-2,3-dihydro-1H-benzo[e][1,4]diazepin-4(5H)-yl)methyl)-N-(5-(4-methylpiperazin-1-yl)pyridin-2-yl)benzamide;
99) (R)-4-((8-chloro-3-methyl-2,5-dioxo-2,3-dihydro-1H-benzo[e][1,4]diazepin-4(5H)-yl)methyl)-N-(5-methylpyrazin-2-yl)benzamide;
100) (R)-4-((8-chloro-2,5-dioxo-3-(pyridin-2-ylmethyl)-2,3-dihydro-1H-benzo[e][1,4]diazepin-4(5H)-yl)methyl)-N-(5-methyl-4H-1,2,4-triazol-3-yl)benzamide
101) (R)-4-((8-chloro-2,5-dioxo-3-(pyridin-2-ylmethyl)-2,3-dihydro-1H-benzo[e][1,4]diazepin-4(5H)-yl)methyl)-N-(3-methyl-1,2,4-thiadiazol-5-yl)benzamide;
102) (R)-4-((8-chloro-2,5-dioxo-3-(pyridin-2-ylmethyl)-2,3-dihydro-1H-benzo[e][1,4]diazepin-4(5H)-yl)methyl)-N-(pyridazin-3-yl)benzamide;
103) (R)-4-((8-chloro-2,5-dioxo-3-(pyridin-2-ylmethyl)-2,3-dihydro-1H-benzo[e][1,4]diazepin-4(5H)-yl)methyl)-N-(6-methoxypyridazin-3-yl)benzamide;
104) (R)-4-((8-chloro-2,5-dioxo-3-(pyridin-2-ylmethyl)-2,3-dihydro-1H-benzo[e][1,4]diazepin-4(5H)-yl)methyl)-N-(5-methyl-1,3,4-thiadiazol-2-yl)benzamide;
105) (R)-4-((8-chloro-2,5-dioxo-3-(pyridin-2-ylmethyl)-2,3-dihydro-1H-benzo[e][1,4]diazepin-4(5H)-yl)methyl)-N-(5-methyl-1,3,4-oxadiazol-2-yl)benzamide;
106) (R)-4-((8-chloro-2,5-dioxo-3-(pyridin-2-ylmethyl)-2,3-dihydro-1H-benzo[e][1,4]diazepin-4(5H)-yl)methyl)-N-(1,3,4-thiadiazol-2-yl)benzamide;
107) (R)-5-((8-chloro-2,5-dioxo-3-(pyridin-2-ylmethyl)-2,3-dihydro-1H-benzo[e][1,4]diazepin-4(5H)-yl)methyl)-N-(pyridin-2-yl)thiophene-2-carboxamide;
108) (R)-5-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)thiophene-2-carboxamide;
109) (R)-5-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)thiophene-2-carboxamide;
110) (R)-5-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)thiophene-2-carboxamide;
111) 4-((8-chloro-2,5-dioxo-3-(pyrazin-2-ylmethyl)-2,3-dihydro-1H-benzo[e][1,4]diazepin-4(5H)-yl)methyl)-N-(pyridin-2-yl)benzamide;
112) (R)-4-((8-chloro-2,5-dioxo-3-(pyridin-3-ylmethyl)-2,3-dihydro-1H-benzo[e][1,4]diazepin-4(5H)-yl)methyl)-N-(1-(hydroxyimino)ethyl)benzamide;
113) (R)-4-((8-chloro-2,5-dioxo-3-(pyridin-2-ylmethyl)-2,3-dihydro-1H-benzo[e][1,4]diazepin-4(5H)-yl)methyl)-N-(5-methylthiazol-2-yl)benzamide;
114) (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)cyclohexanecarboxamide;
115) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide;

116) (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)cyclohexanecarboxamide;
117) (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)cyclohexanecarboxamide;
118) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide;
119) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylthiazol-2-yl)benzamide;
120) (R)-8-chloro-4-(3-chloro-4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;
121) (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)cyclohexanecarboxamide;
122) (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)cyclohexanecarboxamide;
123) (R)-8-chloro-4-(((1r,4R)-4-(2,3-dihydro-1H-pyrrolo[2,3-b]pyridine-1-carbonyl)cyclohexyl)methyl)-3-(pyridin-2-ylmethyl)-3,4-dihydro-1H-benzo[e][1,4]diazepine-2,5-dione;
124) (R)-8-chloro-3-(pyridin-2-ylmethyl)-4-(((1r,4R)-4-(1,2,3,4-tetrahydro-1,8-naphthyridine-1-carbonyl)cyclohexyl)methyl)-3,4-dihydro-1H-benzo[e][1,4]diazepine-2,5-dione;
125) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide;
126) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide;
127) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyridin-2-yl)benzamide;
128) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)-2-methylbenzamide;
129) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyridin-2-yl)benzamide;
130) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyridin-2-yl)benzamide;
131) (R)-4-((8-chloro-3-(4-methylbenzyl)-2,5-dioxo-2,3-dihydro-1H-benzo[e][1,4]diazepin-4(5H)-yl)methyl)-N-(pyridin-2-yl)benzamide;
132) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide;
133) (R)-4-((8-chloro-2,5-dioxo-3-(pyridin-3-ylmethyl)-2,3-dihydro-1H-benzo[e][1,4]diazepin-4(5H)-yl)methyl)-N-(pyrimidin-2-yl)benzamide;
134) (R)-4-((8-chloro-2,5-dioxo-3-(pyridin-3-ylmethyl)-2,3-dihydro-1H-benzo[e][1,4]diazepin-4(5H)-yl)methyl)-N-(pyrazin-2-yl)benzamide;
135) (R)-4-((8-chloro-2,5-dioxo-3-(pyridin-3-ylmethyl)-2,3-dihydro-1H-benzo[e][1,4]diazepin-4(5H)-yl)methyl)-N-(5-chloropyridin-2-yl)benzamide;
136) (R)-4-((8-chloro-2,5-dioxo-3-(pyridin-3-ylmethyl)-2,3-dihydro-1H-benzo[e][1,4]diazepin-4(5H)-yl)methyl)-N-(3-chloropyridin-2-yl)benzamide;
137) (R)-2-(benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide;
138) (R)-4-((8-chloro-2,5-dioxo-3-(pyridin-3-ylmethyl)-2,3-dihydro-1H-benzo[e][1,4]diazepin-4(5H)-yl)methyl)-N-(5-methoxypyridin-2-yl)benzamide;
139) (R)-4-((8-chloro-2,5-dioxo-3-(pyridin-3-ylmethyl)-2,3-dihydro-1H-benzo[e][1,4]diazepin-4(5H)-yl)methyl)-N-(5-methylpyrimidin-2-yl)benzamide;
140) (R)-4-((8-chloro-2,5-dioxo-3-(pyridin-3-ylmethyl)-2,3-dihydro-1H-benzo[e][1,4]diazepin-4(5H)-yl)methyl)-N-(4-methylpyrimidin-2-yl)benzamide;
141) (R)-4-((8-chloro-2,5-dioxo-3-(pyridin-3-ylmethyl)-2,3-dihydro-1H-benzo[e][1,4]diazepin-4(5H)-yl)methyl)-N-(6-methoxypyrimidin-4-yl)benzamide;
142) (R)-4-((8-chloro-2,5-dioxo-3-(pyridin-3-ylmethyl)-2,3-dihydro-1H-benzo[e][1,4]diazepin-4(5H)-yl)methyl)-N-(5-ethylpyridin-2-yl)benzamide;
143) (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)benzamide;
144) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide;
145) (R)-4-((8-chloro-3-methyl-2,5-dioxo-2,3-dihydro-1H-benzo[e][1,4]diazepin-4(5H)-yl)methyl)-N-(quinazolin-2-yl)benzamide;
146) (R)-4-((8-chloro-3-methyl-2,5-dioxo-2,3-dihydro-1H-benzo[e][1,4]diazepin-4(5H)-yl)methyl)-N-(6-methylpyrazin-2-yl)benzamide;
147) (R)-N-(1H-benzo[d]imidazol-2-yl)-4-((8-chloro-3-methyl-2,5-dioxo-2,3-dihydro-1H-benzo[e][1,4]diazepin-4(5H)-yl)methyl)benzamide;
148) (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide;
149) (R)-5-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)thiophene-2-carboxamide;
150) (R)-5-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)thiophene-2-carboxamide;
151) (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide;
152) (R)-4-((8-chloro-2,5-dioxo-3-(pyridin-2-ylmethyl)-2,3-dihydro-1H-benzo[e][1,4]diazepin-4(5H)-yl)methyl)-N-(pyrazin-2-yl)benzamide;
153) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide;
154) 4-((8-chloro-2,5-dioxo-3-(pyrazin-2-ylmethyl)-2,3-dihydro-1H-benzo[e][1,4]diazepin-4(5H)-yl)methyl)-N-(5-methoxypyridin-2-yl)benzamide;

155) 4-((8-chloro-2,5-dioxo-3-(pyrazin-2-ylmethyl)-2,3-dihydro-1H-benzo[e][1,4]diazepin-4(5H)-yl)methyl)-N-(5-methylpyridin-2-yl)benzamide;
156) 4-((8-chloro-2,5-dioxo-3-(pyrazin-2-ylmethyl)-2,3-dihydro-1H-benzo[e][1,4]diazepin-4(5H)-yl)methyl)-N-(5-methoxypyrimidin-2-yl)benzamide;
157) 4-((8-chloro-2,5-dioxo-3-(pyrazin-2-ylmethyl)-2,3-dihydro-1H-benzo[e][1,4]diazepin-4(5H)-yl)methyl)-N-(5-methylpyrimidin-2-yl)benzamide;
158) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide;
159) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide;
160) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(3-fluoropyridin-2-yl)benzamide;
161) (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)cyclohexanecarboxamide;
162) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide;
163) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)-2-methylbenzamide;
164) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrimidin-2-yl)benzamide;
165) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrazin-2-yl)benzamide;
166) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)-2-methylbenzamide;
167) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrazin-2-yl)benzamide;
168) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrazin-2-yl)benzamide;
169) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl)pyridin-2-yl)benzamide;
170) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrimidin-2-yl)benzamide;
171) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrimidin-2-yl)benzamide;
172) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide;
173) (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)-2-methylbenzamide;
174) (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)-2-methoxybenzamide;
175) (R)-2-bromo-4-((8-chloro-3-methyl-2,5-dioxo-2,3-dihydro-1H-benzo[e][1,4]diazepin-4(5H)-yl)methyl)-N-(5-(trifluoromethyl)pyridin-2-yl)benzamide;
176) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)benzamide;
177) (R)-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)-2-methylbenzamide;
178) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)benzamide;
179) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(methylsulfonyl)pyridin-2-yl)benzamide;
180) (R)-8-chloro-4-(3-chloro-4-(3,3-dimethyl-5-(trifluoromethyl)-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;
181) (1R,4r)-4-(((R)-8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)cyclohexanecarboxamide;
182) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(methylsulfonyl)pyridin-2-yl)benzamide;
183) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methoxypyridin-2-yl)benzamide;
184) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(pyridin-2-yl)benzamide;
185) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-fluoropyridin-2-yl)benzamide;
186) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methylpyridin-2-yl)benzamide;
187) (R)-8-chloro-4-(4-(2,3-dihydro-1H-pyrrolo[2,3-b]pyridine-1-carbonyl)-3-fluorobenzyl)-3-(pyridin-2-ylmethyl)-3,4-dihydro-1H-benzo[e][1,4]diazepine-2,5-dione;
188) (R)-8-chloro-4-(3-fluoro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;
189) (R)-2-chloro-4-((8-chloro-2,5-dioxo-3-(pyridin-2-ylmethyl)-2,3-dihydro-1H-benzo[e][1,4]diazepin-4(5H)-yl)methyl)benzoic acid;
190) (R)-4-((8-chloro-2,5-dioxo-3-(pyridin-2-ylmethyl)-2,3-dihydro-1H-benzo[e][1,4]diazepin-4(5H)-yl)methyl)-2-methylbenzoic acid;
191) (R)-2,6-dichloro-4-((8-chloro-2,5-dioxo-3-(pyridin-2-ylmethyl)-2,3-dihydro-1H-benzo[e][1,4]diazepin-4(5H)-yl)methyl)benzoic acid;

192) (R)-4-((8-chloro-2,5-dioxo-3-(pyridin-2-ylmethyl)-2,3-dihydro-1H-benzo[e][1,4]diazepin-4(5H)-yl)methyl)-2-methoxybenzoic acid;
193) (R)-4-((8-chloro-2,5-dioxo-3-(pyridin-2-ylmethyl)-2,3-dihydro-1H-benzo[e][1,4]diazepin-4(5H)-yl)methyl)-2-(pyridin-4-yl)benzoic acid;
194) (R)-5-((8-chloro-2,5-dioxo-3-(pyridin-2-ylmethyl)-2,3-dihydro-1H-benzo[e][1,4]diazepin-4(5H)-yl)methyl)-3'-methoxy-[1,1'-biphenyl]-2-carboxylic acid;
195) (R)-2-(benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)benzoic acid;
196) (R)-5-((8-chloro-2,5-dioxo-3-(pyridin-2-ylmethyl)-2,3-dihydro-1H-benzo[e][1,4]diazepin-4(5H)-yl)methyl)-4'-fluoro-[1,1'-biphenyl]-2-carboxylic acid;
197) (R)-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid;
198) (R)-5-((8-chloro-2,5-dioxo-3-(pyridin-2-ylmethyl)-2,3-dihydro-1H-benzo[e][1,4]diazepin-4(5H)-yl)methyl)-4'-methoxy-[1,1'-biphenyl]-2-carboxylic acid;
199) (R)-5-((8-chloro-2,5-dioxo-3-(pyridin-2-ylmethyl)-2,3-dihydro-1H-benzo[e][1,4]diazepin-4(5H)-yl)methyl)-4'-methyl-[1,1'-biphenyl]-2-carboxylic acid;
200) (R)-5-((8-chloro-2,5-dioxo-3-(pyridin-2-ylmethyl)-2,3-dihydro-1H-benzo[e][1,4]diazepin-4(5H)-yl)methyl)-3'-methyl-[1,1'-biphenyl]-2-carboxylic acid;
201) (R)-4'-chloro-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid;
202) (R)-3'-chloro-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid;
203) (R)-5-((8-chloro-2,5-dioxo-3-(pyridin-2-ylmethyl)-2,3-dihydro-1H-benzo[e][1,4]diazepin-4(5H)-yl)methyl)-3'-fluoro-[1,1'-biphenyl]-2-carboxylic acid;
204) (R)-3'-chloro-5-((8-chloro-2,5-dioxo-3-(pyridin-2-ylmethyl)-2,3-dihydro-1H-benzo[e][1,4]diazepin-4(5H)-yl)methyl)-4'-fluoro-[1,1'-biphenyl]-2-carboxylic acid;
205) (R)-4-((8-chloro-2,5-dioxo-3-(pyridin-2-ylmethyl)-2,3-dihydro-1H-benzo[e][1,4]diazepin-4(5H)-yl)methyl)-2-(pyridin-3-yl)benzoic acid;
206) (R)-4'-acetamido-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid;
207) (R)-5-((8-chloro-2,5-dioxo-3-(pyridin-2-ylmethyl)-2,3-dihydro-1H-benzo[e][1,4]diazepin-4(5H)-yl)methyl)-4'-(methylcarbamoyl)-[1,1'-biphenyl]-2-carboxylic acid;
208) (R)-5-((8-chloro-2,5-dioxo-3-(pyridin-2-ylmethyl)-2,3-dihydro-1H-benzo[e][1,4]diazepin-4(5H)-yl)methyl)-3'-(methylcarbamoyl)-[1,1'-biphenyl]-2-carboxylic acid;
209) (R)-3'-acetamido-5-((8-chloro-2,5-dioxo-3-(pyridin-2-ylmethyl)-2,3-dihydro-1H-benzo[e][1,4]diazepin-4(5H)-yl)methyl)-[1,1'-biphenyl]-2-carboxylic acid;
210) (R)-4-((8-chloro-2,5-dioxo-3-(pyridin-2-ylmethyl)-2,3-dihydro-1H-benzo[e][1,4]diazepin-4(5H)-yl)methyl)-2-(1H-pyrazol-4-yl)benzoic acid;
211) (R)-4-((8-chloro-2,5-dioxo-3-(pyridin-2-ylmethyl)-2,3-dihydro-1H-benzo[e][1,4]diazepin-4(5H)-yl)methyl)-2-(1-methyl-1H-pyrazol-5-yl)benzoic acid;
212) 4-(((R)-8-chloro-2,5-dioxo-3-(pyridin-2-ylmethyl)-2,3-dihydro-1H-benzo[e][1,4]diazepin-4(5H)-yl)methyl)-2-(3,5-dimethylisoxazol-4-yl)benzoic acid;
213) (R)-4-((8-chloro-2,5-dioxo-3-(pyridin-2-ylmethyl)-2,3-dihydro-1H-benzo[e][1,4]diazepin-4(5H)-yl)methyl)-2-(1-methyl-1H-pyrazol-4-yl)benzoic acid;
214) (R)-4-((8-chloro-3-(2-hydroxyethyl)-2,5-dioxo-2,3-dihydro-1H-benzo[e][1,4]diazepin-4(5H)-yl)methyl)-N-(5-methylpyridin-2-yl)benzamide;
215) (R)-4-((8-chloro-3-(2-morpholinoethyl)-2,5-dioxo-2,3-dihydro-1H-benzo[e][1,4]diazepin-4(5H)-yl)methyl)-N-(5-methylpyridin-2-yl)benzamide;
216) (R)-4-((8-chloro-2,5-dioxo-3-(2-(piperidin-1-yl)ethyl)-2,3-dihydro-1H-benzo[e][1,4]diazepin-4(5H)-yl)methyl)-N-(5-methylpyridin-2-yl)benzamide;
217) (R)-4-((8-chloro-3-(2-(4-hydroxypiperidin-1-yl)ethyl)-2,5-dioxo-2,3-dihydro-1H-benzo[e][1,4]diazepin-4(5H)-yl)methyl)-N-(5-methylpyridin-2-yl)benzamide;
218) (R)-4-((8-chloro-3-(2-(4-methylpiperazin-1-yl)ethyl)-2,5-dioxo-2,3-dihydro-1H-benzo[e][1,4]diazepin-4(5H)-yl)methyl)-N-(5-methylpyridin-2-yl)benzamide;
219) (R)-4-((8-chloro-2,5-dioxo-3-(2-(3-oxopiperazin-1-yl)ethyl)-2,3-dihydro-1H-benzo[e][1,4]diazepin-4(5H)-yl)methyl)-N-(5-methylpyridin-2-yl)benzamide;
220) (R)-4-((8-chloro-3-(2-(dimethylamino)ethyl)-2,5-dioxo-2,3-dihydro-1H-benzo[e][1,4]diazepin-4(5H)-yl)methyl)-N-(5-methylpyridin-2-yl)benzamide;
221) (R)-8-chloro-4-(4-picolinoylbenzyl)-3-(pyridin-2-ylmethyl)-3,4-dihydro-1H-benzo[e][1,4]diazepine-2,5-dione;
222) (R)-8-chloro-4-(4-(5-methylpicolinoyl)benzyl)-3-(pyridin-2-ylmethyl)-3,4-dihydro-1H-benzo[e][1,4]diazepine-2,5-dione;
223) (R)-8-chloro-4-((4-picolinoylcyclohexyl)methyl)-3-(pyridin-2-ylmethyl)-3,4-dihydro-1H-benzo[e][1,4]diazepine-2,5-dione;
224) (R)-8-chloro-4-(4-(4-methylpicolinoyl)benzyl)-3-(pyridin-2-ylmethyl)-3,4-dihydro-1H-benzo[e][1,4]diazepine-2,5-dione;
225) (R)-8-chloro-4-(4-(6-methylpicolinoyl)benzyl)-3-(pyridin-2-ylmethyl)-3,4-dihydro-1H-benzo[e][1,4]diazepine-2,5-dione;
226) (R)-8-chloro-4-(3-fluoro-4-picolinoylbenzyl)-3-(pyridin-2-ylmethyl)-3,4-dihydro-1H-benzo[e][1,4]diazepine-2,5-dione;
227) (R)-8-chloro-4-(3-chloro-4-picolinoylbenzyl)-3-(pyridin-2-ylmethyl)-3,4-dihydro-1H-benzo[e][1,4]diazepine-2,5-dione;
228) (R)-8-chloro-4-(3-methyl-4-picolinoylbenzyl)-3-(pyridin-2-ylmethyl)-3,4-dihydro-1H-benzo[e][1,4]diazepine-2,5-dione;
229) (R)-8-chloro-4-(3-fluoro-4-(3-methylpicolinoyl)benzyl)-3-(pyridin-2-ylmethyl)-3,4-dihydro-1H-benzo[e][1,4]diazepine-2,5-dione;
230) (R)-8-chloro-4-(3-methoxy-4-picolinoylbenzyl)-3-(pyridin-2-ylmethyl)-3,4-dihydro-1H-benzo[e][1,4]diazepine-2,5-dione;
231) (R)—N-acetyl-4-((8-chloro-2,5-dioxo-3-(pyridin-2-ylmethyl)-2,3-dihydro-1H-benzo[e][1,4]diazepin-4(5H)-yl)methyl)benzamide;
232) (R)-8-chloro-4-(4-(2-oxopyrrolidine-1-carbonyl)benzyl)-3-(pyridin-2-ylmethyl)-3,4-dihydro-1H-benzo[e][1,4]diazepine-2,5-dione;
233) (S)-4-((8-chloro-3-(3,4-dichlorobenzyl)-2,5-dioxo-2,3-dihydro-1H-benzo[e][1,4]diazepin-4(5H)-yl)methyl)benzamide;

234) (R)-4-((8-chloro-2,5-dioxo-3-(pyridin-3-ylmethyl)-2,3-dihydro-1H-benzo[e][1,4]diazepin-4(5H)-yl)methyl)-N,N-dimethylbenzamide;
235) (R)-4-((8-chloro-2,5-dioxo-3-(pyridin-3-ylmethyl)-2,3-dihydro-1H-benzo[e][1,4]diazepin-4(5H)-yl)methyl)benzamide;
236) (R)-4-((8-chloro-2,5-dioxo-3-(pyridin-2-ylmethyl)-2,3-dihydro-1H-benzo[e][1,4]diazepin-4(5H)-yl)methyl)benzamide;
237) (R)-4-((8-cyano-2,5-dioxo-3-(pyridin-3-ylmethyl)-2,3-dihydro-1H-benzo[e][1,4]diazepin-4(5H)-yl)methyl)-N-(pyridin-2-yl)benzamide hydrochloride;
238) (R)-4-((8-chloro-2,5-dioxo-3-(pyridin-3-ylmethyl)-2,3-dihydro-1H-benzo[e][1,4]diazepin-4(5H)-yl)methyl)-N-(phenylsulfonyl)benzamide;
239) (R)-4-((8-chloro-2,5-dioxo-3-(pyridin-3-ylmethyl)-2,3-dihydro-1H-benzo[e][1,4]diazepin-4(5H)-yl)methyl)-N-(methylsulfonyl)benzamide;
240) (R)-4-((8-chloro-2,5-dioxo-3-(pyridin-3-ylmethyl)-2,3-dihydro-1H-benzo[e][1,4]diazepin-4(5H)-yl)methyl)-N-((4-chlorophenyl)sulfonyl)benzamide;
241) (R)-4-((8-chloro-2,5-dioxo-3-(pyridin-3-ylmethyl)-2,3-dihydro-1H-benzo[e][1,4]diazepin-4(5H)-yl)methyl)-N-((4-methoxyphenyl)sulfonyl)benzamide;
242) (R)-4-((8-chloro-2,5-dioxo-3-(pyridin-3-ylmethyl)-2,3-dihydro-1H-benzo[e][1,4]diazepin-4(5H)-yl)methyl)-N-tosylbenzamide;
243) (R)-4-((8-amino-3-methyl-2,5-dioxo-2,3-dihydro-1H-benzo[e][1,4]diazepin-4(5H)-yl)methyl)-N-(5-methylpyridin-2-yl)benzamide;
244) (R)-4-((8-acetamido-3-methyl-2,5-dioxo-2,3-dihydro-1H-benzo[e][1,4]diazepin-4(5H)-yl)methyl)-N-(5-methylpyridin-2-yl)benzamide;
245) (R)-4-((8-(3-methoxypropanamido)-3-methyl-2,5-dioxo-2,3-dihydro-1H-benzo[e][1,4]diazepin-4(5H)-yl)methyl)-N-(5-methylpyridin-2-yl)benzamide;
246) (R)-4-((8-isobutyramido-3-methyl-2,5-dioxo-2,3-dihydro-1H-benzo[e][1,4]diazepin-4(5H)-yl)methyl)-N-(5-methylpyridin-2-yl)benzamide;
247) (R)-5-methyl-N-(3-methyl-4-((5-methylpyridin-2-yl)carbamoyl)benzyl)-2,5-dioxo-2,3,4,5-tetrahydro-1H-benzo[e][1,4]diazepin-8-yl)isoxazole-3-carboxamide;
248) (R)—N-(3-methyl-4-(4-(5-methylpyridin-2-yl)carbamoyl)benzyl)-2,5-dioxo-2,3,4,5-tetrahydro-1H-benzo[e][1,4]diazepin-8-yl)picolinamide;
249) (R)—N-(3-methyl-4-(4-(5-methylpyridin-2-yl)carbamoyl)benzyl)-2,5-dioxo-2,3,4,5-tetrahydro-1H-benzo[e][1,4]diazepin-8-yl)nicotinamide;
250) (R)-4-((8-chloro-2-oxo-3-(pyridin-2-ylmethyl)-2,3-dihydro-1H-benzo[e][1,4]diazepin-4(5H)-yl)sulfonyl)-N-(5-methylpyridin-2-yl)benzamide;
251) (R)-4-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide;
252) (S)-4-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide;
253) (S)-4-((8-chloro-2-oxo-3-(pyridin-2-ylmethyl)-2,3-dihydro-1H-benzo[e][1,4]diazepin-4(5H)-yl)sulfonyl)-N-(5-methoxypyridin-2-yl)benzamide;
254) (S)-4-((8-chloro-2-oxo-3-(pyridin-2-ylmethyl)-2,3-dihydro-1H-benzo[e][1,4]diazepin-4(5H)-yl)sulfonyl)-N-(5-methylpyrimidin-2-yl)benzamide;
255) (R)-4-((8-chloro-2-oxo-3-(pyridin-2-ylmethyl)-2,3-dihydro-1H-benzo[e][1,4]diazepin-4(5H)-yl)sulfonyl)-N-(5-methoxypyridin-2-yl)benzamide;
256) (R)-4-((8-chloro-2-oxo-3-(pyridin-2-ylmethyl)-2,3-dihydro-1H-benzo[e][1,4]diazepin-4(5H)-yl)sulfonyl)-N-(5-methylpyrimidin-2-yl)benzamide;
257) (R)-4-((8-chloro-2-oxo-3-(pyridin-2-ylmethyl)-2,3-dihydro-1H-benzo[e][1,4]diazepin-4(5H)-yl)sulfonyl)-N-(5-methoxypyrimidin-2-yl)benzamide;
258) (R)-4-(8-chloro-2-oxo-3-(pyridin-2-ylmethyl)-2,3,4,5-tetrahydro-1H-benzo[e][1,4]diazepine-4-carbonyl)-N-(pyridin-2-yl)benzamide;
259) (R)-3-((8-chloro-2-oxo-3-(pyridin-2-ylmethyl)-2,3-dihydro-1H-benzo[e][1,4]diazepin-4(5H)-yl)sulfonyl)-N-(pyridin-2-yl)benzamide;
260) (R)-4-((8-chloro-2-oxo-3-(pyridin-2-ylmethyl)-2,3-dihydro-1H-benzo[e][1,4]diazepin-4(5H)-yl)methyl)-N-(pyridin-2-yl)benzamide;
261) (R)-4-((8-chloro-2,5-dioxo-3-(pyridin-2-ylmethyl)-2,3-dihydro-1H-benzo[e][1,4]diazepin-4(5H)-yl)methyl)-2-(picolinamido)benzoic acid;
262) (R)-2-acetamido-4-((8-chloro-2,5-dioxo-3-(pyridin-2-ylmethyl)-2,3-dihydro-1H-benzo[e][1,4]diazepin-4(5H)-yl)methyl)benzoic acid;
263) (R)-4-((8-chloro-2,5-dioxo-3-(pyridin-2-ylmethyl)-2,3-dihydro-1H-benzo[e][1,4]diazepin-4(5H)-yl)methyl)-2-(2-methoxyacetamido)benzoic acid;
264) (R)-4-((8-chloro-2,5-dioxo-3-(pyridin-2-ylmethyl)-2,3-dihydro-1H-benzo[e][1,4]diazepin-4(5H)-yl)methyl)-2-cyclohexanecarboxamido)benzoic acid;
265) (R)-4-((8-chloro-2,5-dioxo-3-(pyridin-2-ylmethyl)-2,3-dihydro-1H-benzo[e][1,4]diazepin-4(5H)-yl)methyl)-2-(2-(dimethylamino)acetamido)benzoic acid;
266) (R)-4-((8-chloro-2,5-dioxo-3-(pyridin-2-ylmethyl)-2,3-dihydro-1H-benzo[e][1,4]diazepin-4(5H)-yl)methyl)-2-(3-methoxypropanamido)benzoic acid;
267) (R)-4-((8-chloro-2,5-dioxo-3-(pyridin-2-ylmethyl)-2,3-dihydro-1H-benzo[e][1,4]diazepin-4(5H)-yl)methyl)-2-(isonicotinamido)benzoic acid;
268) (R)-4-((8-chloro-2,5-dioxo-3-(pyridin-2-ylmethyl)-2,3-dihydro-1H-benzo[e][1,4]diazepin-4(5H)-yl)methyl)-2-(nicotinamido)benzoic acid;
269) (R)-4-((8-chloro-2,5-dioxo-3-(pyridin-2-ylmethyl)-2,3-dihydro-1H-benzo[e][1,4]diazepin-4(5H)-yl)methyl)-2-(2-morpholinoacetamido)benzoic acid;
270) (R)-4-((8-chloro-2,5-dioxo-3-(pyridin-2-ylmethyl)-2,3-dihydro-1H-benzo[e][1,4]diazepin-4(5H)-yl)methyl)-2-(1-methylpiperidine-4-carboxamido)benzoic acid;
271) (R)-4-((8-chloro-2,5-dioxo-3-(pyridin-2-ylmethyl)-2,3-dihydro-1H-benzo[e][1,4]diazepin-4(5H)-yl)methyl)-2-(2-(4-methylpiperazin-1-yl)acetamido)benzoic acid;
272) (R)-4-((8-chloro-2,5-dioxo-3-(pyridin-2-ylmethyl)-2,3-dihydro-1H-benzo[e][1,4]diazepin-4(5H)-yl)methyl)-2-(3-(dimethylamino)propanamido)benzoic acid;
273) (R)-4-((8-chloro-2,5-dioxo-3-(pyridin-2-ylmethyl)-2,3-dihydro-1H-benzo[e][1,4]diazepin-4(5H)-yl)methyl)-2-(2-(1-methylpiperidin-4-yl)acetamido)benzoic acid;
274) (R)-4-((8-chloro-2,5-dioxo-3-(pyridin-2-ylmethyl)-2,3-dihydro-1H-benzo[e][1,4]diazepin-4(5H)-yl)methyl)-2-(tetrahydro-2H-pyran-4-carboxamido)benzoic acid;
275) (R)-4-((8-chloro-2,5-dioxo-3-(pyridin-2-ylmethyl)-2,3-dihydro-1H-benzo[e][1,4]diazepin-4(5H)-yl)methyl)-2-(2-(pyrrolidin-1-yl)acetamido)benzoic acid;

276) (R)-4-((8-chloro-2,5-dioxo-3-(pyridin-2-ylmethyl)-2,3-dihydro-1H-benzo[e][1,4]diazepin-4(5H)-yl)methyl)-2-(2-hydroxyacetamido)benzoic acid;
277) (R)-4-(4-aminobenzyl)-8-chloro-3-(pyridin-2-ylmethyl)-3,4-dihydro-1H-benzo[e][1,4]diazepine-2,5-dione;
278) (R)-4-(4-amino-3,5-dimethylbenzyl)-8-chloro-3-(pyridin-2-ylmethyl)-3,4-dihydro-1H-benzo[e][1,4]diazepine-2,5-dione;
279) N-((1R,4r)-4-(((R)-8-chloro-2,5-dioxo-3-(pyridin-2-ylmethyl)-2,3-dihydro-1H-benzo[e][1,4]diazepin-4(5H)-yl)methyl)cyclohexyl)-5-methylpicolinamide;
280) (R)-tert-butyl (4-((8-chloro-2,5-dioxo-3-(pyridin-2-ylmethyl)-2,3-dihydro-1H-benzo[e][1,4]diazepin-4(5H)-yl)methyl)phenyl)carbamate;
281) (R)—N-(4-((8-chloro-2,5-dioxo-3-(pyridin-2-ylmethyl)-2,3-dihydro-1H-benzo[e][1,4]diazepin-4(5H)-yl)methyl)phenyl)picolinamide;
282) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-4-methylpicolinamide;
283) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-6-methylpicolinamide;
284) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-3-methylpicolinamide;
285) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-5-methylpicolinamide;
286) (R)-3-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide;
287) (R)-4-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide;
288) (R)-5-chloro-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide;
289) N-((1R,4r)-4-(((R)-8-chloro-2,5-dioxo-3-(pyridin-2-ylmethyl)-2,3-dihydro-1H-benzo[e][1,4]diazepin-4(5H)-yl)methyl)cyclohexyl)picolinamide;
290) (R)—N-(4-((8-chloro-2,5-dioxo-3-(pyridin-2-ylmethyl)-2,3-dihydro-1H-benzo[e][1,4]diazepin-4(5H)-yl)methyl)-2,6-dimethylphenyl)picolinamide;
291) (R)—N-(4-((8-chloro-2,5-dioxo-3-(pyridin-2-ylmethyl)-2,3-dihydro-1H-benzo[e][1,4]diazepin-4(5H)-yl)methyl)-2,6-dimethylphenyl)-5-methylpicolinamide;
292) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-2-hydroxynicotinamide;
293) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-2-hydroxyacetamide;
294) (R)—N-(4-((8-chloro-2,5-dioxo-3-(pyridin-2-ylmethyl)-2,3-dihydro-1H-benzo[e][1,4]diazepin-4(5H)-yl)methyl)phenyl)pyrimidine-4-carboxamide;
295) (R)—N-(4-((8-chloro-2,5-dioxo-3-(pyridin-2-ylmethyl)-2,3-dihydro-1H-benzo[e][1,4]diazepin-4(5H)-yl)methyl)phenyl)pyrazine-2-carboxamide;
296) (R)—N-(4-((8-chloro-2,5-dioxo-3-(pyridin-2-ylmethyl)-2,3-dihydro-1H-benzo[e][1,4]diazepin-4(5H)-yl)methyl)phenyl)thiazole-2-carboxamide;
297) (R)—N-(4-((8-chloro-2,5-dioxo-3-(pyridin-2-ylmethyl)-2,3-dihydro-1H-benzo[e][1,4]diazepin-4(5H)-yl)methyl)phenyl)thiazole-4-carboxamide;
298) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-5-methylisoxazole-3-carboxamide;
299) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-1H-imidazole-2-carboxamide;
300) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-1-methyl-1H-imidazole-2-carboxamide;
301) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-1H-imidazole-4-carboxamide;
302) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-1-methyl-1H-imidazole-4-carboxamide;
303) (R)—N-(3-((8-chloro-2,5-dioxo-3-(pyridin-2-ylmethyl)-2,3-dihydro-1H-benzo[e][1,4]diazepin-4(5H)-yl)methyl)phenyl)picolinamide;
304) (R)—N-(3-((8-chloro-2,5-dioxo-3-(pyridin-2-ylmethyl)-2,3-dihydro-1H-benzo[e][1,4]diazepin-4(5H)-yl)methyl)phenyl)-2-methoxyacetamide;
305) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-2-mercaptoacetamide;
306) (R)—N-(4-((8-chloro-2,5-dioxo-3-(pyridin-2-ylmethyl)-2,3-dihydro-1H-benzo[e][1,4]diazepin-4(5H)-yl)methyl)phenyl)methanesulfonamide;
307) (R)—N-(4-((8-chloro-2,5-dioxo-3-(pyridin-2-ylmethyl)-2,3-dihydro-1H-benzo[e][1,4]diazepin-4(5H)-yl)methyl)phenyl)-2-methoxyacetamide;
308) (R)—N-(3-((8-chloro-2,5-dioxo-3-(pyridin-2-ylmethyl)-2,3-dihydro-1H-benzo[e][1,4]diazepin-4(5H)-yl)methyl)phenyl)pyridine-2-sulfonamide;
309) (R)-8-chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione;
310) (R)-8-chloro-3-(pyridin-2-ylmethyl)-4-(4-(quinoline-8-carbonyl)benzyl)-3,4-dihydro-1H-benzo[e][1,4]diazepine-2,5-dione;
311) (R)-8-chloro-4-(4-(1-methyl-1H-imidazole-2-carbonyl)benzyl)-3-(pyridin-2-ylmethyl)-3,4-dihydro-1H-benzo[e][1,4]diazepine-2,5-dione;
312) (R)-8-chloro-4-(4-(1-methyl-1H-imidazole-4-carbonyl)benzyl)-3-(pyridin-2-ylmethyl)-3,4-dihydro-1H-benzo[e][1,4]diazepine-2,5-dione;
313) (R)-8-chloro-4-(4-(6-methylimidazo[1,2-a]pyridine-8-carbonyl)benzyl)-3-(pyridin-2-ylmethyl)-3,4-dihydro-1H-benzo[e][1,4]diazepine-2,5-dione;
314) (R)-4-(4-([1,2,4]triazolo[1,5-a]pyridine-8-carbonyl)benzyl)-8-chloro-3-(pyridin-2-ylmethyl)-3,4-dihydro-1H-benzo[e][1,4]diazepine-2,5-dione;
315) 4-(4-(1H-pyrrolo[3,2-b]pyridine-3-carbonyl)benzyl)-8-chloro-3-(pyridin-2-ylmethyl)-3,4-dihydro-1H-benzo[e][1,4]diazepine-2,5-dione;
316) (R)-8-chloro-3-(pyridin-2-ylmethyl)-4-(((r,4R)-4-(quinoline-8-carbonyl)cyclohexyl)methyl)-3,4-dihydro-1H-benzo[e][1,4]diazepine-2,5-dione;
317) (R)-8-chloro-4-(((1r,4R)-4-(1-methyl-1H-pyrrolo[3,2-b]pyridine-3-carbonyl)cyclohexyl)methyl)-3-(pyridin-2-ylmethyl)-3,4-dihydro-1H-benzo[e][1,4]diazepine-2,5-dione;
318) (R)-8-chloro-4-(((1r,4R)-4-(1-methyl-1H-imidazole-2-carbonyl)cyclohexyl)methyl)-3-(pyridin-2-ylmethyl)-3,4-dihydro-1H-benzo[e][1,4]diazepine-2,5-dione;

319) (R)-8-chloro-4-(((1r,4R)-4-(1-methyl-1H-imidazole-4-carbonyl)cyclohexyl)methyl)-3-(pyridin-2-ylmethyl)-3,4-dihydro-1H-benzo[e][1,4]diazepine-2,5-dione;
320) (R)-8-chloro-4-(4-(imidazo[1,2-a]pyridine-8-carbonyl)benzyl)-3-(pyridin-2-ylmethyl)-3,4-dihydro-1H-benzo[e][1,4]diazepine-2,5-dione;
321) (R)-8-chloro-4-(((1r,4R)-4-(imidazo[1,2-a]pyridine-8-carbonyl)cyclohexyl)methyl)-3-(pyridin-2-ylmethyl)-3,4-dihydro-1H-benzo[e][1,4]diazepine-2,5-dione;
322) (S)-4-((8-chloro-2,5-dioxo-3-(thiazol-4-ylmethyl)-2,3-dihydro-1H-benzo[e][1,4]diazepin-4(5H)-yl)methyl)-N-(5-methylpyridin-2-yl)benzamide;
323) (R)-4-((8-chloro-2,5-dioxo-3-(thiophen-2-ylmethyl)-2,3-dihydro-1H-benzo[e][1,4]diazepin-4(5H)-yl)methyl)-N-(5-methylpyridin-2-yl)benzamide;
324) (R)-4-((8-chloro-2,5-dioxo-3-phenyl-2,3-dihydro-1H-benzo[e][1,4]diazepin-4(5H)-yl)methyl)-N-(pyridin-2-yl)benzamide;
325) (R)-4-((8-chloro-3-(4-methoxybenzyl)-2,5-dioxo-2,3-dihydro-1H-benzo[e][1,4]diazepin-4(5H)-yl)methyl)-N-(pyridin-2-yl)benzamide;
326) 4-((8-chloro-2,5-dioxo-3-((tetrahydro-2H-pyran-4-yl)methyl)-2,3-dihydro-1H-benzo[e][1,4]diazepin-4(5H)-yl)methyl)-N-(pyridin-2-yl)benzamide;
327) (R)-4-((3-(3,4-dichlorobenzyl)-2,5-dioxo-8-(trifluoromethyl)-2,3-dihydro-1H-benzo[e][1,4]diazepin-4(5H)-yl)methyl)-N-(pyridin-2-yl)benzamide;
328) (R)-4-((2,5-dioxo-3-(pyridin-3-ylmethyl)-2,3-dihydro-1H-benzo[e][1,4]diazepin-4(5H)-yl)methyl)-N-(pyridin-2-yl)benzamide;
329) (R)-4-((7-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide;
330) (R)-4-((9-chloro-2,5-dioxo-3-(pyridin-3-ylmethyl)-2,3-dihydro-1H-benzo[e][1,4]diazepin-4(5H)-yl)methyl)-N-(pyridin-2-yl)benzamide;
331) (R)-4-((8-chloro-3-(3-fluorobenzyl)-2,5-dioxo-2,3-dihydro-1H-benzo[e][1,4]diazepin-4(5H)-yl)methyl)-N-(pyridin-2-yl)benzamide;
332) (R)-4-((8-chloro-3-isobutyl-2,5-dioxo-2,3-dihydro-1H-benzo[e][1,4]diazepin-4(5H)-yl)methyl)-N-(pyridin-2-yl)benzamide;
333) (R)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)cyclohexanecarboxamide;
334) (S)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide;
335) (R)-4-((2,5-dioxo-3-(pyridin-3-ylmethyl)-2,3-dihydro-1H-pyrido[3,4-e][1,4]diazepin-4(5H)-yl)methyl)-N-(pyridin-2-yl)benzamide;
336) (R)-4-((8-chloro-2,5-dioxo-3-(pyridin-3-ylmethyl)-2,3-dihydro-1H-benzo[e][1,4]diazepin-4(5H)-yl)methyl)-N-(pyridin-2-yl)benzenesulfonamide;
337) (R)-8-chloro-4-((1-oxo-2-(pyridin-2-yl)-1,2,3,4-tetrahydroisoquinolin-6-yl)methyl)-3-(pyridin-2-ylmethyl)-3,4-dihydro-1H-benzo[e][1,4]diazepine-2,5-dione;
338) (R)-2-(4-methoxybenzyloxy)-4-((8-chloro-3-methyl-2,5-dioxo-2,3-dihydro-1H-benzo[e][1,4]diazepin-4(5H)-yl)methyl)benzoic acid;
339) (R)-4-((3-methyl-8-(methylsulfonamido)-2,5-dioxo-2,3-dihydro-1H-benzo[e][1,4]diazepin-4(5H)-yl)methyl)-N-(5-methylpyridin-2-yl)benzamide;
340) (R)-4-((8-chloro-2,5-dioxo-3-(pyridin-2-ylmethyl)-2,3-dihydro-1H-benzo[e][1,4]diazepin-4(5H)-yl)methyl)-N-hydroxybenzamide;
341) 8-Chloro-4-(4-(hydroxymethyl)benzyl)-3-(pyridin-2-ylmethyl)-3,4-dihydro-1H-benzo[e][1,4]diazepine-2,5-dione;
342) (R)-4-((8-Chloro-2,5-dioxo-3-(pyridin-2-ylmethyl)-2,3-dihydro-1H-benzo[e][1,4]diazepin-4(5H)-yl)methyl)-N-(pyridin-2-yl)piperidine-1-carboxamide;
343) (R)-8-chloro-4-((1-(1-methyl-1H-pyrrolo[3,2-b]pyridine-3-carbonyl)piperidin-4-yl)methyl)-3-(pyridin-2-ylmethyl)-3,4-dihydro-1H-benzo[e][1,4]diazepine-2,5-dione;
344) (R)-4-((3-Bromo-1-methyl-1H-indazol-6-yl)methyl)-8-chloro-3-(pyridin-2-ylmethyl)-3,4-dihydro-1H-benzo[e][1,4]diazepine-2,5-dione;
345) (R)-3-Amino-N-(4-((8-chloro-2,5-dioxo-3-(pyridin-2-ylmethyl)-2,3-dihydro-1H-benzo[e][1,4]diazepin-4(5H)-yl)methyl)phenyl)picolinamide;
346) (R)-8-Chloro-4-(4-(4-oxopyrido[3,2-d]pyrimidin-3(4H)-yl)benzyl)-3-(pyridin-2-ylmethyl)-3,4-dihydro-1H-benzo[e][1,4]diazepine-2,5-dione;
347) (R)-8-Chloro-4-(4-(2-methyl-4-oxopyrido[3,2-d]pyrimidin-3(4H)-yl)benzyl)-3-(pyridin-2-ylmethyl)-3,4-dihydro-1H-benzo[e][1,4]diazepine-2,5-dione;
348) (R)-4-((8-chloro-2,5-dioxo-3-(pyridin-2-ylmethyl)-2,3-dihydro-1H-benzo[e][1,4]diazepin-4(5H)-yl)methyl)-N-(5-(piperazin-1-yl)pyridin-2-yl)benzamide hydrochloride;
349) (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyrimidin-2-yl)benzamide;
350) (R)-8-chloro-4-(4-(8-oxo-5,6-dihydro-1,7-naphthyridin-7(8H)-yl)benzyl)-3-(pyridin-2-ylmethyl)-3,4-dihydro-1H-benzo[e][1,4]diazepine-2,5-dione;
351) (R)-8-chloro-4-(4-(7-oxo-5H-pyrrolo[3,4-b]pyridin-6(7H)-yl)benzyl)-3-(pyridin-2-ylmethyl)-3,4-dihydro-1H-benzo[e][1,4]diazepine-2,5-dione;
352) (R)-8-chloro-4-((1-oxo-2-(pyridin-2-yl)isoindolin-5-yl)methyl)-3-(pyridin-2-ylmethyl)-3,4-dihydro-1H-benzo[e][1,4]diazepine-2,5-dione;
353) (R)-8-chloro-4-((1-(pyridin-2-ylamino)isoquinolin-6-yl)methyl)-3-(pyridin-2-ylmethyl)-3,4-dihydro-1H-benzo[e][1,4]diazepine-2,5-dione;
354) 8-chloro-4-(1-(4-(imidazo[1,2-a]pyridine-8-carbonyl)phenyl)cyclopropyl)-3-methyl-3,4-dihydro-1H-benzo[e][1,4]diazepine-2,5-dione;
355) (3R)-8-chloro-4-(4-(hydroxy(pyridin-2-yl)methyl)benzyl)-3-(pyridin-2-ylmethyl)-3,4-dihydro-1H-benzo[e][1,4]diazepine-2,5-dione;
356) (R)-8-chloro-4-(4-((hydroxyimino)(pyridin-2-yl)methyl)benzyl)-3-(pyridin-2-ylmethyl)-3,4-dihydro-1H-benzo[e][1,4]diazepine-2,5-dione;
357) (R)-8-chloro-4-(4-((hydroxyimino)(pyridin-2-yl)methyl)benzyl)-3-(pyridin-2-ylmethyl)-3,4-dihydro-1H-benzo[e][1,4]diazepine-2,5-dione;
358) (R)-2-(benzo[d][1,3]dioxol-5-yl)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide;
359) (R)-2-amino-4-((8-chloro-2,5-dioxo-3-(pyridin-2-ylmethyl)-2,3-dihydro-1H-benzo[e][1,4]diazepin-4(5H)-yl)methyl)benzoic acid;
360) 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)benzoic acid;

361) 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-(trifluoromethyl)pyridin-2-yl)benzamide;

362) 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methylpyridin-2-yl)benzamide;

363) 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methoxypyridin-2-yl)benzamide; and 364) 2-chloro-4-(1-((R)-8-chloro-2,5-dioxo-3-(pyridin-2-ylmethyl)-2,3-dihydro-1H-benzo[e][1,4]diazepin-4(5H)-yl)ethyl)-N-(5-methylpyridin-2-yl)benzamide, or a pharmaceutically acceptable salt thereof.

14. The compound of claim 13, which is selected from 1) (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide;

2) (R)-8-chloro-4-(3-chloro-4-(1H-pyrrolo[2,3-b]pyridine-1-carbonyl)benzyl)-3-(pyridin-2-ylmethyl)-3,4-dihydro-1H-benzo[e][1,4]diazepine-2,5-dione;

3) (R)-8-chloro-4-(3-chloro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;

4) (R)-8-chloro-4-(4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;

5) (R)-8-chloro-4-(4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;

6) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide;

7) (R)-4-((8-chloro-2,5-dioxo-3-(pyridin-2-ylmethyl)-2,3-dihydro-1H-benzo[e][1,4]diazepin-4(5H)-yl)methyl)-N-(5-ethylpyridin-2-yl)benzamide;

8) (S)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide;

9) (R)-8-chloro-4-(3-chloro-4-(3,3-dimethyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;

10) (R)-4-((8-chloro-2,5-dioxo-3-(pyridin-2-ylmethyl)-2,3-dihydro-1H-benzo[e][1,4]diazepin-4(5H)-yl)methyl)-N-(5-morpholinopyridin-2-yl)benzamide;

11) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide;

12) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide;

13) (R)-8-chloro-4-(3-chloro-4-(2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;

14) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide;

15) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide;

16) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyridin-2-yl)benzamide;

17) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)-2-methylbenzamide;

18) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyridin-2-yl)benzamide;

19) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyridin-2-yl)benzamide;

20) (R)-4-((8-chloro-2,5-dioxo-3-(pyridin-2-ylmethyl)-2,3-dihydro-1H-benzo[e][1,4]diazepin-4(5H)-yl)methyl)-N-(pyridin-2-yl)benzamide;

21) (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide;

22) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide;

23) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide;

24) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide;

25) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(3-fluoropyridin-2-yl)benzamide;

26) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide;

27) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)-2-methylbenzamide;

28) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrimidin-2-yl)benzamide;

29) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrazin-2-yl)benzamide;

30) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)-2-methylbenzamide;

31) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrazin-2-yl)benzamide;

32) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrazin-2-yl)benzamide;

33) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl)pyridin-2-yl)benzamide;

34) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrimidin-2-yl)benzamide;
35) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrimidin-2-yl)benzamide;
36) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)benzamide;
37) (R)-4-((8-chloro-2,5-dioxo-3-(pyridin-2-ylmethyl)-2,3-dihydro-1H-benzo[e][1,4]diazepin-4(5H)-yl)methyl)-N-(5-fluoropyridin-2-yl)-2-methylbenzamide;
38) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrimidin-2-yl)benzamide;
39) (R)-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)-2-methylbenzamide;
40) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)benzamide;
41) (R)-8-chloro-4-(3-chloro-4-(3,3-dimethyl-5-(trifluoromethyl)-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;
42) (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide;
43) (R)-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide;
44) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide;
45) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methoxypyridin-2-yl)benzamide;
46) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(pyridin-2-yl)benzamide;
47) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-fluoropyridin-2-yl)benzamide;
48) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methylpyridin-2-yl)benzamide;
49) (R)-8-chloro-4-(3-fluoro-4-(5-methyl-2,3-dihydro-1H-pyrrolo[2,3-b]pyridine-1-carbonyl)benzyl)-3-(pyridin-2-ylmethyl)-3,4-dihydro-1H-benzo[e][1,4]diazepine-2,5-dione;
50) (R)-8-chloro-4-(4-(5-methylpicolinoyl)benzyl)-3-(pyridin-2-ylmethyl)-3,4-dihydro-1H-benzo[e][1,4]diazepine-2,5-dione;
51) (R)-8-chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione;
52) (R)-8-chloro-4-(((1r,4R)-4-(1-methyl-1H-pyrrolo[3,2-b]pyridin-3-carbonyl)cyclohexyl)methyl)-3-(pyridin-2-ylmethyl)-3,4-dihydro-1H-benzo[e][1,4]diazepine-2,5-dione;
53) (R)-8-chloro-4-(4-(imidazo[1,2-a]pyridine-8-carbonyl)benzyl)-3-(pyridin-2-ylmethyl)-3,4-dihydro-1H-benzo[e][1,4]diazepine-2,5-dione; and
54) (R)-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyrimidin-2-yl)benzamide, or a pharmaceutically acceptable salt thereof.

15. The compound of claim 13, which is selected from:
1) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)benzamide;
2) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyridin-2-yl)benzamide;
3) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)benzamide;
4) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyridin-2-yl)benzamide;
5) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyridin-2-yl)-2-methylbenzamide;
6) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyridin-2-yl)benzamide;
7) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methylpyrazin-2-yl)benzamide;
8) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)benzamide;
9) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-(trifluoromethyl)pyridin-2-yl)benzamide;
10) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrazin-2-yl)-2-methylbenzamide;
11) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-methylpyrazin-2-yl)benzamide;
12) (R)-4-((8-chloro-2,5-dioxo-3-(pyridin-2-ylmethyl)-2,3-dihydro-1H-benzo[e][1,4]diazepin-4(5H)-yl)methyl)-N-(5-methoxypyrimidin-2-yl)-2-methylbenzamide;
13) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methylpyrazin-2-yl)benzamide;
14) (R)-4-((8-chloro-2,5-dioxo-3-(pyridin-2-ylmethyl)-2,3-dihydro-1H-benzo[e][1,4]diazepin-4(5H)-yl)methyl)-2-methoxy-N-(5-methoxypyrazin-2-yl)benzamide;
15) (R)-4-((8-chloro-2,5-dioxo-3-(pyridin-2-ylmethyl)-2,3-dihydro-1H-benzo[e][1,4]diazepin-4(5H)-yl)methyl)-2-methyl-N-(5-(trifluoromethyl)pyridin-2-yl)benzamide;
16) (R)-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)-2-methylbenzamide;
17) (R)-2-chloro-4-((8-chloro-2,5-dioxo-3-(pyridin-2-ylmethyl)-2,3-dihydro-1H-benzo[e][1,4]diazepin-4(5H)-yl)methyl)-N-(5-cyanopyridin-2-yl)benzamide;

18) (R)-4-((8-chloro-2,5-dioxo-3-(pyridin-2-ylmethyl)-2,3-dihydro-1H-benzo[e][1,4]diazepin-4(5H)-yl)methyl)-2-fluoro-N-(5-methoxypyridin-2-yl)benzamide; and
19) (R)-8-chloro-4-(4-(1-methyl-1H-pyrrolo[3,2-b]pyridine-3-carbonyl)benzyl)-3-(pyridin-2-ylmethyl)-3,4-dihydro-1H-benzo[e][1,4]diazepine-2,5-dione, or a pharmaceutically acceptable salt thereof.

16. A pharmaceutical composition comprising the compound of claim 1, or a pharmaceutically acceptable salt thereof, and a pharmaceutically acceptable carrier.

17. A pharmaceutical composition comprising the compound of claim 13, or a pharmaceutically acceptable salt thereof, and a pharmaceutically acceptable carrier.

18. A pharmaceutical composition comprising the compound of claim 14, or a pharmaceutically acceptable salt thereof, and a pharmaceutically acceptable carrier.

19. A method of treating *C. difficile* infection (CDI) in a human in need thereof, comprising the step of: administering to said human a therapeutically effective amount of the compound of claim 1.

20. A method of treating *C. difficile* infection (CDI) in a human in need thereof, comprising the step of: administering to said human a therapeutically effective amount of the compound of claim 13.

21. A method of treating *C. difficile* infection (CDI) in a human in need thereof, comprising the step of: administering to said human a therapeutically effective amount of the compound of claim 14.

22. A method of treating *C. difficile* infection (CDI) in a human in need thereof, comprising the steps of: (a) administering to said human a therapeutically effective amount of the compound of claim 1; and (b) administering to said human a therapeutically effective amount of an additional therapeutic agent useful for the treatment of CDI.

23. A method of treating *C. difficile* infection (CDI) in a human in need thereof, comprising the steps of: (a) administering to said human a therapeutically effective amount of the compound of claim 13; and (b) administering to said human a therapeutically effective amount of an additional therapeutic agent useful for the treatment of CDI.

24. A method of treating *C. difficile* infection (CDI) in a human in need thereof, comprising the steps of: (a) administering to said human a therapeutically effective amount of the compound of claim 14; and (b) administering to said human a therapeutically effective amount of an additional therapeutic agent useful for the treatment of CDI.

25. A method of preventing a relapse of a prior *C. difficile* infection (CDI) in a human, comprising the step of: administering to said human a therapeutically effective amount of the compound of claim 1.

26. A method of preventing a relapse of a prior *C. difficile* infection (CDI) in a human, comprising the step of: administering to said human a therapeutically effective amount of the compound of claim 13.

27. A method of preventing a relapse of a prior *C. difficile* infection (CDI) in a human, comprising the step of: administering to said human a therapeutically effective amount of the compound of claim 14.

* * * * *